US012338449B2

(12) United States Patent
Loiler

(10) Patent No.: US 12,338,449 B2
(45) Date of Patent: Jun. 24, 2025

(54) ENHANCED MODIFIED VIRAL CAPSID PROTEINS

(71) Applicant: Research Institute at Nationwide Children's Hospital, Columbus, OH (US)

(72) Inventor: Scott Allen Loiler, Columbus, OH (US)

(73) Assignee: Research Institute at Nationwide Children's Hospital, Columbus, OH (US)

(*) Notice: Subject to any disclaimer, the term of this patent is extended or adjusted under 35 U.S.C. 154(b) by 1170 days.

(21) Appl. No.: 16/619,450

(22) PCT Filed: Jun. 4, 2018

(86) PCT No.: PCT/US2018/035906
§ 371 (c)(1),
(2) Date: Dec. 4, 2019

(87) PCT Pub. No.: WO2018/226602
PCT Pub. Date: Dec. 13, 2018

(65) Prior Publication Data
US 2020/0157570 A1 May 21, 2020

Related U.S. Application Data

(60) Provisional application No. 62/562,058, filed on Sep. 22, 2017, provisional application No. 62/515,468, filed on Jun. 5, 2017.

(51) Int. Cl.
*C12N 9/22* (2006.01)
*A61K 47/65* (2017.01)
*A61K 48/00* (2006.01)
*A61P 21/00* (2006.01)
*C07K 14/005* (2006.01)
*C12N 15/11* (2006.01)
*C12N 15/85* (2006.01)
*C12N 15/86* (2006.01)

(52) U.S. Cl.
CPC .............. *C12N 15/86* (2013.01); *A61K 47/65* (2017.08); *A61K 48/005* (2013.01); *A61P 21/00* (2018.01); *C07K 14/005* (2013.01); *C12N 9/22* (2013.01); *C12N 15/11* (2013.01); *C12N 15/85* (2013.01); *C07K 2319/92* (2013.01); *C12N 2310/20* (2017.05); *C12N 2750/14122* (2013.01); *C12N 2750/14143* (2013.01); *C12N 2800/107* (2013.01)

(58) Field of Classification Search
CPC .......... C12N 15/86; C12N 9/22; C12N 15/11; C12N 15/85; C12N 2310/20; C12N 2750/14122; C12N 2750/14143; C12N 2800/107; A61K 47/65; A61K 48/005; A61P 21/00; C07K 14/005; C07K 2319/92
See application file for complete search history.

(56) References Cited

U.S. PATENT DOCUMENTS

| | | | |
|---|---|---|---|
| 2001/0016355 A1 | 8/2001 | Samulski et al. | |
| 2013/0150287 A1 | 6/2013 | Ahn et al. | |
| 2014/0271652 A1* | 9/2014 | Scoville | C07K 7/06 424/139.1 |
| 2014/0273232 A1 | 9/2014 | Zhang et al. | |
| 2014/0335158 A1 | 11/2014 | Rao | |
| 2018/0037877 A1* | 2/2018 | Gao | C12N 15/11 |
| 2020/0080112 A1* | 3/2020 | Zhang | A61K 9/1271 |

FOREIGN PATENT DOCUMENTS

| | | | |
|---|---|---|---|
| WO | WO-2014/093635 A1 | 6/2014 | |
| WO | WO-2016131009 A1* | 8/2016 | .......... A61K 48/005 |
| WO | WO-2017083852 A1* | 5/2017 | ............ A61K 35/30 |
| WO | WO-2017165859 A1* | 9/2017 | .......... A61K 48/005 |
| WO | WO-2018/035387 A1 | 2/2018 | |

OTHER PUBLICATIONS

Chew et al "A multifunctional AAV-CRISPR-Cas9 and its host response" (Nature Methods Oct. 2016, vol. 13, No. 10, pp. 868-874 and attached "Online Methods"). (Year: 2016).*
International Search Report and Written Opinion issued in PCT Application No. PCT/US2018/035906 dated Aug. 30, 2018, 18 pages.
Li et al., "Precise Correction of the Dystrophin Gene in Duchenne Muscular Dystrophy Patient Induced Pluripotent Stem Cells by TALEN and CRISPR-Cas9", Stem Cells Reports, Jan. 13, 2015, vol. 4, No. 1, pp. 43-54.
Stevens et al., "Design of a Split Intein with Exceptional Protein Splicing Activity", Journal of the American Chemical Society, 2016, 138, pp. 2162-2165.
Ann Ran, et al., "In vivo genome editing using *Staphylococcus aureus* Cas9", Nature, Apr. 9, 2015, vol. 520, pp. 186-191.
Ann Ran, F., "Adaptation of CRISPR nucleases for eukaryotic applications", Analytical Biochemistry, 2016, 5 pages.
Aubrey, et al., "An Inducible Lentiviral Guide RNA Platform Enables the Identification of Tumor-Essential Genes and Tumor-Promoting Mutations in Vivo", Cell Reports, 2015, 10, pp. 1422-1432.
Barnard, et al., "Gene Therapy for Choroideremia Using an Adeno-Associated Viral (AAV) Vector", Cold Spring Harbor Perspectives in Medicine, 2015, 5, a017293.

(Continued)

*Primary Examiner* — Catherine S Hibbert
(74) *Attorney, Agent, or Firm* — Foley & Lardner LLP

(57) ABSTRACT

Modified capsid proteins, isolated polynucleotides, methods for the preparation of modified capsid proteins, recombinant viral particles, recombinant expression systems for the generation of modified viral particles, and methods of gene editing and regulation are provided herein.

26 Claims, 18 Drawing Sheets
Specification includes a Sequence Listing.

(56) References Cited

OTHER PUBLICATIONS

Cho, et al., "Analysis of off-target effects of CRISPR/Cas-derived RNA-guided endonucleases and nickases", Genome Research, 2014, 24, pp. 132-141.
Corti, et al., "B-Cell depletion is protective against anti-AAV capsid immune response: a human subject case study", Molecular Therapy—Methods & Clinical Development, 2014, 1, 14033.
Davis, et al., "Small molecule-triggered Cas9 protein with improved genome-editing specificity", Nature Chemical Biology, May 2015, vol. 11, pp. 316-318.
Fu, et al., "Improving CRISPR-Cas nuclease specificity using truncated guide RNAs", Nature Biotechnology, Mar. 2014, vol. 32, No. 3, pp. 279-284.
Haddley, K., "Alipogene Tiparvovec for the Treatment of Lipoprotein Lipase Deficiency", Drugs of Today, 2013, 49(3), pp. 161-170.
MacLaren, et al., "Retinal gene therapy in patients with choroideremia: initial findings from a phase 1/2 clinical trial", Lancet, Mar. 29, 2014, vol. 383, pp. 1129-1137.
Monahan, et al., "Employing a Gain-of-Function Factor IX Variant R338L to Advance the Efficacy and Safety of Hemophilia B Human Gene Therapy: Preclinical Evaluation Supporting an Ongoing Adeno-Associated Virus Clinical Trial", Human Gene Therapy, Feb. 2015, 26, pp. 69-81.
Nicolson, et al., "Recombinant Adeno-Associated Virus Utilizes Host Cell Nuclear Import Machinery to Enter the Nucleus", Journal of Virology, 2014, 88, pp. 4132-4144.
Nihongaki, et al., "CRISPR-Cas9-based Photoactivatable Transcription System", Chemistry & Biology, 2015, 22, pp. 169-174.
Nishimasu, et al., "Crystal Structure of *Staphylococcus aureus* Cas9", Cell, 2015, 162, pp. 1113-1126.
Polstein, et al., "A light-inducible CRISPR-Cas9 system for control of endogenous gene activation", Nature Chemical Biology, Mar. 2015, vol. 11, pp. 198-200.
Simonelli, et al., "Gene Therapy for Leber's Congenital Amaurosis is Safe and Effective Through 1.5 Years After Vector Administration", Molecular Therapy, 2010, vol. 18, No. 3, pp. 643-650.
Smith, et al., "Phase I/II Trial of Adeno-Associated Virus-Mediated Alpha-Glucosidase Gene Therapy to the Diaphragm for Chronic Respiratory Failure in Pompe Disease: Initial Safety and Ventilatory Outcomes", Human Gene Therapy, Jun. 2013, 24, pp. 630-640.
Stevens, et al., "Design of a Split Intein with Exceptional Protein Splicing Activity", JACS, 2016, 138, pp. 2162-2165.
Tenney, et al. "AAV8 capsid variable regions at the two-fold symmetry axis contribute to high liver transduction by mediating nuclear entry and capsid uncoating", Virology, 454-455, 2014, pp. 227-236.
Truong, et al., "Development of an intein-mediated split-Cas9 system for gene therapy", Nucleic Acids Research, 2015, vol. 43, No. 13, pp. 6450-6458.
Wood, et al., "Intein Applications: From Protein Purification and Labeling to Metabolic Control Methods", Journal of Biological Chemistry, May 23, 2014, vol. 289, No. 21, pp. 14512-14519.
Wyvekens, et al., "Dimeric CRISPR RNA-Guided FokI-dCas9 Nucleases Directed by Truncated gRNAs for Highly Specific Genome Editing", Human Gene Therapy, 2015, vol. 26, No. 7, pp. 425-431.
Zetsche, et al., "A split-Cas9 architecture for inducible genome editing and transcription modulation", Nature Biotechnology, Feb. 2015, vol. 33, No. 2, pp. 139-142.
Zetsche, et al., "Cpf1 Is a Single RNA-Guided Endonuclease of a Class 2 CRISPR-Cas System", Cell, 2015, 163, pp. 759-771.
Zhu, et al., "The iCRISPR Platform for Rapid Genome Editing in Human Pluripotent Stem Cells", Methods in Enzymology, 2014, vol. 546, pp. 215-250.

\* cited by examiner

ENHANCED MODIFIED VIRAL CAPSID PROTEINS

CROSS REFERENCE TO RELATED APPLICATIONS

This application is a National Stage Application of PCT/US2018/035906, filed Jun. 4, 2018, which claims the benefit under 35 U.S.C. § 119(e) to U.S. Provisional Application No. 62/515,468, filed Jun. 5, 2017, and U.S. Provisional Application No. 62/562,058, filed Sep. 22, 2017, the contents of each of which are incorporated herein by reference in their entireties.

SEQUENCE LISTING

The instant application contains a Sequence Listing which has been submitted electronically in ASCII format and is hereby incorporated by reference in its entirety. Said ASCII copy, created on Feb. 27, 2023, is named 106887-7092_SL.txt and is 291,477 bytes in size.

BACKGROUND

The development of efficient and reliable ways to make specific, safe, and targeted changes to the genome of living cells with minimal off-target effects is a long-standing goal for biomedical researchers. Recently, a new tool based on a bacterial CRISPR-associated protein-9 nuclease (Cas9) has generated considerable excitement for its potential to efficiently perform gene editing and regulation.

Cas9 protein is a large enzyme that must be delivered efficiently to target tissues and cells to mediate gene repair through the CRISPR system and current CRISPR/Cas9 gene correction protocols suffer from a number of draw backs. Long term expression of Cas9 can elicit host immune responses. An additional guide RNA must usually be delivered via a separate vector due to packaging constraints.

Another constraint with the CRISPR/Cas9 system is that one increases the risk for genetic modifications into alternative regions of the genome other than at the target site, due to Cas9 nicking sequences other than the gRNA target. These "off-target" sites may be critical to normal cell function and disruption of some regions may lead aberrant cell growth. The optimal embodiment of the CRISPR/Cas9 system is to have the Cas9 protein only transiently expressed to reduce the chances of "off-target" gene rearrangements. Thus, there is a significant safety concern for using methods of CRISPR gene editing with AAV.

The present disclosure addresses the limitations of the prior art and provides related advantages as well.

SUMMARY

This disclosure relates to modified capsid proteins, isolated polynucleotides, methods for the preparation of modified capsid proteins, recombinant viral particles, recombinant expression systems for the generation of modified viral particles, and methods of gene editing, and the products and processes for producing them.

In some aspects, the disclosure relates to a modified viral capsid protein that comprises, or alternatively consists essentially of, or yet further consists of, a viral capsid protein having a Cas9 protein or an equivalent thereof conjugated to the interior surface of the viral capsid protein. In other aspects, the disclosure relates to a modified viral capsid protein that comprises, or alternatively consists essentially of, or yet further consists of, a viral capsid protein having a Cas9 protein or an equivalent thereof conjugated to the exterior surface of the viral capsid protein. In one aspect the capsid and/or Cas9 proteins are labeled. Also provided herein are compositions comprising a plurality of the modified capsid proteins that have the same or different viral capsids or Cas9 proteins attached to the interior, exterior, or both, of the viral capsid. In one aspect the capsid and/or Cas9 proteins are labeled.

Also disclosed herein is an isolated polynucleotide encoding a modified viral capsid protein that comprises, or alternatively consists essentially of, or yet further consists of, a viral capsid protein having a Cas9 protein or an equivalent thereof conjugated to the surface of the viral capsid protein. In some aspects, the surface is the exterior surface of the viral capsid protein. In one aspect the polynucleotide is labeled. In other aspects, the surface is the interior surface of the viral capsid protein. In one aspect the polynucleotide is labeled. In some aspects, the Cas9 protein or an equivalent thereof has been conjugated to the viral capsid protein via modular intein based assembly. Also provided herein are compositions comprising a plurality of the polynucleotides that encode the same or different viral capsids or Cas9 proteins attached to the interior, exterior, or both, of the viral capsid.

Provided herein is a method of preparing a modified viral capsid protein that comprises, or alternatively consists essentially of, or yet further consists of, a viral capsid protein having a Cas9 protein or an equivalent thereof conjugated to the interior surface of the viral capsid protein. Also provided herein is a method of preparing a modified capsid protein that comprises, or alternatively consists essentially of, or yet further consists of, a viral capsid protein having a Cas9 protein or an equivalent thereof conjugated to the exterior surface of the viral capsid protein. In one aspect, the method comprises coupling the Cas9 protein or an equivalent thereof to the viral capsid protein. Alternatively, the method comprises expressing a recombinant fusion polynucleotide encoding Cas9 or an equivalent thereof and one or more viral capsid proteins, in a system that provides the helper functions for the preparation of viral particles. In one aspect, the viral particles are isolated from the system. In a further aspect, a label is added to the components of the systems.

Also provided herein is a method of preparing a modified viral capsid protein that comprises, consists of, or consists essentially of coupling (i) a fusion protein comprising a Cas9 protein or an equivalent thereof and an N-terminal fragment of a split intein to (ii) a fusion protein comprising a viral capsid protein and a C-terminal fragment of a split intein under conditions suitable for modular intein based assembly. In another aspect, provided herein is a method of preparing a modified viral capsid protein that comprises, consists of, or consists essentially of coupling (i) a fusion protein comprising a Cas9 protein or an equivalent thereof and a C-terminal fragment of a split intein to (ii) a fusion protein comprising a viral capsid protein and an N-terminal fragment of a split intein under conditions suitable for modular intein based assembly. In some aspects, the modular intein based assembly comprises, consists of, or consists essentially of a fast intein system wherein at least one of the N-terminal split intein fragment and the C-terminal split intein fragment is derived from a fast intein. In some aspects, the split intein fragments are modified to enhance stability, efficiency, speed of ligation, and/or function. In some aspects, the modular intein based assembly comprises, consists of, or consists essentially of a fast intein system wherein at least one of the N-terminal split intein fragment and the C-terminal split intein fragment is derived from a fast intein. In a particular aspect, the modular intein based assembly comprises, consists of, or consists essentially of a consensus fast (Cfa) intein system wherein at least one of the N-terminal split intein fragment and the C-terminal split intein fragment is derived from a Cfa intein. In one aspect, one or more components of the modified capsid proteins are labeled.

Disclosed herein is a recombinant viral particle that comprises or alternatively consists essentially of, or yet further consists of, a modified capsid protein that comprises, or alternatively consists essentially of, or yet further consists of, a viral capsid protein having a Cas9 protein or an equivalent thereof conjugated to the surface of the viral capsid protein, and one or more polynucleotides encapsidated within the capsid. In some aspects, the surface is the exterior surface of the viral capsid protein. In other aspects, the surface is the interior surface of the viral capsid protein. In particular aspects, the recombinant viral particle comprises or alternatively consists essentially of 5 or more modified capsid proteins per viral particle (and/or per modified viral capsid). In other aspects, the recombinant viral particle comprises or alternatively consists essentially of between 1 and 5 modified capsid proteins per viral particle (and/or per modified viral capsid). In one aspect, one or more components of the modified capsid proteins are labeled.

Further disclosed herein is a recombinant expression system for the generation of a modified viral particle expressing Cas9 or an equivalent thereof on the viral particle capsid surface, the system comprising, or alternatively consisting essentially of, or yet further consisting of: (a) a plasmid comprising a DNA sequence encoding a fusion protein, the fusion protein comprising the Cas9 or the equivalent thereof and a viral capsid protein; and (b) a helper plasmid. In another aspect, disclosed herein is a recombinant expression system for the generation of a modified viral particle expressing Cas9 or an equivalent thereof on the viral particle capsid surface, the system comprising, or alternatively consisting essentially of, or yet further consisting of. (a) a plasmid comprising a DNA sequence encoding a fusion protein, the fusion protein comprising the Cas9 or the equivalent thereof and an N-terminal fragment of a split intein; (b) a plasmid comprising a DNA sequence encoding a fusion protein, the fusion protein comprising a modified viral capsid protein and a C-terminal fragment of a split intein; and (c) a helper plasmid. In some aspects, the surface is the exterior surface of the viral capsid protein. In other aspects, the surface is the interior surface of the viral capsid protein. In one aspect, one or more components of the system are labeled.

Also disclosed herein is a method of gene editing or gene regulation comprising contacting a cell or tissue with a recombinant viral particle, the viral particle comprising, or alternatively consisting essentially of, or yet further consisting of, a modified capsid protein that comprises, or alternatively consists essentially of, or yet further consists of, a viral capsid protein having a Cas9 protein or an equivalent thereof conjugated to the surface of the viral capsid protein, that may optionally be labeled. In some aspects, the surface is the exterior surface of the viral capsid protein. In other aspects, the surface is the interior surface of the viral capsid protein. In some aspects, the recombinant viral particle further comprises one or more polynucleotides encapsidated within the modified viral capsid, that may optionally be labeled. In other aspects, the method further comprises contacting the cell or tissue with a second viral particle comprising one or more polynucleotides, that may optionally be labeled. In another aspect, the method further comprises contacting the cell or tissue with one or more polynucleotides, that may optionally be labeled. The contacting can be in vitro, ex vivo, or in vivo.

This disclosure also provides compositions comprising a carrier and one or more of a modified protein, a polynucleotide, vector, plasmid, host cell, or expression system, as well as a plurality of one or more of the modified protein, a polynucleotide, vector, plasmid, host cell, or expression system, that may be the same or different from each other. Further provided is a kit comprising one or more of a modified protein, a polynucleotide, vector, plasmid, host cell, or expression system, as well as a plurality of one or more of the modified protein, a polynucleotide, vector, plasmid, host cell, or expression system, that may be the same or different from each other, and instructions for use.

Further disclosed herein is a method of gene editing or gene regulation in a subject in need thereof, comprising, or alternatively consisting essentially of, or yet further consisting of, administering to the subject an effective amount of a recombinant viral particle that comprises, or alternatively consists essentially of, or yet further consists of, a modified capsid protein that comprises, or alternatively consists essentially of, or yet further consists of, a viral capsid protein having a Cas9 protein or an equivalent thereof conjugated to the interior surface of the viral capsid protein, and one or more polynucleotides encapsidated within the capsid. In one aspect, the viral particle or a component thereof is labeled.

BRIEF DESCRIPTION OF THE FIGURES

FIG. 12A displays an internal side view of 12 capsid monomers (various shades of gray). The 5 insertion sites are identified on each monomer with white arrowheads. FIG. 12B displays a top view of the capsid monomers (various shades of gray). The 5 insertion sites are identified on each monomer with white arrowheads.

FIG. 13A depicts an saCas9-Cfa intein protein map. Signal peptide (SP), saCas9, CfaN intein are shown. FIG. 13B depicts a VP2-Cfa intein protein map. CfaC and VP2 are shown.

FIG. 15A: Lysate of HEK293 cells transfected with the various listed plasmids were run on a 4-12% gradient gel and probed with anti-AAV antibody (B1). FIG. 15B: Lysate of HEK293 cells transfected with the various listed plasmids were run on a 4-12% gradient gel and probed with an anti-OLLAS antibody for the detection of OLLAS tagged Cas9 protein.

FIG. 16A: Sypro stained protein gel of purified viruses. AAVrh74 is a control virus; VP2-Cfa$^C$, intein linker fusion with VP2; VP2-228, OLLAS linker fused to internal facing region of VP2 at position 228. FIG. 16B: Western probed with anti-AAV antibody (lanes 2-4) and Western probed with an anti-OLLAS tag antibody (lanes 6-8).

FIG. 17A is a schematic of GeoCas9-Cfa$^N$. FIG. 17B is a schematic of the Cfa$^C$-VP2 construct. Trans-splicing of split intein allows the assembly of GeoCas9-VP2.

DETAILED DESCRIPTION

Figure 1:
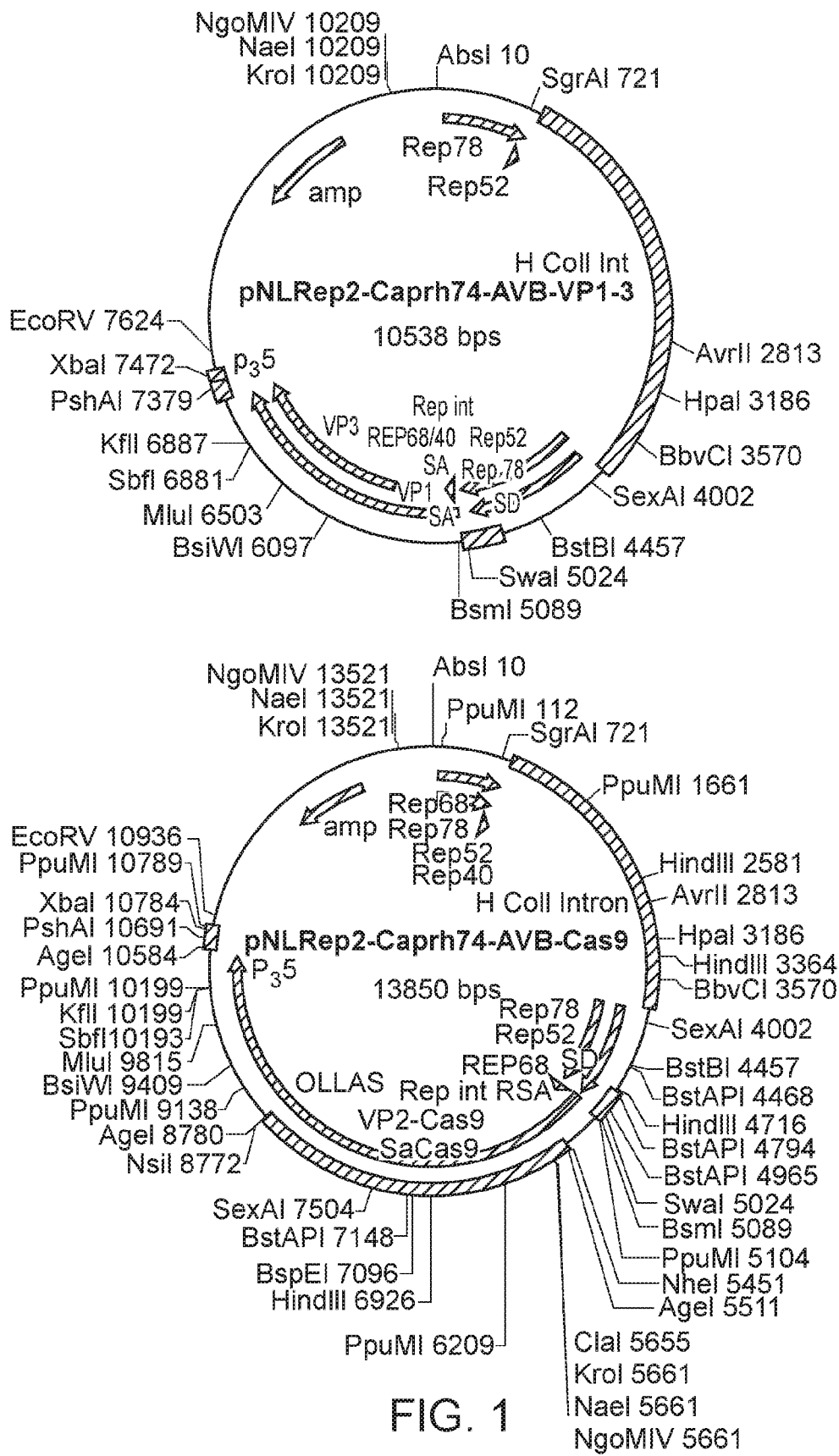
FIG. 1 depicts two exemplary constructs: the first encoding VPs1 and 3 of an AAV and the second encoding a VP2-Cas9 fusion protein for exterior Cas9 expression.

Embodiments according to the present disclosure will be described more fully hereinafter. Aspects of the disclosure may, however, be embodied in different forms and should not be construed as limited to the embodiments set forth herein. Rather, these embodiments are provided so that this disclosure will be thorough and complete, and will fully convey the scope of the invention to those skilled in the art. The terminology used in the description herein is for the purpose of describing particular embodiments only and is not intended to be limiting.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein. While not explicitly defined below, such terms should be interpreted according to their common meaning.

The terminology used in the description herein is for the purpose of describing particular embodiments only and is not intended to be limiting of the invention. All publications, patent applications, patents and other references mentioned herein are incorporated by reference in their entirety.

The practice of the present technology will employ, unless otherwise indicated, conventional techniques of tissue culture, immunology, molecular biology, microbiology, cell biology, and recombinant DNA, which are within the skill of the art.

Unless the context indicates otherwise, it is specifically intended that the various features of the invention described herein can be used in any combination. Moreover, the disclosure also contemplates that in some embodiments, any feature or combination of features set forth herein can be excluded or omitted. To illustrate, if the specification states that a complex comprises components A, B and C, it is specifically intended that any of A, B or C, or a combination thereof, can be omitted and disclaimed singularly or in any combination.

Unless explicitly indicated otherwise, all specified embodiments, features, and terms intend to include both the recited embodiment, feature, or term and biological equivalents thereof.

All numerical designations, e.g., pH, temperature, time, concentration, and molecular weight, including ranges, are approximations which are varied (+) or (−) by increments of 1.0 or 0.1, as appropriate, or alternatively by a variation of +/−15%, or alternatively 10%, or alternatively 5%, or alternatively 2%. It is to be understood, although not always explicitly stated, that all numerical designations are preceded by the term "about". It also is to be understood, although not always explicitly stated, that the reagents described herein are merely exemplary and that equivalents of such are known in the art.

Throughout this disclosure, various publications, patents and published patent specifications are referenced by an identifying citation or by an Arabic numeral. The full citation for the publications identified by an Arabic numeral are found immediately preceding the claims. The disclosures of these publications, patents and published patent specifications are hereby incorporated by reference into the present disclosure in their entirety to more fully describe the state of the art to which this invention pertains.

Definitions

The practice of the present technology will employ, unless otherwise indicated, conventional techniques of organic chemistry, pharmacology, immunology, molecular biology, microbiology, cell biology and recombinant DNA, which are within the skill of the art. See, e.g., Sambrook, Fritsch and Maniatis, Molecular Cloning: A Laboratory Manual, 2$^{nd}$ edition (1989); Current Protocols In Molecular Biology (F. M. Ausubel, et al. eds., (1987)); the series Methods in Enzymology (Academic Press, Inc.): PCR 2: A Practical Approach (M. J. MacPherson, B. D. Hames and G. R. Taylor eds. (1995)), Harlow and Lane, eds. (1988) Antibodies, a Laboratory Manual, and Animal Cell Culture (R. I. Freshney, ed. (1987)).

As used herein, the singular forms "a," "an" and "the" are intended to include the plural forms as well, unless the context clearly indicates otherwise.

As used herein, the term "comprising" is intended to mean that the compositions and methods include the recited elements, but do not exclude others. As used herein, the transitional phrase consisting essentially of (and grammatical variants) is to be interpreted as encompassing the recited materials or steps and those that do not materially affect the basic and novel characteristic(s) of the recited embodiment. Thus, the term "consisting essentially of" as used herein should not be interpreted as equivalent to "comprising." "Consisting of" shall mean excluding more than trace elements of other ingredients and substantial method steps for administering the compositions disclosed herein. Aspects defined by each of these transition terms are within the scope of the present disclosure.

The term "about," as used herein when referring to a measurable value such as an amount or concentration and the like, is meant to encompass variations of 20%, 10%, 5%, 1%, 0.5%, or even 0.1% of the specified amount.

The terms or "acceptable," "effective," or "sufficient" when used to describe the selection of any components, ranges, dose forms, etc. disclosed herein intend that said component, range, dose form, etc. is suitable for the disclosed purpose.

Also as used herein, "and/or" refers to and encompasses any and all possible combinations of one or more of the associated listed items, as well as the lack of combinations when interpreted in the alternative ("or").

The term "adeno-associated virus" or "AAV" as used herein refers to a member of the class of viruses associated with this name and belonging to the genus dependoparvovirus, family Parvoviridae. Multiple serotypes of this virus are known to be suitable for gene delivery; all known serotypes can infect cells from various tissue types. At least 11 sequentially numbered, AAV serotypes are known in the art. Non-limiting exemplary serotypes useful in the methods disclosed herein include any of the 11 serotypes, e.g., AAV2, AAV8, AAV9, or variant serotypes, e.g., AAV-DJ. The AAV particle comprises three major viral proteins: VP1, VP2 and VP3.

The term "Cas9" refers to a CRISPR associated endonuclease referred to by this name. Non-limiting exemplary Cas9s are provided herein, e.g., the Cas9 provided for in UniProtKB G3ECR1 (CAS9_STRTR) or the *Staphylococcus aureus* Cas9 encoded by the protein sequence described herein, e.g., SEQ ID NO: 3, as well as the nuclease dead Cas9 encoded by the protein sequence SEQ ID NO: 40, orthologs and biological equivalents each thereof. Orthologs include but are not limited to *Streptococcus pyogenes* Cas9 ("spCas9"), e.g., SEQ ID NO: 18; Cas 9 from *Streptococcus thermophiles, Legionella pneumophilia, Neisseria lactamica, Neisseria meningitides, Francisella novicida*; and Cpf1 (SEQ ID NO: 19) (which performs cutting functions analogous to Cas9) from various bacterial species including *Acidaminococcus* spp. and *Francisella novicida* U112.

The term "cell" as used herein may refer to either a prokaryotic or eukaryotic cell, optionally obtained from a subject or a commercially available source. In some embodiments, the cell is an isolated cell.

"Eukaryotic cells" comprise all of the life kingdoms except monera. They can be easily distinguished through a membrane-bound nucleus. Animals, plants, fungi, and protists are eukaryotes or organisms whose cells are organized into complex structures by internal membranes and a cytoskeleton. The most characteristic membrane-bound structure is the nucleus. Unless specifically recited, the term "host" includes a eukaryotic host, including, for example, yeast, higher plant, insect and mammalian cells. Non-limiting examples of eukaryotic cells or hosts include simian, bovine, porcine, murine, rat, avian, reptilian and human, e.g., HEK293 cells and 293T cells.

"Prokaryotic cells" that usually lack a nucleus or any other membrane-bound organelles and are divided into two domains, bacteria and archaea. In addition to chromosomal DNA, these cells can also contain genetic information in a circular loop called on episome. Bacterial cells are very small, roughly the size of an animal mitochondrion (about 1-2 m in diameter and 10 m long). Prokaryotic cells feature three major shapes: rod shaped, spherical, and spiral. Instead of going through elaborate replication processes like eukaryotes, bacterial cells divide by binary fission. Examples include but are not limited to *Bacillus* bacteria, *E. coli* bacterium, and *Salmonella* bacterium.

As used herein, the term "CRISPR" refers to a technique of sequence specific genetic manipulation relying on the clustered regularly interspaced short palindromic repeats pathway. CRISPR can be used to perform gene editing and/or gene regulation, as well as to simply target proteins to a specific genomic location. Gene editing refers to a type of genetic engineering in which the nucleotide sequence of a target polynucleotide is changed through introduction of deletions, insertions, or base substitutions to the polynucleotide sequence. In some aspects, CRISPR-mediated gene editing utilizes the pathways of nonhomologous end-joining (NHEJ) or homologous recombination to perform the edits. Gene regulation refers to increasing or decreasing the production of specific gene products such as protein or RNA.

The term "gRNA" or "guide RNA" as used herein refers to the guide RNA sequences used to target specific genes for correction employing the CRISPR technique. Techniques of designing gRNAs and donor therapeutic polynucleotides for target specificity are well known in the art. For example, Doench, J., et al. Nature biotechnology 2014; 32(12):1262-7, Mohr, S. et al. (2016) FEBS Journal 283: 3232-38, and Graham, D., et al. Genome Biol. 2015; 16: 260. gRNA comprises or alternatively consists essentially of, or yet further consists of a fusion polynucleotide comprising CRISPR RNA (crRNA) and trans-activating CRIPSPR RNA (tracrRNA); or a polynucleotide comprising CRISPR RNA (crRNA) and trans-activating CRIPSPR RNA (tracrRNA). In some aspects, a gRNA is synthetic (Kelley, M. et al. (2016) J of Biotechnology 233 (2016) 74-83). As used herein, a biological equivalent of a gRNA includes but is not limited to polynucleotides or targeting molecules that can guide a Cas9 or equivalent thereof to a specific nucleotide sequence such as a specific region of a cell's genome. In some embodiments, the biological equivalent comprises a spacer sequence.

The term "repair template" as used herein refers to a polynucleotide comprising a desired sequence to be repaired in the target sequence. In some embodiments, the mechanism of repair is homology-directed repair. In some embodiments, the repair template comprises the desired edit as well as additional homologous sequence immediately upstream and downstream of the target (termed left & right homology arms). In some embodiments, the length of each homology arm is dependent on the size of the change being introduced, with larger insertions requiring longer homology arms. In some embodiments, the repair template is a single-stranded oligonucleotide, a double-stranded oligonucleotide, or a double-stranded DNA plasmid. Methods of designing repair templates are known in the art (see, e.g., Paquet, D. et al., Nature. 2016 May 5; 533(7601):125-9, incorporated herein by reference). In some embodiments, the repair template does not include the PAM sequence present in the genomic DNA to prevent the repair template from being a suitable target for Cas9 cleavage.

The term "encode" as it is applied to nucleic acid sequences refers to a polynucleotide which is said to "encode" a polypeptide if, in its native state or when manipulated by methods well known to those skilled in the art, can be transcribed and/or translated to produce the mRNA for the polypeptide and/or a fragment thereof. The antisense strand is the complement of such a nucleic acid, and the encoding sequence can be deduced therefrom.

The terms "equivalent" or "biological equivalent" are used interchangeably when referring to a particular molecule, biological, or cellular material and intend those having minimal homology while still maintaining desired structure or functionality. Non-limiting examples of equivalent polypeptides, include a polypeptide having at least 60%, or alternatively at least 65%, or alternatively at least 70%, or alternatively at least 75%, or alternatively 80%, or alternatively at least 85%, or alternatively at least 90%, or alternatively at least 95% identity thereto or for polypeptide sequences, or a polypeptide which is encoded by a polynucleotide or its complement that hybridizes under conditions of high stringency to a polynucleotide encoding such polypeptide sequences. Conditions of high stringency are described herein and incorporated herein by reference. Alternatively, an equivalent thereof is a polypeptide encoded by a polynucleotide or a complement thereto, having at least 70%, or alternatively at least 75%, or alternatively 80%, or alternatively at least 85%, or alternatively at least 90%, or alternatively at least 95% identity, or at least 97% sequence identity to the reference polynucleotide, e.g., the wild-type polynucleotide.

Non-limiting examples of equivalent polynucleotides, include a polynucleotide having at least 60%, or alternatively at least 65%, or alternatively at least 70%, or alternatively at least 75%, or alternatively 80%, or alternatively at least 85%, or alternatively at least 90%, or alternatively at least 95%, or alternatively at least 97%, identity to a reference polynucleotide. An equivalent also intends a polynucleotide or its complement that hybridizes under conditions of high stringency to a reference polynucleotide.

As used herein, the term "functional" may be used to modify any molecule, biological, or cellular material to intend that it accomplishes a particular, specified effect.

A polynucleotide or polynucleotide region (or a polypeptide or polypeptide region) having a certain percentage (for example, 80%, 85%, 90%, or 95%) of "sequence identity" to another sequence means that, when aligned, that percentage of bases (or amino acids) are the same in comparing the two sequences. The alignment and the percent homology or sequence identity can be determined using software programs known in the art, for example those described in Current Protocols in Molecular Biology (Ausubel et al., eds. 1987) Supplement 30, section 7.7.18, Table 7.7.1. In certain embodiments, default parameters are used for alignment. A non-limiting exemplary alignment program is BLAST, using default parameters. In particular, exemplary programs include BLASTN and BLASTP, using the following default parameters: Genetic code=standard; filter=none; strand=both; cutoff=60; expect=10; Matrix=BLOSUM62;

Descriptions=50 sequences; sort by=HIGH SCORE; Databases=non-redundant, GenBank+EMBL+DDBJ+PDB+GenBank CDS translations+SwissProtein+SPupdate+PIR. Details of these programs can be found at the following Internet address: ncbi.nlm.nih.gov/cgi-bin/BLAST. Sequence identity and percent identity can be determined by incorporating them into clustalW (available at the web address:genome.jp/tools/clustalw/, last accessed on Jan. 13, 2017).

"Homology" or "identity" or "similarity" refers to sequence similarity between two peptides or between two nucleic acid molecules. Homology can be determined by comparing a position in each sequence that may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40% identity, or alternatively less than 25% identity, with one of the sequences of the present disclosure.

"Homology" or "identity" or "similarity" can also refer to two nucleic acid molecules that hybridize under stringent conditions.

"Hybridization" refers to a reaction in which one or more polynucleotides react to form a complex that is stabilized via hydrogen bonding between the bases of the nucleotide residues. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these. A hybridization reaction may constitute a step in a more extensive process, such as the initiation of a PCR reaction, or the enzymatic cleavage of a polynucleotide by a ribozyme.

Examples of stringent hybridization conditions include: incubation temperatures of about 25° C. to about 37° C.; hybridization buffer concentrations of about 6×SSC to about 10×SSC; formamide concentrations of about 0% to about 25%; and wash solutions from about 4×SSC to about 8×SSC. Examples of moderate hybridization conditions include: incubation temperatures of about 40° C. to about 50° C.; buffer concentrations of about 9×SSC to about 2×SSC; formamide concentrations of about 30% to about 50%; and wash solutions of about 5×SSC to about 2×SSC. Examples of high stringency conditions include: incubation temperatures of about 55° C. to about 68° C.; buffer concentrations of about 1×SSC to about 0.1×SSC; formamide concentrations of about 55% to about 75%; and wash solutions of about 1×SSC, 0.1×SSC, or deionized water. In general, hybridization incubation times are from 5 minutes to 24 hours, with 1, 2, or more washing steps, and wash incubation times are about 1, 2, or 15 minutes. SSC is 0.15 M NaCl and 15 mM citrate buffer. It is understood that equivalents of SSC using other buffer systems can be employed.

As used herein, "expression" refers to the process by which polynucleotides are transcribed into mRNA and/or the process by which the transcribed mRNA is subsequently being translated into peptides, polypeptides, or proteins. If the polynucleotide is derived from genomic DNA, expression may include splicing of the mRNA in an eukaryotic cell.

An "intein" is a segment of a protein or polypeptide that is able to excise itself and join the remaining portion(s) (the "exteins") with a peptide bond. In some embodiments, the intein excision/splicing process begins with an N-O or N-S shift when the side chain of the first residue (a serine, threonine, or cysteine) of an intein portion of a precursor protein nucleophilically attacks the peptide bond of the residue immediately upstream (i.e., the final residue of the N-extein) to form a linear ester or thioester intermediate. In some embodiments, a transesterification occurs when the side chain of the first residue of the C-extein attacks the newly formed ester or thioester to free the N-terminal end of the intein. In some embodiments, this forms a branched intermediate in which the N-extein and C-extein are attached. In some embodiments, the last residue of the intein is an asparagine, and the amide nitrogen atom of this side chain cleaves apart the peptide bond between the intein and the C-extein, resulting in a free intein segment with a terminal cyclic imide. Finally, in some embodiments, the free amino group of the C-extein attacks the ester or thioester linking the N- and C-exteins together. Thus, in some embodiments, an O-N or S-N shift produces a peptide bond and the functional, ligated protein.

As used herein, an "intein system" refers to a system comprising an intein-based protein splicing mechanism whereby an intervening intein protein domain excises itself from a host protein in a traceless manner such that the flanking polypeptide sequences (called exteins) are ligated together via a normal peptide bond. As used herein "modular intein based ligation," "modular intein based assembly," and "split intein" are used interchangeably to refer in intein systems wherein the intein is split into two fragments, an N-terminal fragment and a C-terminal fragment, and each fragment is fused to an extein such as Cas9 or a viral capsid protein. Under appropriate conditions, the split intein-extein fusions are co-expressed or mixed together and the intein ligation reaction is catalyzed, resulting a fusion of the two exteins and excision of the split intein fragments.

As used herein, a "fast intein" system is an intein system that is capable of a fast rate of protein trans-splicing (Neel, S. et al. Journal of the American Chemical Society (2012), 134 (28), 11338-11341, incorporated herein by reference). For example, a fast rate is a rate of about $t_{1/2}<5$ seconds at 30° C., about $t_{1/2}<10$ seconds at 30° C., about $t_{1/2}<20$ seconds at 30° C., about $t_{1/2}<50$ seconds at 30° C., about $t_{1/2}<100$ seconds at 30° C., about $t_{1/2}<200$ seconds at 30° C., about $t_{1/2}<300$ seconds at 30° C., about $t_{1/2}<400$ seconds at 30° C., about $t_{1/2}<500$ seconds at 30° C., about $t_{1/2}<600$ seconds at 30° C., about $t_{1/2}<700$ seconds at 30° C., about $t_{1/2}<800$ seconds at 30° C., about $t_{1/2}<900$ seconds at 30° C., or about $t_{1/2}<1000$ seconds at 30° C. In a particular embodiment, the fast rate is about $t_{1/2}<400$ seconds at 30° C. Fast intein systems include but are not limited to consensus fast intein systems and systems comprising one or more accelerator residues. Nonlimiting examples of accelerator residues include K70, M75, and M81 of SEQ ID NO: 60 (Stevens, A. et al. J. Am. Chem. Soc., 2016, 138 (7), pp 2162-2165). Exemplary fast inteins include but are not limited to the consensus fast intein (Cfa) (SEQ ID NO: 60), Npu, Ava, and Mcht. An exemplary N-terminal fragment of an intein is $Cfa^N$ (amino acid residues 1-101 of SEQ ID NO: 60). An exemplary C-terminal fragment of intein is $Cfa^C$ (amino acid residues 102-136 of SEQ ID NO: 60). In one embodiment, the fast intein can be further modified with a photocaged cysteine amino acid residue resulting in an intein ligation reaction that is photoactivatable (Ren, W. et al. J Am Chem Soc. 2015 Feb. 18; 137(6):2155-8).

The terms "consensus fast" and "consensus fast assembly" (Cfa) refer to a fast intein protein assembly system that utilizes the consensus design approach of Stevens et al., J Am Chem Soc. 2016 Feb. 24; 138(7): 2162-2165 (incorporated herein by reference). This approach results in a robust system with enhanced stability and activity compared to other split protein assembly systems. Using batch mutagenesis, Stevens et al. conducted a detailed analysis of the difference in splicing rates between the Npu (fast) and Ssp (slow) split inteins of the DnaE family and found that most impactful residues lie on the second shell of the protein, directly adjacent to the active site. These residues were then used to generate an alignment of 73 naturally occurring DnaE inteins that are predicted to be fast. The consensus sequence from this alignment demonstrates both rapid protein splicing and unprecedented thermal and chaotropic stability. For example, the Cfa intein can catalyze rapid ligations at temperatures up to 80° C. and in the presence of harsh chemicals. Moreover, when fused to various proteins including antibody heavy chains, the N-terminal fragment of Cfa exhibits increased expression levels relative to other N-intein fusions. Cfa has also been used to ligate two secreted proteins from co-transfected HEK293 cells in the culture media. By producing the Cas9 protein in a more native bacterial expression system such as the Cfa sytem, large quantities of purified protein can be generated while reducing the risk of protease degradation.

The term "isolated" as used herein refers to molecules or biologicals or cellular materials being substantially free from other materials.

As used herein, the terms "nucleic acid sequence" and "polynucleotide" are used interchangeably to refer to a polymeric form of nucleotides of any length, either ribonucleotides or deoxyribonucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases.

The term "promoter" as used herein refers to any sequence that regulates the expression of a coding sequence, such as a gene. Promoters may be constitutive, inducible, repressible, or tissue-specific, for example. A "promoter" is a control sequence that is a region of a polynucleotide sequence at which initiation and rate of transcription are controlled. It may contain genetic elements at which regulatory proteins and molecules may bind such as RNA polymerase and other transcription factors. Non-limiting exemplary promoters include CMV promoter (e.g., SEQ ID NO: 41, base pairs numbered 140 to 774 of SEQ ID NO: 7, or an equivalent of each thereof) and U6 promoter (e.g., SEQ ID NO: 42, base pairs numbered 4404 to 4395 of SEQ ID NO: 8, or an equivalent of each thereof). Additional non-limiting exemplary promoters with certain target specificity are provided herein below including but not limited to CMV, EF1a, SV40 (e.g., base pairs numbered 3434-3702 of SEQ ID NO: 7), PGK1 (human or mouse), P5 (e.g., base pairs numbered 10749 to 10828 of SEQ ID NO: 5), Ubc, human beta actin, CAG, TRE, UAS, Ac5, Polyhedrin, CaMKIIa, Gal1, 10, TEF1, GDS, ADH1, CaMV35S, Ubi, H1, U6, and Alpha-1-antitrypsin. Synthetically-derived promoters may be used for ubiquitous or tissue specific expression. Further, virus-derived promoters, some of which are noted above, may be useful in the methods disclosed herein, e.g., CMV, HIV, adenovirus, and AAV promoters.

The term "protein", "peptide" and "polypeptide" are used interchangeably and in their broadest sense to refer to a compound of two or more subunits of amino acids, amino acid analogs or peptidomimetics. The subunits may be linked by peptide bonds. In another aspect, the subunit may be linked by other bonds, e.g., ester, ether, etc. A protein or peptide must contain at least two amino acids and no limitation is placed on the maximum number of amino acids which may comprise a protein's or peptide's sequence. As used herein the term "amino acid" refers to either natural and/or unnatural or synthetic amino acids, including glycine and both the D and L optical isomers, amino acid analogs and peptidomimetics.

As used herein, the term "linker" refers to a moiety that joins two or more functional domains or domain fragments of a polypeptide, protein, or peptide. In the context of a chimeric fusion protein, the linker functions to join two or more polypeptides derived from two or more distinct proteins. In some embodiments, a linker is comprised of amino acids (i.e. "peptide linker"). In some embodiments, a linker functions to maintain cooperative inter-domain interactions and/or preserve biological activity of the component polypeptide(s), protein(s), or peptide(s). Non-limiting examples of linkers are provided herein and described in Chen, X. et al., Adv Drug Deliv Rev. 2013 Oct. 15; 65(10): 1357-1369 (incorporated herein by reference). In some embodiments, the linker is encoded by a polynucleotide.

As used herein, the term "recombinant expression system" refers to a genetic construct or constructs for the expression of certain genetic material formed by recombination.

A "gene delivery vehicle" is defined as any molecule that can carry inserted polynucleotides into a host cell. Examples of gene delivery vehicles are liposomes, micelles biocompatible polymers, including natural polymers and synthetic polymers; lipoproteins; polypeptides; polysaccharides; lipopolysaccharides; artificial viral envelopes; metal particles; and bacteria, or viruses, such as baculovirus, adenovirus and retrovirus, bacteriophage, cosmid, plasmid, fungal vectors and other recombination vehicles typically used in the art which have been described for expression in a variety of eukaryotic and prokaryotic hosts, and may be used for gene therapy as well as for simple protein expression.

A polynucleotide disclosed herein can be delivered to a cell or tissue using a gene delivery vehicle. "Gene delivery," "gene transfer," "transducing," and the like as used herein, are terms referring to the introduction of an exogenous polynucleotide (sometimes referred to as a "transgene") into a host cell, irrespective of the method used for the introduction. Such methods include a variety of well-known techniques such as vector-mediated gene transfer (by, e.g., viral infection/transfection, or various other protein-based or lipid-based gene delivery complexes) as well as techniques facilitating the delivery of "naked" polynucleotides (such as electroporation, "gene gun" delivery and various other techniques used for the introduction of polynucleotides). The introduced polynucleotide may be stably or transiently maintained in the host cell. Stable maintenance typically requires that the introduced polynucleotide either contains an origin of replication compatible with the host cell or integrates into a replicon of the host cell such as an extra-chromosomal replicon (e.g., a plasmid) or a nuclear or mitochondrial chromosome. A number of vectors are known to be capable of mediating transfer of genes to mammalian cells, as is known in the art and described herein.

A "plasmid" is an extra-chromosomal DNA molecule separate from the chromosomal DNA which is capable of replicating independently of the chromosomal DNA. In many cases, it is circular and double-stranded. Plasmids provide a mechanism for horizontal gene transfer within a population of microbes and typically provide a selective advantage under a given environmental state. Plasmids may carry genes that provide resistance to naturally occurring antibiotics in a competitive environmental niche, or alternatively the proteins produced may act as toxins under similar circumstances.

"Plasmids" used in genetic engineering are called "plasmid vectors". Many plasmids are commercially available for such uses. The gene to be replicated is inserted into copies of a plasmid containing genes that make cells resistant to particular antibiotics and a multiple cloning site (MCS, or polylinker), which is a short region containing several commonly used restriction sites allowing the easy insertion of DNA fragments at this location. Another major use of plasmids is to make large amounts of proteins. In this case, researchers grow bacteria containing a plasmid harboring the gene of interest. Just as the bacterium produces proteins to confer its antibiotic resistance, it can also be induced to produce large amounts of proteins from the inserted gene.

A "yeast artificial chromosome" or "YAC" refers to a vector used to clone large DNA fragments (larger than 100 kb and up to 3000 kb). It is an artificially constructed chromosome and contains the telomeric, centromeric, and replication origin sequences needed for replication and preservation in yeast cells. Built using an initial circular plasmid, they are linearized by using restriction enzymes, and then DNA ligase can add a sequence or gene of interest within the linear molecule by the use of cohesive ends. Yeast expression vectors, such as YACs, YIps (yeast integrating plasmid), and YEps (yeast episomal plasmid), are extremely useful as one can get eukaryotic protein products with posttranslational modifications as yeasts are themselves eukaryotic cells, however YACs have been found to be more unstable than BACs, producing chimeric effects.

A "viral vector" is defined as a recombinantly produced virus or viral particle that comprises a polynucleotide to be delivered into a host cell, either in vivo, ex vivo or in vitro.

Examples of viral vectors include retroviral vectors, adenovirus vectors, adeno-associated virus vectors, alphavirus vectors and the like. Infectious tobacco mosaic virus (TMV)-based vectors can be used to manufacturer proteins and have been reported to express Griffithsin in tobacco leaves (O'Keefe et al. (2009) Proc. Nat. Acad. Sci. USA 106(15):6099-6104). Alphavirus vectors, such as Semliki Forest virus-based vectors and Sindbis virus-based vectors, have also been developed for use in gene therapy and immunotherapy. See, Schlesinger & Dubensky (1999) Curr. Opin. Biotechnol. 5:434-439 and Ying et al. (1999) Nat. Med. 5(7):823-827. In aspects where gene transfer is mediated by a retroviral vector, a vector construct refers to the polynucleotide comprising the retroviral genome or part thereof, and a therapeutic gene. Further details as to modern methods of vectors for use in gene transfer may be found in, for example, Kotterman et al. (2015) Viral Vectors for Gene Therapy: Translational and Clinical Outlook Annual Review of Biomedical Engineering 17.

As used herein, "retroviral mediated gene transfer" or "retroviral transduction" carries the same meaning and refers to the process by which a gene or nucleic acid sequences are stably transferred into the host cell by virtue of the virus entering the cell and integrating its genome into the host cell genome. The virus can enter the host cell via its normal mechanism of infection or be modified such that it binds to a different host cell surface receptor or ligand to enter the cell. As used herein, retroviral vector refers to a viral particle capable of introducing exogenous nucleic acid into a cell through a viral or viral-like entry mechanism.

Retroviruses carry their genetic information in the form of RNA; however, once the virus infects a cell, the RNA is reverse-transcribed into the DNA form which integrates into the genomic DNA of the infected cell. The integrated DNA form is called a provirus.

In aspects where gene transfer is mediated by a DNA viral vector, such as an adenovirus (Ad) or adeno-associated virus (AAV), a vector construct refers to the polynucleotide comprising the viral genome or part thereof, and a transgene. Adenoviruses (Ads) are a relatively well characterized, homogenous group of viruses, including over 50 serotypes. Ads do not require integration into the host cell genome. Recombinant Ad derived vectors, particularly those that reduce the potential for recombination and generation of wild-type virus, have also been constructed. Such vectors are commercially available from sources such as Takara Bio USA (Mountain View, CA), Vector Biolabs (Philadelphia, PA), and Creative Biogene (Shirley, NY). Wild-type AAV has high infectivity and specificity integrating into the host cell's genome. See, Wold and Toth (2013) Curr. Gene. Ther. 13(6):421-433, Hermonat & Muzyczka (1984) Proc. Natl. Acad. Sci. USA 81:6466-6470, and Lebkowski et al. (1988) Mol. Cell. Biol. 8:3988-3996.

Vectors that contain both a promoter and a cloning site into which a polynucleotide can be operatively linked are well known in the art. Such vectors are capable of transcribing RNA in vitro or in vivo, and are commercially available from sources such as Agilent Technologies (Santa Clara, Calif.) and Promega Biotech (Madison, Wis.). In order to optimize expression and/or in vitro transcription, it may be necessary to remove, add or alter 5' and/or 3' untranslated portions of the clones to eliminate extra, potential inappropriate alternative translation initiation codons or other sequences that may interfere with or reduce expression, either at the level of transcription or translation. Alternatively, consensus ribosome binding sites can be inserted immediately 5' of the start codon to enhance expression.

Gene delivery vehicles also include DNA/liposome complexes, micelles and targeted viral protein-DNA complexes. Liposomes that also comprise a targeting antibody or fragment thereof can be used in the methods disclosed herein. In addition to the delivery of polynucleotides to a cell or cell population, direct introduction of the proteins described herein to the cell or cell population can be done by the non-limiting technique of protein transfection, alternatively culturing conditions that can enhance the expression and/or promote the activity of the proteins disclosed herein are other non-limiting techniques.

As used herein, the term "signal peptide" or "signal polypeptide" intends an amino acid sequence usually present at the N-terminal end of newly synthesized secretory or membrane polypeptides or proteins. It acts to direct the polypeptide to a specific cellular location, e.g., across a cell membrane, into a cell membrane, or into the nucleus. In some embodiments, the signal peptide is removed following localization. Examples of signal peptides are well known in the art. Non-limiting examples are those described in U.S. Pat. Nos. 8,853,381, 5,958,736, and 8,795,965.

As used herein, the term "viral capsid" or "capsid" refers to the proteinaceous shell or coat of a viral particle. Capsids function to encapsidate, protect, transport, and release into host cell a viral genome. Capsids are generally comprised of oligomeric structural subunits of protein ("capsid proteins"). As used herein, the term "encapsidated" means enclosed within a viral capsid.

As used herein, the term "helper" in reference to a virus or plasmid refers to a virus or plasmid used to provide the additional components necessary for replication and packaging of a viral particle or recombinant viral particle, such as the modified AAV disclosed herein. The components encoded by a helper virus may include any genes required for virion assembly, encapsidation, genome replication, and/or packaging. For example, the helper virus may encode necessary enzymes for the replication of the viral genome. Non-limiting examples of helper viruses and plasmids suitable for use with AAV constructs include pHELP (plasmid), adenovirus (virus), or herpesvirus (virus).

As used herein, the term "exterior" in reference to a viral capsid protein refers to the surface, domain, region, or terminal end of the capsid protein that is exterior-facing in an assembled viral capsid. As known to those of skill in the art, a "viral capsid protein" is the protein shell of the virus. A "modified" capsid protein is a protein having an amino acid sequence that has been altered from the wild-type sequence. The term "interior" in reference to a viral capsid protein refers to the surface, domain, region, or terminal end (amino-terminus end or carboxy terminus) of the capsid protein that is interior-facing in an assembled viral capsid. When used in reference to an assembled viral capsid, the term "interior" refers to the encapsidated space inside the viral capsid and the inward-facing surface of the capsid that is exposed to the enclosed space. The interior space is encapsidated by viral capsid proteins and may comprise nucleic acids such as the viral genome, viral proteins, proteins of the host or packaging cell, and any other components or factors packaged or encapsidated during replication, virion assembly, encapsidation, and/or packaging.

As used herein, the term "conjugated" refers to any method of attaching, coupling, fusing, and/or linking a viral capsid protein to a Cas9 protein or an equivalent thereof. Non-limiting examples of conjugation include recombinant fusion proteins wherein the Cas9 protein or an equivalent thereof and the viral capsid protein are encoded by a single polynucleotide that comprises the genes for both the Cas9 protein or an equivalent thereof and the viral capsid protein, modular intein based assembly of a Cas9-intein protein and a viral capsid-intein protein, posttranslational modification that causes a chemical bond to form between a Cas9 protein or equivalent thereof and the viral capsid protein, and linkage of a Cas9 or equivalent thereof and a viral capsid protein via one or more linkers. In some embodiments, conjugation may be a temporary or transient state of association between the viral capsid protein and the equivalent thereof. For example, the Cas9 or an equivalent thereof may be transiently linked to the viral capsid protein via a polymer sensitive to a change in pH or ion gradient at a later step in infection or within a particular cell microenvironment, such as oxime linkage (see, e.g., Jin et al. Biomacromolecules, 2011, 12 (10), pp 3460-3468 and Yoshida et al. Expert Opin Drug Deliv. 2013 November; 10(11): 1497-1513).

As used herein, the term "label" intends a directly or indirectly detectable compound or composition that is conjugated directly or indirectly to the composition to be detected, e.g., polynucleotide or protein such as an antibody so as to generate a "labeled" composition. The term also includes sequences conjugated to the polynucleotide that will provide a signal upon expression of the inserted sequences, such as green fluorescent protein (GFP) and the like and therefore be detectable. The label may be detectable by itself (e.g., radioisotope labels or fluorescent labels) or, in the case of an enzymatic label, may catalyze chemical alteration of a substrate compound or composition which is detectable. The labels can be suitable for small scale detection or more suitable for high-throughput screening. As such, suitable labels include, but are not limited to radioisotopes, fluorochromes, chemiluminescent compounds, dyes, and proteins, including enzymes. The label may be simply detected or it may be quantified. A response that is simply detected generally comprises a response whose existence merely is confirmed, whereas a response that is quantified generally comprises a response having a quantifiable (e.g., numerically reportable) value such as an intensity, polarization, and/or other property. In luminescence or fluoresecence assays, the detectable response may be generated directly using a luminophore or fluorophore associated with an assay component actually involved in binding, or indirectly using a luminophore or fluorophore associated with another (e.g., reporter or indicator) component.

Examples of luminescent labels that produce signals include, but are not limited to bioluminescence and chemiluminescence. Detectable luminescence response generally comprises a change in, or an occurrence of, a luminescence signal. Suitable methods and luminophores for luminescently labeling assay components are known in the art and described for example in Haugland, Richard P. (1996) Handbook of Fluorescent Probes and Research Chemicals ($6^{th}$ ed.). Examples of luminescent probes include, but are not limited to, aequorin and luciferases.

Examples of suitable fluorescent labels include, but are not limited to, fluorescein, rhodamine, tetramethylrhodamine, eosin, erythrosin, coumarin, methyl-coumarins, pyrene, Malacite green, stilbene, Lucifer Yellow, Cascade Blue™., and Texas Red. Other suitable optical dyes are described in the Haugland, Richard P. (1996) Handbook of Fluorescent Probes and Research Chemicals ($6^{th}$ ed.).

In another aspect, the fluorescent label is functionalized to facilitate covalent attachment to a cellular component present in or on the surface of the cell or tissue such as a cell surface marker. Suitable functional groups, including, but not are limited to, isothiocyanate groups, amino groups, haloacetyl groups, maleimides, succinimidyl esters, and sulfonyl halides, all of which may be used to attach the fluorescent label to a second molecule. The choice of the functional group of the fluorescent label will depend on the site of attachment to either a linker, the agent, the marker, or the second labeling agent.

Attachment of the fluorescent label may be either directly to the cellular component or compound or alternatively, can by via a linker. Suitable binding pairs for use in indirectly linking the fluorescent label to the intermediate include, but are not limited to, antigens/antibodies, e.g., rhodamine/anti-rhodamine, biotin/avidin and biotin/strepavidin.

The phrase "solid support" refers to non-aqueous surfaces such as "culture plates" "gene chips" or "microarrays." Such gene chips or microarrays can be used for diagnostic and therapeutic purposes by a number of techniques known to one of skill in the art. In one technique, oligonucleotides are attached and arrayed on a gene chip for determining the DNA sequence by the hybridization approach, such as that outlined in U.S. Pat. Nos. 6,025,136 and 6,018,041. The polynucleotides of the present disclosure can be modified to probes, which in turn can be used for detection of a genetic sequence. Such techniques have been described, for example, in U.S. Pat. Nos. 5,968,740 and 5,858,659. A probe also can be attached or affixed to an electrode surface for the electrochemical detection of nucleic acid sequences such as described by Kayem et al. U.S. Pat. No. 5,952,172 and by Kelley et al. (1999) Nucleic Acids Res. 27:4830-4837.

A "composition" is intended to mean a combination of active polypeptide, polynucleotide or antibody and another compound or composition, inert (e.g., a detectable label) or active (e.g., a gene delivery vehicle).

A "pharmaceutical composition" is intended to include the combination of an active polypeptide, polynucleotide or antibody with a carrier, inert or active such as a solid support, making the composition suitable for diagnostic or therapeutic use in vitro, in vivo or ex vivo.

As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. The compositions also can include stabilizers and preservatives. For examples of carriers, stabilizers and adjuvants, see Martin (1975) Remington's Pharm. Sci., 15th Ed. (Mack Publ. Co., Easton).

A "subject" of diagnosis or treatment is a cell or an animal such as a mammal, or a human. A subject is not limited to a specific species and includes non-human animals subject to diagnosis or treatment and are those subject to infections or animal models, for example, simians, murines, such as, rats, mice, chinchilla, canine, such as dogs, leporids, such as rabbits, livestock, sport animals, and pets. Human patients are included within the term as well.

The term "tissue" is used herein to refer to tissue of a living or deceased organism or any tissue derived from or designed to mimic a living or deceased organism. The tissue may be healthy, diseased, and/or have genetic mutations. The biological tissue may include any single tissue (e.g., a collection of cells that may be interconnected) or a group of tissues making up an organ or part or region of the body of an organism. The tissue may comprise a homogeneous cellular material or it may be a composite structure such as that found in regions of the body including the thorax which for instance can include lung tissue, skeletal tissue, and/or muscle tissue. Exemplary tissues include, but are not limited to those derived from liver, lung, thyroid, skin, pancreas, blood vessels, bladder, kidneys, brain, biliary tree, duodenum, abdominal aorta, iliac vein, heart and intestines, including any combination thereof.

As used herein, "treating" or "treatment" of a disease in a subject refers to (1) preventing the symptoms or disease from occurring in a subject that is predisposed or does not yet display symptoms of the disease; (2) inhibiting the disease or arresting its development; or (3) ameliorating or causing regression of the disease or the symptoms of the disease. As understood in the art, "treatment" is an approach for obtaining beneficial or desired results, including clinical results. For the purposes of the present technology, beneficial or desired results can include one or more, but are not limited to, alleviation or amelioration of one or more symptoms, diminishment of extent of a condition (including a disease), stabilized (i.e., not worsening) state of a condition (including disease), delay or slowing of condition (including disease), progression, amelioration or palliation of the condition (including disease), states and remission (whether partial or total), whether detectable or undetectable.

A number of effector elements are disclosed herein. The nature and function of these effector elements are commonly understood in the art and a number of these effector elements are commercially available. Where relevant, non-limiting exemplary sequences thereof are disclosed herein and further description thereof is provided herein below.

Modes of Carrying Out the Disclosure

The methods and compositions of this disclosure provide several advantages over known compositions and methods. For example, the methods and compositions of this disclosure provide one or more of the following: (1) efficient and targeted delivery of functional Cas9 or an equivalent thereof to target cells, (2) reduced size constraints on packaging and delivery through use of a single vector, (3) limiting the duration of Cas9 activity, thereby reducing off-target gene edits that arise over time, (4) limiting the duration of expression and exposure of Cas9 or the equivalent thereof to the immune system and its responses which may target transduced cells and reduce transduced cell number over time, (5) improve the long-term safety profile of in vivo gene editing, and (6) and enable treatment strategies for many heretofore challenging diseases to treat.

Modified Viral Capsids and Methods of Preparation

Disclosed herein is a modified viral capsid protein comprising, or alternatively consisting essentially of, or yet further consisting of a viral capsid protein having a Cas9 protein or an equivalent thereof conjugated to the interior surface, interior facing domain, or the interior-facing terminal end of the viral capsid protein. In some aspects, conjugation comprises or alternatively consists essentially of, or yet further consists of, a fusion protein, e.g., a fusion of a Cas9 protein or an equivalent thereof with a viral capsid protein wherein the Cas9 protein or an equivalent thereof is fused to the interior surface of the viral capsid protein. Also disclosed herein is a modified viral capsid protein comprising, or alternatively consisting essentially of, or yet further consisting of a viral capsid protein having a Cas9 protein or an equivalent thereof conjugated to the exterior surface, exterior facing domain, or the exterior-facing terminal end of the viral capsid protein. In some aspects, conjugation comprises or alternatively consists essentially of, or yet further consists of, a fusion protein, e.g., a fusion of a Cas9 protein or an equivalent thereof with a viral capsid protein wherein the Cas9 protein or an equivalent thereof is fused to the exterior surface of the viral capsid protein.

In one aspect, the Cas9 or equivalent thereof is fused to the inner surface of a VP2 protein. In some aspects, the Cas9 protein or equivalent thereof is fused or inserted into a VP2 protein at amino acid position 228, 350, 419, 684, or 689 of SEQ ID NO: 59. In some aspects, the Cas9 protein or equivalent thereof is fused or inserted into a VP2 protein at amino acid position 90, 213, 282, 547, and 552 of SEQ ID NO: 39. Non-limiting examples of fusions of Cas9 and VP2 include SEQ ID NO: 45, SEQ ID NO: 46, SEQ ID NO: 47, SEQ ID NO: 48, and SEQ ID NO: 49. In other aspects, conjugation comprises or alternatively consists essentially of, or yet further consists of, posttranslational modifications that cause a bond between a viral capsid protein and a Cas9 or an equivalent thereof, e.g., covalent bonds, hydrogen bonds, or ionic bonds. In some aspects, conjugation comprises or alternatively consists essentially of, or yet further consists of, coating the interior surface of assembled viral particles with a Cas9 or an equivalent thereof.

In another aspect, the Cas9 or equivalent thereof is fused to the outer surface of a VP2 protein. In some aspects, the Cas9 protein or equivalent thereof is fused or inserted into a VP2 protein at the amino terminal end of the VP2 protein. Non-limiting examples of fusions of Cas9 and VP2 include SEQ ID NO: 36, nucleotide base pairs numbered 5037 to 10565 of SEQ ID NO: 2, base pairs numbered 5532 to 10574 of SEQ ID NO: 5, and equivalents of each thereof. In other aspects, conjugation comprises or alternatively consists essentially of, or yet further consists of, posttranslational modifications that cause a bond between a viral capsid protein and a Cas9 or an equivalent thereof, e.g., covalent bonds, hydrogen bonds, or ionic bonds. In some aspects, conjugation comprises or alternatively consists essentially of, or yet further consists of, coating the interior surface of assembled viral particles with a Cas9 or an equivalent thereof.

In a further aspect, the modified viral capsid as described herein, is coupled to a detectable label for ease of detection. Non-limiting examples of such labels are known in the art and described herein. In one aspect, the detectable label is not a naturally occurring, detectable compound such as a fluorescent polynucleotide or amino acid.

In one aspect, conjugation comprises or alternatively consists essentially of, or yet further consists of, attaching a Cas9 or equivalent thereof to the interior or exterior surface of a viral capsid protein via one or more linkers. In some aspects, the linkers are flexible or rigid. In some aspects, the linkers are self-cleaving protein spacers that allow the Cas9 protein to be released from the capsid efficiently during pH changes that occur after cell infection. In one aspect, a biotin ligase is used to join the purified protein moiety with the purified viral preparation. Additional examples of conjugation of a protein with a capsid protein are described in Stachler et al. (2008) Site-specific modification of AAV vector particles with biophysical probes and targeting ligands using biotin ligase. Mol. Ther. 16:1467-1473, doi: 10.1038/mt.2008.129, and Wei et al. (2012) Conjugation of paclitaxel on adeno-associated virus (AAV) nanoparticles for co-delivery of genes and drugs. Eur. J. Pharm. Sci. 46: 167-172, doi:10.1016/j.ejps.2012.02.022.

In one aspect, a Cas9 protein or an equivalent thereof is conjugated to a viral capsid protein via a biotin linker. In some embodiments, *Escherichia coli* enzyme biotin ligase (BirA), ligates biotin to a 15-amino-acid biotin acceptor peptide (BAP) in a sequence-specific manner. In some embodiments, use of a ketone isotere of biotin as a cofactor allows for ligation of a peptide to a BAP-modified AAV capsid. In some embodiments, ketones are absent from AAV, allowing BAP-modified AAV particles to be tagged with the ketone peptide and then specifically conjugated to hydrazide- or hydroxylamine-functionalized molecules.

In some aspects, the conjugation of a Cas9 protein or an equivalent thereof to a viral capsid protein can be reversed or altered via exposure to a change in pH or an ion gradient. In some embodiments, the Cas9 protein or an equivalent thereof is conjugated to the viral capsid protein via a pH sensitive polymer or a linker comprising a pH sensitive functional group. Exemplary pH sensitive polymers include but are not limited to aminoalkyl methacrylate copolymer, poly(methacrylic acid-co-methyl methacrylate), triblock copolymer (PEG-OPCL-PEG) consisting of hydrophilic poly(ethylene glycol) (PEG) and hydrophobic oxime-tethered polycaprolactone (OPCL) and hydroxypropyl-methylcellulose phthalate. Exemplary pH sensitive functional groups include but are not limited to hydrazine, acetal, orthoester, and vinyl ether. In some embodiments, the Cas9 protein or an equivalent thereof is conjugated to the viral capsid protein via an ion-sensitive resin. Exemplary ion-sensitive resins include but are not limited to poly(ethylacrylate-methylmethacrylate-trimethylammonioethyl methacrylate chloride) copolymers, poly(N-isopropylacrylamide), and ion exchange resins as described in Yoshida et al. Expert Opin Drug Deliv. 2013 November; 10(11): 1497-1513. In some embodiments, the pH or ion gradient within the viral capsid, within the transduced cell, or within a microenvironment within the transduced cell triggers Cas9 or the equivalent thereof to be released from conjugation.

In some aspects, the modified capsid protein further comprises, or alternatively consists essentially of, or yet further consists of, a spacer region between the Cas9 or an equivalent thereof and the viral capsid protein to minimize any steric hindrance on viral capsid assembly and/or formation. If the Cas9 is coupled, inserted, or attached within the capsid protein rather than at a terminal end of the capsid protein, a plurality of spacer regions may be included to allow more flexibility or space. The one or more spacer regions may flank one or both ends of the Cas9 protein or the equivalent thereof. In one aspect, the spacer region comprises or alternatively consists essentially of, or yet further consists of, a peptide. In some aspects, the peptide is between 1 and 100 amino acids in length, between 1 and 50 amino acids in length, between 1 and 30 amino acids in length, between 1 and 20 amino acids in length, between 1 and 10 amino acids in length, between 1 and 5 amino acids in length, between 5 and 10 amino acids in length, between 5 and 15 amino acids in length, or between 20 and 40 amino acids in length. As used herein, a "spacer" includes a peptide sequence comprising a "linker." In one aspect, the spacer region is encoded by a polynucleotide comprising SEQ ID NO: 9 or an equivalent thereof. In another aspect, the linker is G4S (SEQ ID NO. 51) encoded by nucleotide sequence ggcggaggaggcagc (SEQ ID NO: 52) and with the amino acid sequence GGGGS (SEQ ID NO: 51). Equivalents of G4S (SEQ ID NO: 51) include multimers of varying lengths including but not limited to the 15-mer (G4S)3 (SEQ ID NO: 53), the 18-mer GGSSRSSSSGGGGSGGGG (SEQ ID NO: 54) (Andris-Widhopf et al., 2011) and the 20-mer (G4S)4 (SEQ ID NO: 55) (Schaefer et al., 2010). In yet another aspect, the number of G's in the G4S (SEQ ID NO: 51) linker can be decreased to three consecutive G's ("GGGS" disclosed as SEQ ID NO: 56). Nonlimiting examples of additional flexible linkers suitable for use in the modified capsid include KESGSVSSEQLAQFRSLD (SEQ ID NO: 31) and EGKSSGSGSESKST (SEQ ID NO: 32) which have been applied for the construction of a bioactive scFv (Bird, R. E. et al. Science 242, 423-426 (1988)). Additional examples of other linkers suitable for use in the modified capsid include but are not limited to (Gly)8 (SEQ ID NO: 33), consisting of glycine residues, GSAGSAAGSGEF (SEQ ID NO: 34), an empirical rigid linker with the sequence of A(EAAAK)n A (n=2-5) (SEQ ID NO: 35) and a linker with α-helical conformation and stabilized by the Glu—-Lys+ salt bridges within segments. Additional methods of producing linkers and descriptions of the above linkers are found, for example, in Sabourin, M. et al. (2007) Yeast 24:39-45, doi:10.1002/yea.1431; Waldo, G. S. et al. (1999) Nat Biotechnol. 17:691-695, doi:10.1038/10904 (1999); Arai et al. (2001) Protein Eng. 14:529-532; and Arai et al. (2004) Proteins 57:829-838.

In some aspects, conjugation comprises or alternatively consists essentially of, or yet further consists of, attaching or coupling a Cas9 or equivalent thereof to the interior or exterior surface of a viral capsid protein via an intein mediated ligation. Intein excision is a protein splicing mechanism whereby an intervening intein protein domain excises itself from a host protein in a traceless manner such that the flanking polypeptide sequences (called exteins) are ligated together via a normal peptide bond. In modular intein based ligation or assembly methods, this process is exploited by splitting the intein into two fragments, an N-terminal fragment and a C-terminal fragment, and fusing each fragment to an extein such as Cas9 or a viral capsid protein. Under appropriate conditions, the split intein-extein fusions co-expressed or mixed together and the intein ligation reaction is catalyzed, resulting a fusion of the two exteins and excision of the split intein fragments. In some embodiments, the intein is a fast intein that is capable of a fast rate of protein trans-splicing (e.g., about $t_{1/2}$<400 seconds at 30° C.) (Neel, S. et al. Journal of the American Chemical Society (2012), 134 (28), 11338-11341). In some embodiments, a fast intein contains one or more accelerator residues (K70, M75, and M81 of SEQ ID NO: 60) (Stevens, A. et al. J. Am. Chem. Soc., 2016, 138 (7), pp 2162-2165). Exemplary fast inteins include but are not limited to the consensus fast intein (Cfa) (SEQ ID NO: 60), Npu, Ava, and Mcht. An exemplary N-terminal fragment of an intein is $Cfa^N$ (amino acid residues 1-101 of SEQ ID NO: 60). An exemplary C-terminal fragment of intein is $Cfa^C$ (amino acid residues 102-136 of SEQ ID NO: 60). In one embodiment, the fast intein can be further modified with a photocaged cysteine amino acid residue resulting in an intein ligation reaction that is photoactivatable (Ren, W. et al. J Am Chem Soc. 2015 Feb. 18; 137(6):2155-8).

Traditional intein ligation reactions need to be performed in optimal conditions of pH and ionic salt strength to function with usable efficiency. These conditions are not found inside eukaryotic cells. In contrast to traditional inteins, the ligation reaction for modified inteins such as Cfa and fast inteins can be catalyzed inside transfected cells without the need for subsequent isolation and purification into optimized buffer systems. Modified and fast inteins can function under a wide range of temperatures, pH, and buffers. Importantly, in order to produce an internal Cas9 or equivalent thereof ligated to a viral capsid protein, the split intein ligation reaction must be performed inside the transfected cell to allow protein ligation to occur before the virus is completely formed. Other, traditional intein forms are non-functional inside the environment of the transfected cell and would not produce the fusion product.

Exemplary appropriate conditions for catalyzing efficient intein ligation reactions for modified and fast inteins, including Cfa, include but are not limited to (i) co-incubation of equal volumes of N-terminal and C-terminal intein fusion proteins in a suitable splicing buffer (e.g., 100 mM sodium phosphates, 150 mM NaCl, 1 mM EDTA, pH 7.2 with 2 mM TCEP) at 30°-37° C.; (ii) co-expression of N-terminal and C-terminal intein fusion proteins in a suitable mammalian cell line for protein expression (e.g., HEK293); and (iii) co-expression of N-terminal and C-terminal intein fusion proteins in a suitable mammalian cell line for viral assembly and packaging (e.g., HEK293). Trans-splicing can be monitored by HPLC. In some aspects, the Cas9-intein and/or viral capsid protein-intein is produced in bacteria. In some aspects, the Cas9-intein and/or viral capsid protein-intein is produced in eukaryotic cells (e.g., HEK293).

In one aspect, the viral capsid protein is selected from the group of an adenoviral (Ad) capsid protein, an adeno-associated virus (AAV) capsid protein, or a lentivirus capsid or envelope protein. Non-limiting examples of Ad capsid proteins include hexon (protein II), penton base (protein III) and fibre (protein IV) and proteins IIIa, VI, VIII and IX or an equivalent of each thereof. These sequences are known in the art and described for example in Athappilly F K, et al., J Mol Biol 1994; 242:430-455. Non-limiting examples of AAV viral proteins include VP1 (SEQ ID NO: 37), VP2 (SEQ ID NO: 39), and VP3 (SEQ ID NO: 38), or an equivalent of each thereof. Nonlimiting examples of lentiviral capsid and envelope proteins include P24 capsid protein CA and P9 capsid protein NC, VSVG and equivalents of each thereof. In one aspect, the modified viral capsid protein comprises AAV VP2, or an equivalent thereof.

In some aspects, the Cas9 protein is a S. aureus Cas9 (e.g., SEQ ID NO: 3, SEQ ID NO: 50) or an equivalent thereof. In other aspects, the Cas9 protein is a Streptococcus pyogenes (SP) SpCas9 (SEQ ID NO: 18) with the PAM sequence NGG (SEQ ID NO: 20), SpCas9 D1135E variant with the PAM sequence NGG (SEQ ID NO: 21) (reduced NAG binding), SpCas9 VRER variant with the PAM sequence NGCG (SEQ ID NO: 22), SpCas9 EQR variant with the PAM sequence NGAG (SEQ ID NO: 23), SpCas9 VQR variant with PAM sequences NGAN (SEQ ID NO: 24) or NGNG (SEQ ID NO: 25), Staphylococcus aureus (SA) SaCas9 with PAM sequences NNGRRT (SEQ ID NO: 26) or NNGRR(N) wherein the (N) is optional (SEQ ID NO: 27), Neisseria meningitidis (NM) Cas9 with the PAM sequence of NNNNGATT (SEQ ID NO: 28), Streptococcus thermophilus (ST) Cas9 with the PAM sequence NNAGAAW (SEQ ID NO: 29), Treponema denticola (TD) Cas9 with the PAM sequence NAAAAC (SEQ ID NO: 30), or a Cas protein from another bacterial species such as Prevotella, Acidaminococcus, Lachnospiraceae, or Francisella. Equivalents of Cas9 include but are not limited to Cas9s derived from the Cas enzymes listed above and/or Cas9s with modifications that affect the protein's function, targeting specificity, size (e.g., truncation mutations), localization, and/or reduce off-target effects such as a nuclease dead Cas9 (dCas9, SEQ ID NO: 40) that is enzymatically inactive but can bind but cannot cleave DNA, a Cas9 nickase (Cas9n) in which one of the two nuclease domains are inactivated (either RuvC or HNH) rendering the enzyme capable of cleaving only one strand of target DNA, a nuclease dead Cas9 fused to the non-specific endonuclease FokI (dCas9-Fok1), spCas9 VQR, EQR and VRER variants that recognize novel NGG (SEQ ID NO: 20) PAM sequences, and non-Cas9 CRISPR endonuclease Cpf1 which leaves a 5 nucleotide 5' overhang 18 base pairs from the PAM sequence when cleaving DNA (SEQ ID NO: 10). In some aspects, the Cas9 protein is C2C2, which is a single-component programmable RNA-guided RNA-targeting CRISPR effector (Abudayyeh, O. et al. (2016) Science 353: 6299). In other aspects, the Cas9 protein comprises or consists of SEQ ID NO: 3 or SEQ ID NO: 50, or an equivalent of each thereof. In some aspects, Cas9 can be modified to be resistant to protease degradation or cleavage. Methods for designing protease resistant proteins are known in the art, as described in Fruchart-Gaillard, C. et al. (2012) PLoS One 7:e39166; Hu, W. et al. Enzyme Microb Technol 97, 82-89 (2017); Kukenshoner, T. et al. (2014) J Struct Biol 186:335-348 (2014); Li, Y. et al. (2013) J Biotechnol. 163:401-407; and Werner, H. M. et al. (2016) Chembiochem 17:712-718.

In some embodiments, the Cas9 or equivalent thereof is a thermostable Cas9. A non-limiting example of a thermostable Cas9 is GeoCas9 from Geobacillus stearothermophilus. Thermostable Cas9 is active at higher temperatures than SpCas9 (70° C. versus 45° C. for SpCas9) and has increased stability in human serum (up to a maximum of 30% serum tolerated compared to about 0% serum tolerated for SpCas9). GeoCas9 has a PAM sequence of CRAA (where R=A or G) and a spacer length of 22 nt. GeoCas9 is available from, for example, Addgene (pET-MBP-NLS-Geo_st; Addgene ID 87703).

In some embodiments, the Cas9 or equivalent thereof is capable of targeting and/or editing RNA. For example, in some embodiments, the Cas9 or equivalent thereof is Cas13, nuclease dead Cas13 (dCas13), C2c2, Cas13a, or Cas9. See, e.g., Gootenberg, et al., Science. 2017 Nov. 24; 358(6366): 1019-1027; Abudayyeh, et al. Nature. 2017 Oct. 12; 550 (7675):280-284; and Strutt et al., eLife. 2018; 7: e32724 (each incorporated herein by reference). In some embodiments, the Cas9 or equivalent thereof does not require the presence of a PAM sequence in the target sequence.

In some embodiments, the modified viral capsid protein thereof may further comprise one or more signal peptides. In some embodiments, the signal peptide is conjugated to the Cas9 or equivalent thereof. In a particular embodiment, one or more signal peptides are fused to the N-terminus of Cas9 or an equivalent thereof. In another embodiment, one or more signal peptides are fused to the C-terminus of Cas9 or an equivalent thereof. In some embodiments, one or more signal peptides are conjugated to both the N and C-termini of Cas9 or an equivalent thereof. In some embodiments, the signal is inserted within the Cas9 or an equivalent thereof. In a particular embodiment, the signal is a nuclear localization signal to aid in the localization of the modified viral capsid protein to the nucleus. An exemplary Cas9 with nuclear localization signals is found in U.S. Pat. No. 8,795,965.

In some aspects, the disclosure provides one or more isolated polynucleotides encoding a modified viral capsid protein comprising, or alternatively consisting essentially of, or yet further consisting of a viral capsid protein having a Cas9 protein or an equivalent thereof conjugated to the interior surface, interior facing domain, or the interior-facing terminal end of the viral capsid protein. In other aspects, the disclosure provides one or more isolated polynucleotides encoding a modified viral capsid protein comprising, or alternatively consisting essentially of, or yet further consisting of a viral capsid protein having a Cas9 protein or an equivalent thereof conjugated to the exterior surface, exterior facing domain, or the exterior-facing terminal end of the viral capsid protein. In one aspect, the polynucleotide encodes a fusion protein wherein a single polynucleotide comprises or alternatively consists essentially of, or yet further consists of a polynucleotide encoding a Cas9 protein or an equivalent thereof and a polynucleotide encoding a viral capsid protein. In a further aspect, the polynucleotide encoding a fusion protein further comprises a polynucleotide sequence encoding a spacer region and/or linker between or flanking the Cas9 or an equivalent thereof and the viral capsid protein. In one aspect, the Cas9 encoded by the polynucleotide is saCas9 and the viral capsid protein encoded by the polynucleotide is VP2. In another aspect, the polynucleotide encodes the Cas9 protein comprising or consisting of SEQ ID NO: 3 or SEQ ID NO: 50. In other aspects, two or more distinct polynucleotides encode the Cas9 protein or an equivalent thereof and the capsid protein. In some aspects, the polynucleotide encoding the Cas9 and/or viral capsid protein is codon-optimized for expression in humans.

In a further aspect, the polynucleotides are operatively coupled to regulatory sequences necessary for the replication and/or expression, e.g., a promoters and optionally enhancers. Non-limiting examples of such are disclosed herein, e.g., U6 promoter.

In a further aspect, the polynucleotides are contained within a gene expression vehicle, a vector, such as a viral vector or plasmid. Non-limiting examples are known in the art and briefly described herein. As is apparent to the skilled artisan, the polynucleotides are contained in the gene expression vehicles in the appropriate orientation for expression of the polynucleotides.

In a further aspect, the polynucleotides are attached to a detectable label. Non-limiting examples of labels are described herein.

In a further aspect, the two or more distinct polynucleotides are on the same or different plasmids. In yet another aspect, one of the two distinct polynucleotides further comprises one or more spacer regions and/or linkers. In one aspect, linkers flank both the amino and carboxy terminal ends of the Cas9 or equivalent thereof. In other aspects, a single linker flanks either the amino or the carboxy terminal end of the Cas9 or equivalent thereof.

In addition, provided herein is a vector or host cell comprising the one or more isolated polynucleotides encoding a modified viral capsid protein comprising or alternatively consisting essentially of, or yet further consisting of a viral capsid protein having a Cas9 protein or an equivalent thereof conjugated to the interior surface, interior facing domain, or the interior-facing terminal end of the viral capsid protein. Also provided herein is a vector or host cell comprising the one or more isolated polynucleotides encoding a modified viral capsid protein comprising or alternatively consisting essentially of, or yet further consisting of a viral capsid protein having a Cas9 protein or an equivalent thereof conjugated to the exterior surface, exterior facing domain, or the exterior-facing terminal end of the viral capsid protein. In some aspects, the vector or host cell further comprises additional plasmids necessary for the production and assembly of viral particles and/or plasmids encoding components for gene editing. Non-limiting examples of vectors or host cells include HEK293 cells, 293T cells, or an equivalent of each thereof, commercially available viral packaging cells, e.g., 293AAV cells (Cell Biolabs, Inc.) or Phoenix packaging cells (ATTC). In some aspects, the vector or host cells further comprise a helper plasmid encoding genes necessary for viral replication, packaging, assembly, and/or encapsidation.

Some aspects of this disclosure relate to methods of preparing a modified viral capsid protein comprising, or alternatively consisting essentially of, or yet further consisting of a viral capsid protein having a Cas9 protein or an equivalent thereof conjugated to the interior surface, interior facing domain, or the interior-facing terminal end of the viral capsid protein, the method comprising or alternatively consisting essentially of, or yet further consisting of, coupling the Cas9 protein or an equivalent thereof to the viral capsid protein. In some aspects, coupling comprises or alternatively consists essentially of, or yet further consists of, posttranslational modifications that cause a bond between a viral capsid protein and a Cas9 or an equivalent thereof, e.g., covalent bonds, hydrogen bonds, or ionic bonds. In some aspects, coupling comprises or alternatively consists essentially of, or yet further consists of, coating the interior surface of assembled viral particles with a Cas9 or an equivalent thereof. In one aspect, coupling comprises or alternatively consists essentially of, or yet further consists of, attaching a Cas9 or equivalent thereof to the interior or exterior surface of a viral capsid protein via one or more linkers. In some aspects, the linkers are the same or different. In additional aspects, the linkers are flexible or rigid. In one aspect, the one or more linkers flank both the amino and carboxy terminal ends of the Cas9 or equivalent thereof. In other aspects, a linker flanks either the amino or the carboxy terminal end of the Cas9 or equivalent thereof. In some aspects, the Cas9 or an equivalent thereof and/or a linker is coupled to a VP2 protein at amino acid position 228, 350, 419, 684, or 689 (of SEQ ID NO: 59). In some aspects, the Cas9 or an equivalent thereof and/or a linker is coupled to a VP2 protein at amino acid position 90, 213, 282, 547, and 552 of SEQ ID NO: 39. Non-limiting examples of Cas9 coupled to VP2 include SEQ ID NO: 45, SEQ ID NO: 46, SEQ ID NO: 47, SEQ ID NO: 48, and SEQ ID NO: 49 and equivalents of each thereof.

Some aspects of this disclosure provide a method of preparing a modified viral capsid protein, the protein comprising or alternatively consisting essentially of, or yet further consisting of, a viral capsid protein having a Cas9 protein or an equivalent thereof conjugated to the interior surface, interior facing domain, or the interior-facing terminal end of the viral capsid protein, the method comprising or alternatively consisting essentially of, or yet further consisting of, expressing one or more isolated polypeptide encoding the modified viral capsid protein. Other aspects of this disclosure provide a method of preparing a modified viral capsid protein, the protein comprising or alternatively consisting essentially of, or yet further consisting of a viral capsid protein having a Cas9 protein or an equivalent thereof conjugated to the exterior surface, exterior facing domain, or the exterior-facing terminal end of the viral capsid protein, the method comprising or alternatively consisting essentially of, or yet further consisting of, expressing one or more isolated polypeptide encoding the modified viral capsid protein. In one aspect, the isolated polypeptide encodes SEQ ID NO: 45, SEQ ID NO: 46, SEQ ID NO: 47, SEQ ID NO: 48, or SEQ ID NO: 49.

In some aspects, the Cas9 protein or an equivalent thereof, a viral capsid protein, or the modified viral capsid protein conjugated to Cas9 are further modified to reduce protease degradation of Cas9. In some aspects, protease cleavage sites within the Cas9 sequence are mutated to prevent cleavage. In some aspects, one or more viral capsid proteins is mutated to eliminate some or all of its endogenous cleavage activity. In some aspects, the modified viral capsid protein is produced in the presence of one or more protease inhibitors.

Modified Viral Particles Expressing Cas9 on the Interior or Exterior Capsid Surface Also provided herein are recombinant or modified viral particles comprising or alternatively consisting essentially of a modified capsid wherein the modified capsid comprises a modified viral capsid protein comprising or alternatively consisting essentially of, or yet further consisting of a viral capsid protein having a Cas9 protein or an equivalent thereof conjugated to the interior surface, interior facing domain, or the interior-facing terminal end of the viral capsid protein. Also provided herein are recombinant or modified viral particles comprising or alternatively consisting essentially of a modified capsid wherein the modified capsid comprises a modified viral capsid protein comprising or alternatively consisting essentially of, or yet further consisting of a viral capsid protein having a Cas9 protein or an equivalent thereof conjugated to the exterior surface, exterior facing domain, or the exterior-facing terminal end of the viral capsid protein. In some aspects, the modified viral particle further comprises one or more polynucleotides encapsidated within the capsid. In some aspects, at least one of the polynucleotides comprises or consists essentially of, or yet further consists of a polynucleotide encoding a guide RNA (gRNA). In some aspects, at least one of the polynucleotides comprises or alternatively consists essentially of, or yet further consists of a therapeutic polynucleotide. As used herein, the term "therapeutic polynucleotide" intends a replacement polynucleotide that can be for genetic modification of a target cell genome. Alternatively, the therapeutic polynucleotide encodes a therapeutic polypeptide.

In some aspects, the polynucleotide encoding the gRNA comprises or alternatively consists essentially of, or yet further consists of a fusion polynucleotide comprising CRISPR RNA (crRNA) and trans-activating CRIPSPR RNA (tracrRNA); or a polynucleotide comprising CRISPR RNA (crRNA) and trans-activating CRIPSPR RNA (tracrRNA). In one aspect, the polynucleotide encoding the gRNA comprises or consists of SEQ ID NO: 8 or an equivalent thereof. In some aspects, the gRNA is specific for a region of DNA that is in need of gene editing and/or gene regulation. In a further aspect the gRNA further comprises a detectable label.

In some aspects, the recombinant viral particle further comprising a therapeutic polynucleotide. The therapeutic polynucleotide is any polypeptide that can be used to target a DNA sequence in need of editing, provide a repair template for a DNA sequence in need of editing, or provide a replacement for a DNA sequence in need of editing. In further aspects, the therapeutic polypeptide comprises a wild-type sequence of a gene in need of editing. In a further aspect the therapeutic polynucleotide further comprises a detectable label.

Disclosed herein is a recombinant expression system for the generation of a modified viral particle expressing Cas9 or an equivalent thereof on the viral particle's interior or exterior capsid surface, the system comprising or alternatively consisting essentially of, or yet further consisting of (a) a plasmid comprising a DNA sequence encoding a fusion protein, the fusion protein comprising the Cas9 or the equivalent thereof and a viral capsid protein; and (b) a helper plasmid. In some aspects, the viral capsid is selected from the group of an adenoviral (Ad) capsid protein, an adeno-associated virus (AAV) capsid protein, or a lentivirus. Non-limiting examples of Ad capsid proteins include hexon (protein II), penton base (protein III) and fibre (protein IV) and proteins IIIa, VI, VIII and IX or an equivalent of each thereof. Non-limiting examples of AAV viral proteins include VP1, VP2, and VP3, or an equivalent of each thereof. Non limiting examples of VP1 include SEQ ID NO: 37, DNA base pairs numbered 5037 to 7253 of SEQ ID NO: 1, base pairs numbered 5037 to 7253 of SEQ ID NO: 4, and equivalents of each thereof. Nonlimiting examples of VP2 include SEQ ID NO: 39, base pairs numbered 8786 to 10574 of SEQ ID NO: 5, and equivalents of each thereof. Non-limiting examples of VP3 include SEQ ID NO: 38, base pairs numbered 5646 to 7253 of SEQ ID NO: 1, base pairs numbered 5646 to 7253 of SEQ ID NO: 1, and an equivalent of each thereof. Non-limiting examples of lentiviral capsid proteins include P24 capsid protein CA, P9 capsid protein NC, lentiviral envelope protein VSVG, and equivalents of each thereof. In some aspects, the modified capsid protein comprises one or more of AAV VP1, VP2, and VP3, or an equivalent of each thereof. In one aspect, the modified viral capsid protein comprises VP2, or an equivalent thereof. Non-limiting examples of Ad capsid proteins include hexon (protein II), penton base (protein III) and fibre (protein IV) and proteins IIIa, VI, VIII and IX or an equivalent of each thereof. Non-limiting examples of AAV viral proteins include VP1, VP2, and VP3, or an equivalent of each thereof. Non-limiting examples of lentiviral capsid proteins include P24 capsid protein CA and P9 capsid protein NC and equivalents of each thereof.

In some aspects, the Cas9 protein is a *S. aureus* Cas9 or an equivalent thereof. In other aspects, the Cas9 protein is a *Streptococcus pyogenes* (SP) SpCas9 with the PAM sequence NGG (SEQ ID NO: 20), SpCas9 D1135E variant with the PAM sequence NGG (SEQ ID NO: 21) (reduced NAG binding), SpCas9 VRER variant with the PAM sequence NGCG (SEQ ID NO: 22), SpCas9 EQR variant with the PAM sequence NGAG (SEQ ID NO: 23), SpCas9 VQR variant with PAM sequences NGAN (SEQ ID NO: 24) or NGNG (SEQ ID NO: 25), *Staphylococcus aureus* (SA)

SaCas9 with PAM sequences NNGRRT (SEQ ID NO: 26) or NNGRR(N) (SEQ ID NO: 27), *Neisseria meningitidis* (NM) Cas9 with the PAM sequence of NNNNGATT (SEQ ID NO: 28), *Streptococcus thermophilus* (ST) Cas9 with the PAM sequence NNAGAAW (SEQ ID NO: 29), *Treponema denticola* (TD) Cas9 with the PAM sequence NAAAAC (SEQ ID NO: 30), or a Cas protein from another bacterial species such as *Prevotella, Acidaminococcus, Lachnospiraceae,* or *Francisella*. In the above sequences, N stands for any nucleotide. Equivalents of Cas9 include but are not limited to Cas9s with modifications that affect the protein's function, targeting specificity, size, localization, and/or reduce off-target effects such as a nuclease dead Cas9 (dCas9) that is enzymatically inactive but can bind but cannot cleave DNA, a Cas9 nickase (Cas9n) in which one of the two nuclease domains are inactivated (either RuvC or HNH) rendering the enzyme capable of cleaving only one strand of target DNA, a nuclease dead Cas9 fused to the non-specific endonuclease FokI (dCas9-Fok1), spCas9 VQR, EQR and VRER variants that recognize novel NGG (SEQ ID NO: 20) PAM sequences, and non-Cas9 CRISPR endonuclease Cpf1 which leaves a 5 nucleotide 5' overhang 18 base pairs from the PAM sequence when cleaving DNA. In some aspects, the Cas9 protein is C2C2, which is a single-component programmable RNA-guided RNA-targeting CRISPR effector (Abudayyeh, O. et al. (2016) Science 353: 6299). In other aspects, the Cas9 protein comprises or consists of SEQ ID NO: 3 or SEQ ID NO: 50, or an equivalent of each thereof. In some aspects, Cas9 is modified to be resistant to protease degradation or cleavage. Methods for designing protease resistant proteins are known in the art, as described in Fruchart-Gaillard, C. et al. (2012) PLoS One 7:e39166; Hu, W. et al. Enzyme Microb Technol 97, 82-89 (2017); Kukenshoner, T. et al. (2014) J Struct Biol 186:335-348 (2014); Li, Y. et al. (2013) J Biotechnol. 163:401-407; and Werner, H. M. et al. (2016) Chembiochem 17:712-718.

In some aspects, recombinant expression system comprises a fusion protein comprising or alternatively consisting essentially of, or yet further consisting of, Cas9 and VP2. In additional aspects, the recombinant expression system comprises or alternatively consists essentially of, or yet further consists of a plasmid comprising or consisting of a DNA sequence encoding the fusion proteins SEQ ID NO: 45, SEQ ID NO: 46, SEQ ID NO: 47, SEQ ID NO: 48, SEQ ID NO: 49 or an equivalent of each thereof. In some aspects, the recombinant expression system comprises or alternatively consists essentially of, or yet further consists of a helper plasmid comprising or consisting of a DNA sequence selected from the group of SEQ ID NO: 1, SEQ ID NO: 4, SEQ ID NO: 57 or an equivalent of each thereof. In a further aspect, the helper plasmid comprises or consists of SEQ ID NO: 6 or an equivalent thereof. In some aspects, the recombinant expression system comprises or alternatively consists essentially of, or yet further consists of a DNA sequence selected from the group of a DNA sequence encoding VP2, a DNA sequence encoding Cas9, a DNA sequence encoding SEQ ID NO: 45, SEQ ID NO: 46, SEQ ID NO: 47, SEQ ID NO: 48, SEQ ID NO: 49, or an equivalent of each thereof. In some aspects, the recombinant expression system comprises a helper plasmid comprising a DNA sequence selected from the group of a DNA sequence encoding VP1, a DNA sequence encoding VP3, or a DNA sequence encoding both VP1 and VP3, or an equivalent of each thereof.

The modified virus, e.g., AAV, can be packaged using a viral packaging system such as a retroviral, adenoviral, herpes virus, or baculovirus packaging system. In some embodiments, packaging is achieved by using a helper virus or helper plasmid and a cell line. The helper virus or helper plasmid contains elements and sequences that facilitate the delivery of genetic materials into cells. In another aspect, the helper plasmid or a polynucleotide comprising the helper plasmid is stably incorporated into the genome of a packaging cell line, such that the packaging cell line does not require additional transfection with a helper plasmid.

A helper plasmid may comprise, for example, at least one viral helper DNA sequence derived from a replication-incompetent viral genome encoding in trans all virion proteins required to package a replication incompetent virus, such as AAV, and for producing virion proteins capable of packaging the replication-incompetent AAV at high titer, without the production of replication-competent AAV. The viral DNA sequence lacks the region encoding the native enhancer and/or promoter of the viral 5' LTR of the virus, and lacks both the psi function sequence responsible for packaging helper genome and the 3' LTR, but encodes a foreign polyadenylation site, for example the SV40 polyadenylation site, and a foreign enhancer and/or promoter which directs efficient transcription in a cell type where virus production is desired. The virus is a leukemia virus such as a Moloney Murine Leukemia Virus (MMLV), the Human Immunodeficiency Virus (HIV), or the Gibbon Ape Leukemia virus (GALV). The foreign enhancer and promoter may be the human cytomegalovirus (HCMV) immediate early (IE) enhancer and promoter, the enhancer and promoter (U3 region) of the Moloney Murine Sarcoma Virus (MMSV), the U3 region of Rous Sarcoma Virus (RSV), the U3 region of Spleen Focus Forming Virus (SFFV), or the HCMV IE enhancer joined to the native Moloney Murine Leukemia Virus (MMLV) promoter. The helper plasmid may consist of two retroviral helper DNA sequences encoded by plasmid based expression vectors, for example where a first helper sequence contains a cDNA encoding the gag and pol proteins of ecotropic MMLV or GALV and a second helper sequence contains a cDNA encoding the env protein. The Env gene, which determines the host range, may be derived from the genes encoding xenotropic, amphotropic, ecotropic, polytropic (mink focus forming) or 10A1 murine leukemia virus env proteins, or the Gibbon Ape Leukemia Virus (GALV env protein, the Human Immunodeficiency Virus env (gp160) protein, the Vesicular Stomatitus Virus (VSV) G protein, the Human T cell leukemia (HTLV) type I and II env gene products, chimeric envelope gene derived from combinations of one or more of the aforementioned env genes or chimeric envelope genes encoding the cytoplasmic and transmembrane of the aforementioned env gene products and a monoclonal antibody directed against a specific surface molecule on a desired target cell.

In the packaging process, the helper plasmids and the plasmids encoding the AAV viral proteins are transiently cotransfected into a first population of mammalian cells that are capable of producing virus, such as human embryonic kidney cells, for example 293 cells (ATCC No. CRL1573, ATCC, Rockville, Md.) to produce high titer recombinant retrovirus-containing supernatants. In another method of the present disclosure, this transiently transfected first population of cells is then cocultivated with mammalian target cells, for example human lymphocytes, to transduce the target cells with the foreign gene at high efficiencies.

In another aspect, the helper plasmids are stably expressed in a first population of mammalian cells that are capable of producing virus, such as human embryonic kidney cells, for example 293 cells. The plasmids are introduced into cells in an episomally maintained plasmid. High titer modified AAV containing supernatants are produced, and the modified AAV may be purified out or maintained in this high titer supernatant for use in the methods of treatment disclosed herein below.

In further aspects, the recombinant expression system further comprises a polynucleotide encoding one or more guide RNAs. In other aspects, the recombinant expression system further comprises a therapeutic polynucleotide.

Also disclosed herein is a method of producing modified AAV expressing Cas9 or an equivalent thereof on its interior or exterior capsid surface comprising transfecting one or more cells with a recombinant expression system consisting essentially of, or yet further consisting of (a) a plasmid comprising a DNA sequence encoding a fusion protein, the fusion protein comprising the Cas9 or the equivalent thereof and a viral capsid protein; and (b) a helper plasmid. In some aspects, the method comprises an HEK293 or a similar cell transfected with plasmids that encode for VP1+VP3 and, in a separate reading frame, the VP2-Cas9 fusion protein. In addition, the targeting vector containing the gRNA sequence and, if needed, additional therapeutic polynucleotide. In another aspect, the method further comprises transfection of the HEK or similar cell with an additional helper plasmid that provides the viral helper function found in Adenovirus (E1A, E1B, E2A, E40RF6 and VA RNAs) or Herpes virus (among other viruses as well) to enable efficient AAV production.

The AAV and Helper genes can be provided as separate plasmids or combined into multiples or a single plasmid if desired. The genes can be stably introduced into cells to generate stable packing cell lines in another embodiment. Alternatively, the genes can be introduced into cells using viral vectors like baculo-virus or herpes virus to amplify and deliver large quantities of the needed genes to adherent or suspension grown cells.

Provided herein is a modified AAV particle expressing Cas9 or an equivalent thereof on its interior or exterior capsid surface produced by a method of transfecting one or more cells with a recombinant expression system consisting essentially of, or yet further consisting of (a) a plasmid comprising a DNA sequence encoding a fusion protein, the fusion protein comprising the Cas9 or the equivalent thereof and a viral capsid protein; and (b) a helper plasmid. In some aspects, the AAV particle comprises Cas9 or an equivalent thereof conjugated to the interior of VP2. In other aspects, the AAV particle comprises Cas9 or an equivalent thereof conjugated to VP1 or VP3.

The present disclosure relates to a modified adeno-associated virus (AAV) expressing Cas9 on its interior or exterior capsid surface and methods of making and using said modified AAV. A non-limiting examples of such are disclosed herein, as well as biological equivalents of such. Non-limiting example of a suitable biological equivalents include a polynucleotide having at least 70%, or alternatively 75%, or alternatively at least 80%, or alternatively at least 85%, or alternatively at least 90%, or alternatively at least 95% sequence identity of the various elements.

Aspects of the disclosure relate to a modified adeno-associated virus (AAV) expressing Cas9 on its interior capsid surface comprising an AAV viral protein selected from the group of VP1, VP2, and VP3 fused to Cas9. In some embodiments, the AAV viral protein is VP2. In some embodiments, the Cas9 is S. aureus Cas9 or Cpf1. In further embodiments, the Cas9 comprises the amino acid sequence provided in SEQ ID NO: 3 or SEQ ID NO: 50 or an equivalent of each thereof. In some embodiments, the modified AAV comprises and/or encapsidates one or more guide RNAs or polynucleotides encoding said guide RNAs.

Further aspects of the disclosure relate to a recombinant expression system for the generation of such a modified AAV. In some embodiments the recombinant expression system comprises a plurality of plasmids; the plurality encoding all of the AAV viral proteins —VP1, VP2, and VP3. In some embodiments, each viral protein is encoded in a different plasmid. In some embodiments, one or more viral proteins is encoded in the same plasmid. In some embodiments, at least one viral protein is encoded as a fusion protein with Cas9.

Accordingly, embodiments disclosed herein relate to a recombinant expression system for the generation of a modified AAV expressing Cas9 on its interior or exterior capsid surface comprising: (a) a plasmid comprising a DNA sequence encoding a fusion protein comprising Cas9 and an AAV viral protein selected from the group of VP1, VP2, and VP3, and (b) a plasmid comprising a DNA sequence encoding any AAV viral proteins selected from the group of VP1, VP2, and VP3 not comprised in the fusion protein of plasmid (a). In some embodiments, the fusion protein comprises VP2. In some embodiments, the Cas9 is S. aureus Cas9 or Cpf1. In further embodiments, the Cas9 comprises the amino acid sequence provided in SEQ ID NO: 3 or SEQ ID NO: 50. In some embodiments, plasmid (a) comprises a DNA sequence encoding SEQ ID NO: 45, SEQ ID NO: 46, SEQ ID NO: 47, SEQ ID NO: 48, SEQ ID NO: 49 or an equivalent of each thereof. In some embodiments, plasmid (b) comprises a DNA sequence selected from the group of SEQ ID NO: 1, SEQ ID NO: 4, and SEQ ID NO: 57. In some embodiments, the recombinant expression system further comprises a helper virus or helper plasmid. In some embodiments, the helper plasmid comprises the DNA sequence provided in SEQ ID NO: 6. In some embodiments, the recombinant expression further comprises a plasmid comprising a DNA sequence encoding one or more guide RNAs.

Some aspects of the disclosure relate to methods of producing the modified AAVs using the recombinant expression system disclosed herein. Aspects relate to a method of producing a modified AAV expressing Cas9 on its interior or exterior capsid surface by transfecting one or more cells with the recombinant expression system disclosed herein. In some embodiments, the one or more cells are HEK293 cells.

Compositions

This disclosure also provides a composition comprising a carrier and one or more of any of the disclosed isolated polynucleotides, viral vectors, packaging systems, and recombinant virus as described herein a carrier. In some embodiments, the carrier comprises a compound or composition, inert (for example, a detectable agent or label) or active, such as an adjuvant, diluent, binder, stabilizer, buffers, salts, lipophilic solvents, preservative, adjuvant or the like. Carriers also include pharmaceutical excipients and additives proteins, peptides, amino acids, lipids, and carbohydrates (e.g., sugars, including monosaccharides, di-, tri-, tetra-, and oligosaccharides; derivatized sugars such as alditols, aldonic acids, esterified sugars and the like; and polysaccharides or sugar polymers), which can be present singly or in combination, comprising alone or in combination 1-99.99% by weight or volume. Exemplary protein excipients include serum albumin such as human serum albumin (HSA), recombinant human albumin (rHA), gelatin, casein, and the like. Representative amino acid/antibody components, which can also function in a buffering capacity, include alanine, glycine, arginine, betaine, histidine, glutamic acid, aspartic acid, cysteine, lysine, leucine, isoleucine, valine, methionine, phenylalanine, aspartame, and the like. Carbohydrate excipients are also intended within the scope of this disclosure, examples of which include but are not limited to monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol) and myoinositol.

The term carrier further includes a buffer or a pH adjusting agent; typically, the buffer is a salt prepared from an organic acid or base. Representative buffers include but are not limited to organic acid salts such as salts of citric acid, ascorbic acid, gluconic acid, carbonic acid, tartaric acid, succinic acid, acetic acid, or phthalic acid; Tris, tromethamine hydrochloride, or phosphate buffers. Additional carriers include polymeric excipients/additives such as polyvinylpyrrolidones, ficolls (a polymeric sugar), dextrates (e.g., cyclodextrins, such as 2-hydroxypropyl-.quadrature.-cyclodextrin), polyethylene glycols, flavoring agents, antimicrobial agents, sweeteners, antioxidants, antistatic agents, surfactants (e.g., polysorbates such as "TWEEN 20" and "TWEEN 80"), lipids (e.g., phospholipids, fatty acids), steroids (e.g., cholesterol), and chelating agents (e.g., EDTA).

In some embodiments, the carrier is a pharmaceutically acceptable carrier. As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. The compositions also can include stabilizers and preservatives and any of the above noted carriers with the additional proviso that they be acceptable for use in vivo. For examples of carriers, stabilizers and adjuvants, see Martin REMINGTON'S PHARM. SCI., 15th Ed. (Mack Publ. Co., Easton (1975) and Williams & Williams, (1995), and in the "PHYSICIAN'S DESK REFERENCE", $52^{nd}$ ed., Medical Economics, Montvale, N.J. (1998).

This disclosure also provides an article of manufacture, comprising packaging material and at least one vial comprising a solution of at least one agent or composition with the prescribed buffers and/or preservatives, optionally in an aqueous diluent, wherein said packaging material comprises a label that indicates that such solution can be held over a period of 1, 2, 3, 4, 5, 6, 9, 12, 18, 20, 24, 30, 36, 40, 48, 54, 60, 66, 72 hours or greater. The disclosure further comprises an article of manufacture, comprising packaging material, a first vial comprising at least one agent or composition and a second vial comprising an aqueous diluent of prescribed buffer or preservative, wherein said packaging material comprises a label that instructs a patient to reconstitute the therapeutic in the aqueous diluent to form a solution that can be held over a period of twenty-four hours or greater.

The formulations of the present disclosure can be prepared by a process which comprises mixing at least one agent or composition and a preservative selected from the group consisting of phenol, m-cresol, p-cresol, o-cresol, chlorocresol, benzyl alcohol, alkylparaben, (methyl, ethyl, propyl, butyl and the like), benzalkonium chloride, benzethonium chloride, sodium dehydroacetate and thimerosal or mixtures thereof in an aqueous diluent. Mixing of the antibody and preservative in an aqueous diluent is carried out using conventional dissolution and mixing procedures. For example, a measured amount of at least one antibody in buffered solution is combined with the desired preservative in a buffered solution in quantities sufficient to provide the antibody and preservative at the desired concentrations. Variations of this process would be recognized by one of skill in the art, e.g., the order the components are added, whether additional additives are used, the temperature and pH at which the formulation is prepared, are all factors that can be optimized for the concentration and means of administration used.

The compositions and formulations can be provided to patients as clear solutions or as dual vials comprising a vial of agent or composition that is reconstituted with a second vial containing the aqueous diluent. Either a single solution vial or dual vial requiring reconstitution can be reused multiple times and can suffice for a single or multiple cycles of patient treatment and thus provides a more convenient treatment regimen than currently available. Recognized devices comprising these single vial systems include pen-injector devices for delivery of a solution such as BD Pens, BD Autojectore, Humaject®, NovoPen®, B-D®Pen, AutoPen®, and OptiPen®, GenotropinPen®, Genotronorm Pen®, Humatro Pen®, Reco-Pen®, Roferon Pen®, Biojector®, iject®, J-tip Needle-Free Injector®, Intraject®, Medi-Ject®, e.g., as made or developed by Becton Dickensen (Franklin Lakes, N.J. available at bectondickenson.com), Disetronic (Burgdorf, Switzerland, available at disetronic-.com; Bioject, Portland, Oregon (available at bioject.com); National Medical Products, Weston Medical (Peterborough, UK, available at weston-medical.com), Medi-Ject Corp (Minneapolis, Minn., available at mediject.com).

Methods of delivery include but are not limited to intra-arterial, intra-muscular, and intravenous. In a specific embodiment, it may be desirable to administer the pharmaceutical compositions and/or cells of the disclosure locally to the area in need of treatment; this may be achieved by, for example, and not by way of limitation, local infusion during surgery, by injection or by means of a catheter. In some embodiments, the compositions or cells are administered by intravenous injection. In a further embodiment, the compositions or cells are administered by intramuscular injection. The compositions may be administered in one injection or in multiple injections. Furthermore, they may also be directly injected into ischemic areas of the diseased limb.

Solutions containing the cells can be prepared in suitable diluents such as water, ethanol, glycerol, liquid polyethylene glycol(s), various oils, and/or mixtures thereof, and others known to those skilled in the art.

Prevention or inhibition of growth of microorganisms in the formulations may be achieved through the addition of one or more antimicrobial agents such as chlorobutanol, ascorbic acid, parabens, thermerosal, or the like. It may also be preferable to include agents that alter the tonicity such as sugars or salts.

Modified AAV Capsids and Particles

The present disclosure provides also provides a specific embodiment, e.g., a modified adeno-associated virus (AAV) expressing Cas9 on its interior or exterior capsid surface and methods of making the modified AAV and using the modified AAV. Adeno-associated virus (AAV) vectors are replication defective viruses that are engineered to deliver genetic cargo efficiently to cells. They are non-enveloped viruses that in their vector form only possess the inverted terminal repeats (ITR) of the original virus. The structural and enzymatic AAV proteins are supplied "in trans" by additional plasmids and are transfected together into a cell to generate the engineered particles for gene delivery. AAVs have been widely utilized for genetic therapy—and more specifically with CRISPR/Cas9 systems—due to their safety and efficiency. AAV efficiently infects a variety of cells and during the infection process the capsid binds to and enters the nucleus where the vector genome is delivered.

The AAV structural particle is composed of 60 protein molecules made up of VP1, VP2 and VP3. Each particle contains approximately 5 VP1 proteins, 5 VP2 proteins and 50 VP3 proteins ordered into an icosahedral structure. It has been shown that AAV2 particles can support the insertion of peptides and proteins at various sites within the capsid structure. The ability to introduce unique peptides into the capsid has led to the development of AAV particles with altered tropism, which allows the virus to bind and infect cells and tissues that may normally be refractory to infection. In addition, large peptides and even functional proteins have been introduced into the capsid of AAV2 vectors with varying levels of success. A functional green fluorescent protein (GFP, 30 kD MW) containing AAV capsid was generated and produced infectious virus that was used to track cell infections.

One of the constraints with AAV vectors for gene delivery is the size limitation of the genetic insert that can be efficiently packaged into particles. For example, the size of the wild-type AAV2 genome is 4679 bases of single stranded DNA. Packaging even one of the new smaller variants of Cas9 (*Staphylococcus aureus* Cas9, SaCas9, 130 kD MW) requires approximately 3255 bp just for the coding region. Adding a ubiquitous or tissue specific promoter to the construct may add another 500-800 bp. Include another 500 bp for a poly A addition sequence and the ITR's and the vector is close to the packaging capacity of an AAV particle. To achieve functional CRISPR/Cas9 gene correction a guide RNA ("gRNA") with the target sequence must also be included. To have this RNA expressed further requires a minimal polIII promoter and termination sequence. In some embodiments, these elements are too large to be combined together into an AAV vector that is efficiently packaged. Thus, in some embodiments, one can choose to package the Cas9 construct and guide RNA expression cassettes into separate vectors, but, for them to be functional, both viruses must infect the same target cells.

Rather than direct delivery, Applicant has generated plasmids to produce a modified AAV expressing Cas9 on its interior capsid surface. During the normal course of AAV infection of a cell, the particle surface contains nuclear localization sequences, which direct the virus to traffic to the nucleus. Upon binding the nuclear pore complex the particle enters the nucleus and uncoats the vector genome. AAV capsid proteins are very stable inside the nucleus and can be found for many weeks after infection. By engineering an AAV vector to express the Cas9 enzyme on the interior capsid surface of the virus particle, one eliminates the need to package the Cas9 polynucleotide coding region within the particle and would allow the delivery of both a Cas9 protein and the guide RNA expression cassette within a single vector particle. In some aspects, the Cas9 or equivalent thereof is attached to a VP2 protein at amino acid position 228, 350, 419, 684, or 689 of SEQ ID NO: 59. In some aspects, the Cas9 or an equivalent thereof is attached to a VP2 protein at amino acid position 90, 213, 282, 547, and 552 of SEQ ID NO: 39.

Aspects of the disclosure relate to a modified adeno-associated virus (AAV) expressing Cas9 on its interior or exterior surface comprising an AAV viral protein selected from the group of VP1, VP2, and VP3 fused to Cas9. In some embodiments, the AAV viral protein is VP2. In some embodiments, the Cas9 is *S. aureus* Cas9 or Cpf1. In further embodiments, the Cas9 comprises the amino acid sequence provided in SEQ ID NO: 3, SEQ ID NO: 50, or an equivalent of each thereof. In some embodiments, the modified AAV comprises and/or encapsidates one or more guide RNAs or polynucleotides encoding said guide RNAs. It is appreciated by those skilled in the art that gRNAs can be generated for target specificity to target a specific gene, optionally a gene associated with a disease, disorder, or condition. Thus, in combination with Cas9, the guide RNAs facilitate the target specificity of the CRISPR/Cas9 system.

Further aspects of the disclosure relate to a recombinant expression system for the generation of such a modified AAV. In some embodiments the recombinant expression system comprises a plurality of plasmids; the plurality encoding all of the AAV viral proteins —VP1, VP2, and VP3. In some embodiments, each viral protein is encoded in a different plasmid. In some embodiments, one or more viral proteins is encoded in the same plasmid. In some embodiments, at least one viral protein is encoded as a fusion protein with Cas9.

Accordingly, embodiments disclosed herein relate to a recombinant expression system for the generation of a modified AAV expressing Cas9 on its interior or exterior capsid surface comprising: (a) a plasmid comprising a DNA sequence encoding a fusion protein comprising Cas9 and an AAV viral protein selected from the group of VP1, VP2, and VP3, and (b) a plasmid comprising a DNA sequence encoding any AAV viral proteins selected from the group of VP1, VP2, and VP3 not comprised in the fusion protein of plasmid (a). In some embodiments, the fusion protein comprises VP2. In some embodiments, the Cas9 is *S. aureus* Cas9 or Cpf1. In further embodiments, the Cas9 comprises the amino acid sequence provided in SEQ ID NO: 3, SEQ ID NO: 50, or an equivalent of each thereof. In embodiments wherein the Cas9 is conjugated to the interior surface of the viral capsid protein, plasmid (a) comprises a DNA sequence encoding SEQ ID NO: 45, SEQ ID NO: 46, SEQ ID NO: 47, SEQ ID NO: 48, SEQ ID NO: 49, or an equivalent of each thereof. In embodiments wherein the Cas9 is conjugated to the exterior surface of the viral capsid protein, plasmid (a) comprises a DNA sequence encoding SEQ ID NO: 2 or SEQ ID NO: 5. In some embodiments, plasmid (b) comprises a DNA sequence selected from the group of SEQ ID NO: 1, SEQ ID NO: 4, or SEQ ID NO: 57. In some embodiments, the recombinant expression system further comprises a helper virus or helper plasmid. In some embodiments, the helper plasmid comprises the DNA sequence provided in SEQ ID NO: 6. In some embodiments, the recombinant expression further comprises a plasmid comprising a DNA sequence encoding one or more guide RNAs.

Some aspects relate to methods of producing the modified AAVs using the recombinant expression system disclosed herein. Aspects relate to a method of producing a modified AAV expressing Cas9 on its interior or exterior capsid surface by transfecting one or more cells with the recombinant expression system disclosed herein. In some embodiments, the one or more cells are HEK293 cells.

Still further aspects relate to methods of treating a subject having a disease, disorder, or condition comprising administering the modified AAV disclosed herein to the subject. In some embodiments, the disease, disorder, or condition is selected from the group of hemophilia, muscular dystrophy, multiple sclerosis, alpha-i-antitrypsin, amyotrophic lateral sclerosis, Alzheimer's, spinal muscular atrophy, cystic fibrosis, HIV, thalassemia, choroideremia, Parkinson's, Leber congenital amaurosis, macular degeneration, aromatic amino acid decarboxylase deficiency, achromatopsia, Crigler Najjar syndrome, Pompe disease, X-linked retinoschisis, homozygous familial hypercholesteremia, Batten disease, retinal degeneration, ornithine transcarbamylase deficiency, mucopolysarccharidosis (I-IX), hepatitis B, and hepatitis C. In some embodiments, the hemophilia is characterized by one or more of factor VIII or factor IX deficiency. In some embodiments, the muscular dystrophy is selected from Becker muscular dystrophy, congenital muscular dystrophy, Duchenne muscular dystrophy, distal muscular dystrophy, Emery-Dreifuss muscular dystrophy, facioscapulohumeral muscular dystrophy, limb-girdle muscular dystrophy, myotonic muscular dystrophy, and oculopharyngeal muscular dystrophy.

Methods of Administering Modified Viral Particles

Provided herein is a non-human transgenic animal comprising a modified viral capsid protein comprising or alternatively consisting essentially of, or yet further consisting of a viral capsid protein having a Cas9 protein or an equivalent thereof conjugated to the interior surface, interior facing domain, or the interior-facing terminal end of the viral capsid protein. Also provided herein is a non-human transgenic animal comprising a modified or recombinant viral particle comprising or alternatively consisting essentially of a modified capsid wherein the modified capsid comprises a modified viral capsid protein comprising or alternatively consisting essentially of, or yet further consisting of a viral capsid protein having a Cas9 protein or an equivalent thereof conjugated to the interior surface, interior facing domain, or the interior-facing terminal end of the viral capsid protein and one or more polynucleotides encapsidated within the capsid.

Disclosed herein is a method of gene editing comprising contacting a cell with recombinant viral particle comprising or alternatively consisting essentially of a modified capsid wherein the modified capsid comprises a modified viral capsid protein comprising or alternatively consisting essentially of, or yet further consisting of a viral capsid protein having a Cas9 protein or an equivalent thereof conjugated to the interior surface, interior facing domain, or the interior-facing terminal end of the viral capsid protein and one or more polynucleotides encapsidated within the capsid. In some aspects, the contact is in vitro. In other aspects, the contact is in vivo. In some aspects, the contact is in vivo or in vitro. In some aspects, at least one of the polynucleotides comprises or consists essentially of, or yet further consists of a polynucleotide encoding a guide RNA (gRNA). In some aspects, at least one of the polynucleotides comprises or alternatively consists essentially of, or yet further consists of a therapeutic polypeptide.

Further disclosed herein is a method of gene editing in a subject in need thereof, comprising administering to the subject an effective amount recombinant viral particle comprising or alternatively consisting essentially of a modified capsid wherein the modified capsid comprises a modified viral capsid protein comprising or alternatively consisting essentially of, or yet further consisting of a viral capsid protein having a Cas9 protein or an equivalent thereof conjugated to the interior surface, interior facing domain, or the interior-facing terminal end of the viral capsid protein and one or more polynucleotides encapsidated within the capsid. In some aspects, at least one of the polynucleotides comprises or consists essentially of, or yet further consists of a polynucleotide encoding a guide RNA (gRNA). In some aspects, at least one of the polynucleotides comprises or alternatively consists essentially of, or yet further consists of a therapeutic polypeptide.

Provided herein is a non-human transgenic animal comprising a modified viral capsid protein comprising or alternatively consisting essentially of, or yet further consisting of a viral capsid protein having a Cas9 protein or an equivalent thereof conjugated to the exterior surface, exterior facing domain, or the exterior-facing terminal end of the viral capsid protein. Also provided herein is a non-human transgenic animal comprising a modified or recombinant viral particle comprising or alternatively consisting essentially of a modified capsid wherein the modified capsid comprises a modified viral capsid protein comprising or alternatively consisting essentially of, or yet further consisting of a viral capsid protein having a Cas9 protein or an equivalent thereof conjugated to the exterior surface, exterior facing domain, or the exterior-facing terminal end of the viral capsid protein and one or more polynucleotides encapsidated within the capsid.

Disclosed herein is a method of gene editing comprising contacting a cell with recombinant viral particle comprising or alternatively consisting essentially of a modified capsid wherein the modified capsid comprises a modified viral capsid protein comprising or alternatively consisting essentially of, or yet further consisting of a viral capsid protein having a Cas9 protein or an equivalent thereof conjugated to the exterior surface, exterior facing domain, or the exterior-facing terminal end of the viral capsid protein and one or more polynucleotides encapsidated within the capsid. In some aspects, the contact is in vitro. In other aspects, the contact is in vivo. In some aspects, the contact is in vivo or in vitro. In some aspects, at least one of the polynucleotides comprises or consists essentially of, or yet further consists of a polynucleotide encoding a guide RNA (gRNA). In some aspects, at least one of the polynucleotides comprises or alternatively consists essentially of, or yet further consists of a therapeutic polypeptide.

In some embodiments, one or more isolated cells or expanded populations of isolated cells that has been edited or contacted according to a method described herein is administered to a subject in need thereof. In some embodiments, the cells are autologous to the subject. In other embodiments, the cells are allogenic to the subject. In some embodiments, an effective amount of the cells or population of cells is administered to the subject. In certain embodiments, about 1-1000 million cells are administered to the subject in the methods described herein. Alternatively, about 1-900 million cells, about 1-800 million cells, about 1-700 million cells, about 1-600 million cells, about 1-500 million cells, about 1-400 million cells, about 1-300 million cells, about 1-200 million cells, about 1-100 million cells, about 10-900 million cells, about 10-800 million cells, about 10-700 million cells, about 10-600 million cells, about 10-500 million cells, about 10-400 million cells, about 10-300 million cells, about 10-200 million cells, about 10-100 million cells, 30-900 million cells, about 30-800 million cells, about 30-700 million cells, about 30-600 million cells, about 30-500 million cells, about 30-400 million cells, about 30-300 million cells, about 30-200 million cells, about 30-100 million cells, about 50-900 million cells, about 50-800 million cells, about 50-700 million cells, about 50-600 million cells, about 50-500 million cells, about 50-400 million cells, about 50-300 million cells, about 50-200 million cells, about 50-150 million cells, about 50-100 million cells, 100-900 million cells, about 100-800 million cells, about 100-700 million cells, about 100-600 million cells, about 100-500 million cells, about 100-400 million cells, about 100-300 million cells, or about 100-200 million cells are administered to the subject in the methods described herein.

Further disclosed herein is a method of gene editing in a subject in need thereof, comprising administering to the subject an effective amount recombinant viral particle comprising or alternatively consisting essentially of a modified capsid wherein the modified capsid comprises a modified viral capsid protein comprising or alternatively consisting essentially of, or yet further consisting of a viral capsid protein having a Cas9 protein or an equivalent thereof conjugated to the exterior surface, exterior facing domain, or the exterior-facing terminal end of the viral capsid protein and one or more polynucleotides encapsidated within the capsid. In some aspects, at least one of the polynucleotides comprises or consists essentially of, or yet further consists of a polynucleotide encoding a guide RNA (gRNA). In some aspects, at least one of the polynucleotides comprises or alternatively consists essentially of, or yet further consists of a therapeutic polypeptide.

In some aspects, the polynucleotide encoding the gRNA comprises or alternatively consists essentially of, or yet further consists of a fusion polynucleotide comprising CRISPR RNA (crRNA) and trans-activating CRIPSPR RNA (tracrRNA); or a polynucleotide comprising CRISPR RNA (crRNA) and trans-activating CRIPSPR RNA (tracrRNA). In one aspect, the polynucleotide encoding the gRNA comprises or consists of SEQ ID NO: 8 or an equivalent thereof. In some aspects, the gRNA is specific for a region of DNA that is in need of gene editing in the subject or cell in need thereof.

In some aspects, the recombinant viral particle further comprising a therapeutic polynucleotide. The therapeutic polynucleotide is any polypeptide that can be used to target a DNA sequence in need of editing, provide a repair template for a DNA sequence in need of editing, or provide a replacement for a DNA sequence in need of editing. In further aspects, the therapeutic polypeptide comprises a wild-type sequence of a gene in need of editing in the subject or cell in need thereof.

Still further aspects relate to methods of treating a subject having a disease, disorder, or condition comprising administering the modified AAV disclosed herein to the subject. In some aspects, the disease, disorder, or condition is selected from the group of hemophilia, muscular dystrophy, multiple sclerosis, alpha-i-antitrypsin, amyotrophic lateral sclerosis, Alzheimer's, spinal muscular atrophy, cystic fibrosis, HIV, thalassemia, choroideremia, Parkinson's, Leber congenital amaurosis, macular degeneration, aromatic amino acid decarboxylase deficiency, achromatopsia, Crigler Najjar syndrome, Pompe disease, X-linked retinoschisis, homozygous familial hypercholesteremia, Batten disease, retinal degeneration, ornithine transcarbamylase deficiency, mucopolysarccharidosis (I-IX), hepatitis B, and hepatitis C. In one aspect, the hemophilia is characterized by one or more of factor VIII or factor IX deficiency. In some aspects, the muscular dystrophy is selected from Becker muscular dystrophy, congenital muscular dystrophy, Duchenne muscular dystrophy, distal muscular dystrophy, Emery-Dreifuss muscular dystrophy, facioscapulohumeral muscular dystrophy, limb-girdle muscular dystrophy, myotonic muscular dystrophy, and oculopharyngeal muscular dystrophy.

In some aspects, guide RNA and/or the therapeutic polynucleotide is designed and/or selected to treat a disease, disorder, or condition selected from the group of hemophilia, muscular dystrophy, multiple sclerosis, alpha-i-antitrypsin, amyotrophic lateral sclerosis, Alzheimer's, spinal muscular atrophy, cystic fibrosis, HIV, thalassemia, choroideremia, Parkinson's, Leber congenital amaurosis, macular degeneration, aromatic amino acid decarboxylase deficiency, achromatopsia, Crigler Najjar syndrome, Pompe disease, X-linked retinoschisis, homozygous familial hypercholesteremia, Batten disease, retinal degeneration, ornithine transcarbamylase deficiency, mucopolysarccharidosis (I-IX), hepatitis B, and hepatitis C. In one aspect, the hemophilia is characterized by one or more of factor VIII or factor IX deficiency. In some aspects, the muscular dystrophy is selected from Becker muscular dystrophy, congenital muscular dystrophy, Duchenne muscular dystrophy, distal muscular dystrophy, Emery-Dreifuss muscular dystrophy, facioscapulohumeral muscular dystrophy, limb-girdle muscular dystrophy, myotonic muscular dystrophy, and oculopharyngeal muscular dystrophy.

Figure 4:
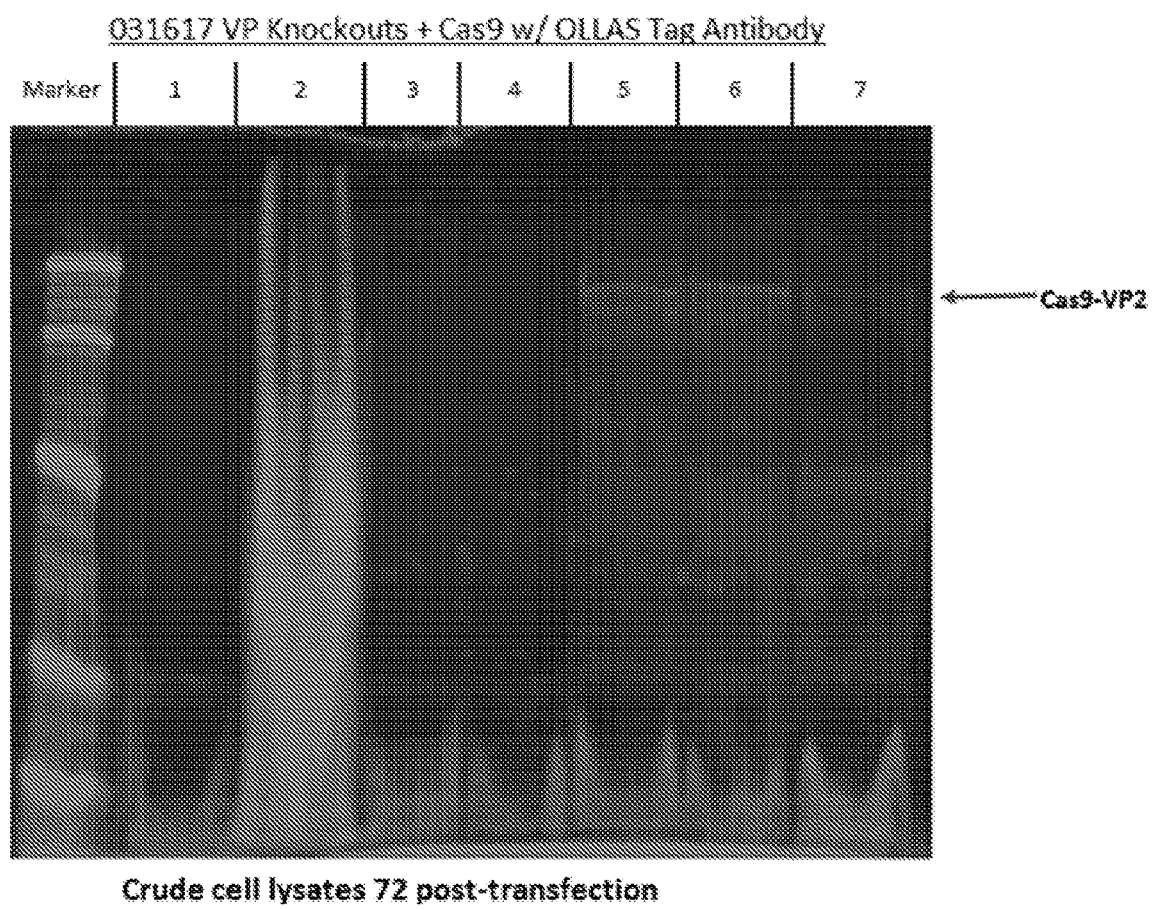
FIG. 4 depicts a Western blot from HEK293 cells transfected with various plasmids. The plasmid in the first lane (after the ladder lane) is an AAV control2 plasmid that expresses normal AAV proteins (VP1, VP2, and VP3 which are approximately 87, 72, and 62 kDa respectively). The plasmid in lane 2 is a Cas9 control plasmid that expresses a Cas9 control protein of approximately 127 kDa. The plasmid in lane 3 is a VP1-3 control2 plasmid that expresses only VP1 and VP3 proteins. The plasmid in lane 4 is a VP2-control2 plasmid that expresses only normal VP2 protein. The plasmid in lane 5 is VP2-Cas9 plasmid that expresses only Cas9-VP2 fusion proteins of approximately 193 kDa in size. The plasmid in lane 6 is VP2-cas9 help plasmid that expresses only Cas9-VP2 fusion protein and adenovirus helper proteins. The plasmid in lane 7 is Cas9 virus that expresses Cas9-VP2 fusion protein as well as VP1 and VP3 proteins. Cell lysates were harvested 72 hours after transfection in RIPA buffer with protease inhibitors. Samples of each lysate were run on 4-12% gradient gel and probed with an anti-OLLAS antibody for the detection of OLLAS tagged Cas9 protein. Lane 2 shows a protein loading artifact with the sample which masked the detection of the positive control Cas9 protein. Lanes 5-7 clearly show the expression of the large Cas9-VP2 fusion protein as expected.
Figure 5:
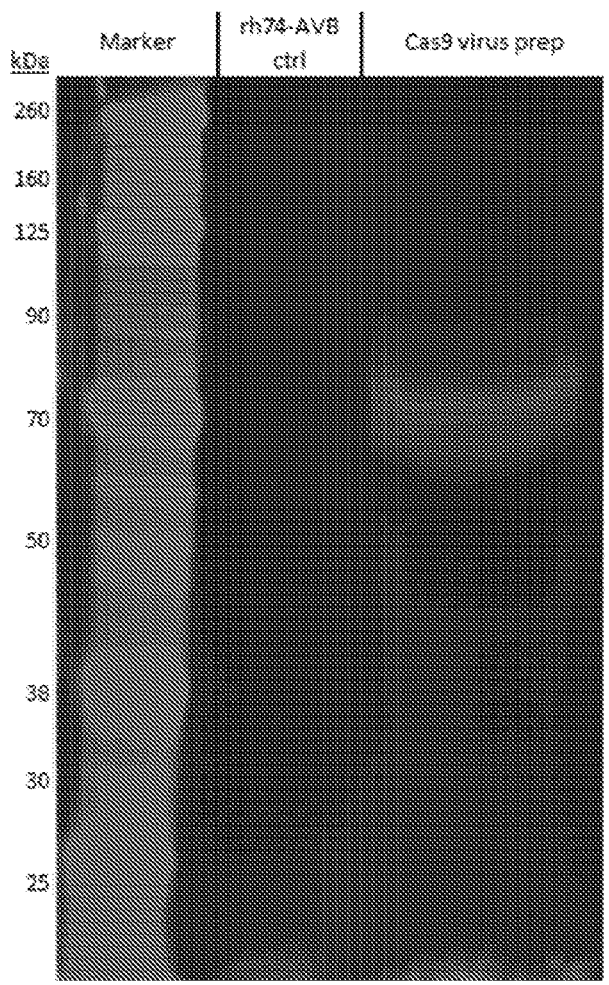
FIG. 5 depicts a Western blot of crude virus preparations of rh74-AVB control and Cas9 virus. Samples of each lysate were run on 4-12% gradient gel and probed with an anti-OLLAS antibody for the detection of OLLAS tagged Cas9 protein. Lane 2 shows a lower molecular weight protein than expected. This lower molecular weight band may be the result of protease degradation of the Cas9-VP2 fusion protein during the purification or may be non-specific binding of the anti-OLLAS antibody with the abundant VP3 protein which is also seen Western blots from crude lysate samples.
Figure 6:
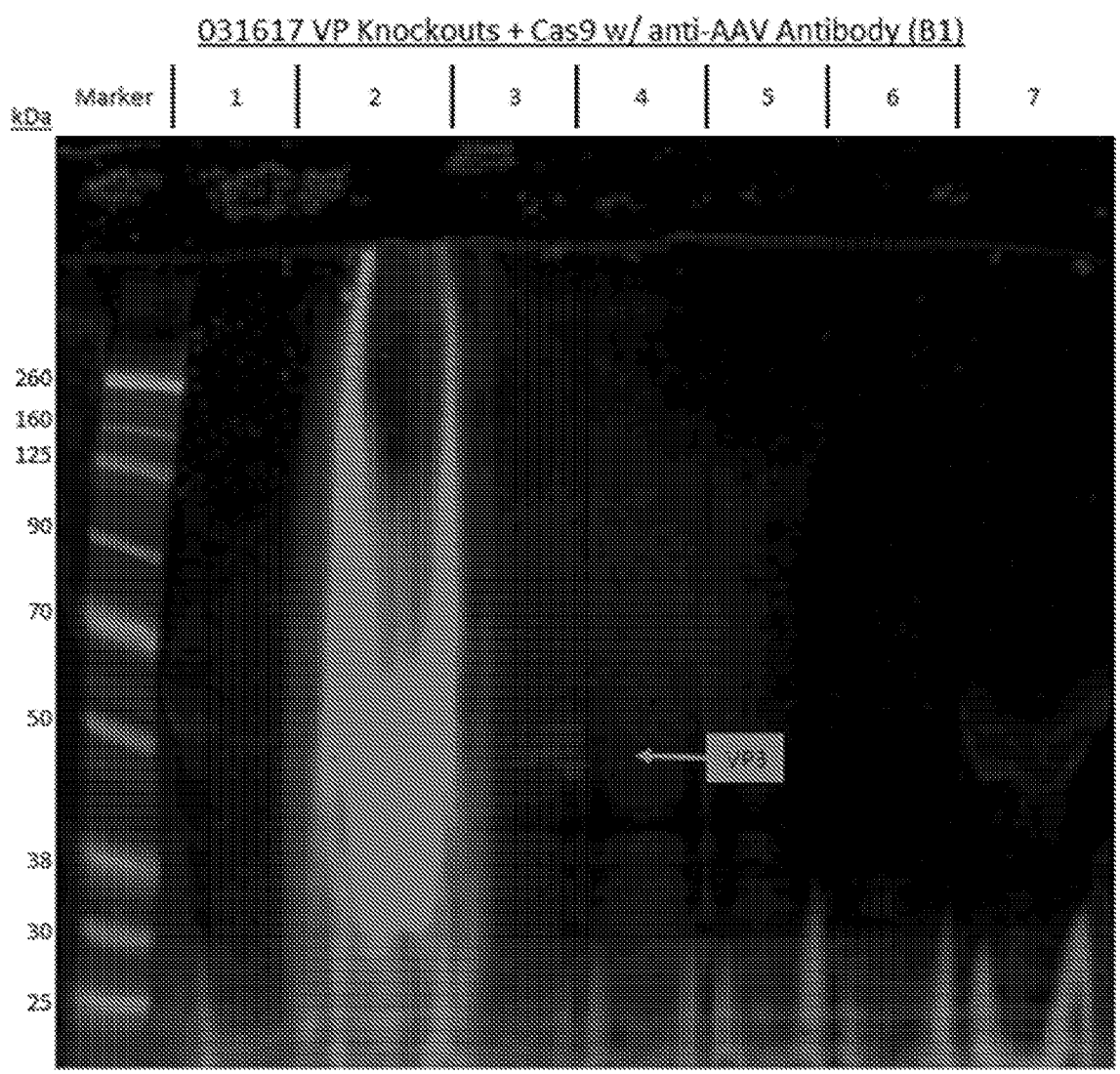
FIG. 6 depicts a Western blot from HEK293 cells transfected with the various plasmids listed below. In the first lane after the ladder, the plasmid is an AAV control2 plasmid that expresses normal AAV proteins (VP1, VP2, and VP3 which are approximately 87, 72, and 62 kDa respectively). The plasmid in lane 2 is a Cas9 control plasmid that expresses a Cas9 control protein of approximately 127 kDa. The plasmid in lane 3 is a VP1-3 control2 plasmid that expresses only VP1 and VP3 proteins. The plasmid in lane 4 is a VP2-control2 plasmid that expresses only normal VP2 protein. The plasmid in lane 5 is VP2-Cas9 plasmid that expresses only Cas9-VP2 fusion proteins of approximately 193 kDa in size. The plasmid in lane 6 is VP2-cas9 help plasmid that expresses only Cas9-VP2 fusion protein and adenovirus helper proteins. The plasmid in lane 7 is Cas9 virus that expresses Cas9-VP2 fusion protein as well as VP1 and VP3 proteins. Cell lysates were harvested 72 hours after transfection in RIPA buffer with protease inhibitors. Samples of each lysate were run on 4-12% gradient gel and probed with an anti-AAV antibody for the detection of AAV proteins. Lane 2 shows a protein loading artifact with the sample. Lane 3 shows the expression of the most abundant VP3 protein as expected. The viral proteins in the positive control sample (lane1) and the viral proteins in lanes 4-7 were not abundant enough to detect in this image.
Figure 7:
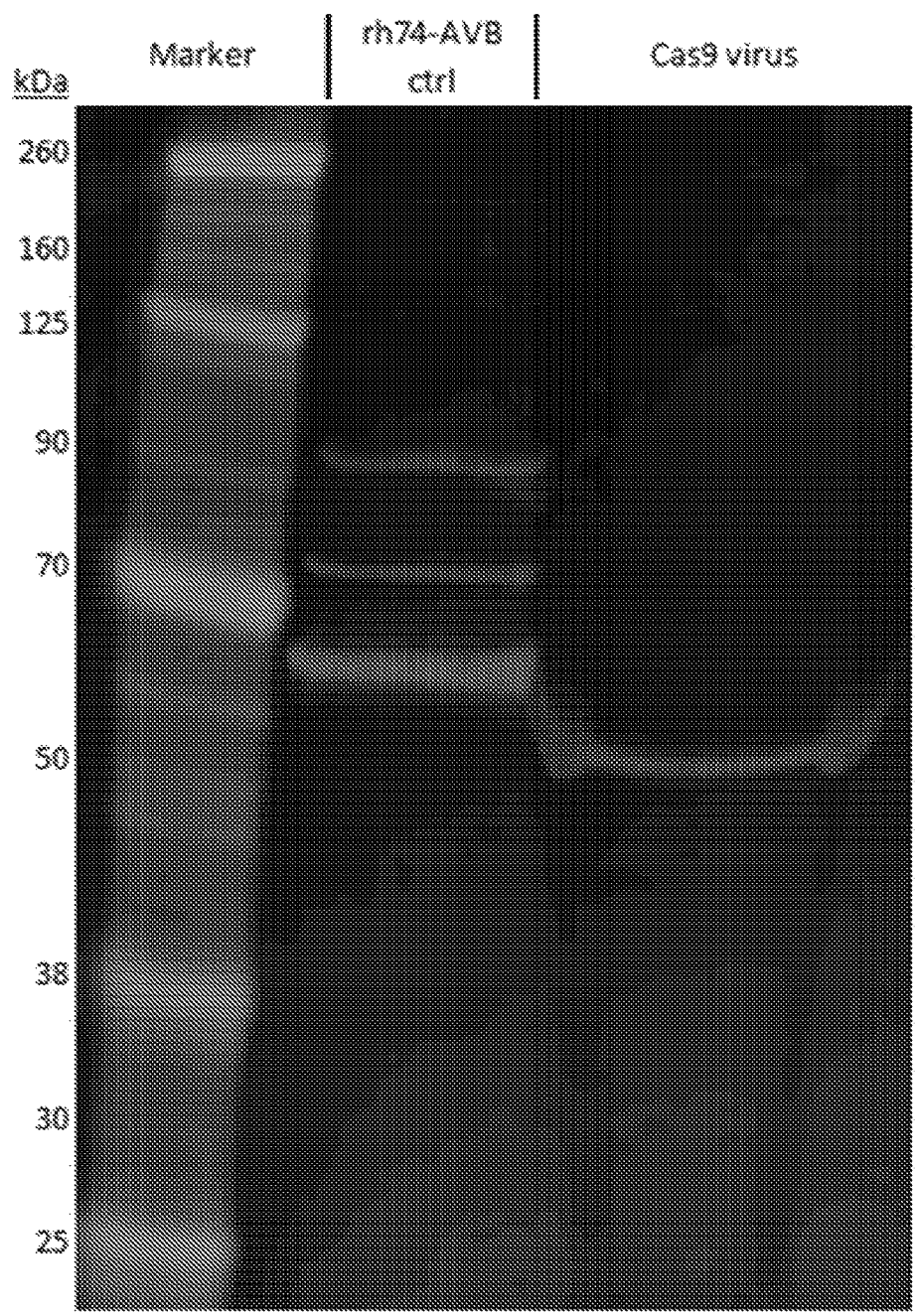
FIG. 7 depicts a Western blot of crude virus preps of rh74-AVB control and Cas9 virus probed with the anti-AAV antibody (B1). Samples of each lysate were run on 4-12% gradient gel and probed with an anti-AAV antibody for the detection of AAV proteins. Lane 1 shows the correct size viral proteins from a purified prep of control AAVrh74 virus. Lane 2 shows a lower molecular weight protein. This lower molecular weight band is likely the most abundant VP3 protein that is affected by residual salts or proteins in the crude virus preparation that affected the migration.
Figure 8:
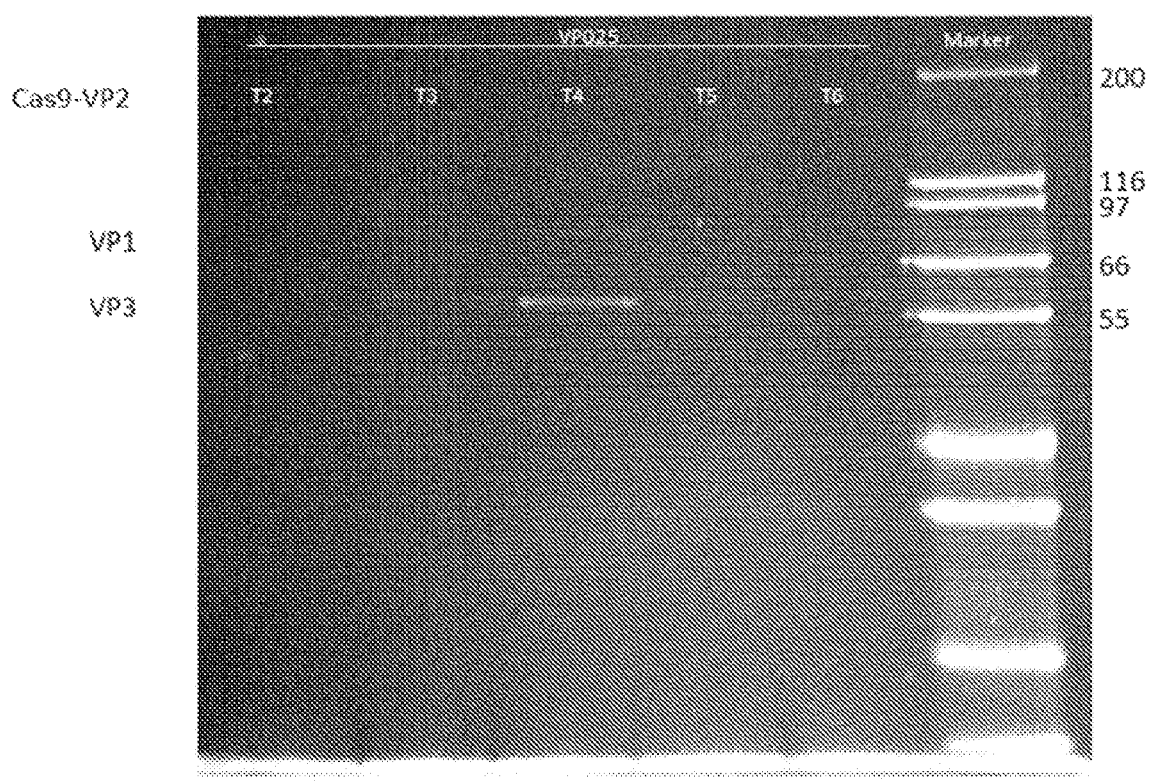
FIG. 8 shows aliquots of chromatography fractions after purification before pooling and concentration. The samples are run on acrylamide gel and visualized with SYPRO stain. The virus fractions are too dilute to visualize the Cas9-VP2 fusion protein (193 kDa) and only the VP1 (87 kDa) and VP3 (62 kDa) proteins are visible.

In some aspects, the guide RNA and/or the therapeutic polynucleotide is designed and/or selected to target or repair a gene selected from the group of Factor VIII (F8, NM_000132, NM_019863), Factor IX (F9, NM_000133, NM_001313913), dystrophin (DMD, NM_000109, NM_004006, NM 004007, NM_004009, NM_004010), dysferlin (DYSF, NM_001130455, NM_001130976, NM_001130977, NM_001130978, NM_001130979), emerin (EMD, NM_000117), lamin A/C (LMNA, NM_001257374, NM_001282624, NM_001282625, NM_001282626, NM_005572), double homeobox 4 (DUX4, NM_001205218, NM_001278056, NM_001293798, NM_001306068), myotonin-protein kinase (MDPK, NM_001081560, NM_001081562, NM_001081563, NM_001288764, NM_001288765), cellular nucleic acid-binding protein (CNBP, NM_003418, NM_001127192, NM_001127193, NM 001127194, NM_001127195), polyadenylate-binding protein-2 (PABP-2, NM_004643), Alpha-1-antitrypsin, superoxide dismutase (SOD1, NM_000454), alsin (ALS2, NM_001135745, NM_020919), helicase senataxin (SETX, NM_015046), spatacsin (SPG11, NM_001160227, NM_025137), RNA-binding protein FUS/TLS (FUS, NM_001010850, NM_001170634, NM_001170937, NM_004960), Vesicle-associated membrane protein-associated protein B/C (VAPB, NM_001195677, NM_004738), angiogenin (ANG, NM_001145, NM_001097577), TAR DNA-binding protein 43 (TARDBP, NM_007375), Polyphosphoinositide phosphatase (FIG. 4, NM_014845), optineurin (OPTN, NM_001008211, NM_001008212, NM_001008213, NM_021980), ataxin-2 (ATXN2, NP_001297050, NP_001297052, NP_002964), valosin-containing protein (VCP, NM_007126), ubiquilin-2 (UBQLN2, NM_013444), sigma-1 receptor (SIGMARI, NM_001282205, NM_001282206, NM_001282207, NM_001282208, NM_001282209), Charged multivesicular body protein 2b (CHMP2B, NM_001244644, NM_014043), profilin-1 (PFN1, NM_005022), Receptor tyrosine-protein kinase erbB-4 (ERBB4, NM_001042599, NM_005235), Heterogeneous nuclear ribonucleoprotein A1 (HNRNPA1, NM_002136, NM_031157), matrin-3 (MATR3, NM_199189, NM_001194954, NM_001194955, NM_001194956, NM_001282278), tubulin alpha-4A chain (TUBA4A, NM_001278552, NM_006000), chromosome 9 open reading frame 72 (C9orf72, NM_145005, NM_001256054, NM_018325), CHCD10, SQSTM1 (NM_001142298), TBK1, apolipoprotein E (NM_001302691, NM_000041, NM_001302688, NM_001302689, NM_001302690), SMN1 (NM_000344), SMN2 (NM_017411, NM 022875, NM_022876, NM_022877), CTFR (NM_000492), beta globin HBB PDB, CHM, alpha-synuclein (SNCA, NM_000345), parkin (PRKN, NM_004562), leucine-rich repeat kinase 2 (LRRK2 or dardarin, NM_198578), PTEN-induced putative kinase 1 (PINK1, NM_032409), DJ-1 (NM_001123377), acid maltase (NM_000152), UDP-glucuronosyltransferase 1 (NM_000463), PPT-1 (NM_000310), or ATP13A2 (NM_001141973).

Additional aspects of the disclosure relate to compositions comprising a carrier and the modified virus described in the embodiments disclosed herein.

As described herein, pharmaceutical compositions of the present disclosure may comprise a modified viral particle expressing Cas9 on its interior or exterior capsid surface as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present disclosure may be formulated for oral, intravenous, topical, enteral, and/or parenteral administration. In certain embodiments, the compositions of the present disclosure are formulated for intravenous administration.

It is appreciated by those skilled in the art that gRNAs can be generated for target specificity to target a specific gene, optionally a gene associated with a disease, disorder, or condition. Thus, in combination with Cas9, the guide RNAs facilitate the target specificity of the CRISPR/Cas9 system. Further aspects such as promoter choice, as discussed above, may provide additional mechanisms of achieving target specificity—e.g., selecting a promoter for the guide RNA encoding polynucleotide that facilitates expression in a particular organ or tissue. Accordingly, the selection of suitable gRNAs for the particular disease, disorder, or condition is contemplated herein.

Administration of the modified AAV or compositions can be effected in one dose, continuously or intermittently throughout the course of treatment. Administration may be through any suitable mode of administration, including but not limited to: intravenous, intra-arterial, intramuscular, intracardiac, intrathecal, subventricular, epidural, intracerebral, intracerebroventricular, sub-retinal, intravitreal, intraarticular, intraocular, intraperitoneal, intrauterine, intradermal, subcutaneous, transdermal, transmuccosal, and inhalation.

Methods of determining the most effective means and dosage of administration are known to those of skill in the art and will vary with the composition used for therapy, the purpose of the therapy and the subject being treated. Single or multiple administrations can be carried out with the dose level and pattern being selected by the treating physician. It is noted that dosage may be impacted by the route of administration. Suitable dosage formulations and methods of administering the agents are known in the art. Non-limiting examples of such suitable dosages may be as low as 1E+9 vector genomes to as much as 1E+17 vector genomes per administration.

In some embodiments of the methods described herein, the number of adenoviral particles administered to the subject ranges administered to the subject ranges from about $10^9$ to about $10^{17}$. In particular embodiments, about $10^{10}$ to about $10^{12}$, about $10^{11}$ to about $10^{13}$, about $10^{11}$ to about $10^{12}$, about $10^{11}$ to about $10^{14}$, about $5 \times 10^{11}$ to about $5 \times 10^{12}$, or about $10^{12}$ to about $10^{13}$ adenoviral particles are administered to the subject.

In a further aspect, the modified viral particle and compositions of the disclosure can be administered in combination with other treatments, e.g., those approved treatments suitable for the particular disease, disorder, or condition. A non-limiting example includes the treatment of muscular dystrophy with a combination of the modified viral particle and one or more steroids.

This administration of the modified viral particle or compositions of the disclosure can be done to generate an animal model of the desired disease, disorder, or condition for experimental and screening assays.

Successful treatment and/or repair is determined when one or more of the following is detected: alleviation or amelioration of one or more of symptoms of the treated subject's disease, disorder, or condition, diminishment of extent of the subject's disease, disorder, or condition, stabilized (i.e., not worsening) state of a disease, disorder, or condition, delay or slowing of the progression of the disease, disorder, or condition, and amelioration or palliation of the disease, disorder, or condition. In some embodiments, success of treatment is determined by detecting the presence repaired target polynucleotide in one or more cells, tissues, or organs isolated from the subject. In some embodiments, success of treatment is determined by detecting the presence polypeptide encoded by the repaired target polynucleotide in one or more cells, tissues, or organs isolated from the subject.

In some embodiments, the ratio of repaired target polynucleotide or polypeptide to unrepaired target polynucleotide or polypeptide in a successfully treated cell, tissue, organ or subject is about 1.5:1, about 2:1, about 3:1, about 4:1, about 5:1, about 6:1, about 7:1, about 8:1, about 9:1, about 10:1, about 20:1, about 50:1, about 100:1, about 1000:1, about 10,000:1, about 100,000:1, or about 1,000,000:1. The amount or ratio of repaired target polynucleotide or polypeptide can be determined by any method known in the art, including but not limited to Western blot, Northern blot, Southern blot, PCR, sequencing, mass spectrometry, flow cytometry, immunohistochemistry, immunofluorescence, fluorescence in situ hybridization, next generation sequencing, immunoblot, and ELISA.

Kits

The agents described herein may, in some embodiments, be assembled into pharmaceutical or diagnostic or research kits to facilitate their use in therapeutic, diagnostic or research applications. In some embodiments, the kits of the present disclosure include one or more of: modified viral capsid proteins, isolated polynucleotides, vectors, host cells, recombinant viral particles, recombinant expression systems, modified AAV, modified cells, isolated tissues, compositions, or pharmaceutical compositions as described herein.

In some embodiments, a kit further comprises instructions for use. Specifically, such kits may include one or more agents described herein, along with instructions describing the intended application and the proper use of these agents. As an example, in one embodiment, the kit may include instructions for mixing one or more components of the kit and/or isolating and mixing a sample and applying to a subject. In certain embodiments, agents in a kit are in a pharmaceutical formulation and dosage suitable for a particular application and for a method of administration of the agents. Kits for research purposes may contain the components in appropriate concentrations or quantities for running various experiments.

The kit may be designed to facilitate use of the methods described herein and can take many forms. Each of the compositions of the kit, where applicable, may be provided in liquid form (e.g., in solution), or in solid form, (e.g., a dry powder). In certain cases, some of the compositions may be constitutable or otherwise processable (e.g., to an active form), for example, by the addition of a suitable solvent or other species (for example, water or a cell culture medium), which may or may not be provided with the kit. In some embodiments, the compositions may be provided in a preservation solution (e.g., cryopreservation solution). Non-limiting examples of preservation solutions include DMSO, paraformaldehyde, and CryoStor® (Stem Cell Technologies, Vancouver, Canada). In some embodiments, the preservation solution contains an amount of metalloprotease inhibitors.

As used herein, "instructions" can define a component of instruction and/or promotion, and typically involve written instructions on or associated with packaging of the claimed method or composition. Instructions also can include any oral or electronic instructions provided in any manner such that a user will clearly recognize that the instructions are to be associated with the kit, for example, audiovisual (e.g., videotape, DVD, etc.), internet, and/or web-based communications, etc. In some embodiments, the written instructions are in a form prescribed by a governmental agency regulating the manufacture, use or sale of pharmaceuticals or biological products, which instructions can also reflect approval by the agency of manufacture, use or sale for animal administration.

In some embodiments, the kit contains any one or more of the components described herein in one or more containers. Thus, in some embodiments, the kit may include a container housing agents described herein. The agents may be in the form of a liquid, gel or solid (powder). The agents may be prepared sterilely, packaged in syringe and shipped refrigerated. Alternatively, it may be housed in a vial or other container for storage. A second container may have other agents prepared sterilely. Alternatively, the kit may include the active agents premixed and shipped in a syringe, vial, tube, or other container. The kit may have one or more or all of the components required to administer the agents to a subject, such as a syringe, topical application devices, or IV needle tubing and bag.

The therapies as described herein can be combined with appropriate diagnostic techniques to identify and select patients for the therapy. For example, a genetic test to identify a mutation in a muscular dystrophy gene can be provided. Thus, patients harboring a mutation can be identified as suitable for therapy.

Examples

The following examples are non-limiting and illustrative of procedures which can be used in various instances in carrying the disclosure into effect. Additionally, all references disclosed herein below are incorporated by reference in their entirety.

Without being bound by theory, it is expected that use of the methods and compositions disclosed herein maintain normal viral tropism while allowing a Cas9 protein or an equivalent thereof to be transiently delivered as a stable component of an AAV particle. Without being bound by theory, it is further expected that the interior location of the Cas9 or equivalent thereof will reduce the risks of steric hindrance, protease degradation, and immune recognition and/or response. In addition, the disclosed methods and compositions allow efficient and targeted delivery of functional Cas9 or equivalent thereof with improved size constraints for the encapsidated polynucleotide.

Example 1—Generation of AAV Particles with Cas9 Exterior Surface Expression

Figure 2:
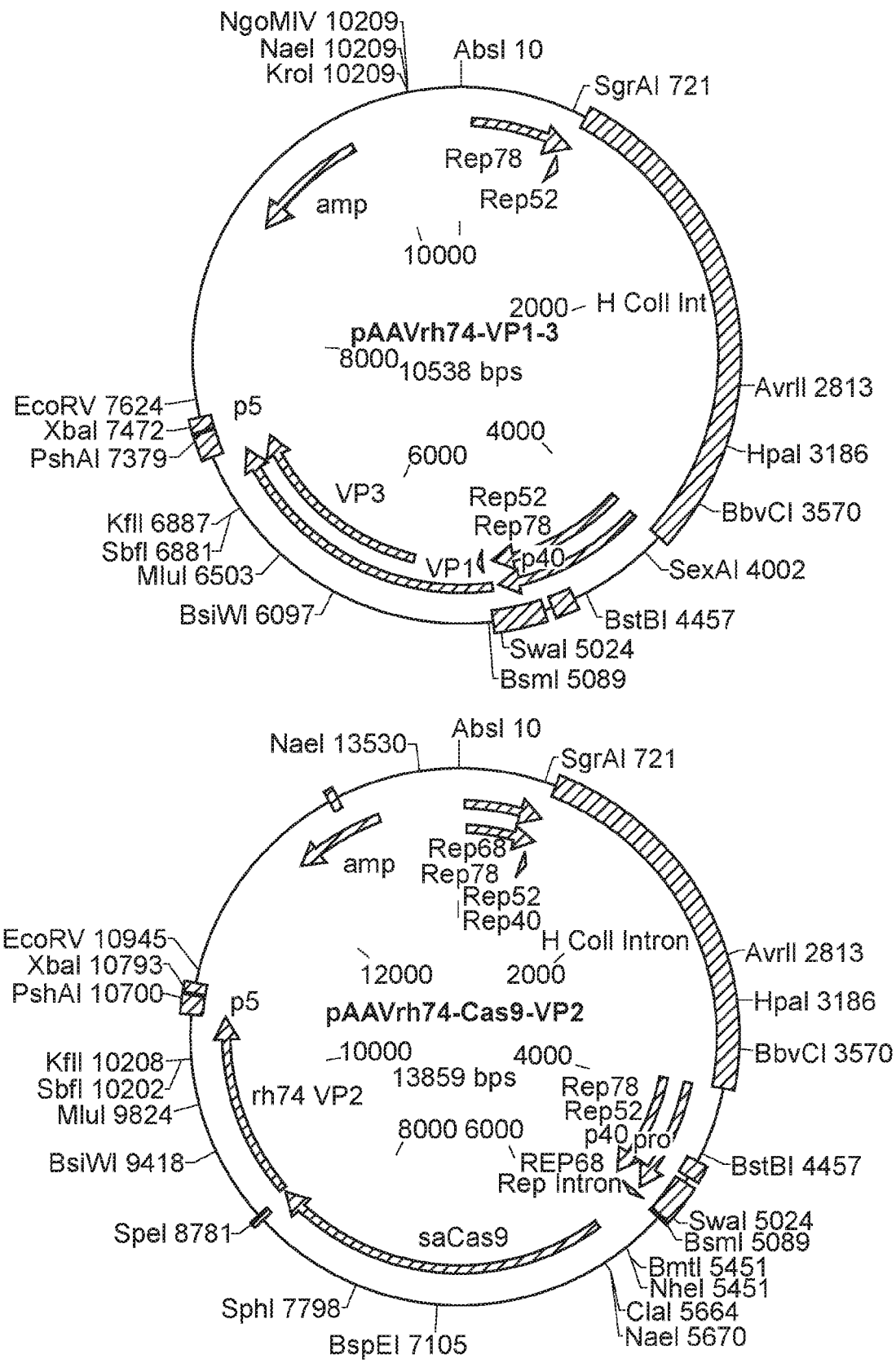
FIG. 2 depicts four exemplary constructs: the first encoding VPs1 and 3 of an AAV, the second encoding a VP2-Cas9 fusion protein for exterior Cas9 expression, the third encoding a helper plasmid comprising the genes necessary for packaging the virus, and the fourth encoding a reporter gene (luciferase) for detecting the virus.
Figure 2:
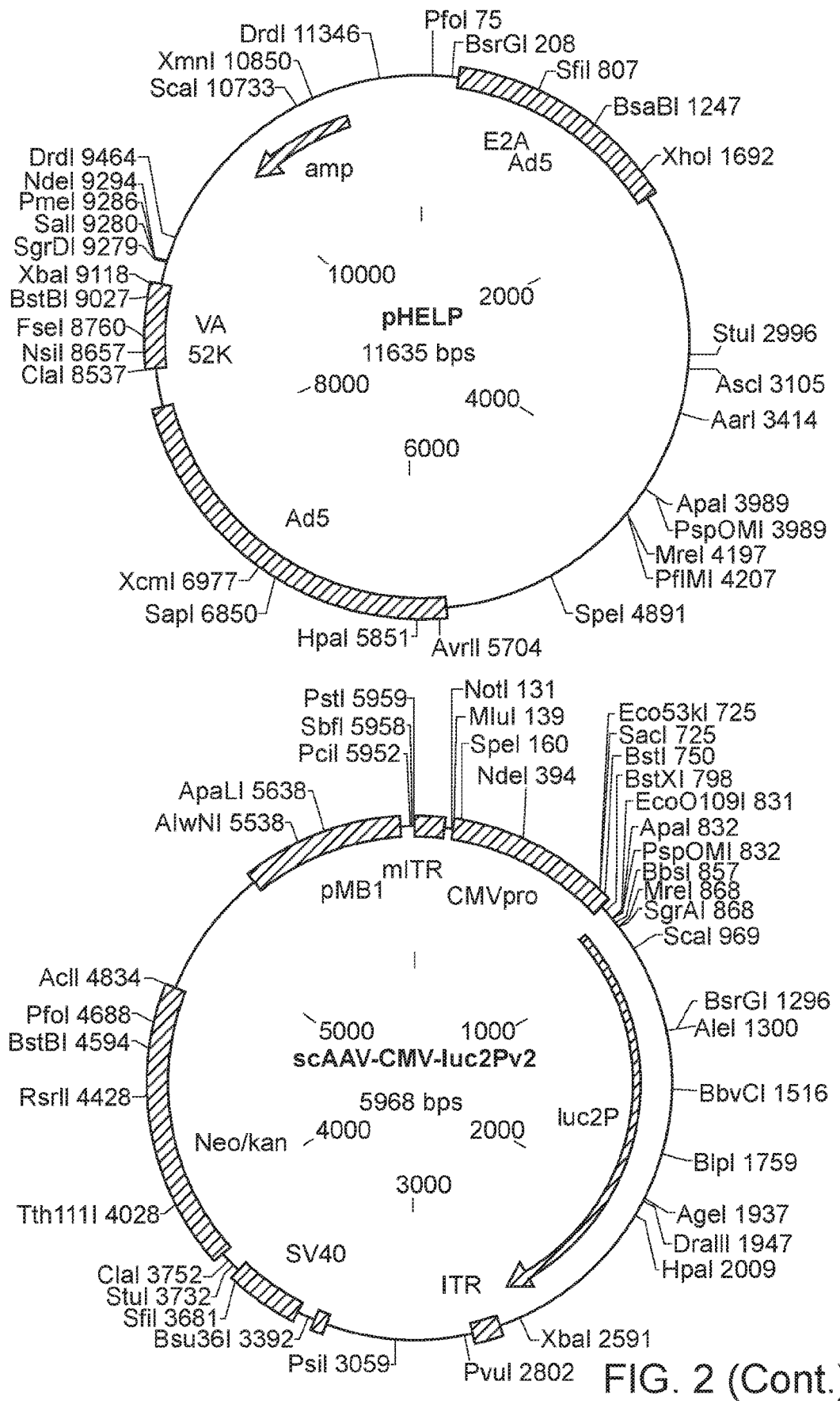
Figure 3:
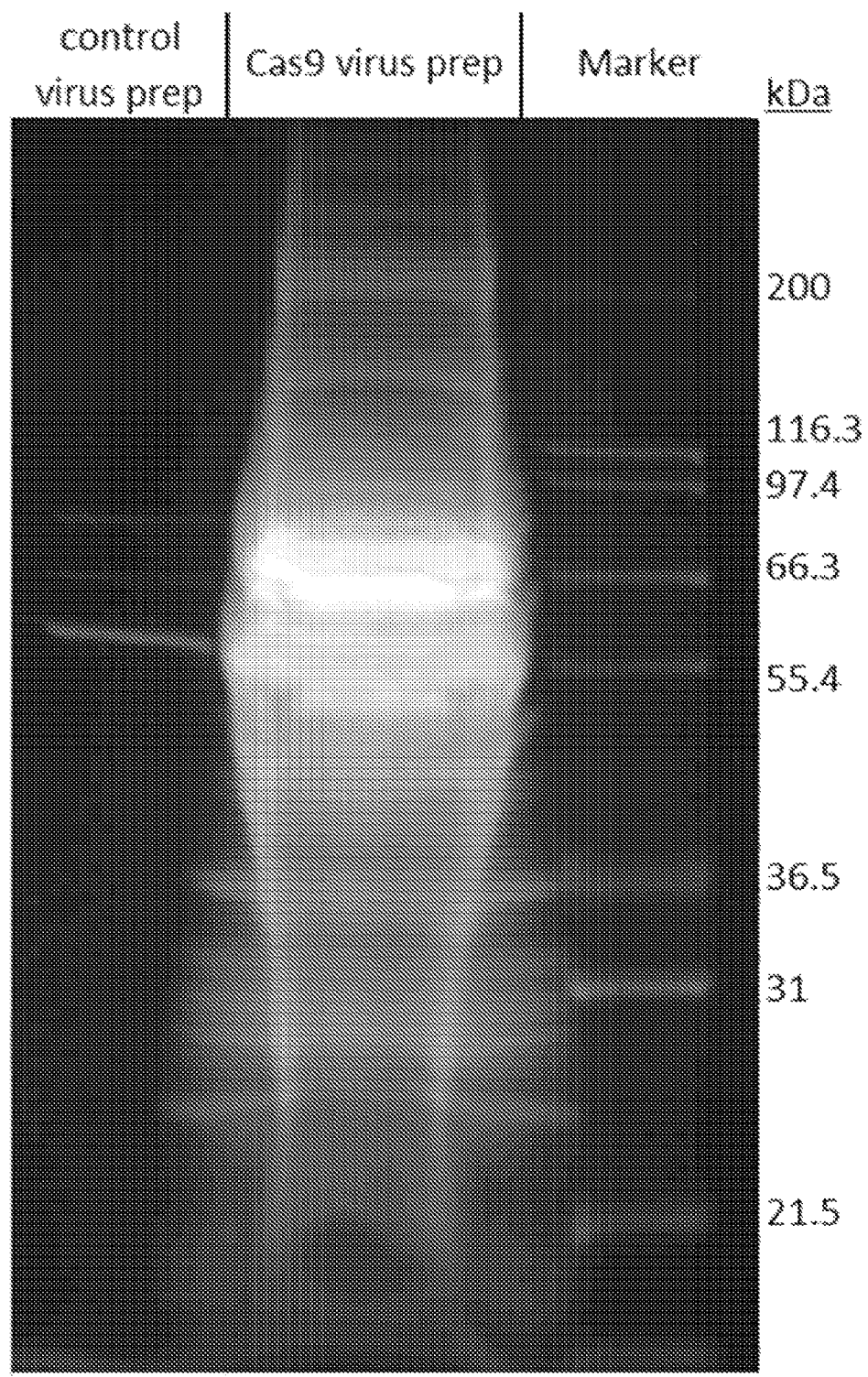
FIG. 3 depicts a SYPRO stained gel from a crude cell lysate of a Cas9-VP2 virus preparation. The goal of this gel was to determine whether the large 193 kDa Cas9-VP2 fusion protein would be visible. This gel shows the abundance of VP1 and VP3 proteins in the gel.
Figure 9:
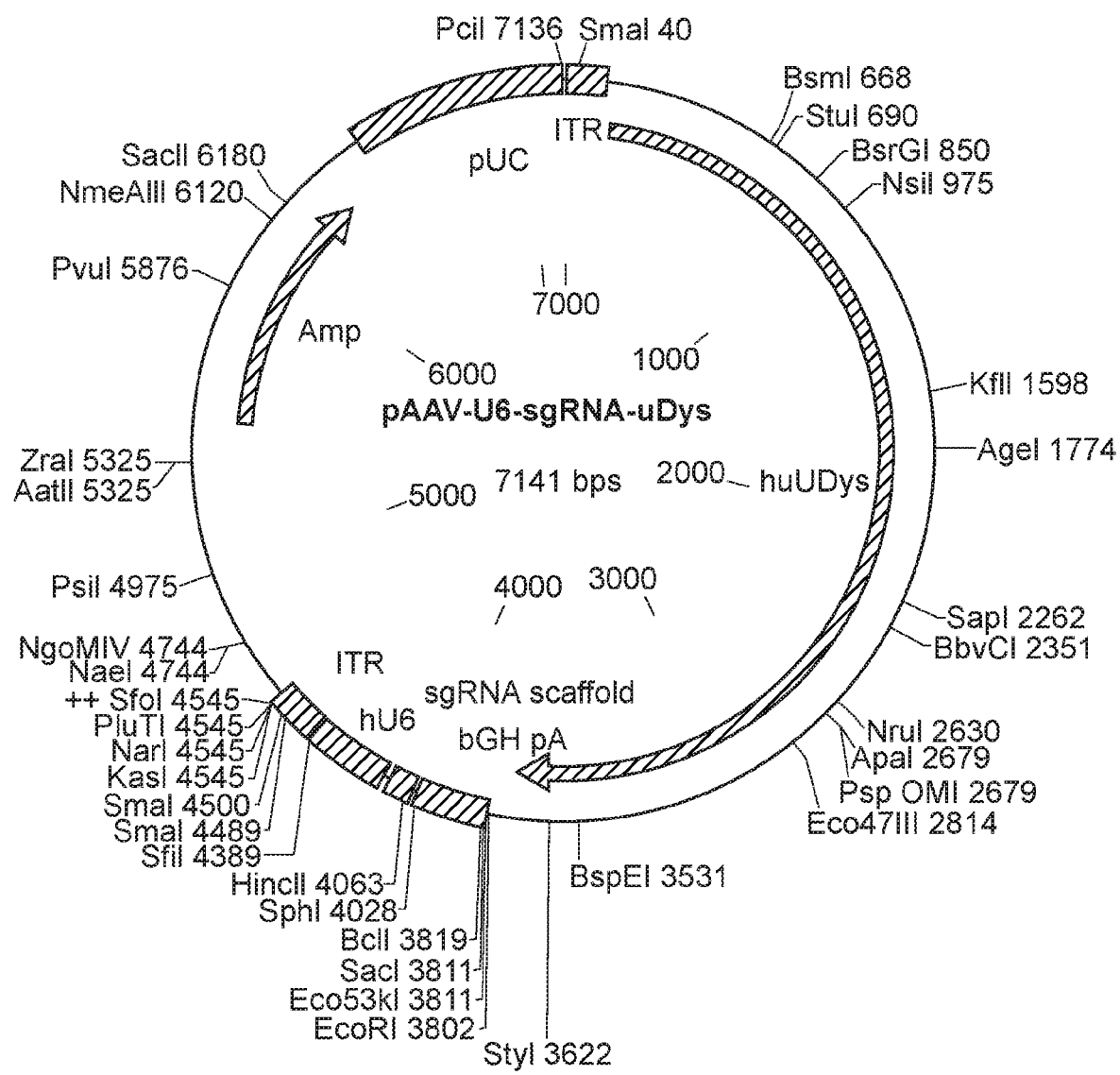
FIG. 9 depicts an exemplary construct encoding a guide RNA under the control of a U6 promoter. The construct is pAV-U6-sgRNA-uDys.
Figure 10:
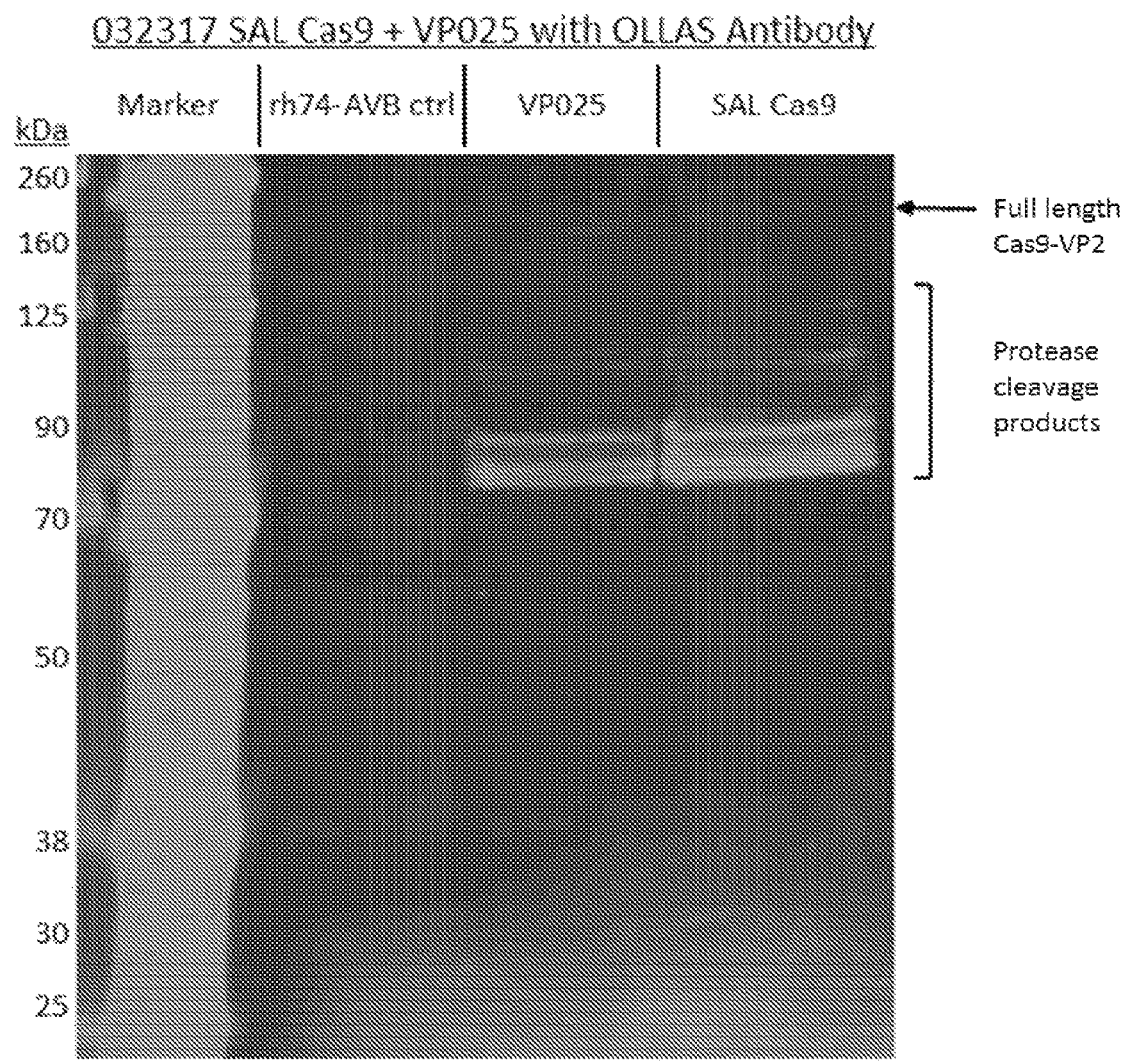
FIG. 10 depicts a Western blot of crude virus preps. VP025 is a larger prep of virus that was purified via standard protocol. SAL Cas9 was a smaller virus prep where the cells were lysed after 72 hours and then purified by standard protocol to purify virus from inside the cell before release into the media. The OLLAS tag is only detecting proteins that contain the specific OLLAS tag sequence which would indicate the presence of lower molecular weight protein likely formed by protease cleavage during production or purification. A small amount of full length Cas9-VP2 protein is faintly visible. The Cas9 fusion protein is 193 kDa and the Cas9 alone is 127 kDa.
Figure 11:
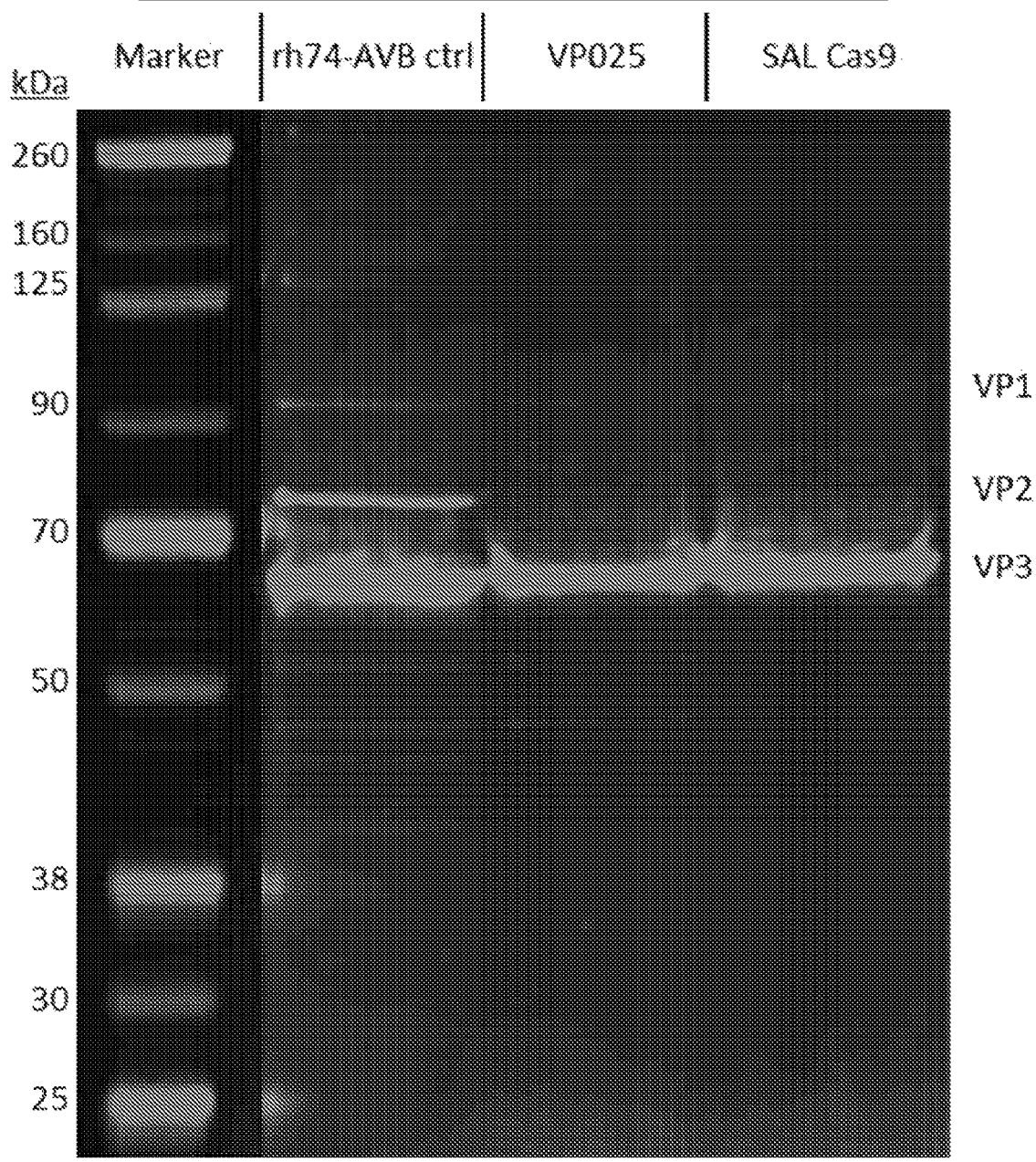
FIG. 11 depicts a Western blot of crude virus preps. VP025 is a larger prep of virus that was purified via standard protocol. SAL Cas9 was a smaller virus prep where the cells were lysed after 72 hours and then purified by standard protocol to purify virus from inside the cell before release into the media. The B1 antibody detects AAV specific capsid proteins. The AAVrh74 control virus lane shows the presence of all three virus capsid proteins whereas the VP025 and SAL Cas9 lanes only show the presence of VP3 and VP1 alone with some degradation proteins of lower molecular weight between 60-80 kDa.

Applicant constructed two plasmids according to the schematic provided in FIG. 1. The sequences for these plasmids is provided as SEQ ID NO: 1, encoding the proteins for VP1 (SEQ ID NO: 37) and VP3 (SEQ ID NO: 38), and SEQ ID NO: 2 or SEQ ID NO: 5, encoding the protein for a Cas9-VP2 fusion (SEQ ID NO: 36). Applicant constructed additional plasmids according to the schematic provided in FIGS. 2 and 9. The sequences for these plasmids is provided as SEQ ID NO: 4, encoding VP1 AND VP3, SEQ ID NO: 2, encoding a VP2-Cas9 fusion, SEQ ID NO: 5, encoding a VP2-Cas9 fusion with an OLLAS epitope tag, SEQ ID NO: 6, encoding a helper plasmid, SEQ ID NO: 7, encoding a reporter (luciferase), and SEQ ID NO: 8, encoding a gRNA. Non limiting examples of VP1 sequences include SEQ ID NO: 37, DNA base pairs numbered 5037 to 7253 of SEQ ID NO: 1, base pairs numbered 5037 to 7253 of SEQ ID NO: 4, and equivalents of each thereof. Non-limiting examples of VP2 sequences include SEQ ID NO: 39, base pairs numbered 8786 to 10574 of SEQ ID NO: 5, and equivalents of each thereof. Nonlimiting examples of VP3 sequences include SEQ ID NO: 38, base pairs numbered 5646 to 7253 of SEQ ID NO: 1, base pairs numbered 5646 to 7253 of SEQ ID NO: 1, and an equivalent of each thereof. Nonlimiting examples of Cas9-VP2 fusion sequences include SEQ ID NO: 36, base pairs numbered 5532 to 1074 of SEQ ID NO: 5, base pairs numbered 5532 to 10565 of SEQ ID NO: 2, and equivalents of each thereof.

HEK293 cells are transfected with plasmids that encode for VP1+VP3 and in a separate plasmid, the Cas9-VP2 fusion protein (e.g., SEQ ID NO: 1 and SEQ ID NO: 2). In addition, the targeting vector containing the guide RNA sequence and, if needed, additional therapeutic polypeptide encoding a DNA repair template or other DNA sequence required for gene modification is also transfected or co-transfected into the HEK293 cells (e.g., SEQ ID NO: 8). An additional plasmid can be transfected or co-transfected that provides the viral helper function found in Adenovirus (E1A, E1B, E2A, E40RF6 and VA RNAs) or Herpes virus (among other viruses as well) to enable efficient AAV production. Alternatively, the AAV and Helper genes can be provided as separate plasmids or combined into multiples or a single plasmid if desired. Alternatively, the genes can be stably introduced into cells to generate stable packing cell lines. Alternatively, the genes can also be introduced into cells using viral vectors like baculo-virus or herpes virus to amplify and deliver large quantities of the needed genes to adherent or suspension grown cells.

For transfection, suspension adapted HEK293 cells are grown in serum free 293Expi media to a concentration of 5E+6 cells/mL. Cells are transfected with the plasmids as described above (e.g., pAAVrh74-Cas9-VP2, pAAVrh74-VP1-3, pHELP and scAAV-CMV-luc2Pv2 plasmids) using polyethylenimine (PEI) using standard transfection methods.

Briefly, the plasmid DNA is mixed with Opti-mem media separately and the PEI is mixed with Opti-mem separately. The diluted DNA and PEI mixes and combined, vortexed briefly and allowed to sit at room temperature for ten minutes for complex formation. The transfection mix is then added to the cells and the cells are incubated in shake flasks at 135 rpm and 37 degrees in a humidified incubator. Following transfection, the HEK293 cells are cultured to produce supernatant containing viral particles. Four days after transfection the virus is recovered from the media using depth filtration with a 0.45-micron filter (Millipore) and concentrated using a 100kD MWCO spin concentrator (Pierce) and purified by iodixanol gradient (15-57%) ultracentrifugation (68,000 rpm, 18 degrees, 1 hour) and column chromatography (GE).

To identify expression of the intended proteins (e.g., VP1, VP3, and Cas9-VP2 fusion), a western blot is performed. A western blot is also performed to qualitatively analyze viral particles in rAAV fraction and final samples and to determine purity. Briefly, a BOLT SDS-Page gel method is performed. First, samples of viral supernatant are prepared in 1.5 mL epp tubes by adding 1 μl Bolt DTT reducing agent, 2.5 μl Bolt NuPAGE LDS 4X loading dye, and 6.5 μl of sample into each tube and pipette up and down to mix. Next, the samples are denatured by placing the tubes into a heat block set at 95° C. for 10 minutes. The Mini Gel Tank Electrophoresis system is assembled by placing the cassette into the tank and make sure the electrodes are on opposite sides. The comb and tape is removed the 10% Bis-Tris gel. The 1X MOPS SDS running buffer by adding 20 mL of Bolt MOPS SDS 20X running buffer to 380 mL dH2O. After heating the samples for 10 minutes, the tubes are cooled on ice for 1 minute and then centrifuge to get rid of any condensation. 10 μl of the denatured samples is added into each well. 10 μl of a standard ladder such as 1X Mark 12 standard is added to the last well of the SDS-PAGE gel. The gel is run at 165 volts, 500 mA (constant), for 45 minutes. The staining solution is prepared by adding 100 mL of 7.5% Acetic Acid and 10 μl SYPRO orange into a gel staining box and the gel is stained on a rocker set 60 rpm at room temperature for 1 hour. Once the gel is done shaking, the 7.5% Acetic Acid is replaced and the gel is stained with 75 mL of fresh 7.5% Acetic Acid for 5-10 minutes to wash residue from gel. An image of the gel is captured using an imaging system. Appropriate expression of the recombinant viral system is indicated by detecting bands that correspond to the predicted size of the expressed viral proteins. For example, VP1, VP2, and VP3 are approximately 87, 72, and 62 kDa respectively. saCas9 is approximately 127 kDa. The VP2-Cas9 fusion protein is approximately 193 kDa in size.

Example 2—Exemplary System for Correction of Muscular Dystrophy

In this example, plasmids are used to supply: 1) the genes encoding the AAV structural and enzymatic proteins, 2) the genes encoding the Adenovirus helper proteins and RNAs and 3) the vector genome to be packaged into the AAV particle. The three plasmids are normally transfected into HEK293 cells that have nucleotides 1-4344 of Adenovirus 5 stably integrated into chromosome 19 and express the Ad proteins E1A and E1B. The virus is then harvested from the cells several days after transfection and purified by ultracentrifugation, chromatography or combinations of similar methods. Normally all three viral capsid proteins, VP1, VP2 and VP3 (VP1, VP2, and VP3 which are approximately 87, 72, and 62 kDa respectively) are produced from a single gene with significant overlap in coding regions. To prevent a large protein insertion from disrupting the production of the required VP1 protein, Applicants separated the genes onto two separate plasmids. The first plasmid encodes the normal VP1 and VP3 proteins while the VP2, which normally uses ACG as the start codon has been modified to GCG. Additional alternative start codons 3' to the normal start codon were also modified to prevent production of truncated VP2 products. The second plasmid has mutated the start codons of VP1 and VP3 from ATG to CTG and the start codon of VP2 was changed from ACG to ATG. A restriction site was also added to SaCas9 in the same reading frame as VP2. The gene was sub-cloned into the VP2 expression plasmid along with an OLLAS (E. coli OmpF Linker and mouse Langerin fusion Sequence) epitope tag, which serves as a linker region, and sensitive detection peptide sequence. For this example, AAVrh74 was selected as the serotype for muscle-directed gene editing based on previously shown muscle cell tropism but AAV9 is a suitable alternative.

Figure 15A:
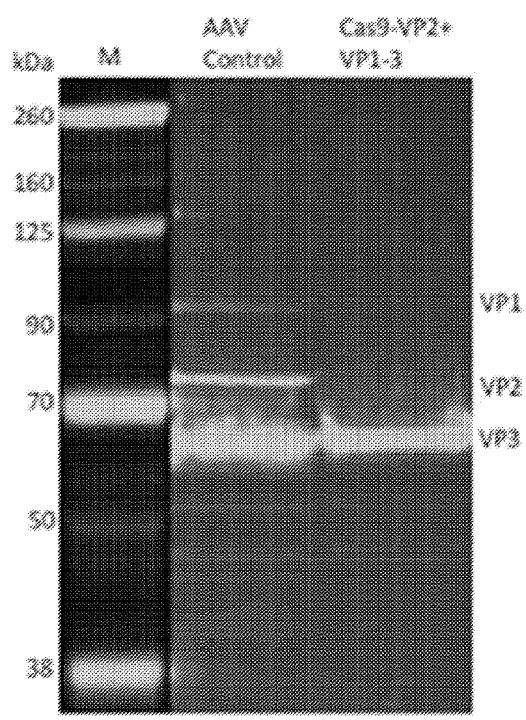
FIGS. 15A-15B depict Cas9-VP2 cleavage products.
Figure 15B:
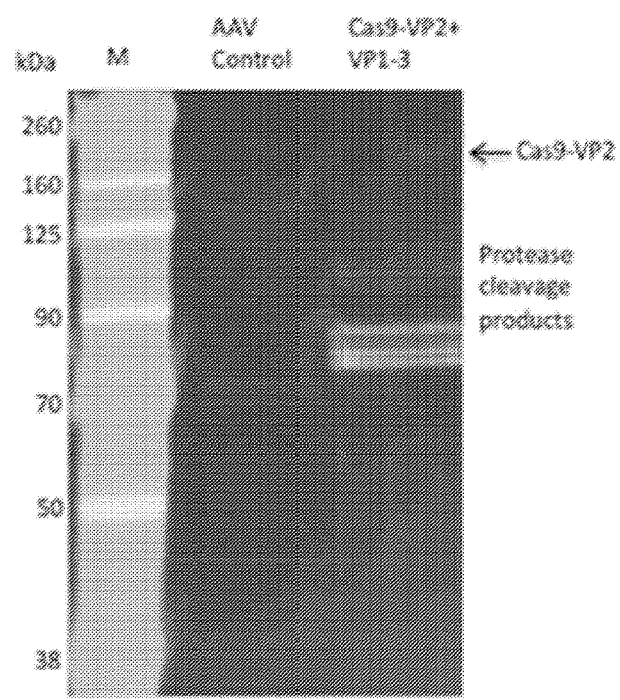

After transfection of the capsid expression plasmids into HEK293 cells, virus was purified and run on Western blots (FIG. 15) probed with either the anti-AAV antibody B1 (FIG. 15A) or the anti-OLLAS antibody (FIG. 15B). FIG. 15A shows the expectedly abundant VP3 band in both lanes and faint VP1 bands, which are often seen when VP2 is overexpressed (see FIG. 15A, AAV control lane). The expected higher molecular weight (192 kDa) band of VP2 is not seen when probed with B1 antibody (FIG. 15A) however a faint band of the expected size is seen with the more sensitive anti-OLLAS antibody (FIG. 15B). Without being bound by theory, lower molecular weight products appear to be the result of cleavage of the VP2 fusion protein. HEK293 cells infected with purified AAVrh74-Cas9 virus showed equal or greater infectivity based on GFP expression and 2-3 fold higher luciferase expression than control AAVrh74 virus (MOI of 20,000 particles per cell for both viruses).

An AAV9 VP2 fusion protein containing the GeoCas9 sequence as well as a separate AAV9 VP1/3 expression plasmid and package a GFP reporter vector containing an sgRNA expression (without Cas9 gene) cassette for dystrophin gene editing. Correction of mutations in in the dystrophin gene will be our initial test system due to the presence of multiple disease models of Duchenne muscular dystrophy in both mice and pigs.

Crude lysates will be harvested with protease inhibitors and run on Western gels to detect the virus capsid proteins and the OLLAS tagged GeoCas9 protein. Full length VP2-GeoCas9 protein should be approximately 195 kDa band by Western blot. Crude virus lysates will be purified by iodixanol gradient and assayed by Western blot to determine if full length VP2 fusion protein is incorporated into purified particles. Viruses will be titered for packaged genomes and infectivity assays will be performed to determine relative infectious titers. Gene editing efficiency in cells transduced with AAV9-GeoCas9 will be performed using the PCR and T7 endonuclease I (T7E1) assays. Next generation sequencing (NGS) can also be performed to determine the editing events. The AAV9-GeoCas9 will then be tested for in vivo gene editing in mice using AAVrh74 packaged with SaCas9 gene and sgRNAs. A large panel of human myoblast cell lines with known mutations that will be targeted for correction. In addition, mdx mice will be used that carry a point mutation in exon 23, resulting in formation of a premature stop codon and disruption of dystrophin expression. Homozygous females and heterozygous males exhibit similar myopathology and will be used for initial gene editing studies (n=10 mice per group (5 males and 5 females per group)). In addition, a panel of human cell lines with the EGFP gene stably integrated can be used to edit the active site between amino acids 65-67 of EGFP and knockout expression. Gene editing efficiency will be quantified by the loss of GFP fluorescence using flow cytometry. Similarly, the EGFP gene will be targeted in the transgenic EGFP mouse (C57BL/6-Tg(CAG-EGFP)1Osb/J, Jackson Labs) for in vivo gene editing. Equal numbers of male and female animals will be used throughout the studies to determine editing efficiency in both sexes (n=10 mice per group (5 males and 5 females per group)).

In some embodiments, partial cleavage products observed during purification require optimization of protease inhibitors and conditions that prevent or minimize protease activity during production and purification. In addition, AAV9 capsid may contain an endogenous protease activity similar to that seen in AAV2 vectors and require mutation of the active site to permit full-length GeoCas9 expression. Applicants have designed point mutations in the capsid protein to disrupt the external protease activity. The homologous residues in a VP2 fusion (AAV9-E564) as well as VP1-3 capsids will be mutated to either alanine or glutamine to test their effect on Cas9 stability. If cleavage products are detected, protein sequencing and analysis will be used to determine the sequence ends of the cleavage products. Identification of the cleavage sequence will allow the design of amino acid substitutions in the VP2 fusion protein to eliminate the cleavage event.

Example 3—Design of VP2-Cas9i

AAV has been shown to be a very efficient delivery vehicle of genes into cells in vivo. One area of research that has not been actively investigated is the use of AAV as a delivery vehicle of proteins into cells in vivo. To reduce the risks steric hindrance and protease degradation Applicant has developed an alternative to packaging the saCas9 gene in the AAV viral genome or displaying saCas9 protein on the surface of AAV: AAV particles that display the saCas9 protein on the inner surface of the particle. By enclosing the Cas9 protein inside the particle, the enzyme is shielded from circulating immune recognition and potential protease degradation. This alternative also prevents the Cas9 protein from affecting normal AAV-receptor binding to target cells that may occur with surface exposed Cas9. Five discrete amino acid positions that are located on the inner surface of VP2 are tested to determine if insertions at these positions allow for stable particle formation. Once stable insertion sites are identified, Cas9 sequence is inserted and the resulting modified viral particle is tested to characterize particle stability, infectivity and functional Cas9 activity. This method results in an efficient protein delivery system that shields the Cas9 enzyme from immune surveillance and degradation while simultaneously delivering the CRISPR targeting sequences for gene correction. AAV shielded Cas9 containing particles can deliver functional Cas9 protein to cells. The approaches described herein provide a greater understanding of the locations for large protein insertions within the interior of AAV. Such knowledge provides, for the first time, a method for the efficient and protected delivery of protein cargo to cells in vivo.

Characterization of internal VP2-Cas9i fusion proteins and particle stability. Once optimal VP2 insertion sites and linker sequences are identified, full virus particles are produced and tested for stability and packaging efficiency. Test batches of virus with the Cas9 insertions of VP2 using the VP2 and VP1+VP3 expression plasmids along with a reporter vector and test for stable virus formation are produced and assayed by qPCR titer and Western blot. Without being bound by theory, the space requirements for packaging the Cas9 protein internally may adversely affect the packaging capacity of vector genomes. Virus particles with internally positioned Cas9 protein (AAV-Cas9i) are produced to test various size ITR containing vector genomes to determine the size of vector genomes that can be efficiently packaged by AAV-Cas9i particles.

Identifying internal regions of VP2 capsid that tolerates insertions of peptide linkers. The crystal structures of many serotypes of AAV have been identified down to less than 4-angstrom resolution. In addition to the crystal structures, many investigators have made numerous mutations in the amino acids that have helped develop our understanding for the locations of key residues within the capsid responsible for vital functions of the virus. No one has yet reported on the key internally positioned residues that allow for the insertions of peptides and proteins within the AAV particle. By identifying the sites that accept insertions and produce stable particles, the work disclosed herein opens a new area of research in capsid modification and protein delivery.

Figure 12A:
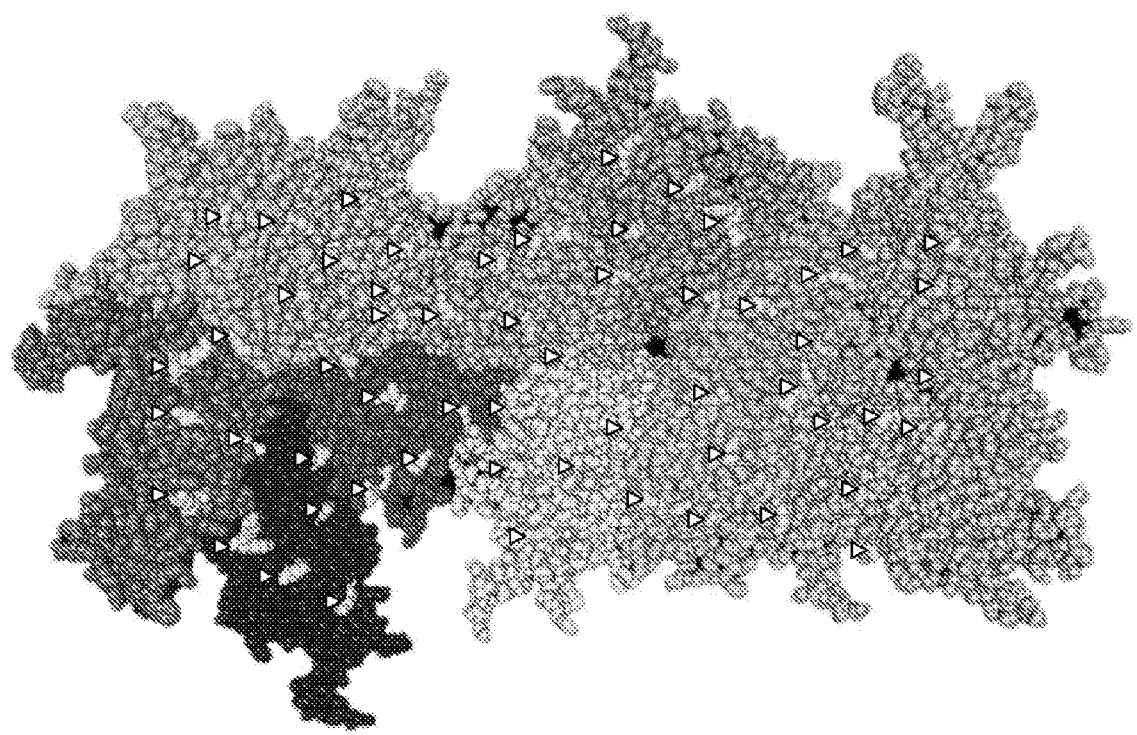
FIGS. 12A-12B depicts crystal structures of AAV8.
Figure 12B:
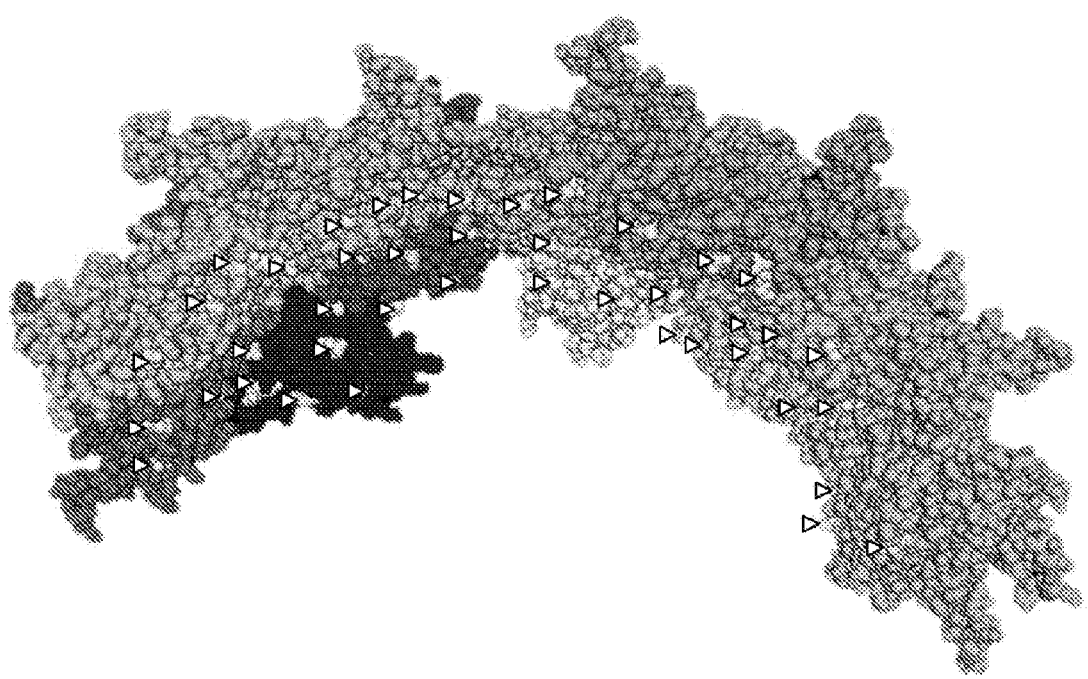
Figure 13A:
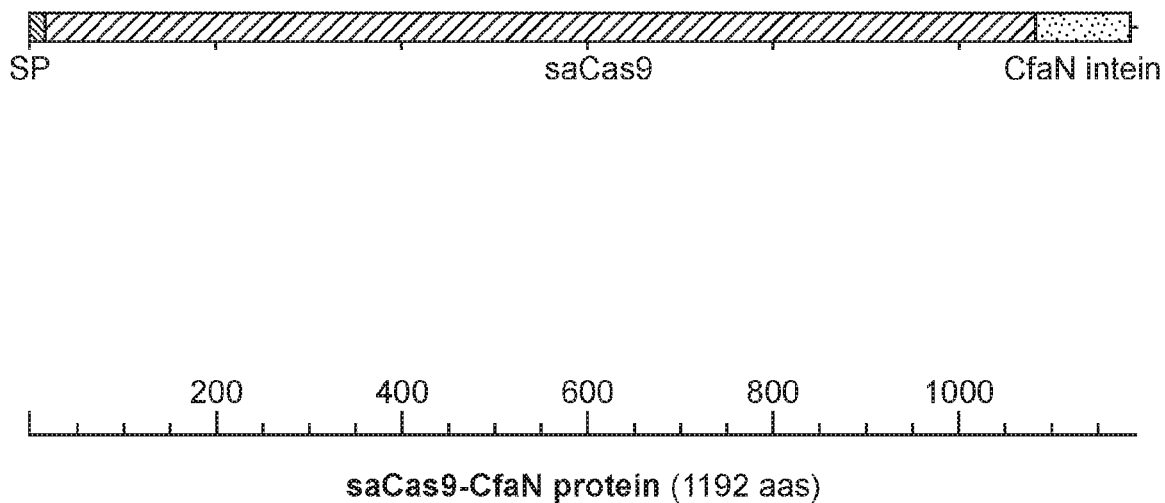
FIGS. 13A-13B This figure depicts exemplary split intein fusions of saCas9 and VP2.
Figure 13B:
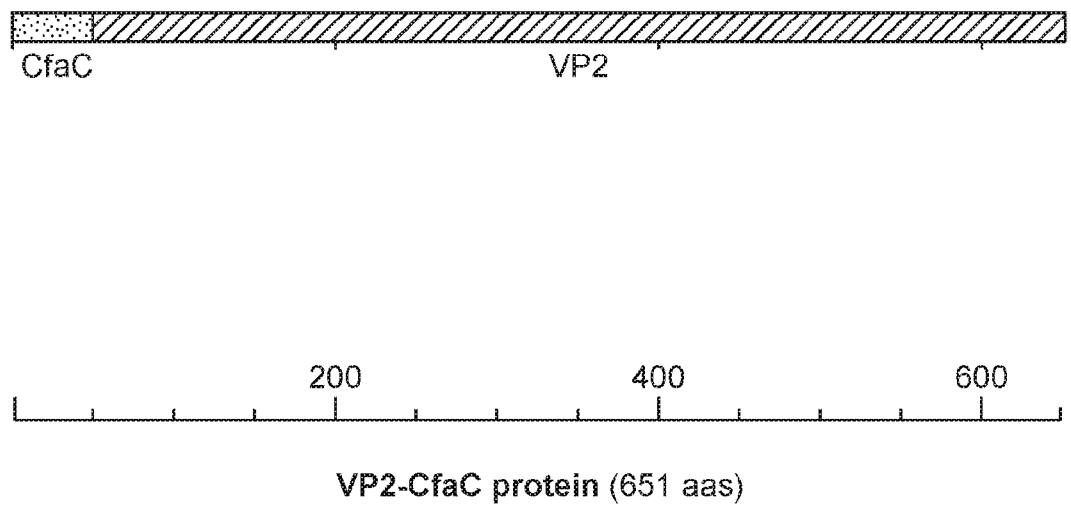
Figure 14:
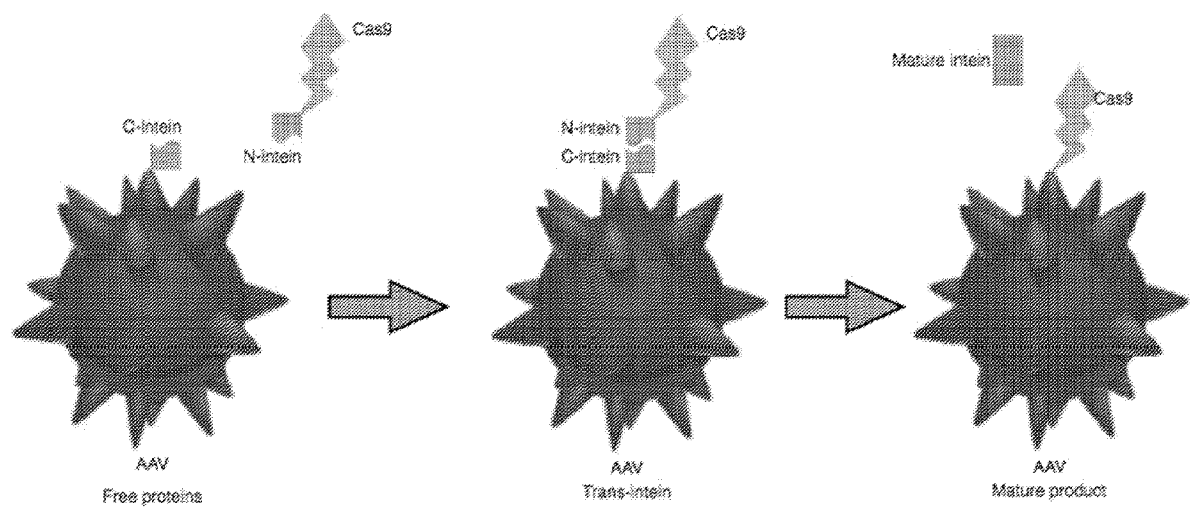
FIG. 14 This figure depicts a flow diagram of intein mediated ligation of Cas9 protein with the exterior surface of the particle.

Mutations and insertions are introduced into 5 discrete sites identified on the inner surface of the VP2 protein. The five sites were selected based upon the close homology of AAVrh74 with that of AAV8 whose crystal structure has been resolved to 2.6 angstroms. Selection of sites was made not only based upon their inner surface exposure but to minimize the impact of surrounding secondary structures that may be interacting with the sites by charge or be involved in the 2-fold, 3-fold and 5-fold axis of symmetry that are important for structural integrity and packaging of DNA. Flexible linker sequences can be cloned into the 5 sites of VP2 to simulate the introduction of a large protein insertion. The positions of the 5 identified sites are numbered based upon the start of VP protein (SEQ ID NO: 59) and are: 228, 350, 419, 684 and 689. The equivalents of these sites in VP2 (SEQ ID NO: 39) are positions 90, 213, 282, 547, and 552. The locations of the 5 sites are shown in the structures in FIG. 12. Once the sites that allow for peptide insertions are identified, Cas9 sequence is inserted into the VP2 plasmids for activity testing. The ability of Cas9-VP2 protein alone is characterized, before producing virus, to mediate site-specific cleavage reactions to identify peptide linkers that allow for functional activity of Cas9 when linked to VP2. The VP2-Cas9i plasmids are tested for their ability to mediate site-specific cleavage reactions by transfecting with a test guide RNA vector into HEK293 cells. These results allow a determination of optimal linker sequences between the Cas9 protein and the VP2 protein to allow for cleavage reactions to occur. Longer, or flexible, or self-cleaving linkers can be tested for optimal Cas9 activity in vitro.

AAV-Cas9i infectivity and site-specific cleavage activity in HEK293 cells and DMD patient cells. In order to show the utility of AAV-Cas9i particles, the infectivity and cleavage activity in cells is tested. The Cas9 protein must be able to escape from the confines of the virus particle after infection and be positioned to allow for DNA and RNA binding in the nucleus. In a particular embodiment, there is sufficient room (i.e. space) inside the viral capsid to package a vector that delivers the guide RNA and the optional therapeutic polypeptide to perform cleavage/editing reactions with one virus. The packaging capacity needed to deliver a functional guide RNA and targeting sequence is roughly 500 base pairs between the ITRs.

Small ITR vector constructs are packaged starting with a 500 bp insert between the ITRs and determine if packaging occurs by qPCR titers. The size of the vectors is gradually increased to determine the upper limit on packaging capacity. Once the upper limit of packaging is known, we will package targeting vectors for in vitro test infections. When infectivity is established, AAV-Cas9i virus is produced containing dystrophin specific sgRNA sequences targeting exons 50 and 54 to test for saCas9 functional activity of gene editing of dystrophin. The gene targeting efficiency is tested by PCR and the Surveyor/Cell enzymatic assay from immortalized myoblasts of DMD patient biopsies and indel formation and dystrophin expression is measured.

AAV-Cas9i virus provides a novel method for efficient protein delivery in vivo. In addition, important information can be obtained through the identification of internal sites within the capsid that allow for peptide and protein insertions. The step-wise approach of evaluating insertion sites followed by linker optimization of VP2-Cas9 constructs followed by Cas9 activity assays allows the design of a stable vector in a linear order. It is difficult to predict the space requirements for Cas9 protein and vector DNA. Without being bound by theory, only one Cas9 protein needs to be packaged per particle for functional activity. Therefore, the plasmid ratios of Cas9-VP2 and VP1-3 plasmids during the virus production can be modified such that instead of 5 or more Cas9-VP2 proteins per virus particle (or per viral capsid), the modified viral particle comprises between 1 to 5 Cas9-VP2 proteins per virus particle (or per viral capsid). Modification of plasmid ratios has been used before to generate mosaic virus particles with altered tropism. By altering the plasmid ratios, AAV-Cas9i virus is generated with fewer than 5 Cas9 proteins per particle. If the packaging capacity limitations prevent effective packaging of vector genomes containing the minimal guide RNA and optional therapeutic polynucleotides, then a two-virus system can be used to deliver (1) a virus with the Cas9 protein and (2) a virus with the guide RNA and optional therapeutic polynucleotide. The two-virus system requires co-infection of a single target cell but increases the safety by limiting the duration of Cas9 activity to weeks instead of the lifetime of the transduced cell.

Example 4—Protease-Resistant Methods of Internal Cas9 AAV Fusion Protein Production and Purification Modified Cas9 (e.g., saCas9) is a bacterially derived enzyme that in eukaryotic systems is typically expressed from a plasmid or vector DNA inside a cell where it is rapidly shuttled to the nucleus after translation. In the modified viral particles disclosed herein, the internal VP2-Cas9 (VP2-Cas9i) protein becomes part of a fully formed virus particle, which is released into the culture media where it is harvested and purified. The modified viral particle is expected to encounter proteases during the production and purification from the cells and media used during production. In addition, two different protease activities were identified as part of the capsid of AAV (Wu et al. 2000; Salganik et al. 2012). One protease activity involves the autolytic proteolysis of the capsid during low pH (<5.5). The other protease activity is not pH dependent and was shown to cleave an external substrate.

To identify protease cleavage sites, proteomic analysis is performed on low-molecular weight fusion protein products excised from a SYPRO stained gel. The protein sequencing information informs a determination of whether the cleavage events are caused by a known protease or potentially by an endogenous capsid protease activity. The sequence also is utilized to design amino acid substitutions in the VP2-Cas9i protein to eliminate the cleavage event. Various amino acid substitutions are tested for: 1) reducing VP2-Cas9i cleavage, 2) allowing stable virus particle formation and 3) maintaining Cas9 functional activity. The VP2-Cas9i construct is in a single plasmid, which allows for rapid site directed mutagenesis to change amino acid sequences and perform test transfections. Amino acid modifications are tested in transient transfections of serum-free suspension grown HEK293 cells followed by cell lysis and Western blots using either Cas9 or AAV specific primary antibodies to detect full-length VP2-Cas9i protein. The ability the protease-resistant modified fusion proteins to form viral particles capable of infecting cells is tested by packaging a reporter construct expressing a luciferase-enhanced yellow fluorescent fusion protein (luc-EYFP) and measuring gene expression. Further functional testing of the modified fusion proteins is performed by producing VP2-Cas9i virus containing DENN Domain Containing 4C (DENND4C) specific sgRNA sequences to test for saCas9 functional activity of gene editing of DENND4C (Chari et al. 2017). The gene targeting efficiency is tested by PCR adding Illumina barcodes and sequencing adapters followed by sequencing using Illumina MiSeq and measure indel formation using published sgRNA and primer sequences.

Production and Purification of Cas9-VP2 Virus with Protease Inhibitors

To identify and predict potential proteases responsible for cleavage products, queries of the VP2-Cas9i protein sequence are run through protease sequence databases. To block activity of these proteases, transfections and virus purifications are performed in the presence of various protease inhibitors. The effectiveness of the inhibitors is assayed by western blot to determine if fewer degradation products (identifiable by lower molecular weight compared to the predicted size of VP2-Cas9i) are produced by this method. VX-765 is a potent and selective inhibitor of Caspase belonging to the ICE/caspase-1 subfamily and is currently in clinical trials (Wannamaker et al. 2007; Tanoury et al. 2008). Test transfections with the addition of VX-765 (as well as other pan-protease inhibitors) are performed to see if protease inhibitors reduce the formation of lower molecular weight products seen after purification. A VP2-Cas9i expression plasmid is transfected into HEK293 cells in the presence of protease inhibitors, cell lysates are isolated 48 hours after transfection, and Western blots are run with Cas9 or AAV specific antibodies to determine the size of the VP2-Cas9i protein produced.

Subsequent steps in the purification process can also lead to degradation of the saCas9 product such as changes in pH and detergents. Samples are taken at each step of the purification process to determine if any additional processes contribute to degrading the VP2-Cas9i capsid. A wide variety of purification procedures can be used, including various ion-exchange and affinity columns, iodixanol and CsCl gradients and tangential-flow filtration can be used to amend the purification process to one that is less harsh and more suitable for efficient purification of the full-length VP2-Cas9i product. VP2-Cas9i virus produced by a modified method of reducing protease degradation is then tested for function. The ability of virus to infect cells is tested by packaging a reporter construct expressing a luciferase-enhanced yellow fluorescent fusion protein (luc-EYFP) and measuring gene expression.

When infectivity is established, Cas9 activity is tested using the DENND4C sgRNA and MiSeq as described herein.

Modify Amino Acids Required for Endogenous AAV Capsid Protease Activity

Two separate protease activities were identified in the capsid of AAV2 (Wu et al. 200; Salganik et al. 2012). One of the protease activities was found to be pH dependent and was only active pH 5.5 and lower. The protease activity resulted in autocleavage of the capsid protein and can be involved in the normal infection process encountered in endosomes. The other protease activity was not pH dependent and was active on external substrates. Mutation of the glutamic acid at position 563 of AAV2 has been shown to specifically disrupt the external protease activity. Without being bound by theory, this external protease activity can be the source of Cas9 degradation seen during virus production.

Applicant has designed point mutations in the capsid protein to disrupt the external protease activity. The homologous residue in the VP2-Cas9i fusion proteins as well as VP1-3 capsid proteins is also mutated to either alanine or glutamine to test their effect on Cas9 stability. Once mutated, the modified expression plasmids are transfected into HEK293 cells in the presence or absence of protease inhibitors. Cell lysates are isolated 48 hours after transfection and run Western blots with Cas9 or AAV specific antibodies to determine the size of the fusion protein produced. Next, the ability of these modified particles to infect cells is tested by packaging a reporter construct expressing a luciferase-enhanced yellow fluorescent fusion protein (luc-EYFP) and measuring gene expression. When infectivity is established, Cas9 activity is tested using the DENND4C sgRNA and MiSeq as described above.

Figure 18:
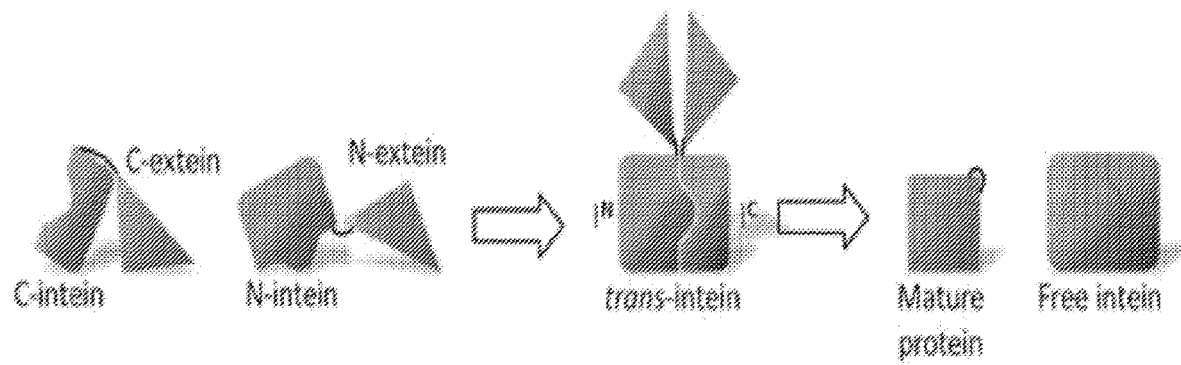
FIG. 18 is a diagram of intein splicing and protein ligation. Trans-splicing of split intein occurs after assembly of the intein fragments.

Example 4—Modular Assembly of Internal Cas9 AAV by Split-Intein Protein Splicing Protein trans-splicing (PTS) is a novel technology used to link two proteins together via intein-extein protein self-splicing reactions (Borra et al. 2017; Stevens et al. 2016; Truong et al. 2015, FIG. 18). Inteins are intervening sequences that excise themselves from precursor proteins and ligate the surrounding sequences together (Kane et al. 1990; Hirata et al. 1990; Perler 2002). PTS is an alternative approach to producing a large VP2-Cas9i fusion protein. The PTS design is a modular assembly system where the two proteins are produced separately and joined together in a separate reaction. The production and purification conditions can be optimized for each protein in separate reactions. The purified proteins are then mixed and an assembly reaction occurs. The objective of this example is to produce Cas9-intein and AAV-intein proteins, mix and assemble the purified proteins into AAV-Cas9i particles and determine infectivity and Cas9 activity.

Figure 16A:
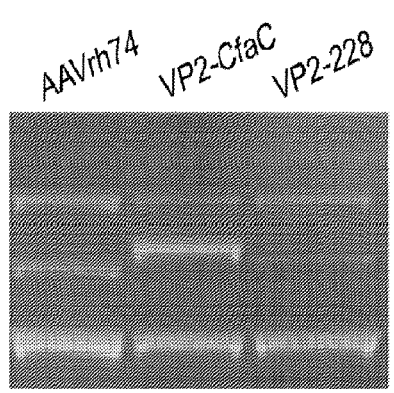
FIGS. 16A-16B depicts protein and Western gels.
Figure 16B:
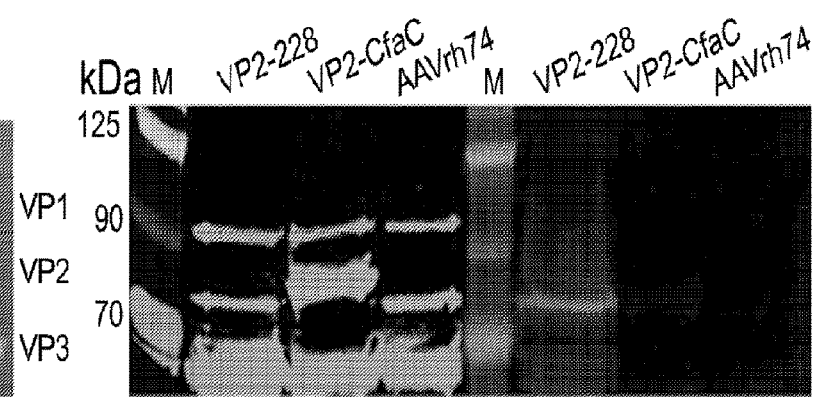
Figure 17A:
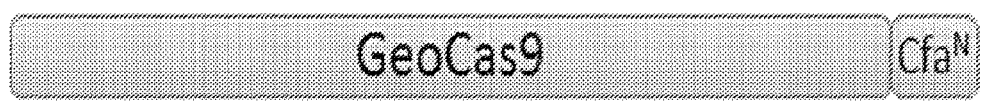
FIGS. 17A-17B are schematics of constructs.
Figure 17B:

First, Cas9-intein (e.g., saCas9-intein) and AAV VP2-intein particles are produced in separate reactions. Next, both components are mixed together and measured for purity, stability and infectivity of the product. The purity and infectivity of the resulting product guides selection of alternative splice junction sequences and/or peptide linker additions that may be required to facilitate rapid ligation and functional AAV and Cas9 activities. The rationale for this example is to develop a modular assembly of AAV-Cas9i and reduce the potential for product instability while providing the platform for rapid modification and optimization. These methods provide, for the first time, a tool for the modular creation of AAV particles that deliver functional saCas9 protein to cells for the purpose of gene editing and/or gene regulation. The modular assembly approach also allows the rapid testing of alternate Cas9, Cpf1 or Zinc finger nuclease proteins or even targeting ligands displayed on the interior of AAV for efficient delivery. The data shown in FIG. 16 demonstrates successful incorporation and virus production of the $Cfa^C$-intein fused to the VP2 protein of AAVrh74 serotype virus. A size increase of VP2 to 77 kDa from 72 kDa in the control AAVrh74 virus is also shown. Examine Split-Intein-Cas9 Purity and Stability Produced in Bacteria Cells Inteins are naturally occurring intervening sequences that catalyze a protein splicing reaction in a similar manner to introns in RNA68. Inteins are found in all forms of life with 113 known to be present in eukaryotes (InBase) (Perler 2002). The two inteins self-catalytically cleave out of the precursor protein and ligate the surrounding extein fragments with a native peptide bond (Vila-Perello et al. 2010). Trans-splicing split inteins are naturally derived or artificially created forms where the inteins are part of two separate proteins and direct the joining, splicing and ligation reactions resulting in the ligation of two separate proteins into one. The inteins identified from *Nostoc punctiforme* DnaE have shown remarkably rapid kinetics of splicing and ligation reactions (Cheriyan et al. 2013). In addition, traceless splicing reactions can be obtained with variant inteins leaving no intervening peptide sequences. The joining of two proteins can be achieved with almost any sequence and is only affected by the kinetics of ligation. Recent efforts to engineer split inteins with enhanced stability and activity have resulted in inteins with exceptional properties named consensus fast DnaE intein sequence (Cfa) (Stevens et al. 2016). The Cfa intein can catalyze rapid ligations at temperatures up to 80° C. and in harsh chemicals. Cfa has also been used to ligate two secreted proteins from co-transfected HEK293 cells in the culture media. By producing the Cas9 protein in a more native bacterial expression system, large quantities of purified protein can be generated while reducing the risk of protease degradation.

$Cfa^N$ intein is cloned to the carboxy terminus and/or amino-terminus of Cas9 (e.g., saCas9) along with a 6×His-tag (SEQ ID NO: 61) for purification and isolation of purified protein from bacteria or from yeast culture. In some embodiments, CfaN intein is cloned to the carboxy terminus of Cas9. $Cfa^C$ intein is cloned to either the amino terminus of VP2 or an insertion site of VP2 appropriate for internal expression within the assembled capsid (e.g., position 228, 350, 419, 684 and 689) and the modified VP2 is transfected into HEK293 cells to produce purified VP2-intein protein. The purified saCas9-intein and VP2-intein proteins are formulated in phosphate buffered saline (PBS) and tested in ligation reactions. The purified Cas9-intein and the VP2-intein are mixed and ligation reaction kinetics over time in PBS are monitored by Western blot. Once the reaction conditions for stable ligation of the Cas9-intein to the VP2-intein are determined, a VP2-intein containing AAV particle is produced by co-transfecting the VP1-3, Ad-HELP and AAV vector plasmids into HEK293 cells and purifying virus particles. The AAV-intein particles are mixed with the Cas9-intein in PBS to allow for the extein ligation. The purified Cas9-AAV particles are analyzed by Western blot for ligation of Cas9 with VP2 protein to determine efficiency of ligation and relative abundance of Cas9 compared to VP1, VP2 and VP3 proteins. The saCas9 and VP2 proteins should be found in a 1:1 ratio if efficient ligation has occurred. If a lower ratio is found, then reaction conditions of time and temperature can be adjusted to improve the ratio of ligation. The amino terminus of VP2 should be accessible for efficient intein based ligation to Cas9 proteins.

Based on the crystal structure of various serotypes of AAV, it is expected that the amino terminus of VP2 will be at or closely associated with the external region of the full virus particle. In addition, when GFP-VP2 containing AAV was examined microscopically, fluorescently decorated particles were visible during in vitro cell infections. Additionally, alternative sites of surface exposed amino acids within VP1 or VP2 can be mutated to include a Cfa intein region to provide a target site for the ligation reaction with Cas9 instead of the amino terminus of VP2.

Examine Split-Intein-saCas9 Purity and Stability Produced in HEK293

Split Cas9 proteins utilizing intein ligation reactions have been successfully tested and produced functional activity after delivery of the components to cells via two separate AAV vectors (Truong et al. 2015). In addition, Stevens et al. have co-expressed split intein components of a monoclonal heavy chain antibody-intein and a secreted peptide-intein and shown efficient ligation of the components in the medium following four days of expression at 37° C. (Stevens et al. 2016). HEK293 cells are normally used to produce AAV vectors due to their relative ease of efficient plasmid transfection and their endogenous expression of the Adenovirus E1A and E1B proteins required for AAV production. A simplified alternative method of producing saCas9-AAV particles via split intein mediated ligation is to co-transfect the saCas9-intein plasmid along with the AAV-intein component plasmids into HEK293 cells and purify AAV-Cas9i directly from the medium. Co-transfection into HEK293 cells eliminates separate production, ligation and purification steps to produce AAV-Cas9i particles. In addition, co-transfection into HEK293 allows for the rapid testing of various linkers for optimization of expression and function as well as alternative Cas9 proteins. Post-translational modifications (PTMs) are very different in bacteria than eukaryotic organisms (Delley et al. 2017; Brown et al. 2017; Bastos et al. 2017). SaCas9-intein produced in HEK293 cells retain eukaryotic PTMs and are less likely to be recognized as foreign.

$Cfa^N$ intein is cloned into the carboxy and/or amino terminus of Cas9 and ligated into a standard eukaryotic expression plasmid. $Cfa^C$ intein is further cloned to the insertion site of VP2 appropriate for internal expression within the assembled capsid (e.g., position 228, 350, 419, 684 and 689). These plasmids are co-transfected into HEK293 cells and the efficiency of ligation to produce a full-length VP2-Cas9i protein is determined. Once the reaction conditions for stable ligation of the Cas9-intein to the VP2-intein are determined in HEK293 cells, a modified particle is produced by including the VP1-3, Ad-HELP and AAV vector plasmids into the transfection of HEK293 cells and purifying the virus particles. Virus purification is performed utilizing standard iodixanol step gradient purification to isolate complete virus particles from contaminating cellular and adenovirus helper proteins followed by dialysis into a formulation buffer of PBS and poloxamer. The addition of 0.001% poloxamer to the formulation buffer helps to reduce adsorption of virus onto surfaces.

The intein mediated protein trans-splicing technology for joining two proteins together will provide an efficient method to link saCas9 to the interior-facing surface of AAV for delivery to cells. The two protein components can be produced separately by the most desirable and efficient methods as described above. Expression of Cas9-intein protein in bacteria provides a simplified method for producing large quantities of pure protein that can be rapidly ligated to AAV-intein capsids. Expression of the saCas9-intein protein in HEK293 cells overcomes the potential issues of PTMs. Another benefit of HEK293 cell production of the protein is that the saCas9-intein protein can be produced in a separate reaction and purified alone under optimal conditions for production and purification and then mixed with purified AAV-intein particles in a later ligation reaction to yield the final internal Cas9 AAV product. The utility of the split-intein system for protein ligation is that alternative Cas9 enzymes or other proteins can be efficiently produced and delivered by AAV vectors in vivo which allows for the rapid development and testing of endless numbers of molecules. In the same regard, a variety of linkers can be generated and tested to help overcome any spacing issues between Cas9 and AAV. If the infectivity of AAV is diminished by these modifications, longer protein linkers can be used to reposition the Cas9 either in a flexible or stable conformation. If the Cas9 activity is affected after infection of the cell, self-cleaving protein spacers can be used that allow the Cas9 protein to be released from the capsid efficiently during pH changes that occur after cell infection.

Example 5—Treatment of Muscular Dystrophy with AAV Expressing Interior Cas9

Duchenne muscular dystrophy is an inherited X-linked recessive gene defect that affects approximately 1 in 5000 newborn males. The gene is 2.2 megabases (MB) in length and contains 79 exons. Truncated forms of the DMD gene have been tested as a gene replacement strategy but the truncated form does not provide full functionality. By developing methods to accurately correct the myriad of gene mutations that are specific in each individual a fully functional dystrophin gene can be restored for these patients.

The CRISPR/Cas9 system allows for simple replacement of the targeting sequence to provide specific gene correction. The disclosed AAV delivery system is used to efficiently target every major muscle with a single intravenous administration, and provides a robust therapeutic strategy to treat DMD.

A mouse model mdx is used to demonstrate the effectiveness of treating muscular dystrophy with the modified viral particle and the methods disclosed herein. Mdx mice bear a frame-disrupting mutation in the DMD gene which compromises the muscle myofibers and results in muscle deterioration. One strategy for potential gene repair is to remove at least one exon from the DMD gene, thus producing a truncated mRNA that is still in frame and produces a dystrophin protein that is at least partially functional. To directly edit the DMD gene in mice, a gene therapy approach with a modified AAV viral particle is used to deliver one or more a guide RNAs capable of directing Cas9 to excise exon 23 of the mouse DMD gene, concurrently with delivery a Cas9-viral capsid fusion protein. Because the AAV will ultimately be used to target skeletal muscle, an AAV with skeletal muscle tropism should be used such as AAV1, AAV6, AAV7, AAV8, or AAV9.

Modified Cas9 AAV particles are prepared as described above. Briefly, HEK293T cells are co-transfected with four plasmids. The first plasmid encodes AAV viral capsid proteins VP1 and VP3 with VP2 deleted (e.g., SEQ ID NO: 1, SEQ ID NO: 2, or SEQ ID NO: 4). The second plasmid encodes a VP2-saCas9i fusion protein (e.g., SEQ ID NO: 45-49). The third plasmid encodes viral assembly helper genes (e.g., SEQ ID NO: 6). The fourth plasmid encodes the guide RNA targeting the DMD gene under the control of a U6 promoter or another appropriate promoter for expression in the tissue of interest (e.g., SEQ ID NO: 8). Alternatively, a cell line in which necessary viral assembly genes such as the genes encoded in the first and/or third plasmids are stably introduced can be used in lieu of co-transfection with plasmids encoding those genes.

Methods for designing guide RNA sequences for targeting exon 23 of the mouse Dmd gene are known in the art. For example, see Tabebordbar, M. et al. (2016) Science 351 (6271):407-411. Exemplary guide RNA target sequences appropriate for saCas9 cleavage of Dmd exon 23 are disclosed as SEQ ID NOs: 10-17. SEQ ID NOs: 10-17 target genomic sequences flanking exon 23, resulting of excision of exon 23. These sequences are cloned into the fourth plasmid, a scaffold guide RNA plasmid, to be packaged into the assembled modified viral particle. Control guide RNAs are also prepared that do not target the Dmd gene.

Following co-transfection, assembled modified viral particles are harvested and tested for VP2-saCas9 protein expression, as well as expression of VP1 and VP3 by western blot as described in Example 1. The packaged virus is also assayed for viral titer which should range from about 10^8 GC/mL to 10ƒGC/mL, with titer optimally of about 10—GC/mL. Viral titer can be assayed by western blot or by viral genome copy number by qPCR and compared to copy number standard samples. Following confirmation of fusion protein expression and sufficient viral titer, the modified viral particles are administered ex vivo to cells harvested from mdx mice to confirm efficient excision of exon 23. The harvested cells from the mdx mice (e.g., muscle cells, muscle stem cells, liver cells, fibroblasts, adipose stem cells, or any other cells compatible with the AAV serotype used) bear the genomic Dmd mutation. Upon transduction with the modified viral particles, they can be assayed for efficient exon 23 excision by PCR using primers that span the deletion region. Efficient operation of the CRISPR system can be measured by comparing the relative levels of PCR products of primers that span exon 23, primers within exon 23, and products where one primer is outside the deleted region and the other is inside the deleted region of exon 23. Efficient excision will be demonstrated the primers spanning exon 23 produce the most abundant product. Additional confirmation of efficient CRISPR activity can be ascertained by western blot for the repaired Dystrophin protein product.

Following confirmation of the CRISPR system's efficient excision, the modified viral particles can be administered ex vivo or in vitro to muscle stem or progenitor cells from the mdx mice such as satellite cells. Upon exon 23 excision, the CRISPR modified cells are transplanted back into the mice via intramuscular injection. Effectiveness of cell therapy with the cells treated with modified AAV is measured by improved muscle morphology, decreases in sarcolemmal localization of the multimeric dystrophin-glycoprotein complex and neuronal nitric-oxide synthase, as well as detection of Dystrophin expression.

Alternatively, the modified viral particles can be administered in vivo to muscle tissue through localized tissue injection such as intramuscular injection, intraperitoneal injection, systemic injection, or by tail vein injection. Effectiveness of viral gene therapy with the modified saCas9 AAV is measured by improved muscle morphology, decreases in sarcolemmal localization of the multimeric dystrophin-glycoprotein complex and neuronal nitric-oxide synthase, as well as detection of Dystrophin expression.

To treat muscular dystrophy in humans, guide RNAs are designed that target one or more of the following genes that cause muscular dystrophy: dystrophin (DMD, NM_000109, NM_004006, NM 004007, NM_004009, NM_004010), dysferlin (DYSF, NM_001130455, NM_001130976, NM_001130977, NM_001130978, NM_001130979), emerin (EMD, NM_000117), lamin A/C (LMNA, NM_001257374, NM_001282624, NM_001282625, NM_001282626, NM_005572), double homeobox 4 (DUX4, NM_001205218, NM_001278056, NM_001293798, NM_001306068), myotonin-protein kinase (MDPK, NM_001081560, NM_001081562, NM_001081563, NM_001288764, NM_001288765), cellular nucleic acid-binding protein (CNBP, NM_003418, NM_001127192, NM_001127193, NM_001127194, NM_001127195), polyadenylate-binding protein-2 (PABP-2, NM_004643). The guide RNA is designed to direct Cas9 to excise an exon via non-homologous end joining (NHEJ) causing an in frame truncation product that produces a functional protein product. Alternatively, the guide RNA can be designed to repair a gene via homology directed repair. This method uses a therapeutic DNA encoding a wild-type DNA sequence or replacement sequence to be used as a template for repair of the cleaved region.

Modified viral particles with interior Cas9 and encapsulating a polynucleotide comprising the guide RNA, and, optionally, the therapeutic template DNA, are prepared as described above. Viral protein expression and titer are assayed by western blot and PCR as described above. Efficiency of CRISPR—mediated gene editing is assayed by designing PCR primers that detect the repaired DNA fragment. Viral particles are administered to muscle tissue via intramuscular injection or systemic delivery. Expression of repaired gene product can be detected by PCR, histological staining, or western blot of treated muscle tissue.

Successful treatment and/or repair is determined when one or more of the following is detected: alleviation or amelioration of one or more of symptoms of muscular dystrophy, stabilized (i.e., not worsening) state of muscular dystrophy, delay or slowing of the progression of muscular dystrophy, and amelioration or palliation of muscular dystrophy. In some embodiments, success of treatment is determined by detecting the presence repaired target polynucleotide in one or more cells, tissues, or organs isolated from the subject. In some embodiments, success of treatment is determined by detecting the presence polypeptide encoded by the repaired target polynucleotide in one or more cells, tissues, or organs isolated from the subject. In some embodiments, the repaired polynucleotide or polypeptide is detected in muscle tissue of the treated subject.

Example 6—Treatment of Hemophilia

To treat hemophilia, guide RNAs are designed to direct CRISPR-mediated gene repair to Factor VIII (F8, NM 000132, NM_019863) or Factor IX (F9, NM_000133, NM_001313913). Additionally, therapeutic polynucleotides are prepared to provide templates for repair of Factor VIII (F8, NM_000132, NM_019863) or Factor IX (F9, NM_000133, NM_001313913). Modified viral particles with interior Cas9 and encapsulating a polynucleotide comprising the guide RNA and the therapeutic template DNA, are prepared as described above. Viral protein expression and titer are assayed by western blot and PCR as described above. Efficiency of CRISPR—mediated gene editing is determined by designing PCR primers that detect the repaired DNA fragment. In one aspect, modified viral particles are administered to stem cells, hepatocyte precursor cells, or hepatocytes to correct the factor VIII or IX genes. Alternatively, modified viral particles are administered directly to a subject with hemophilia by injection directly into the liver or by systemic delivery. Successful gene repair is detected by detecting functional Factor VIII or Factor IX protein within the treated cell or subject with hemophilia. In some embodiments, successful treatment is determined by detecting improved clotting function in the treated subject.

EQUIVALENTS

Unless otherwise defined, all technical and scientific terms used herein have the same meaning as commonly understood by one of ordinary skill in the art to which this disclosure belongs.

The inventions illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed.

Thus, it should be understood that although the present disclosure has been specifically disclosed by preferred embodiments and optional features, modification, improvement and variation of the inventions embodied therein herein disclosed may be resorted to by those skilled in the art, and that such modifications, improvements and variations are considered to be within the scope of this invention. The materials, methods, and examples provided here are representative of preferred embodiments, are exemplary, and are not intended as limitations on the scope of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

All publications, patent applications, patents, and other references mentioned herein are expressly incorporated by reference in their entirety, including all formulas and figures, to the same extent as if each were incorporated by reference individually. In case of conflict, the present specification, including definitions, will control.

Other embodiments are set forth within the following claims.

REFERENCES

The following articles are referenced in the disclosure hereinabove and are incorporated by reference, in their entirety:

1. Agbandje-McKenna, M. & Kleinschmidt, J. AAV capsid structure and cell interactions. Methods Mol Biol 807, 47-92, doi:10.1007/978-1-61779-370-73 (2011).
2. Alipour, M., Hosseinkhani, S., Sheikhnejad, R. & Cheraghi, R. Nano-biomimetic carriers are implicated in mechanistic evaluation of intracellular gene delivery. Sci Rep 7, 41507, doi:10.1038/srep41507 (2017).
3. Aubrey, B. J. et al. An inducible lentiviral guide RNA platform enables the identification of tumor-essential genes and tumor-promoting mutations in vivo. Cell Rep 10, 1422-1432, doi:10.1016/j.celrep.2015.02.002 (2015).
4. Aydemir, F. et al. Mutants at the 2-Fold Interface of Adeno-associated Virus Type 2 (AAV2) Structural Proteins Suggest a Role in Viral Transcription for AAV Capsids. J Virol 90, 7196-7204, doi:10.1128/JVI.00493-16 (2016).
5. Barnard, A. R., Groppe, M. & MacLaren, R. E. Gene therapy for choroideremia using an adeno-associated viral (AAV) vector. Cold Spring Harb Perspect Med 5, a017293, doi:10.1101/cshperspect.a017293 (2014).
6. Barrangou, R. et al. CRISPR provides acquired resistance against viruses in prokaryotes. Science 315, 1709-1712, doi:10.1126/science.1138140 (2007).
7. Bastos, P. A., da Costa, J. P. & Vitorino, R. A glimpse into the modulation of post-translational modifications of human-colonizing bacteria. J Proteomics 152, 254-275, doi:10.1016/j.jprot.2016.11.005 (2017).
8. Becerra, S. P., Rose, J. A., Hardy, M., Baroudy, B. M. & Anderson, C. W. Direct mapping of adeno-associated virus capsid proteins B and C: a possible ACG initiation codon. Proc Natl Acad Sci USA 82, 7919-7923 (1985).
9. Bengtsson, N. E. et al. Muscle-specific CRISPR/Cas9 dystrophin gene editing ameliorates pathophysiology in a mouse model for Duchenne muscular dystrophy. Nat Commun 8, 14454, doi:10.1038/ncomms14454 (2017).
10. Bleker, S., Sonntag, F. & Kleinschmidt, J. A. Mutational analysis of narrow pores at the fivefold symmetry axes of adeno-associated virus type 2 capsids reveals a dual role in genome packaging and activation of phospholipase A2 activity. J Virol 79, 2528-2540, doi:10.1128/JVI.79.4.2528-2540.2005 (2005).
11. Bolotin, A., Quinquis, B., Sorokin, A. & Ehrlich, S. D. Clustered regularly interspaced short palindrome repeats (CRISPRs) have spacers of extrachromosomal origin. Microbiology 151, 2551-2561, doi:10.1099/mic.0.28048-0 (2005).
12. Borra, R. & Camarero, J. A. Protein Chemical Modification Inside Living Cells Using Split Inteins. Methods Mol Biol 1495, 111-130, doi:10.1007/978-1-4939-6451-2_8 (2017).
13. Brown, C. W. et al. Large-scale analysis of post-translational modifications in *E. coli* under glucose-limiting conditions. BMC Genomics 18, 301, doi:10.1186/s12864-017-3676-8 (2017).
14. Chari, R., Yeo, N. C., Chavez, A. & Church, G. M. sgRNA Scorer 2.0: A Species-Independent Model To Predict CRISPR/Cas9 Activity. ACS Synth Biol 6, 902-904, doi:10.1021/acssynbio.6b00343 (2017).
15. Chen, X., Bai, Y., Zaro, J. L. & Shen, W. C. Design of an in vivo cleavable disulfide linker in recombinant fusion proteins. Biotechniques 49, 513-518, doi:10.2144/000113450 (2010).
16. Chen, X., Lee, H. F., Zaro, J. L. & Shen, W. C. Effects of receptor binding on plasma half-life of bifunctional transferrin fusion proteins. Mol Pharm 8, 457-465, doi:10.1021/mp1003064 (2011).
17. Chen, X., Zaro, J. L. & Shen, W. C. Fusion protein linkers: property, design and functionality. Adv Drug Deliv Rev 65, 1357-1369, doi:10.1016/j.addr.2012.09.039 (2013).
18. Cheriyan, M. & Perler, F. B. Protein splicing: A versatile tool for drug discovery. Adv Drug Deliv Rev 61, 899-907, doi:10.1016/j.addr.2009.04.021 (2009).
19. Cheriyan, M., Pedamallu, C. S., Tori, K. & Perler, F. Faster protein splicing with the *Nostoc punctiforme* DnaE intein using non-native extein residues. J Biol Chem 288, 6202-6211, doi:10.1074/jbc.M112.433094 (2013).
20. Chew, W. L. et al. A multifunctional AAV-CRISPR-Cas9 and its host response. Nat Methods 13, 868-874, doi:10.1038/nmeth.3993 (2016).
21. Cho, S. W. et al. Analysis of off-target effects of CRISPR/Cas-derived RNA-guided endonucleases and nickases. Genome Res 24, 132-141, doi:10.1101/gr.162339.113 (2014).

22. Chylinski, K., Le Rhun, A. & Charpentier, E. The tracrRNA and Cas9 families of type II CRISPR-Cas immunity systems. RNA Biol 10, 726-737, doi:10.4161/rna.24321 (2013).
23. Corti, M. et al. B-Cell Depletion is Protective Against Anti-AAV Capsid Immune Response: A Human Subject Case Study. Mol Ther Methods Clin Dev 1, doi:10.1038/mtm.2014.33 (2014).
24. Davis, K. M., Pattanayak, V., Thompson, D. B., Zuris, J. A. & Liu, D. R. Small molecule-triggered Cas9 protein with improved genome-editing specificity. Nat Chem Biol 11, 316-318, doi:10.1038/nchembio.1793 (2015).
25. Delley, C. L., Muller, A., Ziemski, M. & Weber-Ban, E. Prokaryotic ubiquitin-like protein and its ligase/deligase enyzmes. J Mol Biol, doi:10.1016/j.jmb.2017.04.020 (2017).
26. Deltcheva, E. et al. CRISPR RNA maturation by trans-encoded small RNA and host factor RNase III. Nature 471, 602-607, doi:10.1038/nature09886 (2011).
27. Fu, Y., Sander, J. D., Reyon, D., Cascio, V. M. & Joung, J. K. Improving CRISPR-Cas nuclease specificity using truncated guide RNAs. Nat Biotechnol 32, 279-284, doi:10.1038/nbt.2808 (2014).
28. Garneau, J. E. et al. The CRISPR/Cas bacterial immune system cleaves bacteriophage and plasmid DNA. Nature 468, 67-71, doi:10.1038/nature09523 (2010).
29. Gasiunas, G., Barrangou, R., Horvath, P. & Siksnys, V. Cas9-crRNA ribonucleoprotein complex mediates specific DNA cleavage for adaptive immunity in bacteria. Proc Natl Acad Sci USA 109, E2579-2586, doi:10.1073/pnas.1208507109 (2012).
30. Haddley, K. Alipogene tiparvovec for the treatment of lipoprotein lipase deficiency. Drugs Today (Barc) 49, 161-170, doi:10.1358/dot.2013.49.3.1937398 (2013).
31. Halder, S. et al. Structure of neurotropic adeno-associated virus AAVrh.8. J Struct Biol 192, 21-36, doi:10.1016/j.jsb.2015.08.017 (2015).
32. Hirata, R. et al. Molecular structure of a gene, VMA1, encoding the catalytic subunit of H(+)-translocating adenosine triphosphatase from vacuolar membranes of Saccharomyces cerevisiae. J Biol Chem 265, 6726-6733 (1990).
33. Jansen, R., Embden, J. D., Gaastra, W. & Schouls, L. M. Identification of genes that are associated with DNA repeats in prokaryotes. Mol Microbiol 43, 1565-1575 (2002).
34. Jinek, M. et al. A programmable dual-RNA-guided DNA endonuclease in adaptive bacterial immunity. Science 337, 816-821, doi:10.1126/science.1225829 (2012).
35. Kane, P. M. et al. Protein splicing converts the yeast TFP1 gene product to the 69-kD subunit of the vacuolar H(+)-adenosine triphosphatase. Science 250, 651-657 (1990).
36. Kim, E. et al. In vivo genome editing with a small Cas9 orthologue derived from Campylobacter jejuni. Nat Commun 8, 14500, doi:10.1038/ncomms14500 (2017).
37. Kim, S., Kim, D., Cho, S. W., Kim, J. & Kim, J. S. Highly efficient RNA-guided genome editing in human cells via delivery of purified Cas9 ribonucleoproteins. Genome Res 24, 1012-1019, doi:10.1101/gr.171322.113 (2014).
38. Kronenberg, S., Bottcher, B., von der Lieth, C. W., Bleker, S. & Kleinschmidt, J. A. A conformational change in the adeno-associated virus type 2 capsid leads to the exposure of hidden VP1 N termini. J Virol 79, 5296-5303, doi:10.1128/JVI.79.9.5296-5303.2005 (2005).
39. Li, W. et al. Engineering and Selection of Shuffled AAV Genomes: A New Strategy for Producing Targeted Biological Nanoparticles. Mol Ther 16, 1252-1260, doi:10.1038/mt.2008.100 (2008).
40. Lin, Y. H. et al. Approach To Deliver Two Antioxidant Enzymes with Mesoporous Silica Nanoparticles into Cells. ACS Appl Mater Interfaces 8, 17944-17954, doi:10.1021/acsami.6b05834 (2016).
41. Loiler, S. A. et al. Targeting recombinant adeno-associated virus vectors to enhance gene transfer to pancreatic islets and liver. Gene Ther 10, 1551-1558, doi:10.1038/sj.gt.3302046 (2003).
42. Long, C. et al. Prevention of muscular dystrophy in mice by CRISPR/Cas9-mediated editing of germline DNA. Science 345, 1184-1188, doi:10.1126/science.1254445 (2014).
43. MacLaren, R. E. et al. Retinal gene therapy in patients with choroideremia: initial findings from a phase 1/2 clinical trial. Lancet 383, 1129-1137, doi:10.1016/50140-6736(13)62117-0 (2014).
44. Monahan, P. E. et al. Employing a gain-of-function factor IX variant R338L to advance the efficacy and safety of hemophilia B human gene therapy: preclinical evaluation supporting an ongoing adeno-associated virus clinical trial. Hum Gene Ther 26, 69-81, doi:10.1089/hum.2014.106 (2015).
45. Muralidhar, S., Becerra, S. P. & Rose, J. A. Site-directed mutagenesis of adeno-associated virus type 2 structural protein initiation codons: effects on regulation of synthesis and biological activity. J Virol 68, 170-176 (1994).
46. Nicolson, S. C. & Samulski, R. J. Recombinant adeno-associated virus utilizes host cell nuclear import machinery to enter the nucleus. J Virol 88, 4132-4144, doi:10.1128/JVI.02660-13 (2014).
47. Nihongaki, Y., Yamamoto, S., Kawano, F., Suzuki, H. & Sato, M. CRISPR-Cas9-based photoactivatable transcription system. Chem Biol 22, 169-174, doi:10.1016/j.chembiol.2014.12.011 (2015).
48. Nishimasu, H. et al. Crystal Structure of Staphylococcus aureus Cas9. Cell 162, 1113-1126, doi:10.1016/j.cell.2015.08.007 (2015).
49. Perler, F. B. InBase: the Intein Database. Nucleic Acids Res 30, 383-384 (2002).
50. Polstein, L. R. & Gersbach, C. A. A light-inducible CRISPR-Cas9 system for control of endogenous gene activation. Nat Chem Biol 11, 198-200, doi:10.1038/nchembio.1753 (2015).
51. Rabinowitz, J. E. et al. Cross-dressing the virion: the transcapsidation of adeno-associated virus serotypes functionally defines subgroups. J Virol 78, 4421-4432 (2004).
52. Ran, F. A. et al. In vivo genome editing using Staphylococcus aureus Cas9. Nature 520, 186-191, doi:10.1038/nature14299 (2015).
53. Ran, F. A. Adaptation of CRISPR nucleases for eukaryotic applications. Analytical Biochemistry (2016) S0003-2697(16)30354-2.
54. Ried, M. U., Girod, A., Leike, K., Buning, H. & Hallek, M. Adeno-associated virus capsids displaying immunoglobulin-binding domains permit antibody-mediated vector retargeting to specific cell surface receptors. J Virol 76, 4559-4566 (2002).
55. Salganik, M. et al. Evidence for pH-dependent protease activity in the adeno-associated virus capsid. J Virol 86, 11877-11885, doi:10.1128/JVI.01717-12 (2012).

56. Sapranauskas, R. et al. The *Streptococcus thermophilus* CRISPR/Cas system provides immunity in *Escherichia coli*. Nucleic Acids Res 39, 9275-9282, doi:10.1093/nar/gkr606 (2011).
57. Schmidt, M. et al. Molecular characterization of the heparin-dependent transduction domain on the capsid of a novel adeno-associated virus isolate, AAV(VR-942). J Virol 82, 8911-8916, doi:10.1128/JVI.00672-08 (2008).
58. Shi, W., Arnold, G. S. & Bartlett, J. S. Insertional mutagenesis of the adeno-associated virus type 2 (AAV2) capsid gene and generation of AAV2 vectors targeted to alternative cell-surface receptors. Hum Gene Ther 12, 1697-1711, doi:10.1089/104303401750476212 (2001).
59. Simonelli, F. et al. Gene therapy for Leber's congenital amaurosis is safe and effective through 1.5 years after vector administration. Mol Ther 18, 643-650, doi:10.1038/mt.2009.277 (2010).
60. Smith, B. K. et al. Phase I/II trial of adeno-associated virus-mediated alpha-glucosidase gene therapy to the diaphragm for chronic respiratory failure in Pompe disease: initial safety and ventilatory outcomes. Hum Gene Ther 24, 630-640, doi:10.1089/hum.2012.250 (2013).
61. Stachler, M. D., Chen, I., Ting, A. Y. & Bartlett, J. S. Site-specific modification of AAV vector particles with biophysical probes and targeting ligands using biotin ligase. Mol Ther 16, 1467-1473, doi:10.1038/mt.2008.129 (2008).
62. Stevens, A. J. et al. Design of a Split Intein with Exceptional Protein Splicing Activity. J Am Chem Soc 138, 2162-2165, doi:10.1021/jacs.5b13528 (2016).
63. Tanoury, G. J., Chen, M., Dong, Y., Forslund, R. E. & Magdziak, D. Development of a novel Pd-catalyzed N-acyl vinylogous carbamate synthesis for the key intermediate of ICE inhibitor VX-765. Org Lett 10, 185-188, doi:10.1021/ol702532h (2008).
64. Tenney, R. M., Bell, C. L. & Wilson, J. M. AAV8 capsid variable regions at the two-fold symmetry axis contribute to high liver transduction by mediating nuclear entry and capsid uncoating. Virology 454-455, 227-236, doi:10.1016/j.virol.2014.02.017 (2014).
65. Truong, D. J. et al. Development of an intein-mediated split-Cas9 system for gene therapy. Nucleic Acids Res 43, 6450-6458, doi:10.1093/nar/gkv601 (2015).
66. Tseng, Y. S. et al. Adeno-associated virus serotype 1 (AAV1)- and AAV5-antibody complex structures reveal evolutionary commonalities in parvovirus antigenic reactivity. J Virol 89, 1794-1808, doi:10.1128/JVI.02710-14 (2015).
67. Tseng, Y. S. et al. Generation and characterization of anti-Adeno-associated virus serotype 8 (AAV8) and anti-AAV9 monoclonal antibodies. J Virol Methods 236, 105-110, doi:10.1016/j.jviromet.2016.07.009 (2016).
68. Vila-Perello, M. & Muir, T. W. Biological applications of protein splicing. Cell 143, 191-200, doi:10.1016/j.cell.2010.09.031 (2010).
69. Wannamaker, W. et al. (S)-1-((S)-2-{[1-(4-amino-3-chloro-phenyl)-methanoyl]-amino}-3,3-dimethyl-butanoy l)-pyrrolidine-2-carboxylic acid ((2R,3S)-2-ethoxy-5-oxo-tetrahydro-furan-3-yl)-amide (VX-765), an orally available selective interleukin (IL)-converting enzyme/caspase-1 inhibitor, exhibits potent anti-inflammatory activities by inhibiting the release of IL-1beta and IL-18. J Pharmacol Exp Ther 321, 509-516, doi:10.1124/jpet.106.111344 (2007).
70. Warrington, K. H., Jr. et al. Adeno-associated virus type 2 VP2 capsid protein is nonessential and can tolerate large peptide insertions at its N terminus. J Virol 78, 6595-6609, doi:10.1128/JVI.78.12.6595-6609.2004 (2004).
71. White, K. et al. Engineering adeno-associated virus 2 vectors for targeted gene delivery to atherosclerotic lesions. Gene Ther 15, 443-451, doi:10.1038/sj.gt.3303077 (2008).
72. Wright, A. V. et al. Rational design of a split-Cas9 enzyme complex. Proc Natl Acad Sci USA 112, 2984-2989, doi:10.1073/pnas.1501698112 (2015).
73. Wu, P. et al. Mutational analysis of the adeno-associated virus type 2 (AAV2) capsid gene and construction of AAV2 vectors with altered tropism. J Virol 74, 8635-8647 (2000).
74. Wyvekens, N., Topkar, V. V., Khayter, C., Joung, J. K. & Tsai, S. Q. Dimeric CRISPR RNA-Guided FokI-dCas9 Nucleases Directed by Truncated gRNAs for Highly Specific Genome Editing. Hum Gene Ther 26, 425-431, doi:10.1089/hum.2015.084 (2015).
75. Zetsche, B. et al. Cpf1 is a single RNA-guided endonuclease of a class 2 CRISPR-Cas system. Cell 163, 759-771, doi:10.1016/j.cell.2015.09.038 (2015).
76. Zetsche, B., Volz, S. E. & Zhang, F. A split-Cas9 architecture for inducible genome editing and transcription modulation. Nat Biotechnol 33, 139-142, doi:10.1038/nbt.3149 (2015).
77. Zhu, Z., Gonzalez, F. & Huangfu, D. The iCRISPR platform for rapid genome editing in human pluripotent stem cells. Methods Enzymol 546, 215-250, doi:10.1016/B978-0-12-801185-0.00011-8 (2014).

SEQUENCE LISTING
A description of the non-limiting exemplary vectors and the sequences thereof discussed herein is provided herein below:

pNL-Rep2-Caprh74-AVB-VP1-3

| | |
|---|---|
| LOCUS | pNLRep2-Caprh74- 10538 bp DNA circular SYN 23-MAR-2016 |
| DEFINITION | Knocks out VP2 expression, 5448 A-G |
| ACCESSION | pNLRep2-Caprh74- |
| ORGANISM | Unknown |
| REFERENCE | 1 (bases 1 to 10538) |
| COMMENT | SECID/File created by Clone Manager, Scientific & Educational Software |
| COMMENT | SECNOTES|GenBank 10538 bp DNA circular 20-MAR-2015 |
| FEATURES | Location/Qualifiers |

-continued

SEQUENCE LISTING
A description of the non-limiting exemplary vectors and the sequences thereof
discussed herein is provided herein below:

```
misc_feature      84..815
                  /note = "Rep78 5"
                  /SECDrawAs = "Gene"
                  /SECStyleId = 1
                  /SECName = "Rep78"
                  /SECDescr = "Rep78 5"

misc_feature      756..815
                  /note = "Rep52 5"
                  /SECDrawAs = "Gene"
                  /SECStyleId = 1
                  /SECName = "Rep52"
                  /SECDescr = "Rep52 5"

misc_feature      816..3886
                  /note = "Human Collagen Intron"
                  /SECDrawAs = "Region"
                  /SECStyleId = 1
                  /SECName = "H Coll Int"
                  /SECDescr = "Human Collagen Intron"

misc_feature      3887..5017
                  /note = "Rep52 3"
                  /SECDrawAs = "Gene"
                  /SECStyleId = 1
                  /SECName = "Rep52"
                  /SECDescr = "Rep52 3"

misc_feature      3887..5017
                  /note = "Rep78 3"
                  /SECDrawAs = "Gene"
                  /SECStyleId = 1
                  /SECName = "Rep78"
                  /SECDescr = "Rep78 3"

misc_feature      4741..4742
                  /note = "splice donor"
                  /SECDrawAs = "Region"
                  /SECStyleId = 1
                  /SECName = "SD"
                  /SECDescr = "splice donor"

misc_feature      4741..5061
                  /note = "Rep INTRON"
                  /SECDrawAs = "Region"
                  /SECStyleId = 1
                  /SECName = "Rep int"
                  /SECDescr = "Rep INTRON"

misc_feature      5033..5034
                  /note = "splice acceptor"
                  /SECDrawAs = "Region"
                  /SECStyleId = 1
                  /SECName = "SA"
                  /SECDescr = "splice acceptor"

CDS               5037..7253
                  /gene = "VP1"
                  /SECDrawAs = "Gene"
                  /SECStyleId = 1
                  /SECName = "VP1"

misc_feature      5060..5061
                  /note = "splice acceptor"
                  /SECDrawAs = "Region"
                  /SECStyleId = 1
                  /SECName = "SA"
                  /SECDescr = "splice acceptor"

misc_feature      5062..5086
                  /note = "REP68/40 3' end AAV2 wt is RLARGHSL (SEQ ID NO: 43) with
                  rh.74
                  capsid it is RLARGQPL ! (SEQ ID NO: 44)"
                  /SECDrawAs = "Gene"
```

```
                    SEQUENCE LISTING
     A description of the non-limiting exemplary vectors and the sequences thereof
                    discussed herein is provided herein below:

/SECStyleId = 1
                    /SECName = "REP68/40"
                    /SECDescr = "REP68/40 3' end AAV2 wt is RLARGHSL (SEQ ID NO: 43)
                    with rh.74 capsid it is RLARGQPL ! (SEQ ID NO: 44)"

CDS                 5646..7253
                    /gene = "VP3"
                    /SECDrawAs = "Gene"
                    /SECStyleId = 1 misc_feature        complement(7254..7411)
                    /note = "3' UTR"
                    /SECDrawAs = "Region"
                    /SECStyleId = 1
                    /SECName = "3"
                    /SECDescr = "3' UTR"

misc_feature        7428..7507
                    /note = "p5 Promoter"
                    /SECDrawAs = "Region"
                    /SECStyleId = 1
                    /SECName = "p5"
                    /SECDescr = "p5 Promoter"

CDS                 complement(8893..9753)
                    /gene = "amp"
                    /SECDrawAs = "Gene"
                    /SECStyleId = 1
                    /SECName = "amp"

ORIGIN (SEQ ID NO: 1)
        1   cgggccccce ctcgaggtcg acggtatcgg gggagctcgc agggtctcca ttttgaagcg
       61   ggaggtttga acgcgcagcc gccatgccgg ggttttacga gattgtgatt aaggtcccca
      121   gcgaccttga cgagcatctg cccggcattt ctgacagctt tgtgaactgg gtggccgaga
      181   aggaatggga gttgccgcca gattctgaca tggatctgaa tctgattgag caggcacccc
      241   tgaccgtggc cgagaagctg cagcgcgact ttctgacgga atggcgccgt gtgagtaagg
      301   ccccggaggc tcttttcttt gtgcaatttg agaagggaga gagctacttc cacatgcacg
      361   tgctcgtgga aaccaccggg gtgaaatcca tggttttggg acgtttcctg agtcagattc
      421   gcgaaaaact gattcagaga atttaccgcg gatcgagcc gactttgcca aactggttcg
      481   cggtcacaaa gaccagaaat ggcgccggag gcgggaacaa ggtggtggat gagtgctaca
      541   tccccaatta cttgctcccc aaaacccagc ctgagctcca gtgggcgtgg actaatatgg
      601   aacagtattt aagcgcctgt ttgaatctca cggagcgtaa acggttggtg gcgcagcatc
      661   tgacgcacgt gtcgcagacg caggagcaga acaaagagaa tcagaatccc aattctgatg
      721   cgccggtgat cagatcaaaa acttcagcca ggtacatgga gctggtcggg tggctcgtgg
      781   acaagggat tacctcggag aagcagtgga tccaggtgag taattgcaa agccaaacac
      841   caccatttgc cgagcacttt agagtttaca ggtttgtttc tcttgaccct caaaacaaac
      901   ctgtgaggca tagggagtat tgctatccct taagaattca ccccagtgt gcccatcaaa
      961   acctcccagg ctgagtctgc acagttgaag gaggaaggat aggaatggga gggtcgatgg
     1021   gtgaaagcat gattctctta accagtccag attatcaggt aatcccttca acaaccacca
     1081   cccactcccct gggcaatcca gctggagttt acagacagac ttagctggct atagcaccac
     1141   cgtgctactc tctgttcttc ctggttgctc aaatgcccta gaaaagtgga acaggtgagc
     1201   atcaactcac agggctctat gctggctgct gctgcgaggg atgttatgct atagtaccag
     1261   gggccaccat tccataggca cttcctgtgt ttaatacct atatgcttta cttcatctca
     1321   tcttcctcca tatcctgaga ggtggttcta ttcttctccc cattttacgg atgaaaaaac
```

```
1381   cgagacacag aaaggtgaaa tagcttaaga taaatggtgc cttgcagcct tagactctgg 1441   tggcctctag ttaatgtggg aaattaaggg tgaggggatt ggcagctgat ggagggtgca 1501   gggtgccaga cagaggcgtt tagctctgat cccttagcaa tagagagtcc ttgtaggcac 1561   ttggtcaggc gagtgatgcg atgaaagctg tgtttaagaa agattatgct ttctgctgat 1621   ttcatacccc caacacccaa gctctgaggc ccctcctcac aggtccttgc agggctggcc 1681   aaaataaagc agcttcactc cgttgtgctg ctttccagct aatgtgtctg tttggcagaa 1741   gtttccctca aaggcagatc agtgaaataa gcagaagcct cgaccccct ttgtcagcca 1801   gagctgctga agtgccttgc cccagggtca ctttgtgtga ggggattaga gagcactggg 1861   gctgccaaga aacactgccg tttctacaga ttagcaggac gctggcttgt ggccttctag 1921   cgaggctcag agctgcggtg ccctagtct gcatgggcta aagacaagct ccatctcctg 1981   tccttgttcc ctccttcctg ggcacagccg ccctgcttct tggttctctc tgttggttcc 2041   tgtccgcacg gtagttaggc tggcagcgtg tgtaggattt ggcttagaag attgacaaca 2101   ttgcctttga gcccttcttt gctactcctc cctctcccct cccatcagac tcctctctgg 2161   agtctgctct gcgaggcctc tgctctgtgg tatcccagca gccttctcag ccttgacttc 2221   cagaagggggg ctgtgcagtg tccggggtgt gcaggcccca gacacggggt aggctcatgg 2281   agatccaagt gctgatctag tgtcaaggct ggcctggaga ctgggctggg ttggtgtctg 2341   cctgctgtgg tcatgtgccc tcccttgggc ctgtatcctc tctccagact tgctgcaggg 2401   agaggtggca gatgtcagcc tagttctggc ctctcagagc agcatggcag ctcccttca 2461   ctcaggccca ggctgggccc tcctgctggc tgaccctgg ggagagggtg ctccagagct 2521   ccccaaggaa cagcttcccg aagcagccag gccagcccag aggggctgtg gccaatcctg 2581   aagctttatg ttcctgctga cattttttct aagttttctc ttgctttcct cttaaatgcc 2641   aatctggaga gtctccgtta ggagaaatgg accccagcca ggaagaaagag ttgagttgta 2701   tttaaaacac gagctccccc taaagcatcc ttctttagct tctaaggaga ggcagagact 2761   gacaggcagg actcagcagg aaaaggtacc cccctgacct gtcagtcag gccctaggcc 2821   cagctccacc cagcctgtgg cccccagagt ttcggtaaag agttccctgg gccttaagga 2881   accttgagag agcatttgag gggtgccacc acaaacttgg cagaaaaaac cctcccctc 2941   caagtccagt cctagagaag gagctggcaa ccttgccttg ctttgtaagc aaaagcctct 3001   tagggcttga gctcagatgt agtgtttgag ctgtggctgg tgccctgccc catcagggag 3061   ccaatggtag acatcctatg ggcatctttg ttttccgtaa gagcaggctg tctggggatg 3121   ggccagagga agaggcgacc tggagtcaac caagaggagg ccttaaccaa gccttaacca 3181   cagaggttaa ccaagccttg aaagcgcttc ccctgagca ggcaggaagc actgagtcca 3241   catggttgcc tcgctgtttc atttccttac actcaattct ctcagtcttt aaatgatcac 3301   ttggccttga agttacggat atttggggtc tgaactgaag ttgaagaaaa gaggaaatga 3361   tttaagcttt gtttaagatt aggggccagg tgcggtggct cacgcctgta atcccagcac 3421   cttgggagcc tgaggcgggt ggatcacctg aggtcaggag ttccagacca gcctggccaa 3481   catagcaaaa cccagtctct actaaaaata acaataaaaa aattagccag gtgtggtgac 3541   acatgcctgt aatcccagtt actcaggagg ctgaggcaga attgcttgaa cttgagaggt
```

SEQUENCE LISTING
A description of the non-limiting exemplary vectors and the sequences thereof
discussed herein is provided herein below:

```
3601  ggaggttgta gtgagccaag accgcaccac tgcactccag cctggcgaca gagccagact 3661  ccgtctcaaa acaacaaca aaaaagatta gaagaagccc attactgcct tctggccacc 3721  cactcgcaca gacaccaaaa ctgcagccca cacctcgcca tcctcgtgct ctgccctggg 3781  acaccccagg cacagtgtgt ccttcgtttt ctgtaagggt gggctggag cagggacgga 3841  cagggcctgt gggcacctct catggtcact tccttcttgc tcacaggagg accaggcctc 3901  atacatctcc ttcaatgcgg cctccaactc gcggtcccaa atcaaggctg ccttggacaa 3961  tgcgggaaag attatgagcc tgactaaaac cgcccccgac tacctggtgg gccagcagcc 4021  cgtggaggac atttccagca atcggattta taaaattttg aactaaacg ggtacgatcc 4081  ccaatatgcg gcttccgtct ttctgggatg ggccacgaaa aagttcggca agaggaacac 4141  catctggctg tttgggcctg caactaccgg gaagaccaac atcgcggagg ccatagccca 4201  cactgtgccc ttctacgggt gcgtaaactg gaccaatgag aactttccct tcaacgactg 4261  tgtcgacaag atggtgatct ggtgggagga ggggaagatg accgccaagt tcgtggagtc 4321  ggccaaagcc attctcggag gaagcaaggt gcgcgtggac cagaaatgca agtcctcggc 4381  ccagatagac ccgactcccg tgatcgtcac ctccaacacc aacatgtgcg ccgtgattga 4441  cgggaactca acgaccttcg aacaccagca gccgttgcaa gaccggatgt tcaaatttga 4501  actcacccgc cgtctggatc atgactttgg gaaggtcacc aagcaggaag tcaaagactt 4561  tttccggtgg gcaaaggatc acgtggttga ggtggagcat gaattctacg tcaaaaaggg 4621  tggagccaag aaaagacccg cccccagtga cgcagatata agtgagccca acgggtgcg 4681  cgagtcagtt gcgcagccat cgacgtcaga cgcggaagct tcgatcaact acgcagacag 4741  gtaccaaaac aaatgttctc gtcacgtggg catgaatctg atgctgtttc cctgcagaca 4801  atgcgagaga atgaatcaga attcaaatat ctgcttcact cacggacaga aagactgttt 4861  agagtgcttt cccgtgtcag aatctcaacc cgtttctgtc gtcaaaaagg cgtatcagaa 4921  actgtgctac attcatcata tcatgggaaa ggtgccagac gcttgcactg cctgcgatct 4981  ggtcaatgtg gatttggatg actgcatctt tgaacaataa atgatttaaa tcaggtatgg 5041  ctgccgatgg ttatcttcca gattggctcg aggacaacct ctctgagggc attcgcgagt 5101  ggtgggacct gaaacctgga gccccgaaac ccaaagccaa ccagcaaaag caggacaacg 5161  gccggggtct ggtgcttcct ggctacaagt acctcggacc cttcaacgga ctcgacaagg 5221  gggagcccgt caacgcggcg gacgcagcgg ccctcgagca cgacaaggcc tacgaccagc 5281  agctccaagc gggtgacaat ccgtacctgc ggtataatca cgccgacgcc gagtttcagg 5341  agcgtctgca agaagatacg tcttttgggg gcaacctcgg gcgcgcagtc ttccaggcca 5401  aaaagcgggt tctcgaacct ctgggcctgg ttgaatcgcc ggttaaggcg gctcctggaa 5461  agaagagacc ggtagagcca tcaccccagc gctctccaga ctcctctacg ggcatcggca 5521  agaaaggcca gcagcccgca aaaagagac tcaattttgg gcagactggc gactcagagt 5581  cagtccccga ccctcaacca atcgagaac caccagcagg ccctctggt ctgggatctg 5641  gtacaatggc tgcaggcggt ggcgctccaa tggcagacaa taacgaaggc gccgacggag 5701  tgggtagttc ctcaggaaat tggcattgcg attccacatg gctgggcgac agagtcatca 5761  ccaccagcac ccgcacctgg gccctgccca cctacaacaa ccacctctac aagcaaatct 5821  ccaacgggac ctcgggagga gcaccaacg acaacaccta cttcggctac agcaccccct
```

SEQUENCE LISTING
A description of the non-limiting exemplary vectors and the sequences thereof
discussed herein is provided herein below:

```
5881  gggggtattt tgacttcaac agattccact gccactttc accacgtgac tggcagcgac
5941  tcatcaacaa caactgggga ttccggccca agaggctcaa cttcaagctc ttcaacatcc
6001  aagtcaagga ggtcacgcag aatgaaggca ccaagaccat cgccaataac cttaccagca
6061  cgattcaggt ctttacggac tcggaatacc agctcccgta cgtgctcggc tcggcgcacc
6121  agggctgcct gcctccgttc ccggcggacg tcttcatgat tcctcagtac gggtacctga
6181  ctctgaacaa tggcagtcag gctgtgggcc ggtcgtcctt ctactgcctg gagtactttc
6241  cttctcaaat gctgagaacg ggcaacaact ttgaattcag ctacaacttc gaggacgtgc
6301  ccttccacag cagctacgcg cacagccaga gcctggaccg gctgatgaac cctctcatcg
6361  accagtactt gtactacctg tcccggactc aaagcacggg cggtactgca ggaactcagc
6421  agttgctatt ttctcaggcc gggcctaaca acatgtcggc tcaggccaag aactggctac
6481  ccggtccctg ctaccggcag caacgcgtct ccacgacact gtcgcagaac aacaacagca
6541  actttgcctg gacgggtgcc accaagtatc atctgaatgg cagagactct ctggtgaatc
6601  ctggcgttgc catggctacc cacaaggacg acgaagagcg attttttcca tccagcggag
6661  tcttaatgtt tgggaaacag ggagctggaa aagacaacgt ggactatagc agcgtgatgc
6721  taaccagcga ggaagaaata aagaccacca acccagtggc cacagaacag tacggcgtgg
6781  tggccgataa cctgcaacag caaaacgccg ctcctattgt aggggccgtc aatagtcaag
6841  gagccttacc tggcatggtg tggcagaacc gggacgtgta cctgcagggt cccatctggg
6901  ccaagattcc tcatacggac ggcaactttc atccctcgcc gctgatggga ggctttggac
6961  tgaagcatcc gcctcctcag atcctgatta aaaacacacc tgttcccgcg gatcctccga
7021  ccaccttcag ccaggccaag ctggcttctt tcatcacgca gtacagtacc ggccaggtca
7081  gcgtggagat cgagtgggag ctgcagaagg agaacagcaa acgctggaac ccagagattc
7141  agtacacttc caactactac aaatctacaa atgtggactt tgctgtcaat actgagggta
7201  cttattccga gcctcgcccc attggcaccc gttacctcac ccgtaatctg taattacatg
7261  ttaatcaata aaccggttaa ttcgtttcag ttgaactttg gtctcctgtc cttcttatct
7321  tatcggttac catagaaact ggttacttat taactgcttg gtgcgcttcg cgataaaaga
7381  cttacgtcat cgggttaccc ctagtgatgg agcggccgct ttcagttgaa ctttggtctc
7441  tgcgtatttc tttcttatct agtttccatg ctctagaggt cctgtattag aggtcacgtg
7501  agtgttttgc gacattttgc gacaccatgt ggtcacgctg ggtatttaag cccgagtgag
7561  cacgcagggt ctccattttg aagcggagg tttgaacgcg cagccgccaa gccgaattct
7621  gcagatatcc atcacactgg cggccgctcg actagagcgg ccgccaccgc ggtggagctc
7681  cagcttttgt tccctttagt gagggttaat tgcgcgcttg gcgtaatcat ggtcatagct
7741  gtttcctgtg tgaaattgtt atccgctcac aattccacac aacatacgag ccggaagcat
7801  aaagtgtaaa gcctggggtg cctaatgagt gagctaactc acattaattg cgttgcgctc
7861  actgcccgct ttccagtcgg gaaacctgtc gtgccagctg cattaatgaa tcggccaacg
7921  cgcggggaga ggcggtttgc gtattgggcg ctcttccgct tcctcgctca ctgactcgct
7981  gcgctcggtc gttcggctgc ggcgagcggt atcagctcac tcaaaggcgg taatacggtt
8041  atccacagaa tcaggggata acgcaggaaa gaacatgtga gcaaaaggcc agcaaaaggc
```

SEQUENCE LISTING
A description of the non-limiting exemplary vectors and the sequences thereof discussed herein is provided herein below:

```
8101  caggaaccgt aaaaaggccg cgttgctggc gttttcccat aggctccgcc ccctgacga
8161  gcatcacaaa aatcgacgct caagtcagag gtggcgaaac ccgacaggac tataaagata
8221  ccaggcgttt ccccctggaa gctccctcgt gcgctctcct gttccgaccc tgccgcttac
8281  cggatacctg tccgcctttc tcccttcggg aagcgtggcg ctttctcata gctcacgctg
8341  taggtatctc agttcggtgt aggtcgttcg ctccaagctg gctgtgtgc acgaaccccc
8401  cgttcagccc gaccgctgcg ccttatccgg taactatcgt cttgagtcca acccggtaag
8461  acacgactta tcgccactgg cagcagccac tggtaacagg attagcagag cgaggtatgt
8521  aggcggtgct acagagttct tgaagtggtg gcctaactac ggctacacta agaacagt
8581  atttggtatc tgcgctctgc tgaagccagt taccttcgga aaaagagttg gtagctcttg
8641  atccggcaaa caaaccaccg ctggtagcgg tggttttttt gtttgcaagc agcagattac
8701  gcgcagaaaa aaaggatctc aagaagatcc tttgatcttt tctacggggt ctgacgctca
8761  gtggaacgaa aactcacgtt aagggatttt ggtcatgaga ttatcaaaaa ggatcttcac
8821  ctagatcctt ttaaattaaa aatgaagttt taaatcaatc taagtatat atgagtaaac
8881  ttggtctgac agttaccaat gcttaatcag tgaggcacct atctcagcga tctgtctatt
8941  tcgttcatcc atagttgcct gactccccgt cgtgtagata actacgatac gggagggctt
9001  accatctggc cccagtgctg caatgatacc gcgagaccca cgctcaccgg ctccagattt
9061  atcagcaata aaccagccag ccggaagggc cgagcgcaga agtggtcctg caactttatc
9121  cgcctccatc cagtctatta attgttgccg ggaagctaga gtaagtagtt cgccagttaa
9181  tagtttgcgc aacgttgttg ccattgctac aggcatcgtg gtgtcacgct cgtcgtttgg
9241  tatggcttca ttcagctccg gttcccaacg atcaaggcga gttacatgat cccccatgtt
9301  gtgcaaaaaa gcggttagct ccttcggtcc tccgatcgtt gtcagaagta agttggccgc
9361  agtgttatca ctcatggtta tggcagcact gcataattct cttactgtca tgccatccgt
9421  aagatgcttt tctgtgactg gtgagtactc aaccaagtca ttctgagaat agtgtatgcg
9481  gcgaccgagt tgctcttgcc cggcgtcaat acgggataat accgcgccac atagcagaac
9541  tttaaaagtg ctcatcattg gaaaacgttc ttcggggcga aaactctcaa ggatcttacc
9601  gctgttgaga tccagttcga tgtaacccac tcgtgcaccc aactgatctt cagcatcttt
9661  tactttcacc agcgtttctg ggtgagcaaa aacaggaagg caaaatgccg caaaaaaggg
9721  aataagggcg acacggaaat gttgaatact catactcttc ctttttcaat attattgaag
9781  catttatcag ggttattgtc tcatgagcgg atacatattt gaatgtattt agaaaaataa
9841  acaaataggg gttccgcgca catttccccg aaaagtgcca cctaaattgt aagcgttaat
9901  attttgttaa aattcgcgtt aaattttgt taaatcagct cattttttaa ccaataggcc
9961  gaaatcggca aaatccctta taatcaaaa gaatagaccg agatagggt gagtgttgtt
10021 ccagtttgga acaagagtcc actattaaag aacgtggact ccaacgtcaa agggcgaaaa
10081 accgtctatc agggcgatgg cccactacgt gaaccatcac cctaatcaag ttttttgggg
10141 tcgaggtgcc gtaaagcact aaatcggaac cctaaaggga gcccccgatt tagagcttga
10201 cggggaaagc cggcgaacgt ggcgagaaag gaagggaaga agcgaaagg agcgggcgct
10261 agggcgctgg caagtgtagc ggtcacgctg cgcgtaacca ccacacccgc cgcgcttaat
10321 gcgccgctac agggcgcgtc ccattcgcca ttcaggctgc gcaactgttg ggaagggcga
```

SEQUENCE LISTING
A description of the non-limiting exemplary vectors and the sequences thereof discussed herein is provided herein below:

```
10381  tcggtgcggg cctcttcgct attacgccag ctggcgaaag ggggatgtgc tgcaaggcga 10441  ttaagttggg taacgccagg gttttcccag tcacgacgtt gtaaaacgac ggccagtgag 10501  cgcgcgtaat acgactcact atagggcgaa ttgggtac
``` pNL-Rep2-Caprh74-AVB-VP1-3

| | |
|---|---|
| LOCUS | pNLRep2-Caprh74- 13850 bp DNA circular SYN 23-MAR-2016 |
| DEFINITION | Ligation of pX601-AAV-CMV--N 696 to 4011 product cut NheI..6 to NsiI..3331 into pNLRep2-Caprh74-AVB-VP2-NN cut NsiI..5464 to NheI..5451 |
| ACCESSION | pNLRep2-Caprh74- |
| ORGANISM | Unknown |
| REFERENCE | 1 (bases 1 to 13850) |
| COMMENT | SECNOTES\|Vector molecule: pNLRep2-Caprh74-AVB-VP2-NN cut NsiI..5464 to NheI..5451<br>Fragment ends: NsiI and NheI<br>Fragment size: 10525<br>Insert molecule: pX601-AAV-CMV--N 696 to 4011 product cut NheI..6 to NsiI..3331<br>Fragment ends: NheI and NsiI<br>Fragment size: 3325 |
| FEATURES | Location/Qualifiers |
| misc_feature | 84..815<br>/note = "Rep68 5"<br>/SECDrawAs = "Gene"<br>/SECStyleId = 1<br>/SECName = "Rep68"<br>/SECDescr = "Rep68 5" |
| misc_feature | 84..815<br>/note = "Rep78 5"<br>/SECDrawAs = "Gene"<br>/SECStyleId = 1<br>/SECName = "Rep78"<br>/SECDescr = "Rep78 5" |
| misc_feature | 756..815<br>/note = "Rep40 5"<br>/SECDrawAs = "Gene"<br>/SECStyleId = 1<br>/SECName = "Rep40"<br>/SECDescr = "Rep40 5" |
| misc_feature | 756..815<br>/note = "Rep52 5"<br>/SECDrawAs = "Gene"<br>/SECStyleId = 1<br>/SECName = "Rep52"<br>/SECDescr = "Rep52 5" |
| misc_feature | 816..3886<br>/note = "Human Collagen Intron"<br>/SECDrawAs = "Region"<br>/SECStyleId = 1<br>/SECName = "H Coll Intron"<br>/SECDescr = "Human Collagen Intron" |
| misc_feature | 3887..5017<br>/note = "Rep52 3"<br>/SECDrawAs = "Gene"<br>/SECStyleId = 1<br>/SECName = "Rep52"<br>/SECDescr = "Rep52 3" |
| misc_feature | 3887..5017 |

SEQUENCE LISTING
A description of the non-limiting exemplary vectors and the sequences thereof discussed herein is provided herein below:

```
                         /note = "Rep78 3"
                         /SECDrawAs = "Gene"
                         /SECStyleId = 1
                         /SECName = "Rep78"
                         /SECDescr = "Rep78 3"
misc_feature             4741..4742
                         /note = "splice donor"
                         /SECDrawAs = "Region"
                         /SECStyleId = 1
                         /SECName = "SD"
                         /SECDescr = "splice donor"
misc_feature             4741..5061
                         /note = "Rep INTRON"
                         /SECDrawAs = "Region"
                         /SECStyleId = 1
                         /SECName = "Rep intron"
                         /SECDescr = "Rep INTRON"
misc_feature             5033..5034
                         /note = "splice acceptor"
                         /SECDrawAs = "Region"
                         /SECStyleId = 1
                         /SECName = "SA"
                         /SECDescr = "splice acceptor"
CDS                      5037..10565
                         /gene = "VP2-Cas9"
                         /product = "fusion protein"
                         /SECDrawAs = "Gene"
                         /SECStyleId = 1
                         /SECName = "VP2-Cas9"
                         /SECDescr = "fusion protein"
misc_feature             5060..5061
                         /note = "splice acceptor"
                         /SECDrawAs = "Region"
                         /SECStyleId = 1
                         /SECName = "SA"
                         /SECDescr = "splice acceptor"
misc_feature             5062..5086
                         /note = "REP68/40 3' end AAV2 wt is RLARGHSL (SEQ ID NO: 43) with
                         rh.74
                         capsid it is RLARGQPL ! (SEQ ID NO: 44)"
                         /SECDrawAs = "Gene"
                         /SECStyleId = 1
                         /SECName = "REP68"
                         /SECDescr = "REP68/40 3' end AAV2 wt is RLARGHSL (SEQ ID NO: 43)
                         with rh.74 capsid it is RLARGQPL ! (SEQ ID NO 44)"
misc_feature             5084..5086
                         /note = "Rep 68/40 stop"
                         /SECDrawAs = "Region"
                         /SECStyleId = 1
                         /SECName = "Rep"
                         /SECDescr = "Rep 68/40 stop"
CDS                      5457..8772
                         /gene = "saCas9"
                         /SECDrawAs = "Region"
                         /SECStyleId = 1
                         /SECName = "saCas9"
misc_feature             8730..8771
                         /gene = "OLLAS"
                         /product = "epitope tag"
                         /SECDrawAs = "Region"
                         /SECStyleId = 1
misc_feature             complement(10566..10723)
                         /note = "3' UTR"
                         /SECDrawAs = "Region"
                         /SECStyleId = 1
```

SEQUENCE LISTING
A description of the non-limiting exemplary vectors and the sequences thereof discussed herein is provided herein below:

```
                        /SECName = "3"
                        /SECDescr = "3' UTR"
misc_feature    10740..10819
                        /note = "p5 Promoter"
                        /SECDrawAs = "Region"
                        /SECStyleId = 1
                        /SECName = "p5"
                        /SECDescr = "p5 Promoter"
CDS             complement(12205..13065)
                        /gene = "amp"
                        /SECDrawAs = "Gene"
                        /SECStyleId = 1
                        /SECName = "amp"

ORIGIN (SEQ ID NO: 2)
        1   cgggccccc  ctcgaggtcg  acggtatcgg  gggagctcgc  agggtctcca  ttttgaagcg
       61   ggaggtttga  acgcgcagcc  gccatgccgg  ggttttacga  gattgtgatt  aaggtcccca
      121   gcgaccttga  cgagcatctg  cccggcattt  ctgacagctt  tgtgaactgg  gtggccgaga
      181   aggaatggga  gttgccgcca  gattctgaca  tggatctgaa  tctgattgag  caggcacccc
      241   tgaccgtggc  cgagaagctg  cagcgcgact  tcctgacgga  atggcgccgt  gtgagtaagg
      301   cccccggaggc  tctttctttt  gtgcaatttg  agaagggaga  gagctacttc  cacatgcacg
      361   tgctcgtgga  aaccaccggg  gtgaaatcca  tggttttggg  acgtttcctg  agtcagattc
      421   gcgaaaaact  gattcagaga  atttaccgcg  ggatcgagcc  gactttgcca  aactggttcg
      481   cggtcacaaa  gaccagaaat  ggcgccggag  gcgggaacaa  ggtggtggat  gagtgctaca
      541   tccccaatta  cttgctcccc  aaaacccagc  ctgagctcca  gtgggcgtgg  actaatatgg
      601   aacagtattt  aagcgcctgt  tgaatctca   cggagcgtaa  acggttggtg  gcgcagcatc
      661   tgacgcacgt  gtcgcagacg  caggagcaga  acaaagagaa  tcagaatccc  aattctgatg
      721   cgccggtgat  cagatcaaaa  acttcagcca  ggtacatgga  gctggtcggg  tggctcgtgg
      781   acaaggggat  tacctcggag  aagcagtgga  tccaggtgag  taattgacaa  agccaaacac
      841   caccatttgc  cgagcacttt  agagtttaca  ggtttgtttc  tcttgaccct  caaaacaaac
      901   ctgtgaggca  tagggagtat  tgctatccct  taagaattca  ccccagtgt   gcccatcaaa
      961   acctcccagg  ctgagtctgc  acagttgaag  gaggaaggat  aggaatggga  gggtcgatgg
     1021   gtgaaagcat  gattctctta  accagtccag  attatcaggt  aatcccttca  acaaccacca
     1081   cccactccct  gggcaatcca  gctggagttt  acagacagac  ttagctggct  atagcaccac
     1141   cgtgctactc  tctgttcttc  ctggttgctc  aaatgcccta  gaaagtgga   acaggtgagc
     1201   atcaactcac  agggctctat  gctggctgct  gctgcgaggg  atgttatgct  atagtaccag
     1261   gggccaccat  tccataggca  cttcctgtgt  ttaatacct   atatgcttta  cttcatctca
     1321   tcttcctcca  tatcctgaga  ggtggttcta  ttcttctccc  cattttacgg  atgaaaaaac
     1381   cgagacacag  aaaggtgaaa  tagcttaaga  taaatggtgc  cttgcagcct  tagactctgg
     1441   tggcctctag  ttaatgtggg  aaattaaggg  tgaggggatt  ggcagctgat  ggagggtgca
     1501   gggtgccaga  cagaggcgtt  tagctctgat  cccttagcaa  tagagagtcc  ttgtaggcac
     1561   ttggtcaggc  gagtgatgcg  atgaaagctg  tgtttaagaa  agattatgct  ttctgctgat
     1621   ttcataccc   caacacccaa  gctctgaggc  ccctcctcac  aggtccttgc  agggctggcc
     1681   aaaataaagc  agcttcactc  cgttgtgctg  ctttccagct  aatgtgtctg  tttggcagaa
```

SEQUENCE LISTING
A description of the non-limiting exemplary vectors and the sequences thereof
discussed herein is provided herein below:

```
1741   gtttccctca aaggcagatc agtgaaataa gcagaagcct cgacccccct tgtcagcca 1801   gagctgctga agtgccttgc cccagggtca ctttgtgtga ggggattaga gagcactggg 1861   gctgccaaga aacactgccg tttctacaga ttagcaggac gctggcttgt ggccttctag 1921   cgaggctcag agctgcggtg gccctagtct gcatgggcta agacaagct ccatctcctg 1981   tccttgttcc ctccttcctg ggcacagccg ccctgcttct tggttctctc tgttggttcc 2041   tgtccgcacg gtagttaggc tggcagcgtg tgtaggattt ggcttagaag attgacaaca 2101   ttgcctttga gcccttcttt gctactcctc cctctcccct cccatcagac tcctctctgg 2161   agtctgctct gcgaggcctc tgctctgtgg tatcccagca gccttctcag ccttgacttc 2221   cagaagggg ctgtgcagtg tccggggtgt gcaggcccca gacacggggt aggctcatgg 2281   agatccaagt gctgatctag tgtcaaggct ggcctggaga ctgggctggg ttggtgtctg 2341   cctgctgtgg tcatgtgccc tcccttgggc ctgtatcctc tctccagact tgctgcaggg 2401   agaggtggca gatgtcagcc tagttctggc ctctcagagc agcatggcag ctcccttca 2461   ctcaggccca ggctgggccc tcctgctggc tgaccctgg ggagagggtg ctccagagct 2521   ccccaaggaa cagcttcccg aagcagccag gccagcccag aggggctgtg gccaatcctg 2581   aagctttatg ttcctgctga cattttttct aagttttctc ttgcttttcct cttaaatgcc 2641   aatctggaga gtctccgtta ggagaaatgg accccagcca ggaagaagag ttgagttgta 2701   tttaaaacac gagctccccc taaagcatcc ttctttagct tctaaggaga ggcagagact 2761   gacaggcagg actcagcagg aaaaggtacc cccctgacct gctcagtcag gccctaggcc 2821   cagctccacc cagcctgtgg cccccagagt ttcggtaaag agttccctgg gccttaagga 2881   accttgagag agcatttgag gggtgccacc acaaacttgg cagaaaaaac cctccccctc 2941   caagtccagt cctagagaag gagctggcaa ccttgccttg ctttgtaagc aaaagcctct 3001   tagggcttga gctcagatgt agtgtttgag ctgtggctgg tgccctgccc catcagggag 3061   ccaatggtag acatcctatg ggcatctttg ttttccgtaa gagcaggctg tctggggatg 3121   ggccagagga agaggcgacc tggagtcaac caagaggagg ccttaaccaa gccttaacca 3181   cagaggttaa ccaagccttg aaagcgcttc cccctgagca ggcaggaagc actgagtcca 3241   catggttgcc tcgctgtttc atttccttac actcaattct ctcagtcttt aaatgatcac 3301   ttggccttga agttacggat atttggggtc tgaactgaag ttgaagaaaa gaggaaatga 3361   tttaagcttt gtttaagatt aggggccagg tgcggtggct cacgcctgta atcccagcac 3421   cttgggagcc tgaggcgggt ggatcacctg aggtcaggag ttccagacca gcctggccaa 3481   catagcaaaa cccagtctct actaaaaata caataaaaa aattagccag gtgtggtgac 3541   acatgcctgt aatcccagtt actcaggagg ctgaggcaga attgcttgaa cttgagaggt 3601   ggaggttgta gtgagccaag accgcaccac tgcactccag cctggcgaca gagccagact 3661   ccgtctcaaa aacaacaaca aaaagatta gaagaagccc attactgcct tctggccacc 3721   cactcgcaca gacaccaaaa ctgcagccca cacctcgcca tcctcgtgct ctgccctggg 3781   acaccccagg cacagtgtgt ccttcgtttt ctgtaagggt gggctgggag cagggacgga 3841   cagggcctgt gggcacctct catggtcact tccttcttgc tcacaggagg accaggcctc 3901   atacatctcc ttcaatgcgg cctccaactc gcggtcccaa atcaaggctg ccttggacaa 3961   tgcgggaaag attatgagcc tgactaaaac cgccccgac tacctggtgg gccagcagcc
```

SEQUENCE LISTING
A description of the non-limiting exemplary vectors and the sequences thereof
discussed herein is provided herein below:

```
4021  cgtggaggac atttccagca atcggattta taaaattttg gaactaaacg ggtacgatcc
4081  ccaatatgcg gcttccgtct ttctgggatg ggccacgaaa aagttcggca agaggaacac
4141  catctggctg tttgggcctg caactaccgg gaagaccaac atcgcggagg ccatagccca
4201  cactgtgccc ttctacgggt gcgtaaactg gaccaatgag aactttccct tcaacgactg
4261  tgtcgacaag atggtgatct ggtgggagga ggggaagatg accgccaagg tcgtggagtc
4321  ggccaaagcc attctcggag gaagcaaggt gcgcgtggac cagaaatgca agtcctcggc
4381  ccagatagac ccgactcccg tgatcgtcac ctccaacacc aacatgtgcg ccgtgattga
4441  cgggaactca acgaccttcg aacaccagca gccgttgcaa gaccggatgt tcaaatttga
4501  actcacccgc cgtctggatc atgactttgg gaaggtcacc aagcaggaag tcaaagactt
4561  tttccggtgg gcaaaggatc acgtggttga ggtggagcat gaattctacg tcaaaaaggg
4621  tggagccaag aaaagacccg cccccagtga cgcagatata agtgagccca acgggtgcg
4681  cgagtcagtt gcgcagccat cgacgtcaga cgcggaagct tcgatcaact acgcagacag
4741  gtaccaaaac aaatgttctc gtcacgtggg catgaatctg atgctgtttc cctgcagaca
4801  atgcgagaga atgaatcaga attcaaatat ctgcttcact cacggacaga aagactgttt
4861  agagtgcttt cccgtgtcag aatctcaacc cgtttctgtc gtcaaaaagg cgtatcagaa
4921  actgtgctac attcatcata tcatgggaaa ggtgccagac gcttgcactg cctgcgatct
4981  ggtcaatgtg gatttggatg actgcatctt tgaacaataa atgatttaaa tcaggtatgg
5041  ctgccgatgg ttatcttcca gattggctcg aggacaacct ctctgagggc attcgcgagt
5101  ggtgggacct gaaacctgga gccccgaaac ccaaagccaa ccagcaaaag caggacaacg
5161  gccggggtct ggtgcttcct ggctacaagt acctcggacc cttcaacgga ctcgacaagg
5221  gggagcccgt caacgcggcg gacgcagcgg ccctcgagca cgacaaggcc tacgaccagc
5281  agctccaagc gggtgacaat ccgtacctgc ggtataatca cgccgacgcc gagtttcagg
5341  agcgtctgca agaagatacg tcttttgggg gcaacctcgg gcgcgcagtc ttccaggcca
5401  aaaagcgggt tctcgaacct ctgggcctgg ttgaatcgcc ggttaagatg ctagcggcg
5461  gtaggcgtgt acggtgggag gtctatataa gcagagctct ctggctaact accggtgcca
5521  ccatggcccc aaagaagaag cggaaggtcg gtatccacgg agtcccagca gccaagcgga
5581  actacatcct gggcctggac atcggcatca ccagcgtggg ctacggcatc atcgactacg
5641  agacacggga cgtgatcgat gccggcgtgc ggctgttcaa agaggccaac gtggaaaaca
5701  acgagggcag gcggagcaag agaggcgcca gaaggctgaa gcggcggagg cggcatagaa
5761  tccagagagt gaagaagctg ctgttcgact acaacctgct gaccgaccac agcgagctga
5821  gcggcatcaa cccctacgag gccagagtga agggcctgag ccagaagctg agcgaggaag
5881  agttctctgc cgccctgctg cacctggcca agagaagagg cgtgcacaac gtgaacgagg
5941  tggaagagga caccggcaac gagctgtcca ccaaagagca gatcagccgg aacagcaagg
6001  ccctggaaga gaaatacgtg gccgaactgc agctggaacg gctgaagaaa gacggcgaag
6061  tgcggggcag catcaacaga ttcaagacca gcgactacgt gaaagaagcc aaacagctgc
6121  tgaaggtgca gaaggcctac caccagctgg accagagctt catcgacacc tacatcgacc
6181  tgctggaaac ccggcggacc tactatgagg gacctggcga gggcagcccc ttcggctgga
```

SEQUENCE LISTING
A description of the non-limiting exemplary vectors and the sequences thereof discussed herein is provided herein below:

```
6241  aggacatcaa agaatggtac gagatgctga tgggccactg cacctacttc cccgaggaac
6301  tgcggagcgt gaagtacgcc tacaacgccg acctgtacaa cgccctgaac gacctgaaca
6361  atctcgtgat caccagggac gagaacgaga agctggaata ttacgagaag ttccagatca
6421  tcgagaacgt gttcaagcag aagaagaagc ccaccctgaa gcagatcgcc aaagaaatcc
6481  tcgtgaacga agaggatatt aagggctaca gagtgaccag caccggcaag cccgagttca
6541  ccaacctgaa ggtgtaccac gacatcaagg acattaccgc ccggaaagag attattgaga
6601  acgccgagct gctggatcag attgccaaga tcctgaccat ctaccagagc agcgaggaca
6661  tccaggaaga actgaccaat ctgaactccg agctgaccca ggaagagatc gagcagatct
6721  ctaatctgaa gggctatacc ggcacccaca acctgagcct gaaggccatc aacctgatcc
6781  tggacgagct gtggcacacc aacgacaacc agatcgctat cttcaaccgg ctgaagctgg
6841  tgcccaagaa ggtggacctg tcccagcaga agagatccc caccaccctg gtggacgact
6901  tcatcctgag ccccgtcgtg aagagaagct catccagag catcaaagtg atcaacgcca
6961  tcatcaagaa gtacggcctg cccaacgaca tcattatcga gctggcccgc gagaagaact
7021  ccaaggacgc ccagaaaatg atcaacgaga tgcagaagcg gaaccggcag accaacgagc
7081  ggatcgagga aatcatccgg accaccggca agagaacgc caagtacctg atcgagaaga
7141  tcaagctgca cgacatgcag gaaggcaagt gcctgtacag cctggaagcc atccctctgg
7201  aagatctgct gaacaacccc ttcaactatg aggtggacca catcatcccc agaagcgtgt
7261  ccttcgacaa cagcttcaac aacaaggtgc tcgtgaagca ggaagaaaac agcaagaagg
7321  gcaaccggac cccattccag tacctgagca gcagcgacag caagatcagc tacgaaacct
7381  tcaagaagca catcctgaat ctggccaagg gcaagggcag aatcagcaag accaagaaag
7441  agtatctgct ggaagaacgg gacatcaaca ggttctccgt gcagaaagac ttcatcaacc
7501  ggaacctggt ggataccaga tacgccacca gaggcctgat gaacctgctg cggagctact
7561  tcagagtgaa caacctggac gtgaaagtga agtccatcaa tggcggcttc accagctttc
7621  tgcggcggaa gtggaagttt aagaaagagc ggaacaaggg gtacaagcac cacgccgagg
7681  acgccctgat cattgccaac gccgatttca tcttcaaaga gtggaagaaa ctggacaagg
7741  ccaaaaaagt gatggaaaac cagatgttcg aggaaaagca ggccgagagc atgcccgaga
7801  tcgaaaccga gcaggagtac aaagagatct tcatcacccc caccagatc aagcacatta
7861  aggacttcaa ggactacaag tacagccacc gggtggacaa gaagcctaat agagagctga
7921  ttaacgacac cctgtactcc acccggaagg acgacaaggg caacaccctg atcgtgaaca
7981  atctgaacgg cctgtacgac aaggacaatg acaagctgaa aaagctgatc aacaagagcc
8041  ccgaaaagct gctgatgtac caccacgacc cccagaccta ccagaaactg aagctgatta
8101  tggaacagta cggcgacgag aagaatcccc tgtacaagta ctacgaggaa accgggaact
8161  acctgaccaa gtactccaaa aaggacaacg gccccgtgat caagaagatt aagtattacg
8221  gcaacaaact gaacgcccat ctggacatca ccgacgacta ccccaacagc agaaacaagg
8281  tcgtgaagct gtccctgaag ccctacagat tcgacgtgta cctggacaat ggcgtgtaca
8341  agttcgtgac cgtgaagaat ctggatgtga tcaaaaaaga aaactactac gaagtgaata
8401  gcaagtgcta tgaggaagct aagaagctga aagaagatcag caaccaggcc gagtttatcg
8461  cctccttcta caacaacgat ctgatcaaga tcaacggcga gctgtataga gtgatcggcg
```

SEQUENCE LISTING
A description of the non-limiting exemplary vectors and the sequences thereof
discussed herein is provided herein below:

```
8521   tgaacaacga cctgctgaac cggatcgaag tgaacatgat cgacatcacc taccgcgagt
8581   acctggaaaa catgaacgac aagaggcccc ccaggatcat taagacaatc gcctccaaga
8641   cccagagcat taagaagtac agcacagaca ttctgggcaa cctgtatgaa gtgaaatcta
8701   agaagcaccc tcagatcatc aaaaagggca gcggcttcgc caacgagctg ggccctagac
8761   tgatgggaaa gatgcataga ccgtagagc catcacccca gcgctctcca gactcctcta
8821   cgggcatcgg caagaaaggc cagcagcccg caaaaaagag actcaatttt gggcagactg
8881   gcgactcaga gtcagtcccc gaccctcaac caatcggaga accaccagca ggcccctctg
8941   gtctgggatc tggtacaatg gctgcaggcg gtggcgctcc aatggcagac aataacgaag
9001   gcgccgacgg agtgggtagt tcctcaggaa attggcattg cgattccaca tggctgggcg
9061   acagagtcat caccaccagc acccgcacct gggccctgcc cacctacaac aaccacctct
9121   acaagcaaat ctccaacggg acctcgggag aagcaccaa cgacaacacc tacttcggct
9181   acagcacccc ctgggggtat tttgacttca acagattcca ctgccacttt tcaccacgtg
9241   actggcagcg actcatcaac aacaactggg gattccggcc caagaggctc aacttcaagc
9301   tcttcaacat ccaagtcaag gaggtcacgc agaatgaagg caccaagacc atcgccaata
9361   accttaccag cacgattcag gtctttacgg actcggaata ccagctcccg tacgtgctcg
9421   gctcggcgca ccagggctgc ctgcctccgt tcccggcgga cgtcttcatg attcctcagt
9481   acgggtacct gactctgaac aatggcagtc aggctgtggg ccggtcgtcc ttctactgcc
9541   tggagtactt tccttctcaa atgctgagaa cgggcaacaa ctttgaattc agctacaact
9601   tcgaggacgt gcccttccac agcagctacg cgcacagcca gagcctggac cggctgatga
9661   accctctcat cgaccagtac ttgtactacc tgtcccggac tcaaagcacg ggcggtactg
9721   caggaactca gcagttgcta ttttctcagg ccgggcctaa caacatgtcg gctcaggcca
9781   agaactggct acccggtccc tgctaccggc agcaacgcgt ctccacgaca ctgtcgcaga
9841   acaacaacag caactttgcc tggacgggtg ccaccaagta tcatctgaat ggcagagact
9901   ctctggtgaa tcctggcgtt gccatggcta cccacaagga cgacgaagag cgatttttc
9961   catccagcgg agtcttaatg tttgggaaac agggagctgg aaaagacaac gtggactata
10021  gcagcgtgat gctaaccagc gaggaagaaa taaagaccac caaccagtg gccacagaac
10081  agtacggcgt ggtggccgat aacctgcaac agcaaaacgc cgctcctatt gtaggggccg
10141  tcaatagtca aggagcctta cctggcatgg tgtggcagaa ccgggacgtg tacctgcagg
10201  gtcccatctg gccaagatt cctcatacgg acggcaactt tcatccctcg ccgctgatgg
10261  gaggctttgg actgaagcat ccgcctcctc agatcctgat taaaaacaca cctgttcccg
10321  cggatcctcc gaccaccttc agcaggcca agctggcttc tttcatcacg cagtacagta
10381  ccggccaggt cagcgtggag atcgagtggg agctgcagaa ggagaacagc aaacgctgga
10441  acccagagat tcagtacact tccaactact acaaatctac aaatgtggac tttgctgtca
10501  atactgaggg tacttattcc gagcctcgcc ccattggcac ccgttacctc acccgtaatc
10561  tgtaattaca tgttaatcaa taaaccggtt aattcgtttc agttgaactt tggtctcctg
10621  tccttcttat cttatcggtt accatagaaa ctggttactt attaactgct tggtgcgctt
10681  cgcgataaaa gacttacgtc atcgggttac ccctagtgat ggagcggccg ctttcagttg
```

SEQUENCE LISTING
A description of the non-limiting exemplary vectors and the sequences thereof
discussed herein is provided herein below:

```
10741  aactttggtc tctgcgtatt tctttcttat ctagtttcca tgctctagag gtcctgtatt
10801  agaggtcacg tgagtgtttt gcgacatttt gcgacaccat gtggtcacgc tgggtattta
10861  agcccgagtg agcacgcagg gtctccattt tgaagcggga ggtttgaacg cgcagccgcc
10921  aagccgaatt ctgcagatat ccatcacact ggcggccgct cgactagagc ggccgccacc
10981  gcggtggagc tccagctttt gttcccttta gtgagggtta attgcgcgct tggcgtaatc
11041  atggtcatag ctgtttcctg tgtgaaattg ttatccgctc acaattccac acaacatacg
11101  agccggaagc ataaagtgta aagcctgggg tgcctaatga gtgagctaac tcacattaat
11161  tgcgttgcgc tcactgcccg ctttccagtc gggaaacctg tcgtgccagc tgcattaatg
11221  aatcggccaa cgcgcgggga gaggcggttt gcgtattggg cgctcttccg cttcctcgct
11281  cactgactcg ctgcgctcgg tcgttcggct gcggcgagcg gtatcagctc actcaaaggc
11341  ggtaatacgg ttatccacag aatcagggga taacgcagga agaacatgt gagcaaaagg
11401  ccagcaaaag gccaggaacc gtaaaaaggc cgcgttgctg gcgtttttcc ataggctccg
11461  ccccectgac gagcatcaca aaaatcgacg ctcaagtcag aggtggcgaa acccgacagg
11521  actataaaga taccaggcgt ttccccctgg aagctccctc gtgcgctctc ctgttccgac
11581  cctgccgctt accggatacc tgtccgcctt tctcccttcg ggaagcgtgg cgctttctca
11641  tagctcacgc tgtaggtatc tcagttcggt gtaggtcgtt cgctccaagc tgggctgtgt
11701  gcacgaaccc cccgttcagc ccgaccgctg cgccttatcc ggtaactatc gtcttgagtc
11761  caacccggta agacacgact tatcgccact ggcagcagcc actggtaaca ggattagcag
11821  agcgaggtat gtaggcggtg ctacagagtt cttgaagtgg tggcctaact acggctacac
11881  tagaagaaca gtatttggta tctgcgctct gctgaagcca gttaccttcg gaaaaagagt
11941  tggtagctct tgatccggca acaaaccac cgctggtagc ggtggttttt ttgtttgcaa
12001  gcagcagatt acgcgcagaa aaaaaggatc tcaagaagat cctttgatct tttctacggg
12061  gtctgacgct cagtggaacg aaaactcacg ttaagggatt ttggtcatga gattatcaaa
12121  aaggatcttc acctagatcc ttttaaatta aaaatgaagt tttaaatcaa tctaaagtat
12181  atatgagtaa acttggtctg acagttacca atgcttaatc agtgaggcac ctatctcagc
12241  gatctgtcta tttcgttcat ccatagttgc ctgactcccc gtcgtgtaga taactacgat
12301  acgggagggc ttaccatctg gccccagtgc tgcaatgata ccgcgagacc cacgctcacc
12361  ggctccagat ttatcagcaa taaaccagcc agccggaagg gccgagcgca gaagtggtcc
12421  tgcaacttta tccgcctcca tccagtctat taattgttgc cgggaagcta gagtaagtag
12481  ttcgccagtt aatagtttgc gcaacgttgt tgccattgct acaggcatcg tggtgtcacg
12541  ctcgtcgttt ggtatggctt cattcagctc cggttcccaa cgatcaaggc gagttacatg
12601  atcccccatg ttgtgcaaaa aagcggttag ctccttcggt cctccgatcg ttgtcagaag
12661  taagttggcc gcagtgttat cactcatggt tatggcagca ctgcataatt ctcttactgt
12721  catgccatcc gtaagatgct tttctgtgac tggtgagtac tcaaccaagt cattctgaga
12781  atagtgtatg cggcgaccga gttgctcttg cccggcgtca atacgggata taccgcgcc
12841  acatagcaga actttaaaag tgctcatcat tggaaaacgt tcttcggggc gaaaactctc
12901  aaggatctta ccgctgttga gatccagttc gatgtaaccc actcgtgcac ccaactgatc
12961  ttcagcatct tttactttca ccagcgtttc tgggtgagca aaaacaggaa ggcaaaatgc
```

SEQUENCE LISTING
A description of the non-limiting exemplary vectors and the sequences thereof
discussed herein is provided herein below:

```
13021  cgcaaaaaag ggaataaggg cgacacggaa atgttgaata ctcatactct tccttttca
13081  atattattga agcatttatc agggttattg tctcatgagc ggatacatat ttgaatgtat
13141  ttagaaaaat aaacaaatag gggttccgcg cacatttccc cgaaaagtgc cacctaaatt
13201  gtaagcgtta atattttgtt aaaattcgcg ttaaatttt gttaaatcag ctcatttttt
13261  aaccaatagg ccgaaatcgg caaatccct tataaatcaa agaatagac cgagataggg
13321  ttgagtgttg ttccagtttg gaacaagagt ccactattaa agaacgtgga ctccaacgtc
13381  aaagggcgaa aaaccgtcta tcagggcgat ggcccactac gtgaaccatc accctaatca
13441  agttttttgg ggtcgaggtg ccgtaaagca ctaaatcgga accctaaagg gagcccccga
13501  tttagagctt gacggggaaa gccggcgaac gtggcgagaa aggaaggaa gaaagcgaaa
13561  ggagcgggcg ctagggcgct ggcaagtgta gcggtcacgc tgcgcgtaac caccacaccc
13621  gccgcgctta atgcgccgct acagggcgcg tcccattcgc cattcaggct gcgcaactgt
13681  tgggaagggc gatcggtgcg ggcctcttcg ctattacgcc agctggcgaa aggggatgt
13741  gctgcaaggc gattaagttg ggtaacgcca gggttttccc agtcacgacg ttgtaaaacg
13801  acggccagtg agcgcgcgta atacgactca ctatagggcg aattgggtac
```

Staph aureus Cas9 (saCas9)
(SEQ ID NO: 3)
GGRRVRWEVYISRALWLTTGATMAPKKKRKVGIHGVPAAKRNYILGLDIGITSVGY
GIIDYETRDVIDAGVRLFKEANVENNEGRRSKRGARRLKRRRRHRIQRVKKLLFDYN
LLTDHSELSGINPYEARVKGLSQKLSEEEFSAALLHLAKRRGVHNVNEVEEDTGNEL
STKEQISRNSKALEEKYVAELQLERLKKDGEVRGSINRFKTSDYVKEAKQLLKVQKA
YHQLDQSFIDTYIDLLETRRTYYEGPGEGSPFGWKDIKEWYEMLMGHCTYFPEELRS
VKYAYNADLYNALNDLNNLVITRDENEKLEYYEKFQIIENVFKQKKKPTLKQIAKEI
LVNEEDIKGYRVTSTGKPEFTNLKVYHDIKDITARKEIIENAELLDQIAKILTIYQSSED
IQEELTNLNSELTQEEIEQISNLKGYTGTHNLSLKAINLILDELWHTNDNQIAIFNRLKL
VPKKVDLSQQKEIPTTLVDDFILSPVVKRSFIQSIKVINAIIKKYGLPNDIIIELAREKNS
KDAQKMINEMQKRNRQTNERIEEIIRTTGKENAKYLIEKIKLHDMQEGKCLYSLEMP
LEDLLNNPFNYEVDHIIPRSVSFDNSFNNKVLVKQEENSKKGNRTPFQYLSSSDSKISY
ETFKKHILNLAKGKGRISKTKKEYLLEERDINRFSVQKDFINRNLVDTRYATRGLMN
LLRSYFRVNNLDVKVKSINGGFTSFLRRKWKFKKERNKGYKHHAEDALIIANADFIF
KEWKKLDKAKKVMENQMFEEKQAESMPEIETEQEYKEIFITPHQIKHIKDFKDYKYS
HRVDKKPNRELINDTLYSTRKDDKGNTLIVNNLNGLYDKDNDKLKKLINKSPEKLL
MYHHDPQTYQKLKLIMEQYGDEKNPLYKYYEETGNYLTKYSKKDNGPVIKKIKYY
GNKLNAHLDITDDYPNSRNKVVKLSLKPYRFDVYLDNGVYKFVTVKNLDVIKKENY
YEVNSKCYEEAKKLKKISNQAEFIASFYNNDLIKINGELYRVIGVNNDLLNRIEVNMI
DITYREYLENMNDKRPPRIIKTIASKTQSIKKYSTDILGNLYEVKSKKEEPQIIKKGSGFA
NELGPRLMGK pAAVrh74-VP1-3

LOCUS           pAAVrh74-VP1-3 10538 bp DNA circular SYN 19-SEP-2016
DEFINITION      Knocks out VP2 expression, 5448 A-G
ACCESSION       pAAVrh74-VP1-3
REFERENCE       1 (bases 1 to 10538)
FEATURES        Location/Qualifiers
misc_feature    84..815
                /note = "Rep78 5"
misc_feature    756..815
                /note = "Rep52 5"
misc_feature    816..3886
                /note = "Human Collagen Intron"
misc_feature    3887..5017
                /note = "Rep52 3"
```

SEQUENCE LISTING
A description of the non-limiting exemplary vectors and the sequences thereof discussed herein is provided herein below:

```
misc_feature      3887..5017
                  /note = "Rep78 3"

misc_feature      4534..4686
                  /gene = "p40"

misc_feature      4741..4742
                  /note = "splice donor"

misc_feature      4741..5061
                  /note = "Rep INTRON"

misc_feature      5033..5034
                  /note = "splice acceptor"

CDS               5037. 7253
                  /gene = "VP1"

misc_feature      5060..5061
                  /note = "splice acceptor"

CDS               5646..7253
                  /gene = "VP3"

misc_feature      complement(7254..7411)
                  /note = "3' UTR"

misc_feature      7428..7507
                  /note = "p5 Promoter"

CDS               complement(8893..9753)
                  /gene = "amp"

ORIGIN (SEQ ID NO: 4)
    1  cgggcccccc ctcgaggtcg acggtatcgg gggagctcgc agggtctcca ttttgaagcg
   61  ggaggtttga acgcgcagcc gccatgccgg ggttttacga gattgtgatt aaggtcccca
  121  gcgaccttga cgagcatctg cccggcattt ctgacagctt tgtgaactgg gtggccgaga
  181  aggaatggga gttgccgcca gattctgaca tggatctgaa tctgattgag caggcaccc
  241  tgaccgtggc cgagaagctg cagcgcgact ttctgacgga atggcgccgt gtgagtaagg
  301  ccccggaggc tcttttcttt gtgcaatttg agaagggaga gagctacttc cacatgcacg
  361  tgctcgtgga aaccaccggg gtgaaatcca tggttttggg acgtttcctg agtcagattc
  421  gcgaaaaact gattcagaga atttaccgcg ggatcgagcc gactttgcca aactggttcg
  481  cggtcacaaa gaccagaaat ggcgccggag gcgggaacaa ggtggtggat gagtgctaca
  541  tccccaatta cttgctcccc aaaacccagc tgagctcca gtgggcgtgg actaatatgg
  601  aacagtattt aagcgcctgt ttgaatctca cggagcgtaa acggttggtg gcgcagcatc
  661  tgacgcacgt gtcgcagacg caggagcaga acaaagagaa tcagaatccc aattctgatg
  721  cgccggtgat cagatcaaaa acttcagcca ggtacatgga gctggtcggg tggctcgtgg
  781  acaaggggat tacctcggag aagcagtgga tccaggtgag taattgacaa agccaaacac
  841  caccatttgc cgagcacttt agagtttaca ggtttgtttc tcttgaccct caaaacaaac
  901  ctgtgaggca tagggagtat tgctatccct taagaattca cccccagtgt gcccatcaaa
  961  acctcccagg ctgagtctgc acagttgaag gaggaaggat aggaatggga gggtcgatgg
 1021  gtgaaagcat gattctctta accagtccag attatcaggt aatcccttca acaaccacca
 1081  cccactccct gggcaatcca gctggagttt acagacagac ttagctggct atagcaccac
 1141  cgtgctactc tctgttcttc ctggttgctc aaatgcccta gaaaagtgga acaggtgagc
```

```
1201  atcaactcac agggctctat gctggctgct gctgcgaggg atgttatgct atagtaccag
1261  gggccaccat tccataggca cttcctgtgt ttaatacccct atatgcttta cttcatctca
1321  tcttcctcca tatcctgaga ggtggttcta ttcttctccc cattttacgg atgaaaaaac
1381  cgagacacag aaaggtgaaa tagcttaaga taaatggtgc cttgcagcct tagactctgg
1441  tggcctctag ttaatgtggg aaattaaggg tgaggggatt ggcagctgat ggagggtgca
1501  gggtgccaga cagaggcgtt tagctctgat cccttagcaa tagagagtcc ttgtaggcac
1561  ttggtcaggc gagtgatgcg atgaaagctg tgtttaagaa agattatgct ttctgctgat
1621  ttcatacccc caacacccaa gctctgaggc ccctcctcac aggtccttgc agggctggcc
1681  aaaataaagc agcttcactc cgttgtgctg ctttccagct aatgtgtctg tttggcagaa
1741  gtttccctca aaggcagatc agtgaaataa gcagaagcct cgaccccccct ttgtcagcca
1801  gagctgctga agtgccttgc cccagggtca ctttgtgtga ggggattaga gagcactggg
1861  gctgccaaga aacactgccg tttctacaga ttagcaggac gctggcttgt ggccttctag
1921  cgaggctcag agctgcggtg gcccccagtct gcatgggcta aagacaagct ccatctcctg
1981  tccttgttcc ctccttcctg ggcacagccg ccctgcttct tggttctctc tgttggttcc
2041  tgtccgcacg gtagttaggc tggcagcgtg tgtaggattt ggcttagaag attgacaaca
2101  ttgcctttga gcccttcttt gctactcctc cctctcccct cccatcagac tcctctctgg
2161  agtctgctct gcgaggcctc tgctctgtgg tatcccagca gccttctcag ccttgacttc
2221  cagaaggggg ctgtgcagtg tccggggtgt gcaggcccca gacacggggt aggctcatgg
2281  agatccaagt gctgatctag tgtcaaggct ggcctggaga ctgggctggg ttggtgtctg
2341  cctgctgtgg tcatgtgccc tcccttgggc ctgtatcctc tctccagact tgctgcaggg
2401  agaggtggca gatgtcagcc tagttctggc ctctcagagc agcatggcag ctccctttca
2461  ctcaggccca ggctgggccc tcctgctggc tgaccccctgg ggagagggtg ctccagagct
2521  ccccaaggaa cagcttcccg aagcagccag gccagcccag aggggctgtg gccaatcctg
2581  aagctttatg ttcctgctga catttttttct aagttttctc ttgctttcct cttaaatgcc
2641  aatctggaga gtctccgtta ggagaaatgg acccccagcca ggaagaagag ttgagttgta
2701  tttaaaacac gagctcccccc taaagcatcc ttctttagct tctaaggaga ggcagagact
2761  gacaggcagg actcagcagg aaaaggtacc cccctgacct gctcagtcag gccctaggcc
2821  cagctccacc cagcctgtgg cccccagagt ttcggtaaag agttccctgg gccttaagga
2881  accttgagag agcatttgag gggtgccacc acaaacttgg cagaaaaaac cctccccctc
2941  caagtccagt cctagagaag gagctggcaa ccttgccttg ctttgtaagc aaaagcctct
3001  tagggcttga gctcagatgt agtgtttgag ctgtggctgg tgccctgccc catcagggag
3061  ccaatggtag acatcctatg ggcatctttg ttttccgtaa gagcaggctg tctggggatg
3121  ggccagagga agaggcgacc tggagtcaac caagaggagg ccttaaccaa gccttaacca
3181  cagaggttaa ccaagccttg aaagcgcttc cccctgagca ggcaggaagc actgagtcca
3241  catggttgcc tcgctgtttc atttccttac actcaattct ctcagtcttt aaatgatcac
3301  ttggccttga agttacggat atttggggtc tgaactgaag ttgaagaaaa gaggaaatga
3361  tttaagcttt gtttaagatt aggggccagg tgcggtggct cacgcctgta atcccagcac
3421  cttgggagcc tgaggcgggt ggatcacctg aggtcaggag ttccagacca gcctggccaa
```

```
3481  catagcaaaa cccagtctct actaaaaata acaataaaaa aattagccag gtgtggtgac
3541  acatgcctgt aatcccagtt actcaggagg ctgaggcaga attgcttgaa cttgagaggt
3601  ggaggttgta gtgagccaag accgcaccac tgcactccag cctggcgaca gagccagact
3661  ccgtctcaaa acaacaaca aaaagatta gaagaagccc attactgcct tctggccacc
3721  cactcgcaca gacaccaaaa ctgcagccca cacctcgcca tcctcgtgct ctgccctggg
3781  acaccccagg cacagtgtgt ccttcgtttt ctgtaagggt gggctgggag cagggacgga
3841  cagggcctgt gggcacctct catggtcact tccttcttgc tcacaggagg accaggcctc
3901  atacatctcc ttcaatgcgg cctccaactc gcggtcccaa atcaaggctg ccttggacaa
3961  tgcgggaaag attatgagcc tgactaaaac cgcccccgac tacctggtgg gccagcagcc
4021  cgtggaggac atttccagca atcggattta taaaattttg gaactaaacg ggtacgatcc
4081  ccaatatgcg gcttccgtct ttctgggatg gccacgaaa aagttcggca agaggaacac
4141  catctggctg tttgggcctg caactaccgg gaagaccaac atcgcggagg ccatagccca
4201  cactgtgccc ttctacgggt gcgtaaactg gaccaatgag aactttccct tcaacgactg
4261  tgtcgacaag atggtgatct ggtgggagga gggaagatg accgccaagg tcgtggagtc
4321  ggccaaagcc attctcggag gaagcaaggt gcgcgtggac cagaaatgca agtcctcggc
4381  ccagatagac ccgactcccg tgatcgtcac ctccaacacc aacatgtgcg ccgtgattga
4441  cgggaactca acgaccttcg aacaccagca gccgttgcaa gaccggatgt tcaaatttga
4501  actcacccgc cgtctggatc atgactttgg gaaggtcacc aagcaggaag tcaaagactt
4561  tttccggtgg gcaaaggatc acgtggttga ggtggagcat gaattctacg tcaaaaaggg
4621  tggagccaag aaaagacccg cccccagtga cgcagatata agtgagccca acgggtgcg
4681  cgagtcagtt gcgcagccat cgacgtcaga cgcggaagct tcgatcaact acgcagacag
4741  gtaccaaaac aaatgttctc gtcacgtggg catgaatctg atgctgtttc cctgcagaca
4801  atgcgagaga atgaatcaga attcaaatat ctgcttcact cacggacaga aagactgttt
4861  agagtgcttt cccgtgtcag aatctcaacc cgtttctgtc gtcaaaaagg cgtatcagaa
4921  actgtgctac attcatcata tcatgggaaa ggtgccagac gcttgcactg cctgcgatct
4981  ggtcaatgtg gatttggatg actgcatctt tgaacaataa atgatttaaa tcaggtatgg
5041  ctgccgatgg ttatcttcca gattggctcg aggacaacct ctctgagggc attcgcgagt
5101  ggtgggacct gaaacctgga gccccgaaac ccaaagccaa ccagcaaaag caggacaacg
5161  gccggggtct ggtgcttcct ggctacaagt acctcggacc cttcaacgga ctcgacaagg
5221  gggagcccgt caacgcggcg gacgcagcgg ccctcgagca cgacaaggcc tacgaccagc
5281  agctccaagc gggtgacaat ccgtacctgc ggtataatca cgccgacgcc gagtttcagg
5341  agcgtctgca agaagatacg tcttttgggg gcaacctcgg gcgcgcagtc ttccaggcca
5401  aaaagcgggt tctcgaacct ctgggcctgg ttgaatcgcc ggttaaggcg gctcctggaa
5461  agaagagacc ggtagagcca tcaccccagc gctctccaga ctcctctacg ggcatcggca
5521  agaaaggcca gcagcccgca aaaagagac tcaattttgg gcagactggc gactcagagt
5581  cagtccccga ccctcaacca atcggagaac caccagcagg cccctctggt ctgggatctg
5641  gtacaatggc tgcaggcggt ggcgctccaa tggcagacaa taacgaaggc gccgacggag
```

SEQUENCE LISTING
A description of the non-limiting exemplary vectors and the sequences thereof
discussed herein is provided herein below:

```
5701  tgggtagttc ctcaggaaat tggcattgcg attccacatg gctgggcgac agagtcatca
5761  ccaccagcac ccgcacctgg gccctgccca cctacaacaa ccacctctac aagcaaatct
5821  ccaacgggac ctcgggagga agcaccaacg acaacaccta cttcggctac agcaccccct
5881  gggggtattt tgacttcaac agattccact gccacttttc accacgtgac tggcagcgac
5941  tcatcaacaa caactgggga ttccggccca agaggctcaa cttcaagctc ttcaacatcc
6001  aagtcaagga ggtcacgcag aatgaaggca ccaagaccat cgccaataac cttaccagca
6061  cgattcaggt ctttacggac tcggaatacc agctcccgta cgtgctcggc tcggcgcacc
6121  agggctgcct gcctccgttc ccggcggacg tcttcatgat tcctcagtac gggtacctga
6181  ctctgaacaa tggcagtcag gctgtgggcc ggtcgtcctt ctactgcctg gagtactttc
6241  cttctcaaat gctgagaacg ggcaacaact ttgaattcag ctacaacttc gaggacgtgc
6301  ccttccacag cagctacgcg cacagccaga gcctggaccg gctgatgaac cctctcatcg
6361  accagtactt gtactacctg tcccggactc aaagcacggg cggtactgca ggaactcagc
6421  agttgctatt ttctcaggcc gggcctaaca acatgtcggc tcaggccaag aactggctac
6481  ccggtccctg ctaccggcag caacgcgtct ccacgacact gtcgcagaac aacaacagca
6541  actttgcctg gacgggtgcc accaagtatc atctgaatgg cagagactct ctggtgaatc
6601  ctggcgttgc catggctacc cacaaggacg acgaagagcg attttttcca tccagcggag
6661  tcttaatgtt tgggaaacag ggagctggaa aagacaacgt ggactatagc agcgtgatgc
6721  taaccagcga ggaagaaata aagaccacca acccagtggc cacagaacag tacggcgtgg
6781  tggccgataa cctgcaacag caaaacgccg ctcctattgt aggggccgtc aatagtcaag
6841  gagccttacc tggcatggtg tggcagaacc gggacgtgta cctgcagggt cccatctggg
6901  ccaagattcc tcatacggac ggcaactttc atcctcgcc gctgatggga ggctttggac
6961  tgaagcatcc gcctcctcag atcctgatta aaaacacacc tgttcccgcg gatcctccga
7021  ccaccttcag ccaggccaag ctggcttctt tcatcacgca gtacagtacc ggccaggtca
7081  gcgtggagat cgagtgggag ctgcagaagg agaacagcaa acgctggaac ccagagattc
7141  agtacacttc caactactac aaatctacaa atgtggactt tgctgtcaat actgagggta
7201  cttattccga gcctcgcccc attggcaccc gttacctcac ccgtaatctg taattacatg
7261  ttaatcaata aaccggttaa ttcgtttcag ttgaactttg gtctcctgtc cttcttatct
7321  tatcggttac catagaaact ggttacttat taactgcttg gtgcgcttcg cgataaaaga
7381  cttacgtcat cgggttaccc ctagtgatgg agcggccgct ttcagttgaa ctttggtctc
7441  tgcgtatttc tttcttatct agtttccatg ctctagaggt cctgtattag aggtcacgtg
7501  agtgttttgc gacattttgc gacaccatgt ggtcacgctg ggtatttaag cccgagtgag
7561  cacgcagggt ctccattttg aagcgggagg tttgaacgcg cagccgccaa gccgaattct
7621  gcagatatcc atcacactgg cggccgctcg actagagcgg ccgccaccgc ggtggagctc
7681  cagcttttgt tccctttagt gagggttaat tgcgcgcttg gcgtaatcat ggtcatagct
7741  gtttcctgtg tgaaattgtt atccgctcac aattccacac aacatacgag ccggaagcat
7801  aaagtgtaaa gcctggggtg cctaatgagt gagctaactc acattaattg cgttgcgctc
7861  actgcccgct ttccagtcgg gaaacctgtc gtgccagctg cattaatgaa tcggccaacg
7921  cgcggggaga ggcggtttgc gtattgggcg ctcttccgct tcctcgctca ctgactcgct
```

SEQUENCE LISTING
A description of the non-limiting exemplary vectors and the sequences thereof discussed herein is provided herein below:

```
7981 gcgctcggtc gttcggctgc ggcgagcggt atcagctcac tcaaaggcgg taatacggtt
8041 atccacagaa tcaggggata acgcaggaaa gaacatgtga gcaaaaggcc agcaaaaggc
8101 caggaaccgt aaaaaggccg cgttgctggc gtttttccat aggctccgcc cccctgacga
8161 gcatcacaaa aatcgacgct caagtcagag gtggcgaaac ccgacaggac tataaagata
8221 ccaggcgttt ccccctggaa gctccctcgt gcgctctcct gttccgaccc tgccgcttac
8281 cggatacctg tccgcctttc tcccttcggg aagcgtggcg ctttctcata gctcacgctg
8341 taggtatctc agttcggtgt aggtcgttcg ctccaagctg gctgtgtgc acgaaccccc
8401 cgttcagccc gaccgctgcg ccttatccgg taactatcgt cttgagtcca acccggtaag
8461 acacgactta tcgccactgg cagcagccac tggtaacagg attagcagag cgaggtatgt
8521 aggcggtgct acagagttct tgaagtggtg gcctaactac ggctacacta agaacagt
8581 atttggtatc tgcgctctgc tgaagccagt taccttcgga aaagagttg gtagctcttg
8641 atccggcaaa caaaccaccg ctggtagcgg tggtttttt gtttgcaagc agcagattac
8701 gcgcagaaaa aaaggatctc aagaagatcc tttgatcttt tctacggggt ctgacgctca
8761 gtggaacgaa aactcacgtt aagggatttt ggtcatgaga ttatcaaaaa ggatcttcac
8821 ctagatcctt ttaaattaaa aatgaagttt taaatcaatc taagtatat atgagtaaac
8881 ttggtctgac agttaccaat gcttaatcag tgaggcacct atctcagcga tctgtctatt
8941 tcgttcatcc atagttgcct gactccccgt cgtgtagata actacgatac gggagggctt
9001 accatctggc cccagtgctg caatgatacc gcgagaccca cgctcaccgg ctccagattt
9061 atcagcaata aaccagccag ccggaagggc cgagcgcaga agtggtcctg caactttatc
9121 cgcctccatc cagtctatta attgttgccg ggaagctaga gtaagtagtt cgccagttaa
9181 tagtttgcgc aacgttgttg ccattgctac aggcatcgtg gtgtcacgct cgtcgtttgg
9241 tatggcttca ttcagctccg gttcccaacg atcaaggcga gttacatgat cccccatgtt
9301 gtgcaaaaaa gcggttagct ccttcggtcc tccgatcgtt gtcagaagta agttggccgc
9361 agtgttatca ctcatggtta tggcagcact gcataattct cttactgtca tgccatccgt
9421 aagatgcttt tctgtgactg gtgagtactc aaccaagtca ttctgagaat agtgtatgcg
9481 gcgaccgagt tgctcttgcc cggcgtcaat acgggataat accgcgccac atagcagaac
9541 tttaaaagtg ctcatcattg gaaaacgttc ttcggggcga aaactctcaa ggatcttacc
9601 gctgttgaga tccagttcga tgtaacccac tcgtgcaccc aactgatctt cagcatcttt
9661 tactttcacc agcgtttctg ggtgagcaaa aacaggaagg caaaatgccg caaaaaaggg
9721 aataagggcg acacggaaat gttgaatact catactcttc cttttcaat attattgaag
9781 catttatcag ggttattgtc tcatgagcgg atacatattt gaatgtattt agaaaaataa
9841 acaaataggg gttccgcgca catttccccg aaaagtgcca cctaaattgt aagcgttaat
9901 attttgttaa aattcgcgtt aaattttgt taaatcagct cattttttaa ccaataggcc
9961 gaaatcggca aaatccctta taatcaaaa gaatagaccg agatagggtt gagtgttgtt
10021 ccagtttgga acaagagtcc actattaaag aacgtggact ccaacgtcaa agggcgaaaa
10081 accgtctatc agggcgatgg cccactacgt gaaccatcac cctaatcaag ttttttgggg
10141 tcgaggtgcc gtaaagcact aaatcggaac cctaaaggga gcccccgatt tagagcttga
```

```
                              SEQUENCE LISTING
        A description of the non-limiting exemplary vectors and the sequences thereof
                     discussed herein is provided herein below:

10201   cggggaaagc cggcgaacgt ggcgagaaag gaagggaaga aagcgaaagg agcgggcgct 10261   agggcgctgg caagtgtagc ggtcacgctg cgcgtaacca ccacaccgc cgcgcttaat 10321   gcgccgctac agggcgcgtc ccattcgcca ttcaggctgc gcaactgttg ggaagggcga 10381   tcggtgcggg cctcttcgct attacgccag ctggcgaaag ggggatgtgc tgcaaggcga 10441   ttaagttggg taacgccagg gttttcccag tcacgacgtt gtaaaacgac ggccagtgag 10501   cgcgcgtaat acgactcact atagggcgaa ttgggtac
``` pAAVrh74-Cas9-VP2

| | |
|---|---|
| LOCUS | pAAVrh74-Cas9-VP 13859 bp DNA circular SYN 09-MAR-2017 |
| REFERENCE | 1 (bases 1 to 13859) |
| FEATURES | Location/Qualifiers |
| misc_feature | 84..815<br>/note = "Rep68 5" |
| misc_feature | 84..815<br>/note = "Rep78 5" |
| misc_feature | 756..815<br>/note = "Rep40 5" |
| misc_feature | 756..815<br>/note = "Rep52 5" |
| misc_feature | 816..3886<br>/note = "Human Collagen Intron" |
| misc_feature | 3887..5017<br>/note = "Rep52 3" |
| misc_feature | 3887..5017<br>/note = "Rep78 3" |
| misc_feature | 4534..4686<br>/gene = "p40 pro" |
| misc_feature | 4741..4742<br>/note = "splice donor" |
| misc_feature | 4741..5061<br>/note = "Rep INTRON" |
| misc_feature | 5033..5034<br>/note = "splice acceptor" |
| misc_feature | 5060..5061<br>/note = "splice acceptor" |
| misc_feature | 5084..5086<br>/note = "Rep 68/40 stop" |
| CDS | 5532..8781<br>/gene = "saCas9" |
| misc_feature | 8739..8780<br>/product = "OLLAS tag epitope tag" |
| CDS | 8786..10574<br>/gene = "rh74 cap"<br>/codon_start = 3<br>/translation = "DR" |
| misc_feature | complement(10575..10732)<br>/note = "3' UTR" |
| misc_feature | 10749..10828<br>/note = "p5 Promoter" |

SEQUENCE LISTING
A description of the non-limiting exemplary vectors and the sequences thereof discussed herein is provided herein below:

```
CDS             complement(12214..13074)
                /gene = "amp"

ORIGIN (SEQ ID NO: 5)
     1  cgggccccc  ctcgaggtcg  acggtatcgg  gggagctcgc  agggtctcca  ttttgaagcg
    61  ggaggtttga  acgcgcagcc  gccatgccgg  ggttttacga  gattgtgatt  aaggtcccca
   121  gcgaccttga  cgagcatctg  cccggcattt  ctgacagctt  tgtgaactgg  gtggccgaga
   181  aggaatggga  gttgccgcca  gattctgaca  tggatctgaa  tctgattgag  caggcacccc
   241  tgaccgtggc  cgagaagctg  cagcgcgact  ttctgacgga  atggcgccgt  gtgagtaagg
   301  ccccggaggc  tcttttcttt  gtgcaatttg  agaagggaga  gagctacttc  cacatgcacg
   361  tgctcgtgga  aaccaccggg  gtgaaatcca  tggttttggg  acgtttcctg  agtcagattc
   421  gcgaaaaact  gattcagaga  atttaccgcg  ggatcgagcc  gactttgcca  aactggttcg
   481  cggtcacaaa  gaccagaaat  ggcgccggag  gcgggaacaa  ggtggtggat  gagtgctaca
   541  tcccccaatta  cttgctcccc  aaaacccagc  ctgagctcca  gtgggcgtgg  actaatatgg
   601  aacagtattt  aagcgcctgt  ttgaatctca  cggagcgtaa  acggttggtg  gcgcagcatc
   661  tgacgcacgt  gtcgcagacg  caggagcaga  acaaagagaa  tcagaatccc  aattctgatg
   721  cgccggtgat  cagatcaaaa  acttcagcca  ggtacatgga  gctggtcggg  tggctcgtgg
   781  acaaggggat  tacctcggag  aagcagtgga  tccaggtgag  taattgacaa  agccaaacac
   841  caccatttgc  cgagcacttt  agagtttaca  ggtttgtttc  tcttgaccct  caaaacaaac
   901  ctgtgaggca  tagggagtat  tgctatccct  taagaattca  ccccccagtgt  gcccatcaaa
   961  acctcccagg  ctgagtctgc  acagttgaag  gaggaaggat  aggaatggga  gggtcgatgg
  1021  gtgaaagcat  gattctctta  accagtccag  attatcaggt  aatcccttca  acaaccacca
  1081  cccactccct  gggcaatcca  gctggagttt  acagacagac  ttagctggct  atagcaccac
  1141  cgtgctactc  tctgttcttc  ctggttgctc  aaatgcccta  gaaaagtgga  acaggtgagc
  1201  atcaactcac  agggctctat  gctggctgct  gctgcgaggg  atgttatgct  atagtaccag
  1261  gggccaccat  tccataggca  cttcctgtgt  ttaataccct  atatgcttta  cttcatctca
  1321  tcttcctcca  tatcctgaga  ggtggttcta  ttcttctccc  cattttacgg  atgaaaaaac
  1381  cgagacacag  aaaggtgaaa  tagcttaaga  taaatggtgc  cttgcagcct  tagactctgg
  1441  tggcctctag  ttaatgtggg  aaattaaggg  tgaggggatt  ggcagctgat  ggagggtgca
  1501  gggtgccaga  cagaggcgtt  tagctctgat  cccttagcaa  tagagagtcc  ttgtaggcac
  1561  ttggtcaggc  gagtgatgcg  atgaaagctg  tgtttaagaa  agattatgct  ttctgctgat
  1621  ttcataccccc  caacacccaa  gctctgaggc  ccctcctcac  aggtccttgc  agggctggcc
  1681  aaaataaagc  agcttcactc  cgttgtgctg  ctttccagct  aatgtgtctg  tttggcagaa
  1741  gtttccctca  aaggcagatc  agtgaaataa  gcagaagcct  cgaccccct  ttgtcagcca
  1801  gagctgctga  agtgccttgc  cccagggtca  ctttgtgtga  ggggattaga  gagcactggg
  1861  gctgccaaga  aacactgccg  tttctacaga  ttagcaggac  gctggcttgt  ggccttctag
  1921  cgaggctcag  agctgcggtg  gccctagtct  gcatgggcta  aagacaagct  ccatctcctg
  1981  tccttgttcc  ctccttcctg  ggcacagccg  ccctgcttct  tggttctctc  tgttggttcc
  2041  tgtccgcacg  gtagttaggc  tggcagcgtg  tgtaggattt  ggcttagaag  attgacaaca
```

-continued

SEQUENCE LISTING
A description of the non-limiting exemplary vectors and the sequences thereof discussed herein is provided herein below:

```
2101  ttgcctttga gcccttcttt gctactcctc cctctccct cccatcagac tcctctctgg 2161  agtctgctct gcgaggcctc tgctctgtgg tatcccagca gccttctcag ccttgacttc 2221  cagaagggg ctgtgcagtg tccggggtgt gcaggcccca gacacggggt aggctcatgg 2281  agatccaagt gctgatctag tgtcaaggct ggcctggaga ctgggctggg ttggtgtctg 2341  cctgctgtgg tcatgtgccc tcccttgggc ctgtatcctc tctccagact tgctgcaggg 2401  agaggtggca gatgtcagcc tagttctggc ctctcagagc agcatggcag ctcccttca 2461  ctcaggccca ggctgggccc tcctgctggc tgaccctgg ggagagggtg ctccagagct 2521  ccccaaggaa cagcttcccg aagcagccag gccagcccag aggggctgtg gccaatcctg 2581  aagctttatg ttcctgctga cattttttct aagttttctc ttgctttcct cttaaatgcc 2641  aatctggaga gtctccgtta ggagaaatgg accccagcca ggaagaagag ttgagttgta 2701  tttaaaacac gagctccccc taaagcatcc ttctttagct tctaaggaga ggcagagact 2761  gacaggcagg actcagcagg aaaaggtacc cccctgacct gctcagtcag gccctaggcc 2821  cagctccacc cagcctgtgg cccccagagt ttcggtaaag agttccctgg gccttaagga 2881  accttgagag agcatttgag gggtgccacc acaaacttgg cagaaaaaac cctcccctc 2941  caagtccagt cctagagaag gagctggcaa ccttgccttg ctttgtaagc aaaagcctct 3001  tagggcttga gctcagatgt agtgtttgag ctgtggctgg tgccctgccc catcagggag 3061  ccaatggtag acatcctatg ggcatctttg ttttccgtaa gagcaggctg tctggggatg 3121  ggccagagga agaggcgacc tggagtcaac caagaggagg ccttaaccaa gccttaacca 3181  cagaggttaa ccaagccttg aaagcgcttc cccctgagca ggcaggaagc actgagtcca 3241  catggttgcc tcgctgtttc atttccttac actcaattct ctcagtcttt aaatgatcac 3301  ttggccttga agttacggat atttggggtc tgaactgaag ttgaagaaaa gaggaaatga 3361  tttaagcttt gtttaagatt aggggccagg tgcggtggct cacgcctgta atcccagcac 3421  cttgggagcc tgaggcgggt ggatcacctg aggtcaggag ttccagacca gcctggccaa 3481  catagcaaaa cccagtctct actaaaaata acaataaaaa aattagccag gtgtggtgac 3541  acatgcctgt aatcccagtt actcaggagg ctgaggcaga attgcttgaa cttgagaggt 3601  ggaggttgta gtgagccaag accgcaccac tgcactccag cctggcgaca gagccagact 3661  ccgtctcaaa aacaacaaca aaaagatta gaagaagccc attactgcct tctggccacc 3721  cactcgcaca gacaccaaaa ctgcagccca cacctcgcca tcctcgtgct ctgccctggg 3781  acaccccagg cacagtgtgt ccttcgtttt ctgtaagggt gggctgggag cagggacgga 3841  cagggcctgt gggcacctct catggtcact tccttcttgc tcacaggagg accaggcctc 3901  atacatctcc ttcaatgcgg cctccaactc gcggtcccaa atcaaggctg ccttggacaa 3961  tgcgggaaag attatgagcc tgactaaaac cgcccccgac tacctggtgg gccagcagcc 4021  cgtggaggac atttccagca atcggattta taaaattttg gaactaaacg ggtacgatcc 4081  ccaatatgcg gcttccgtct ttctgggatg ggccacgaaa aagttcggca agaggaacac 4141  catctggctg tttgggcctg caactaccgg gaagaccaac atcgcggagg ccatagccca 4201  cactgtgccc ttctacgggt gcgtaaactg gaccaatgag aactttccct tcaacgactg 4261  tgtcgacaag atggtgatct ggtgggagga gggaagatg accgccaagg tcgtggagtc 4321  ggccaaagcc attctcggag gaagcaaggt gcgcgtggac cagaaatgca agtcctcggc
```

SEQUENCE LISTING
A description of the non-limiting exemplary vectors and the sequences thereof discussed herein is provided herein below:

```
4381  ccagatagac cgactcccg tgatcgtcac ctccaacacc aacatgtgcg ccgtgattga
4441  cgggaactca acgaccttcg aacaccagca gccgttgcaa gaccggatgt tcaaatttga
4501  actcacccgc cgtctggatc atgactttgg gaaggtcacc aagcaggaag tcaaagactt
4561  tttccggtgg gcaaaggatc acgtggttga ggtggagcat gaattctacg tcaaaaaggg
4621  tggagccaag aaaagacccg cccccagtga cgcagatata agtgagccca acgggtgcg
4681  cgagtcagtt gcgcagccat cgacgtcaga cgcggaagct tcgatcaact acgcagacag
4741  gtaccaaaac aaatgttctc gtcacgtggg catgaatctg atgctgtttc cctgcagaca
4801  atgcgagaga atgaatcaga attcaaatat ctgcttcact cacggacaga aagactgttt
4861  agagtgcttt cccgtgtcag aatctcaacc cgtttctgtc gtcaaaaagg cgtatcagaa
4921  actgtgctac attcatcata tcatgggaaa ggtgccagac gcttgcactg cctgcgatct
4981  ggtcaatgtg gatttggatg actgcatctt tgaacaataa atgatttaaa tcaggtctgg
5041  ctgccgatgg ttatcttcca gattggctcg aggacaacct ctctgagggc attcgcgagt
5101  ggtgggacct gaaacctgga gccccgaaac ccaaagccaa ccagcaaaag caggacaacg
5161  gccgggtct ggtgcttcct ggctacaagt acctcggacc cttcaacgga ctcgacaagg
5221  gggagcccgt caacgcggcg gacgcagcgg ccctcgagca cgacaaggcc tacgaccagc
5281  agctccaagc gggtgacaat ccgtacctgc ggtataatca cgccgacgcc gagtttcagg
5341  agcgtctgca agaagatacg tcttttgggg gcaacctcgg gcgcgcagtc ttccaggcca
5401  aaaagcgggt tctcgaacct ctgggcctgg ttgaatcgcc ggttaagatg gctagcggaa
5461  ctagcggcgg taggcgtgta cggtgggagg tctatataag cagagctctc tggctaacta
5521  ccggtgccac catggcccca aagaagaagc ggaaggtcgg tatccacgga gtcccagcag
5581  ccaagcggaa ctacatcctg ggcctggaca tcggcatcac cagcgtgggc tacggcatca
5641  tcgactacga gacacgggac gtgatcgatg ccggcgtgcg gctgttcaaa gaggccaacg
5701  tggaaaacaa cgagggcagg cggagcaaga gaggcgccag aaggctgaag cggcggaggc
5761  ggcatagaat ccagagagtg aagaagctgc tgttcgacta caacctgctg accgaccaca
5821  gcgagctgag cggcatcaac ccctacgagg ccagagtgaa gggcctgagc cagaagctga
5881  gcgaggaaga gttctctgcc gccctgctgc acctggccaa gagaagaggc gtgcacaacg
5941  tgaacgaggt ggaagaggac accggcaacg agctgtccac caaagagcag atcagccgga
6001  acagcaaggc cctggaagag aaatacgtgg ccgaactgca gctggaacgg ctgaagaaag
6061  acggcgaagt gcggggcagc atcaacagat tcaagaccag cgactacgtg aaagaagcca
6121  aacagctgct gaaggtgcag aaggcctacc accagctgga ccagagcttc atcgacacct
6181  acatcgacct gctggaaacc cggcggacct actatgaggg acctggcgag ggcagcccct
6241  tcggctggaa ggacatcaaa gaatggtacg agatgctgat gggccactgc acctacttcc
6301  ccgaggaact gcggagcgtg aagtacgcct acaacgccga cctgtacaac gccctgaacg
6361  acctgaacaa tctcgtgatc accagggacg agaacgagaa gctggaatat tacgagaagt
6421  tccagatcat cgagaacgtg ttcaagcaga agaagaagcc caccctgaag cagatcgcca
6481  aagaaatcct cgtgaacgaa gaggatatta agggctacag agtgaccagc accggcaagc
6541  ccgagttcac caacctgaag gtgtaccacg acatcaagga cattaccgcc cggaaagaga
```

```
6601  ttattgagaa cgccgagctg ctggatcaga ttgccaagat cctgaccatc taccagagca
6661  gcgaggacat ccaggaagaa ctgaccaatc tgaactccga gctgacccag gaagagatcg
6721  agcagatctc taatctgaag ggctataccg gcacccacaa cctgagcctg aaggccatca
6781  acctgatcct ggacgagctg tggcacacca acgacaacca gatcgctatc ttcaaccggc
6841  tgaagctggt gcccaagaag gtggacctgt cccagcagaa agagatcccc accaccctgg
6901  tggacgactt catcctgagc cccgtcgtga agagaagctt catccagagc atcaaagtga
6961  tcaacgccat catcaagaag tacgcctgcc caacgacat cattatcgag ctggcccgcg
7021  agaagaactc caaggacgcc cagaaaatga tcaacgagat gcagaagcgg aaccggcaga
7081  ccaacgagcg gatcgaggaa atcatccgga ccaccggcaa agagaacgcc aagtacctga
7141  tcgagaagat caagctgcac gacatgcagg aaggcaagtg cctgtacagc ctggaagcca
7201  tccctctgga agatctgctg aacaacccct tcaactatga ggtgaccac atcatcccca
7261  gaagcgtgtc cttcgacaac agcttcaaca acaaggtgct cgtgaagcag aagaaaaaca
7321  gcaagaaggg caaccggacc ccattccagt acctgagcag cagcgacagc aagatcagct
7381  acgaaacctt caagaagcac atcctgaatc tggccaaggg caagggcaga atcagcaaga
7441  ccaagaaaga gtatctgctg gaagaacggg acatcaacag gttctccgtg cagaaagact
7501  tcatcaaccg gaacctggtg gataccagat acgccaccag aggcctgatg aacctgctgc
7561  ggagctactt cagagtgaac aacctggacg tgaaagtgaa gtccatcaat ggcggcttca
7621  ccagctttct gcggcggaag tggaagttta gaaagagcg gaacaagggg tacaagcacc
7681  acgccgagga cgcccctgatc attgccaacg ccgatttcat cttcaaagag tggaagaaac
7741  tggacaaggc caaaaagtg atggaaaacc agatgttcga ggaaaagcag gccgagagca
7801  tgcccgagat cgaaaccgag caggagtaca agagatctt catcacccc caccagatca
7861  agcacattaa ggacttcaag gactacaagt acagccaccg ggtggacaag aagcctaata
7921  gagagctgat taacgacacc ctgtactcca cccggaagga cgacaagggc aacaccctga
7981  tcgtgaacaa tctgaacggc ctgtacgaca aggacaatga caagctgaaa aagctgatca
8041  acaagagccc cgaaaagctg ctgatgtacc accacgaccc ccagacctac cagaaactga
8101  agctgattat ggaacagtac ggcgacgaga gaatcccct gtacaagtac tacgaggaaa
8161  ccgggaacta cctgaccaag tactccaaaa aggacaacgg ccccgtgatc aagaagatta
8221  agtattacgg caacaaactg aacgcccatc tggacatcac cgacgactac cccaacagca
8281  gaaacaaggt cgtgaagctg tccctgaagc cctacagatt cgacgtgtac ctggacaatg
8341  gcgtgtacaa gttcgtgacc gtgaagaatc tggatgtgat caaaaaagaa aactactacg
8401  aagtgaatag caagtgctat gaggaagcta agaagctgaa gaagatcagc aaccaggccg
8461  agtttatcgc ctccttctac aacaacgatc tgatcaagat caacggcgag ctgtatagag
8521  tgatcggcgt gaacaacgac ctgctgaacc ggatcgaagt gaacatgatc gacatcacct
8581  accgcgagta cctggaaaac atgaacgaca gaggccccc caggatcatt aagacaatcg
8641  cctccaagac ccagagcatt aagaagtaca gcacagacat tctgggcaac ctgtatgaag
8701  tgaaatctaa gaagcaccct cagatcatca aaaagggcag cggcttcgcc aacgagctgg
8761  gccctagact gatgggaaag actagtagac cggtagagcc atcaccccag cgctctccag
8821  actcctctac gggcatcggc aagaaaggcc agcagcccgc aaaaaagaga ctcaattttg
```

SEQUENCE LISTING
A description of the non-limiting exemplary vectors and the sequences thereof discussed herein is provided herein below:

```
 8881  ggcagactgg cgactcagag tcagtccccg accctcaacc aatcggagaa ccaccagcag
 8941  gcccctctgg tctgggatct ggtacactgg ctgcaggcgg tggcgctcca ctggcagaca
 9001  ataacgaagg cgccgacgga gtgggtagtt cctcaggaaa ttggcattgc gattccacat
 9061  ggctgggcga cagagtcatc accaccagca cccgcacctg ggccctgccc acctacaaca
 9121  accacctcta caagcaaatc tccaacggga cctcgggagg aagcaccaac gacaacacct
 9181  acttcggcta cagcaccccc tgggggtatt ttgacttcaa cagattccac tgccactttt
 9241  caccacgtga ctggcagcga ctcatcaaca caactgggg attccggccc aagaggctca
 9301  acttcaagct cttcaacatc caagtcaagg aggtcacgca gaatgaaggc accaagacca
 9361  tcgccaataa ccttaccagc acgattcagg tctttacgga ctcggaatac cagctcccgt
 9421  acgtgctcgg ctcggcgcac cagggctgcc tgcctccgtt cccggcgac gtcttcatga
 9481  ttcctcagta cgggtacctg actctgaaca atggcagtca ggctgtgggc cggtcgtcct
 9541  tctactgcct ggagtacttt ccttctcaaa tgctgagaac gggcaacaac tttgaattca
 9601  gctacaactt cgaggacgtg cccttccaca gcagctacgc gcacagccag agcctggacc
 9661  ggctgatgaa ccctctcatc gaccagtact tgtactacct gtcccggact caaagcacgg
 9721  gcggtactgc aggaactcag cagttgctat tttctcaggc cgggcctaac aacatgtcgg
 9781  ctcaggccaa gaactggcta cccggtccct gctaccggca gcaacgcgtc tccacgacac
 9841  tgtcgcagaa caacaacagc aactttgcct ggacgggtgc caccaagtat catctgaatg
 9901  gcagagactc tctggtgaat cctggcgttg ccatggctac ccacaaggac gacgaagagc
 9961  gattttttcc atccagcgga gtcttaatgt ttgggaaaca gggagctgga aaagacaacg
10021  tggactatag cagcgtgatg ctaaccagcg aggaagaaat aaagaccacc aacccagtgg
10081  ccacagaaca gtacggcgtg gtggccgata acctgcaaca gcaaaacgcc gctcctattg
10141  taggggccgt caatagtcaa ggagccttac ctggcatggt gtggcagaac cgggacgtgt
10201  acctgcaggg tcccatctgg gccaagattc tcatacgga cggcaacttt catccctcgc
10261  cgctgatggg aggctttgga ctgaagcatc cgcctcctca gatcctgatt aaaaacacac
10321  ctgttcccgc ggatcctccg accaccttca gccaggccaa gctggcttct ttcatcacgc
10381  agtacagtac cggccaggtc agcgtggaga tcgagtggga gctgcagaag gagaacagca
10441  aacgctggaa cccagagatt cagtacactt ccaactacta caatctaca aatgtggact
10501  ttgctgtcaa tactgagggt acttattccg agcctcgccc cattggcacc cgttacctca
10561  cccgtaatct gtaattacat gttaatcaat aaaccggtta attcgtttca gttgaacttt
10621  ggtctcctgt ccttcttatc ttatcggtta ccatagaaac tggttactta ttaactgctt
10681  ggtgcgcttc gcgataaaag acttacgtca tcgggttacc cctagtgatg agcggccgc
10741  tttcagttga actttggtct ctgcgtattt ctttcttatc tagtttccat gctctagagg
10801  tcctgtatta gaggtcacgt gagtgttttg cgacattttg cgacaccatg tggtcacgct
10861  gggtatttaa gcccgagtga gcacgcaggg tctccatttt gaagcgggag gtttgaacgc
10921  gcagccgcca agccgaattc tgcagatatc catcacactg gcggccgctc gactagagcg
10981  gccgccaccg cggtggagct ccagcttttg ttccctttag tgagggttaa ttgcgcgctt
11041  ggcgtaatca tggtcatagc tgtttcctgt gtgaaattgt tatccgctca caattccaca
```

SEQUENCE LISTING

A description of the non-limiting exemplary vectors and the sequences thereof discussed herein is provided herein below:

```
11101  caacatacga gccggaagca taaagtgtaa agcctggggt gcctaatgag tgagctaact
11161  cacattaatt gcgttgcgct cactgcccgc tttccagtcg ggaaacctgt cgtgccagct
11221  gcattaatga atcggccaac gcgcggggag aggcggtttg cgtattgggc gctcttccgc
11281  ttcctcgctc actgactcgc tgcgctcggt cgttcggctg cggcgagcgg tatcagctca
11341  ctcaaaggcg gtaatacggt tatccacaga atcaggggat aacgcaggaa agaacatgtg
11401  agcaaaaggc cagcaaaagg ccaggaaccg taaaaaggcc gcgttgctgg cgtttttcca
11461  taggctccgc ccccctgacg agcatcacaa aaatcgacgc tcaagtcaga ggtggcgaaa
11521  cccgacagga ctataaagat accaggcgtt tcccctgga agctccctcg tgcgctctcc
11581  tgttccgacc ctgccgctta ccggatacct gtccgccttt ctcccttcgg aagcgtggc
11641  gctttctcat agctcacgct gtaggtatct cagttcggtg taggtcgttc gctccaagct
11701  gggctgtgtg cacgaacccc ccgttcagcc cgaccgctgc gccttatccg gtaactatcg
11761  tcttgagtcc aacccggtaa gacacgactt atcgccactg gcagcagcca ctggtaacag
11821  gattagcaga gcgaggtatg taggcggtgc tacagagttc ttgaagtggt ggcctaacta
11881  cggctacact agaagaacag tatttggtat ctgcgctctg ctgaagccag ttaccttcgg
11941  aaaaagagtt ggtagctctt gatccggcaa acaaaccacc gctggtagcg gtggttttt
12001  tgtttgcaag cagcagatta cgcgcagaaa aaaggatct caagaagatc ctttgatctt
12061  ttctacgggg tctgacgctc agtggaacga aaactcacgt taagggattt tggtcatgag
12121  attatcaaaa aggatcttca cctagatcct tttaaattaa aaatgaagtt ttaaatcaat
12181  ctaaagtata tatgagtaaa cttggtctga cagttaccaa tgcttaatca gtgaggcacc
12241  tatctcagcg atctgtctat ttcgttcatc catagttgcc tgactccccg tcgtgtagat
12301  aactacgata cgggagggct taccatctgg ccccagtgct gcaatgatac cgcgagaccc
12361  acgctcaccg gctccagatt tatcagcaat aaaccagcca gccggaaggg ccgagcgcag
12421  aagtggtcct gcaactttat ccgcctccat ccagtctatt aattgttgcc gggaagctag
12481  agtaagtagt tcgccagtta atagtttgcg caacgttgtt gccattgcta caggcatcgt
12541  ggtgtcacgc tcgtcgtttg gtatggcttc attcagctcc ggttcccaac gatcaaggcg
12601  agttacatga tcccccatgt tgtgcaaaaa agcggttagc tccttcggtc ctccgatcgt
12661  tgtcagaagt aagttggccg cagtgttatc actcatggtt atggcagcac tgcataattc
12721  tcttactgtc atgccatccg taagatgctt ttctgtgact ggtgagtact caaccaagtc
12781  attctgagaa tagtgtatgc ggcgaccgag ttgctcttgc ccggcgtcaa tacgggataa
12841  taccgcgcca catagcagaa ctttaaaagt gctcatcatt ggaaaacgtt cttcggggcg
12901  aaaactctca aggatcttac cgctgttgag atccagttcg atgtaaccca ctcgtgcacc
12961  caactgatct tcagcatctt ttactttcac cagcgtttct gggtgagcaa aaacaggaag
13021  gcaaaatgcc gcaaaaaagg gaataagggc gacacggaaa tgttgaatac tcatactctt
13081  cctttttcaa tattattgaa gcatttatca gggttattgt ctcatgagcg gatacatatt
13141  tgaatgtatt tagaaaaata aacaataggg gttccgcgc acatttcccc gaaaagtgcc
13201  acctaaattg taagcgttaa tattttgtta aaattcgcgt taaatttttg ttaaatcagc
13261  tcatttttta accaataggc cgaaatcggc aaaatccctt ataaatcaaa agaatagacc
13321  gagataggggt tgagtgttgt tccagtttgg aacaagagtc cactattaaa gaacgtggac
```

SEQUENCE LISTING
A description of the non-limiting exemplary vectors and the sequences thereof
discussed herein is provided herein below:

```
13381  tccaacgtca aagggcgaaa aaccgtctat cagggcgatg gcccactacg tgaaccatca 13441  ccctaatcaa gttttttggg gtcgaggtgc cgtaaagcac taaatcggaa ccctaaaggg 13501  agcccccgat ttagagcttg acggggaaag ccggcgaacg tggcgagaaa ggaagggaag 13561  aaagcgaaag gagcgggcgc tagggcgctg gcaagtgtag cggtcacgct gcgcgtaacc 13621  accacacccg ccgcgcttaa tgcgccgcta cagggcgcgt cccattcgcc attcaggctg 13681  cgcaactgtt gggaagggcg atcggtgcgg gcctcttcgc tattacgcca gctggcgaaa 13741  gggggatgtg ctgcaaggcg attaagttgg gtaacgccag gttttccca gtcacgacgt 13801  tgtaaaacga cggccagtga gcgcgcgtaa tacgactcac tatagggcga attgggtac
``` pHELP

| | |
|---|---|
| LOCUS | pHELP 11635 bp DNA circular SYN 19-JUL-2016 |
| REFERENCE | 1 (bases 1 to 11635) |
| FEATURES | Location/Qualifiers |
| misc_feature | complement(258..1841)<br>/note = "Ad5 E2A DBP" |
| misc_feature | 839..903<br>/note = "E2A Primer/probe Region" |
| misc_feature | 5647..8267<br>/note = "Ad5 E4 Gene" |
| misc_feature | complement(8546..8662)<br>/note = "52K Partial" |
| misc_feature | 8661..9121<br>/note = "VA RNA Region" |
| CDS | complement(10182..11042)<br>/gene = "amp" |

ORIGIN (SEQ ID NO: 6)

```
  1  ggtacccaac tccatgctta acagtcccca ggtacagccc accctgcgtc gcaaccagga 61  acagctctac agcttcctgg agcgccactc gccctacttc cgcagccaca gtgcgcagat 121  taggagcgcc acttcttttt gtcacttgaa aaacatgtaa aaataatgta ctaggagaca 181  ctttcaataa aggcaaatgt ttttatttgt acactctcgg gtgattattt accccccacc 241  cttgccgtct gcgccgttta aaaatcaaag gggttctgcc gcgcatcgct atgcgccact 301  ggcagggaca cgttgcgata ctggtgttta gtgctccact taaactcagg cacaaccatc 361  cgcggcagct cggtgaagtt ttcactccac aggctgcgca ccatcaccaa cgcgtttagc 421  aggtcgggcg ccgatatctt gaagtcgcag ttggggcctc cgccctgcgc gcgcgagttg 481  cgatacacag ggttgcagca ctggaacact atcagcgccg ggtggtgcac gctggccagc 541  acgctcttgt cggagatcag atccgcgtcc aggtcctccg cgttgctcag ggcgaacgga 601  gtcaactttg gtagctgcct tcccaaaaag ggtgcatgcc caggctttga gttgcactcg 661  caccgtagtg gcatcagaag gtgaccgtgc ccgtctgggg cgttaggata cagcgcctgc 721  atgaaagcct tgatctgctt aaaagccacc tgagcctttg cgccttcaga agaacatg 781  ccgcaagact tgccggaaaa ctgattggcc ggacaggccg tcatgcac gcagcacctt 841  gcgtcggtgt tggagatctg caccacattt cggccccacc ggttcttcac gatcttggcc 901  ttgctagact gctccttcag cgcgcgctgc ccgttttcgc tcgtcacatc catttcaatc
```

```
 961 acgtgctcct tatttatcat aatgctcccg tgtagacact taagctcgcc ttcgatctca
1021 gcgcagcggt gcagccacaa cgcgcagccc gtgggctcgt ggtgcttgta ggttacctct
1081 gcaaacgact gcaggtacgc ctgcaggaat cgccccatca tcgtcacaaa ggtcttgttg
1141 ctggtgaagg tcagctgcaa cccgcggtgc tcctcgttta gccaggtctt gcatacggcc
1201 gccagagctt ccacttggtc aggcagtagc ttgaagtttg cctttagatc gttatccacg
1261 tggtacttgt ccatcaacgc gcgcgcagcc tccatgccct tctcccacgc agacacgatc
1321 ggcaggctca gcgggtttat caccgtgctt tcactttccg cttcactgga ctcttccttt
1381 tcctcttgcg tccgcatacc ccgcgccact gggtcgtctt cattcagccg ccgcaccgtg
1441 cgcttacctc ccttgccgtg cttgattagc accggtgggt tgctgaaacc caccatttgt
1501 agcgccacat cttctctttc ttcctcgctg tccacgatca cctctgggga tggcgggcgc
1561 tcgggcttgg gagaggggcg cttcttttc tttttggacg caatggccaa atccgccgtc
1621 gaggtcgatg gccgcgggct gggtgtgcgc ggcaccagcg catcttgtga cgagtcttct
1681 tcgtcctcgg actcgagacg ccgcctcagc cgctttttg ggggcgcgcg gggaggcggc
1741 ggcgacggcg acggggacga cacgtcctcc atggttggtg gacgtcgcgc cgcaccgcgt
1801 ccgcgctcgg gggtggtttc gcgctgctcc tcttcccgac tggccatttc cttctcctat
1861 aggcagaaaa agatcatgga gtcagtcgag aaggaggaca gcctaaccgc ccccttgag
1921 ttcgccacca ccgcctccac cgatgccgcc aacgcgccta ccaccttccc cgtcgaggca
1981 cccccgcttg aggaggagga agtgattatc gagcaggacc caggttttgt aagcgaagac
2041 gacgaggatc gctcagtacc aacagaggat aaaaagcaag accaggacga cgcagaggca
2101 aacgaggaac aagtcgggcg gggggaccaa aggcatggcg actacctaga tgtgggagac
2161 gacgtgctgt tgaagcatct gcagcgccag tgcgccatta tctgcgacgc gttgcaagag
2221 cgcagcgatg tgcccctcgc catagcggat gtcagccttg cctacgaacg ccacctgttc
2281 tcaccgcgcg tacccccaa acgccaagaa aacggcacat gcgagcccaa cccgcgcctc
2341 aacttctacc ccgtatttgc cgtgccagag gtgcttgcca cctatcacat cttttccaa
2401 aactgcaaga taccctatc ctgccgtgcc aaccgcagcc gagcggacaa gcagctggcc
2461 ttgcggcagg gcgctgtcat acctgatatc gcctcgctcg acgaagtgcc aaaaatcttt
2521 gagggtcttg gacgcgacga gaaacgcgcg gcaaacgctc tgcaacaaga aacagcgaa
2581 aatgaaagtc actgtggagt gctggtggaa cttgagggtg acaacgcgcg cctagccgtg
2641 ctgaaacgca gcatcgaggt cacccacttt gcctacccgg cacttaacct accccccaag
2701 gttatgagca cagtcatgag cgagctgatc gtgcgccgtg cacgacccct ggagagggat
2761 gcaaacttgc aagaacaaac cgaggagggc ctaccgcag ttggcgatga gcagctggcg
2821 cgctggcttg agacgcgcga gcctgccgac ttggaggagc gacgcaagct aatgatggcc
2881 gcagtgcttg ttaccgtgga gcttgagtgc atgcagcggt tctttgctga cccggagatg
2941 cagcgcaagc tagaggaaac gttgcactac acctttcgcc agggctacgt gcgccaggcc
3001 tgcaaaattt ccaacgtgga gctctgcaac ctggtctcct accttggaat tttgcacgaa
3061 aaccgcctcg ggcaaaacgt gcttcattcc acgctcaagg gcgaggcgcg ccgcgactac
3121 gtccgcgact gcgtttactt atttctgtgc tacacctggc aaacggccat gggcgtgtgg
```

```
3181  cagcaatgcc tggaggagcg caacctaaag gagctgcaga agctgctaaa gcaaaacttg 3241  aaggacctat ggacggcctt caacgagcgc tccgtggccg cgcacctggc ggacattatc 3301  ttccccgaac gcctgcttaa aaccctgcaa cagggtctgc cagacttcac cagtcaaagc 3361  atgttgcaaa actttaggaa ctttatccta gagcgttcag gaattctgcc cgccacctgc 3421  tgtgcgcttc ctagcgactt tgtgcccatt aagtaccgtg aatgccctcc gccgctttgg 3481  ggtcactgct accttctgca gctagccaac taccttgcct accactccga catcatggaa 3541  gacgtgagcg gtgacggcct actggagtgt cactgtcgct gcaacctatg caccccgcac 3601  cgctccctgg tctgcaattc gcaactgctt agcgaaagtc aaattatcgg tacctttgag 3661  ctgcagggtc cctcgcctga cgaaaagtcc gcggctccgg ggttgaaact cactccgggg 3721  ctgtggacgt cggcttacct tcgcaaattt gtacctgagg actaccacgc cacgagatt 3781  aggttctacg aagaccaatc ccgcccgcca aatgcggagc ttaccgcctg cgtcattacc 3841  cagggccaca tccttggcca attgcaagcc atcaacaaag cccgccaaga gtttctgcta 3901  cgaaagggac gggggttta cctggacccc cagtccggcg aggagctcaa cccaatcccc 3961  ccgccgccgc agccctatca gcagccgcgg gcccttgctt cccaggatgg cacccaaaaa 4021  gaagctgcag ctgccgccgc cgccacccac ggacgaggag gaatactggg acagtcaggc 4081  agaggaggtt ttggacgagg aggaggagat gatggaagac tgggacagcc tagacgaagc 4141  ttccgaggcc gaagaggtgt cagacgaaac accgtcaccc tcggtcgcat tccctcgcc 4201  ggcgccccag aaattggcaa ccgttcccag catcgctaca acctccgctc ctcaggcgcc 4261  gccggcactg cctgttcgcc gacccaaccg tagatgggac accactgaa ccagggccgg 4321  taagtctaag cagccgccgc cgttagccca agagcaacaa cagcgccaag gctaccgctc 4381  gtggcgcggg cacaagaacg ccatagttgc ttgcttgcaa gactgtgggg gcaacatctc 4441  cttcgcccgc cgctttcttc tctaccatca cggcgtggcc ttcccccgta acatcctgca 4501  ttactaccgt catctctaca gcccctactg caccggcggc agcggcagcg cagcaacag 4561  cagcggtcac acagaagcaa aggcgaccgg atagcaagac tctgacaaag cccaagaaat 4621  ccacagcggc ggcagcagca ggaggaggag cgctgcgtct ggcgcccaac gaacccgtat 4681  cgaccgcga gcttagaaat aggatttttc ccactctgta tgctatattt caacaaagca 4741  ggggccaaga acaagagctg aaaataaaaa acaggtctct gcgctccctc acccgcagct 4801  gcctgtatca caaagcgaa gatcagcttc ggcgcacgct ggaagacgcg gaggctctct 4861  tcagcaaata ctgcgcgctg actcttaagg actagtttcg cgcccttttct caaatttaag 4921  cgcgaaaact acgtcatctc cagcggccac acccggcgcc agcacctgtc gtcagcgcca 4981  ttatgagcaa ggaaattccc acgccctaca tgtggagtta ccagccacaa atgggacttg 5041  cggctggagc tgcccaagac tactcaaccc gaataaacta catgagcgcg ggaccccaca 5101  tgatatcccg ggtcaacgga atccgcgccc accgaaaccg aattctcctc gaacaggcgg 5161  ctattaccac cacacctcgt aataacctta atccccgtag ttggcccgct gccctggtgt 5221  accaggaaag tcccgctccc accactgtgg tacttcccag agacgcccag gccgaagttc 5281  agatgactaa ctcaggggcg cagcttgcgg gcggctttcg tcacagggtg cggtcgcccg 5341  ggcgttttag gcggagtaa cttgcatgta ttgggaattg tagttttttt aaaatgggaa 5401  gtgacgtatc gtgggaaaac ggaagtgaag atttgaggaa gttgtgggtt ttttggcttt
```

SEQUENCE LISTING
A description of the non-limiting exemplary vectors and the sequences thereof
discussed herein is provided herein below:

```
5461  cgtttctggg cgtaggttcg cgtgcggttt tctgggtgtt ttttgtggac tttaaccgtt
5521  acgtcatttt ttagtcctat atatactcgc tctgtacttg gcccttttta cactgtgact
5581  gattgagctg gtgccgtgtc gagtggtgtt ttttaatagg ttttttact ggtaaggctg
5641  actgttatgg ctgccgctgt ggaagcgctg tatgttgttc tggagcggga gggtgctatt
5701  ttgcctaggc aggagggttt ttcaggtgtt tatgtgtttt tctctcctat taattttgtt
5761  atacctccta tgggggctgt aatgttgtct ctacgcctgc gggtatgtat tcccccgggc
5821  tatttcggtc gcttttttagc actgaccgat gttaaccaac ctgatgtgtt taccgagtct
5881  tacattatga ctccggacat gaccgaggaa ctgtcggtgg tgcttttaa tcacggtgac
5941  cagttttttt acggtcacgc cggcatggcc gtagtccgtc ttatgcttat aagggttgtt
6001  tttcctgttg taagacaggc ttctaatgtt taaatgtttt tttttttgtt attttatttt
6061  gtgtttaatg caggaacccg cagacatgtt tgagagaaaa atggtgtctt tttctgtggt
6121  ggttccggaa cttacctgcc tttatctgca tgagcatgac tacgatgtgc ttgcttttt
6181  gcgcgaggct ttgcctgatt ttttgagcag caccttgcat tttatatcgc cgcccatgca
6241  acaagcttac ataggggcta cgctggttag catagctccg agtatgcgtg tcataatcag
6301  tgtgggttct tttgtcatgg ttcctggcgg ggaagtggcc gcgctggtcc gtgcagacct
6361  gcacgattat gttcagctgg ccctgcgaag ggacctacgg gatcgcggta tttttgttaa
6421  tgttccgctt ttgaatctta tacaggtctg tgaggaacct gaattttgc aatcatgatt
6481  cgctgcttga ggctgaaggt ggagggcgct ctggagcaga ttttacaat ggccggactt
6541  aatattcggg atttgcttag agacatattg ataaggtggc gagatgaaaa ttatttgggc
6601  atggttgaag gtgctggaat gtttatagag gagattcacc ctgaagggtt tagcctttac
6661  gtccacttgg acgtgagggc agtttgcctt ttggaagcca ttgtgcaaca tcttacaaat
6721  gccattatct gttctttggc tgtagagttt gaccacgcca ccggagggga gcgcgttcac
6781  ttaatagatc ttcattttga ggttttggat aatctttggg aataaaaaaa aaaaaacatg
6841  gttcttccag ctcttcccgc tcctcccgtg tgtgactcgc agaacgaatg tgtaggttgg
6901  ctgggtgtgg cttattctgc ggtggtggat gttatcaggg cagcggcgca tgaaggagtt
6961  tacatagaac ccgaagccag ggggcgcctg gatgctttga gagagtggat atactacaac
7021  tactacacag agcgagctaa gcgacgagac cggagacgca gatctgtttg tcacgcccgc
7081  acctggtttt gcttcaggaa atatgactac gtccggcgtt ccatttggca tgacactacg
7141  accaacacga tctcggttgt ctcggcgcac tccgtacagt agggatcgcc tacctccttt
7201  tgagacagag acccgcgcta ccatactgga ggatcatccg ctgctgcccg aatgtaacac
7261  tttgacaatg cacaacgtga gttacgtgcg aggtcttccc tgcagtgtgg gatttacgct
7321  gattcaggaa tgggttgttc cctgggatat ggttctgacg cgggaggagc ttgtaatcct
7381  gaggaagtgt atgcacgtgt gcctgtgttg tgccaacatt gatatcatga cgagcatgat
7441  gatccatggt tacgagtcct gggctctcca ctgtcattgt tccagtcccg gttccctgca
7501  gtgcatagcc ggcgggcagg ttttggccag ctggtttagg atggtggtgg atggcgccat
7561  gtttaatcag aggtttatat ggtaccggga ggtggtgaat tacaacatgc caaaagaggt
7621  aatgtttatg tccagcgtgt ttatgagggg tcgccactta atctacctgc gcttgtggta
```

-continued

SEQUENCE LISTING
A description of the non-limiting exemplary vectors and the sequences thereof
discussed herein is provided herein below:

```
7681  tgatggccac gtgggttctg tggtccccgc catgagcttt ggatacagcg ccttgcactg 7741  tgggattttg aacaatattg tggtgctgtg ctgcagttac tgtgctgatt taagtgagat 7801  cagggtgcgc tgctgtgccc ggaggacaag gcgtctcatg ctgcgggcgg tgcgaatcat 7861  cgctgaggag accactgcca tgttgtattc ctgcaggacg gagcggcggc ggcagcagtt 7921  tattcgcgcg ctgctgcagc accaccgccc tatcctgatg cacgattatg actctacccc 7981  catgtaggcg tggacttccc cttcgccgcc cgttgagcaa ccgcaagttg acagcagcc 8041  tgtggctcag cagctggaca gcgacatgaa cttaagcgag ctgcccgggg agtttattaa 8101  tatcactgat gagcgtttgg ctcgacagga accgtgtgg aatataacac ctaagaatat 8161  gtctgttacc catgatatga tgcttttta ggccagccgg ggagaaagga ctgtgtactc 8221  tgtgtgttgg gagggaggtg gcaggttgaa tactagggtt ctgtgagttt gattaaggta 8281  cggtgatcaa tataagctat gtggtggtgg ggctatacta ctgaatgaaa aatgacttga 8341  aattttctgc aattgaaaaa taaacacgtt gaaacataac atgcaacagg ttcacgattc 8401  tttattcctg ggcaatgtag gagaaggtgt aagagttggt agcaaaagtt tcagtggtgt 8461  attttccact ttcccaggac catgtaaaag acatagagta agtgcttacc tcgctagttt 8521  ctgtggattc actagaatcg atgtaggatg ttgcccctcc tgacgcggta ggagaagggg 8581  agggtgccct gcatgtctgc cgctgctctt gctcttgccg ctgctgagga ggggggcgca 8641  tctgccgcag caccggatgc atctgggaaa agcaaaaaag gggctcgtcc ctgtttccgg 8701  aggaatttgc aagcggggtc ttgcatgacg gggaggcaaa ccccgttcg ccgcagtccg 8761  gccggcccga gactcgaacc ggggtcctg cgactcaacc cttggaaaat aaccctccgg 8821  ctacagggag cgagccactt aatgctttcg ctttccagcc taaccgctta cgccgcgcgc 8881  ggccagtggc caaaaaagct agcgcagcag ccgccgcgcc tggaaggaag ccaaaaggag 8941  cgctcccccg ttgtctgacg tcgcacacct gggttcgaca cgcgggcggt aaccgcatgg 9001  atcacggcgg acggccggat ccggggttcg aacccggtc gtccgccatg atacccttgc 9061  gaatttatcc accagaccac ggaagagtgc ccgcttacag gctctccttt tgcacggtct 9121  agagcgtcaa cgactgcgca cgcctcaccg gccagagcgt cccgaccatg gagcactttt 9181  tgccgctgcg caacatctgg aaccgcgtcc gcgactttcc gcgcgcctcc accaccgccg 9241  ccggcatcac ctggatgtcc aggtacatct acggattacg tcgacgttta aaccatatga 9301  tcagctcact caaaggcggt aatacggtta ccacagaat cagggataa cgcaggaaag 9361  aacatgtgag caaaaggcca gcaaaaggcc aggaaccgta aaaaggccgc gttgctggcg 9421  ttttccata ggctccgccc ccctgacgag catcacaaaa atcgacgctc aagtcagagg 9481  tggcgaaacc cgacaggact ataaagatac caggcgtttc ccctggaag ctccctcgtg 9541  cgctctcctg ttccgaccct gccgcttacc ggatacctgt ccgcctttct cccttcggga 9601  agcgtggcgc tttctcatag ctcacgctgt aggtatctca gttcggtgta ggtcgttcgc 9661  tccaagctgg gctgtgtgca cgaaccccc gttcagcccg accgctgcgc cttatccggt 9721  aactatcgtc ttgagtccaa cccggtaaga cacgacttat cgccactggc agcagccact 9781  ggtaacagga ttagcagagc gaggtatgta ggcggtgcta cagagttctt gaagtggtgg 9841  cctaactacg gctacactag aagaacagta tttggtatct gcgctctgct gaagccagtt 9901  accttcggaa aaagagttgg tagctcttga tccggcaaac aaaccaccgc tggtagcggt
```

SEQUENCE LISTING
A description of the non-limiting exemplary vectors and the sequences thereof discussed herein is provided herein below:

```
 9961 ggttttttg tttgcaagca gcagattacg cgcagaaaaa aaggatctca agaagatcct
10021 ttgatctttt ctacggggtc tgacgctcag tggaacgaaa actcacgtta agggattttg
10081 gtcatgagat tatcaaaaag gatcttcacc tagatccttt taaattaaaa atgaagtttt
10141 aaatcaatct aaagtatata tgagtaaact tggtctgaca gttaccaatg cttaatcagt
10201 gaggcaccta tctcagcgat ctgtctattt cgttcatcca tagttgcctg actccccgtc
10261 gtgtagataa ctacgatacg ggagggctta ccatctggcc ccagtgctgc aatgataccg
10321 cgagacccac gctcaccggc tccagattta tcagcaataa accagccagc cggaagggcc
10381 gagcgcagaa gtggtcctgc aactttatcc gcctccatcc agtctattaa ttgttgccgg
10441 gaagctagag taagtagttc gccagttaat agtttgcgca acgttgttgc cattgctaca
10501 ggcatcgtgg tgtcacgctc gtcgtttggt atggcttcat tcagctccgg ttcccaacga
10561 tcaaggcgag ttacatgatc ccccatgttg tgcaaaaaag cggttagctc cttcggtcct
10621 ccgatcgttg tcagaagtaa gttggccgca gtgttatcac tcatggttat ggcagcactg
10681 cataattctc ttactgtcat gccatccgta agatgctttt ctgtgactgg tgagtactca
10741 accaagtcat tctgagaata gtgtatgcgg cgaccgagtt gctcttgccc ggcgtcaata
10801 cgggataata ccgcgccaca tagcagaact ttaaaagtgc tcatcattgg aaaacgttct
10861 tcggggcgaa aactctcaag gatcttaccg ctgttgagat ccagttcgat gtaacccact
10921 cgtgcaccca actgatcttc agcatctttt actttcacca gcgtttctgg gtgagcaaaa
10981 acaggaaggc aaaatgccgc aaaaaaggga ataagggcga cacggaaatg ttgaatactc
11041 atactcttcc ttttcaata ttattgaagc atttatcagg gttattgtct catgagcgga
11101 tacatatttg aatgtattta gaaaaataaa caaatagggg ttccgcgcac atttccccga
11161 aaagtgccac ctaaattgta agcgttaata ttttgttaaa attcgcgtta aattttgtt
11221 aaatcagctc attttttaac caataggccg aaatcggcaa aatcccttat aaatcaaaag
11281 aatagaccga gatagggttg agtgttgttc cagtttggaa caagagtcca ctattaaaga
11341 acgtggactc caacgtcaaa gggcgaaaaa ccgtctatca gggcgatggc ccactacgtg
11401 aaccatcacc ctaatcaagt tttttggggt cgaggtgccg taaagcacta atcggaacc
11461 ctaaagggag cccccgattt agagcttgac ggggaaagcc ggcgaacgtg gcgagaaagg
11521 aagggaagaa agcgaaagga gcgggcgcta gggcgctggc aagtgtagcg gtcacgctgc
11581 gcgtaaccac cacacccgcc gcgcttaatg cgccgctaca gggcgcgatg gatcc
``` scAAV-CMV-luc2Pv2

| | |
|---|---|
| LOCUS | scAAV-CMV-luc2Pv 5968 bp DNA circular SYN 08-DEC-2014 |
| REFERENCE | 1 (bases 1 to 5968) |
| FEATURES | Location/Qualifiers |
| misc_feature | 1..106<br>/gene = "mITR" |
| misc_feature | 140..774<br>/gene = "CMVpro" |
| CDS | 806..2581<br>/gene = "luc2P" |

SEQUENCE LISTING
A description of the non-limiting exemplary vectors and the sequences thereof discussed herein is provided herein below:

| | | |
|---|---|---|
| misc_feature | 2668..2771 | /note = "3' ITR" |
| misc_feature | 3319..3360 | /note = "Bacterial promoter" |
| misc_feature | 3434..3702 | /note = "SV40 promoter" |
| misc_feature | 3785..4579 | /note = "Neo/Kan" |
| misc_feature | 4581..4833 | /note = "HSV tk polyA" |
| misc_feature | 5325..5912 | /note = "pMB1 ori" |

ORIGIN (SEQ ID NO: 7)

```
   1 ctgcgcgctc gctcgctcac tgaggccgcc cgggcaaagc ccgggcgtcg ggcgaccttt
  61 ggtcgcccgg cctcagtgag cgagcgagcg cgcagagagg gagtggccaa ctccatcact
 121 aggggttcct gcggccgcac gcgttgacat tgattattga ctagttatta atagtaatca
 181 attacggggt cattagttca tagcccatat atggagttcc gcgttacata acttacggta
 241 aatggcccgc ctggctgacc gcccaacgac ccccgcccat tgacgtcaat aatgacgtat
 301 gttcccatag taacgccaat agggactttc cattgacgtc aatgggtgga ctatttacgg
 361 taaactgccc acttggcagt acatcaagtg tatcatatgc caagtacgcc ccctattgac
 421 gtcaatgacg gtaaatggcc cgcctggcat tatgcccagt acatgacctt atgggacttt
 481 cctacttggc agtacatcta cgtattagtc atcgctatta ccatggtgat gcggttttgg
 541 cagtacatca atgggcgtgg atagcggttt gactcacggg gatttccaag tctccacccc
 601 attgacgtca atgggagttt gttttggcac caaaatcaac gggactttcc aaaatgtcgt
 661 aacaactccg ccccattgac gcaaatgggc ggtaggcgtg tacggtggga ggtctatata
 721 agcagagctc tctggctaac tagagaaccc actgcttact ggcttatcga aattaatacg
 781 actcactata gggagaccca agctcatgga agatgccaaa acattaagag agggcccagc
 841 gccattctac ccactcgaag acgggaccgc cggcgagcag ctgcacaaag ccatgaagcg
 901 ctacgccctg gtgcccggca ccatcgcctt taccgacgca catatcgagg tggacattac
 961 ctacgccgag tacttcgaga tgagcgttcg gctggcagaa gctatgaagc gctatgggct
1021 gaatacaaac catcggatcg tggtgtgcag cgagaatagc ttgcagttct tcatgcccgt
1081 gttgggtgcc ctgttcatcg gtgtggctgt ggccccagct aacgacatct acaacgagcg
1141 cgagctgctg aacagcatgg gcatcagcca gcccaccgtc gtattcgtga gcaagaaagg
1201 gctgcaaaag atcctcaacg tgcaaaagaa gctaccgatc atacaaaaga tcatcatcat
1261 ggatagcaag accgactacc agggcttcca aagcatgtac accttcgtga cttcccattt
1321 gccacccggc ttcaacgagt acgacttcgt gcccgagagc ttcgaccggg acaaaaccat
1381 cgccctgatc atgaacagta gtggcagtac cggattgccc aagggcgtag ccctaccgca
1441 ccgcaccgct tgtgtccgat tcagtcatgc ccgcgacccc atcttcggca accagatcat
1501 ccccgacacc gctatcctca gcgtggtgcc atttcaccac ggcttcggca tgttcaccac
1561 gctgggctac ttgatctgcg gctttcgggt cgtgctcatg taccgcttcg aggaggagct
1621 attcttgcgc agcttgcaag actataagat tcaatctgcc ctgctggtgc ccacactatt
```

```
1681  tagcttcttc gctaagagca ctctcatcga caagtacgac ctaagcaact tgcacgagat
1741  cgccagcggc ggggcgccgc tcagcaagga ggtaggtgag gccgtggcca aacgcttcca
1801  cctaccaggc atccgccagg gctacggcct gacagaaaca accagcgcca ttctgatcac
1861  ccccgaaggg gacgacaagc ctggcgcagt aggcaaggtg gtgcccttct tcgaggctaa
1921  ggtggtggac ttggacaccg gtaagacact gggtgtgaac cagcgcggcg agctgtgcgt
1981  ccgtggcccc atgatcatga gcggctacgt taacaacccc gaggctacaa acgctctcat
2041  cgacaaggac ggctggctgc acagcggcga catcgcctac tgggacgagg acgagcactt
2101  cttcatcgtg gaccggctga agagcctgat caaatacaag ggctaccagg tagccccagc
2161  cgaactggag agcatcctgc tgcaacaccc caacatcttc gacgccgggg tcgccggcct
2221  gcccgacgac gatgccggcg agctgccccg cgcagtcgtc gtgctggaac acggtaaaac
2281  catgaccgag aaggagatcg tggactatgt ggccagccag gttacaaccg ccaagaagct
2341  gcgcggtggt gttgtgttcg tggacgaggt gcctaaagga ctgaccggca agttggacgc
2401  ccgcaagatc cgcgagattc tcattaaggc caagaagggc ggcaagatcg ccgtgaattc
2461  tcacggcttc cctcccgagg tggaggagca ggccgccggc accctgccca tgagctgcgc
2521  ccaggagagc ggcatggata cacccctgc tgcttgcgcc agcgccagga tcaacgtcta
2581  aggccgcgac tctagagcat ggctacgtag ataagtagca tggcgggtta atcattaact
2641  acaaggaacc cctagtgatg gagttggcca ctccctctct gcgcgctcgc tcgctcactg
2701  aggccgggcg accaaaggtc gcccgacgcc cgggctttgc ccgggcggcc tcagtgagcg
2761  agcgagcgcg ccagctggcg taatagcgaa gaggcccgca ccgatcgccc ttcccaacag
2821  ttgcgcagcc tgaatggcga atggaattcc agacgattga gcgtcaaaat gtaggtattt
2881  ccatgagcgt ttttcctgtt gcaatggctg gcggtaatat tgttctggat attaccagca
2941  aggccgatag tttgagttct tctactcagg caagtgatgt tattactaat caaagaagta
3001  ttgcgacaac ggttaatttg cgtgatggac agactctttt actcggtggc ctcactgatt
3061  ataaaaacac ttctcaggat tctggcgtac cgttcctgtc taaaatccct ttaatcggcc
3121  tcctgtttag ctcccgctct gattctaacg aggaaagcac gttatacgtg ctcgtcaaag
3181  caaccatagt acgcgccctg tagcggcgca ttaagcgcgg cgggtgtggt ggttacgcgc
3241  agcgtgaccg ctacacttgc cagcgcccta gcgcccgctc ctttcgcttt cttcccttcc
3301  tttctcgcca cgttcgccat cttcaaatat gtatccgctc atgagacaat aaccctgata
3361  aatgcttcaa taatattgaa aaaggaagag tcctgaggcg gaaagaacca gctgtggaat
3421  gtgtgtcagt tagggtgtgg aaagtcccca ggctccccag caggcagaag tatgcaaagc
3481  atgcatctca attagtcagc aaccaggtgt ggaaagtccc caggctcccc agcaggcaga
3541  agtatgcaaa gcatgcatct caattagtca gcaaccatag tcccgcccct aactccgccc
3601  atcccgcccc taactccgcc cagttccgcc cattctccgc cccatggctg actaattttt
3661  tttatttatg cagaggccga ggccgcctcg gcctctgagc tattccagaa gtagtgagga
3721  ggcttttttg gaggcctagg cttttgcaaa gatcgatcaa gagacaggat gaggatcgtt
3781  tcgcatgatt gaacaagatg gattgcacgc aggttctccg gccgcttggg tggagaggct
3841  attcggctat gactgggcac aacagacaat cggctgctct gatgccgccg tgttccggct
3901  gtcagcgcag gggcgcccgg ttcttttttgt caagaccgac ctgtccggtg ccctgaatga
```

SEQUENCE LISTING
A description of the non-limiting exemplary vectors and the sequences thereof discussed herein is provided herein below:

```
3961  actgcaagac gaggcagcgc ggctatcgtg gctggccacg acgggcgttc cttgcgcagc
4021  tgtgctcgac gttgtcactg aagcgggaag ggactggctg ctattgggcg aagtgccggg
4081  gcaggatctc ctgtcatctc accttgctcc tgccgagaaa gtatccatca tggctgatgc
4141  aatgcggcgg ctgcatacgc ttgatccggc tacctgccca ttcgaccacc aagcgaaaca
4201  tcgcatcgag cgagcacgta ctcggatgga agccggtctt gtcgatcagg atgatctgga
4261  cgaagagcat caggggctcg cgccagccga actgttcgcc aggctcaagg cgagcatgcc
4321  cgacggcgag gatctcgtcg tgacccatgg cgatgcctgc ttgccgaata tcatggtgga
4381  aaatggccgc ttttctggat tcatcgactg tggccggctg ggtgtggcgg accgctatca
4441  ggacatagcg ttggctaccc gtgatattgc tgaagagctt ggcggcgaat gggctgaccg
4501  cttcctcgtg ctttacggta tcgccgctcc cgattcgcag cgcatcgcct tctatcgcct
4561  tcttgacgag ttcttctgag cgggactctg gggttcgaaa tgaccgacca agcgacgccc
4621  aacctgccat cacgagattt cgattccacc gccgccttct atgaaaggtt gggcttcgga
4681  atcgttttcc gggacgccgg ctggatgatc ctccagcgcg gggatctcat gctggagttc
4741  ttcgcccacc ctaggggag gctaactgaa acacggaagg agacaatacc ggaaggaacc
4801  cgcgctatga cggcaataaa aagacagaat aaaaacgttg cgcaaactat taactggcga
4861  actacttact ctagcttccc ggcaacaatt aatagactgg atggaggcgg ataaagttgc
4921  aggaccactt ctgcgctcgg cccttccggc tggctggttt attgctgata atctggagc
4981  cggtgagcgt gggtctcgcg gtatcattgc agcactgggg ccagatggta agccctcccg
5041  tatcgtagtt atctacacga cggggagtca ggcaactatg gatgaacgaa atagacagat
5101  cgctgagata ggtgcctcac tgattaagca ttggtaactg tcagaccaag tttactcata
5161  tatactttag attgatttaa aacttcattt ttaatttaaa aggatctagg tgaagatcct
5221  ttttgataat ctcatgacca aaatccctta acgtgagttt cgttccact gagcgtcaga
5281  ccccgtagaa aagatcaaag gatcttcttg agatcctttt tttctgcgcg taatctgctg
5341  cttgcaaaca aaaaaaccac cgctaccagc ggtggtttgt ttgccggatc aagagctacc
5401  aactctttt ccgaaggtaa ctggcttcag cagagcgcag ataccaaata ctgtccttct
5461  agtgtagccg tagttaggcc accacttcaa gaactctgta gcaccgccta catacctcgc
5521  tctgctaatc ctgttaccag tggctgctgc cagtggcgat aagtcgtgtc ttaccgggtt
5581  ggactcaaga cgatagttac cggataaggc gcagcggtcg ggctgaacgg ggggttcgtg
5641  cacacagccc agcttggagc gaacgaccta ccgaactg atatacctac agcgtgagct
5701  atgagaaagc gccacgcttc ccgaagggag aaaggcggac aggtatccgg taagcggcag
5761  ggtcggaaca ggagagcgca cgagggagct tccaggggga aacgcctggt atctttatag
5821  tcctgtcggg tttcgccacc tctgacttga gcgtcgattt ttgtgatgct cgtcaggggg
5881  gcggagccta tggaaaaacg ccagcaacgc ggcctttta cggttcctgg ccttttgctg
5941  gccttttgct cacatgtcct gcaggcag
``` pAAV-U6-sgRNA-uD

LOCUS       pAAV-U6-sgRNA-uD 7141 bp DNA circular SYN 23-MAR-2017
DEFINITION  pAAV-U6-sgRNA-uDys Circularized -continued SEQUENCE LISTING
A description of the non-limiting exemplary vectors and the sequences thereof
discussed herein is provided herein below:

| FEATURES | Location/Qualifiers |
|---|---|
| misc_feature | 1..130<br>/gene = "ITR" |
| misc_feature | 162..3742<br>/note = "huUDys" |
| misc_feature | 3808..4039<br>/gene = "bGH pA" |
| misc_feature | complement(4046..4126)<br>/gene = "sgRNA scaffold" |
| misc_feature | complement(4147..4395)<br>/gene = "hU6" |
| misc_feature | 4404..4544<br>/gene = "ITR" |
| CDS | 5461..6321<br>/gene = "Amp" |
| misc_feature | 6469..7136<br>/gene = "pUC" |

ORIGIN (SEQ ID NO: 8)

```
   1 cctgcaggca gctgcgcgct cgctcgctca ctgaggccgc ccgggcgtcg ggcgaccttt
  61 ggtcgcccgg cctcagtgag cgagcgagcg cgcagagagg gagtggccaa ctccatcact
 121 aggggttcct gcggcctcta gactcgacat gggccgccac catgctgtgg tgggaggagg
 181 tggaggattg ttatgaaagg gaggacgtgc agaagaagac ttttaccaag tgggtgaacg
 241 ctcagttcag caaatttggg aagcagcaca tcgagaatct gttttccgac ctgcaggatg
 301 ggagacggct gctggatctg ctggaaggac tgactggcca gaagctgccc aaagagaagg
 361 ggagcactag ggtgcacgcc ctgaacaacg tgaacaaagc tctgagagtg ctgcagaaca
 421 acaacgtgga tctggtgaat attggcagta ctgatatcgt ggacgggaac cacaaactga
 481 cactgggcct gatctggaac attattctgc actggcaggt gaaaaatgtg atgaagaaca
 541 tcatggccgg gctgcagcag accaattccg agaagatcct gctgtcttgg gtgcggcaga
 601 gcacccgcaa ctatccccag gtgaacgtga ttaacttcac tacatcctgg agcgacgggc
 661 tggccctgaa tgctctgatt cacagccaca ggcctgatct gttcgactgg aatagcgtgg
 721 tgtgccagca gtctgccaca cagcgcctgg aacatgcctt caatatcgct cggtaccagc
 781 tggggatcga aaaactgctg gacccagagg atgtggacac tacatacccc gataaaaagt
 841 ctattctgat gtacattact agcctgttcc aggtgctgcc acagcaggtg tctattgaag
 901 ccattcagga ggtggaaatg ctgccccgcc cccccaaagt gactaaagag gagcattac
 961 agctgcatca tcagatgcat tacagccagc agattaccgt gagcctggct cagggatatg
1021 agcgcaccag tagtccaaaa ccacggttca gtcctacgc ttatacccag gctgcctacg
1081 tgacaactag cgaccctact agatccccct ttccatccca gcacctggag ccccagagg
1141 acaagagctt tgggtccagc ctgatggaaa gcgaggtgaa tctggatcgg taccagacag
1201 ccctggagga ggtgctgagc tggctgctga gtgctgaaga cactgcag gcccagggcg
1261 aaatttccaa tgacgtgaa gtggtgaagg atcagttcca cacacgag ggctatatga
1321 tggacctgac agctcaccag gggcgcgtgg caatatcct gcagctgggc tctaaactga
1381 tcggcaccgg gaaactgagt gaggacgagg aaacagaagt gcaggagcag atgaacctgc
```

SEQUENCE LISTING
A description of the non-limiting exemplary vectors and the sequences thereof
discussed herein is provided herein below:

```
1441  tgaacagccg ctgggagtgt ctgagagtgg ctagtatgga gaagcagtcc aacctgcacc
1501  gggtgctgat ggacctgcag aaccagaaac tgaaagagct gaacgactgg ctgacaaaga
1561  ctgaggaacg cacaaggaag atggaggagg agccactggg acccgacctg gaggatctga
1621  agagacaggt gcagcagcat aaggtgctgc aggaggatct ggaacaggag caggtgcggg
1681  tgaactccct gacacatatg gtggtggtgg tggacgaatc tagtggagat cacgccaccg
1741  ccgccctgga ggaacagctg aaggtgctgg gggaccggtg ggccaacatt gccggtgga
1801  ccgaggacag gtgggtgctg ctgcaggaca tcctgctgaa atggcagagg ctgaccgagg
1861  agcagtgtct gtttagtgct tggctgagcg agaaagagga cgccgtgaac aagatccaca
1921  caaccggctt taaggatcag aacgaaatgc tgtctagcct gcagaaactg gctgtgctga
1981  aggccgatct ggagaaaaag aagcagagca tgggcaaact gtatagcctg aaacaggacc
2041  tgctgagcac cctgaagaac aagagcgtga cccagaagac agaagcctgg ctggataact
2101  ttgcccgctg ctgggacaac ctggtgcaga aactggagaa aagtacagct cagatctctc
2161  aggctgtgac cacaacccag cctagcctga cccagacaac cgtgatggaa accgtgacca
2221  ccgtgacaac ccgcgaacag atcctggtga acatgccca ggaagagctg ccacctccac
2281  ctccccagaa gaagagaacc ctggagcggc tgcaggagct gcaggaagcc actgacgaac
2341  tggaccctga agctgaggcag gccgaagtga ttaaggggtc ttggcagcct gtgggcgatc
2401  tgctgattga ttccctgcag gaccacctgg aaaaggtgaa ggctctgaga ggcgaaattg
2461  ctccactgaa ggagaacgtg agtcatgtga acgatctggc tagacagctg acaacactgg
2521  gcatccagct gagcccatac aatctgagca cactggagga cctgaatacc aggtggaagc
2581  tgctgcaggt ggctgtggaa gacggggtgc ggcagctgca tgaggcccat cgccgacttcg
2641  gaccagccag ccagcacttt ctgagcacat ccgtgcaggg gccctgggag agggccattt
2701  ctcccaacaa ggtgccctac tatattaatc acgagaccca gaccacttgt tgggaccatc
2761  ccaagatgac agaactgtac cagtccctgg ccgatctgaa caacgtgagg tttagcgctt
2821  acagaaccgc tatgaagctg agacggctgc agaaggccct gtgcctggat ctgctgtccc
2881  tgtccgccgc ctgcgatgcc ctggatcagc ataatctgaa gcagaacgat cagccaatgg
2941  atatcctgca gatcatcaac tgcctgacca ctatctacga caggctggag caggagcaca
3001  acaacctggt gaacgtgcct ctgtgcgtgg atatgtgcct gaactggctg ctgaacgtgt
3061  atgacactgg gcgcaccggc cggatcagag tgctgagttt aaaactggg attatctccc
3121  tgtgtaaggc ccacctggag gacaagtaca ggtacctgtt caagcaggtg gctagtagca
3181  ctggattttg tgaccagcgc cgcctgggac tgctgctgca tgatagtatc cagattccta
3241  gacagctggg agaggtggct agtttcggag gatctaacat cgaacccagc gtgcgcagct
3301  gtttccagtt tgccaataac aaacctgaaa tcgaggctgc tctgttcctg gattggatgc
3361  gcctggaacc acagagcatg gtgtggctgc ctgtgctgca cagagtggct gccgccgaaa
3421  ctgccaagca ccaggctaaa tgcaacatct gcaaggaatg tcccattatc ggctttcgct
3481  acaggagtct gaaacatttt aactacgata tttgccagag ctgcttcttt tccggaagag
3541  tggccaaagg acacaagatg cactacccta tggtggaata ttgcacccca actacatctg
3601  gcgaagatgt gcgcgatttt gccaaggtgc tgaagaataa gtttcggact aagaggtact
```

SEQUENCE LISTING
A description of the non-limiting exemplary vectors and the sequences thereof discussed herein is provided herein below:

```
3661  tcgccaagca cccccgcatg gggtatctgc cagtgcagac agtgctggaa ggagacaata
3721  tggagaccga tacaatgtga gcggccgcaa taaaagatct ttattttcat tagatctgtg
3781  tgttggtttt tgtgtgtct agaattccta gagctcgctg atcagcctcg actgtgcctt
3841  ctagttgcca gccatctgtt gtttgcccct ccccccgtgcc ttccttgacc ctggaaggtg
3901  ccactcccac tgtcctttcc taataaaatg aggaaattgc atcgcattgt ctgagtaggt
3961  gtcattctat tctgggggt gggtgggc aggacagcaa gggggaggat tgggaagaga
4021  atagcaggca tgctggggag gtaccaaaaa tctcgccaac aagttgacga gataaacacg
4081  gcattttgcc ttgttttagt agattctgtt tccagagtac taaaactgag acctgccgtg
4141  gtctccggtg tttcgtcctt tccacaagat atataaagcc aagaaatcga atactttca
4201  agttacggta agcatatgat agtccatttt aaaacataat tttaaaactg caaactaccc
4261  aagaaattat tactttctac gtcacgtatt ttgtactaat atctttgtgt ttacagtcaa
4321  attaattcca attatctctc taacagcctt gtatcgtata tgcaaatatg aaggaatcat
4381  gggaaatagg ccctcgcggc cgcaggaacc cctagtgatg gagttggcca ctccctctct
4441  gcgcgctcgc tcgctcactg aggccgggcg accaaaggtc gcccgacgcc cgggctttgc
4501  ccgggcggcc tcagtgagcg agcgagcgcg cagctgcctg caggggcgcc tgatgcggta
4561  tttctcctt acgcatctgt gcggtatttc acaccgcata cgtcaaagca accatagtac
4621  gcgccctgta gcggcgcatt aagcgcggcg ggtgtggtgg ttacgcgcag cgtgaccgct
4681  acacttgcca gcgccctagc gcccgctcct ttcgctttct tcccttcctt tctcgccacg
4741  ttcgccggct ttccccgtca agctctaaat cggggggctcc ctttagggtt ccgatttagt
4801  gctttacggc acctcgaccc caaaaaactt gatttgggtg atggttcacg tagtgggcca
4861  tcgccctgat agacggtttt tcgccctttg acgttggagt ccacgttctt taatagtgga
4921  ctcttgttcc aaactggaac aacactcaac cctatctcgg gctattcttt tgatttataa
4981  gggattttgc cgatttcggc ctattggtta aaaaatgagc tgatttaaca aaaatttaac
5041  gcgaatttta caaaatatt aacgtttaca attttatggt gcactctcag tacaatctgc
5101  tctgatgccg catagttaag ccagccccga cacccgccaa cacccgctga cgcgccctga
5161  cgggcttgtc tgctcccggc atccgcttac agacaagctg tgaccgtctc cgggagctgc
5221  atgtgtcaga ggttttcacc gtcatcaccg aaacgcgcga cgaaagg cctcgtgata
5281  cgcctatttt tataggttaa tgtcatgata ataatggttt cttagacgtc aggtggcact
5341  tttcggggaa atgtgcgcgg aaccccctatt tgtttatttt tctaaataca ttcaaatatg
5401  tatccgctca tgagacaata accctgataa atgcttcaat aatattgaaa aaggaagagt
5461  atgagtattc aacatttccg tgtcgccctt attcccttt ttgcggcatt ttgccttcct
5521  gtttttgctc acccagaaac gctggtgaaa gtaaaagatg ctgaagatca gttgggtgca
5581  cgagtgggtt acatcgaact ggatctcaac agcggtaaga tccttgagag ttttcgcccc
5641  gaagaacgtt ttccaatgat gagcactttt aaagttctgc tatgtggcgc ggtattatcc
5701  cgtattgacg ccgggcaaga gcaactcggt cgccgcatac actattctca gaatgacttg
5761  gttgagtact caccagtcac agaaaagcat cttacggatg gcatgacagt aagagaatta
5821  tgcagtgctg ccataaccat gagtgataac actgcggcca acttacttct gacaacgatc
5881  ggaggaccga aggagctaac cgcttttttg cacaacatgg gggatcatgt aactcgcctt
```

SEQUENCE LISTING
A description of the non-limiting exemplary vectors and the sequences thereof discussed herein is provided herein below:

```
5941  gatcgttggg aaccggagct gaatgaagcc ataccaaacg acgagcgtga caccacgatg 6001  cctgtagcaa tggcaacaac gttgcgcaaa ctattaactg gcgaactact tactctagct 6061  tcccggcaac aattaataga ctggatggag gcggataaag ttgcaggacc acttctgcgc 6121  tcggcccttc cggctggctg gtttattgct gataaatctg gagccggtga gcgtggaagc 6181  cgcggtatca ttgcagcact ggggccagat ggtaagccct cccgtatcgt agttatctac 6241  acgacgggga gtcaggcaac tatggatgaa cgaaatagac agatcgctga gataggtgcc 6301  tcactgatta agcattggta actgtcagac caagtttact catatatact ttagattgat 6361  ttaaaacttc attttaatt taaaaggatc taggtgaaga tcctttttga taatctcatg 6421  accaaaatcc cttaacgtga gttttcgttc cactgagcgt cagacccgt agaaaagatc 6481  aaaggatctt cttgagatcc ttttttctg cgcgtaatct gctgcttgca acaaaaaaa 6541  ccaccgctac cagcggtggt ttgtttgccg gatcaagagc taccaactct ttttccgaag 6601  gtaactggct tcagcagagc gcagatacca aatactgtcc ttctagtgta gccgtagtta 6661  ggccaccact tcaagaactc tgtagcaccg cctacatacc tcgctctgct aatcctgtta 6721  ccagtggctg ctgccagtgg cgataagtcg tgtcttaccg ggttggactc aagacgatag 6781  ttaccggata aggcgcagcg gtcgggctga acggggggtt cgtgcacaca gcccagcttg 6841  gagcgaacga cctacaccga actgagatac ctacagcgtg agctatgaga aagcgccacg 6901  cttcccgaag ggagaaaggc ggacaggtat ccggtaagcg gcagggtcgg aacaggagag 6961  cgcacgaggg agcttccagg gggaaacgcc tggtatcttt atagtcctgt cgggtttcgc 7021  cacctctgac ttgagcgtcg atttttgtga tgctcgtcag ggggggcggag cctatggaaa 7081  aacgccagca acgcggcctt tttacggttc ctggcctttt gctggccttt tgctcacatg 7141  t
```

Spacer (SEQ ID NO: 9)
gcctccaagacccagagcattaagaagtacagcacagacattctgggcaacctgtatgaagtgaaatctaagaagcaccctcagatcatcaaaaagggcagcggcttcgccaacgagctgggccctagactgatgggaaagactagtagaccggtagagccatcaccccagcgc Dmd gRNA 1 (SEQ ID NO: 10)
ATATAATAGAAATTATTCAT Dmd gRNA 2 (SEQ ID NO: 11)
TAATATGCCCTGTAATATAA Dmd gRNA 3 (SEQ ID NO: 12)
TGATATCATCAATATCTTTG Dmd gRNA 4 (SEQ ID NO: 13)
GCAATTAATTGGAAAATGTG Dmd gRNA 5 (SEQ ID NO: 14)
CTTTAAGC TTAGGTAAAATCA Dmd gRNA 6 (SEQ ID NO: 15)
CAGTAATGTGTCATACC TT C Dmd gRNA 7 (SEQ ID NO: 16)
CAGGGCATATTATATTTAGA Dmd gRNA 8 (SEQ ID NO: 17)
CAAAAGCCAAATCTATTTCA spCas9 (SEQ ID NO: 18)
>sp|Q99ZW2|CAS9_STRP1 CRISPR-associated endonuclease Cas9/Csn1 OS = *Streptococcus*

SEQUENCE LISTING
A description of the non-limiting exemplary vectors and the sequences thereof
discussed herein is provided herein below:

*pyogenes* serotype M1 GN = cas9 PE = 1 SV = 1
MDKKYSIGLDIGTNSVGWAVITDEYKVPSKKFKVLGNTDRHSIKKNLIGALLFDSGE
TAEATRLKRTARRRYTRRKNRICYLQEIFSNEMAKVDDSFFIIRLEESFLVEEDKKHE
RHPIFGNIVDEVAYHEKYPTIYHLRKKLVDSTDKADLRLIYLALAHMIKFRGHFLIEG
DLNPDNSDVDKLFIQLVQTYNQLFEENPINASGVDAKAILSARLSKSRRLENLIAQLP
GEKKNGLFGNLIALSLGLTPNFKSNFDLAEDAKLQLSKDTYDDDLDNLLAQIGDQYA
DLFLAAKNLSDAILLSDILRVNTEITKAPLSASMIKRYDEHHQDLTLLKALVRQQLPE
KYKEIFFDQSKNGYAGYIDGGASQEEFYKFIKPILEKMDGTEELLVKLNREDLLRKQR
TFDNGSIPHQIHLGELHAILRRQEDFYPFLKDNREKIEKILTFRIPYYVGPLARGNSRFA
WMTRKSEETITPWNFEEVVDKGASAQSFIERMTNFDKNLPNEKVLPKHSLLYEYFTV
YNELTKVKYVTEGMRKPAFLSGEQKKAIVDLLFKTNRKVTVKQLKEDYFKKIECFD
SVEISGVEDRFNASLGTYHDLLKIIKDKDFLDNEENEDILEDIVLTLTLFEDREMIEERL
KTYAHLFDDKVMKQLKRRRYTGWGRLSRKLINGIRDKQSGKTILDFLKSDGFANRN
FMQLIHDDSLTFKEDIQKAQVSGQGDSLHEHIANLAGSPAIKKGILQTVKVVDELVK
VMGRHKPENIVIEMARENQTTQKGQKNSRERMKRIEEGIKELGSQILKEHPVENTQL
QNEKLYLYYLQNGRDMYVDQELDINRLSDYDVDHIVPQSFLKDDSIDNKVLTRSDK
NRGKSDNVPSEEVVKKMKNYWRQLLNAKLITQRKFDNLTKAERGGLSELDKAGFIK
RQLVETRQITKHVAQILDSRMNTKYDENDKLIREVKVITLKSKLVSDFRKDFQFYKV
REINNYHHAHDAYLNAVVGTALIKKYPKLESEFVYGDYKVYDVRKMIAKSEQEIGK
ATAKYFFEYSNIMNEEKTEITLANGEIRKRPLIETNGETGEIVWDKGRDEATVRKVLSM
PQVNIVKKTEVQTGGFSKESILPKRNSDKLIARKKDWDPKKYGGFDSPTVAYSVLVV
AKVEKGKSKKLKSVKELLGITIMERSSFEKNPIDFLEAKGYKEVKKDLIIKLPKYSLFE
LENGRKRMLASAGELQKGNELALPSKYVNFLYLASHYEKLKGSPEDNEQKQLFVEQ
HKHYLDEIIEQISEFSKRVILADANLDKVLSAYNKEIRDKPIREQAENIIEILFTLTNLGA
PAAFKYFDTTIDRKRYTSTKEVLDATLIHQSITGLYETRIDLSQLGGD Cpf1 (SEQ ID NO: 19)
CPF1 FRATN CRISPR-associated endonuclease Cpf1 OS = *Francisella tularensis* subsp.
novicida (strain U112) GN = cpf1 PE = 1 SV = 1
MSIYQEFVNKYSLSKTLRFELIPQGKTLENIKARGLILDDEKRAKDYKKAKQIIDKYH
QFFWEILSSVCISEDLLQNYSDVYFKLKKSDDDNLQKDFKSAKDTIKKQISEYIKDSE
KFKNLFNQNLIDAKKGQESDLILWLKQSKDNGIELFKANSDITDIDEALEIIKSFKGWT
TYFKGEHENRKNVYSSNDIPTSITYRIVDDNLPKELENKAKYESLKDKAPEAINYEQIK
KDLAEELTEDIDYKTSEVNQRVFSLDEVFEIANENNYLNQSGITKFNTIIGGKEVNGEN
TKRKGINEYINLYSQQINDKTLKKYKMSVLFKQILSDTESKSFVIDKLEDDSDVVTTM
QSFYEQIAAFKTVEEKSIKETLSLLFDDLKAQKLDLSKIYFKNDKSLTDLSQQVFDDY
SVIGTAVLEYITQQIAPKNLDNPSKKEQELIAKKTEKAKYLSLETIKLALEEENKHRDI
DKQCRFEEILANFAAIPMIFDEIAQNKDNLAQISIKYQNQGKKDLLQASAEDDVKAIK
DLLDQTNNLLEIKLKIEHISQSEDKANILDKDEHFYLVFEECYFELANIVPLYNKIRNYI
TQKPYSDEKFKLNEENSTLANGWDKNKEPDNTAILFIKDDKYYLGVMNKKNNKIFD
DKAIKENKGEGYKKIVYKLLPGANKMLPKVFFSAKSIKFYNPSEDILRIRNHSTHTKN
GSPQKGYEKFEFNIEDCRKFIDEYKQSISKHPEWKDFGERFSDTQRYNSIDEFYREVE
NQGYKLTFENISESYIDSVVNQGKLYLFQIYNKDFSAYSKGRPNLHTLYWKALFDER
NLQDVVYKLNGEAELFYRKQSIPKKITHPAKEAIANKNKDNPKKESVFEYDLIKDKR
FTEDKFFFHCPITINFKSSGANKENDEINLLLKEKANDVHILSIDRGERHLAYYTLVDG
KGNIIKQDTFNIIGNDRMKTNYHDKLAAIEKDRDSARKDWKKINNIKEMKEGYLSQV
VHEIAKLVIEYNAIVVFEDLNEGFKRGREKVEKQVYQKLEKMLIEKLNYLVEKDNEF
DKTGGVLRAYQLTAPEETFKKMGKQTGIIYYVPAGFTSKICPVTGEVNQLYPKYESV
SKSQEFFSKEDKICYNLDKGYFEESEDYKNEGDKAAKGKWTIASFGSRLINFRNSDKN
HNWDTREVYPTKELEKLLKDYSIEYGHGECIKAAICGESDKKFFAKLTSVLNTILQM
RNSKTGTELDYLISPVADVNGNFFDSRQAPKNMPQDADANGAYHIGLKGLMLLGRI
KNNQEGKKLNLVIKNEEYFEFVQNRNN SpCas9 PAM (SEQ ID NO: 20)
NGG SpCas9 D1135E variant PAM (SEQ ID NO: 21)
NGG SpCas9 VRER variant PAM (SEQ ID NO: 22)
NGCG SpCas9 EQR variant PAM (SEQ ID NO: 23)
NGAG SpCas9 VQR variant PAM 1 (SEQ ID NO: 24)
NGAN SpCas9 VQR variant PAM 1 (SEQ ID NO: 25)
NGNG SaCas9 PAM 1 (SEQ ID NO: 26)
NNGRRT SaCas9 PAM 2 (SEQ ID NO: 27)

```
                       SEQUENCE LISTING
   A description of the non-limiting exemplary vectors and the sequences thereof
                      discussed herein is provided herein below:
```

NNGRR(N)

NMCas9 PAM (SEQ ID NO: 28)
NNNNGATT

STCas9 PAM (SEQ ID NO: 29)
NNAGAAW

TD Cas9 PAM (SEQ ID NO: 30)
NAAAAC

Linker 1 (SEQ ID NO: 31)
KESGSVSSEQLAQFRSLD

Linker 2 (SEQ ID NO: 32)
EGKSSGSGSESKST

Linker 3 (SEQ ID NO: 33)
GGGGGGGG

Linker 4 (SEQ ID NO: 34)
GSAGSAAGSGEF

Linker 5 (SEQ ID NO: 35)
A(EAAAK)nA (n = 2-5)

saCas9-VP2 fusion peptide for exterior capsid expression (SEQ ID NO: 36)
(pNLRep2-Caprh74-AVB-VP2NN-VP3knock-Cas9update starting at bp 5532)
MAPKKKRKVGIHGVPAAKRNYILGLDIGITSVGYGIIDYETRDVIDAGVR
LFKEANVENNEGRRSKRGARRLKRRRRHRIQRVKKLLFDYNLLTDHSELS
GINPYEARVKGLSQKLSEEEFSAALLHLAKRRGVHNVNEVEEDTGNELST
KEQISRNSKALEEKYVAELQLERLKKDGEVRGSINRFKTSDYVKEAKQLL
KVQKAYHQLDQSFIDTYIDLLETRRTYYEGPGEGSPFGWKDIKEWYEMLM
GHCTYFPEELRSVKYAYNADLYNALNDLNNLVITRDENEKLEYYEKFQII
ENVFKQKKKPTLKQIAKEILVNEEDIKGYRVTSTGKPEFTNLKVYHDIKD
ITARKEIIENAELLDQIAKILTIYQSSEDIQEELTNLNSELTQEEIEQIS
NLKGYTGTHNLSLKAINLILDELWHTNDNQIAIFNRLKLVPKKVDLSQQK
EIPTTLVDDFILSPVVKRSFIQSIKVINAIIKKYGLPNDIIIELAREKNS
KDAQKMINEMQKRNRQTNERIEEIIRTTGKENAKYLIEKIKLHDMQEGKC
LYSLEAIPLEDLLNNPFNYEVDHIIPRSVSFDNSFNNKVLVKQEENSKKG
NRTPFQYLSSSDSKISYETFKKHILNLAKGKGRISKTKKEYLLEERDINR
FSVQKDFINRNLVDTRYATRGLMNLLRSYFRVNNLDVKVKSINGGFTSFL
RRKWKFKKERNKGYKEEHAEDALIIANADFIFKEWKKLDKAKKVMENQWE
EKQAESMPEIETEQEYKEIFITPHQIKHIKDFKDYKYSHRVDKKPNRELI
NDTLYSTRKDDKGNTLIVNNLNGLYDKDNDKLKKLINKSPEKLLMYHHDP
QTYQKLKLIMEQYGDEKNPLYKYYEETGNYLTKYSKKDNGPVIKKIKYYG
NKLNAHLDITDDYPNSRNKVVKLSLKPYRFDVYLDNGVYKFVTVKNLDVI
KKENYYEVNSKCYEEAKKLKKISNQAEFIASFYNNDLIKINGELYRVIGV
NNDLLNRIEVNMIDITYREYLENMNDKRPPRIIKTIASKTQSIKKYSTDI
LGNLYEVKSKKHPQIIKKGSGFANELGPRLMGKTSTAPGKKRPVEPSPQR
SPDSSTGIGKKGQQPAKKRLNFGQTGDSESVPDPQPIGEPPAGPSGLGSG
TLAAGGGAPLADNNEGADGVGSSSGNWHCDSTWLGDRVITTSTRTWALPT
YNNHLYKQISNGTSGGSTNDNTYFGYSTPWGYFDFNRFHCHFSPRDWQRL
INNNWGFRPKRLNFKLFNIQVKEVTQNEGTKTIANNLTSTIQVFTDSEYQ
LPYVLGSAHQGCLPPFPADVFMIPQYGYLTLNNGSQAVGRSSFYCLEYFP
SQMLRTGNNFEFSYNFEDVPFHSSYAHSQSLDRLMNPLIDQYLYYLSRTQ
STGGTAGTQQLLFSQAGPNNMSAQAKNWLPGPCYRQQRVSTTLSQNNNSN
FAWTGATKYHLNGRDSLVNPGVAMATHKDDEERFFPSSGVLMFGKQGAGK
DNVDYSSVMLTSEEEIKTTNPVATEQYGVVADNLQQQNAAPIVGAVNSQG
ALPGMVWQNRDVYLQGPIWAKIPHTDGNFHPSPLMGGFGLKHPPPQILIK
NTPVPADPPTTFSQAKLASFITQYSTGQVSVEIEWELQKENSKRWNPEIQ
YTSNYYKSTNVDFAVNTEGTYSEPRPIGTRYLTRNL VP1 protein (SEQ ID NO: 37)
Translation of VP1 (pAAVrh74-VP1-3 starting at bp 5037)
MAADGYLPDWLEDNLSEGIREWWDLKPGAPKPKANQQKQDNGRGLVLPGY
KYLGPFNGLDKGEPVNAADAAALEHDKAYDQQLQAGDNPYLRYNHADAEF
QERLQEDTSFGGNLGRAVFQAKKRVLEPLGLVESPVKAAPGKKRPVEPSP
QRSPDSSTGIGKKGQQPAKKRLNFGQTGDSESVPDPQPIGEPPAGPSGLG
SGTMAAGGGAPMADNNEGADGVGSSSGNWHCDSTWLGDRVITTSTRTWAL
PTYNNHLYKQISNGTSGGSTNDNTYFGYSTPWGYFDFNRFHCHFSPRDWQ
RLINNNWGFRPKRLNFKLFNIQVKEVTQNEGTKTIANNLTSTIQVFTDSE
YQLPYVLGSAHQGCLPPFPADVFMIPQYGYLTLNNGSQAVGRSSFYCLEY
FPSQMLRTGNNFEFSYNFEDVPFHSSYAHSQSLDRLMNPLIDQYLYYLSR
TQSTGGTAGTQQLLFSQAGPNNMSAQAKNWLPGPCYRQQRVSTTLSQNNN

```
SNFAWTGATKYHLNGRDSLVNPGVAMATHKDDEERFFPSSGVLMFGKQGA
GKDNVDYSSVMLTSEEEIKTTNPVATEQYGVVADNLQQQNAAPIVGAVNS
QGALPGMVWQNRDVYLQGPIWAKIPHTDGNFHPSPLMGGFGLKHPPPQIL
IKNTPVPADPPTTFSQAKLASFITQYSTGQVSVEIEWELQKENSKRWNPE
IQYTSNYYKSTNVDFAVNTEGTYSEPRPIGTRYLTRNL

VP3 protein (SEQ ID NO: 38)
Translation of VP3 (pAAVrh74-VP1-3 starting at bp 5646)
MAAGGGAPMADNNEGADGVGSSSGNWHCDSTWLGDRVITTSTRTWALPTY
NNHLYKQISNGTSGGSTNDNTYFGYSTPWGYFDFNRFHCHFSPRDWQRLI
NNNWGFRPKRLNFKLFNIQVKEVTQNEGTKTIANNLTSTIQVFTDSEYQL
PYVLGSAHQGCLPPFPADVFMIPQYGYLTLNNGSQAVGRSSFYCLEYFPS
QMLRTGNNFEFSYNFEDVPFHSSYAHSQSLDRLMNPLIDQYLYYLSRTQS
TGGTAGTQQLLFSQAGPNNMSAQAKNWLPGPCYRQQRVSTTLSQNNNSNF
AWTGATKYHLNGRDSLVNPGVAMATHKDDEERFFPSSGVLMFGKQGAGKD
NVDYSSVMLTSEEEIKTTNPVATEQYGVVADNLQQQNAAPIVGAVNSQGA
LPGMVWQNRDVYLQGPIWAKIPHTDGNFHPSPLMGGFGLKHPPPQILIKN
TPVPADPPTTFSQAKLASFITQYSTGQVSVEIEWELQKENSKRWNPEIQY
TSNYYKSTNVDFAVNTEGTYSEPRPIGTRYLTRNL VP2 protein (SEQ ID NO: 39)
Translation of VP2 (pNLRep2-Caprh74-AVB-VP2 starting at bp 5448)
MASGKKRSVEPSPQRSPDSSTGIGKKGQQPAKKRLNFGQTGDSESVPDPQ
PIGEPPAGPSGLGSGTMAAGGGAPMADNNEGADGVGSSSGNWHCDSTWLG
DRVITTSTRTWALPTYNNHLYKQISNGTSGGSTNDNTYFGYSTPWGYFDF
NRFHCHFSPRDWQRLINNNWGFRPKRLNFKLFNIQVKEVTQNEGTKTIAN
NLTSTIQVFTDSEYQLPYVLGSAHQGCLPPFPADVFMIPQYGYLTLNNGS
QAVGRSSFYCLEYFPSQMLRTGNNFEFSYNFEDVPFHSSYAHSQSLDRLM
NPLIDQYLYYLSRTQSTGGTAGTQQLLFSQAGPNNMSAQAKNWLPGPCYR
QQRVSTTLSQNNNSNFAWTGATKYHLNGRDSLVNPGVAMATHKDDEERFF
PSSGVLMFGKQGAGKDNVDYSSVMLTSEEEIKTTNPVATEQYGVVADNLQ
QQNAAPIVGAVNSQGALPGMVWQNRDVYLQGPIWAKIPHTDGNFHPSPLM
GGFGLKHPPPQILIKNTPVPADPPTTFSQAKLASFITQYSTGQVSVEIEW
ELQKENSKRWNPEIQYTSNYYKSTNVDFAVNTEGTYSEPRPIGTRYLTRNL dSaCas9 protein (SEQ ID NO: 40)
Translation of dSaCas9 (pX603-AAV-CMV-NLS-dSaCas9-NLS-3xHA-bGHpA starting at
bp 700)
MGGRRVRWEVYISRALWLTTGATMAPKKKRKVGIHGVPAAKRNYILGLAI
GITSVGYGIlDYETRDVIDAGVRLFKEANVENNEGRRSKRGARRLKRRRR
HRIQRVKKLLFDYNLLTDHSELSGINPYEARVKGLSQKLSEEEFSAALLH
LAKRRGVHNVNEVEEDTGNELSTKEQISRNSKALEEKYVAELQLERLKKD
GEVRGSINRFKTSDYVKEAKQLLKVQKAYHQLDQSFIDTYIDLLETRRTY
YEGPGEGSPFGWKDIKEWYEMLMGHCTYFPEELRSVKYAYNADLYNALND
LNNLVITRDENEKLEYYEKFQIIENVFKQKKKPTLKQIAKEILVNEEDIK
GYRVTSTGKPEFTNLKVYHDIKDITARKEIIENAELLDQIAKILTIYQSS
EDIQEELTNLNSELTQEEIEQISNLKGYTGTHNLSLKAINLILDELWHTN
DNQIAIFNRLKLVPKKVDLSQQKEIPTTLVDDFILSPVVKRSFIQSIKVI
NAIIKKYGLPNDIIIELAREKNSKDAQKMINEMQKRNRQTNERIEEIIRT
TGKENAKYLIEKIKLHDMQEGKCLYSLEAIPLEDLLNNPFNYEVDHIIPR
SVSFDNSFNNKVLVKQEEASKKGNRTPFQYLSSSDSKISYETFKKHILNL
AKGKGRISKTKKEYLLEERDINRFSVQKDFINRNLVDTRYATRGLMNLLR
SYFRVNNLDVKVKSINGGFTSFLRRKWKFKKERNKGYKHHAEDALIIANA
DFIFKEWKKLDKAKKVMENQMFEEKQAESMPEIETEQEYKEIFITPHQIK
HIKDFKDYKYSHRVDKKPNRELINDTLYSTRKDDKGNTLIVNNLNGLYDK
DNDKLKKLINKSPEKLLMYHHDPQTYQKLKLIMEQYGDEKNPLYKYYEET
GNYLTKYSKKDNGPVIKKIKYYGNKLNAHLDITDDYPNSRNKVVKLSLKP
YRFDVYLDNGVYKFVTVKNLDVIKKENYYEVNSKCYEEAKKLKKISNQAE
FIASFYNNDLIKINGELYRVIGVNNDLLNRIEVNMIDITYREYLENMNDK
RPPRIIKTIASKTQSIKKYSTDILGNLYEVKSKKHPQIIKKGKRPAATKK
AGQAKKKKGSYPYDVPDYAYPYDVPDYAYPYDVPDYA CMV promoter (SEQ ID NO: 41)
TAGTAATCAATTACGGGGTCATTAGTTCATAGCCCATATATGGAGTTCCGCGTTA
CATAACTTACGGTAAATGGCCCGCCTGGCTGACCGCCCAACGACCCCCGCCCATT
GACGTCAATAATGACGTATGTTCCCATAGTAACGCCAATAGGGACTTTCCATTGA
CGTCAATGGGTGGAGTATTTACGGTAAACTGCCCACTTGGCAGTACATCAAGTGT
ATCATATGCCAAGTACGCCCCCTATTGACGTCAATGACGGTAAATGGCCCGCCTG
GCATTATGCCCAGTACATGACCTTATGGGACTTTCCTACTTGGCAGTACATCTAC
GTATTAGTCATCGCTATTACCATGGTGATGCGGTTTTGGCAGTACATCAATGGGC
GTGGATAGCGGTTTGACTCACGGGGATTTCCAAGTCTCCACCCCATTGACGTCAA
TGGGAGTTTGTTTTGGCACCAAAATCAACGGGACTTTCCAAAATGTCGTAACAAC
TCCGCCCCATTGACGCAAATGGGCGGTAGGCGTGTACGGTGGGAGGTCTATATA
AGCAGAGCTGGTTTAGTGAACCGTCAG
```

SEQUENCE LISTING
A description of the non-limiting exemplary vectors and the sequences thereof discussed herein is provided herein below:

U6 promoter (SEQ ID NO: 42)
```
ggtg tttcgtcctt tccacaagat atataaagcc aagaaatcga atactttca
agttacggta agcatatgat agtccatttt aaaacataat tttaaaactg caaactaccc
aagaaattat tactttctac gtcacgtatt ttgtactaat atctttgtgt ttacagtcaa
attaattcca attatctctc taacagcctt gtatcgtata tgcaaatatg aaggaatcat
gggaaatagg ccctc
```

228Cas9VP2 fusion protein (SEQ ID NO: 45)
Translation of VP2 (pNLRep2-Caprh74-AVB-VP2-NN-VP3 knockSpe starting at bp 5448)
```
MASGTSRPVEPSPQRSPDSSTGIGKKGQQPAKKRLNFGQTGDSESVPDPQ
PIGEPPAGPSGLGSGTLAAGGGAPLADNNEGADGVGSSGGGGGSMAPKK
KRKVGIHGVPAAKRNYILGLDIGITSVGYGIIDYETRDVIDAGVRLFKEA
NVENNEGRRSKRGARRLKRRRHRIQRVKKLLFDYNLLTDHSELSGINPY
EARVKGLSQKLSEEEFSAALLHLAKRRGVHNVNEVEEDTGNELSTKEQIS
RNSKALEEKYVAELQLERLKKDGEVRGSINRFKTSDYVKEAKQLLKVQKA
YHQLDQSFIDTYIDLLETRRTYYEGPGEGSPFGWKDIKEWYEMLMGHCTY
FPEELRSVKYAYNADLYNALNDLNNLVITRDENEKLEYYEKFQIIENVFK
QKKKPTLKQIAKEILVNEEDIKGYRVTSTGKPEFTNLKVYHDIKDITARK
EIIENAELLDQIAKILTIYQSSEDIQEELTNLNSELTQEEIEQISNLKGY
TGTHNLSLKAINLILDELWHTNDNQIAIFNRLKLVPKKVDLSQQKEIPTT
LVDDFILSPVVKRSFIQSIKVINAIIKKYGLPNDIIIELAREKNSKDAQK
MINEMQKRNRQTNERIEEIIRTTGKENAKYLIEKIKLHDMQEGKCLYSLE
AIPLEDLLNNPFNYEVDHIIPRSVSFDNSFNNKVLVKQEENSKKGNRTPF
QYLSSSDSKISYETFKKHILNLAKGKGRISKTKKEYLLEERDINRFSVQK
DFINRNLVDTRYATRGLMNLLRSYFRVNNLDVKVKSINGGFTSFLRRKWK
FKKERNKGYKHHAEDALIIANADFIFKEWKKLDKAKKVMENQMFEEKQAE
SMPEIETEQEYKEIFITPHQIKHIKDFKDYKYSHRVDKKPNRELINDTLY
STRKDDKGNTLIVNNLNGLYDKDNDKLKKLINKSPEKLLMYHHDPQTYQK
LKLIMEQYGDEKNPLYKYYEETGNYLTKYSKKDNGPVIKKIKYYGNKLNA
HLDITDDYPNSRNKVVKLSLKPYRFDVYLDNGVYKFVTVKNLDVIKKENY
YEVNSKCYEEAKKLKKISNQAEFIASFYNNDLIKINGELYRVIGVNNDLL
NRIEVNMIDITYREYLENMNDKRPPRIIKTIASKTQSIKKYSTDILGNLY
EVKSKKHPQIIKKGSGFANELGPRLMGKGGGGSNWHCDSTWLGDRVITTS
TRTWALPTYNNHLYKQISNGTSGGSTNDNTYFGYSTPWGYFDFNRPHCHF
SPRDWQRLINNNWGFRPKRLNFKLFNIQVKEVTQNEGTKTIANNLTSTIQ
VFTDSEYQLPYVLGSAHQGCLPPFPADVFMIPQYGYLTLNNGSQAVGRSS
FYCLEYFPSQMLRTGNNFEFSYNFEDVPFHSSYAHSQSLDRLMNPLIDQY
LYYLSRTQSTGGTAGTQQLLFSQAGPNNMSAQAKNWLPGPCYRQQRVSTT
LSQNNNSNFAWTGATKYHLNGRDSLVNPGVAMATHKDDEERFFPSSGVLM
FGKQGAGKDNVDYSSVMLTSEEEIKTTNPVATEQYGVVADNLQQQNAAPI
VGAVNSQGALPGMVWQNRDVYLQGPIWAKIPHTDGNFHPSPLMGGFGLKH
PPPQILIKNTPVPADPPTTFSQAKLASFITQYSTGQVSVEIEWELQKENS
KRWNPEIQYTSNYYKSTNVDFAVNTEGTYSEPRPIGTRYLTRNL
```

350Cas9VP2 fusion protein (SEQ ID NO: 46)
Translation of VP2 (pNLRep2-Caprh74-AVB-VP2-NN-VP3 knockSpe starting at bp 5448)
```
MASGTSRPVEPSPQRSPDSSTGIGKKGQQPAKKRLNFGQTGDSESVPDPQ
PIGEPPAGPSGLGSGTLAAGGGAPLADNNEGADGVGSSGNWHCDSTWLG
DRVITTSTRTWALPTYNNHLYKQISNGTSGGSTNDNTYFGYSTPWGYFDF
NRFHCHFSPRDWQRLINNNWGFRPKRLNFKLFNIQVKEVTQNEGTKTIAN
NLTSTIQVFTDSEGGGGSMAPKKKRKVGIHGVPAAKRNYILGLDIGITSV
GYGIIDYETRDVIDAGVRLFKEANVENNEGRRSKRGARRLKRRRHRIQR
VKKLLFDYNLLTDHSELSGINPYEARVKGLSQKLSEEEFSAALLHLAKRR
GVHNVNEVEEDTGNELSTKEQISRNSKALEEKYVAELQLERLKKDGEVRG
SINRFKTSDYVKEAKQLLKVQKAYHQLDQSFIDTYIDLLETRRTYYEGPG
EGSPFGWKDIKEWYEMLMGHCTYFPEELRSVKYAYNADLYNALNDLNNLV
ITRDENEKLEYYEKFQIIENVFKQKKKPTLKQIAKEILVNEEDIKGYRVT
STGKPEFTNLKVYHDIKDITARKEIIENAELLDQIAKILTIYQSSEDIQE
ELTNLNSELTQEEIEQISNLKGYTGTHNLSLKAINLILDELWHTNDNQIA
IFNRLKLVPKKVDLSQQKEIPTTLVDDFILSPVVKRSFIQSIKVINAIIK
KYGLPNDIIIELAREKNSKDAQKMINEMQKRNRQTNERIEEIIRTTGKEN
AKYLIEKIKLHDMQEGKCLYSLEAIPLEDLLNNPFNYEVDHIIPRSVSFD
NSFNNKVLVKQEENSKKGNRTPFQYLSSSDSKISYETFKKHILNLAKGKG
RISKTKKEYLLEERDINRFSVQKDFINRNLVDTRYATRGLMNLLRSYFRV
NNLDVKVKSINGGFTSFLRRKWKFKKERNKGYKHHAEDALIIANADFIFK
EWKKLDKAKKVMENQMFEEKQAESMPEIETEQEYKEIFITPHQIKHIKDF
KDYKYSHRVDKKPNRELINDTLYSTRKDDKGNTLIVNNLNGLYDKDNDKL
KKUNKSPEKLLMYHTIDPQTYQKLKLIMEQYGDEKNPLYKYYEETGNYLT
KYSKKDNGPVIKKIKYYGNKLNAHLDITDDYPNSRNKVVKLSLKPYRFDV
YLDNGVYKFVTVKNLDVIKKENYYEVNSKCYEEAKKLKKISNQAEFIASF
YNNDLIKINGELYRVIGVNNDLLNRIEVNMIDITYREYLENMNDKRPPRI
IKTIASKTQSIKKYSTDILGNLYEVKSKKHPQIIKKGSGFANELGPRLMG
KGGGGSYQLPYVLGSAHQGCLPPFPADVFMIPQYGYLTLNNGSQAVGRSS
FYCLEYFPSQMLRTGNNFEFSYNFEDVPFHSSYAHSQSLDRLMNPLIDQY
LYYLSRTQSTGGTAGTQQLLFSQAGPNNMSAQAKNWLPGPCYRQQRVSTT
```

SEQUENCE LISTING
A description of the non-limiting exemplary vectors and the sequences thereof
discussed herein is provided herein below:

```
LSQNNNSNFAWTGATKYHLNGRDSLVNPGVAMATHKDDEERFFPSSGVLM
FGKQGAGKDNVDYSSVMLTSEEEIKTTNPVATEQYGVVADNLQQQNAAPI
VGAVNSQGALPGMVWQNRDVYLQGPIWAKIPHTDGNFHPSPLMGGFGLKH
PPPQILIKNTPVPADPPTTFSQAKLASFITQYSTGQVSVEIEWELQKENS
KRWNPEIQYTSNYYKSTNVDFAVNTEGTYSEPRPIGTRYLTRNL

419Cas9VP2 fusion protein (SEQ ID NO: 47)
Translation of VP2 (pNLRep2-Caprh74-AVB-VP2-NN-VP3 knockSpe starting at bp 5448)
MASGTSRPVEPSPQRSPDSSTGIGKKGQQPAKKRLNFGQTGDSESVPDPQ
PIGEPPAGPSGLGSGTLAAGGGAPLADNNEGADGVGSSSGNWHCDSTWLG
DRVITTSTRTWALPTYNNULYKQISNGTSGGSTNDNTYFGYSTPWGYFDF
NRFHCHFSPRDWQRLINNNWGFRPKRLNFKLFNIQVKEVTQNEGTKTIAN
NLTSTIQVFTDSEYQLPYVLGSAHQGCLPPFPADVFMIPQYGYLTLNNGS
QAVGRSSFYCLEYFPSQMLRTGNNFEFSYNFEGGGGSMAPKKKRKVGIEG
VPAAKRNYILGLDIGITSVGYGIIDYETRDVIDAGVRLFKEANVENNEGR
RSKRGARRLKRRRHRIQRVKKLLFDYNLLTDHSELSGINPYEARVKGLS
QKLSEEEFSAALLHLAKRRGVHNVNEVEEDTGNELSTKEQISRNSKALEE
KYVAELQLERLKKDGEVRGSINRFKTSDYVKEAKQLLKVQKAYHQLDQSF
IDTYIDLLETRRTYYEGPGEGSPFGWKDIKEWYEMLMGHCTYFPEELRSV
KYAYNADLYNALNDLNNLVITRDENEKLEYYEKFQIIENVFKQKKKPTLK
QIAKEILVNEEDIKGYRVTSTGKPEFTNLKVYHDIKDITARKEIIENAEL
LDQIAKILTIYQSSEDIQEELTNLNSELTQEEIEQISNLKGYTGTHNLSL
KAINLILDELWHTNDNQIAIFNRLKLVPKKVDLSQQKEIPTTLVDDFILS
PVVKRSFIQSIKVINAIIKKYGLPNDIIIELAREKNSKDAQKMINEMQKR
NRQTNERIEEIIRTTGKENAKYLIEKIKLHDMQEGKCLYSLEAIPLEDLL
NNPFNYEVDHIIPRSVSFDNSFNNKVLVKQEENSKKGNRTPFQYLSSSDS
KISYETFKKHILNLAKGKGRISKTKKEYLLEERDINRFSVQKDFINRNLV
DTRYATRGLMNLLRSYFRVNNLDVKVKSINGGFTSFLRRKWKFKKERNKG
YKHHAEDALIIANADFIFKEWKKLDKAKKVMENQMFEEKQAESMPEIETE
QEYKEIFITPHQIKHIKDFKDYKYSHRVDKKPNRELINDTLYSTRKDDKG
NTLIVNNLGLYDKDNDKLKKLINKSPEKLLMYHHDPQTYQKLKLIMEQY
GDEKNPLYKYYEETGNYLTKYSKKDNGPVIKKIKYYGNKLNAHLDITDDY
PNSRNKVVKLSLKPYRFDVYLDNGVYKFVTVKNLDVIKKENYYEVNSKCY
EEAKKLKKISNQAEFIASFYNNDLIKINGELYRVIGVNNDLLNRIEVNMI
DITYREYLENMNDKRPPRIIKTIASKTQSIKKYSTDILGNLYEVKSKKHP
QIIKKGSGFANELGPRLMGKGGGGSDVPFHSSYAHSQSLDRLMNPLIDQY
LYYLSRTQSTGGTAGTQQLLFSQAGPNNMSAQAKNWLPGCYRQQRVSTT
LSQNNNSNFAWTGATKYHLNGRDSLVNPGVAMATHKDDEERFFPSSGVLM
FGKQGAGKDNVDYSSVMLTSEEEIKTTNPVATEQYGVVADNLQQQNAAPI
VGAVNSQGALPGMVWQNRDVYLQGPIWAKIPHTDGNFHPSPLMGGFGLKH
PPPQILIKNTPVPADPPTTFSQAKLASFITQYSTGQVSVEIEWELQKENS
KRWNPEIQYTSNYYKSTNVDFAVNTEGTYSEPRPIGTRYLTRNL 684Cas9VP2 fusion protein (SEQ ID NO: 48)
Translation of VP2 (pNLRep2-Capr1174-AVB-VP2-NN-VP3 knockSpe starting at bp 5448)
MASGTSRPVEPSPQRSPDSSTGIGKKGQQPAKKRLNFGQTGDSESVPDPQ
PIGEPPAGPSGLGSGTLAAGGGAPLADNNEGADGVGSSSGNWHCDSTWLG
DRVITTSTRTWALPTYNNHLYKQISNGTSGGSTNDNTYFGYSTPWGYFDF
NRFHCHFSPRDWQRLINNNWGFRPKRLNFKLFNIQVKEVTQNEGTKTIAN
NLTSTIQVFTDSEYQLPYVLGSAHQGCLPPFPADVFMIPQYGYLTLNNGS
QAVGRSSFYCLEYFPSQMLRTGNNFEFSYNFEDVPFHSSYAHSQSLDRLM
NPLIDQYLYYLSRTQSTGGTAGTQQLLFSQAGPNNMSAQAKNWLPGCYR
QQRVSTTLSQNNNSNFAWTGATKYHLNGRDSLVNPGVAMATHKDDEERFF
PSSGVLMFGKQGAGKDNVDYSSWILTSEEEIKTTNPVATEQYGVVADNLQ
QQNAAPIVGAVNSQGALPGMVWQNRDVYLQGPIWAKIPHTDGNFHPSPLM
GGFGLKHPPPQILIKNTPVPADPPTTFSQAKLASFITQYSTGQVSVEGGG
GSMAPKKKRKVGIHGVPAAKRNYILGLDIGITSVGYGIIDYETRDVIDAG
VRLFKEANVENNEGRRSKRGARRLKRRRHRIQRVKKLLFDYNLLTDHSE
LSGINPYEARVKGLSQKLSEEEFSAALLHLAKRRGVHNVNEVEEDTGNEL
STKEQISRNSKALEEKYVAELQLERLKKDGEVRGSINRFKTSDYVKEAKQ
LLKVQKAYHQLDQSFIDTYIDLLETRRTYYEGPGEGSPFGWKDIKEWYEM
LMGHCTYFPEELRSVKYAYNADLYNALNDLNNLVITRDENEKLEYYEKFQ
IIENVFKQKKKPTLKQIAKEILVNEEDIKGYRVTSTGKPEFTNLKVYHDI
KDITARKEIIENAELLDQIAKILTIYQSSEDIQEELTNLNSELTQEEIEQ
ISNLKGYTGTHNLSLKAINLILDELWHTNDNQIAIFNRLKLVPKKVDLSQ
QKEIPTTLVDDFILSPVVKRSFIQSIKVINAIIKKYGLPNDIIIELAREK
NSKDAQKMINEMQKRNRQTNERIEEIIRTTGKENAKYLIEKIKLHDMQEG
KCLYSLEAIPLEDLLNNPFNYEVDHIIPRSVSFDNSFNNKVLVKQEENSK
KGNRTPFQYLSSSDSKISYETFKKHILNLAKGKGRISKTKKEYLLEERDI
NRFSVQKDFINRNLVDTRYATRGLMNLLRSYFRVNNLDVKVKSINGGFTS
FLRRKWKFKKERNKGYKHHAEDALIIANADFIFKEWKKLDKAKKVMENQM
FEEKQAESMPEIETEQEYKEIFITPHQIKHIKDFKDYKYSHRVDKKPNRE
LINDTLYSTRKDDKGNTLIVNNLGLYDKDNDKLKKLINKSPEKLLMYHH
DPQTYQKLKLIMEQYGDEKNPLYKYYEETGNYLTKYSKKDNGPVIKKIKY
YGNKLNAHLDITDDYPNSRNKVVKLSLKPYRFDVYLDNGVYKFVTVKNLD
```

SEQUENCE LISTING
A description of the non-limiting exemplary vectors and the sequences thereof
discussed herein is provided herein below:

```
VIKKENYYEVNSKCYEEAKKLKKISNQAEFIASFYNNDLIKINGELYRVI
GVNNDLLNRIEVNMIDITYREYLENMNDKRPPRIIKTIASKTQSIKKYST
DILGNLYEVKSKKHPQIIKKGSGFANELGPRLMGKGGGGSIEWELQKENS
KRWNPEIQYTSNYYKSTNVDFAVNTEGTYSEPRPIGTRYLTRNL

689Cas9VP2 fusion protein (SEQ ID NO: 49)
Translation of VP2 (pNLRep2-Caprh74-AVB-VP2-NN-VP3 knockSpe starting at bp 5448)
MASGTSRPVEPSPQRSPDSSTGIGKKGQQPAKKRLNFGQTGDSESVPDPQ
PIGEPPAGPSGLGSGTLAAGGGAPLADNNEGADGVGSSSGNWHCDSTWLG
DRVITTSTRTWALPTYNNHLYKQISNGTSGGSTNDNTYFGYSTPWGYFDF
NRFHCHFSPRDWQRLINNNWGFRPKRLNFKLFNIQVKEVTQNEGTKTIAN
NLTSTIQVFTDSEYQLPYVLGSAHQGCLPPFPADVFMIPQYGYLTLNNGS
QAVGRSSFYCLEYFPSQMLRTGNNFEFSYNFEDVPFHSSYAHSQSLDRLM
NPLIDQYLYYLSRTQSTGGTAGTQQLLFSQAGPNNMSAQAKNWLPGPCYR
QQRVSTTLSQNNNSNFAWTGATKYHLNGRDSLVNPGVAMATHKDDEERFF
PSSGVLMFGKQGAGKDNVDYSSVMLTSEEEIKTTNPVATEQYGVVADNLQ
QQNAAPIVGAVNSQGALPGMVWQNRDVYLQGPIWAKIPHTDGNFHPSPLM
GGFGLKHPPPQILIKNTPVPADPPTTFSQAKLASFITQYSTGQVSVEIEW
ELGGGGSMAPKKKRKVGIHGVPAAKRNYILGLDIGITSVGYGIIDYETRD
VIDAGVRLFKEANVENNEGRRSKRGARRLKRRRRHRIQRVKKLLFDYNLL
TDHSELSGINPYEARVKGLSQKLSEEEFSAALLHLAKRRGVHNVNEVEED
TGNELSTKEQISRNSKALEEKYVAELQLERLKKDGEVRGSINRFKTSDYV
KEAKQLLKVQKAYHQLDQSFIDTYIDLLETRRTYYEGPGEGSPFGWKDIK
EWYEMLMGHCTYFPEELRSVKYAYNADLYNALNDLNNLVITRDENEKLEY
YEKFQIIENVFKQKKKPTLKQIAKEILVNEEDIKGYRVTSTGKPEFTNLK
VYHDIKDITARKEIIENAELLDQIAKILTIYQSSEDIQEELTNLNSELTQ
EEIEQISNLKGYTGTHNLSLKAINLILDELWHTNDNQIAIFNRLKLVPKK
VDLSQQKEIPTTLVDDFILSPVVKRSFIQSIKVINAIIKKYGLPNDIIIE
LAREKNSKDAQKMINEMQKRNRQTNERIEEIIRTTGKENAKYLIEKIKLH
DMQEGKCLYSLEAIPLEDLLNNPFNYEVDHIIPRSVSFDNSFNNKVLVKQ
EENSKKGNRTPFQYLSSSDSKISYETFKKHILNLAKGKGRISKTKKEYLL
EERDINRFSVQKDFINRNLVDTRYATRGLMNLLRSYFRVNNLDVKVKSIN
GGFTSFLRRKWKFKKERNKGYKHHAEDALIIANADFIFKEWKKLDKAKKV
MENQMFEEKQAESMPEIETEQEYKEIFITPHQIKHIKDFKDYKYSHRVDK
KPNRELINDTLYSTRKDDKGNTLIVNNLNGLYDKDNDKLKKLINKSPEKL
LMYHHDPQTYQKLKLIMEQYGDEKNPLYKYYEETGNYLTKYSKKDNGPVI
KKIKYYGNKLNAHLDITDDYPNSRNKVVKLSLKPYRFDVYLDNGVYKFVT
VKNLDVIKKENYYEVNSKCYEEAKKLKKISNQAEFIASFYNNDLIKINGE
LYRVIGVNNDLLNRIEVNMIDITYREYLENMNDKRPPRIIKTIASKTQSI
KKYSTDILGNLYEVKSKKHPQIIKKGSGFANELGPRLMGKGGGGSQKENS
KRWNPEIQYTSNYYKSTNVDFAVNTEGTYSEPRPIGTRYLTRNL saCas9 version 2 (SEQ ID NO: 50)
Translation of saCas9 (pNLRep2-Caprh74-AVB-VP2NN-VP3knock-Cas9update starting at
bp 5532)
MAPKKKRKVGIHGVPAAKRNYILGLDIGITSVGYGIIDYETRDVIDAGVR
LFKEANVENNEGRRSKRGARRLKRRRRHRIQRVKKLLFDYNLLTDHSELS
GINPYEARVKGLSQKLSEEEFSAALLHLAKRRGVHNVNEVEEDTGNELST
KEQISRNSKALEEKYVAELQLERLKKDGEVRGSINRFKTSDYVKEAKQLL
KVQKAYHQLDQSFIDTYIDLLETRRTYYEGPGEGSPFGWKDIKEWYEMLM
GHCTYFPEELRSVKYAYNADLYNALNDLNNLVITRDENEKLEYYEKFQII
ENVFKQKKKPTLKQIAKEILVNEEDIKGYRVTSTGKPEFTNLKVYHDIKD
ITARKEIIENAELLDQIAKILTIYQSSEDIQEELTNLNSELTQEEIEQIS
NLKGYTGTHNLSLKAINLILDELWHTNDNQIAIFNRLKLVPKKVDLSQQK
EIPTTLVDDFILSPVVKRSFIQSIKVINAIIKKYGLPNDIIIELAREKNS
KDAQKMINEMQKRNRQTNERIEEIIRTTGKENAKYLIEKIKLHDMQEGKC
LYSLEIPPLEDLLNNPFNYEVDHIIPRSVSFDNSFNNKVLVKQEENSKKG
NRTPFQYLSSSDSKISYETFKKHILNLAKGKGRISKTKKEYLLEERDINR
FSVQKDFINRNLVDTRYATRGLMNLLRSYFRVNNLDVKVKSINGGFTSFL
RRKWKFKKERNKGYKEIHAEDALIIANADFIFKEWKKLDKAKKVMENQWE
EKQAESMPEIETEQEYKEIFITPHQIKHIKDFKDYKYSHRVDKKPNRELI
NDTLYSTRKDDKGNTLIVNNLNGLYDKDNDKLKKLINKSPEKLLMYHHDP
QTYQKLKLIMEQYGDEKNPLYKYYEETGNYLTKYSKKDNGPVIKKIKYYG
NKLNAHLDITDDYPNSRNKVVKLSLKPYRFDVYLDNGVYKFVTVKNLDVI
KKENYYEVNSKCYEEAKKLKKISNQAEFIASFYNNDLIKINGELYRVIGV
NNDLLNRIEVNMIDITYREYLENMNDKRPPRIIKTIASKTQSIKKYSTDI
LGNLYEVKSKKHPQIIKKGSGFANELGPRLMGK G4S Linker peptide (SEQ ID NO: 51)
GGGGS G4S Linker polynucleotide (SEQ ID NO: 52)
ggcggaggaggcagc 15-mer G4S Linker (SEQ ID NO: 53)
```

SEQUENCE LISTING
A description of the non-limiting exemplary vectors and the sequences thereof
discussed herein is provided herein below:

(GGGGS)3

18-mer G4S Linker (SEQ ID NO: 54)
GGSSRSSSSGGGGSGGGG 20-mer G4S Linker (SEQ ID NO: 55)
(GGGGS)4

G3S Linker (SEQ ID NO: 56)
GGGS pAAVrh74-VP1-3 Knock out of VP2 expression, 5448 A-G (SEQ ID NO: 57)
CGGGCCCCCCCTCGAGGTCGACGGTATCGGGGGAGCTCGCAGGGTCTCCA
TTTTGAAGCGGGAGGTTTGAACGCGCAGCCGCCATGCCGGGTTTTACGA
GATTGTGATTAAGGTCCCCAGCGACCTTGACGAGCATCTGCCCGGCATTT
CTGACAGCTTTGTGAACTGGGTGGCCGAGAAGGAATGGGAGTTGCCGCCA
GATTCTGACATGGATCTGAATCTGATTGAGCAGGCACCCCTGACCGTGGC
CGAGAAGCTGCAGCGCGACTTTCTGACGGAATGGCGCCGTGTGAGTAAGG
CCCCGGAGGCTCTTTTCTTTGTGCAATTTGAGAAGGGAGAGAGCTACTTC
CACATGCACGTGCTCGTGGAAACCACCGGGGTGAAATCCATGGTTTTGGG
ACGTTTCCTGAGTCAGATTCGCGAAAAACTGATTCAGAGAATTTACCGCG
GGATCGAGCCGACTTTGCCAAACTGGTTCGCGGTCACAAAGACCAGAAAT
GGCGCCGGAGGCGGGAACAAGGTGGTGGATGAGTGCTACATCCCCAATTA
CTTGCTCCCAAAACCCAGCCTGAGCTCCAGTGGGCGTGGACTAATATGG
AACAGTATTTAAGCGCCTGTTTGAATCTCACGGAGCGTAAACGGTTGGTG
GCGCAGCATCTGACGCACGTGTCGCAGACGCAGGAGCAGAACAAAGAGAA
TCAGAATCCCAATTCTGATGCGCCGGTGATCAGATCAAAAACTTCAGCCA
GGTACATGGAGCTGGTCGGGTGGCTCGTGGACAAGGGGATTACCTCGGAG
AAGCAGTGGATCCAGGTGAGTAATTGACAAAGCCAAACACCACCATTTGC
CGAGCACTTTAGAGTTTACAGGTTTGTTTCTCTTGACCCTCAAAACAAAC
CTGTGAGGCATAGGGAGTATTGCTATCCCTTAAGAATTCACCCCCAGTGT
GCCCATCAAAACCTCCCAGGCTGAGTCTGCACAGTTGAAGGAGGAAGGAT
AGGAATGGGAGGGTCGATGGGTGAAAGCATGATTCTCTTAACCAGTCCAG
ATTATCAGGTAATCCCTTCAACAACCACCACCCACTCCCTGGGCAATCCA
GCTGGAGTTTACAGACAGACTTAGCTGGCTATAGCACCACCGTGCTACTC
TCTGTTCTTCCTGGTTGCTCAAATGCCCTAGAAAAGTGGAACAGGTGAGC
ATCAACTCACAGGGCTCTATGCTGGCTGCTGCTGCGAGGGATGTTATGCT
ATAGTACCAGGGGCCACCATTCCATAGGCACTTCCTGTGTTTAATACCCT
ATATGCTTTACTTCATCTCATCTTCCTCCATATCCTGAGAGGTGGTTCTA
TTCTTCTCCCCATTTTACGGATGAAAAAACCGAGACACAGAAAGGTGAAA
TAGCTTAAGATAAATGGTGCCTTGCAGCCTTAGACTCTGGTGGCCTCTAG
TTAATGTGGGAAATTAAGGGTGAGGGGATTGGCAGCTGATGGAGGGTGCA
GGGTGCCAGACAGAGGCGTTTAGCTCTGATCCCTTAGCAATAGAGAGTCC
TTGTAGGCACTTGGTCAGGCGAGTGATGCGATGAAAGCTGTGTTTAAGAA
AGATTATGCTTTCTGCTGATTTCATACCCCCAACACCCAAGCTCTGAGGC
CCCTCCTCACAGGTCCTTGCAGGGCTGGCCAAAATAAAGCAGCTTCACTC
CGTTGTGCTGCTTTCCAGCTAATGTGTCTGTTTGGCAGAAGTTTCCCTCA
AAGGCAGATCAGTGAAATAAGCAGAAGCCTCGACCCCCCTTTGTCAGCCA
GAGCTGCTGAAGTGCCTTGCCCCAGGGTCACTTTGTGTGAGGGGATTAGA
GAGCACTGGGGCTGCCAAGAAACACTGCCGTTTCTACAGATTAGCAGGAC
GCTGGCTTGTGGCCTTCTAGCGAGGCTCAGAGCTGCGGTGGCCCTAGTCT
GCATGGGCTAAAGACAAGCTCCATCTCCTGTCCTTGTTCCCTCCTTCCTG
GGCACAGCCGCCCTGCTTCTTGGTTCTCTCTGTTGGTTCCTGTCCGCACG
GTAGTTAGGCTGGCAGCGTGTGTAGGATTTGGCTTAGAAGATTGACAACA
TTGCCTTTGAGCCCTTCTTTGCTACTCCTCCCTCTCCCCTCCCATCAGAC
TCCTCTCTGGAGTCTGCTCTGCGAGGCCTCTGCTCTGTGGTATCCCAGCA
GCCTTCTCAGCCTTGACTTCCAGAAGGGGGCTGTGCAGTGTCCGGGGTGT
GCAGGCCCCAGACACGGGGTAGGCTCATGGAGATCCAAGTGCTGATCTAG
TGTCAAGGCTGGCCTGGAGACTGGGCTGGGTTGGTGTCTGCCTGCTGTGG
TCATGTGCCCTCCCTTGGGCCTGTATCCTCTCTCCAGACTTGCTGCAGGG
AGAGGTGGCAGATGTCAGCCTAGTTCTGGCCTCTCAGAGCAGCATGGCAG
CTCCCTTTCACTCAGGCCCAGGCTGGGCCCTCCTGCTGGCTGACCCCTGG
GGAGAGGGTGCTCCAGAGCTCCCCAAGGAACAGCTTCCCGAAGCAGCCAG
GCCAGCCCAGAGGGGCTGTGGCCAATCCTGAAGCTTTATGTTCCTGCTGA
CATTTTTTCTAAGTTTTCTCTTGCTTTCCTCTTAAATGCCAATCTGGAGA
GTCTCCGTTAGGAGAAATGGACCCCAGCCAGGAAGAAGAGTTGAGTTGTA
TTTAAAACACGAGCTCCCCCTAAAGCATCCTTCTTTAGCTTCTAAGGAGA
GGCAGAGACTGACAGGCAGGACTCAGCAGGAAAAGGTACCCCCCTGACCT
GCTCAGTCAGGCCCTAGGCCCAGCTCCACCCAGCCTGTGGCCCCCAGAGT
TTCGGTAAAGAGTTCCCTGGGCCTTAAGGAACCTTGAGAGAGCATTTGAG
GGGTGCCACCACAAACTTGGCAGAAAAAACCCTCCCCCTCCAAGTCCAGT
CCTAGAGAAGGAGCTGGCAACCTTGCCTTGCTTTGTAAGCAAAAGCCTCT
TAGGGCTTGAGCTCAGATGTAGTGTTTGAGCTGTGGCTGGTGCCCTGCCC
CATCAGGGAGCCAATGGTAGACATCCTATGGGCATCTTTGTTTTCCGTAA
GAGCAGGCTGTCTGGGGATGGGCCAGAGGAAGAGGCGACCTGGAGTCAAC SEQUENCE LISTING
A description of the non-limiting exemplary vectors and the sequences thereof
discussed herein is provided herein below:

```
CAAGAGGAGGCCTTAACCAAGCCTTAACCACAGAGGTTAACCAAGCCTTG
AAAGCGCTTCCCCCTGAGCAGGCAGGAAGCACTGAGTCCACATGGTTGCC
TCGCTGTTTCATTTCCTTACACTCAATTCTCTCAGTCTTTAAATGATCAC
TTGGCCTTGAAGTTACGGATATTTGGGGTCTGAACTGAAGTTGAAGAAAA
GAGGAAATGATTTAAGCTTTGTTTAAGATTAGGGGCCAGGTGCGGTGGCT
CACGCCTGTAATCCCAGCACCTTGGGAGCCTGAGGCGGGTGGATCACCTG
AGGTCAGGAGTTCCAGACCAGCCTGGCCAACATAGCAAAACCCAGTCTCT
ACTAAAAATAACAATAAAAAAATTAGCCAGGTGTGGTGACACATGCCTGT
AATCCCAGTTACTCAGGAGGCTGAGGCAGAATTGCTTGAACTTGAGAGGT
GGAGGTTGTAGTGAGCCAAGACCGCACCACTGCACTCCAGCCTGGCGACA
GAGCCAGACTCCGTCTCAAAAACAACAACAAAAAAGATTAGAAGAAGCCC
ATTACTGCCTTCTGGCCACCCACTCGCACAGACACCAAAACTGCAGCCCA
CACCTCGCCATCCTCGTGCTCTGCCCTGGGACACCCCAGGCACAGTGTGT
CCTTCGTTTTCTGTAAGGGTGGGCTGGGAGCAGGGACGGACAGGGCCTGT
GGGCACCTCTCATGGTCACTTCCTTCTTGCTCACAGGAGGACCAGGCCTC
ATACATCTCCTTCAATGCGGCCTCCAACTCGCGGTCCCAAATCAAGGCTG
CCTTGGACAATGCGGGAAAGATTATGAGCCTGACTAAAACCGCCCCCGAC
TACCTGGTGGGCCAGCAGCCCGTGGAGGACATTTCCAGCAATCGGATTTA
TAAAATTTTGGAACTAAACGGGTACGATCCCCAATATGCGGCTTCCGTCT
TTCTGGGATGGGCCACGAAAAAGTTCGGCAAGAGGAACACCATCTGGCTG
TTTGGGCCTGCAACTACCGGGAAGACCAACATCGCGGAGGCCATAGCCCA
CACTGTGCCCTTCTACGGGTGCGTAAACTGGACCAATGAGAACTTTCCCT
TCAACGACTGTGTCGACAAGATGGTGATCTGGTGGGAGGAGGGGAAGATG
ACCGCCAAGGTCGTGGAGTCGCCAAAGCCATTCTCGGAGGAAGCAAGGT
GCGCGTGGACCAGAAATGCAAGTCCTCGGCCCAGATAGACCCGACTCCCG
TGATCGTCACCTCCAACACCAACATGTGCGCCGTGATTGACGGGAACTCA
ACGACCTTCGAACACCAGCAGCCGTTGCAAGACCGGATGTTCAAATTTGA
ACTCACCCGCCGTCTGGATCATGACTTTGGGAAGGTCACCAAGCAGGAAG
TCAAAGACTTTTTCCGGTGGGCAAAGGATCACGTGGTTGAGGTGGAGCAT
GAATTCTACGTCAAAAAGGGTGGAGCCAAGAAAAGACCCGCCCCCAGTGA
CGCAGATATAAGTGAGCCCAAACGGGTGCGCGAGTCAGTTGCGCAGCCAT
CGACGTCAGACGCGGAAGCTTCGATCAACTACGCAGACAGGTACCAAAAC
AAATGTTCTCGTCACGTGGGCATGAATCTGATGCTGTTTCCCTGCAGACA
ATGCGAGAGAATGAATCAGAATTCAAATATCTGCTTCACTCACGGACAGA
AAGACTGTTTAGAGTGCTTTCCCGTGTCAGAATCTCAACCCGTTTCTGTC
GTCAAAAAGGCGTATCAGAAACTGTGCTACATTCATCATATCATGGGAAA
GGTGCCAGACGCTTGCACTGCCTGCGATCTGGTCAATGTGGATTTGGATG
ACTGCATCTTTGAACAATAAATGATTTAAATCAGGTATGGCTGCCGATGG
TTATCTTCCAGATTGGCTCGAGGACAACCTCTCTGAGGGCATTCGCGAGT
GGTGGGACCTGAAACCTGGAGCCCCGAAACCCAAAGCCAACCAGCAAAAG
CAGGACAACGGCCGGGGTCTGGTGCTTCCTGGCTACAAGTACCTCGGACC
CTTCAACGGACTCGACAAGGGGGAGCCCGTCAACGCGGCGGACGCAGCGG
CCCTCGAGCACGACAAGGCCTACGACCAGCAGCTCCAAGCGGGTGACAAT
CCGTACCTGCGGTATAATCACGCCGACGCCGAGTTTCAGGAGCGTCTGCA
AGAAGATACGTCTTTTGGGGGCAACCTCGGGCGCGCAGTCTTCCAGGCCA
AAAAGCGGGTTCTCGAACCTCTGGGCCTGGTTGAATCGCCGGTTAAGGCG
GCTCCTGGAAAGAAGAGACCGGTAGAGCCATCACCCCAGCGCTCTCCAGA
CTCCTCTACGGGCATCGGCAAGAAAGGCCAGCAGCCCGCAAAAAAGAGAC
TCAATTTTGGGCAGACTGGCGACTCAGAGTCAGTCCCGACCCTCAACCA
ATCGGAGAACCACCAGCAGGCCCCTCTGGTCTGGGATCTGGTACAATGGC
TGCAGGCGGTGGCGCTCCAATGGCAGACAATAACGAAGGCGCCGACGGAG
TGGGTAGTTCCTCAGGAAATTGGCATTGCGATTCCACATGGCTGGGCGAC
AGAGTCATCACCACCAGCACCCGCACCTGGGCCCTGCCCACCTACAACAA
CCACCTCTACAAGCAAATCTCCAACGGGACCTCGGGAGGAAGCACCAACG
ACAACACCTACTTCGGCTACAGCACCCCCTGGGGGTATTTTGACTTCAAC
AGATTCCACTGCCACTTTTCACCACGTGACTGGCAGCGACTCATCAACAA
CAACTGGGGATTCCGGCCCAAGAGGCTCAACTTCAAGCTCTTCAACATCC
AAGTCAAGGAGGTCACGCAGAATGAAGGCACCAAGACCATCGCCAATAAC
CTTACCAGCACGATTCAGGTCTTTACGGACTCGGAATACCAGCTCCCGTA
CGTGCTCGGCTCGGCGCACCAGGGCTGCCTGCCTCCGTTCCCGGCGGACG
TCTTCATGATTCCTCAGTACGGGTACCTGACTCTGAACAATGGCAGTCAG
GCTGTGGGCCGGTCGTCCTTCTACTGCCTGGAGTACTTTCCTTCTCAAAT
GCTGAGAACGGGCAACAACTTTGAATTCAGCTACAACTTCGAGGACGTGC
CCTTCCACAGCAGCTACGCGCACAGCCAGAGCCTGGACCGGCTGATGAAC
CCTCTCATCGACCAGTACTTGTACTACCTGTCCCGGACTCAAAGCACGGG
CGGTACTGCAGGAACTCAGCAGTTGCTATTTTCTCAGGCCGGGCCTAACA
ACATGTCGGCTCAGGCCAAGAACTGGCTACCCGGTCCCTGCTACCGGCAG
CAACGCGTCTCCACGACACTGTCGCAGAACAACAACAGCAACTTTGCCTG
GACGGGTGCCACCAAGTATCATCTGAATGGCAGAGACTCTCTGGTGAATC
CTGGCGTTGCCATGGCTACCCACAAGGACGACGAAGAGCGATTTTTTCCA
TCCAGCGGAGTCTTAATGTTTGGGAAACAGGGAGCTGGAAAAGACAACGT
GGACTATAGCAGCGTGATGCTAACCAGCGAGGAAGAAATAAAGACCACCA
ACCCAGTGGCCACAGAACAGTACGGCGTGGTGGCCGATAACCTGCAACAG
CAAAACGCCGCTCCTATTGTAGGGGCCGTCAATAGTCAAGGAGCCTTACC
TGGCATGGTGTGGCAGAACCGGGACGTGTACCTGCAGGGTCCCATCTGGG
```

SEQUENCE LISTING
A description of the non-limiting exemplary vectors and the sequences thereof discussed herein is provided herein below:

```
CCAAGATTCCTCATACGGACGGCAACTTTCATCCCTCGCCGCTGATGGGA
GGCTTTGGACTGAAGCATCCGCCTCCTCAGATCCTGATTAAAAACACACC
TGTTCCCGCGGATCCTCCGACCACCTTCAGCCAGGCCAAGCTGGCTTCTT
TCATCACGCAGTACAGTACCGGCCAGGTCAGCGTGGAGATCGAGTGGGAG
CTGCAGAAGGAGAACAGCAAACGCTGGAACCCAGAGATTCAGTACACTTC
CAACTACTACAAATCTACAAATGTGGACTTTGCTGTCAATACTGAGGGTA
CTTATTCCGAGCCTCGCCCCATTGGCACCCGTTACCTCACCCGTAATCTG
TAATTACATGTTAATCAATAAACCGGTTAATTCGTTTCAGTTGAACTTTG
GTCTCCTGTCCTTCTTATCTTATCGGTTACCATAGAAACTGGTTACTTAT
TAACTGCTTGGTGCGCTTCGCGATAAAAGACTTACGTCATCGGGTTACCC
CTAGTGATGGAGCGGCCGCTTTCAGTTGAACTTTGGTCTCTGCGTATTTC
TTTCTTATCTAGTTTCCATGCTCTAGAGGTCCTGTATTAGAGGTCACGTG
AGTGTTTTGCGACATTTTGCGACACCATGTGGTCACGCTGGGTATTTAAG
CCCGAGTGAGCACGCAGGGTCTCCATTTTGAAGCGGGAGGTTTGAACGCG
CAGCCGCCAAGCCGAATTCTGCAGATATCCATCACACTGGCGGCCGCTCG
ACTAGAGCGGCCGCCACCGCGGTGGAGCTCCAGCTTTTGTTCCCTTTAGT
GAGGGTTAATTGCGCGCTTGGCGTAATCATGGTCATAGCTGTTTCCTGTG
TGAAATTGTTATCCGCTCACAATTCCACACAACATACGAGCCGGAAGCAT
AAAGTGTAAAGCCTGGGGTGCCTAATGAGTGAGCTAACTCACATTAATTG
CGTTGCGCTCACTGCCCGCTTTCCAGTCGGGAAACCTGTCGTGCCAGCTG
CATTAATGAATCGGCCAACGCGCGGGGAGAGGCGGTTTGCGTATTGGGCG
CTCTTCCGCTTCCTCGCTCACTGACTCGCTGCGCTCGGTCGTTCGGCTGC
GGCGAGCGGTATCAGCTCACTCAAAGGCGGTAATACGGTTATCCACAGAA
TCAGGGGATAACGCAGGAAAGAACATGTGAGCAAAAGGCCAGCAAAAGGC
CAGGAACCGTAAAAAGGCCGCGTTGCTGGCGTTTTTCCATAGGCTCCGCC
CCCCTGACGAGCATCACAAAAATCGACGCTCAAGTCAGAGGTGGCGAAAC
CCGACAGGACTATAAAGATACCAGGCGTTTCCCCCTGGAAGCTCCCTCGT
GCGCTCTCCTGTTCCGACCCTGCCGCTTACCGGATACCTGTCCGCCTTTC
TCCCTTCGGGAAGCGTGGCGCTTTCTCATAGCTCACGCTGTAGGTATCTC
AGTTCGGTGTAGGTCGTTCGCTCCAAGCTGGGCTGTGTGCACGAACCCCC
CGTTCAGCCCGACCGCTGCGCCTTATCCGGTAACTATCGTCTTGAGTCCA
ACCCGGTAAGACACGACTTATCGCCACTGGCAGCAGCCACTGGTAACAGG
ATTAGCAGAGCGAGGTATGTAGGCGGTGCTACAGAGTTCTTGAAGTGGTG
GCCTAACTACGGCTACACTAGAAGAACAGTATTTGGTATCTGCGCTCTGC
TGAAGCCAGTTACCTTCGGAAAAAGAGTTGGTAGCTCTTGATCCGGCAAA
CAAACCACCGCTGGTAGCGGTGGTTTTTTTGTTTGCAAGCAGCAGATTAC
GCGCAGAAAAAAAGGATCTCAAGAAGATCCTTTGATCTTTTCTACGGGGT
CTGACGCTCAGTGGAACGAAAACTCACGTTAAGGGATTTTGGTCATGAGA
TTATCAAAAAGGATCTTCACCTAGATCCTTTTAAATTAAAAATGAAGTTT
TAAATCAATCTAAAGTATATATGAGTAAACTTGGTCTGACAGTTACCAAT
GCTTAATCAGTGAGGCACCTATCTCAGCGATCTGTCTATTTCGTTCATCC
ATAGTTGCCTGACTCCCCGTCGTGTAGATAACTACGATACGGGAGGGCTT
ACCATCTGGCCCCAGTGCTGCAATGATACCGCGAGACCCACGCTCACCGG
CTCCAGATTTATCAGCAATAAACCAGCCAGCCGGAAGGGCCGAGCGCAGA
AGTGGTCCTGCAACTTTATCCGCCTCCATCCAGTCTATTAATTGTTGCCG
GGAAGCTAGAGTAAGTAGTTCGCCAGTTAATAGTTTGCGCAACGTTGTTG
CCATTGCTACAGGCATCGTGGTGTCACGCTCGTCGTTTGGTATGGCTTCA
TTCAGCTCCGGTTCCCAACGATCAAGGCGAGTTACATGATCCCCCATGTT
GTGCAAAAAAGCGGTTAGCTCCTTCGGTCCTCCGATCGTTGTCAGAAGTA
AGTTGGCCGCAGTGTTATCACTCATGGTTATGGCAGCACTGCATAATTCT
CTTACTGTCATGCCATCCGTAAGATGCTTTTCTGTGACTGGTGAGTACTC
AACCAAGTCATTCTGAGAATAGTGTATGCGGCGACCGAGTTGCTCTTGCC
CGGCGTCAATACGGGATAATACCGCGCCACATAGCAGAACTTTAAAAGTG
CTCATCATTGGAAAACGTTCTTCGGGGCGAAAACTCTCAAGGATCTTACC
GCTGTTGAGATCCAGTTCGATGTAACCCACTCGTGCACCCAACTGATCTT
CAGCATCTTTTACTTTCACCAGCGTTTCTGGGTGAGCAAAAACAGGAAGG
CAAAATGCCGCAAAAAAGGGAATAAGGGCGACACGGAAATGTTGAATACT
CATACTCTTCCTTTTTCAATATTATTGAAGCATTTATCAGGGTTATTGTC
TCATGAGCGGATACATATTTGAATGTATTTAGAAAAATAAACAAATAGGG
GTTCCGCGCACATTTCCCCGAAAAGTGCCACCTAAATTGTAAGCGTTAAT
ATTTTGTTAAAATTCGCGTTAAATTTTGTTAAATCAGCTCATTTTTTAA
CCAATAGGCCGAAATCGGCAAAATCCCTTATAAATCAAAAGAATAGACCG
AGATAGGGTTGAGTGTTGTTCCAGTTTGGAACAAGAGTCCACTATTAAAG
AACGTGGACTCCAACGTCAAAGGGCGAAAAACCGTCTATCAGGGCGATGG
CCCACTACGTGAACCATCACCCTAATCAAGTTTTTTGGGGTCGAGGTGCC
GTAAAGCACTAAATCGGAACCCTAAAGGGAGCCCCCGATTTAGAGCTTGA
CGGGGAAAGCCGGCGAACGTGGCGAGAAAGGAAGGGAAGAAAGCGAAAGG
AGCGGGCGCTAGGGCGCTGGCAAGTGTAGCGGTCACGCTGCGCGTAACCA
CCACACCCGCCGCGCTTAATGCGCCGCTACAGGGCGCGTCCCATTCGCCA
TTCAGGCTGCGCAACTGTTGGGAAGGGCGATCGGTGCGGGCCTCTTCGCT
ATTACGCCAGCTGGCGAAAGGGGGATGTGCTGCAAGGCGATTAAGTTGGG
TAACGCCAGGGTTTTCCCAGTCACGACGTTGTAAAACGACGGCCAGTGAG
CGCGCGTAATACGACTCACTATAGGGCGAATTGGGTAC
```

Full VP Gene (SEQ ID NO: 58)

SEQUENCE LISTING
A description of the non-limiting exemplary vectors and the sequences thereof discussed herein is provided herein below:

```
>AAVrh74 VP1 capsid gene rh74 cap
ATGGCTGCCGATGGTTATCTTCCAGATTGGCTCGAGGACAACCTCTCTGA
GGGCATTCGCGAGTGGTGGGACCTGAAACCTGGAGCCCCGAAACCCAAG
CCAACCAGCAAAAGCAGGACAACGGCCGGGGTCTGGTGCTTCCTGGCTAC
AAGTACCTCGGACCCTTCAACGGACTCGACAAGGGGGAGCCCGTCAACGC
GGCGGACGCAGCGGCCCTCGAGCACGACAAGGCCTACGACCAGCAGCTCC
AAGCGGGTGACAATCCGTACCTGCGGTATAATCACGCCGACGCCGAGTTT
CAGGAGCGTCTGCAAGAAGATACGTCTTTTGGGGGCAACCTCGGGCGCGC
AGTCTTCCAGGCCAAAAAGCGGGTTCTCGAACCTCTGGGCTGGTTGAAT
CGCCGGTTAAGACGGCTCCTGGAAAGAAGAGACCGGTAGAGCCATCACCC
CAGCGCTCTCCAGACTCCTCTACGGGCATCGGCAAGAAAGGCCAGCAGCC
CGCAAAAAAGAGACTCAATTTTGGGCAGACTGGCGACTCAGAGTCAGTCC
CCGACCCTCAACCAATCGGAGAACCACCAGCAGGCCCCTCTGGTCTGGGA
TCTGGTACAATGGCTGCAGGCGGTGGCGCTCCAATGGCAGACAATAACGA
AGGCGCCGACGGAGTGGGTAGTTCCTCAGGAAATTGGCATTGCGATTCCA
CATGGCTGGGCGACAGAGTCATCACCACCAGCACCCGCACCTGGGCCCTG
CCCACCTACAACAACCACCTCTACAAGCAAATCTCCAACGGGACCTCGGG
AGGAAGCACCAACGACAACACCTACTTCGGCTACAGCACCCCCTGGGGGT
ATTTTGACTTCAACAGATTCCACTGCCACTTTTCACCACGTGACTGGCAG
CGACTCATCAACAACAACTGGGGATTCCGGCCCAAGAGGCTCAACTTCAA
GCTCTTCAACATCCAAGTCAAGGAGGTCACGCAGAATGAAGGCACCAAGA
CCATCGCCAATAACCTTACCAGCACGATTCAGGTCTTTACGGACTCGGAA
TACCAGCTCCCGTACGTGCTCGGCTCGGCGCACCAGGGCTGCCTGCCTCC
GTTCCCGGCGGACGTCTTCATGATTCCTCAGTACGGGTACCTGACTCTGA
ACAATGGCAGTCAGGCTGTGGGCCGGTCGTCCTTCTACTGCCTGGAGTAC
TTTCCTTCTCAAATGCTGAGAACGGGCAACAACTTTGAATTCAGCTACAA
CTTCGAGGACGTGCCCTTCCACAGCAGCTACGCGCACAGCCAGAGCCTGG
ACCGGCTGATGAACCCTCTCATCGACCAGTACTTGTACTACCTGTCCCGG
ACTCAAAGCACGGGCGGTACTGCAGGAACTCAGCAGTTGCTATTTTCTCA
GGCCGGGCCTAACAACATGTCGGCTCAGGCCAAGAACTGGCTACCCGGTC
CCTGCTACCGGCAGCAACGCGTCTCCACGACACTGTCGCAGAACAACAAC
AGCAACTTTGCCTGGACGGGTGCCACCAAGTATCATCTGAATGGCAGAGA
CTCTCTGGTGAATCCTGGCGTTGCCATGGCTACCCACAAGGACGACGAAG
AGCGATTTTTTCCATCCAGCGGAGTCTTAATGTTTGGGAAACAGGGAGCT
GGAAAAGACAACGTGGACTATAGCAGCGTGATGCTAACCAGCGAGGAAGA
AATAAAGACCACCAACCCAGTGGCCACAGAACAGTACGGCGTGGTGGCCG
ATAACCTGCAACAGCAAAACGCCGCTCCTATTGTAGGGGCCGTCAATAGT
CAAGGAGCCTTACCTGGCATGGTGTGGCAGAACCGGGACGTGTACCTGCA
GGGTCCCATCTGGGCCAAGATTCCTCATACGGACGGCAACTTTCATCCCT
CGCCGCTGATGGGAGGCTTTGGACTGAAGCATCCGCCTCCTCAGATCCTG
ATTAAAAACACACCTGTTCCCGCGGATCCTCCGACCACCTTCAATCAGGC
CAAGCTGGCTTCTTTCATCACGCAGTACAGTACCGGCCAGGTCAGCGTGG
AGATCGAGTGGGAGCTGCAGAAGGAGAACAGCAAACGCTGGAACCCAGAG
ATTCAGTACACTTCCAACTACTACAAATCTACAAATGTGGACTTTGCTGT
CAATACTGAGGGTACTTATTCCGAGCCTCGCCCCATTGGCACCCGTTACC
TCACCCGTAATCTGTAA Full VP Protein (SEQ ID NO: 59)
>AAVrh74 VP1 protein Translation of rh74 cap
>Alternative start site for VP2  =  aa 137
>Insertion site 1  =  aa 228
>Insertion site 2  =  aa 350
>Insertion site 3  =  aa 419
>Insertion site 4  =  aa 684
>Insertion site 5  =  aa 689
MAADGYLPDWLEDNLSEGIREWWDLKPGAPKPKANQQKQDNGRGLVLPGY
KYLGPFNGLDKGEPVNAADAAALEHDKAYDQQLQAGDNPYLRYNHADAEF
QERLQEDTSFGGNLGRAVFQAKKRVLEPLGLVESPVKTAPGKKRPVEPSP
QRSPDSSTGIGKKGQQPAKKRLNFGQTGDSESVPDPQPIGEPPAGPSGLG
SGTMAAGGGAPMADNNEGADGVGSSSGNWHCDSTWLGDRVITTSTRTWAL
PTYNNHLYKQISNGTSGGSTNDNTYFGYSTPWGYFDFNRFHCHFSPRDWQ
RLINNNWGFRPKRLNFKLFNIQVKEVTQNEGTKTIANNLTSTIQVFTDSE
YQLPYVLGSAHQGCLPPFPADVFMIPQYGYLTLNNGSQAVGRSSFYCLEY
FPSQMLRTGNNFEFSYNFEDVPFHSSYAHSQSLDRLMNPLIDQYLYYLSR
TQSTGGTAGTQQLLFSQAGPNNMSAQAKNWLPGPCYRQQRVSTTLSQNNN
SNFAWTGATKYHLNGRDSLVNPGVAMATHKDDEERFFPSSGVLMFGKQGA
GKDNVDYSSVMLTSEEEIKTTNPVATEQYGVVADNLQQQNAAPIVGAVNS
QGALPGMVWQNRDVYLQGPIWAKIPHTDGNFHPSPLMGGFGLKHPPPQIL
IKNTPVPADPPTTFNQAKLASFITQYSTGQVSVEIEWELQKENSKRWNPE
IQYTSNYYKSTNVDFAVNTEGTYSEPRPIGTRYLTRNL Cfa split intein (SEQ ID NO: 60)
>Cfa^N  =  aa 1-101
>Cfa^C  =  aa 102-136
>accelerator lysine residue  =  aa 70 (underline)
```

SEQUENCE LISTING
A description of the non-limiting exemplary vectors and the sequences thereof
discussed herein is provided herein below:

>accelerator met residue 1 = aa 75 (underline)
>accelerator met residue 2 = aa 81 (underline)
CLSYDTEILTVEYGFLPIGKIVEERIECTVYTVDKNGFVYTQPIAQWHNRGEQEVFEY
CLEDGSIIRATKDHKFMTTDGQMLPIDEIFERGLDLKQVDGLPVKIISRKSLGTQNVY
DIGVEKDHNFLLKNGLVASN

SEQUENCE LISTING

<160> NUMBER OF SEQ ID NOS: 61

<210> SEQ ID NO 1
<211> LENGTH: 10538
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 1 cgggccccc ctcgaggtcg acggtatcgg gggagctcgc agggtctcca ttttgaagcg      60
ggaggtttga acgcgcagcc gccatgccgg ggttttacga gattgtgatt aaggtcccca    120
gcgaccttga cgagcatctg cccggcattt ctgacagctt tgtgaactgg gtggccgaga    180
aggaatggga gttgccgcca gattctgaca tggatctgaa tctgattgag caggcacccc    240
tgaccgtggc cgagaagctg cagcgcgact ttctgacgga atggcgccgt gtgagtaagg    300
ccccggaggc tcttttcttt gtgcaatttg agaagggaga gagctacttc cacatgcacg    360
tgctcgtgga aaccaccggg gtgaaatcca tggttttggg acgtttcctg agtcagattc    420
gcgaaaaact gattcagaga atttaccgcg ggatcgagcc gactttgcca aactggttcg    480
cggtcacaaa gaccagaaat ggcgccggag gcgggaacaa ggtggtggat gagtgctaca    540
tccccaatta cttgctcccc aaaacccagc ctgagctcca gtgggcgtgg actaatatgg    600
aacagtattt aagcgcctgt ttgaatctca cggagcgtaa acggttggtg gcgcagcatc    660
tgacgcacgt gtcgcagacg caggagcaga acaaagagaa tcagaatccc aattctgatg    720
cgccggtgat cagatcaaaa acttcagcca ggtacatgga gctggtcggg tggctcgtgg    780 acaagggat tacctcggag aagcagtgga tccaggtgag taattgacaa agccaaacac    840
caccatttgc cgagcacttt agagtttaca ggtttgtttc tcttgacccct caaaacaaac    900 ctgtgaggca tagggagtat tgctatccct taagaattca cccccagtgt gcccatcaaa    960
acctcccagg ctgagtctgc acagttgaag gaggaaggat aggaatggga gggtcgatgg   1020
gtgaaagcat gattctctta accagtccag attatcaggt aatcccttca acaaccacca   1080
cccactccct gggcaatcca gctggagttt acagacagac ttagctggct atagcaccac   1140
cgtgctactc tctgttcttc ctggttgctc aaatgcccta gaaaagtgga acaggtgagc   1200
atcaactcac agggctctat gctggctgct gctgcgaggg atgttatgct atagtaccag   1260
gggccaccat tccataggca cttcctgtgt ttaatacccct atatgcttta cttcatctca   1320
tcttcctcca tatcctgaga ggtggttcta ttcttctccc cattttacgg atgaaaaaac   1380
cgagacacag aaaggtgaaa tagcttaaga taaatggtgc cttgcagcct tagactctgg   1440
tggcctctag ttaatgtggg aaattaaggg tgaggggatt ggcagctgat ggagggtgca   1500

```
gggtgccaga cagaggcgtt tagctctgat cccttagcaa tagagagtcc ttgtaggcac    1560
ttggtcaggc gagtgatgcg atgaaagctg tgtttaagaa agattatgct ttctgctgat    1620 ttcataccccc caacacccaa gctctgaggc ccctcctcac aggtccttgc agggctggcc    1680
aaaataaagc agcttcactc cgttgtgctg ctttccagct aatgtgtctg tttggcagaa    1740
gtttccctca aaggcagatc agtgaaataa gcagaagcct cgacccccct tgtcagcca    1800 gagctgctga agtgccttgc cccagggtca ctttgtgtga ggggattaga gagcactggg    1860
gctgccaaga aacactgccg tttctacaga ttagcaggac gctggcttgt ggccttctag    1920
cgaggctcag agctgcggtg gccctagtct gcatgggcta aagacaagct ccatctcctg    1980
tccttgttcc ctccttcctg ggcacagccg ccctgcttct tggttctctc tgttggttcc    2040
tgtccgcacg gtagttaggc tggcagcgtg tgtaggattt ggcttagaag attgacaaca    2100
ttgcctttga gcccttcttt gctactcctc cctctcccct cccatcagac tcctctctgg    2160
agtctgctct gcgaggcctc tgctctgtgg tatcccagca gccttctcag ccttgacttc    2220
cagaaggggg ctgtgcagtg tccggggtgt gcaggcccca gacacggggt aggctcatgg    2280
agatccaagt gctgatctag tgtcaaggct ggcctggaga ctgggctggg ttggtgtctg    2340
cctgctgtgg tcatgtgccc tcccttgggc ctgtatcctc tctccagact tgctgcaggg    2400
agaggtggca gatgtcagcc tagttctggc ctctcagagc agcatggcag ctcccttcca    2460
ctcaggccca ggctgggccc tcctgctggc tgaccctggg ggagagggtg ctccagagct    2520
ccccaaggaa cagcttcccg aagcagccag gccagcccag aggggctgtg gccaatcctg    2580
aagctttatg ttcctgctga cattttttct aagttttctc ttgctttcct cttaaatgcc    2640
aatctggaga gtctccgtta ggagaaatgg accccagcca ggaagaagag ttgagttgta    2700
tttaaaacac gagctccccc taaagcatcc ttctttagct tctaaggaga ggcagagact    2760
gacaggcagg actcagcagg aaaaggtacc cccctgacct gctcagtcag gccctaggcc    2820
cagctccacc cagcctgtgg cccccagagt ttcggtaaag agttccctgg gccttaagga    2880
accttgagag agcatttgag gggtgccacc acaaacttgg cagaaaaaac cctccccctc    2940
caagtccagt cctagagaag gagctggcaa ccttgccttg cttttgtaagc aaaagcctct    3000 tagggcttga gctcagatgt agtgtttgag ctgtggctgg tgccctgccc catcagggag    3060
ccaatggtag acatcctatg ggcatctttg ttttccgtaa gagcaggctg tctgggatg    3120 ggccagagga agaggcgacc tggagtcaac caagaggagg ccttaaccaa gccttaacca    3180
cagaggttaa ccaagccttg aaagcgcttc cccctgagca ggcaggaagc actgagtcca    3240
catggttgcc tcgctgtttc atttccttac actcaattct ctcagtcttt aaatgatcac    3300
ttggccttga agttacggat atttgggggtc tgaactgaag ttgaagaaaa gaggaaatga    3360
tttaagcttt gtttaagatt aggggccagg tgcggtggct cacgcctgta atcccagcac    3420
cttgggagcc tgaggcgggt ggatcacctg aggtcaggag ttccagacca gcctggccaa    3480
catagcaaaa cccagtctct actaaaaata acaataaaaa aattagccag gtgtggtgac    3540
acatgcctgt aatcccagtt actcaggagg ctgaggcaga attgcttgaa cttgagaggt    3600
ggaggttgta gtgagccaag accgcaccac tgcactccag cctggcgaca gagccagact    3660
ccgtctcaaa acaacaaca aaaagatta gaagaagccc attactgcct tctggccacc    3720
cactcgcaca gacaccaaaa ctgcagccca cacctcgcca tcctcgtgct ctgccctggg    3780
acaccccagg cacagtgtgt ccttcgtttt ctgtaagggt gggctgggag cagggacgga    3840
cagggcctgt gggcacctct catggtcact tccttcttgc tcacaggagg accaggcctc    3900
```

```
atacatctcc ttcaatgcgg cctccaactc gcggtcccaa atcaaggctg ccttggacaa    3960
tgcgggaaag attatgagcc tgactaaaac cgccccgac tacctggtgg ccagcagcc      4020 cgtggaggac atttccagca atcggattta taaaattttg gaactaaacg ggtacgatcc    4080
ccaatatgcg gcttccgtct ttctgggatg ggccacgaaa aagttcggca agaggaacac    4140
catctggctg tttgggcctg caactaccgg gaagaccaac atcgcggagg ccatagccca    4200
cactgtgccc ttctacgggt gcgtaaactg gaccaatgag aactttccct tcaacgactg    4260
tgtcgacaag atggtgatct ggtgggagga ggggaagatg accgccaagg tcgtggagtc    4320
ggccaaagcc attctcggag gaagcaaggt gcgcgtggac cagaaatgca agtcctcggc    4380
ccagatagac ccgactcccg tgatcgtcac ctccaacacc aacatgtgcg ccgtgattga    4440
cgggaactca acgaccttcg aacaccagca gccgttgcaa gaccggatgt tcaaatttga    4500
actcacccgc cgtctggatc atgactttgg gaaggtcacc aagcaggaag tcaaagactt    4560
tttccggtgg gcaaaggatc acgtggttga ggtggagcat gaattctacg tcaaaaaggg    4620
tggagccaag aaaagacccg ccccccagtga cgcagatata agtgagccca acgggtgcg    4680 cgagtcagtt gcgcagccat cgacgtcaga cgcggaagct tcgatcaact acgcagacag    4740
gtaccaaaac aaatgttctc gtcacgtggg catgaatctg atgctgtttc cctgcagaca    4800
atgcgagaga atgaatcaga attcaaatat ctgcttcact cacggacaga aagactgttt    4860
agagtgcttt cccgtgtcag aatctcaacc cgtttctgtc gtcaaaaagg cgtatcagaa    4920
actgtgctac attcatcata tcatgggaaa ggtgccagac gcttgcactg cctgcgatct    4980
ggtcaatgtg gatttggatg actgcatctt tgaacaataa atgatttaaa tcaggtatgg    5040
ctgccgatgg ttatcttcca gattggctcg aggacaaacct ctctgagggc attcgcgagt    5100
ggtgggacct gaaacctgga gccccgaaac ccaaagccaa ccagcaaaag caggacaacg    5160
gccgggtctc ggtgcttcct ggctacaagt acctcggacc cttcaacgga ctcgacaagg    5220
gggagcccgt caacgcggcg gacgcagcgg ccctcgagca cgacaaggcc tacgaccagc    5280
agctccaagc gggtgacaat ccgtacctgc ggtataatca cgccgacgcc gagtttcagg    5340
agcgtctgca agaagatacg tcttttgggg gcaacctcgg gcgcgcagtc ttccaggcca    5400
aaaagcgggt tctcgaacct ctgggcctgg ttgaatcgcc ggttaaggcg gctcctggaa    5460
agaagagacc ggtagagcca tcaccccagc gctctccaga ctcctctacg ggcatcggca    5520
agaaaggcca gcagcccgca aaaaagagac tcaattttgg gcagactggc gactcagagt    5580
cagtccccga ccctcaacca atcggagaac caccagcagg cccctctggt ctgggatctg    5640
gtacaatggc tgcaggcggt ggcgctccaa tggcagacaa taacgaaggc gccgacggag    5700
tgggtagttc ctcaggaaat tggcattgcg attccacatg gctgggcgac agagtcatca    5760
ccaccagcac ccgcacctgg gccctgccca cctacaacaa ccacctctac aagcaaatct    5820
ccaacgggac ctcgggagga agcaccaacg acaacaccta cttcggctac agcaccccct    5880
gggggtattt tgacttcaac agattccact gccacttttc accacgtgac tggcagcgac    5940
tcatcaacaa caactgggga ttccggccca gaggctcaa cttcaagctc ttcaacatcc    6000
aagtcaagga ggtcacgcag aatgaaggca ccaagaccat cgccaataac cttaccagca    6060
cgattcaggt ctttacggac tcggaatacc agctcccgta cgtgctcggc tcggcgcacc    6120
agggctgcct gcctccgttc ccggcggacg tcttcatgat tcctcagtac gggtacctga    6180
ctctgaacaa tggcagtcag gctgtgggcc ggtcgtcctt ctactgcctg gagtactttc    6240
```

```
cttctcaaat gctgagaacg ggcaacaact ttgaattcag ctacaacttc gaggacgtgc   6300
ccttccacag cagctacgcg cacagccaga gcctggaccg gctgatgaac cctctcatcg   6360
accagtactt gtactacctg tcccggactc aaagcacggg cggtactgca ggaactcagc   6420
agttgctatt ttctcaggcc gggcctaaca acatgtcggc tcaggccaag aactggctac   6480
ccggtccctg ctaccggcag caacgcgtct ccacgacact gtcgcagaac aacaacagca   6540
actttgcctg gacgggtgcc accaagtatc atctgaatgg cagagactct ctggtgaatc   6600
ctggcgttgc catggctacc cacaaggacg acgaagagcg attttttcca tccagcggag   6660
tcttaatgtt tgggaaacag ggagctggaa aagacaacgt ggactatagc agcgtgatgc   6720
taaccagcga ggaagaaata aagaccacca acccagtggc cacagaacag tacggcgtgg   6780
tggccgataa cctgcaacag caaaacgccg ctcctattgt aggggccgtc aatagtcaag   6840
gagccttacc tggcatggtg tggcagaacc gggacgtgta cctgcagggt cccatctggg   6900
ccaagattcc tcatacggac ggcaactttc atccctcgcc gctgatggga ggctttggac   6960
tgaagcatcc gcctcctcag atcctgatta aaaacacacc tgttcccgcg gatcctccga   7020
ccaccttcag ccaggccaag ctggcttctt tcatcacgca gtacagtacc ggccaggtca   7080
gcgtggagat cgagtgggag ctgcagaagg agaacagcaa acgctggaac ccagagattc   7140
agtacacttc caactactac aaatctacaa atgtggactt tgctgtcaat actgagggta   7200
cttattccga gcctcgcccc attggcaccc gttacctcac ccgtaatctg taattacatg   7260
ttaatcaata aaccggttaa ttcgtttcag ttgaactttg gtctcctgtc cttcttatct   7320
tatcggttac catagaaact ggttacttat taactgcttg gtgcgcttcg cgataaaaga   7380
cttacgtcat cgggttaccc ctagtgatgg agcggccgct ttcagttgaa ctttggtctc   7440
tgcgtatttc tttcttatct agtttccatg ctctagaggt cctgtattag aggtcacgtg   7500
agtgttttgc gacattttgc gacaccatgt ggtcacgctg gtatttaag cccgagtgag   7560 cacgcagggt ctccattttg aagcgggagg tttgaacgcg cagccgccaa gccgaattct   7620
gcagatatcc atcacactgg cggccgctcg actagagcgg ccgccaccgc ggtggagctc   7680
cagcttttgt tccctttagt gagggttaat tgcgcgcttg gcgtaatcat ggtcatagct   7740
gtttcctgtg tgaaattgtt atccgctcac aattccacac aacatacgag ccggaagcat   7800
aaagtgtaaa gcctggggtg cctaatgagt gagctaactc acattaattg cgttgcgctc   7860
actgcccgct ttccagtcgg gaaacctgtc gtgccagctg cattaatgaa tcggccaacg   7920
cgcggggaga ggcggtttgc gtattgggcg ctcttccgct tcctcgctca ctgactcgct   7980
gcgctcggtc gttcggctgc ggcgagcggt atcagctcac tcaaaggcgg taatacggtt   8040
atccacagaa tcaggggata acgcaggaaa gaacatgtga gcaaaaggcc agcaaaaggc   8100
caggaaccgt aaaaaggccg cgttgctggc gtttttccat aggctccgcc cccctgacga   8160
gcatcacaaa aatcgacgct caagtcagag gtggcgaaac ccgacaggac tataaagata   8220
ccaggcgttt ccccctggaa gctccctcgt gcgctctcct gttccgaccc tgccgcttac   8280
cggatacctg tccgcctttc tcccttcggg aagcgtggcg ctttctcata gctcacgctg   8340
taggtatctc agttcggtgt aggtcgttcg ctccaagctg ggctgtgtgc acgaaccccc   8400
cgttcagccc gaccgctgcg ccttatccgg taactatcgt cttgagtcca acccggtaag   8460
acacgactta tcgccactgg cagcagccac tggtaacagg attagcagag cgaggtatgt   8520
aggcggtgct acagagttct tgaagtggtg gcctaactac ggctacacta agaacagt    8580 atttggtatc tgcgctctgc tgaagccagt taccttcgga aaagagttg gtagctcttg    8640
```

```
atccggcaaa caaaccaccg ctggtagcgg tggttttttt gtttgcaagc agcagattac    8700
gcgcagaaaa aaggatctc aagaagatcc tttgatcttt tctacggggt ctgacgctca    8760
gtggaacgaa aactcacgtt aagggatttt ggtcatgaga ttatcaaaaa ggatcttcac    8820
ctagatcctt ttaaattaaa aatgaagttt taaatcaatc taaagtatat atgagtaaac    8880
ttggtctgac agttaccaat gcttaatcag tgaggcacct atctcagcga tctgtctatt    8940
tcgttcatcc atagttgcct gactccccgt cgtgtagata actacgatac gggagggctt    9000
accatctggc cccagtgctg caatgatacc gcgagaccca cgctcaccgg ctccagattt    9060
atcagcaata aaccagccag ccggaagggc cgagcgcaga agtggtcctg caactttatc    9120
cgcctccatc cagtctatta attgttgccg ggaagctaga gtaagtagtt cgccagttaa    9180
tagtttgcgc aacgttgttg ccattgctac aggcatcgtg gtgtcacgct cgtcgtttgg    9240
tatggcttca ttcagctccg gttcccaacg atcaaggcga gttacatgat cccccatgtt    9300
gtgcaaaaaa gcggttagct ccttcggtcc tccgatcgtt gtcagaagta agttggccgc    9360
agtgttatca ctcatggtta tggcagcact gcataattct cttactgtca tgccatccgt    9420
aagatgcttt tctgtgactg gtgagtactc aaccaagtca ttctgagaat agtgtatgcg    9480
gcgaccgagt tgctcttgcc cggcgtcaat acgggataat accgcgccac atagcagaac    9540
tttaaaagtg ctcatcattg gaaaacgttc ttcggggcga aaactctcaa ggatcttacc    9600
gctgttgaga tccagttcga tgtaacccac tcgtgcaccc aactgatctt cagcatcttt    9660
tactttcacc agcgtttctg ggtgagcaaa aacaggaagg caaaatgccg caaaaaaggg    9720
aataagggcg acacggaaat gttgaatact catactcttc ctttttcaat attattgaag    9780
catttatcag ggttattgtc tcatgagcgg atacatattt gaatgtattt agaaaaataa    9840
acaaataggg gttccgcgca catttccccg aaaagtgcca cctaaattgt aagcgttaat    9900
attttgttaa aattcgcgtt aaattttgt taaatcagct catttttaa ccaataggcc    9960 gaaatcggca aaatccctta taaatcaaaa gaatagaccg agatagggt gagtgttgtt   10020 ccagtttgga acaagagtcc actattaaag aacgtggact ccaacgtcaa agggcgaaaa   10080
accgtctatc agggcgatgg cccactacgt gaaccatcac cctaatcaag ttttttgggg   10140
tcgaggtgcc gtaaagcact aaatcggaac cctaaaggga gcccccgatt tagagcttga   10200
cggggaaagc cggcgaacgt ggcgagaaag gaagggaaga agcgaaagg agcgggcgct   10260 agggcgctgg caagtgtagc ggtcacgctg cgcgtaacca ccacacccgc cgcgcttaat   10320
gcgccgctac agggcgcgtc ccattcgcca ttcaggctgc gcaactgttg ggaagggcga   10380
tcggtgcggg cctcttcgct attacgccag ctggcgaaag ggggatgtgc tgcaaggcga   10440
ttaagttggg taacgccagg gttttcccag tcacgacgtt gtaaaacgac ggccagtgag   10500
cgcgcgtaat acgactcact atagggcgaa ttgggtac                          10538

<210> SEQ ID NO 2
<211> LENGTH: 13850
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 2 cgggccccccc ctcgaggtcg acggtatcgg gggagctcgc agggtctcca ttttgaagcg    60
```

| | |
|---|---|
| ggaggtttga acgcgcagcc gccatgccgg ggttttacga gattgtgatt aaggtcccca | 120 |
| gcgaccttga cgagcatctg cccggcattt ctgacagctt tgtgaactgg gtggccgaga | 180 |
| aggaatggga gttgccgcca gattctgaca tggatctgaa tctgattgag caggcacccc | 240 |
| tgaccgtggc cgagaagctg cagcgcgact ttctgacgga atggcgccgt gtgagtaagg | 300 |
| ccccggaggc tcttttcttt gtgcaatttg agaagggaga gagctacttc cacatgcacg | 360 |
| tgctcgtgga aaccaccggg gtgaaatcca tggttttggg acgtttcctg agtcagattc | 420 |
| gcgaaaaact gattcagaga atttaccgcg ggatcgagcc gactttgcca aactggttcg | 480 |
| cggtcacaaa gaccagaaat ggcgccgag gcgggaacaa ggtggtggat gagtgctaca | 540 |
| tcccccaatta cttgctcccc aaaacccagc ctgagctcca gtgggcgtgg actaatatgg | 600 |
| aacagtattt aagcgcctgt ttgaatctca cggagcgtaa acggttggtg gcgcagcatc | 660 |
| tgacgcacgt gtcgcagacg caggagcaga acaaagagaa tcagaatccc aattctgatg | 720 |
| cgccggtgat cagatcaaaa acttcagcca ggtacatgga gctggtcggg tggctcgtgg | 780 |
| acaagggat tacctcggag aagcagtgga tccaggtgag taattgacaa agccaaacac | 840 |
| caccatttgc cgagcacttt agagtttaca ggtttgtttc tcttgaccct caaaacaaac | 900 |
| ctgtgaggca taggagtat tgctatccct taagaattca cccccagtgt gcccatcaaa | 960 |
| acctcccagg ctgagtctgc acagttgaag gaggaaggat aggaatggga gggtcgatgg | 1020 |
| gtgaaagcat gattctctta accagtccag attatcaggt aatcccttca acaaccacca | 1080 |
| cccactccct gggcaatcca gctggagttt acagacagac ttagctggct atagcaccac | 1140 |
| cgtgctactc tctgttcttc ctggttgctc aaatgcccta gaaagtgga acaggtgagc | 1200 |
| atcaactcac agggctctat gctggctgct gctgcgaggg atgttatgct atagtaccag | 1260 |
| gggccaccat tccataggca cttcctgtgt ttaatacct atatgcttta cttcatctca | 1320 |
| tcttcctcca tatcctgaga ggtggttcta ttcttctccc cattttacgg atgaaaaaac | 1380 |
| cgagacacag aaaggtgaaa tagcttaaga taaatggtgc cttgcagcct tagactctgg | 1440 |
| tggcctctag ttaatgtggg aaattaaggg tgaggggatt ggcagctgat ggagggtgca | 1500 |
| gggtgccaga cagaggcgtt tagctctgat cccttagcaa tagagagtcc ttgtaggcac | 1560 |
| ttggtcaggc gagtgatgcg atgaaagctg tgtttaagaa agattatgct ttctgctgat | 1620 |
| ttcataccc caacacccaa gctctgaggc ccctcctcac aggtccttgc agggctggcc | 1680 |
| aaaataaagc agcttcactc cgttgtgctg cttttccagct aatgtgtctg tttggcagaa | 1740 |
| gtttccctca aaggcagatc agtgaaataa gcagaagcct cgaccccct tgtcagcca | 1800 |
| gagctgctga agtgccttgc cccagggtca ctttgtgtga ggggattaga gagcactggg | 1860 |
| gctgccaaga aacactgccg tttctacaga ttagcaggac gctggcttgt ggccttctag | 1920 |
| cgaggctcag agctgcggtg gccctagtct gcatgggcta aagacaagct ccatctcctg | 1980 |
| tccttgttcc ctccttcctg gcacagccg ccctgcttct tggttctctc tgttggttcc | 2040 |
| tgtccgcacg gtagttaggc tggcagcgtg tgtaggattt ggcttagaag attgacaaca | 2100 |
| ttgcctttga gccttctttt gctactcctc cctctcccct cccatcagac tcctctctgg | 2160 |
| agtctgctct gcgaggcctc tgctctgtgg tatcccagca gccttctcag ccttgacttc | 2220 |
| cagaaggggg ctgtgcagtg tccggggtgt gcaggcccca gacacggggt aggctcatgg | 2280 |
| agatccaagt gctgatctag tgtcaaggct ggcctggaga ctgggctggg ttggtgtctg | 2340 |
| cctgctgtgg tcatgtgccc tcccttgggc ctgtatcctc tctccagact tgctgcaggg | 2400 |
| agaggtggca gatgtcagcc tagttctggc ctctcagagc agcatggcag ctcccttta | 2460 |

```
ctcaggccca ggctgggccc tcctgctggc tgacccctgg ggagagggtg ctccagagct   2520
ccccaaggaa cagcttcccg aagcagccag gccagcccag aggggctgtg gccaatcctg   2580
aagctttatg ttcctgctga catttttct aagttttctc ttgctttcct cttaaatgcc    2640
aatctggaga gtctccgtta ggagaaatgg accccagcca ggaagaagag ttgagttgta   2700
tttaaaacac gagctccccc taaagcatcc ttctttagct tctaaggaga ggcagagact   2760
gacaggcagg actcagcagg aaaaggtacc cccctgacct gctcagtcag gccctaggcc   2820
cagctccacc cagcctgtgg cccccagagt ttcggtaaag agttccctgg gccttaagga   2880
accttgagag agcatttgag gggtgccacc acaaacttgg cagaaaaaac cctcccctc    2940 caagtccagt cctagagaag gagctggcaa ccttgccttg ctttgtaagc aaaagcctct   3000
tagggcttga gctcagatgt agtgtttgag ctgtggctgg tgccctgccc catcagggag   3060
ccaatggtag acatcctatg ggcatctttg ttttccgtaa gagcaggctg tctggggatg   3120
ggccagagga agaggcgacc tggagtcaac caagaggagg ccttaaccaa gccttaacca   3180
cagaggttaa ccaagccttg aaagcgcttc cccctgagca ggcaggaagc actgagtcca   3240
catggttgcc tcgctgtttc atttccttac actcaattct ctcagtcttt aaatgatcac   3300
ttggccttga agttacggat atttggggtc tgaactgaag ttgaagaaaa gaggaaatga   3360
tttaagcttt gtttaagatt aggggccagg tgcggtggct cacgcctgta atcccagcac   3420
cttgggagcc tgaggcgggt ggatcacctg aggtcaggag ttccagacca gcctggccaa   3480
catagcaaaa cccagtctct actaaaaata caataaaaa aattagccag gtgtggtgac    3540
acatgcctgt aatcccagtt actcaggagg ctgaggcaga attgcttgaa cttgagaggt   3600
ggaggttgta gtgagccaag accgcaccac tgcactccag cctggcgaca gagccagact   3660
ccgtctcaaa acaacaaca aaaagatta gaagaagccc attactgcct tctggccacc     3720
cactcgcaca gacaccaaaa ctgcagccca cacctcgcca tcctcgtgct ctgccctggg   3780 acacccagg cacagtgtgt ccttcgtttt ctgtaagggt gggctgggag cagggacgga    3840
cagggcctgt gggcacctct catggtcact tccttcttgc tcacaggagg accaggcctc   3900
atacatctcc ttcaatgcgg cctccaactc gcggtcccaa atcaaggctg ccttggacaa   3960
tgcgggaaag attatgagcc tgactaaaac cgcccccgac tacctggtgg ccagcagcc    4020 cgtggaggac atttccagca atcggattta taaaattttg gaactaaacg ggtacgatcc   4080
ccaatatgcg gcttccgtct ttctgggatg ggccacgaaa aagttcggca agaggaacac   4140
catctggctg tttgggcctg caactaccgg gaagaccaac atcgcggagg ccatagccca   4200
cactgtgccc ttctacgggt gcgtaaactg gaccaatgag aactttccct tcaacgactg   4260
tgtcgacaag atggtgatct ggtgggagga ggggaagatg accgccaagg tcgtggagtc   4320
ggccaaagcc attctcggag gaagcaaggt gcgcgtggac cagaaatgca agtcctcggc   4380
ccagatagac ccgactcccg tgatcgtcac ctccaacacc aacatgtgcg ccgtgattga   4440
cgggaactca acgaccttcg aacaccagca gccgttgcaa gaccggatgt tcaaatttga   4500
actcacccgc cgtctggatc atgactttgg gaaggtcacc aagcaggaag tcaaagactt   4560
tttccggtgg gcaaaggatc acgtggttga ggtggagcat gaattctacg tcaaaaaggg   4620
tggagccaag aaaagacccg ccccagtga cgcagatata agtgagccca acgggtgcg    4680 cgagtcagtt gcgcagccat cgacgtcaga gcgcgaagct tcgatcaact acgcagacag   4740
gtaccaaaac aaatgttctc gtcacgtggg catgaatctg atgctgtttc cctgcagaca   4800
```

```
atgcgagaga atgaatcaga attcaaatat ctgcttcact cacggacaga aagactgttt    4860
agagtgcttt cccgtgtcag aatctcaacc cgtttctgtc gtcaaaaagg cgtatcagaa    4920
actgtgctac attcatcata tcatgggaaa ggtgccagac gcttgcactg cctgcgatct    4980
ggtcaatgtg gatttggatg actgcatctt tgaacaataa atgatttaaa tcaggtatgg    5040
ctgccgatgg ttatcttcca gattggctcg aggacaacct ctctgagggc attcgcgagt    5100
ggtgggacct gaaacctgga gccccgaaac ccaaagccaa ccagcaaaag caggacaacg    5160
gccggggtct ggtgcttcct ggctacaagt acctcggacc cttcaacgga ctcgacaagg    5220
gggagcccgt caacgcggcg gacgcagcgg ccctcgagca cgacaaggcc tacgaccagc    5280
agctccaagc gggtgacaat ccgtacctgc ggtataatca cgccgacgcc gagtttcagg    5340
agcgtctgca agaagatacg tcttttgggg gcaacctcgg gcgcgcagtc ttccaggcca    5400
aaaagcgggt tctcgaacct ctgggcctgg ttgaatcgcc ggttaagatg gctagcggcg    5460
gtaggcgtgt acggtgggag gtctatataa gcagagctct ctggctaact accggtgcca    5520
ccatggcccc aaagaagaag cggaaggtcg gtatccacgg agtcccagca gccaagcgga    5580
actacatcct gggcctggac atcggcatca ccagcgtggg ctacggcatc atcgactacg    5640
agacacggga cgtgatcgat gccggcgtgc ggctgttcaa agaggccaac gtggaaaaca    5700
acgagggcag gcggagcaag agaggcgcca gaaggctgaa gcggcggagg cggcatagaa    5760
tccagagagt gaagaagctg ctgttcgact acaacctgct gaccgaccac agcgagctga    5820
gcggcatcaa cccctacgag gccagagtga agggcctgag ccagaagctg agcgaggaag    5880
agttctctgc cgccctgctg cacctggcca agagaagagg cgtgcacaac gtgaacgagg    5940
tggaagagga caccggcaac gagctgtcca ccaaagagca gatcagccgg aacagcaagg    6000
ccctggaaga gaaatacgtg gccgaactgc agctggaacg gctgaagaaa gacggcgaag    6060
tgcggggcag catcaacaga ttcaagacca gcgactacgt gaaagaagcc aaacagctgc    6120
tgaaggtgca gaaggcctac caccagctgg accagagctt catcgacacc tacatcgacc    6180
tgctggaaac ccggcggacc tactatgagg gacctggcga gggcagcccc ttcggctgga    6240
aggacatcaa agaatggtac gagatgctga tgggccactg cacctacttc cccgaggaac    6300
tgcggagcgt gaagtacgcc tacaacgccg acctgtacaa cgccctgaac gacctgaaca    6360
atctcgtgat caccagggac gagaacgaga gctggaata ttacgagaag ttccagatca    6420
tcgagaacgt gttcaagcag aagaagaagc ccaccctgaa gcagatcgcc aaagaaatcc    6480
tcgtgaacga agaggatatt aagggctaca gagtgaccag caccggcaag cccgagttca    6540
ccaacctgaa ggtgtaccac gacatcaagg acattaccgc ccggaaagag attattgaga    6600
acgccgagct gctggatcag attgccaaga tcctgaccat ctaccagagc agcgaggaca    6660
tccaggaaga actgaccaat ctgaactccg agctgaccca ggaagagatc gagcagatct    6720
ctaatctgaa gggctatacc ggcacccaca acctgagcct gaaggccatc aacctgatcc    6780
tggacgagct gtggcacacc aacgacaacc agatcgctat cttcaaccgg ctgaagctgg    6840
tgcccaagaa ggtggacctg tcccagcaga agagatcc caccaccctg gtggacgact    6900
tcatcctgag ccccgtcgtg aagagaagct tcatccagag catcaaagtg atcaacgcca    6960
tcatcaagaa gtacggcctg cccaacgaca tcattatcga gctggcccgc gagaagaact    7020
ccaaggacgc ccagaaaatg atcaacgaga tgcagaagcg gaaccggcag accaacgagc    7080
ggatcgagga aatcatccgg accaccgca aagaaacgc caagtacctg atcgagaaga    7140
tcaagctgca cgacatgcag gaaggcaagt gcctgtacag cctggaagcc atccctctgg    7200
```

| | |
|---|---|
| aagatctgct gaacaacccc ttcaactatg aggtggacca catcatcccc agaagcgtgt | 7260 |
| ccttcgacaa cagcttcaac aacaaggtgc tcgtgaagca ggaagaaaac agcaagaagg | 7320 |
| gcaaccggac cccattccag tacctgagca gcagcgacag caagatcagc tacgaaacct | 7380 |
| tcaagaagca catcctgaat ctggccaagg caagggcag aatcagcaag accaagaaag | 7440 |
| agtatctgct ggaagaacgg gacatcaaca ggttctccgt gcagaaagac ttcatcaacc | 7500 |
| ggaacctggt ggataccaga tacgccacca gaggcctgat gaacctgctg cggagctact | 7560 |
| tcagagtgaa caacctggac gtgaaagtga agtccatcaa tggcggcttc accagctttc | 7620 |
| tgcggcggaa gtggaagttt aagaaagagc ggaacaaggg gtacaagcac cacgccgagg | 7680 |
| acgccctgat cattgccaac gccgatttca tcttcaaaga gtggaagaaa ctggacaagg | 7740 |
| ccaaaaaagt gatggaaaac cagatgttcg aggaaaagca ggccgagagc atgcccgaga | 7800 |
| tcgaaaccga gcaggagtac aaagagatct tcatcacccc ccaccagatc aagcacatta | 7860 |
| aggacttcaa ggactacaag tacagccacc gggtggacaa gaagcctaat agagagctga | 7920 |
| ttaacgacac cctgtactcc acccggaagg acgacaaggg caacaccctg atcgtgaaca | 7980 |
| atctgaacgg cctgtacgac aaggacaatg acaagctgaa aaagctgatc aacaagagcc | 8040 |
| ccgaaaagct gctgatgtac caccacgacc cccagaccta ccagaaactg aagctgatta | 8100 |
| tggaacagta cggcgacgag aagaatcccc tgtacaagta ctacgaggaa ccgggaact | 8160 |
| acctgaccaa gtactccaaa aaggacaacg cccccgtgat caagaagatt aagtattacg | 8220 |
| gcaacaaact gaacgcccat ctggacatca ccgacgacta ccccaacagc agaaacaagg | 8280 |
| tcgtgaagct gtccctgaag ccctacagat cgacgtgta cctggacaat ggcgtgtaca | 8340 |
| agttcgtgac cgtgaagaat ctggatgtga tcaaaaaaga aaactactac gaagtgaata | 8400 |
| gcaagtgcta tgaggaagct aagaagctga agaagatcag caaccaggcc gagtttatcg | 8460 |
| cctccttcta caacaacgat ctgatcaaga tcaacggcga gctgtataga gtgatcggcg | 8520 |
| tgaacaacga cctgctgaac cggatcgaag tgaacatgat cgacatcacc taccgcgagt | 8580 |
| acctggaaaa catgaacgac aagaggcccc caggatcat taagacaatc gcctccaaga | 8640 |
| cccagagcat taagaagtac agcacagaca ttctgggcaa cctgtatgaa gtgaaatcta | 8700 |
| agaagcaccc tcagatcatc aaaaagggca gcggcttcgc caacgagctg ggccctagac | 8760 |
| tgatgggaaa gatgcataga ccggtagagc catcacccca gcgctctcca gactcctcta | 8820 |
| cgggcatcgg caagaaaggc cagcagcccg caaaaaagag actcaatttt gggcagactg | 8880 |
| gcgactcaga gtcagtcccc gaccctcaac caatcggaga accaccagca ggcccctctg | 8940 |
| gtctgggatc tggtacaatg gctgcaggcg gtggcgctcc aatggcagac aataacgaag | 9000 |
| gcgccgacgg agtgggtagt tcctcaggaa attggcattg cgattccaca tggctgggcg | 9060 |
| acagagtcat caccaccagc acccgcacct gggccctgcc cacctacaac aaccacctct | 9120 |
| acaagcaaat ctccaacggg acctcggag gaagcaccaa cgacaacacc tacttcggct | 9180 |
| acagcacccc ctgggggtat tttgacttca acagattcca ctgccacttt tcaccacgtg | 9240 |
| actggcagcg actcatcaac aacaactggg gattccggcc caagaggctc aacttcaagc | 9300 |
| tcttcaacat ccagtcaag gaggtcacgc agaatgaagg caccaagacc atcgccaata | 9360 |
| accttaccag cacgattcag gtctttacgg actcggaata ccagctcccg tacgtgctcg | 9420 |
| gctcggcgca ccagggctgc ctgcctccgt tcccggcgga cgtcttcatg attcctcagt | 9480 |
| acgggtacct gactctgaac aatggcagtc aggctgtggg ccggtcgtcc ttctactgcc | 9540 |

```
tggagtactt tccttctcaa atgctgagaa cgggcaacaa ctttgaattc agctacaact   9600
tcgaggacgt gcccttccac agcagctacg cgcacagcca gagcctggac cggctgatga   9660
accctctcat cgaccagtac ttgtactacc tgtcccggac tcaaagcacg ggcggtactg   9720
caggaactca gcagttgcta ttttctcagg ccgggcctaa caacatgtcg gctcaggcca   9780
agaactggct acccggtccc tgctaccggc agcaacgcgt ctccacgaca ctgtcgcaga   9840
acaacaacag caactttgcc tggacgggtg ccaccaagta tcatctgaat ggcagagact   9900
ctctggtgaa tcctggcgtt gccatggcta cccacaagga cgacgaagag cgattttttc   9960
catccagcgg agtcttaatg tttgggaaac agggagctgg aaaagacaac gtggactata  10020
gcagcgtgat gctaaccagc gaggaagaaa taaagaccac caacccagtg gccacagaac  10080 agtacgcgt ggtggccgat aacctgcaac agcaaaacgc cgctcctatt gtaggggccg   10140
tcaatagtca aggagcctta cctggcatgg tgtggcagaa ccgggacgtg tacctgcagg  10200
gtcccatctg ggccaagatt cctcatacgg acggcaactt tcatccctcg ccgctgatgg  10260
gaggctttgg actgaagcat ccgcctcctc agatcctgat taaaaacaca cctgttcccg  10320
cggatcctcc gaccaccttc agccaggcca agctggcttc tttcatcacg cagtacagta  10380
ccggccaggt cagcgtggag atcgagtggg agctgcagaa ggagaacagc aaacgctgga  10440
acccagagat tcagtacact tccaactact acaaatctac aaatgtggac tttgctgtca  10500
atactgaggg tacttattcc gagcctcgcc ccattggcac ccgttacctc acccgtaatc  10560
tgtaattaca tgttaatcaa taaaccggtt aattcgtttc agttgaactt tggtctcctg  10620
tccttcttat cttatcggtt accatagaaa ctggttactt attaactgct tggtgcgctt  10680
cgcgataaaa gacttacgtc atcgggttac ccctagtgat ggagcggccg ctttcagttg  10740
aactttggtc tctgcgtatt tctttcttat ctagtttcca tgctctagag gtcctgtatt  10800
agaggtcacg tgagtgtttt gcgacatttt gcgacaccat gtggtcacgc tgggtattta  10860
agcccgagtg agcacgcagg gtctccattt tgaagcggga ggtttgaacg cgcagccgcc  10920
aagccgaatt ctgcagatat ccatcacact ggcggccgct cgactagagc ggccgccacc  10980
gcggtggagc tccagctttt gttcccttta gtgagggtta attgcgcgct tggcgtaatc  11040
atggtcatag ctgtttcctg tgtgaaattg ttatccgctc acaattccac acaacatacg  11100
agccggaagc ataaagtgta aagcctgggg tgcctaatga gtgagctaac tcacattaat  11160
tgcgttgcgc tcactgcccg ctttccagtc gggaaacctg tcgtgccagc tgcattaatg  11220
aatcggccaa cgcgcgggga gaggcggttt gcgtattggg cgctcttccg cttcctcgct  11280
cactgactcg ctgcgctcgg tcgttcggct gcggcgagcg gtatcagctc actcaaaggc  11340
ggtaatacgg ttatccacag aatcagggga taacgcagga agaacatgt gagcaaaagg   11400 ccagcaaaag gccaggaacc gtaaaaaggc cgcgttgctg gcgtttttcc ataggctccg  11460
cccccctgac gagcatcaca aaaatcgacg ctcaagtcag aggtggcgaa acccgacagg  11520
actataaaga taccaggcgt ttccccctgg aagctccctc gtgcgctctc ctgttccgac  11580
cctgccgctt accggatacc tgtccgcctt tctcccttcg ggaagcgtgg cgctttctca  11640
tagctcacgc tgtaggtatc tcagttcggt gtaggtcgtt cgctccaagc tgggctgtgt  11700
gcacgaaccc cccgttcagc ccgaccgctg cgccttatcc ggtaactatc gtcttgagtc  11760
caacccggta agacacgact tatcgccact ggcagcagcc actggtaaca ggattagcag  11820
agcgaggtat gtaggcggtg ctacagagtt cttgaagtgg tggcctaact acggctacac  11880
tagaagaaca gtatttggta tctgcgctct gctgaagcca gttaccttcg gaaaaagagt  11940
```

```
tggtagctct tgatccggca aacaaaccac cgctggtagc ggtggttttt ttgtttgcaa    12000
gcagcagatt acgcgcagaa aaaaggatc tcaagaagat cctttgatct tttctacggg    12060
gtctgacgct cagtggaacg aaaactcacg ttaagggatt ttggtcatga gattatcaaa    12120
aaggatcttc acctagatcc ttttaaatta aaaatgaagt tttaaatcaa tctaaagtat    12180
atatgagtaa acttggtctg acagttacca atgcttaatc agtgaggcac ctatctcagc    12240
gatctgtcta tttcgttcat ccatagttgc ctgactcccc gtcgtgtaga taactacgat    12300
acgggagggc ttaccatctg gccccagtgc tgcaatgata ccgcgagacc cacgctcacc    12360
ggctccagat ttatcagcaa taaaccagcc agcggaagg gccgagcgca gaagtggtcc    12420
tgcaacttta tccgcctcca tccagtctat taattgttgc cgggaagcta gagtaagtag    12480
ttcgccagtt aatagtttgc gcaacgttgt tgccattgct acaggcatcg tggtgtcacg    12540
ctcgtcgttt ggtatggctt cattcagctc cggttcccaa cgatcaaggc gagttacatg    12600
atcccccatg ttgtgcaaaa aagcggttag ctccttcggt cctccgatcg ttgtcagaag    12660
taagttggcc gcagtgttat cactcatggt tatggcagca ctgcataatt ctcttactgt    12720
catgccatcc gtaagatgct tttctgtgac tggtgagtac tcaaccaagt cattctgaga    12780
atagtgtatg cggcgaccga gttgctcttg cccggcgtca atacgggata taccgcgcc    12840 acatagcaga actttaaaag tgctcatcat tggaaaacgt tcttcgggc gaaaactctc    12900 aaggatctta ccgctgttga gatccagttc gatgtaaccc actcgtgcac ccaactgatc    12960
ttcagcatct tttactttca ccagcgtttc tgggtgagca aaaacaggaa ggcaaaatgc    13020
cgcaaaaaag ggaataaggg cgacacggaa atgttgaata ctcatactct tccttttca    13080 atattattga agcatttatc agggttattg tctcatgagc ggatacatat ttgaatgtat    13140
ttagaaaaat aaacaaatag gggttccgcg cacatttccc cgaaaagtgc cacctaaatt    13200
gtaagcgtta atattttgtt aaaattcgcg ttaaattttt gttaaatcag ctcatttttt    13260
aaccaatagg ccgaaatcgg caaaatccct tataaatcaa agaatagac cgagataggg    13320 ttgagtgttg ttccagtttg gaacaagagt ccactattaa agaacgtgga ctccaacgtc    13380
aaagggcgaa aaaccgtcta tcagggcgat ggcccactac gtgaaccatc accctaatca    13440
agttttttgg ggtcgaggtg ccgtaaagca ctaaatcgga accctaaagg gagcccccga    13500
tttagagctt gacggggaaa gccggcgaac gtggcgagaa aggaagggaa gaaagcgaaa    13560
ggagcgggcg ctagggcgct ggcaagtgta gcggtcacgc tgcgcgtaac caccacaccc    13620
gccgcgctta atgcgccgct acagggcgcg tcccattcgc cattcaggct gcgcaactgt    13680
tgggaagggc gatcggtgcg ggcctcttcg ctattacgcc agctggcgaa agggggatgt    13740
gctgcaaggc gattaagttg ggtaacgcca gggttttccc agtcacgacg ttgtaaaacg    13800
acggccagtg agcgcgcgta atacgactca ctatagggcg aattgggtac                13850
```

<210> SEQ ID NO 3
<211> LENGTH: 1105
<212> TYPE: PRT
<213> ORGANISM: Staphylococcus aureus

<400> SEQUENCE: 3

```
Gly Gly Arg Arg Val Arg Trp Glu Val Tyr Ile Ser Arg Ala Leu Trp
1               5                   10                  15

Leu Thr Thr Gly Ala Thr Met Ala Pro Lys Lys Arg Lys Val Gly
            20                  25                  30
```

```
Ile His Gly Val Pro Ala Ala Lys Arg Asn Tyr Ile Leu Gly Leu Asp
             35                  40                  45

Ile Gly Ile Thr Ser Val Gly Tyr Gly Ile Ile Asp Tyr Glu Thr Arg
 50                  55                  60

Asp Val Ile Asp Ala Gly Val Arg Leu Phe Lys Glu Ala Asn Val Glu
 65                  70                  75                  80

Asn Asn Glu Gly Arg Arg Ser Lys Arg Gly Ala Arg Arg Leu Lys Arg
                 85                  90                  95

Arg Arg Arg His Arg Ile Gln Arg Val Lys Lys Leu Leu Phe Asp Tyr
                100                 105                 110

Asn Leu Leu Thr Asp His Ser Glu Leu Ser Gly Ile Asn Pro Tyr Glu
             115                 120                 125

Ala Arg Val Lys Gly Leu Ser Gln Lys Leu Ser Glu Glu Glu Phe Ser
130                 135                 140

Ala Ala Leu Leu His Leu Ala Lys Arg Arg Gly Val His Asn Val Asn
145                 150                 155                 160

Glu Val Glu Glu Asp Thr Gly Asn Glu Leu Ser Thr Lys Glu Gln Ile
                165                 170                 175

Ser Arg Asn Ser Lys Ala Leu Glu Glu Lys Tyr Val Ala Glu Leu Gln
                180                 185                 190

Leu Glu Arg Leu Lys Lys Asp Gly Glu Val Arg Gly Ser Ile Asn Arg
            195                 200                 205

Phe Lys Thr Ser Asp Tyr Val Lys Glu Ala Lys Gln Leu Leu Lys Val
        210                 215                 220

Gln Lys Ala Tyr His Gln Leu Asp Gln Ser Phe Ile Asp Thr Tyr Ile
225                 230                 235                 240

Asp Leu Leu Glu Thr Arg Arg Thr Tyr Tyr Glu Gly Pro Gly Glu Gly
                245                 250                 255

Ser Pro Phe Gly Trp Lys Asp Ile Lys Glu Trp Tyr Glu Met Leu Met
                260                 265                 270

Gly His Cys Thr Tyr Phe Pro Glu Glu Leu Arg Ser Val Lys Tyr Ala
            275                 280                 285

Tyr Asn Ala Asp Leu Tyr Asn Ala Leu Asn Asp Leu Asn Asn Leu Val
        290                 295                 300

Ile Thr Arg Asp Glu Asn Glu Lys Leu Glu Tyr Tyr Glu Lys Phe Gln
305                 310                 315                 320

Ile Ile Glu Asn Val Phe Lys Gln Lys Lys Lys Pro Thr Leu Lys Gln
                325                 330                 335

Ile Ala Lys Glu Ile Leu Val Asn Glu Glu Asp Ile Lys Gly Tyr Arg
                340                 345                 350

Val Thr Ser Thr Gly Lys Pro Glu Phe Thr Asn Leu Lys Val Tyr His
            355                 360                 365

Asp Ile Lys Asp Ile Thr Ala Arg Lys Glu Ile Ile Glu Asn Ala Glu
        370                 375                 380

Leu Leu Asp Gln Ile Ala Lys Ile Leu Thr Ile Tyr Gln Ser Ser Glu
385                 390                 395                 400

Asp Ile Gln Glu Glu Leu Thr Asn Leu Asn Ser Glu Leu Thr Gln Glu
                405                 410                 415

Glu Ile Glu Gln Ile Ser Asn Leu Lys Gly Tyr Thr Gly Thr His Asn
                420                 425                 430

Leu Ser Leu Lys Ala Ile Asn Leu Ile Leu Asp Glu Leu Trp His Thr
            435                 440                 445

Asn Asp Asn Gln Ile Ala Ile Phe Asn Arg Leu Lys Leu Val Pro Lys
```

```
            450                 455                 460
Lys Val Asp Leu Ser Gln Gln Lys Glu Ile Pro Thr Thr Leu Val Asp
465                 470                 475                 480

Asp Phe Ile Leu Ser Pro Val Val Lys Arg Ser Phe Ile Gln Ser Ile
                485                 490                 495

Lys Val Ile Asn Ala Ile Ile Lys Lys Tyr Gly Leu Pro Asn Asp Ile
                500                 505                 510

Ile Ile Glu Leu Ala Arg Glu Lys Asn Ser Lys Asp Ala Gln Lys Met
                515                 520                 525

Ile Asn Glu Met Gln Lys Arg Asn Arg Gln Thr Asn Glu Arg Ile Glu
                530                 535                 540

Glu Ile Ile Arg Thr Thr Gly Lys Glu Asn Ala Lys Tyr Leu Ile Glu
545                 550                 555                 560

Lys Ile Lys Leu His Asp Met Gln Glu Gly Lys Cys Leu Tyr Ser Leu
                565                 570                 575

Glu Ala Ile Pro Leu Glu Asp Leu Leu Asn Asn Pro Phe Asn Tyr Glu
                580                 585                 590

Val Asp His Ile Ile Pro Arg Ser Val Ser Phe Asp Asn Ser Phe Asn
                595                 600                 605

Asn Lys Val Leu Val Lys Gln Glu Glu Asn Ser Lys Lys Gly Asn Arg
                610                 615                 620

Thr Pro Phe Gln Tyr Leu Ser Ser Ser Asp Ser Lys Ile Ser Tyr Glu
625                 630                 635                 640

Thr Phe Lys Lys His Ile Leu Asn Leu Ala Lys Gly Lys Gly Arg Ile
                645                 650                 655

Ser Lys Thr Lys Lys Glu Tyr Leu Leu Glu Glu Arg Asp Ile Asn Arg
                660                 665                 670

Phe Ser Val Gln Lys Asp Phe Ile Asn Arg Asn Leu Val Asp Thr Arg
                675                 680                 685

Tyr Ala Thr Arg Gly Leu Met Asn Leu Leu Arg Ser Tyr Phe Arg Val
                690                 695                 700

Asn Asn Leu Asp Val Lys Val Lys Ser Ile Asn Gly Gly Phe Thr Ser
705                 710                 715                 720

Phe Leu Arg Arg Lys Trp Lys Phe Lys Lys Glu Arg Asn Lys Gly Tyr
                725                 730                 735

Lys His His Ala Glu Asp Ala Leu Ile Ile Ala Asn Ala Asp Phe Ile
                740                 745                 750

Phe Lys Glu Trp Lys Lys Leu Asp Lys Ala Lys Lys Val Met Glu Asn
                755                 760                 765

Gln Met Phe Glu Glu Lys Gln Ala Glu Ser Met Pro Glu Ile Glu Thr
                770                 775                 780

Glu Gln Glu Tyr Lys Glu Ile Phe Ile Thr Pro His Gln Ile Lys His
785                 790                 795                 800

Ile Lys Asp Phe Lys Asp Tyr Lys Tyr Ser His Arg Val Asp Lys Lys
                805                 810                 815

Pro Asn Arg Glu Leu Ile Asn Asp Thr Leu Tyr Ser Thr Arg Lys Asp
                820                 825                 830

Asp Lys Gly Asn Thr Leu Ile Val Asn Asn Leu Asn Gly Leu Tyr Asp
                835                 840                 845

Lys Asp Asn Asp Lys Leu Lys Lys Leu Ile Asn Lys Ser Pro Glu Lys
                850                 855                 860

Leu Leu Met Tyr His His Asp Pro Gln Thr Tyr Gln Lys Leu Lys Leu
865                 870                 875                 880
```

```
Ile Met Glu Gln Tyr Gly Asp Glu Lys Asn Pro Leu Tyr Lys Tyr Tyr
                885                 890                 895

Glu Glu Thr Gly Asn Tyr Leu Thr Lys Tyr Ser Lys Lys Asp Asn Gly
            900                 905                 910

Pro Val Ile Lys Lys Ile Lys Tyr Tyr Gly Asn Lys Leu Asn Ala His
        915                 920                 925

Leu Asp Ile Thr Asp Asp Tyr Pro Asn Ser Arg Asn Lys Val Val Lys
    930                 935                 940

Leu Ser Leu Lys Pro Tyr Arg Phe Asp Val Tyr Leu Asp Asn Gly Val
945                 950                 955                 960

Tyr Lys Phe Val Thr Val Lys Asn Leu Asp Val Ile Lys Glu Asn
                965                 970                 975

Tyr Tyr Glu Val Asn Ser Lys Cys Tyr Glu Glu Ala Lys Lys Leu Lys
            980                 985                 990

Lys Ile Ser Asn Gln Ala Glu Phe Ile Ala Ser Phe Tyr Asn Asn Asp
        995                 1000                1005

Leu Ile Lys Ile Asn Gly Glu Leu Tyr Arg Val Ile Gly Val Asn
    1010                1015                1020

Asn Asp Leu Leu Asn Arg Ile Glu Val Asn Met Ile Asp Ile Thr
    1025                1030                1035

Tyr Arg Glu Tyr Leu Glu Asn Met Asn Asp Lys Arg Pro Pro Arg
    1040                1045                1050

Ile Ile Lys Thr Ile Ala Ser Lys Thr Gln Ser Ile Lys Lys Tyr
    1055                1060                1065

Ser Thr Asp Ile Leu Gly Asn Leu Tyr Glu Val Lys Ser Lys Lys
    1070                1075                1080

His Pro Gln Ile Ile Lys Lys Gly Ser Gly Phe Ala Asn Glu Leu
    1085                1090                1095

Gly Pro Arg Leu Met Gly Lys
    1100                1105

<210> SEQ ID NO 4
<211> LENGTH: 10538
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 4
cgggcccccc ctcgaggtcg acggtatcgg gggagctcgc agggtctcca ttttgaagcg      60
ggaggtttga acgcgcagcc gccatgccgg ggttttacga gattgtgatt aaggtcccca     120
gcgaccttga cgagcatctg cccggcattt ctgacagctt tgtgaactgg gtggccgaga     180
aggaatggga gttgccgcca gattctgaca tggatctgaa tctgattgag caggcacccc     240
tgaccgtggc cgagaagctg cagcgcgact ttctgacgga atggcgccgt gtgagtaagg     300
ccccggaggc tctttttctt gtgcaatttg agaagggaga gagctacttc cacatgcacg     360
tgctcgtgga aaccaccggg gtgaaatcca tggttttggg acgtttcctg agtcagattc     420
gcgaaaaact gattcagaga atttaccgcg ggatcgagcc gactttgcca aactggttcg     480
cggtcacaaa gaccagaaat ggcgccggag gcgggaacaa ggtggtggat gagtgctaca     540
tccccaatta cttgctcccc aaaacccagc ctgagctcca gtgggcgtgg actaatatgg     600
aacagtattt aagcgcctgt ttgaatctca cggagcgtaa acggttggtg gcgcagcatc     660
```

```
tgacgcacgt gtcgcagacg caggagcaga acaaagagaa tcagaatccc aattctgatg    720
cgccggtgat cagatcaaaa acttcagcca ggtacatgga gctggtcggg tggctcgtgg    780
acaaggggat tacctcggag aagcagtgga tccaggtgag taattgacaa agccaaacac    840
caccatttgc cgagcacttt agagtttaca ggtttgtttc tcttgacccT caaaacaaac    900
ctgtgaggca tagggagtat tgctatccct taagaattca cccccagtgt gcccatcaaa    960
acctcccagg ctgagtctgc acagttgaag gaggaaggat aggaatggga gggtcgatgg   1020
gtgaaagcat gattctctta accagtccag attatcaggt aatcccttca acaaccacca   1080
cccactccct gggcaatcca gctggagttt acagacagac ttagctggct atagcaccac   1140
cgtgctactc tctgttcttc ctggttgctc aaatgcccta gaaaagtgga acaggtgagc   1200
atcaactcac agggctctat gctggctgct gctgcgaggg atgttatgct atagtaccag   1260
gggccaccat tccataggca cttcctgtgt ttaatacccT atatgcttta cttcatctca   1320
tcttcctcca tatcctgaga ggtggttcta ttcttctccc cattttacgg atgaaaaaac   1380
cgagacacag aaaggtgaaa tagcttaaga taaatggtgc cttgcagcct tagactctgg   1440
tggcctctag ttaatgtggg aaattaaggg tgagggatt ggcagctgat ggagggtgca   1500
gggtgccaga cagaggcgtt tagctctgat cccttagcaa tagagagtcc ttgtaggcac   1560
ttggtcaggc gagtgatgcg atgaaagctg tgtttaagaa agattatgct ttctgctgat   1620
ttcatacccc caacacccaa gctctgaggc ccctcctcac aggtccttgc agggctggcc   1680
aaaataaagc agcttcactc cgttgtgctg ctttccagct aatgtgtctg tttggcagaa   1740
gtttccctca aaggcagatc agtgaaataa gcagaagcct cgaccccccT tgtcagcca   1800
gagctgctga agtgccttgc cccagggtca ctttgtgtga ggggattaga gagcactggg   1860
gctgccaaga aacactgccg tttctacaga ttagcaggac gctggcttgt ggccttctag   1920
cgaggctcag agctgcggtg ccctagtcT gcatgggcta aagacaagct ccatctcctg   1980
tccttgttcc ctccttcctg ggcacagccg ccctgcttct tggttctctc tgttggttcc   2040
tgtccgcacg gtagttaggc tggcagcgtg tgtaggattt ggcttagaag attgacaaca   2100
ttgcctttga gcccttcttt gctactcctc cctctcccT cccatcagac tcctctctgg   2160
agtctgctct gcgaggcctc tgctctgtgg tatcccagca gccttctcag ccttgacttc   2220
cagaagggg ctgtgcagtg tccggggtgt gcaggcccca gacacggggt aggctcatgg   2280
agatccaagt gctgatctag tgtcaaggct ggcctggaga ctgggctggg ttggtgtctg   2340
cctgctgtgg tcatgtgccc tcccttgggc ctgtatcctc tctccagact tgctgcaggg   2400
agaggtggca gatgtcagcc tagttctggc ctctcagagc agcatggcag ctccctttca   2460
ctcaggccca ggctgggccc tcctgctggc tgacccctgg ggagagggtg ctccagagct   2520
ccccaaggaa cagcttcccg aagcagccag gccagcccag aggggctgtg gccaatcctg   2580
aagctttatg ttcctgctga cattttttct aagttttctc ttgctttcct cttaaatgcc   2640
aatctggaga gtctccgtta ggagaaatgg acccccagcca ggaagaagag ttgagttgta   2700
tttaaaacac gagctccccc taaagcatcc ttcttTagct tctaaggaga ggcagagact   2760
gacaggcagg actcagcagg aaaaggtacc cccctgacct gctcagtcag gccctaggcc   2820
cagctccacc cagcctgtgg ccccagagt ttcggtaaag agttccctgg gccttaagga   2880
accttgagag agcatttgag gggtgccacc acaaacttgg cagaaaaaac cctccccctc   2940
caagtccagt cctagagaag gagctggcaa ccttgccttg ctttgtaagc aaaagcctct   3000
```

```
tagggcttga gctcagatgt agtgtttgag ctgtggctgg tgccctgccc catcagggag    3060
ccaatggtag acatcctatg ggcatctttg ttttccgtaa gagcaggctg tctgggatg     3120 ggccagagga agaggcgacc tggagtcaac caagaggagg ccttaaccaa gccttaacca    3180
cagaggttaa ccaagccttg aaagcgcttc ccctgagca ggcaggaagc actgagtcca     3240
catggttgcc tcgctgtttc atttccttac actcaattct ctcagtcttt aaatgatcac    3300
ttggccttga agttacggat atttggggtc tgaactgaag ttgaagaaaa gaggaaatga    3360
tttaagcttt gtttaagatt aggggccagg tgcggtggct cacgcctgta atcccagcac    3420
cttgggagcc tgaggcgggt ggatcacctg aggtcaggag ttccagacca gcctggccaa    3480
catagcaaaa cccagtctct actaaaaata acaataaaaa aattagccag gtgtggtgac    3540
acatgcctgt aatcccagtt actcaggagg ctgaggcaga attgcttgaa cttgagaggt    3600
ggaggttgta gtgagccaag accgcaccac tgcactccag cctggcgaca gagccagact    3660
ccgtctcaaa acaacaaca aaaaagatta gaagaagccc attactgcct tctggccacc     3720
cactcgcaca gacaccaaaa ctgcagccca cacctcgcca tcctcgtgct ctgccctggg    3780 acacccagg cacagtgtgt ccttcgtttt ctgtaagggt gggctgggag cagggacgga     3840
cagggcctgt gggcacctct catggtcact tccttcttgc tcacaggagg accaggcctc    3900
atacatctcc ttcaatgcgg cctccaactc gcggtcccaa atcaaggctg ccttggacaa    3960
tgcgggaaag attatgagcc tgactaaaac cgcccccgac tacctggtgg ccagcagcc    4020 cgtggaggac atttccagca atcggattta taaaattttg gaactaaacg ggtacgatcc    4080
ccaatatgcg gcttccgtct ttctgggatg ggccacgaaa aagttcggca agaggaacac    4140
catctggctg tttgggcctg caactaccgg gaagaccaac atcgcggagg ccatagccca    4200
cactgtgccc ttctacgggt gcgtaaactg gaccaatgag aactttccct tcaacgactg    4260
tgtcgacaag atggtgatct ggtgggagga ggggaagatg accgccaagg tcgtggagtc    4320
ggccaaagcc attctcggag gaagcaaggt gcgcgtggac cagaaatgca agtcctcggc    4380
ccagatagac ccgactcccg tgatcgtcac ctccaacacc aacatgtgcg ccgtgattga    4440
cgggaactca acgaccttcg aacaccagca gccgttgcaa gaccggatgt tcaaatttga    4500
actcacccgc cgtctggatc atgactttgg gaaggtcacc aagcaggaag tcaaagactt    4560
tttccggtgg gcaaaggatc acgtggttga ggtggagcat gaattctacg tcaaaaaggg    4620
tggagccaag aaaagacccg cccccagtga cgcagatata agtgagccca acgggtgcg    4680 cgagtcagtt gcgcagccat cgacgtcaga gcgggaagct tcgatcaact acgcagacag    4740
gtaccaaaac aaatgttctc gtcacgtggg catgaatctg atgctgtttc cctgcagaca    4800
atgcgagaga atgaatcaga attcaaatat ctgcttcact cacggacaga aagactgttt    4860
agagtgcttt cccgtgtcag aatctcaacc cgtttctgtc gtcaaaaagg cgtatcagaa    4920
actgtgctac attcatcata tcatgggaaa ggtgccagac gcttgcactg cctgcgatct    4980
ggtcaatgtg gatttggatg actgcatctt tgaacaataa atgatttaaa tcaggtatgg    5040
ctgccgatgg ttatcttcca gattggctcg aggacaacct ctctgagggc attcgcgagt    5100
ggtgggacct gaaacctgga gccccgaaac ccaaagccaa ccagcaaaag caggacaacg    5160
gccggggtct ggtgcttcct ggctacaagt acctcggacc cttcaacgga ctcgacaagg    5220
gggagcccgt caacgcggcg gacgcagcgg ccctcgagca cgacaaggcc tacgaccagc    5280
agctccaagc gggtgacaat ccgtacctgc ggtataatca cgccgacgcc gagtttcagg    5340
agcgtctgca agaagatacg tcttttgggg gcaacctcgg gcgcgcagtc ttccaggcca    5400
```

```
aaaagcgggt tctcgaacct ctgggcctgg ttgaatcgcc ggttaaggcg gctcctggaa   5460
agaagagacc ggtagagcca tcaccccagc gctctccaga ctcctctacg ggcatcggca   5520
agaaaggcca gcagcccgca aaaaagagac tcaattttgg gcagactggc gactcagagt   5580
cagtccccga ccctcaacca atcggagaac caccagcagg ccctctggt ctgggatctg    5640 gtacaatggc tgcaggcggt ggcgctccaa tggcagacaa taacgaaggc gccgacggag   5700
tgggtagttc ctcaggaaat tggcattgcg attccacatg gctgggcgac agagtcatca   5760
ccaccagcac ccgcacctgg gccctgccca cctacaacaa ccacctctac aagcaaatct   5820
ccaacgggac ctcggggagga agcaccaacg acaacaccta cttcggctac agcaccccct   5880
gggggtattt tgacttcaac agattccact gccacttttc accacgtgac tggcagcgac   5940
tcatcaacaa caactgggga ttccggccca agaggctcaa cttcaagctc ttcaacatcc   6000
aagtcaagga ggtcacgcag aatgaaggca ccaagaccat cgccaataac cttaccagca   6060
cgattcaggt ctttacggac tcggaatacc agctcccgta cgtgctcggc tcggcgcacc   6120
agggctgcct gcctccgttc ccggcggacg tcttcatgat tcctcagtac gggtacctga   6180
ctctgaacaa tggcagtcag gctgtgggcc ggtcgtcctt ctactgcctg gagtactttc   6240
cttctcaaat gctgagaacg ggcaacaact ttgaattcag ctacaacttc gaggacgtgc   6300
ccttccacag cagctacgcg cacagccaga gcctggaccg gctgatgaac cctctcatcg   6360
accagtactt gtactacctg tcccggactc aaagcacggg cggtactgca ggaactcagc   6420
agttgctatt ttctcaggcc gggcctaaca acatgtcggc tcaggccaag aactggctac   6480
ccggtccctg ctaccggcag caacgcgtct ccacgacact gtcgcagaac aacaacagca   6540
actttgcctg gacgggtgcc accaagtatc atctgaatgg cagagactct ctggtgaatc   6600
ctggcgttgc catggctacc cacaaggacg acgaagagcg atttttttcca tccagcggag   6660 tcttaatgtt tgggaaacag ggagctggaa aagacaacgt ggactatagc agcgtgatgc   6720
taaccagcga ggaagaaata aagaccacca acccagtggc cacagaacag tacggcgtgg   6780
tggccgataa cctgcaacag caaaacgccg ctcctattgt agggccgtc aatagtcaag   6840 gagccttacc tggcatggtg tggcagaacc gggacgtgta cctgcagggt cccatctggg   6900
ccaagattcc tcatacggac ggcaacttc atccctcgcc gctgatggga ggctttggac   6960
tgaagcatcc gcctcctcag atcctgatta aaaacacacc tgttcccgcg gatcctccga   7020
ccaccttcag ccaggccaag ctggcttctt tcatcacgca gtacagtacc ggccaggtca   7080
gcgtggagat cgagtgggag ctgcagaagg agaacagcaa acgctggaac ccagagattc   7140
agtacacttc caactactac aaatctacaa atgtggactt tgctgtcaat actgagggta   7200
cttattccga gcctcgcccc attggcaccc gttacctcac ccgtaatctg taattacatg   7260
ttaatcaata aaccggttaa ttcgtttcag ttgaactttg gtctcctgtc cttcttatct   7320
tatcggttac catagaaact ggttacttat taactgcttg gtgcgcttcg cgataaaaga   7380
cttacgtcat cgggttaccc ctagtgatgg agcggccgct ttcagttgaa ctttggtctc   7440
tgcgtatttc tttcttatct agtttccatg ctctagaggt cctgtattag aggtcacgtg   7500
agtgttttgc gacattttgc gacaccatgt ggtcacgctg gtatttaag cccgagtgag   7560 cacgcagggt ctccattttg aagcgggagg tttgaacgcg cagccgccaa gccgaattct   7620
gcagatatcc atcacactgg cggccgctcg actagagcgg ccgccaccgc ggtggagctc   7680
cagcttttgt tccctttagt gagggttaat tgcgcgcttg gcgtaatcat ggtcatagct   7740
```

```
gtttcctgtg tgaaattgtt atccgctcac aattccacac aacatacgag ccggaagcat    7800
aaagtgtaaa gcctggggtg cctaatgagt gagctaactc acattaattg cgttgcgctc    7860
actgcccgct ttccagtcgg gaaacctgtc gtgccagctg cattaatgaa tcggccaacg    7920
cgcggggaga ggcggtttgc gtattgggcg ctcttccgct tcctcgctca ctgactcgct    7980
gcgctcggtc gttcggctgc ggcgagcggt atcagctcac tcaaaggcgg taatacggtt    8040
atccacagaa tcaggggata acgcaggaaa gaacatgtga gcaaaaggcc agcaaaaggc    8100
caggaaccgt aaaaaggccg cgttgctggc gtttttccat aggctccgcc cccctgacga    8160
gcatcacaaa aatcgacgct caagtcagag gtggcgaaac ccgacaggac tataaagata    8220
ccaggcgttt ccccctggaa gctccctcgt gcgctctcct gttccgaccc tgccgcttac    8280
cggatacctg tccgcctttc tcccttcggg aagcgtggcg ctttctcata gctcacgctg    8340
taggtatctc agttcggtgt aggtcgttcg ctccaagctg ggctgtgtgc acgaaccccc    8400
cgttcagccc gaccgctgcg ccttatccgg taactatcgt cttgagtcca acccggtaag    8460
acacgactta tcgccactgg cagcagccac tggtaacagg attagcagag cgaggtatgt    8520
aggcggtgct acagagttct tgaagtggtg gcctaactac ggctacacta agaacagt     8580
atttggtatc tgcgctctgc tgaagccagt taccttcgga aaaagagttg gtagctcttg    8640
atccggcaaa caaccaccg ctggtagcgg tggtttttttt gtttgcaagc agcagattac    8700
gcgcagaaaa aaaggatctc aagaagatcc tttgatcttt tctacggggt ctgacgctca    8760
gtggaacgaa aactcacgtt aagggatttt ggtcatgaga ttatcaaaaa ggatcttcac    8820
ctagatcctt ttaaattaaa aatgaagttt taaatcaatc taaagtatat atgagtaaac    8880
ttggtctgac agttaccaat gcttaatcag tgaggcacct atctcagcga tctgtctatt    8940
tcgttcatcc atagttgcct gactccccgt cgtgtagata actacgatac gggagggctt    9000
accatctggc cccagtgctg caatgatacc gcgagaccca cgctcaccgg ctccagattt    9060
atcagcaata accagccag ccggaagggc cgagcgcaga agtggtcctg caactttatc    9120
cgcctccatc cagtctatta attgttgccg ggaagctaga gtaagtagtt cgccagttaa    9180
tagtttcgc aacgttgttg ccattgctac aggcatcgtg gtgtcacgct cgtcgtttgg    9240
tatggcttca ttcagctccg gttcccaacg atcaaggcga gttacatgat cccccatgtt    9300
gtgcaaaaaa gcggttagct ccttcggtcc tccgatcgtt gtcagaagta agttggccgc    9360
agtgttatca ctcatggtta tggcagcact gcataattct cttactgtca tgccatccgt    9420
aagatgcttt tctgtgactg gtgagtactc aaccaagtca ttctgagaat agtgtatgcg    9480
gcgaccgagt tgctcttgcc cggcgtcaat acgggataat accgcgccac atagcagaac    9540
tttaaaagtg ctcatcattg gaaaacgttc ttcggggcga aaactctcaa ggatcttacc    9600
gctgttgaga tccagttcga tgtaacccac tcgtgcaccc aactgatctt cagcatcttt    9660
tactttcacc agcgtttctg ggtgagcaaa aacaggaagg caaaatgccg caaaaaggg     9720
aataagggcg acacggaaat gttgaatact catactcttc ctttttcaat attattgaag    9780
catttatcag ggttattgtc tcatgagcgg atacatattt gaatgtattt agaaaaataa    9840
acaaataggg gttccgcgca catttccccg aaaagtgcca cctaaattgt aagcgttaat    9900
attttgttaa aattcgcgtt aaattttgt taaatcagct cattttttaa ccaataggcc    9960
gaaatcggca aaatccctta taaatcaaaa gaatagaccg agatagggtt gagtgttgtt   10020
ccagtttgga acaagagtcc actattaaag aacgtggact ccaacgtcaa agggcgaaaa   10080
accgtctatc agggcgatgg cccactacgt gaaccatcac cctaatcaag ttttttgggg   10140
```

```
tcgaggtgcc gtaaagcact aaatcggaac cctaaaggga gcccccgatt tagagcttga    10200
cggggaaagc cggcgaacgt ggcgagaaag gaagggaaga aagcgaaagg agcgggcgct    10260
agggcgctgg caagtgtagc ggtcacgctg cgcgtaacca ccacacccgc cgcgcttaat    10320
gcgccgctac agggcgcgtc ccattcgcca ttcaggctgc gcaactgttg ggaagggcga    10380
tcggtgcggg cctcttcgct attacgccag ctggcgaaag ggggatgtgc tgcaaggcga    10440
ttaagttggg taacgccagg gttttcccag tcacgacgtt gtaaaacgac ggccagtgag    10500
cgcgcgtaat acgactcact atagggcgaa ttgggtac                            10538

<210> SEQ ID NO 5
<211> LENGTH: 13859
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 5 cgggccccc ctcgaggtcg acggtatcgg gggagctcgc agggtctcca ttttgaagcg        60
ggaggtttga acgcgcagcc gccatgccgg ggttttacga gattgtgatt aaggtcccca       120
gcgaccttga cgagcatctg cccggcattt ctgacagctt tgtgaactgg gtggccgaga       180
aggaatggga gttgccgcca gattctgaca tggatctgaa tctgattgag caggcacccc       240
tgaccgtggc cgagaagctg cagcgcgact tctgacggga atggcgccgt gtgagtaagg       300
ccccggaggc tcttttcttt gtgcaatttg agaagggaga gagctacttc cacatgcacg       360
tgctcgtgga aaccaccggg gtgaaatcca tggttttggg acgtttcctg agtcagattc       420
gcgaaaaact gattcagaga atttaccgcg ggatcgagcc gactttgcca aactggttcg       480
cggtcacaaa gaccagaaat ggcgccgag gcgggaacaa ggtggtggat gagtgctaca       540
tccccaatta cttgctcccc aaaacccagc ctgagctcca gtgggcgtgg actaatatgg       600
aacagtattt aagcgcctgt ttgaatctca cggagcgtaa acggttggtg gcgcagcatc       660
tgacgcacgt gtcgcagacg caggagcaga acaaagagaa tcagaatccc aattctgatg       720
cgccggtgat cagatcaaaa acttcagcca ggtacatgga gctggtcggg tggctcgtgg       780 acaagggat tacctcggag aagcagtgga tccaggtgag taattgacaa agccaaacac       840
caccatttgc cgagcacttt agagtttaca ggtttgtttc tcttgaccct caaaacaaac       900
ctgtgaggca tagggagtat tgctatccct taagaattca ccccagtgt gcccatcaaa       960 acctcccagg ctgagtctgc acagttgaag gaggaaggat aggaatggga gggtcgatgg      1020
gtgaaagcat gattctctta accagtccag attatcaggt aatccttca acaaccacca      1080 cccactccct gggcaatcca gctggagttt acagacagac ttagctggct atagcaccac      1140
cgtgctactc tctgttcttc ctggttgctc aaatgcccta gaaaagtgga acaggtgagc      1200
atcaactcac agggctctat gctggctgct gctgcgaggg atgttatgct atagtaccag      1260
gggccaccat tccataggca cttcctgtgt ttaataccct atatgcttta cttcatctca      1320
tcttcctcca tatcctgaga ggtggttcta ttcttctccc cattttacgg atgaaaaaac      1380
cgagacacag aaaggtgaaa tagcttaaga taaatggtgc cttgcagcct tagactctgg      1440
tggcctctag ttaatgtggg aaattaaggg tgagggatt ggcagctgat ggagggtgca      1500
gggtgccaga cagaggcgtt tagctctgat cccttagcaa tagagagtcc ttgtaggcac      1560
```

```
ttggtcaggc gagtgatgcg atgaaagctg tgtttaagaa agattatgct ttctgctgat    1620
ttcatacccc caacacccaa gctctgaggc ccctcctcac aggtccttgc agggctggcc    1680
aaaataaagc agcttcactc cgttgtgctg cttttccagct aatgtgtctg tttggcagaa    1740
gtttccctca aaggcagatc agtgaaataa gcagaagcct cgaccccctc ttgtcagcca    1800
gagctgctga agtgccttgc cccagggtca ctttgtgtga ggggattaga gagcactggg    1860
gctgccaaga aacactgccg tttctacaga ttagcaggac gctggcttgt ggccttctag    1920
cgaggctcag agctgcggtg gccctagtct gcatgggcta aagacaagct ccatctcctg    1980
tccttgttcc ctccttcctg ggcacagccg ccctgcttct tggttctctc tgttggttcc    2040
tgtccgcacg gtagttaggc tggcagcgtg tgtaggattt ggcttagaag attgacaaca    2100
ttgccttttga gcccttcttt gctactcctc cctctcccct cccatcagac tcctctctgg    2160
agtctgctct gcgaggcctc tgctctgtgg tatcccagca gccttctcag ccttgacttc    2220
cagaaggggg ctgtgcagtg tccggggtgt gcaggcccca gacacggggt aggctcatgg    2280
agatccaagt gctgatctag tgtcaaggct ggcctggaga ctgggctggg ttggtgtctg    2340
cctgctgtgg tcatgtgccc tcccttgggc ctgtatcctc tctccagact tgctgcaggg    2400
agaggtggca gatgtcagcc tagttctggc ctctcagagc agcatggcag ctccctttca    2460
ctcaggccca ggctgggccc tcctgctggc tgaccctggg ggagagggtg ctccagagct    2520
ccccaaggaa cagcttcccg aagcagccag gccagcccag aggggctgtg gccaatcctg    2580
aagctttatg ttcctgctga catttttct aagttttctc ttgctttcct cttaaatgcc    2640
aatctggaga gtccgtta ggagaaatgg accccagcca ggaagaagag ttgagttgta    2700
tttaaaacac gagctccccc taaagcatcc ttctttagct tctaaggaga ggcagagact    2760
gacaggcagg actcagcagg aaaaggtacc ccctgacct gctcagtcag gcctaggcc    2820
cagctccacc cagcctgtgg cccccagagt ttcggtaaag agttccctgg gccttaagga    2880
accttgagag agcatttgag gggtgccacc acaaacttgg cagaaaaaac cctcccctc    2940
caagtccagt cctagagaag gagctggcaa ccttgccttg ctttgtaagc aaaagcctct    3000
tagggcttga gctcagatgt agtgtttgag ctgtggctgg tgccctgccc catcaggag    3060
ccaatggtag acatcctatg ggcatctttg ttttccgtaa gagcaggctg tctggggatg    3120
ggccagagga agaggcgacc tggagtcaac caagaggagg ccttaaccaa gccttaacca    3180
cagaggttaa ccaagccttg aaagcgcttc cccctgagca ggcaggaagc actgagtcca    3240
catggttgcc tcgctgtttc atttccttac actcaattct ctcagtcttt aaatgatcac    3300
ttggccttga agttacggat atttggggtc tgaactgaag ttgaagaaaa gaggaaatga    3360
tttaagcttt gtttaagatt aggggccagg tgcggtggct cacgcctgta atcccagcac    3420
cttgggagcc tgaggcgggt ggatcacctg aggtcaggag ttccagacca gcctggccaa    3480
catagcaaaa cccagtctct actaaaaata acaataaaaa aattagccag gtgtggtgac    3540
acatgcctgt aatcccagtt actcaggagg ctgaggcaga attgcttgaa cttgagaggt    3600
ggaggttgta gtgagccaag accgcaccac tgcactccag cctggcgaca gagccagact    3660
ccgtctcaaa aacaacaaca aaaaagatta gaagaagccc attactgcct tctgccacc    3720
cactcgcaca gacaccaaaa ctgcagccca cacctcgcca tcctcgtgct ctgccctggg    3780
acacccagg cacagtgtgt ccttcgtttt ctgtaagggt gggctgggag cagggacgga    3840
cagggcctgt gggcacctct catggtcact tccttcttgc tcacaggagg accaggcctc    3900
atacatctcc ttcaatgcgg cctccaactc gcggtcccaa atcaaggctg ccttggacaa    3960
```

```
tgcgggaaag attatgagcc tgactaaaac cgcccccgac tacctggtgg gccagcagcc    4020
cgtggaggac atttccagca atcggattta taaaattttg gaactaaacg ggtacgatcc    4080
ccaatatgcg gcttccgtct ttctgggatg ggccacgaaa aagttcggca agaggaacac    4140
catctggctg tttgggcctg caactaccgg gaagaccaac atcgcggagg ccatagccca    4200
cactgtgccc ttctacgggt gcgtaaactg gaccaatgag aactttccct tcaacgactg    4260
tgtcgacaag atggtgatct ggtgggagga ggggaagatg accgccaagg tcgtggagtc    4320
ggccaaagcc attctcggag gaagcaaggt gcgcgtggac cagaaatgca agtcctcggc    4380
ccagatagac ccgactcccg tgatcgtcac ctccaacacc aacatgtgcg ccgtgattga    4440
cgggaactca acgaccttcg aacaccagca gccgttgcaa gaccggatgt tcaaatttga    4500
actcacccgc cgtctggatc atgactttgg gaaggtcacc aagcaggaag tcaaagactt    4560
tttccggtgg gcaaaggatc acgtggttga ggtggagcat gaattctacg tcaaaaaggg    4620
tggagccaag aaaagacccg cccccagtga cgcagatata agtgagccca aacgggtgcg    4680
cgagtcagtt gcgcagccat cgacgtcaga cgcggaagct tcgatcaact acgcagacag    4740
gtaccaaaac aaatgttctc gtcacgtggg catgaatctg atgctgtttc cctgcagaca    4800
atgcgagaga atgaatcaga attcaaatat ctgcttcact cacggacaga aagactgttt    4860
agagtgcttt cccgtgtcag aatctcaacc cgtttctgtc gtcaaaaagg cgtatcagaa    4920
actgtgctac attcatcata tcatgggaaa ggtgccagac gcttgcactg cctgcgatct    4980
ggtcaatgtg gatttggatg actgcatctt tgaacaataa atgatttaaa tcaggtctgg    5040
ctgccgatgg ttatcttcca gattggctcg aggacaacct ctctgagggc attcgcgagt    5100
ggtgggacct gaaacctgga gccccgaaac ccaaagccaa ccagcaaaag caggacaacg    5160
gccggggtct ggtgcttcct ggctacaagt acctcggacc cttcaacgga ctcgacaagg    5220
gggagcccgt caacgcggcg gacgcagcgg ccctcgagca cgacaaggcc tacgaccagc    5280
agctccaagc gggtgacaat ccgtacctgc ggtataatca cgccgacgcc gagtttcagg    5340
agcgtctgca agaagatacg tcttttgggg gcaacctcgg gcgcgcagtc ttccaggcca    5400
aaaagcgggt tctcgaacct ctgggcctgg ttgaatcgcc ggttaagatg gctagcggaa    5460
ctagcggcgg taggcgtgta cggtgggagg tctatataag cagagctctc tggctaacta    5520
ccggtgccac catggcccca aagaagaagc ggaaggtcgg tatccacgga gtcccagcag    5580
ccaagcggaa ctacatcctg ggcctggaca tcggcatcac cagcgtgggc tacggcatca    5640
tcgactacga gacacgggac gtgatcgatg ccggcgtgcg gctgttcaaa gaggccaacg    5700
tggaaaacaa cgagggcagg cggagcaaga gaggcgccag aaggctgaag cggcggaggc    5760
ggcatagaat ccagagagtg aagaagctgc tgttcgacta caacctgctg accgaccaca    5820
gcgagctgag cggcatcaac ccctacgagg ccagagtgaa gggcctgagc cagaagctga    5880
gcgaggaaga gttctctgcc gccctgctgc acctggccaa gagaagaggc gtgcacaacg    5940
tgaacgaggt ggaagaggac accggcaacg agctgtccac caaagagcag atcagccgga    6000
acagcaaggc cctggaagag aaatacgtgg ccgaactgca gctggaacgg ctgaagaaag    6060
acggcgaagt gcggggcagc atcaacagat tcaagaccag cgactacgtg aaagaagcca    6120
aacagctgct gaaggtgcag aaggcctacc accagctgga ccagagcttc atcgacacct    6180
acatcgacct gctggaaacc cggcggacct actatgaggg acctggcgag ggcagccctg    6240
tcggctggaa ggacatcaaa gaatggtacg agatgctgat gggccactgc acctacttcc    6300
```

```
ccgaggaact gcggagcgtg aagtacgcct acaacgccga cctgtacaac gccctgaacg   6360
acctgaacaa tctcgtgatc accagggacg agaacgagaa gctggaatat tacgagaagt   6420
tccagatcat cgagaacgtg ttcaagcaga agaagaagcc caccctgaag cagatcgcca   6480
aagaaatcct cgtgaacgaa gaggatatta agggctacag agtgaccagc accggcaagc   6540
ccgagttcac caacctgaag gtgtaccacg acatcaagga cattaccgcc cggaaagaga   6600
ttattgagaa cgccgagctg ctggatcaga ttgccaagat cctgaccatc taccagagca   6660
gcgaggacat ccaggaagaa ctgaccaatc tgaactccga gctgacccag aagagatcg    6720 agcagatctc taatctgaag gctataccg gcacccacaa cctgagcctg aaggccatca    6780
acctgatcct ggacgagctg tggcacacca acgacaacca gatcgctatc ttcaaccggc   6840
tgaagctggt gcccaagaag gtggacctgt cccagcagaa agagatcccc accaccctgg   6900
tggacgactt catcctgagc cccgtcgtga agagaagctt catccagagc atcaaagtga   6960
tcaacgccat catcaagaag tacgcctgc ccaacgacat cattatcgag ctggcccgcg     7020
agaagaactc caaggacgcc cagaaaatga tcaacgagat gcagaagcgg aaccggcaga   7080
ccaacgagcg gatcgaggaa atcatccgga ccaccggcaa agagaacgcc aagtacctga   7140
tcgagaagat caagctgcac gacatgcagg aaggcaagtg cctgtacagc ctggaagcca   7200
tccctctgga agatctgctg aacaacccct tcaactatga ggtggaccac atcatcccca   7260
gaagcgtgtc cttcgacaac agcttcaaca acaaggtgct cgtgaagcag gaagaaaaca   7320
gcaagaaggg caaccggacc ccattccagt acctgagcag cagcgacagc aagatcagct   7380
acgaaacctt caagaagcac atcctgaatc tggccaaggg caagggcaga atcagcaaga   7440
ccaagaaaga gtatctgctg gaagaacggg acatcaacag gttctccgtg cagaaagact   7500
tcatcaaccg gaacctggtg gataccagat acgccaccag aggcctgatg aacctgctgc   7560
ggagctactt cagagtgaac aacctggacg tgaaagtgaa gtccatcaat ggcggcttca   7620 ccagcttct gcggcggaag tgaagtttta agaagagcg gaacaagggg tacaagcacc    7680
acgccgagga cgccctgatc attgccaacg ccgatttcat cttcaaagag tggaagaaac   7740
tggacaaggc caaaaaagtg atggaaaacc agatgttcga ggaaaagcag gccgagagca   7800
tgcccgagat cgaaaccgag caggagtaca agagatctt catcaccccc caccagatca    7860
agcacattaa ggacttcaag gactacaagt acagccaccg ggtggacaag aagcctaata   7920
gagagctgat taacgacacc ctgtactcca cccggaagga cgacaagggc aacaccctga   7980
tcgtgaacaa tctgaacggc ctgtacgaca aggacaatga caagctgaaa aagctgatca   8040
acaagagccc cgaaaagctg ctgatgtacc accacgaccc ccagacctac cagaaactga   8100
agctgattat ggaacagtac ggcgacgaga agaatcccct gtacaagtac tacgaggaaa   8160
ccgggaacta cctgaccaag tactccaaaa aggacaacgg ccccgtgatc aagaagatta   8220
agtattacgg caacaaactg aacgcccatc tggacatcac cgacgactac cccaacagca   8280
gaaacaaggt cgtgaagctg tccctgaagc cctacagatt cgacgtgtac ctggacaatg   8340
gcgtgtacaa gttcgtgacc gtgaagaatc tggatgtgat caaaaaagaa aactactacg   8400
aagtgaatag caagtgctat gaggaagcta agaagctgaa gaagatcagc aaccaggccg   8460
agtttatcgc ctccttctac aacaacgatc tgatcaagat caacggcgag ctgtatagag   8520
tgatcggcgt gaacaacgac ctgctgaacc ggatcgaagt gaacatgatc gacatcaccc   8580
accgcgagta cctggaaaac atgaacgaca agaggccccc caggatcatt aagacaatcg   8640
cctccaagac ccagagcatt aagaagtaca gcacagacat tctgggcaac ctgtatgaag   8700
```

```
tgaaatctaa gaagcaccct cagatcatca aaaagggcag cggcttcgcc aacgagctgg   8760
gccctagact gatgggaaag actagtagac cggtagagcc atcacccag cgctctccag    8820 actcctctac gggcatcggc aagaaaggcc agcagcccgc aaaaaagaga ctcaattttg   8880
ggcagactgg cgactcagag tcagtccccg accctcaacc aatcggagaa ccaccagcag   8940
gcccctctgg tctgggatct ggtacactgg ctgcaggcgg tggcgctcca ctggcagaca   9000
ataacgaagg cgccgacgga gtgggtagtt cctcaggaaa ttggcattgc gattccacat   9060
ggctgggcga cagagtcatc accaccagca cccgcacctg ggccctgccc acctacaaca   9120
accacctcta caagcaaatc tccaacggga cctcggagg aagcaccaac gacaacacct    9180
acttcggcta cagcaccccc tggggtatt ttgacttcaa cagattccac tgccactttt    9240
caccacgtga ctggcagcga ctcatcaaca acaactgggg attccggccc aagaggctca   9300
acttcaagct cttcaacatc caagtcaagg aggtcacgca gaatgaaggc accaagacca   9360
tcgccaataa ccttaccagc acgattcagg tctttacgga ctcggaatac cagctcccgt   9420
acgtgctcgg ctcggcgcac cagggctgcc tgcctccgtt cccggcggac gtcttcatga   9480
ttcctcagta cgggtacctg actctgaaca atggcagtca ggctgtgggc cggtcgtcct   9540
tctactgcct ggagtacttt ccttctcaaa tgctgagaac gggcaacaac tttgaattca   9600
gctacaactt cgaggacgtg cccttccaca gcagctacgc gcacagccag agcctggacc   9660
ggctgatgaa ccctctcatc gaccagtact tgtactacct gtcccggact caaagcacgg   9720
gcggtactgc aggaactcag cagttgctat tttctcaggc cgggcctaac aacatgtcgg   9780
ctcaggccaa gaactggcta cccggtccct gctaccggca gcaacgcgtc tccacgacac   9840
tgtcgcagaa caacaacagc aactttgcct ggacgggtgc caccaagtat catctgaatg   9900
gcagagactc tctggtgaat cctggcgttg ccatggctac ccacaaggac gacgaagagc   9960
gattttttcc atccagcgga gtcttaatgt ttgggaaaca gggagctgga aaagacaacg   10020
tggactatag cagcgtgatg ctaaccagcg aggaagaaat aaagaccacc aacccagtgg   10080
ccacagaaca gtacgcgtg gtggccgata acctgcaaca gcaaaacgcc gctcctattg    10140
taggggccgt caatagtcaa ggagccttac ctggcatggt gtggcagaac cgggacgtgt   10200
acctgcaggg tcccatctgg gccaagattc ctcatacgga cggcaacttt catccctcgc   10260
cgctgatggg aggctttgga ctgaagcatc cgcctcctca gatcctgatt aaaaacacac   10320 tgttcccgc ggatcctccg accaccttca gccaggccaa gctggcttct ttcatcacgc    10380
agtacagtac cggccaggtc agcgtggaga tcgagtggga gctgcagaag gagaacagca   10440
aacgctggaa cccagagatt cagtacactt ccaactacta caaatctaca aatgtggact   10500 tgctgtcaa tactgagggt acttattccg agcctcgccc cattggcacc cgttacctca    10560
cccgtaatct gtaattacat gttaatcaat aaaccggtta attcgtttca gttgaacttt   10620
ggtctcctgt ccttcttatc ttatcggtta ccatagaaac tggttactta ttaactgctt   10680
ggtgcgcttc gcgataaaag acttacgtca tcgggttacc cctagtgatg gagcggccgc   10740
tttcagttga actttggtct ctgcgtattt ctttcttatc tagtttccat gctctagagg   10800
tcctgtatta gaggtcacgt gagtgttttg cgacattttg cgacaccatg tggtcacgct   10860
gggtatttaa gcccgagtga gcacgcaggg tctccatttt gaagcgggag gtttgaacgc   10920
gcagccgcca agccgaattc tgcagatatc catcacactg gcggccgctc gactagagcg   10980
gccgccaccg cggtggagct ccagcttttg ttccctttag tgagggttaa ttgcgcgctt   11040
```

```
ggcgtaatca tggtcatagc tgtttcctgt gtgaaattgt tatccgctca caattccaca   11100
caacatacga gccggaagca taaagtgtaa agcctgggt gcctaatgag tgagctaact    11160
cacattaatt gcgttgcgct cactgcccgc tttccagtcg ggaaacctgt cgtgccagct   11220
gcattaatga atcggccaac gcgcggggag aggcggtttg cgtattgggc gctcttccgc   11280
ttcctcgctc actgactcgc tgcgctcggt cgttcggctg cggcgagcgg tatcagctca   11340
ctcaaaggcg gtaatacggt tatccacaga atcaggggat aacgcaggaa agaacatgtg   11400
agcaaaaggc cagcaaaagg ccaggaaccg taaaaaggcc gcgttgctgg cgtttttcca   11460
taggctccgc cccctgacg agcatcacaa aaatcgacgc tcaagtcaga ggtggcgaaa    11520
cccgacagga ctataaagat accaggcgtt tcccctgga agctccctcg tgcgctctcc    11580
tgttccgacc ctgccgctta ccggatacct gtccgccttt ctcccttcgg aagcgtggc    11640
gctttctcat agctcacgct gtaggtatct cagttcggtg taggtcgttc gctccaagct   11700
gggctgtgtg cacgaacccc cgttcagcc cgaccgctgc gccttatccg gtaactatcg    11760
tcttgagtcc aacccggtaa gacacgactt atcgccactg gcagcagcca ctggtaacag   11820
gattagcaga gcgaggtatg taggcggtgc tacagagttc ttgaagtggt ggcctaacta   11880
cggctacact agaagaacag tatttggtat ctgcgctctg ctgaagccag ttaccttcgg   11940
aaaaagagtt ggtagctctt gatccggcaa acaaaccacc gctggtagcg gtggtttttt   12000
tgtttgcaag cagcagatta cgcgcagaaa aaaggatct caagaagatc ctttgatctt    12060
ttctacgggg tctgacgctc agtggaacga aaactcacgt taagggattt tggtcatgag   12120
attatcaaaa aggatcttca cctagatcct tttaaattaa aaatgaagtt ttaaatcaat   12180
ctaaagtata tatgagtaaa cttggtctga cagttaccaa tgcttaatca gtgaggcacc   12240
tatctcagcg atctgtctat ttcgttcatc catagttgcc tgactccccg tcgtgtagat   12300
aactacgata cgggagggct taccatctgg ccccagtgct gcaatgatac cgcgagaccc   12360
acgctcaccg gctccagatt tatcagcaat aaaccagcca gccggaaggg ccgagcgcag   12420
aagtggtcct gcaactttat ccgcctccat ccagtctatt aattgttgcc gggaagctag   12480
agtaagtagt tcgccagtta atagtttgcg caacgttgtt gccattgcta caggcatcgt   12540
ggtgtcacgc tcgtcgtttg gtatggcttc attcagctcc ggttcccaac gatcaaggcg   12600
agttacatga tcccccatgt tgtgcaaaaa agcggttagc tccttcggtc ctccgatcgt   12660
tgtcagaagt aagttggccg cagtgttatc actcatggtt atggcagcac tgcataattc   12720
tcttactgtc atgccatccg taagatgctt ttctgtgact ggtgagtact caaccaagtc   12780
attctgagaa tagtgtatgc ggcgaccgag ttgctcttgc ccggcgtcaa tacgggataa   12840
taccgcgcca catagcagaa ctttaaaagt gctcatcatt ggaaaacgtt cttcggggcg   12900
aaaactctca aggatcttac cgctgttgag atccagttcg atgtaaccca ctcgtgcacc   12960
caactgatct tcagcatctt ttactttcac cagcgtttct gggtgagcaa aaacaggaag   13020
gcaaaatgcc gcaaaaaagg gaataagggc gacacggaaa tgttgaatac tcatactctt   13080
cctttttcaa tattattgaa gcatttatca gggttattgt ctcatgagcg gatacatatt   13140
tgaatgtatt tagaaaaata aacaaatagg ggttccgcgc acatttcccc gaaaagtgcc   13200
acctaaattg taagcgttaa tattttgtta aaattcgcgt taaattttg ttaaatcagc    13260
tcatttttta accaataggc cgaaatcggc aaaatccctt ataaatcaaa agaatagacc   13320
gagatagggt tgagtgttgt tccagtttgg aacaagagtc cactattaaa gaacgtggac   13380
tccaacgtca aagggcgaaa aaccgtctat cagggcgatg gcccactacg tgaaccatca   13440
```

-continued

```
ccctaatcaa gttttttggg gtcgaggtgc cgtaaagcac taaatcggaa ccctaaaggg    13500
agcccccgat ttagagcttg acggggaaag ccggcgaacg tggcgagaaa ggaagggaag    13560
aaagcgaaag gagcgggcgc tagggcgctg gcaagtgtag cggtcacgct gcgcgtaacc    13620
accacacccg ccgcgcttaa tgcgccgcta cagggcgcgt cccattcgcc attcaggctg    13680
cgcaactgtt gggaagggcg atcggtgcgg gcctcttcgc tattacgcca gctggcgaaa    13740
gggggatgtg ctgcaaggcg attaagttgg gtaacgccag ggttttccca gtcacgacgt    13800
tgtaaaacga cggccagtga gcgcgcgtaa tacgactcac tatagggcga attgggtac     13859
```

<210> SEQ ID NO 6
<211> LENGTH: 11635
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 6

```
ggtacccaac tccatgctta acagtcccca ggtacagccc accctgcgtc gcaaccagga      60
acagctctac agcttcctgg agcgccactc gccctacttc cgcagccaca gtgcgcagat     120
taggagcgcc acttcttttt gtcacttgaa aaacatgtaa aaataatgta ctaggagaca     180
ctttcaataa aggcaaatgt ttttatttgt acactctcgg gtgattattt accccccacc     240
cttgccgtct gcgccgttta aaaatcaaag gggttctgcc gcgcatcgct atgcgccact     300
ggcagggaca cgttgcgata ctggtgttta gtgctccact taaactcagg cacaaccatc     360
cgcggcagct cggtgaagtt ttcactccac aggctgcgca ccatcaccaa cgcgtttagc     420
aggtcgggcg ccgatatctt gaagtcgcag ttggggcctc cgccctgcgc gcgcgagttg     480
cgatacacag ggttgcagca ctggaacact atcagcgccg ggtggtgcac gctggccagc     540
acgctcttgt cggagatcag atccgcgtcc aggtcctccg cgttgctcag ggcgaacgga     600
gtcaactttg gtagctgcct tcccaaaaag ggtgcatgcc caggctttga gttgcactcg     660
caccgtagtg gcatcagaag gtgaccgtgc ccggtctggg cgttaggata cagcgcctgc     720
atgaaagcct tgatctgctt aaaagccacc tgagcctttg cgccttcaga gaagaacatg     780
ccgcaagact tgccggaaaa ctgattggcc ggacaggccg cgtcatgcac gcagcacctt     840
gcgtcggtgt tggagatctg caccacattt cggccccacc ggttcttcac gatcttggcc     900
ttgctagact gctccttcag cgcgcgctgc ccgttttcgc tcgtcacatc catttcaatc     960
acgtgctcct tatttatcat aatgctcccg tgtagacact taagctcgcc ttcgatctca    1020
gcgcagcggt gcagccacaa cgcgcagccc gtgggctcgt ggtgcttgta ggttacctct    1080
gcaaacgact gcaggtacgc ctgcaggaat cgccccatca tcgtcacaaa ggtcttgttg    1140
ctggtgaagg tcagctgcaa cccgcggtgc tcctcgttta gccaggtctt gcatacggcc    1200
gccagagctt ccacttggtc aggcagtagc ttgaagtttg cctttagatc gttatccacg    1260
tggtacttgt ccatcaacgc gcgcgcagcc tccatgccct tctcccacgc agacacgatc    1320
ggcaggctca gcgggtttat caccgtgctt tcactttccg cttcactgga ctcttccttt    1380
tcctcttgcg tccgcatacc ccgcgccact gggtcgtctt cattcagccg ccgcaccgtg    1440
cgcttacctc ccttgccgtg cttgattagc accggtgggt tgctgaaacc caccatttgt    1500
agcgccacat cttctctttc ttcctcgctg tccacgatca cctctgggga tggcgggcgc    1560
```

-continued

```
tcgggcttgg gagaggggcg cttctttttc tttttggacg caatggccaa atccgccgtc    1620
gaggtcgatg gccgcgggct gggtgtgcgc ggcaccagcg catcttgtga cgagtcttct    1680
tcgtcctcgg actcgagacg ccgcctcagc cgcttttttg ggggcgcgcg gggaggcggc    1740
ggcgacggcg acgggacga cacgtcctcc atggttggtg gacgtcgcgc cgcaccgcgt    1800
ccgcgctcgg gggtggtttc gcgctgctcc tcttcccgac tggccatttc cttctcctat    1860
aggcagaaaa agatcatgga gtcagtcgag aaggaggaca gcctaaccgc cccctttgag    1920
ttcgccacca ccgcctccac cgatgccgcc aacgcgccta ccaccttccc cgtcgaggca    1980
cccccgcttg aggaggagga agtgattatc gagcaggacc caggttttgt aagcgaagac    2040
gacgaggatc gctcagtacc aacagaggat aaaaagcaag accaggacga cgcagaggca    2100
aacgaggaac aagtcgggcg gggggaccaa aggcatggcg actacctaga tgtgggagac    2160
gacgtgctgt tgaagcatct gcagcgccag tgcgccatta tctgcgacgc gttgcaagag    2220
cgcagcgatg tgcccctcgc catagcggat gtcagccttg cctacgaacg ccacctgttc    2280
tcaccgcgcg tacccccaa cgccaagaa acggcacat gcgagcccaa cccgcgcctc    2340
aacttctacc ccgtatttgc cgtgccagag gtgcttgcca cctatcacat cttttttccaa    2400 aactgcaaga taccccctatc ctgccgtgcc aaccgcagcc gagcggacaa gcagctggcc    2460
ttgcggcagg gcgctgtcat acctgatatc gcctcgctcg acgaagtgcc aaaaatcttt    2520
gagggtcttg gacgcgacga gaaacgcgcg gcaaacgctc tgcaacaaga aaacagcgaa    2580
aatgaaagtc actgtggagt gctggtggaa cttgagggtg acaacgcgcg cctagccgtg    2640
ctgaaacgca gcatcgaggt cacccacttt gcctacccgg cacttaacct accccccaag    2700
gttatgagca cagtcatgag cgagctgatc gtgcgccgtg cacgaccct ggagagggat    2760 gcaaacttgc aagaacaaac cgaggagggc ctacccgcag ttggcgatga gcagctggcg    2820
cgctggcttg agacgcgcga gcctgccgac ttggaggagc gacgcaagct aatgatggcc    2880
gcagtgcttg ttaccgtgga gcttgagtgc atgcagcggt tctttgctga cccgagatg    2940 cagcgcaagc tagaggaaac gttgcactac acctttcgcc agggctacgt gcgccaggcc    3000
tgcaaaattt ccaacgtgga gctctgcaac ctggtctcct accttggaat tttgcacgaa    3060
aaccgcctcg ggcaaaacgt gcttcattcc acgctcaagg gcgaggcgcg ccgcgactac    3120
gtccgcgact gcgtttactt atttctgtgc tacacctggc aaacggccat gggcgtgtgg    3180
cagcaatgcc tggaggagcg caacctaaag gagctgcaga agctgctaaa gcaaaacttg    3240
aaggacctat ggacggcctt caacgagcgc tccgtggccg cgcacctggc ggacattatc    3300
ttccccgaac gcctgcttaa aaccctgcaa cagggtctgc cagacttcac cagtcaaagc    3360
atgttgcaaa actttaggaa ctttatccta gagcgttcag gaattctgcc cgccacctgc    3420
tgtgcgcttc ctagcgactt tgtgcccatt aagtaccgtg aatgccctcc gccgctttgg    3480
ggtcactgct accttctgca gctagccaac taccttgcct accactccga catcatggaa    3540
gacgtgagcg gtgacggcct actggagtgt cactgtcgct gcaacctatg cacccgcac    3600 cgctccctgg tctgcaattc gcaactgctt agcgaaagtc aaattatcgg tacctttgag    3660
ctgcagggtc cctcgcctga cgaaaagtcc gcggctccgg ggttgaaact cactccgggg    3720
ctgtggacgt cggcttacct tcgcaaattt gtacctgagg actaccacgc ccacgagatt    3780
aggttctacg aagaccaatc ccgcccgcca aatgcggagc ttaccgcctg cgtcattacc    3840
cagggccaca tccttggcca attgcaagcc atcaacaaag cccgcaagaa gtttctgcta    3900
cgaaagggac gggggggttta cctggacccc cagtccggcg aggagctcaa cccaatcccc    3960
```

| | |
|---|---|
| ccgccgccgc agccctatca gcagccgcgg gcccttgctt cccaggatgg cacccaaaaa | 4020 |
| gaagctgcag ctgccgccgc cgccaccac ggacgaggag gaatactggg acagtcaggc | 4080 |
| agaggaggtt ttggacgagg aggaggagat gatggaagac tgggacagcc tagacgaagc | 4140 |
| ttccgaggcc gaagaggtgt cagacgaaac accgtcaccc tcggtcgcat tcccctcgcc | 4200 |
| ggcgcccag aaattggcaa ccgttcccag catcgctaca acctccgctc ctcaggcgcc | 4260 |
| gccggcactg cctgttcgcc gacccaaccg tagatgggac accactggaa ccagggccgg | 4320 |
| taagtctaag cagccgccgc cgttagccca agagcaacaa cagcgccaag gctaccgctc | 4380 |
| gtggcgcggg cacaagaacg ccatagttgc ttgcttgcaa gactgtgggg gcaacatctc | 4440 |
| cttcgcccgc cgctttcttc tctaccatca cggcgtggcc ttcccccgta acatcctgca | 4500 |
| ttactaccgt catctctaca gcccctactg caccggcggc agcggcagcg gcagcaacag | 4560 |
| cagcggtcac acagaagcaa aggcgaccgg atagcaagac tctgacaaag cccaagaaat | 4620 |
| ccacagcggc ggcagcagca ggaggaggag cgctgcgtct ggcgcccaac gaacccgtat | 4680 |
| cgaccgcga gcttagaaat aggattttc ccactctgta tgctatattt caacaaagca | 4740 |
| ggggccaaga acaagagctg aaaataaaaa acaggtctct cgcgctccctc acccgcagct | 4800 |
| gcctgtatca caaaagcgaa gatcagcttc ggcgcacgct ggaagacgcg gaggctctct | 4860 |
| tcagcaaata ctgcgcgctg actcttaagg actagtttcg cgccctttct caaatttaag | 4920 |
| cgcgaaaact acgtcatctc cagcggccac accggcgcc agcacctgtc gtcagcgcca | 4980 |
| ttatgagcaa ggaaattccc acgccctaca tgtggagtta ccagccacaa atgggacttg | 5040 |
| cggctggagc tgcccaagac tactcaaccc gaataaacta catgagcgcg ggaccccaca | 5100 |
| tgatatcccg ggtcaacgga atccgcgccc accgaaaccg aattctcctc gaacaggcgg | 5160 |
| ctattaccac cacacctcgt aataaccta atccccgtag ttggcccgct gccctggtgt | 5220 |
| accaggaaag tcccgctccc accactgtgg tacttcccag agacgcccag gccgaagttc | 5280 |
| agatgactaa ctcaggggcg cagcttgcgg gcggcttcg tcacagggtg cggtcgcccg | 5340 |
| ggcgttttag ggcggagtaa cttgcatgta ttgggaattg tagtttttt aaaatgggaa | 5400 |
| gtgacgtatc gtgggaaaac ggaagtgaag atttgaggaa gttgtgggtt ttttggcttt | 5460 |
| cgtttctggg cgtaggttcg cgtgcggttt tctgggtgtt ttttgtggac tttaaccgtt | 5520 |
| acgtcatttt ttagtcctat atatactcgc tctgtacttg gccctttta cactgtgact | 5580 |
| gattgagctg gtgccgtgtc gagtggtgtt tttaatagg ttttttttact ggtaaggctg | 5640 |
| actgttatgg ctgccgctgt ggaagcgctg tatgttgttc tggagcggga gggtgctatt | 5700 |
| ttgcctaggc aggagggttt ttcaggtgtt tatgtgtttt tctctcctat taattttgtt | 5760 |
| atacctccta tggggctgt aatgttgtct ctacgcctgc gggtatgtat tccccgggc | 5820 |
| tatttcggtc gctttttagc actgaccgat gttaaccaac ctgatgtgtt taccgagtct | 5880 |
| tacattatga ctccggacat gaccgaggaa ctgtcggtgg tgcttttaa tcacggtgac | 5940 |
| cagttttttt acggtcacgc cggcatggcc gtagtccgtc ttatgcttat aagggttgtt | 6000 |
| tttcctgttg taagacaggc ttctaatgtt taaatgtttt ttttttgtt attttatttt | 6060 |
| gtgtttaatg caggaacccg cagacatgtt tgagagaaaa atggtgtctt tttctgtggt | 6120 |
| ggttccggaa cttacctgcc tttatctgca tgagcatgac tacgatgtgc ttgcttttt | 6180 |
| gcgcgaggct ttgcctgatt ttttgagcag caccttgcat tttatatcgc cgcccatgca | 6240 |
| acaagcttac ataggggcta cgctggttag catagctccg agtatgcgtg tcataatcag | 6300 |

```
tgtgggttct tttgtcatgg ttcctggcgg ggaagtggcc gcgctggtcc gtgcagacct    6360
gcacgattat gttcagctgg ccctgcgaag ggacctacgg gatcgcggta tttttgttaa    6420
tgttccgctt ttgaatctta tacaggtctg tgaggaacct gaattttttgc aatcatgatt   6480 cgctgcttga ggctgaaggt ggagggcgct ctggagcaga ttttttacaat ggccggactt   6540 aatattcggg atttgcttag agacatattg ataaggtggc gagatgaaaa ttatttgggc    6600
atggttgaag gtgctggaat gtttatagag gagattcacc ctgaagggtt tagcctttac    6660
gtccacttgg acgtgagggc agtttgcctt ttggaagcca ttgtgcaaca tcttacaaat    6720
gccattatct gttctttggc tgtagagttt gaccacgcca ccggagggga gcgcgttcac    6780
ttaatagatc ttcattttga ggttttggat aatcttttgg aataaaaaaa aaaaaacatg    6840
gttcttccag ctcttcccgc tcctcccgtg tgtgactcgc agaacgaatg tgtaggttgg    6900
ctgggtgtgg cttattctgc ggtggtggat gttatcaggg cagcggcgca tgaaggagtt   6960
tacatagaac ccgaagccag ggggcgcctg gatgctttga gagagtggat atactacaac    7020
tactacacag agcgagctaa gcgacgagac cggagacgca gatctgtttg tcacgcccgc    7080
acctggtttt gcttcaggaa atatgactac gtccggcgtt ccatttggca tgacactacg    7140
accaacacga tctcggttgt ctcggcgcac tccgtacagt agggatcgcc tacctccttt    7200
tgagacagag acccgcgcta ccatactgga ggatcatccg ctgctgcccg aatgtaacac    7260
tttgacaatg cacaacgtga gttacgtgcg aggtcttccc tgcagtgtgg gatttacgct    7320
gattcaggaa tgggttgttc cctgggatat ggttctgacg cgggaggagc ttgtaatcct    7380
gaggaagtgt atgcacgtgt gcctgtgttg tgccaacatt gatatcatga cgagcatgat    7440
gatccatggt tacgagtcct gggctctcca ctgtcattgt tccagtcccg gttccctgca    7500
gtgcatagcc ggcgggcagg ttttggccag ctggtttagg atggtggtgg atggcgccat    7560
gtttaatcag aggtttatat ggtaccggga ggtggtgaat tacaacatgc caaaagaggt    7620
aatgtttatg tccagcgtgt ttatgagggg tcgccactta atctacctgc gcttgtggta    7680
tgatggccac gtgggttctg tggtccccgc catgagcttt ggatacagcg ccttgcactg    7740 tgggatttttg aacaatattg tggtgctgtg ctgcagttac tgtgctgatt taagtgagat   7800
cagggtgcgc tgctgtgccc ggaggacaag gcgtctcatg ctgcgggcgg tgcgaatcat    7860
cgctgaggag accactgcca tgttgtattc ctgcaggacg gagcggcggc ggcagcagtt    7920
tattcgcgcg ctgctgcagc accaccgccc tatcctgatg cacgattatg actctacccc    7980
catgtaggcg tggacttccc cttcgccgcc cgttgagcaa ccgcaagttg gacagcagcc    8040
tgtggctcag cagctggaca gcgacatgaa cttaagcgag ctgcccgggg agtttattaa    8100
tatcactgat gagcgtttgg ctcgacagga aaccgtgtgg aatataacac ctaagaatat    8160
gtctgttacc catgatatga tgcttttttaa ggccagccgg ggagaaagga ctgtgtactc    8220
tgtgtgttgg gagggaggtg gcaggttgaa tactagggtt ctgtgagttt gattaaggta    8280
cggtgatcaa tataagctat gtggtggtgg ggctatacta ctgaatgaaa aatgacttga    8340 aatttttctgc aattgaaaaa taaacacgtt gaaacataac atgcaacagg ttcacgattc    8400
tttattcctg ggcaatgtag agaaggtgt aagagttggt agcaaaagtt tcagtggtgt     8460
attttccact ttcccaggac catgtaaaag acatagagta agtgcttacc tcgctagttt    8520
ctgtggattc actagaatcg atgtaggatg ttgcccctcc tgacgcggta ggagaagggg    8580
agggtgccct gcatgtctgc cgctgctctt gctcttgccg ctgctgagga gggggcgca     8640 tctgccgcag caccggatgc atctgggaaa agcaaaaaag gggctcgtcc ctgtttccgg    8700
```

```
aggaatttgc aagcggggtc ttgcatgacg gggaggcaaa cccccgttcg ccgcagtccg    8760
gccggcccga gactcgaacc gggggtcctg cgactcaacc cttggaaaat aaccctccgg    8820
ctacagggag cgagccactt aatgctttcg ctttccagcc taaccgctta cgccgcgcgc    8880
ggccagtggc caaaaaagct agcgcagcag ccgccgcgcc tggaaggaag ccaaaaggag    8940
cgctcccccg ttgtctgacg tcgcacacct gggttcgaca cgcgggcggt aaccgcatgg    9000
atcacggcgg acggccggat ccggggttcg aaccccggtc gtccgccatg ataccctttgc   9060 gaatttatcc accagaccac ggaagagtgc ccgcttacag gctctccttt tgcacggtct    9120
agagcgtcaa cgactgcgca cgcctcaccg gccagagcgt cccgaccatg gagcactttt    9180
tgccgctgcg caacatctgg aaccgcgtcc gcgactttcc gcgcgcctcc accaccgccg    9240
ccggcatcac ctgatgtgcc aggtacatct acggattacg tcgacgttta aaccatatga    9300
tcagctcact caaaggcggt aatacggtta tccacagaat caggggataa cgcaggaaag    9360
aacatgtgag caaaaggcca gcaaaaggcc aggaaccgta aaaaggccgc gttgctggcg    9420 ttttttccata ggctccgccc ccctgacgag catcacaaaa atcgacgctc aagtcagagg    9480
tggcgaaacc cgacaggact ataaagatac caggcgtttc cccctggaag ctccctcgtg    9540
cgctctcctg ttccgaccct gccgcttacc ggatacctgt ccgcctttct cccttcggga    9600
agcgtggcgc tttctcatag ctcacgctgt aggtatctca gttcggtgta ggtcgttcgc    9660
tccaagctgg gctgtgtgca cgaaccccccc gttcagcccg accgctgcgc cttatccggt    9720
aactatcgtc ttgagtccaa cccggtaaga cacgacttat cgccactggc agcagccact    9780
ggtaacagga ttagcagagc gaggtatgta ggcggtgcta cagagttctt gaagtggtgg    9840
cctaactacg gctacactag aagaacagta tttggtatct gcgctctgct gaagccagtt    9900
accttcggaa aaagagttgg tagctcttga tccggcaaac aaaccaccgc tggtagcggt    9960
ggtttttttg tttgcaagca gcagattacg cgcagaaaaa aaggatctca agaagatcct   10020
ttgatctttt ctacggggtc tgacgctcag tggaacgaaa actcacgtta agggattttg   10080
gtcatgagat tatcaaaaag gatcttcacc tagatccttt taaattaaaa atgaagtttt   10140
aaatcaatct aaagtatata tgagtaaact tggtctgaca gttaccaatg cttaatcagt   10200
gaggcaccta tctcagcgat ctgtctattt cgttcatcca tagttgcctg actccccgtc   10260
gtgtagataa ctacgatacg ggagggctta ccatctggcc ccagtgctgc aatgataccg   10320
cgagacccac gctcaccggc tccagattta tcagcaataa accagccagc cggaagggcc   10380
gagcgcagaa gtggtcctgc aactttatcc gcctccatcc agtctattaa ttgttgccgg   10440
gaagctagag taagtagttc gccagttaat agtttgcgca acgttgttgc cattgctaca   10500
ggcatcgtgg tgtcacgctc gtcgtttggt atggcttcat tcagctccgg ttcccaacga   10560
tcaaggcgag ttacatgatc ccccatgttg tgcaaaaaag cggttagctc cttcggtcct   10620
ccgatcgttg tcagaagtaa gttggccgca gtgttatcac tcatggttat ggcagcactg   10680
cataattctc ttactgtcat gccatccgta agatgctttt ctgtgactgg tgagtactca   10740
accaagtcat tctgagaata gtgtatgcgg cgaccgagtt gctcttgccc ggcgtcaata   10800
cgggataata ccgcgccaca tagcagaact ttaaaagtgc tcatcattgg aaaacgttct   10860
tcggggcgaa aactctcaag gatcttaccg ctgttgagat ccagttcgat gtaacccact   10920
cgtgcaccca actgatcttc agcatctttt actttcacca gcgtttctgg gtgagcaaaa   10980
acaggaaggc aaaatgccgc aaaaaaggga ataagggcga cacggaaatg ttgaatactc   11040
```

| | | | | | |
|---|---|---|---|---|---|
| atactcttcc | tttttcaata | ttattgaagc | atttatcagg | gttattgtct | catgagcgga | 11100 |
| tacatatttg | aatgtattta | gaaaaataaa | caaataggg | ttccgcgcac | atttccccga | 11160 |
| aaagtgccac | ctaaattgta | agcgttaata | ttttgttaaa | attcgcgtta | aattttgtt | 11220 |
| aaatcagctc | atttttaac | caataggccg | aaatcggcaa | aatcccttat | aaatcaaaag | 11280 |
| aatagaccga | gatagggttg | agtgttgttc | cagtttggaa | caagagtcca | ctattaaaga | 11340 |
| acgtggactc | caacgtcaaa | gggcgaaaaa | ccgtctatca | gggcgatggc | ccactacgtg | 11400 |
| aaccatcacc | ctaatcaagt | tttttgggt | cgaggtgccg | taaagcacta | aatcggaacc | 11460 |
| ctaaagggag | cccccgattt | agagcttgac | ggggaaagcc | ggcgaacgtg | gcagaaaagg | 11520 |
| aagggaagaa | agcgaaagga | gcgggcgcta | gggcgctggc | aagtgtagcg | gtcacgctgc | 11580 |
| gcgtaaccac | cacacccgcc | gcgcttaatg | cgccgctaca | gggcgcgatg | gatcc | 11635 |

<210> SEQ ID NO 7
<211> LENGTH: 5968
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 7

| | | | | | |
|---|---|---|---|---|---|
| ctgcgcgctc | gctcgctcac | tgaggccgcc | cgggcaaagc | ccgggcgtcg | ggcgaccttt | 60 |
| ggtcgcccgg | cctcagtgag | cgagcgagcg | cgcagagagg | gagtggccaa | ctccatcact | 120 |
| aggggttcct | gcggccgcac | gcgttgacat | tgattattga | ctagttatta | atagtaatca | 180 |
| attacggggt | cattagttca | tagcccatat | atggagttcc | gcgttacata | acttacggta | 240 |
| aatggcccgc | ctggctgacc | gcccaacgac | ccccgcccat | tgacgtcaat | aatgacgtat | 300 |
| gttcccatag | taacgccaat | agggactttc | cattgacgtc | aatgggtgga | ctatttacgg | 360 |
| taaactgccc | acttggcagt | acatcaagtg | tatcatatgc | caagtacgcc | ccctattgac | 420 |
| gtcaatgacg | gtaaatggcc | cgcctggcat | tatgcccagt | acatgacctt | atgggacttt | 480 |
| cctacttggc | agtacatcta | cgtattagtc | atcgctatta | ccatggtgat | gcggttttgg | 540 |
| cagtacatca | atgggcgtgg | atagcggttt | gactcacggg | gatttccaag | tctccacccc | 600 |
| attgacgtca | atgggagttt | gttttggcac | caaaatcaac | gggactttcc | aaaatgtcgt | 660 |
| aacaactccg | ccccattgac | gcaaatgggc | ggtaggcgtg | tacggtggga | ggtctatata | 720 |
| agcagagctc | tctggctaac | tagagaaccc | actgcttact | ggcttatcga | aattaatacg | 780 |
| actcactata | gggagaccca | agctcatgga | agatgccaaa | aacattaaga | agggcccagc | 840 |
| gccattctac | ccactcgaag | acgggaccgc | cggcgagcag | ctgcacaaag | ccatgaagcg | 900 |
| ctacgccctg | gtgcccggca | ccatcgcctt | taccgacgca | catatcgagg | tggacattac | 960 |
| ctacgccgag | tacttcgaga | tgagcgttcg | gctggcagaa | gctatgaagc | gctatgggct | 1020 |
| gaatacaaac | catcggatcg | tggtgtgcag | cgagaatagc | ttgcagttct | tcatgccgt | 1080 |
| gttgggtgcc | ctgttcatcg | gtgtggctgt | ggccccagct | aacgacatct | acaacgagcg | 1140 |
| cgagctgctg | aacagcatgg | gcatcagcca | gcccaccgtc | gtattcgtga | gcaagaaagg | 1200 |
| gctgcaaaag | atcctcaacg | tgcaaaagaa | gctaccgatc | atacaaaaga | tcatcatcat | 1260 |
| ggatagcaag | accgactacc | agggcttcca | aagcatgtac | accttcgtga | cttcccattt | 1320 |
| gccaccggc | ttcaacgagt | acgacttcgt | gcccgagagc | ttcgaccggg | acaaaaccat | 1380 |
| cgccctgatc | atgaacagta | gtggcagtac | cggattgccc | aagggcgtag | ccctaccgca | 1440 |

```
ccgcaccgct tgtgtccgat tcagtcatgc ccgcgacccc atcttcggca accagatcat   1500
ccccgacacc gctatcctca gcgtggtgcc atttcaccac ggcttcggca tgttcaccac   1560
gctgggctac ttgatctgcg gctttcgggt cgtgctcatg taccgcttcg aggaggagct   1620
attcttgcgc agcttgcaag actataagat tcaatctgcc ctgctggtgc ccacactatt   1680
tagcttcttc gctaagagca ctctcatcga caagtacgac ctaagcaact tgcacgagat   1740
cgccagcggg ggggcgccgc tcagcaagga ggtaggtgag gccgtggcca aacgcttcca   1800
cctaccaggc atccgccagg gctacggcct gacagaaaca accagcgcca ttctgatcac   1860
ccccgaaggg gacgacaagc ctggcgcagt aggcaaggtg gtgcccttct tcgaggctaa   1920
ggtggtggac ttggacaccg gtaagacact gggtgtgaac cagcgcggcg agctgtgcgt   1980
ccgtggcccc atgatcatga gcggctacgt taacaacccc gaggctacaa acgtctcat    2040 cgacaaggac ggctggctgc acagcggcga catcgcctac tgggacgagg acgagcactt   2100
cttcatcgtg gaccggctga agagcctgat caaatacaag ggctaccagg tagccccagc   2160
cgaactggag agcatcctgc tgcaacaccc caacatcttc gacgccgggg tcgccggcct   2220
gcccgacgac gatgccggcg agctgccccg cgcagtcgtc gtgctggaac acggtaaaac   2280
catgaccgag aaggagatcg tggactatgt ggccagccag gttacaaccg ccaagaagct   2340
gcgcggtggt gttgtgttcg tggacgaggt gcctaaagga ctgaccggca agttggacgc   2400
ccgcaagatc cgcgagattc tcattaaggc caagaagggc ggcaagatcg ccgtgaattc   2460
tcacggcttc cctcccgagg tggaggagca ggccgccggc accctgccca tgagctgcgc   2520
ccaggagagc ggcatggata cacccctgc tgcttgcgcc agcgccagga tcaacgtcta   2580
aggccgcgac tctagagcat ggctacgtag ataagtagca tggcgggtta atcattaact   2640
acaaggaacc cctagtgatg gagttggcca ctccctctct gcgcgctcgc tcgctcactg   2700
aggccgggcg accaaaggtc gcccgacgcc gggctttgc ccgggcgcc tcagtgagcg   2760 agcgagcgcg ccagctggcg taatagcgaa gaggcccgca ccgatcgccc ttcccaacag   2820
ttgcgcagcc tgaatggcga atggaattcc agacgattga gcgtcaaaat gtaggtattt   2880
ccatgagcgt ttttcctgtt gcaatggctg cggtaatat tgttctggat attaccagca   2940
aggccgatag tttgagttct tctactcagg caagtgatgt tattactaat caaagaagta   3000
ttgcgacaac ggttaatttg cgtgatggac agactctttt actcggtggc ctcactgatt   3060
ataaaaacac ttctcaggat tctggcgtac cgttcctgtc taaatccct ttaatcggcc   3120 tcctgtttag ctcccgctct gattctaacg aggaaagcac gttatacgtg ctcgtcaaag   3180
caaccatagt acgcgccctg tagcggcgca ttaagcgcgg cgggtgtggt ggttacgcgc   3240
agcgtgaccg ctacacttgc cagcgcccta gcgcccgctc cttcgcttt cttcccttcc   3300 tttctcgcca cgttcgccat cttcaaatat gtatccgctc atgagacaat aaccctgata   3360
aatgcttcaa taatattgaa aaaggaagag tcctgaggcg gaaagaacca gctgtggaat   3420
gtgtgtcagt tagggtgtgg aaagtcccca ggctcccag caggcagaag tatgcaaagc   3480
atgcatctca attagtcagc aaccaggtgt ggaaagtccc caggctcccc agcaggcaga   3540
agtatgcaaa gcatgcatct caattagtca gcaaccatag tcccgcccct aactccgccc   3600
atcccgcccc taactccgcc cagttccgcc cattctccgc cccatggctg actaattttt   3660
tttatttatg cagaggccga ggccgcctcg gcctctgagc tattccagaa gtagtgagga   3720 ggctttttg gaggcctagg cttttgcaaa gatcgatcaa gagacaggat gaggatcgtt   3780
```

```
tcgcatgatt gaacaagatg gattgcacgc aggttctccg gccgcttggg tggagaggct   3840
attcggctat gactgggcac aacagacaat cggctgctct gatgccgccg tgttccggct   3900
gtcagcgcag gggcgcccgg ttcttttttgt caagaccgac ctgtccggtg ccctgaatga   3960
actgcaagac gaggcagcgc ggctatcgtg gctggccacg acgggcgttc cttgcgcagc   4020
tgtgctcgac gttgtcactg aagcgggaag ggactggctg ctattgggcg aagtgccggg   4080
gcaggatctc ctgtcatctc accttgctcc tgccgagaaa gtatccatca tggctgatgc   4140
aatgcggcgg ctgcatacgc ttgatccggc tacctgccca ttcgaccacc aagcgaaaca   4200
tcgcatcgag cgagcacgta ctcggatgga agccggtctt gtcgatcagg atgatctgga   4260
cgaagagcat caggggctcg cgccagccga actgttcgcc aggctcaagg cgagcatgcc   4320
cgacggcgag gatctcgtcg tgacccatgg cgatgcctgc ttgccgaata tcatggtgga   4380
aaatggccgc ttttctggat tcatcgactg tggccggctg ggtgtggcgg accgctatca   4440
ggacatagcg ttggctaccc gtgatattgc tgaagagctt ggcggcgaat gggctgaccg   4500
cttcctcgtg ctttacggta tcgccgctcc cgattcgcag cgcatcgcct tctatcgcct   4560
tcttgacgag ttcttctgag cgggactctg gggttcgaaa tgaccgacca agcgacgccc   4620
aacctgccat cacgagattt cgattccacc gccgccttct atgaaaggtt gggcttcgga   4680
atcgttttcc gggacgccgg ctggatgatc ctccagcgcg ggatctcat gctggagttc   4740
ttcgcccacc ctaggggag gctaactgaa acacggaagg agacaatacc ggaaggaacc   4800
cgcgctatga cggcaataaa aagacagaat aaaaacgttg cgcaaactat taactggcga   4860
actacttact ctagcttccc ggcaacaatt aatagactgg atggaggcgg ataaagttgc   4920
aggaccactt ctgcgctcgg cccttccggc tggctggttt attgctgata atctggagc   4980
cggtgagcgt gggtctcgcg gtatcattgc agcactgggg ccagatggta gccctcccg   5040
tatcgtagtt atctacacga cggggagtca ggcaactatg gatgaacgaa atagacagat   5100
cgctgagata ggtgcctcac tgattaagca ttggtaactg tcagaccaag tttactcata   5160
tatactttag attgatttaa aacttcattt ttaatttaaa aggatctagg tgaagatcct   5220
ttttgataat ctcatgacca aaatccctta acgtgagttt tcgttccact gagcgtcaga   5280
ccccgtagaa aagatcaaag gatcttcttg agatcctttt tttctgcgcg taatctgctg   5340
cttgcaaaca aaaaaaccac cgctaccagc ggtggtttgt ttgccggatc aagagctacc   5400
aactcttttt ccgaaggtaa ctggcttcag cagagcgcag ataccaaata ctgtccttct   5460
agtgtagccg tagttaggcc accacttcaa gaactctgta gcaccgccta catacctcgc   5520
tctgctaatc ctgttaccag tggctgctgc cagtggcgat aagtcgtgtc ttaccgggtt   5580
ggactcaaga cgatagttac cggataaggc gcagcggtcg ggctgaacgg ggggttcgtg   5640
cacacagccc agcttggagc gaacgaccta caccgaactg agatacctac agcgtgagct   5700
atgagaaagc gccacgcttc ccgaagggag aaaggcggac aggtatccgg taagcggcag   5760
ggtcggaaca ggagagcgca cgagggagct tccaggggga aacgcctggt atctttatag   5820
tcctgtcggg tttcgccacc tctgacttga gcgtcgattt ttgtgatgct cgtcaggggg   5880
gcggagccta tggaaaaacg ccagcaacgc ggccttttta cggttcctgg cctttgctg   5940
gccttttgct cacatgtcct gcaggcag                                     5968
```

<210> SEQ ID NO 8  
<211> LENGTH: 7141  
<212> TYPE: DNA  
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 8

| | | | | | | |
|---|---|---|---|---|---|---|
| cctgcaggca | gctgcgcgct | cgctcgctca | ctgaggccgc | ccgggcgtcg | ggcgaccttt | 60 |
| ggtcgcccgg | cctcagtgag | cgagcgagcg | cgcagagagg | gagtggccaa | ctccatcact | 120 |
| aggggttcct | gcggcctcta | gactcgacat | gggccgccac | catgctgtgg | tgggaggagg | 180 |
| tggaggattg | ttatgaaagg | gaggacgtgc | agaagaagac | ttttaccaag | tgggtgaacg | 240 |
| ctcagttcag | caaatttggg | aagcagcaca | tcgagaatct | gttttccgac | ctgcaggatg | 300 |
| ggagacggct | gctggatctg | ctggaaggac | tgactggcca | gaagctgccc | aaagagaagg | 360 |
| ggagcactag | ggtgcacgcc | ctgaacaacg | tgaacaaagc | tctgagagtg | ctgcagaaca | 420 |
| acaacgtgga | tctggtgaat | attggcagta | ctgatatcgt | ggacgggaac | cacaaactga | 480 |
| cactgggcct | gatctggaac | attattctgc | actggcaggt | gaaaaatgtg | atgaagaaca | 540 |
| tcatggccgg | gctgcagcag | accaattccg | agaagatcct | gctgtcttgg | gtgcggcaga | 600 |
| gcacccgcaa | ctatcccag | gtgaacgtga | ttaacttcac | tacatcctgg | agcgacgggc | 660 |
| tggccctgaa | tgctctgatt | cacagccaca | ggcctgatct | gttcgactgg | aatagcgtgg | 720 |
| tgtgccagca | gtctgccaca | cagcgcctgg | aacatgcctt | caatatcgct | cggtaccagc | 780 |
| tggggatcga | aaaactgctg | gacccagagg | atgtggacac | tacataccca | gataaaaagt | 840 |
| ctattctgat | gtacattact | agcctgttcc | aggtgctgcc | acagcaggtg | tctattgaag | 900 |
| ccattcagga | ggtggaaatg | ctgccccgcc | ccccaaagt | gactaaagag | gagcattttc | 960 |
| agctgcatca | tcagatgcat | tacagccagc | agattaccgt | gagcctggct | cagggatatg | 1020 |
| agcgcaccag | tagtccaaaa | ccacggttca | agtcctacgc | ttatacccag | gctgcctacg | 1080 |
| tgacaactag | cgaccctact | agatccccct | ttccatccca | gcacctggag | gccccagagg | 1140 |
| acaagagctt | tgggtccagc | ctgatggaaa | gcgaggtgaa | tctggatcgg | taccagacag | 1200 |
| ccctggagga | ggtgctgagc | tggctgctga | gtgctgaaga | cacactgcag | gcccagggcg | 1260 |
| aaatttccaa | tgacgtggaa | gtggtgaagg | atcgttcca | cacacgag | ggctatatga | 1320 |
| tggacctgac | agctcaccag | gggcgcgtgg | gcaatatcct | gcagctgggc | tctaaactga | 1380 |
| tcggcaccgg | gaaactgagt | gaggacgagg | aaacagaagt | gcaggagcag | atgaacctgc | 1440 |
| tgaacagccg | ctgggagtgt | ctgagagtgg | ctagtatgga | gaagcagtcc | aacctgcacc | 1500 |
| gggtgctgat | ggacctgcag | aaccagaaac | tgaaagagct | gaacgactgg | ctgacaaaga | 1560 |
| ctgaggaacg | cacaaggaag | atggaggagg | agccactggg | acccgacctg | gaggatctga | 1620 |
| agagacaggt | gcagcagcat | aaggtgctgc | aggaggatct | ggaacaggag | caggtgcggg | 1680 |
| tgaactccct | gacacatatg | gtggtggtgg | tggacgaatc | tagtggagat | cacgccaccg | 1740 |
| ccgcctgga | ggaacagctg | aaggtgctgg | gggaccggtg | ggccaacatt | tgccggtgga | 1800 |
| ccgaggacag | gtgggtgctg | ctgcaggaca | tcctgctgaa | atggcagagg | ctgaccgagg | 1860 |
| agcagtgtct | gtttagtgct | tggctgagcg | agaaagagga | cgccgtgaac | aagatccaca | 1920 |
| caaccggctt | taaggatcag | aacgaaatgc | tgtctagcct | gcagaaactg | gctgtgctga | 1980 |
| aggccgatct | ggagaaaaag | aagcagagca | tgggcaaact | gtatagcctg | aaacaggacc | 2040 |
| tgctgagcac | cctgaagaac | aagagcgtga | cccagaagac | agaagcctgg | ctggataact | 2100 |
| ttgcccgctg | ctgggacaac | ctggtgcaga | aactggagaa | aagtacagct | cagatctctc | 2160 |

| | |
|---|---|
| aggctgtgac cacaacccag cctagcctga cccagacaac cgtgatggaa accgtgacca | 2220 |
| ccgtgacaac ccgcgaacag atcctggtga aacatgccca ggaagagctg ccacctccac | 2280 |
| ctccccagaa gaagagaacc ctggagcggc tgcaggagct gcaggaagcc actgacgaac | 2340 |
| tggacctgaa gctgaggcag gccgaagtga ttaaggggtc ttggcagcct gtgggcgatc | 2400 |
| tgctgattga ttccctgcag gaccacctgg aaaaggtgaa ggctctgaga ggcgaaattg | 2460 |
| ctccactgaa ggagaacgtg agtcatgtga acgatctggc tagacagctg acaacactgg | 2520 |
| gcatccagct gagcccatac aatctgagca cactggagga cctgaatacc aggtggaagc | 2580 |
| tgctgcaggt ggctgtggaa gaccgggtgc ggcagctgca tgaggcccat cgcgacttcg | 2640 |
| gaccagccag ccagcacttt ctgagcacat ccgtgcaggg gccctgggag agggccattt | 2700 |
| ctcccaacaa ggtgccctac tatattaatc acgagaccca gaccacttgt tgggaccatc | 2760 |
| ccaagatgac agaactgtac cagtccctgg ccgatctgaa caacgtgagg tttagcgctt | 2820 |
| acagaaccgc tatgaagctg agacggctgc agaaggccct gtgcctggat ctgctgtccc | 2880 |
| tgtccgccgc ctgcgatgcc ctggatcagc ataatctgaa gcagaacgat cagccaatgg | 2940 |
| atatcctgca gatcatcaac tgcctgacca ctatctacga caggctggag caggagcaca | 3000 |
| acaacctggt gaacgtgcct ctgtgcgtgg atatgtgcct gaactggctg ctgaacgtgt | 3060 |
| atgacactgg gcgcaccggc cggatcagag tgctgagttt taaaactggg attatctccc | 3120 |
| tgtgtaaggc ccacctggag gacaagtaca ggtacctgtt caagcaggtg ctagtagca | 3180 |
| ctggattttg tgaccagcgc cgcctgggac tgctgctgca tgatagtatc cagattccta | 3240 |
| gacagctggg agaggtggct agtttcggag gatctaacat cgaacccagc gtgcgcagct | 3300 |
| gtttccagtt tgccaataac aaacctgaaa tcgaggctgc tctgttcctg gattggatgc | 3360 |
| gcctggaacc acagagcatg gtgtggctgc ctgtgctgca cagagtggct gccgccgaaa | 3420 |
| ctgccaagca ccaggctaaa tgcaacatct gcaaggaatg tcccattatc ggctttcgct | 3480 |
| acaggagtct gaaacatttt aactacgata tttgccagag ctgcttcttt tccgaagag | 3540 |
| tggccaaagg acacaagatg cactacccta tggtggaata ttgcaccca actacatctg | 3600 |
| gcgaagatgt gcgcgatttt gccaaggtgc tgaagaataa gtttcggact aagaggtact | 3660 |
| tcgccaagca ccccgcatg gggtatctgc cagtgcagac agtgctggaa ggagacaata | 3720 |
| tggagaccga tacaatgtga gcggccgcaa taaagatct ttattttcat tagatctgtg | 3780 |
| tgttggttt ttgtgtgtct agaattccta gagctcgctg atcagcctcg actgtgcctt | 3840 |
| ctagttgcca gccatctgtt gtttgcccct ccccgtgcc ttccttgacc ctggaaggtg | 3900 |
| ccactcccac tgtcctttcc taataaaatg aggaaattgc atcgcattgt ctgagtaggt | 3960 |
| gtcattctat tctgggggt ggggtgggc aggacagcaa gggggaggat tgggaagaga | 4020 |
| atagcaggca tgctgggag gtaccaaaaa tctcgccaac aagttgacga gataaacacg | 4080 |
| gcatttgcc ttgttttagt agattctgtt tccagagtac taaaactgag acctgccgtg | 4140 |
| gtctccggtg tttcgtcctt tccacaagat atataaagcc aagaaatcga aatactttca | 4200 |
| agttacggta agcatatgat agtccatttt aaaacataat tttaaaactg caaactaccc | 4260 |
| aagaaattat tactttctac gtcacgtatt ttgtactaat atctttgtgt ttacagtcaa | 4320 |
| attaattcca attatctctc taacagcctt gtatcgtata tgcaaatatg aaggaatcat | 4380 |
| gggaaatagg ccctcgcggc cgcaggaacc cctagtgatg gagttggcca ctccctctct | 4440 |
| gcgcgctcgc tcgctcactg aggccgggcg accaaaggtc gcccgacgcc cgggctttgc | 4500 |
| ccgggcggcc tcagtgagcg agcgagcgcg cagctgcctg caggggcgcc tgatgcgta | 4560 |

```
tttctccctt acgcatctgt gcggtatttc acaccgcata cgtcaaagca accatagtac   4620
gcgccctgta gcggcgcatt aagcgcggcg ggtgtggtgg ttacgcgcag cgtgaccgct   4680
acacttgcca gcgccctagc gcccgctcct ttcgctttct tcccttcctt tctcgccacg   4740
ttcgccggct ttccccgtca agctctaaat cgggggctcc ctttagggtt ccgatttagt   4800
gctttacggc acctcgaccc caaaaaactt gatttgggtg atggttcacg tagtgggcca   4860
tcgccctgat agacggtttt tcgccctttg acgttggagt ccacgttctt taatagtgga   4920
ctcttgttcc aaactggaac aacactcaac cctatctcgg gctattcttt tgatttataa   4980
gggattttgc cgatttcggc ctattggtta aaaaatgagc tgatttaaca aaaatttaac   5040
gcgaatttta acaaaatatt aacgtttaca attttatggt gcactctcag tacaatctgc   5100
tctgatgccg catagttaag ccagccccga cacccgccaa cacccgctga cgcgccctga   5160
cgggcttgtc tgctcccggc atccgcttac agacaagctg tgaccgtctc cgggagctgc   5220
atgtgtcaga ggttttcacc gtcatcaccg aaacgcgcga gacgaaaggg cctcgtgata   5280
cgcctatttt tataggttaa tgtcatgata ataatggttt cttagacgtc aggtggcact   5340
tttcggggaa atgtgcgcgg aaccccctatt tgtttatttt tctaaataca ttcaaatatg   5400
tatccgctca tgagacaata accctgataa atgcttcaat aatattgaaa aaggaagagt   5460
atgagtattc aacatttccg tgtcgccctt attcccttt ttgcggcatt ttgccttcct   5520
gtttttgctc acccagaaac gctggtgaaa gtaaaagatg ctgaagatca gttgggtgca   5580
cgagtgggtt acatcgaact ggatctcaac agcggtaaga tccttgagag ttttcgcccc   5640
gaagaacgtt ttccaatgat gagcactttt aaagttctgc tatgtggcgc ggtattatcc   5700
cgtattgacg ccgggcaaga gcaactcggt cgccgcatac actattctca gaatgacttg   5760
gttgagtact caccagtcac agaaaagcat cttacggatg gcatgacagt aagagaatta   5820
tgcagtgctg ccataaccat gagtgataac actgcggcca acttacttct gacaacgatc   5880
ggaggaccga aggagctaac cgcttttttg cacaacatgg gggatcatgt aactcgcctt   5940
gatcgttggg aaccggagct gaatgaagcc ataccaaacg acgagcgtga ccacacgatg   6000
cctgtagcaa tggcaacaac gttgcgcaaa ctattaactg gcgaactact tactctagct   6060
tcccggcaac aattaataga ctggatggag gcggataaag ttgcaggacc acttctgcgc   6120
tcggcccttc cggctggctg gtttattgct gataaatctg gagccggtga gcgtggaagc   6180
cgcggtatca ttgcagcact ggggccagat ggtaagccct cccgtatcgt agttatctac   6240
acgacgggga gtcaggcaac tatggatgaa cgaaatagac agatcgctga tagggtgcc   6300 tcactgatta agcattggta actgtcagac caagtttact catatatact ttagattgat   6360
ttaaaacttc atttttaatt taaaaggatc taggtgaaga tcctttttga taatctcatg   6420
accaaaatcc cttaacgtga gttttcgttc cactgagcgt cagacccgt agaaaagatc   6480 aaaggatctt cttgagatcc ttttttctg cgcgtaatct gctgcttgca acaaaaaaa   6540 ccaccgctac cagcggtggt ttgtttgccg gatcaagagc taccaactct ttttccgaag   6600
gtaactggct tcagcagagc gcagatacca aatactgtcc ttctagtgta gccgtagtta   6660
ggccaccact tcaagaactc tgtagcaccg cctacatacc tcgctctgct aatcctgtta   6720
ccagtggctg ctgccagtgg cgataagtcg tgtcttaccg ggttggactc aagacgatag   6780
ttaccggata aggcgcagcg gtcgggctga acggggggtt cgtgcacaca gcccagcttg   6840
gagcgaacga cctacaccga actgagatac ctacagcgtg agctatgaga aagcgccacg   6900
```

```
cttcccgaag ggagaaaggc ggacaggtat ccggtaagcg gcagggtcgg aacaggagag    6960
cgcacgaggg agcttccagg gggaaacgcc tggtatcttt atagtcctgt cgggtttcgc    7020
cacctctgac ttgagcgtcg attttttgtga tgctcgtcag gggggcggag cctatggaaa   7080
aacgccagca acgcggcctt tttacggttc ctggccttttt gctggccttt tgctcacatg   7140
t                                                                    7141
```

<210> SEQ ID NO 9
<211> LENGTH: 174
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 9

```
gcctccaaga cccagagcat taagaagtac agcacagaca ttctgggcaa cctgtatgaa     60
gtgaaatcta agaagcaccc tcagatcatc aaaaagggca gcggcttcgc caacgagctg    120
ggccctagac tgatgggaaa gactagtaga ccggtagagc catcacccca gcgc          174
```

<210> SEQ ID NO 10
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 10

```
atataataga aattattcat                                                 20
```

<210> SEQ ID NO 11
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 11

```
taatatgccc tgtaatataa                                                 20
```

<210> SEQ ID NO 12
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 12

```
tgatatcatc aatatctttg                                                 20
```

<210> SEQ ID NO 13
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

-continued

<400> SEQUENCE: 13
gcaattaatt ggaaaatgtg                                           20

<210> SEQ ID NO 14
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 14
ctttaagctt aggtaaaatc a                                         21

<210> SEQ ID NO 15
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 15
cagtaatgtg tcataccttc                                           20

<210> SEQ ID NO 16
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 16
cagggcatat tatatttaga                                           20

<210> SEQ ID NO 17
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 17
caaaagccaa atctatttca                                           20

<210> SEQ ID NO 18
<211> LENGTH: 1368
<212> TYPE: PRT
<213> ORGANISM: Streptococcus pyogenes

<400> SEQUENCE: 18

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu

```
                50                  55                  60
    Lys Arg Thr Ala Arg Arg Tyr Thr Arg Arg Lys Asn Arg Ile Cys
    65                  70                  75                  80

Tyr Leu Gln Glu Ile Phe Ser Asn Glu Met Ala Lys Val Asp Asp Ser
                        85                  90                  95

Phe Phe His Arg Leu Glu Glu Ser Phe Leu Val Glu Glu Asp Lys Lys
                        100                 105                 110

His Glu Arg His Pro Ile Phe Gly Asn Ile Val Asp Glu Val Ala Tyr
                        115                 120                 125

His Glu Lys Tyr Pro Thr Ile Tyr His Leu Arg Lys Lys Leu Val Asp
                        130                 135                 140

Ser Thr Asp Lys Ala Asp Leu Arg Leu Ile Tyr Leu Ala Leu Ala His
    145                 150                 155                 160

Met Ile Lys Phe Arg Gly His Phe Leu Ile Glu Gly Asp Leu Asn Pro
                        165                 170                 175

Asp Asn Ser Asp Val Asp Lys Leu Phe Ile Gln Leu Val Gln Thr Tyr
                        180                 185                 190

Asn Gln Leu Phe Glu Glu Asn Pro Ile Asn Ala Ser Gly Val Asp Ala
                        195                 200                 205

Lys Ala Ile Leu Ser Ala Arg Leu Ser Lys Ser Arg Arg Leu Glu Asn
                        210                 215                 220

Leu Ile Ala Gln Leu Pro Gly Glu Lys Lys Asn Gly Leu Phe Gly Asn
    225                 230                 235                 240

Leu Ile Ala Leu Ser Leu Gly Leu Thr Pro Asn Phe Lys Ser Asn Phe
                        245                 250                 255

Asp Leu Ala Glu Asp Ala Lys Leu Gln Leu Ser Lys Asp Thr Tyr Asp
                        260                 265                 270

Asp Asp Leu Asp Asn Leu Leu Ala Gln Ile Gly Asp Gln Tyr Ala Asp
                        275                 280                 285

Leu Phe Leu Ala Ala Lys Asn Leu Ser Asp Ala Ile Leu Leu Ser Asp
                        290                 295                 300

Ile Leu Arg Val Asn Thr Glu Ile Thr Lys Ala Pro Leu Ser Ala Ser
    305                 310                 315                 320

Met Ile Lys Arg Tyr Asp Glu His His Gln Asp Leu Thr Leu Leu Lys
                        325                 330                 335

Ala Leu Val Arg Gln Gln Leu Pro Glu Lys Tyr Lys Glu Ile Phe Phe
                        340                 345                 350

Asp Gln Ser Lys Asn Gly Tyr Ala Gly Tyr Ile Asp Gly Gly Ala Ser
                        355                 360                 365

Gln Glu Glu Phe Tyr Lys Phe Ile Lys Pro Ile Leu Glu Lys Met Asp
                        370                 375                 380

Gly Thr Glu Glu Leu Leu Val Lys Leu Asn Arg Glu Asp Leu Leu Arg
    385                 390                 395                 400

Lys Gln Arg Thr Phe Asp Asn Gly Ser Ile Pro His Gln Ile His Leu
                        405                 410                 415

Gly Glu Leu His Ala Ile Leu Arg Arg Gln Glu Asp Phe Tyr Pro Phe
                        420                 425                 430

Leu Lys Asp Asn Arg Glu Lys Ile Glu Lys Ile Leu Thr Phe Arg Ile
                        435                 440                 445

Pro Tyr Tyr Val Gly Pro Leu Ala Arg Gly Asn Ser Arg Phe Ala Trp
                        450                 455                 460

Met Thr Arg Lys Ser Glu Glu Thr Ile Thr Pro Trp Asn Phe Glu Glu
    465                 470                 475                 480
```

-continued

Val Val Asp Lys Gly Ala Ser Ala Gln Ser Phe Ile Glu Arg Met Thr
            485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
            515                 520                 525

Tyr Val Thr Glu Gly Met Arg Lys Pro Ala Phe Leu Ser Gly Glu Gln
            530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
            565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
            595                 600                 605

Asn Glu Glu Asn Glu Asp Ile Leu Glu Asp Ile Val Leu Thr Leu Thr
            610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
            645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
            675                 680                 685

Ala Asn Arg Asn Phe Met Gln Leu Ile His Asp Asp Ser Leu Thr Phe
            690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
            725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
            755                 760                 765

Thr Thr Gln Lys Gly Gln Lys Asn Ser Arg Glu Arg Met Lys Arg Ile
            770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
            805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
            835                 840                 845

Asp Asp Ser Ile Asp Asn Lys Val Leu Thr Arg Ser Asp Lys Asn Arg
            850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
            885                 890                 895

```
Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
            915                 920                 925

Lys His Val Ala Gln Ile Leu Asp Ser Arg Met Asn Thr Lys Tyr Asp
            930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
                980                 985                 990

Val Gly Thr Ala Leu Ile Lys Lys Tyr Pro Lys Leu Glu Ser Glu Phe
            995                 1000                1005

Val Tyr Gly Asp Tyr Lys Val Tyr Asp Val Arg Lys Met Ile Ala
            1010                1015                1020

Lys Ser Glu Gln Glu Ile Gly Lys Ala Thr Ala Lys Tyr Phe Phe
            1025                1030                1035

Tyr Ser Asn Ile Met Asn Phe Phe Lys Thr Glu Ile Thr Leu Ala
            1040                1045                1050

Asn Gly Glu Ile Arg Lys Arg Pro Leu Ile Glu Thr Asn Gly Glu
            1055                1060                1065

Thr Gly Glu Ile Val Trp Asp Lys Gly Arg Asp Phe Ala Thr Val
            1070                1075                1080

Arg Lys Val Leu Ser Met Pro Gln Val Asn Ile Val Lys Lys Thr
            1085                1090                1095

Glu Val Gln Thr Gly Gly Phe Ser Lys Glu Ser Ile Leu Pro Lys
            1100                1105                1110

Arg Asn Ser Asp Lys Leu Ile Ala Arg Lys Lys Asp Trp Asp Pro
            1115                1120                1125

Lys Lys Tyr Gly Gly Phe Asp Ser Pro Thr Val Ala Tyr Ser Val
            1130                1135                1140

Leu Val Val Ala Lys Val Glu Lys Gly Lys Ser Lys Lys Leu Lys
            1145                1150                1155

Ser Val Lys Glu Leu Leu Gly Ile Thr Ile Met Glu Arg Ser Ser
            1160                1165                1170

Phe Glu Lys Asn Pro Ile Asp Phe Leu Glu Ala Lys Gly Tyr Lys
            1175                1180                1185

Glu Val Lys Lys Asp Leu Ile Ile Lys Leu Pro Lys Tyr Ser Leu
            1190                1195                1200

Phe Glu Leu Glu Asn Gly Arg Lys Arg Met Leu Ala Ser Ala Gly
            1205                1210                1215

Glu Leu Gln Lys Gly Asn Glu Leu Ala Leu Pro Ser Lys Tyr Val
            1220                1225                1230

Asn Phe Leu Tyr Leu Ala Ser His Tyr Glu Lys Leu Lys Gly Ser
            1235                1240                1245

Pro Glu Asp Asn Glu Gln Lys Gln Leu Phe Val Glu Gln His Lys
            1250                1255                1260

His Tyr Leu Asp Glu Ile Ile Glu Gln Ile Ser Glu Phe Ser Lys
            1265                1270                1275

Arg Val Ile Leu Ala Asp Ala Asn Leu Asp Lys Val Leu Ser Ala
            1280                1285                1290

Tyr Asn Lys His Arg Asp Lys Pro Ile Arg Glu Gln Ala Glu Asn
```

```
                    1295                1300                1305

Ile  Ile  His  Leu  Phe  Thr  Leu  Thr  Asn  Leu  Gly  Ala  Pro  Ala  Ala
          1310                1315                1320

Phe  Lys  Tyr  Phe  Asp  Thr  Thr  Ile  Asp  Arg  Lys  Arg  Tyr  Thr  Ser
     1325                1330                1335

Thr  Lys  Glu  Val  Leu  Asp  Ala  Thr  Leu  Ile  His  Gln  Ser  Ile  Thr
1340                1345                1350

Gly  Leu  Tyr  Glu  Thr  Arg  Ile  Asp  Leu  Ser  Gln  Leu  Gly  Gly  Asp
     1355                1360                1365

<210> SEQ ID NO 19
<211> LENGTH: 1300
<212> TYPE: PRT
<213> ORGANISM: Francisella tularensis

<400> SEQUENCE: 19

Met  Ser  Ile  Tyr  Gln  Glu  Phe  Val  Asn  Lys  Tyr  Ser  Leu  Ser  Lys  Thr
1                   5                   10                  15

Leu  Arg  Phe  Glu  Leu  Ile  Pro  Gln  Gly  Lys  Thr  Leu  Glu  Asn  Ile  Lys
               20                  25                  30

Ala  Arg  Gly  Leu  Ile  Leu  Asp  Asp  Glu  Lys  Arg  Ala  Lys  Asp  Tyr  Lys
          35                  40                  45

Lys  Ala  Lys  Gln  Ile  Ile  Asp  Lys  Tyr  His  Gln  Phe  Phe  Ile  Glu  Glu
50                  55                  60

Ile  Leu  Ser  Ser  Val  Cys  Ile  Ser  Glu  Asp  Leu  Leu  Gln  Asn  Tyr  Ser
65                  70                  75                  80

Asp  Val  Tyr  Phe  Lys  Leu  Lys  Lys  Ser  Asp  Asp  Asp  Asn  Leu  Gln  Lys
               85                  90                  95

Asp  Phe  Lys  Ser  Ala  Lys  Asp  Thr  Ile  Lys  Lys  Gln  Ile  Ser  Glu  Tyr
          100                 105                 110

Ile  Lys  Asp  Ser  Glu  Lys  Phe  Lys  Asn  Leu  Phe  Asn  Gln  Asn  Leu  Ile
          115                 120                 125

Asp  Ala  Lys  Lys  Gly  Gln  Glu  Ser  Asp  Leu  Ile  Leu  Trp  Leu  Lys  Gln
130                 135                 140

Ser  Lys  Asp  Asn  Gly  Ile  Glu  Leu  Phe  Lys  Ala  Asn  Ser  Asp  Ile  Thr
145                 150                 155                 160

Asp  Ile  Asp  Glu  Ala  Leu  Glu  Ile  Ile  Lys  Ser  Phe  Lys  Gly  Trp  Thr
               165                 170                 175

Thr  Tyr  Phe  Lys  Gly  Phe  His  Glu  Asn  Arg  Lys  Asn  Val  Tyr  Ser  Ser
          180                 185                 190

Asn  Asp  Ile  Pro  Thr  Ser  Ile  Ile  Tyr  Arg  Ile  Val  Asp  Asp  Asn  Leu
          195                 200                 205

Pro  Lys  Phe  Leu  Glu  Asn  Lys  Ala  Lys  Tyr  Glu  Ser  Leu  Lys  Asp  Lys
210                 215                 220

Ala  Pro  Glu  Ala  Ile  Asn  Tyr  Glu  Gln  Ile  Lys  Lys  Asp  Leu  Ala  Glu
225                 230                 235                 240

Glu  Leu  Thr  Phe  Asp  Ile  Asp  Tyr  Lys  Thr  Ser  Glu  Val  Asn  Gln  Arg
               245                 250                 255

Val  Phe  Ser  Leu  Asp  Glu  Val  Phe  Glu  Ile  Ala  Asn  Phe  Asn  Asn  Tyr
          260                 265                 270

Leu  Asn  Gln  Ser  Gly  Ile  Thr  Lys  Phe  Asn  Thr  Ile  Ile  Gly  Gly  Lys
          275                 280                 285

Phe  Val  Asn  Gly  Glu  Asn  Thr  Lys  Arg  Lys  Gly  Ile  Asn  Glu  Tyr  Ile
290                 295                 300
```

```
Asn Leu Tyr Ser Gln Gln Ile Asn Asp Lys Thr Leu Lys Lys Tyr Lys
305                 310                 315                 320

Met Ser Val Leu Phe Lys Gln Ile Leu Ser Asp Thr Glu Ser Lys Ser
            325                 330                 335

Phe Val Ile Asp Lys Leu Glu Asp Ser Asp Val Val Thr Thr Met
                340                 345                 350

Gln Ser Phe Tyr Glu Gln Ile Ala Ala Phe Lys Thr Val Glu Glu Lys
        355                 360                 365

Ser Ile Lys Glu Thr Leu Ser Leu Leu Phe Asp Asp Leu Lys Ala Gln
370                 375                 380

Lys Leu Asp Leu Ser Lys Ile Tyr Phe Lys Asn Asp Lys Ser Leu Thr
385                 390                 395                 400

Asp Leu Ser Gln Gln Val Phe Asp Asp Tyr Ser Val Ile Gly Thr Ala
                405                 410                 415

Val Leu Glu Tyr Ile Thr Gln Gln Ile Ala Pro Lys Asn Leu Asp Asn
                420                 425                 430

Pro Ser Lys Lys Glu Gln Glu Leu Ile Ala Lys Thr Glu Lys Ala
        435                 440                 445

Lys Tyr Leu Ser Leu Glu Thr Ile Lys Leu Ala Leu Glu Glu Phe Asn
450                 455                 460

Lys His Arg Asp Ile Asp Lys Gln Cys Arg Phe Glu Glu Ile Leu Ala
465                 470                 475                 480

Asn Phe Ala Ala Ile Pro Met Ile Phe Asp Glu Ile Ala Gln Asn Lys
                485                 490                 495

Asp Asn Leu Ala Gln Ile Ser Ile Lys Tyr Gln Asn Gln Gly Lys Lys
            500                 505                 510

Asp Leu Leu Gln Ala Ser Ala Glu Asp Val Lys Ala Ile Lys Asp
            515                 520                 525

Leu Leu Asp Gln Thr Asn Asn Leu Leu His Lys Leu Lys Ile Phe His
530                 535                 540

Ile Ser Gln Ser Glu Asp Lys Ala Asn Ile Leu Asp Lys Asp Glu His
545                 550                 555                 560

Phe Tyr Leu Val Phe Glu Glu Cys Tyr Phe Glu Leu Ala Asn Ile Val
                565                 570                 575

Pro Leu Tyr Asn Lys Ile Arg Asn Tyr Ile Thr Gln Lys Pro Tyr Ser
            580                 585                 590

Asp Glu Lys Phe Lys Leu Asn Phe Glu Asn Ser Thr Leu Ala Asn Gly
        595                 600                 605

Trp Asp Lys Asn Lys Glu Pro Asp Asn Thr Ala Ile Leu Phe Ile Lys
610                 615                 620

Asp Asp Lys Tyr Tyr Leu Gly Val Met Asn Lys Lys Asn Asn Lys Ile
625                 630                 635                 640

Phe Asp Asp Lys Ala Ile Lys Glu Asn Lys Gly Glu Gly Tyr Lys Lys
                645                 650                 655

Ile Val Tyr Lys Leu Leu Pro Gly Ala Asn Lys Met Leu Pro Lys Val
                660                 665                 670

Phe Phe Ser Ala Lys Ser Ile Lys Phe Tyr Asn Pro Ser Glu Asp Ile
                675                 680                 685

Leu Arg Ile Arg Asn His Ser Thr His Thr Lys Asn Gly Ser Pro Gln
            690                 695                 700

Lys Gly Tyr Glu Lys Phe Glu Phe Asn Ile Glu Asp Cys Arg Lys Phe
705                 710                 715                 720

Ile Asp Phe Tyr Lys Gln Ser Ile Ser Lys His Pro Glu Trp Lys Asp
```

```
                725                 730                 735
Phe Gly Phe Arg Phe Ser Asp Thr Gln Arg Tyr Asn Ser Ile Asp Glu
                740                 745                 750

Phe Tyr Arg Glu Val Glu Asn Gln Gly Tyr Lys Leu Thr Phe Glu Asn
                755                 760                 765

Ile Ser Glu Ser Tyr Ile Asp Ser Val Val Asn Gln Gly Lys Leu Tyr
                770                 775                 780

Leu Phe Gln Ile Tyr Asn Lys Asp Phe Ser Ala Tyr Ser Lys Gly Arg
785                 790                 795                 800

Pro Asn Leu His Thr Leu Tyr Trp Lys Ala Leu Phe Asp Glu Arg Asn
                805                 810                 815

Leu Gln Asp Val Val Tyr Lys Leu Asn Gly Glu Ala Glu Leu Phe Tyr
                820                 825                 830

Arg Lys Gln Ser Ile Pro Lys Lys Ile Thr His Pro Ala Lys Glu Ala
                835                 840                 845

Ile Ala Asn Lys Asn Lys Asp Asn Pro Lys Lys Glu Ser Val Phe Glu
                850                 855                 860

Tyr Asp Leu Ile Lys Asp Lys Arg Phe Thr Glu Asp Lys Phe Phe Phe
865                 870                 875                 880

His Cys Pro Ile Thr Ile Asn Phe Lys Ser Ser Gly Ala Asn Lys Phe
                885                 890                 895

Asn Asp Glu Ile Asn Leu Leu Leu Lys Glu Lys Ala Asn Asp Val His
                900                 905                 910

Ile Leu Ser Ile Asp Arg Gly Glu Arg His Leu Ala Tyr Tyr Thr Leu
                915                 920                 925

Val Asp Gly Lys Gly Asn Ile Ile Lys Gln Asp Thr Phe Asn Ile Ile
                930                 935                 940

Gly Asn Asp Arg Met Lys Thr Asn Tyr His Asp Lys Leu Ala Ala Ile
945                 950                 955                 960

Glu Lys Asp Arg Asp Ser Ala Arg Lys Asp Trp Lys Lys Ile Asn Asn
                965                 970                 975

Ile Lys Glu Met Lys Glu Gly Tyr Leu Ser Gln Val Val His Glu Ile
                980                 985                 990

Ala Lys Leu Val Ile Glu Tyr Asn Ala Ile Val Val Phe Glu Asp Leu
                995                 1000                1005

Asn Phe Gly Phe Lys Arg Gly Arg Phe Lys Val Glu Lys Gln Val
                1010                1015                1020

Tyr Gln Lys Leu Glu Lys Met Leu Ile Glu Lys Leu Asn Tyr Leu
                1025                1030                1035

Val Phe Lys Asp Asn Glu Phe Asp Lys Thr Gly Gly Val Leu Arg
                1040                1045                1050

Ala Tyr Gln Leu Thr Ala Pro Phe Glu Thr Phe Lys Lys Met Gly
                1055                1060                1065

Lys Gln Thr Gly Ile Ile Tyr Tyr Val Pro Ala Gly Phe Thr Ser
                1070                1075                1080

Lys Ile Cys Pro Val Thr Gly Phe Val Asn Gln Leu Tyr Pro Lys
                1085                1090                1095

Tyr Glu Ser Val Ser Lys Ser Gln Glu Phe Phe Ser Lys Phe Asp
                1100                1105                1110

Lys Ile Cys Tyr Asn Leu Asp Lys Gly Tyr Phe Glu Phe Ser Phe
                1115                1120                1125

Asp Tyr Lys Asn Phe Gly Asp Lys Ala Ala Lys Gly Lys Trp Thr
                1130                1135                1140
```

```
Ile Ala Ser Phe Gly Ser Arg Leu Ile Asn Phe Arg Asn Ser Asp
    1145            1150                1155
Lys Asn His Asn Trp Asp Thr Arg Glu Val Tyr Pro Thr Lys Glu
    1160            1165                1170
Leu Glu Lys Leu Leu Lys Asp Tyr Ser Ile Glu Tyr Gly His Gly
    1175            1180                1185
Glu Cys Ile Lys Ala Ala Ile Cys Gly Glu Ser Asp Lys Lys Phe
    1190            1195                1200
Phe Ala Lys Leu Thr Ser Val Leu Asn Thr Ile Leu Gln Met Arg
    1205            1210                1215
Asn Ser Lys Thr Gly Thr Glu Leu Asp Tyr Leu Ile Ser Pro Val
    1220            1225                1230
Ala Asp Val Asn Gly Asn Phe Phe Asp Ser Arg Gln Ala Pro Lys
    1235            1240                1245
Asn Met Pro Gln Asp Ala Asp Ala Asn Gly Ala Tyr His Ile Gly
    1250            1255                1260
Leu Lys Gly Leu Met Leu Leu Gly Arg Ile Lys Asn Asn Gln Glu
    1265            1270                1275
Gly Lys Lys Leu Asn Leu Val Ile Lys Asn Glu Glu Tyr Phe Glu
    1280            1285                1290
Phe Val Gln Asn Arg Asn Asn
    1295            1300

<210> SEQ ID NO 20
<211> LENGTH: 3
<212> TYPE: DNA
<213> ORGANISM: Unknown
<220> FEATURE:
<221> NAME/KEY: source
<223> OTHER INFORMATION: /note="Description of Unknown:
      PAM sequence"
<220> FEATURE:
<221> NAME/KEY: modified_base
<222> LOCATION: (1)..(1)
<223> OTHER INFORMATION: a, c, t, g, unknown or other

<400> SEQUENCE: 20 ngg                                                          3

<210> SEQ ID NO 21
<211> LENGTH: 3
<212> TYPE: DNA
<213> ORGANISM: Unknown
<220> FEATURE:
<221> NAME/KEY: source
<223> OTHER INFORMATION: /note="Description of Unknown:
      PAM sequence"
<220> FEATURE:
<221> NAME/KEY: modified_base
<222> LOCATION: (1)..(1)
<223> OTHER INFORMATION: a, c, t, g, unknown or other

<400> SEQUENCE: 21 ngg                                                          3

<210> SEQ ID NO 22
<211> LENGTH: 4
<212> TYPE: DNA
<213> ORGANISM: Unknown
<220> FEATURE:
<221> NAME/KEY: source
<223> OTHER INFORMATION: /note="Description of Unknown:
      PAM sequence"
```

-continued

```
<220> FEATURE:
<221> NAME/KEY: modified_base
<222> LOCATION: (1)..(1)
<223> OTHER INFORMATION: a, c, t, g, unknown or other

<400> SEQUENCE: 22 ngcg                                                                4

<210> SEQ ID NO 23
<211> LENGTH: 4
<212> TYPE: DNA
<213> ORGANISM: Unknown
<220> FEATURE:
<221> NAME/KEY: source
<223> OTHER INFORMATION: /note="Description of Unknown:
      PAM sequence"
<220> FEATURE:
<221> NAME/KEY: modified_base
<222> LOCATION: (1)..(1)
<223> OTHER INFORMATION: a, c, t, g, unknown or other

<400> SEQUENCE: 23 ngag                                                                4

<210> SEQ ID NO 24
<211> LENGTH: 4
<212> TYPE: DNA
<213> ORGANISM: Unknown
<220> FEATURE:
<221> NAME/KEY: source
<223> OTHER INFORMATION: /note="Description of Unknown:
      PAM sequence"
<220> FEATURE:
<221> NAME/KEY: modified_base
<222> LOCATION: (1)..(1)
<223> OTHER INFORMATION: a, c, t, g, unknown or other
<220> FEATURE:
<221> NAME/KEY: modified_base
<222> LOCATION: (4)..(4)
<223> OTHER INFORMATION: a, c, t, g, unknown or other

<400> SEQUENCE: 24 ngan                                                                4

<210> SEQ ID NO 25
<211> LENGTH: 4
<212> TYPE: DNA
<213> ORGANISM: Unknown
<220> FEATURE:
<221> NAME/KEY: source
<223> OTHER INFORMATION: /note="Description of Unknown:
      PAM sequence"
<220> FEATURE:
<221> NAME/KEY: modified_base
<222> LOCATION: (1)..(1)
<223> OTHER INFORMATION: a, c, t, g, unknown or other
<220> FEATURE:
<221> NAME/KEY: modified_base
<222> LOCATION: (3)..(3)
<223> OTHER INFORMATION: a, c, t, g, unknown or other

<400> SEQUENCE: 25 ngng                                                                4

<210> SEQ ID NO 26
<211> LENGTH: 6
<212> TYPE: DNA
<213> ORGANISM: Unknown
<220> FEATURE:
<221> NAME/KEY: source
<223> OTHER INFORMATION: /note="Description of Unknown:
```

```
      PAM sequence"
<220> FEATURE:
<221> NAME/KEY: modified_base
<222> LOCATION: (1)..(2)
<223> OTHER INFORMATION: a, c, t, g, unknown or other

<400> SEQUENCE: 26 nngrrt                                                                            6

<210> SEQ ID NO 27
<211> LENGTH: 6
<212> TYPE: DNA
<213> ORGANISM: Unknown
<220> FEATURE:
<221> NAME/KEY: source
<223> OTHER INFORMATION: /note="Description of Unknown:
      PAM sequence"
<220> FEATURE:
<221> NAME/KEY: modified_base
<222> LOCATION: (1)..(2)
<223> OTHER INFORMATION: a, c, t, g, unknown or other
<220> FEATURE:
<221> NAME/KEY: modified_base
<222> LOCATION: (6)..(6)
<223> OTHER INFORMATION: a, c, t, g, unknown or other
<220> FEATURE:
<221> NAME/KEY: variation
<222> LOCATION: (6)..(6)
<223> OTHER INFORMATION: /replace=" "
<220> FEATURE:
<221> NAME/KEY: misc_feature
<222> LOCATION: (1)..(6)
<223> OTHER INFORMATION: /note="Variant nucleotides given in the
      sequence have no preference with respect to those in the
      annotations for variant positions"

<400> SEQUENCE: 27 nngrrn                                                                            6

<210> SEQ ID NO 28
<211> LENGTH: 8
<212> TYPE: DNA
<213> ORGANISM: Unknown
<220> FEATURE:
<221> NAME/KEY: source
<223> OTHER INFORMATION: /note="Description of Unknown:
      PAM sequence"
<220> FEATURE:
<221> NAME/KEY: modified_base
<222> LOCATION: (1)..(4)
<223> OTHER INFORMATION: a, c, t, g, unknown or other

<400> SEQUENCE: 28 nnnngatt                                                                          8

<210> SEQ ID NO 29
<211> LENGTH: 7
<212> TYPE: DNA
<213> ORGANISM: Unknown
<220> FEATURE:
<221> NAME/KEY: source
<223> OTHER INFORMATION: /note="Description of Unknown:
      PAM sequence"
<220> FEATURE:
<221> NAME/KEY: modified_base
<222> LOCATION: (1)..(2)
<223> OTHER INFORMATION: a, c, t, g, unknown or other

<400> SEQUENCE: 29 nnagaaw                                                                           7
```

-continued

```
<210> SEQ ID NO 30
<211> LENGTH: 6
<212> TYPE: DNA
<213> ORGANISM: Unknown
<220> FEATURE:
<221> NAME/KEY: source
<223> OTHER INFORMATION: /note="Description of Unknown:
      PAM sequence"
<220> FEATURE:
<221> NAME/KEY: modified_base
<222> LOCATION: (1)..(1)
<223> OTHER INFORMATION: a, c, t, g, unknown or other

<400> SEQUENCE: 30 naaaac                                                              6

<210> SEQ ID NO 31
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 31

Lys Glu Ser Gly Ser Val Ser Ser Glu Gln Leu Ala Gln Phe Arg Ser
1               5                   10                  15

Leu Asp

<210> SEQ ID NO 32
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 32

Glu Gly Lys Ser Ser Gly Ser Gly Ser Glu Ser Lys Ser Thr
1               5                   10

<210> SEQ ID NO 33
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 33

Gly Gly Gly Gly Gly Gly Gly Gly
1               5

<210> SEQ ID NO 34
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 34

Gly Ser Ala Gly Ser Ala Ala Gly Ser Gly Glu Phe
1               5                   10
```

```
<210> SEQ ID NO 35
<211> LENGTH: 27
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MISC_FEATURE
<222> LOCATION: (2)..(26)
<223> OTHER INFORMATION: /note="This region may encompass 2-5 "Glu Ala
      Ala Ala Lys" repeating units"

<400> SEQUENCE: 35

Ala Glu Ala Ala Ala Lys Glu Ala Ala Ala Lys Glu Ala Ala Ala Lys
1               5                   10                  15

Glu Ala Ala Ala Lys Glu Ala Ala Ala Lys Ala
            20                  25

<210> SEQ ID NO 36
<211> LENGTH: 1686
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 36

Met Ala Pro Lys Lys Lys Arg Lys Val Gly Ile His Gly Val Pro Ala
1               5                   10                  15

Ala Lys Arg Asn Tyr Ile Leu Gly Leu Asp Ile Gly Ile Thr Ser Val
            20                  25                  30

Gly Tyr Gly Ile Ile Asp Tyr Glu Thr Arg Asp Val Ile Asp Ala Gly
        35                  40                  45

Val Arg Leu Phe Lys Glu Ala Asn Val Glu Asn Asn Glu Gly Arg Arg
    50                  55                  60

Ser Lys Arg Gly Ala Arg Arg Leu Lys Arg Arg Arg His Arg Ile
65                  70                  75                  80

Gln Arg Val Lys Lys Leu Leu Phe Asp Tyr Asn Leu Leu Thr Asp His
                85                  90                  95

Ser Glu Leu Ser Gly Ile Asn Pro Tyr Glu Ala Arg Val Lys Gly Leu
            100                 105                 110

Ser Gln Lys Leu Ser Glu Glu Glu Phe Ser Ala Ala Leu Leu His Leu
        115                 120                 125

Ala Lys Arg Arg Gly Val His Asn Val Asn Glu Val Glu Glu Asp Thr
    130                 135                 140

Gly Asn Glu Leu Ser Thr Lys Glu Gln Ile Ser Arg Asn Ser Lys Ala
145                 150                 155                 160

Leu Glu Glu Lys Tyr Val Ala Glu Leu Gln Leu Glu Arg Leu Lys Lys
                165                 170                 175

Asp Gly Glu Val Arg Gly Ser Ile Asn Arg Phe Lys Thr Ser Asp Tyr
            180                 185                 190

Val Lys Glu Ala Lys Gln Leu Leu Lys Val Gln Lys Ala Tyr His Gln
        195                 200                 205

Leu Asp Gln Ser Phe Ile Asp Thr Tyr Ile Asp Leu Leu Glu Thr Arg
    210                 215                 220

Arg Thr Tyr Tyr Glu Gly Pro Gly Glu Gly Ser Pro Phe Gly Trp Lys
225                 230                 235                 240
```

```
Asp Ile Lys Glu Trp Tyr Glu Met Leu Met Gly His Cys Thr Tyr Phe
                245                 250                 255

Pro Glu Glu Leu Arg Ser Val Lys Tyr Ala Tyr Asn Ala Asp Leu Tyr
            260                 265                 270

Asn Ala Leu Asn Asp Leu Asn Asn Leu Val Ile Thr Arg Asp Glu Asn
        275                 280                 285

Glu Lys Leu Glu Tyr Tyr Glu Lys Phe Gln Ile Ile Glu Asn Val Phe
    290                 295                 300

Lys Gln Lys Lys Lys Pro Thr Leu Lys Gln Ile Ala Lys Glu Ile Leu
305                 310                 315                 320

Val Asn Glu Glu Asp Ile Lys Gly Tyr Arg Val Thr Ser Thr Gly Lys
                325                 330                 335

Pro Glu Phe Thr Asn Leu Lys Val Tyr His Asp Ile Lys Asp Ile Thr
            340                 345                 350

Ala Arg Lys Glu Ile Ile Glu Asn Ala Glu Leu Leu Asp Gln Ile Ala
        355                 360                 365

Lys Ile Leu Thr Ile Tyr Gln Ser Ser Glu Asp Ile Gln Glu Glu Leu
    370                 375                 380

Thr Asn Leu Asn Ser Glu Leu Thr Gln Glu Glu Ile Glu Gln Ile Ser
385                 390                 395                 400

Asn Leu Lys Gly Tyr Thr Gly Thr His Asn Leu Ser Leu Lys Ala Ile
                405                 410                 415

Asn Leu Ile Leu Asp Glu Leu Trp His Thr Asn Asp Asn Gln Ile Ala
            420                 425                 430

Ile Phe Asn Arg Leu Lys Leu Val Pro Lys Lys Val Asp Leu Ser Gln
        435                 440                 445

Gln Lys Glu Ile Pro Thr Thr Leu Val Asp Asp Phe Ile Leu Ser Pro
    450                 455                 460

Val Val Lys Arg Ser Phe Ile Gln Ser Ile Lys Val Ile Asn Ala Ile
465                 470                 475                 480

Ile Lys Lys Tyr Gly Leu Pro Asn Asp Ile Ile Glu Leu Ala Arg
                485                 490                 495

Glu Lys Asn Ser Lys Asp Ala Gln Lys Met Ile Asn Glu Met Gln Lys
            500                 505                 510

Arg Asn Arg Gln Thr Asn Glu Arg Ile Glu Glu Ile Ile Arg Thr Thr
        515                 520                 525

Gly Lys Glu Asn Ala Lys Tyr Leu Ile Glu Lys Ile Lys Leu His Asp
    530                 535                 540

Met Gln Glu Gly Lys Cys Leu Tyr Ser Leu Glu Ala Ile Pro Leu Glu
545                 550                 555                 560

Asp Leu Leu Asn Asn Pro Phe Asn Tyr Glu Val Asp His Ile Ile Pro
                565                 570                 575

Arg Ser Val Ser Phe Asp Asn Ser Phe Asn Asn Lys Val Leu Val Lys
            580                 585                 590

Gln Glu Glu Asn Ser Lys Lys Gly Asn Arg Thr Pro Phe Gln Tyr Leu
        595                 600                 605

Ser Ser Ser Asp Ser Lys Ile Ser Tyr Glu Thr Phe Lys Lys His Ile
    610                 615                 620

Leu Asn Leu Ala Lys Gly Lys Gly Arg Ile Ser Lys Thr Lys Lys Glu
625                 630                 635                 640

Tyr Leu Leu Glu Glu Arg Asp Ile Asn Arg Phe Ser Val Gln Lys Asp
                645                 650                 655
```

Phe Ile Asn Arg Asn Leu Val Asp Thr Arg Tyr Ala Thr Arg Gly Leu
                660                 665                 670

Met Asn Leu Leu Arg Ser Tyr Phe Arg Val Asn Asn Leu Asp Val Lys
        675                 680                 685

Val Lys Ser Ile Asn Gly Gly Phe Thr Ser Phe Leu Arg Arg Lys Trp
690                 695                 700

Lys Phe Lys Lys Glu Arg Asn Lys Gly Tyr Lys His His Ala Glu Asp
705                 710                 715                 720

Ala Leu Ile Ile Ala Asn Ala Asp Phe Ile Phe Lys Glu Trp Lys Lys
                725                 730                 735

Leu Asp Lys Ala Lys Lys Val Met Glu Asn Gln Met Phe Glu Glu Lys
        740                 745                 750

Gln Ala Glu Ser Met Pro Glu Ile Glu Thr Glu Gln Glu Tyr Lys Glu
755                 760                 765

Ile Phe Ile Thr Pro His Gln Ile Lys His Ile Lys Asp Phe Lys Asp
770                 775                 780

Tyr Lys Tyr Ser His Arg Val Asp Lys Lys Pro Asn Arg Glu Leu Ile
785                 790                 795                 800

Asn Asp Thr Leu Tyr Ser Thr Arg Lys Asp Asp Lys Gly Asn Thr Leu
                805                 810                 815

Ile Val Asn Asn Leu Asn Gly Leu Tyr Asp Lys Asp Asn Asp Lys Leu
                820                 825                 830

Lys Lys Leu Ile Asn Lys Ser Pro Glu Lys Leu Leu Met Tyr His His
        835                 840                 845

Asp Pro Gln Thr Tyr Gln Lys Leu Lys Leu Ile Met Glu Gln Tyr Gly
850                 855                 860

Asp Glu Lys Asn Pro Leu Tyr Lys Tyr Tyr Glu Glu Thr Gly Asn Tyr
865                 870                 875                 880

Leu Thr Lys Tyr Ser Lys Lys Asp Asn Gly Pro Val Ile Lys Lys Ile
                885                 890                 895

Lys Tyr Tyr Gly Asn Lys Leu Asn Ala His Leu Asp Ile Thr Asp Asp
                900                 905                 910

Tyr Pro Asn Ser Arg Asn Lys Val Val Lys Leu Ser Leu Lys Pro Tyr
        915                 920                 925

Arg Phe Asp Val Tyr Leu Asp Asn Gly Val Tyr Lys Phe Val Thr Val
930                 935                 940

Lys Asn Leu Asp Val Ile Lys Lys Glu Asn Tyr Tyr Glu Val Asn Ser
945                 950                 955                 960

Lys Cys Tyr Glu Glu Ala Lys Lys Leu Lys Lys Ile Ser Asn Gln Ala
                965                 970                 975

Glu Phe Ile Ala Ser Phe Tyr Asn Asn Asp Leu Ile Lys Ile Asn Gly
        980                 985                 990

Glu Leu Tyr Arg Val Ile Gly Val Asn Asn Asp Leu Leu Asn Arg Ile
        995                 1000                1005

Glu Val Asn Met Ile Asp Ile Thr Tyr Arg Glu Tyr Leu Glu Asn
        1010                1015                1020

Met Asn Asp Lys Arg Pro Pro Arg Ile Ile Lys Thr Ile Ala Ser
        1025                1030                1035

Lys Thr Gln Ser Ile Lys Lys Tyr Ser Thr Asp Ile Leu Gly Asn
        1040                1045                1050

Leu Tyr Glu Val Lys Ser Lys Lys His Pro Gln Ile Ile Lys Lys
        1055                1060                1065

Gly Ser Gly Phe Ala Asn Glu Leu Gly Pro Arg Leu Met Gly Lys

```
                      1070                1075                1080
Thr Ser Thr Ala Pro Gly Lys Lys Arg Pro Val Glu Pro Ser Pro
    1085                1090                1095
Gln Arg Ser Pro Asp Ser Ser Thr Gly Ile Gly Lys Lys Gly Gln
    1100                1105                1110
Gln Pro Ala Lys Lys Arg Leu Asn Phe Gly Gln Thr Gly Asp Ser
    1115                1120                1125
Glu Ser Val Pro Asp Pro Gln Pro Ile Gly Glu Pro Pro Ala Gly
    1130                1135                1140
Pro Ser Gly Leu Gly Ser Gly Thr Leu Ala Ala Gly Gly Gly Ala
    1145                1150                1155
Pro Leu Ala Asp Asn Asn Glu Gly Ala Asp Gly Val Gly Ser Ser
    1160                1165                1170
Ser Gly Asn Trp His Cys Asp Ser Thr Trp Leu Gly Asp Arg Val
    1175                1180                1185
Ile Thr Thr Ser Thr Arg Thr Trp Ala Leu Pro Thr Tyr Asn Asn
    1190                1195                1200
His Leu Tyr Lys Gln Ile Ser Asn Gly Thr Ser Gly Gly Ser Thr
    1205                1210                1215
Asn Asp Asn Thr Tyr Phe Gly Tyr Ser Thr Pro Trp Gly Tyr Phe
    1220                1225                1230
Asp Phe Asn Arg Phe His Cys His Phe Ser Pro Arg Asp Trp Gln
    1235                1240                1245
Arg Leu Ile Asn Asn Asn Trp Gly Phe Arg Pro Lys Arg Leu Asn
    1250                1255                1260
Phe Lys Leu Phe Asn Ile Gln Val Lys Glu Val Thr Gln Asn Glu
    1265                1270                1275
Gly Thr Lys Thr Ile Ala Asn Asn Leu Thr Ser Thr Ile Gln Val
    1280                1285                1290
Phe Thr Asp Ser Glu Tyr Gln Leu Pro Tyr Val Leu Gly Ser Ala
    1295                1300                1305
His Gln Gly Cys Leu Pro Pro Phe Pro Ala Asp Val Phe Met Ile
    1310                1315                1320
Pro Gln Tyr Gly Tyr Leu Thr Leu Asn Asn Gly Ser Gln Ala Val
    1325                1330                1335
Gly Arg Ser Ser Phe Tyr Cys Leu Glu Tyr Phe Pro Ser Gln Met
    1340                1345                1350
Leu Arg Thr Gly Asn Asn Phe Glu Phe Ser Tyr Asn Phe Glu Asp
    1355                1360                1365
Val Pro Phe His Ser Ser Tyr Ala His Ser Gln Ser Leu Asp Arg
    1370                1375                1380
Leu Met Asn Pro Leu Ile Asp Gln Tyr Leu Tyr Tyr Leu Ser Arg
    1385                1390                1395
Thr Gln Ser Thr Gly Gly Thr Ala Gly Thr Gln Gln Leu Leu Phe
    1400                1405                1410
Ser Gln Ala Gly Pro Asn Asn Met Ser Ala Gln Ala Lys Asn Trp
    1415                1420                1425
Leu Pro Gly Pro Cys Tyr Arg Gln Gln Arg Val Ser Thr Thr Leu
    1430                1435                1440
Ser Gln Asn Asn Asn Ser Asn Phe Ala Trp Thr Gly Ala Thr Lys
    1445                1450                1455
Tyr His Leu Asn Gly Arg Asp Ser Leu Val Asn Pro Gly Val Ala
    1460                1465                1470
```

```
Met Ala Thr His Lys Asp Asp Glu Glu Arg Phe Phe Pro Ser Ser
    1475                1480                1485
Gly Val Leu Met Phe Gly Lys Gln Gly Ala Gly Lys Asp Asn Val
    1490                1495                1500
Asp Tyr Ser Ser Val Met Leu Thr Ser Glu Glu Ile Lys Thr
    1505                1510                1515
Thr Asn Pro Val Ala Thr Glu Gln Tyr Gly Val Val Ala Asp Asn
    1520                1525                1530
Leu Gln Gln Gln Asn Ala Ala Pro Ile Val Gly Ala Val Asn Ser
    1535                1540                1545
Gln Gly Ala Leu Pro Gly Met Val Trp Gln Asn Arg Asp Val Tyr
    1550                1555                1560
Leu Gln Gly Pro Ile Trp Ala Lys Ile Pro His Thr Asp Gly Asn
    1565                1570                1575
Phe His Pro Ser Pro Leu Met Gly Gly Phe Gly Leu Lys His Pro
    1580                1585                1590
Pro Pro Gln Ile Leu Ile Lys Asn Thr Pro Val Pro Ala Asp Pro
    1595                1600                1605
Pro Thr Thr Phe Ser Gln Ala Lys Leu Ala Ser Phe Ile Thr Gln
    1610                1615                1620
Tyr Ser Thr Gly Gln Val Ser Val Glu Ile Glu Trp Glu Leu Gln
    1625                1630                1635
Lys Glu Asn Ser Lys Arg Trp Asn Pro Glu Ile Gln Tyr Thr Ser
    1640                1645                1650
Asn Tyr Tyr Lys Ser Thr Asn Val Asp Phe Ala Val Asn Thr Glu
    1655                1660                1665
Gly Thr Tyr Ser Glu Pro Arg Pro Ile Gly Thr Arg Tyr Leu Thr
    1670                1675                1680
Arg Asn Leu
    1685

<210> SEQ ID NO 37
<211> LENGTH: 738
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 37

Met Ala Ala Asp Gly Tyr Leu Pro Asp Trp Leu Glu Asp Asn Leu Ser
1               5                   10                  15
Glu Gly Ile Arg Glu Trp Trp Asp Leu Lys Pro Gly Ala Pro Lys Pro
            20                  25                  30
Lys Ala Asn Gln Gln Lys Gln Asp Asn Gly Arg Gly Leu Val Leu Pro
        35                  40                  45
Gly Tyr Lys Tyr Leu Gly Pro Phe Asn Gly Leu Asp Lys Gly Glu Pro
    50                  55                  60
Val Asn Ala Ala Asp Ala Ala Ala Leu Glu His Asp Lys Ala Tyr Asp
65                  70                  75                  80
Gln Gln Leu Gln Ala Gly Asp Asn Pro Tyr Leu Arg Tyr Asn His Ala
                85                  90                  95
Asp Ala Glu Phe Gln Glu Arg Leu Gln Glu Asp Thr Ser Phe Gly Gly
            100                 105                 110
```

-continued

```
Asn Leu Gly Arg Ala Val Phe Gln Ala Lys Lys Arg Val Leu Glu Pro
            115                 120                 125

Leu Gly Leu Val Glu Ser Pro Val Lys Ala Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Lys Lys Arg Leu Asn Phe Gly Gln
                165                 170                 175

Thr Gly Asp Ser Glu Ser Val Pro Asp Pro Gln Pro Ile Gly Glu Pro
            180                 185                 190

Pro Ala Gly Pro Ser Gly Leu Gly Ser Gly Thr Met Ala Ala Gly Gly
    195                 200                 205

Gly Ala Pro Met Ala Asp Asn Glu Gly Ala Asp Gly Val Gly Ser
210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Asn Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Glu Phe Ser Tyr
                405                 410                 415

Asn Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Ser Arg Thr Gln Ser Thr Gly Gly Thr Ala Gly Thr Gln Gln Leu Leu
    450                 455                 460

Phe Ser Gln Ala Gly Pro Asn Asn Met Ser Ala Gln Ala Lys Asn Trp
465                 470                 475                 480

Leu Pro Gly Pro Cys Tyr Arg Gln Gln Arg Val Ser Thr Thr Leu Ser
                485                 490                 495

Gln Asn Asn Asn Ser Asn Phe Ala Trp Thr Gly Ala Thr Lys Tyr His
            500                 505                 510

Leu Asn Gly Arg Asp Ser Leu Val Asn Pro Gly Val Ala Met Ala Thr
        515                 520                 525

His Lys Asp Asp Glu Glu Arg Phe Phe Pro Ser Ser Gly Val Leu Met
```

```
                530                 535                 540
Phe Gly Lys Gln Gly Ala Gly Lys Asp Asn Val Asp Tyr Ser Ser Val
545                 550                 555                 560

Met Leu Thr Ser Glu Glu Ile Lys Thr Thr Asn Pro Val Ala Thr
                565                 570                 575

Glu Gln Tyr Gly Val Val Ala Asp Asn Leu Gln Gln Asn Ala Ala
                580                 585                 590

Pro Ile Val Gly Ala Val Asn Ser Gln Gly Ala Leu Pro Gly Met Val
                595                 600                 605

Trp Gln Asn Arg Asp Val Tyr Leu Gln Gly Pro Ile Trp Ala Lys Ile
                610                 615                 620

Pro His Thr Asp Gly Asn Phe His Pro Ser Pro Leu Met Gly Gly Phe
625                 630                 635                 640

Gly Leu Lys His Pro Pro Gln Ile Leu Ile Lys Asn Thr Pro Val
                645                 650                 655

Pro Ala Asp Pro Pro Thr Thr Phe Ser Gln Ala Lys Leu Ala Ser Phe
                660                 665                 670

Ile Thr Gln Tyr Ser Thr Gly Gln Val Ser Val Glu Ile Glu Trp Glu
                675                 680                 685

Leu Gln Lys Glu Asn Ser Lys Arg Trp Asn Pro Glu Ile Gln Tyr Thr
                690                 695                 700

Ser Asn Tyr Tyr Lys Ser Thr Asn Val Asp Phe Ala Val Asn Thr Glu
705                 710                 715                 720

Gly Thr Tyr Ser Glu Pro Arg Pro Ile Gly Thr Arg Tyr Leu Thr Arg
                725                 730                 735

Asn Leu

<210> SEQ ID NO 38
<211> LENGTH: 535
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 38

Met Ala Ala Gly Gly Gly Ala Pro Met Ala Asp Asn Asn Glu Gly Ala
1               5                   10                  15

Asp Gly Val Gly Ser Ser Ser Gly Asn Trp His Cys Asp Ser Thr Trp
                20                  25                  30

Leu Gly Asp Arg Val Ile Thr Thr Ser Thr Arg Thr Trp Ala Leu Pro
        35                  40                  45

Thr Tyr Asn Asn His Leu Tyr Lys Gln Ile Ser Asn Gly Thr Ser Gly
    50                  55                  60

Gly Ser Thr Asn Asp Asn Thr Tyr Phe Gly Tyr Ser Thr Pro Trp Gly
65                  70                  75                  80

Tyr Phe Asp Phe Asn Arg Phe His Cys His Phe Ser Pro Arg Asp Trp
                85                  90                  95

Gln Arg Leu Ile Asn Asn Asn Trp Gly Phe Arg Pro Lys Arg Leu Asn
                100                 105                 110

Phe Lys Leu Phe Asn Ile Gln Val Lys Glu Val Thr Gln Asn Glu Gly
        115                 120                 125

Thr Lys Thr Ile Ala Asn Asn Leu Thr Ser Thr Ile Gln Val Phe Thr
    130                 135                 140
```

```
Asp Ser Glu Tyr Gln Leu Pro Tyr Val Leu Gly Ser Ala His Gln Gly
145                 150                 155                 160

Cys Leu Pro Pro Phe Pro Ala Asp Val Phe Met Ile Pro Gln Tyr Gly
                165                 170                 175

Tyr Leu Thr Leu Asn Asn Gly Ser Gln Ala Val Gly Arg Ser Ser Phe
            180                 185                 190

Tyr Cys Leu Glu Tyr Phe Pro Ser Gln Met Leu Arg Thr Gly Asn Asn
        195                 200                 205

Phe Glu Phe Ser Tyr Asn Phe Glu Asp Val Pro Phe His Ser Ser Tyr
    210                 215                 220

Ala His Ser Gln Ser Leu Asp Arg Leu Met Asn Pro Leu Ile Asp Gln
225                 230                 235                 240

Tyr Leu Tyr Tyr Leu Ser Arg Thr Gln Ser Thr Gly Gly Thr Ala Gly
                245                 250                 255

Thr Gln Gln Leu Leu Phe Ser Gln Ala Gly Pro Asn Asn Met Ser Ala
            260                 265                 270

Gln Ala Lys Asn Trp Leu Pro Gly Pro Cys Tyr Arg Gln Gln Arg Val
        275                 280                 285

Ser Thr Thr Leu Ser Gln Asn Asn Asn Ser Asn Phe Ala Trp Thr Gly
    290                 295                 300

Ala Thr Lys Tyr His Leu Asn Gly Arg Asp Ser Leu Val Asn Pro Gly
305                 310                 315                 320

Val Ala Met Ala Thr His Lys Asp Asp Glu Arg Phe Phe Pro Ser
                325                 330                 335

Ser Gly Val Leu Met Phe Gly Lys Gln Gly Ala Gly Lys Asp Asn Val
            340                 345                 350

Asp Tyr Ser Ser Val Met Leu Thr Ser Glu Glu Ile Lys Thr Thr
        355                 360                 365

Asn Pro Val Ala Thr Glu Gln Tyr Gly Val Val Ala Asp Asn Leu Gln
    370                 375                 380

Gln Gln Asn Ala Ala Pro Ile Val Gly Ala Val Asn Ser Gln Gly Ala
385                 390                 395                 400

Leu Pro Gly Met Val Trp Gln Asn Arg Asp Val Tyr Leu Gln Gly Pro
                405                 410                 415

Ile Trp Ala Lys Ile Pro His Thr Asp Gly Asn Phe His Pro Ser Pro
            420                 425                 430

Leu Met Gly Gly Phe Gly Leu Lys His Pro Pro Pro Gln Ile Leu Ile
        435                 440                 445

Lys Asn Thr Pro Val Pro Ala Asp Pro Pro Thr Thr Phe Ser Gln Ala
450                 455                 460

Lys Leu Ala Ser Phe Ile Thr Gln Tyr Ser Thr Gly Gln Val Ser Val
465                 470                 475                 480

Glu Ile Glu Trp Glu Leu Gln Lys Glu Asn Ser Lys Arg Trp Asn Pro
                485                 490                 495

Glu Ile Gln Tyr Thr Ser Asn Tyr Tyr Lys Ser Thr Asn Val Asp Phe
            500                 505                 510

Ala Val Asn Thr Glu Gly Thr Tyr Ser Glu Pro Arg Pro Ile Gly Thr
        515                 520                 525

Arg Tyr Leu Thr Arg Asn Leu
    530                 535

<210> SEQ ID NO 39
<211> LENGTH: 601
<212> TYPE: PRT
```

<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 39

```
Met Ala Ser Gly Lys Lys Arg Ser Val Glu Pro Ser Pro Gln Arg Ser
1               5                   10                  15

Pro Asp Ser Ser Thr Gly Ile Gly Lys Lys Gly Gln Gln Pro Ala Lys
            20                  25                  30

Lys Arg Leu Asn Phe Gly Gln Thr Gly Asp Ser Glu Ser Val Pro Asp
        35                  40                  45

Pro Gln Pro Ile Gly Glu Pro Pro Ala Gly Pro Ser Gly Leu Gly Ser
    50                  55                  60

Gly Thr Met Ala Ala Gly Gly Ala Pro Met Ala Asp Asn Asn Glu
65                  70                  75                  80

Gly Ala Asp Gly Val Gly Ser Ser Gly Asn Trp His Cys Asp Ser
                85                  90                  95

Thr Trp Leu Gly Asp Arg Val Ile Thr Thr Ser Thr Arg Thr Trp Ala
            100                 105                 110

Leu Pro Thr Tyr Asn Asn His Leu Tyr Lys Gln Ile Ser Asn Gly Thr
        115                 120                 125

Ser Gly Gly Ser Thr Asn Asp Asn Thr Tyr Phe Gly Tyr Ser Thr Pro
    130                 135                 140

Trp Gly Tyr Phe Asp Phe Asn Arg Phe His Cys His Phe Ser Pro Arg
145                 150                 155                 160

Asp Trp Gln Arg Leu Ile Asn Asn Trp Gly Phe Arg Pro Lys Arg
                165                 170                 175

Leu Asn Phe Lys Leu Phe Asn Ile Gln Val Lys Glu Val Thr Gln Asn
            180                 185                 190

Glu Gly Thr Lys Thr Ile Ala Asn Asn Leu Thr Ser Thr Ile Gln Val
        195                 200                 205

Phe Thr Asp Ser Glu Tyr Gln Leu Pro Tyr Val Leu Gly Ser Ala His
    210                 215                 220

Gln Gly Cys Leu Pro Pro Phe Pro Ala Asp Val Phe Met Ile Pro Gln
225                 230                 235                 240

Tyr Gly Tyr Leu Thr Leu Asn Asn Gly Ser Gln Ala Val Gly Arg Ser
                245                 250                 255

Ser Phe Tyr Cys Leu Glu Tyr Phe Pro Ser Gln Met Leu Arg Thr Gly
            260                 265                 270

Asn Asn Phe Glu Phe Ser Tyr Asn Phe Glu Asp Val Pro Phe His Ser
        275                 280                 285

Ser Tyr Ala His Ser Gln Ser Leu Asp Arg Leu Met Asn Pro Leu Ile
    290                 295                 300

Asp Gln Tyr Leu Tyr Tyr Leu Ser Arg Thr Gln Ser Thr Gly Gly Thr
305                 310                 315                 320

Ala Gly Thr Gln Gln Leu Leu Phe Ser Gln Ala Gly Pro Asn Asn Met
                325                 330                 335

Ser Ala Gln Ala Lys Asn Trp Leu Pro Gly Pro Cys Tyr Arg Gln Gln
            340                 345                 350

Arg Val Ser Thr Thr Leu Ser Gln Asn Asn Asn Ser Asn Phe Ala Trp
        355                 360                 365

Thr Gly Ala Thr Lys Tyr His Leu Asn Gly Arg Asp Ser Leu Val Asn
    370                 375                 380
```

```
Pro Gly Val Ala Met Ala Thr His Lys Asp Asp Glu Glu Arg Phe Phe
385                 390                 395                 400

Pro Ser Ser Gly Val Leu Met Phe Gly Lys Gln Gly Ala Gly Lys Asp
            405                 410                 415

Asn Val Asp Tyr Ser Ser Val Met Leu Thr Ser Glu Glu Ile Lys
        420                 425                 430

Thr Thr Asn Pro Val Ala Thr Glu Gln Tyr Gly Val Val Ala Asp Asn
        435                 440                 445

Leu Gln Gln Gln Asn Ala Ala Pro Ile Val Gly Ala Val Asn Ser Gln
450                 455                 460

Gly Ala Leu Pro Gly Met Val Trp Gln Asn Arg Asp Val Tyr Leu Gln
465                 470                 475                 480

Gly Pro Ile Trp Ala Lys Ile Pro His Thr Asp Gly Asn Phe His Pro
                485                 490                 495

Ser Pro Leu Met Gly Phe Gly Leu Lys His Pro Pro Gln Ile
            500                 505                 510

Leu Ile Lys Asn Thr Pro Val Pro Ala Asp Pro Thr Thr Phe Ser
        515                 520                 525

Gln Ala Lys Leu Ala Ser Phe Ile Thr Gln Tyr Ser Thr Gly Gln Val
530                 535                 540

Ser Val Glu Ile Glu Trp Glu Leu Gln Lys Glu Asn Ser Lys Arg Trp
545                 550                 555                 560

Asn Pro Glu Ile Gln Tyr Thr Ser Asn Tyr Tyr Lys Ser Thr Asn Val
                565                 570                 575

Asp Phe Ala Val Asn Thr Glu Gly Thr Tyr Ser Glu Pro Arg Pro Ile
                580                 585                 590

Gly Thr Arg Tyr Leu Thr Arg Asn Leu
            595                 600

<210> SEQ ID NO 40
<211> LENGTH: 1137
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 40

Met Gly Gly Arg Arg Val Arg Trp Glu Val Tyr Ile Ser Arg Ala Leu
1               5                   10                  15

Trp Leu Thr Thr Gly Ala Thr Met Ala Pro Lys Lys Arg Lys Val
            20                  25                  30

Gly Ile His Gly Val Pro Ala Ala Lys Arg Asn Tyr Ile Leu Gly Leu
            35                  40                  45

Ala Ile Gly Ile Thr Ser Val Gly Tyr Gly Ile Ile Asp Tyr Glu Thr
50                  55                  60

Arg Asp Val Ile Asp Ala Gly Val Arg Leu Phe Lys Glu Ala Asn Val
65                  70                  75                  80

Glu Asn Asn Glu Gly Arg Arg Ser Lys Arg Gly Ala Arg Arg Leu Lys
                85                  90                  95

Arg Arg Arg Arg His Arg Ile Gln Arg Val Lys Lys Leu Leu Phe Asp
                100                 105                 110

Tyr Asn Leu Leu Thr Asp His Ser Glu Leu Ser Gly Ile Asn Pro Tyr
            115                 120                 125
```

-continued

```
Glu Ala Arg Val Lys Gly Leu Ser Gln Lys Leu Glu Glu Phe
130                 135                 140

Ser Ala Ala Leu Leu His Leu Ala Lys Arg Arg Gly Val His Asn Val
145                 150                 155                 160

Asn Glu Val Glu Glu Asp Thr Gly Asn Glu Leu Ser Thr Lys Glu Gln
                165                 170                 175

Ile Ser Arg Asn Ser Lys Ala Leu Glu Glu Lys Tyr Val Ala Glu Leu
            180                 185                 190

Gln Leu Glu Arg Leu Lys Lys Asp Gly Glu Val Arg Gly Ser Ile Asn
        195                 200                 205

Arg Phe Lys Thr Ser Asp Tyr Val Lys Glu Ala Lys Gln Leu Leu Lys
210                 215                 220

Val Gln Lys Ala Tyr His Gln Leu Asp Gln Ser Phe Ile Asp Thr Tyr
225                 230                 235                 240

Ile Asp Leu Leu Glu Thr Arg Arg Thr Tyr Tyr Glu Gly Pro Gly Glu
                245                 250                 255

Gly Ser Pro Phe Gly Trp Lys Asp Ile Lys Glu Trp Tyr Glu Met Leu
            260                 265                 270

Met Gly His Cys Thr Tyr Phe Pro Glu Glu Leu Arg Ser Val Lys Tyr
        275                 280                 285

Ala Tyr Asn Ala Asp Leu Tyr Asn Ala Leu Asn Asp Leu Asn Asn Leu
290                 295                 300

Val Ile Thr Arg Asp Glu Asn Glu Lys Leu Glu Tyr Tyr Glu Lys Phe
305                 310                 315                 320

Gln Ile Ile Glu Asn Val Phe Lys Gln Lys Lys Pro Thr Leu Lys
            325                 330                 335

Gln Ile Ala Lys Glu Ile Leu Val Asn Glu Glu Asp Ile Lys Gly Tyr
        340                 345                 350

Arg Val Thr Ser Thr Gly Lys Pro Glu Phe Thr Asn Leu Lys Val Tyr
            355                 360                 365

His Asp Ile Lys Asp Ile Thr Ala Arg Lys Glu Ile Ile Glu Asn Ala
        370                 375                 380

Glu Leu Leu Asp Gln Ile Ala Lys Ile Leu Thr Ile Tyr Gln Ser Ser
385                 390                 395                 400

Glu Asp Ile Gln Glu Glu Leu Thr Asn Leu Asn Ser Glu Leu Thr Gln
                405                 410                 415

Glu Glu Ile Glu Gln Ile Ser Asn Leu Lys Gly Tyr Thr Gly Thr His
            420                 425                 430

Asn Leu Ser Leu Lys Ala Ile Asn Leu Ile Leu Asp Glu Leu Trp His
        435                 440                 445

Thr Asn Asp Asn Gln Ile Ala Ile Phe Asn Arg Leu Lys Leu Val Pro
450                 455                 460

Lys Lys Val Asp Leu Ser Gln Gln Lys Glu Ile Pro Thr Thr Leu Val
465                 470                 475                 480

Asp Asp Phe Ile Leu Ser Pro Val Val Lys Arg Ser Phe Ile Gln Ser
                485                 490                 495

Ile Lys Val Ile Asn Ala Ile Ile Lys Lys Tyr Gly Leu Pro Asn Asp
            500                 505                 510

Ile Ile Ile Glu Leu Ala Arg Glu Lys Asn Ser Lys Asp Ala Gln Lys
        515                 520                 525

Met Ile Asn Glu Met Gln Lys Arg Asn Arg Gln Thr Asn Glu Arg Ile
530                 535                 540

Glu Glu Ile Ile Arg Thr Thr Gly Lys Glu Asn Ala Lys Tyr Leu Ile
```

```
              545                 550                 555                 560
        Glu Lys Ile Lys Leu His Asp Met Gln Glu Gly Lys Cys Leu Tyr Ser
                            565                 570                 575

Leu Glu Ala Ile Pro Leu Glu Asp Leu Leu Asn Asn Pro Phe Asn Tyr
                            580                 585                 590

Glu Val Asp His Ile Ile Pro Arg Ser Val Ser Phe Asp Asn Ser Phe
                            595                 600                 605

Asn Asn Lys Val Leu Val Lys Gln Glu Glu Ala Ser Lys Lys Gly Asn
                            610                 615                 620

Arg Thr Pro Phe Gln Tyr Leu Ser Ser Asp Ser Lys Ile Ser Tyr
        625                 630                 635                 640

Glu Thr Phe Lys Lys His Ile Leu Asn Leu Ala Lys Gly Lys Gly Arg
                            645                 650                 655

Ile Ser Lys Thr Lys Lys Glu Tyr Leu Leu Glu Glu Arg Asp Ile Asn
                            660                 665                 670

Arg Phe Ser Val Gln Lys Asp Phe Ile Asn Arg Asn Leu Val Asp Thr
                            675                 680                 685

Arg Tyr Ala Thr Arg Gly Leu Met Asn Leu Leu Arg Ser Tyr Phe Arg
        690                 695                 700

Val Asn Asn Leu Asp Val Lys Val Lys Ser Ile Asn Gly Gly Phe Thr
        705                 710                 715                 720

Ser Phe Leu Arg Arg Lys Trp Lys Phe Lys Lys Glu Arg Asn Lys Gly
                            725                 730                 735

Tyr Lys His His Ala Glu Asp Ala Leu Ile Ile Ala Asn Ala Asp Phe
                            740                 745                 750

Ile Phe Lys Glu Trp Lys Lys Leu Asp Lys Ala Lys Lys Val Met Glu
                            755                 760                 765

Asn Gln Met Phe Glu Glu Lys Gln Ala Glu Ser Met Pro Glu Ile Glu
                            770                 775                 780

Thr Glu Gln Glu Tyr Lys Glu Ile Phe Ile Thr Pro His Gln Ile Lys
        785                 790                 795                 800

His Ile Lys Asp Phe Lys Asp Tyr Lys Tyr Ser His Arg Val Asp Lys
                            805                 810                 815

Lys Pro Asn Arg Glu Leu Ile Asn Asp Thr Leu Tyr Ser Thr Arg Lys
                            820                 825                 830

Asp Asp Lys Gly Asn Thr Leu Ile Val Asn Asn Leu Asn Gly Leu Tyr
                            835                 840                 845

Asp Lys Asp Asn Asp Lys Leu Lys Lys Leu Ile Asn Lys Ser Pro Glu
                            850                 855                 860

Lys Leu Leu Met Tyr His His Asp Pro Gln Thr Tyr Gln Lys Leu Lys
        865                 870                 875                 880

Leu Ile Met Glu Gln Tyr Gly Asp Glu Lys Asn Pro Leu Tyr Lys Tyr
                            885                 890                 895

Tyr Glu Glu Thr Gly Asn Tyr Leu Thr Lys Tyr Ser Lys Lys Asp Asn
                            900                 905                 910

Gly Pro Val Ile Lys Lys Ile Lys Tyr Tyr Gly Asn Lys Leu Asn Ala
                            915                 920                 925

His Leu Asp Ile Thr Asp Asp Tyr Pro Asn Ser Arg Asn Lys Val Val
                            930                 935                 940

Lys Leu Ser Leu Lys Pro Tyr Arg Phe Asp Val Tyr Leu Asp Asn Gly
        945                 950                 955                 960

Val Tyr Lys Phe Val Thr Val Lys Asn Leu Asp Val Ile Lys Lys Glu
                            965                 970                 975
```

```
Asn Tyr Tyr Glu Val Asn Ser Lys Cys Tyr Glu Glu Ala Lys Lys Leu
            980                 985                 990

Lys Lys Ile Ser Asn Gln Ala Glu Phe Ile Ala Ser Phe Tyr Asn Asn
        995                 1000                1005

Asp Leu Ile Lys Ile Asn Gly Glu Leu Tyr Arg Val Ile Gly Val
    1010                1015                1020

Asn Asn Asp Leu Leu Asn Arg Ile Glu Val Asn Met Ile Asp Ile
    1025                1030                1035

Thr Tyr Arg Glu Tyr Leu Glu Asn Met Asn Asp Lys Arg Pro Pro
    1040                1045                1050

Arg Ile Ile Lys Thr Ile Ala Ser Lys Thr Gln Ser Ile Lys Lys
    1055                1060                1065

Tyr Ser Thr Asp Ile Leu Gly Asn Leu Tyr Glu Val Lys Ser Lys
    1070                1075                1080

Lys His Pro Gln Ile Ile Lys Lys Gly Lys Arg Pro Ala Ala Thr
    1085                1090                1095

Lys Lys Ala Gly Gln Ala Lys Lys Lys Lys Gly Ser Tyr Pro Tyr
    1100                1105                1110

Asp Val Pro Asp Tyr Ala Tyr Pro Tyr Asp Val Pro Asp Tyr Ala
    1115                1120                1125

Tyr Pro Tyr Asp Val Pro Asp Tyr Ala
    1130                1135
```

<210> SEQ ID NO 41
<211> LENGTH: 576
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 41

```
tagtaatcaa ttacggggtc attagttcat agcccatata tggagttccg cgttacataa    60
cttacggtaa atggcccgcc tggctgaccg cccaacgacc cccgcccatt gacgtcaata   120
atgacgtatg ttcccatagt aacgccaata gggactttcc attgacgtca atgggtggag   180
tatttacggt aaactgccca cttggcagta catcaagtgt atcatatgcc aagtacgccc   240
cctattgacg tcaatgacgg taaatggccc gcctggcatt atgcccagta catgacctta   300
tgggactttc ctacttggca gtacatctac gtattagtca tcgctattac catggtgatg   360
cggttttggc agtacatcaa tgggcgtgga tagcggtttg actcacgggg atttccaagt   420
ctccacccca ttgacgtcaa tgggagtttg ttttggcacc aaaatcaacg ggactttcca   480
aaatgtcgta caactccgcc ccattgacgc aaatgggcg gtaggcgtgt acggtgggag   540
gtctatataa gcagagctgg tttagtgaac cgtcag                             576
```

<210> SEQ ID NO 42
<211> LENGTH: 249
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 42

```
ggtgtttcgt cctttccaca agatatataa agccaagaaa tcgaaatact ttcaagttac    60
```

```
ggtaagcata tgatagtcca ttttaaaaca taattttaaa actgcaaact acccaagaaa    120
ttattacttt ctacgtcacg tattttgtac taatatcttt gtgtttacag tcaaattaat    180
tccaattatc tctctaacag ccttgtatcg tatatgcaaa tatgaaggaa tcatgggaaa    240
taggccctc                                                           249
```

```
<210> SEQ ID NO 43
<211> LENGTH: 8
<212> TYPE: PRT
<213> ORGANISM: Adeno-associated virus 2

<400> SEQUENCE: 43

Arg Leu Ala Arg Gly His Ser Leu
1               5

<210> SEQ ID NO 44
<211> LENGTH: 8
<212> TYPE: PRT
<213> ORGANISM: Adeno-associated virus 2

<400> SEQUENCE: 44

Arg Leu Ala Arg Gly Gln Pro Leu
1               5

<210> SEQ ID NO 45
<211> LENGTH: 1694
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 45

Met Ala Ser Gly Thr Ser Arg Pro Val Glu Pro Ser Pro Gln Arg Ser
1               5                   10                  15

Pro Asp Ser Ser Thr Gly Ile Gly Lys Lys Gly Gln Gln Pro Ala Lys
            20                  25                  30

Lys Arg Leu Asn Phe Gly Gln Thr Gly Asp Ser Glu Ser Val Pro Asp
        35                  40                  45

Pro Gln Pro Ile Gly Glu Pro Pro Ala Gly Pro Ser Gly Leu Gly Ser
    50                  55                  60

Gly Thr Leu Ala Ala Gly Gly Ala Pro Leu Ala Asp Asn Asn Glu
65                  70                  75                  80

Gly Ala Asp Gly Val Gly Ser Ser Ser Gly Gly Gly Gly Ser Met
                85                  90                  95

Ala Pro Lys Lys Lys Arg Lys Val Gly Ile His Gly Val Pro Ala Ala
            100                 105                 110

Lys Arg Asn Tyr Ile Leu Gly Leu Asp Ile Gly Ile Thr Ser Val Gly
        115                 120                 125

Tyr Gly Ile Ile Asp Tyr Glu Thr Arg Asp Val Ile Asp Ala Gly Val
    130                 135                 140

Arg Leu Phe Lys Glu Ala Asn Val Glu Asn Asn Glu Gly Arg Arg Ser
145                 150                 155                 160

Lys Arg Gly Ala Arg Arg Leu Lys Arg Arg Arg His Arg Ile Gln
            165                 170                 175

Arg Val Lys Lys Leu Leu Phe Asp Tyr Asn Leu Leu Thr Asp His Ser
        180                 185                 190
```

-continued

```
Glu Leu Ser Gly Ile Asn Pro Tyr Glu Ala Arg Val Lys Gly Leu Ser
            195                 200                 205

Gln Lys Leu Ser Glu Glu Phe Ser Ala Ala Leu Leu His Leu Ala
        210                 215                 220

Lys Arg Arg Gly Val His Asn Val Asn Glu Val Glu Glu Asp Thr Gly
225                 230                 235                 240

Asn Glu Leu Ser Thr Lys Glu Gln Ile Ser Arg Asn Ser Lys Ala Leu
            245                 250                 255

Glu Glu Lys Tyr Val Ala Glu Leu Gln Leu Arg Leu Lys Lys Asp
        260                 265                 270

Gly Glu Val Arg Gly Ser Ile Asn Arg Phe Lys Thr Ser Asp Tyr Val
        275                 280                 285

Lys Glu Ala Lys Gln Leu Leu Lys Val Gln Lys Ala Tyr His Gln Leu
        290                 295                 300

Asp Gln Ser Phe Ile Asp Thr Tyr Ile Asp Leu Leu Glu Thr Arg Arg
305                 310                 315                 320

Thr Tyr Tyr Glu Gly Pro Gly Glu Gly Ser Pro Phe Gly Trp Lys Asp
                325                 330                 335

Ile Lys Glu Trp Tyr Glu Met Leu Met Gly His Cys Thr Tyr Phe Pro
            340                 345                 350

Glu Glu Leu Arg Ser Val Lys Tyr Ala Tyr Asn Ala Asp Leu Tyr Asn
        355                 360                 365

Ala Leu Asn Asp Leu Asn Asn Leu Val Ile Thr Arg Asp Glu Asn Glu
        370                 375                 380

Lys Leu Glu Tyr Tyr Glu Lys Phe Gln Ile Ile Glu Asn Val Phe Lys
385                 390                 395                 400

Gln Lys Lys Lys Pro Thr Leu Lys Gln Ile Ala Lys Glu Ile Leu Val
                405                 410                 415

Asn Glu Glu Asp Ile Lys Gly Tyr Arg Val Thr Ser Thr Gly Lys Pro
            420                 425                 430

Glu Phe Thr Asn Leu Lys Val Tyr His Asp Ile Lys Asp Ile Thr Ala
        435                 440                 445

Arg Lys Glu Ile Ile Glu Asn Ala Glu Leu Leu Asp Gln Ile Ala Lys
450                 455                 460

Ile Leu Thr Ile Tyr Gln Ser Ser Glu Asp Ile Gln Glu Glu Leu Thr
465                 470                 475                 480

Asn Leu Asn Ser Glu Leu Thr Gln Glu Glu Ile Glu Gln Ile Ser Asn
            485                 490                 495

Leu Lys Gly Tyr Thr Gly Thr His Asn Leu Ser Leu Lys Ala Ile Asn
        500                 505                 510

Leu Ile Leu Asp Glu Leu Trp His Thr Asn Asp Asn Gln Ile Ala Ile
        515                 520                 525

Phe Asn Arg Leu Lys Leu Val Pro Lys Lys Val Asp Leu Ser Gln Gln
530                 535                 540

Lys Glu Ile Pro Thr Thr Leu Val Asp Asp Phe Ile Leu Ser Pro Val
545                 550                 555                 560

Val Lys Arg Ser Phe Ile Gln Ser Ile Lys Val Ile Asn Ala Ile Ile
                565                 570                 575

Lys Lys Tyr Gly Leu Pro Asn Asp Ile Ile Glu Leu Ala Arg Glu
            580                 585                 590

Lys Asn Ser Lys Asp Ala Gln Lys Met Ile Asn Glu Met Gln Lys Arg
        595                 600                 605

Asn Arg Gln Thr Asn Glu Arg Ile Glu Glu Ile Ile Arg Thr Thr Gly
```

-continued

```
            610                 615                 620
Lys Glu Asn Ala Lys Tyr Leu Ile Glu Lys Ile Lys Leu His Asp Met
625                 630                 635                 640

Gln Glu Gly Lys Cys Leu Tyr Ser Leu Glu Ala Ile Pro Leu Glu Asp
                645                 650                 655

Leu Leu Asn Asn Pro Phe Asn Tyr Glu Val Asp His Ile Ile Pro Arg
            660                 665                 670

Ser Val Ser Phe Asp Asn Ser Phe Asn Asn Lys Val Leu Val Lys Gln
        675                 680                 685

Glu Glu Asn Ser Lys Lys Gly Asn Arg Thr Pro Phe Gln Tyr Leu Ser
690                 695                 700

Ser Ser Asp Ser Lys Ile Ser Tyr Glu Thr Phe Lys Lys His Ile Leu
705                 710                 715                 720

Asn Leu Ala Lys Gly Lys Gly Arg Ile Ser Lys Thr Lys Lys Glu Tyr
                725                 730                 735

Leu Leu Glu Glu Arg Asp Ile Asn Arg Phe Ser Val Gln Lys Asp Phe
            740                 745                 750

Ile Asn Arg Asn Leu Val Asp Thr Arg Tyr Ala Thr Arg Gly Leu Met
        755                 760                 765

Asn Leu Leu Arg Ser Tyr Phe Arg Val Asn Asn Leu Asp Val Lys Val
        770                 775                 780

Lys Ser Ile Asn Gly Gly Phe Thr Ser Phe Leu Arg Arg Lys Trp Lys
785                 790                 795                 800

Phe Lys Lys Glu Arg Asn Lys Gly Tyr Lys His His Ala Glu Asp Ala
                805                 810                 815

Leu Ile Ile Ala Asn Ala Asp Phe Ile Phe Lys Glu Trp Lys Lys Leu
            820                 825                 830

Asp Lys Ala Lys Lys Val Met Glu Asn Gln Met Phe Glu Glu Lys Gln
        835                 840                 845

Ala Glu Ser Met Pro Glu Ile Glu Thr Glu Gln Glu Tyr Lys Glu Ile
        850                 855                 860

Phe Ile Thr Pro His Gln Ile Lys His Ile Lys Asp Phe Lys Asp Tyr
865                 870                 875                 880

Lys Tyr Ser His Arg Val Asp Lys Lys Pro Asn Arg Glu Leu Ile Asn
                885                 890                 895

Asp Thr Leu Tyr Ser Thr Arg Lys Asp Asp Lys Gly Asn Thr Leu Ile
            900                 905                 910

Val Asn Asn Leu Asn Gly Leu Tyr Asp Lys Asp Asn Asp Lys Leu Lys
        915                 920                 925

Lys Leu Ile Asn Lys Ser Pro Glu Lys Leu Leu Met Tyr His His Asp
        930                 935                 940

Pro Gln Thr Tyr Gln Lys Leu Lys Leu Ile Met Glu Gln Tyr Gly Asp
945                 950                 955                 960

Glu Lys Asn Pro Leu Tyr Lys Tyr Tyr Glu Glu Thr Gly Asn Tyr Leu
                965                 970                 975

Thr Lys Tyr Ser Lys Lys Asp Asn Gly Pro Val Ile Lys Lys Ile Lys
            980                 985                 990

Tyr Tyr Gly Asn Lys Leu Asn Ala His Leu Asp Ile Thr Asp Asp Tyr
        995                 1000                1005

Pro Asn Ser Arg Asn Lys Val Val Lys Leu Ser Leu Lys Pro Tyr
        1010                1015                1020

Arg Phe Asp Val Tyr Leu Asp Asn Gly Val Tyr Lys Phe Val Thr
    1025                1030                1035
```

-continued

```
Val Lys Asn Leu Asp Val Ile Lys Lys Glu Asn Tyr Tyr Glu Val
    1040              1045             1050

Asn Ser Lys Cys Tyr Glu Glu Ala Lys Lys Leu Lys Lys Ile Ser
    1055              1060             1065

Asn Gln Ala Glu Phe Ile Ala Ser Phe Tyr Asn Asn Asp Leu Ile
    1070              1075             1080

Lys Ile Asn Gly Glu Leu Tyr Arg Val Ile Gly Val Asn Asn Asp
    1085              1090             1095

Leu Leu Asn Arg Ile Glu Val Asn Met Ile Asp Ile Thr Tyr Arg
    1100              1105             1110

Glu Tyr Leu Glu Asn Met Asn Asp Lys Arg Pro Pro Arg Ile Ile
    1115              1120             1125

Lys Thr Ile Ala Ser Lys Thr Gln Ser Ile Lys Lys Tyr Ser Thr
    1130              1135             1140

Asp Ile Leu Gly Asn Leu Tyr Glu Val Lys Ser Lys Lys His Pro
    1145              1150             1155

Gln Ile Ile Lys Lys Gly Ser Gly Phe Ala Asn Glu Leu Gly Pro
    1160              1165             1170

Arg Leu Met Gly Lys Gly Gly Gly Ser Asn Trp His Cys Asp
    1175              1180             1185

Ser Thr Trp Leu Gly Asp Arg Val Ile Thr Thr Ser Thr Arg Thr
    1190              1195             1200

Trp Ala Leu Pro Thr Tyr Asn Asn His Leu Tyr Lys Gln Ile Ser
    1205              1210             1215

Asn Gly Thr Ser Gly Gly Ser Thr Asn Asp Asn Thr Tyr Phe Gly
    1220              1225             1230

Tyr Ser Thr Pro Trp Gly Tyr Phe Asp Phe Asn Arg Phe His Cys
    1235              1240             1245

His Phe Ser Pro Arg Asp Trp Gln Arg Leu Ile Asn Asn Asn Trp
    1250              1255             1260

Gly Phe Arg Pro Lys Arg Leu Asn Phe Lys Leu Phe Asn Ile Gln
    1265              1270             1275

Val Lys Glu Val Thr Gln Asn Glu Gly Thr Lys Thr Ile Ala Asn
    1280              1285             1290

Asn Leu Thr Ser Thr Ile Gln Val Phe Thr Asp Ser Glu Tyr Gln
    1295              1300             1305

Leu Pro Tyr Val Leu Gly Ser Ala His Gln Gly Cys Leu Pro Pro
    1310              1315             1320

Phe Pro Ala Asp Val Phe Met Ile Pro Gln Tyr Gly Tyr Leu Thr
    1325              1330             1335

Leu Asn Asn Gly Ser Gln Ala Val Gly Arg Ser Ser Phe Tyr Cys
    1340              1345             1350

Leu Glu Tyr Phe Pro Ser Gln Met Leu Arg Thr Gly Asn Asn Phe
    1355              1360             1365

Glu Phe Ser Tyr Asn Phe Glu Asp Val Pro Phe His Ser Ser Tyr
    1370              1375             1380

Ala His Ser Gln Ser Leu Asp Arg Leu Met Asn Pro Leu Ile Asp
    1385              1390             1395

Gln Tyr Leu Tyr Tyr Leu Ser Arg Thr Gln Ser Thr Gly Gly Thr
    1400              1405             1410

Ala Gly Thr Gln Gln Leu Leu Phe Ser Gln Ala Gly Pro Asn Asn
    1415              1420             1425
```

Met Ser Ala Gln Ala Lys Asn Trp Leu Pro Gly Pro Cys Tyr Arg
     1430                1435                1440

Gln Gln Arg Val Ser Thr Thr Leu Ser Gln Asn Asn Asn Ser Asn
     1445                1450                1455

Phe Ala Trp Thr Gly Ala Thr Lys Tyr His Leu Asn Gly Arg Asp
     1460                1465                1470

Ser Leu Val Asn Pro Gly Val Ala Met Ala Thr His Lys Asp Asp
     1475                1480                1485

Glu Glu Arg Phe Phe Pro Ser Ser Gly Val Leu Met Phe Gly Lys
     1490                1495                1500

Gln Gly Ala Gly Lys Asp Asn Val Asp Tyr Ser Ser Val Met Leu
     1505                1510                1515

Thr Ser Glu Glu Glu Ile Lys Thr Thr Asn Pro Val Ala Thr Glu
     1520                1525                1530

Gln Tyr Gly Val Val Ala Asp Asn Leu Gln Gln Gln Asn Ala Ala
     1535                1540                1545

Pro Ile Val Gly Ala Val Asn Ser Gln Gly Ala Leu Pro Gly Met
     1550                1555                1560

Val Trp Gln Asn Arg Asp Val Tyr Leu Gln Gly Pro Ile Trp Ala
     1565                1570                1575

Lys Ile Pro His Thr Asp Gly Asn Phe His Pro Ser Pro Leu Met
     1580                1585                1590

Gly Gly Phe Gly Leu Lys His Pro Pro Pro Gln Ile Leu Ile Lys
     1595                1600                1605

Asn Thr Pro Val Pro Ala Asp Pro Pro Thr Thr Phe Ser Gln Ala
     1610                1615                1620

Lys Leu Ala Ser Phe Ile Thr Gln Tyr Ser Thr Gly Gln Val Ser
     1625                1630                1635

Val Glu Ile Glu Trp Glu Leu Gln Lys Glu Asn Ser Lys Arg Trp
     1640                1645                1650

Asn Pro Glu Ile Gln Tyr Thr Ser Asn Tyr Tyr Lys Ser Thr Asn
     1655                1660                1665

Val Asp Phe Ala Val Asn Thr Glu Gly Thr Tyr Ser Glu Pro Arg
     1670                1675                1680

Pro Ile Gly Thr Arg Tyr Leu Thr Arg Asn Leu
     1685                1690

<210> SEQ ID NO 46
<211> LENGTH: 1694
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 46

Met Ala Ser Gly Thr Ser Arg Pro Val Glu Pro Ser Pro Gln Arg Ser
1               5                   10                  15

Pro Asp Ser Ser Thr Gly Ile Gly Lys Lys Gly Gln Gln Pro Ala Lys
            20                  25                  30

Lys Arg Leu Asn Phe Gly Gln Thr Gly Asp Ser Glu Ser Val Pro Asp
        35                  40                  45

Pro Gln Pro Ile Gly Glu Pro Pro Ala Gly Pro Ser Gly Leu Gly Ser
    50                  55                  60

Gly Thr Leu Ala Ala Gly Gly Gly Ala Pro Leu Ala Asp Asn Asn Glu

-continued

```
            65                  70                  75                  80
Gly Ala Asp Gly Val Gly Ser Ser Ser Gly Asn Trp His Cys Asp Ser
                    85                  90                  95
Thr Trp Leu Gly Asp Arg Val Ile Thr Thr Ser Thr Arg Thr Trp Ala
                100                 105                 110
Leu Pro Thr Tyr Asn Asn His Leu Tyr Lys Gln Ile Ser Asn Gly Thr
                115                 120                 125
Ser Gly Gly Ser Thr Asn Asp Asn Thr Tyr Phe Gly Tyr Ser Thr Pro
            130                 135                 140
Trp Gly Tyr Phe Asp Phe Asn Arg Phe His Cys His Phe Ser Pro Arg
145                 150                 155                 160
Asp Trp Gln Arg Leu Ile Asn Asn Asn Trp Gly Phe Arg Pro Lys Arg
                165                 170                 175
Leu Asn Phe Lys Leu Phe Asn Ile Gln Val Lys Glu Val Thr Gln Asn
                180                 185                 190
Glu Gly Thr Lys Thr Ile Ala Asn Asn Leu Thr Ser Thr Ile Gln Val
                195                 200                 205
Phe Thr Asp Ser Glu Gly Gly Gly Ser Met Ala Pro Lys Lys Lys
    210                 215                 220
Arg Lys Val Gly Ile His Gly Val Pro Ala Ala Lys Arg Asn Tyr Ile
225                 230                 235                 240
Leu Gly Leu Asp Ile Gly Ile Thr Ser Val Gly Tyr Gly Ile Ile Asp
                245                 250                 255
Tyr Glu Thr Arg Asp Val Ile Asp Ala Gly Val Arg Leu Phe Lys Glu
                260                 265                 270
Ala Asn Val Glu Asn Asn Glu Gly Arg Arg Ser Lys Arg Gly Ala Arg
            275                 280                 285
Arg Leu Lys Arg Arg Arg His Arg Ile Gln Arg Val Lys Lys Leu
            290                 295                 300
Leu Phe Asp Tyr Asn Leu Leu Thr Asp His Ser Glu Leu Ser Gly Ile
305                 310                 315                 320
Asn Pro Tyr Glu Ala Arg Val Lys Gly Leu Ser Gln Lys Leu Ser Glu
                325                 330                 335
Glu Glu Phe Ser Ala Ala Leu Leu His Leu Ala Lys Arg Arg Gly Val
                340                 345                 350
His Asn Val Asn Glu Val Glu Glu Asp Thr Gly Asn Glu Leu Ser Thr
            355                 360                 365
Lys Glu Gln Ile Ser Arg Asn Ser Lys Ala Leu Glu Glu Lys Tyr Val
            370                 375                 380
Ala Glu Leu Gln Leu Glu Arg Leu Lys Lys Asp Gly Glu Val Arg Gly
385                 390                 395                 400
Ser Ile Asn Arg Phe Lys Thr Ser Asp Tyr Val Lys Glu Ala Lys Gln
                405                 410                 415
Leu Leu Lys Val Gln Lys Ala Tyr His Gln Leu Asp Gln Ser Phe Ile
                420                 425                 430
Asp Thr Tyr Ile Asp Leu Leu Glu Thr Arg Arg Thr Tyr Tyr Glu Gly
            435                 440                 445
Pro Gly Glu Gly Ser Pro Phe Gly Trp Lys Asp Ile Lys Glu Trp Tyr
            450                 455                 460
Glu Met Leu Met Gly His Cys Thr Tyr Phe Pro Glu Glu Leu Arg Ser
465                 470                 475                 480
Val Lys Tyr Ala Tyr Asn Ala Asp Leu Tyr Asn Ala Leu Asn Asp Leu
                485                 490                 495
```

```
Asn Asn Leu Val Ile Thr Arg Asp Glu Asn Glu Lys Leu Glu Tyr Tyr
            500                 505                 510

Glu Lys Phe Gln Ile Ile Glu Asn Val Phe Lys Gln Lys Lys Lys Pro
            515                 520                 525

Thr Leu Lys Gln Ile Ala Lys Glu Ile Leu Val Asn Glu Glu Asp Ile
            530                 535                 540

Lys Gly Tyr Arg Val Thr Ser Thr Gly Lys Pro Glu Phe Thr Asn Leu
545                 550                 555                 560

Lys Val Tyr His Asp Ile Lys Asp Ile Thr Ala Arg Lys Glu Ile Ile
                565                 570                 575

Glu Asn Ala Glu Leu Leu Asp Gln Ile Ala Lys Ile Leu Thr Ile Tyr
            580                 585                 590

Gln Ser Ser Glu Asp Ile Gln Glu Glu Leu Thr Asn Leu Asn Ser Glu
            595                 600                 605

Leu Thr Gln Glu Glu Ile Glu Gln Ile Ser Asn Leu Lys Gly Tyr Thr
            610                 615                 620

Gly Thr His Asn Leu Ser Leu Lys Ala Ile Asn Leu Ile Leu Asp Glu
625                 630                 635                 640

Leu Trp His Thr Asn Asp Asn Gln Ile Ala Ile Phe Asn Arg Leu Lys
                645                 650                 655

Leu Val Pro Lys Lys Val Asp Leu Ser Gln Gln Lys Glu Ile Pro Thr
            660                 665                 670

Thr Leu Val Asp Asp Phe Ile Leu Ser Pro Val Val Lys Arg Ser Phe
            675                 680                 685

Ile Gln Ser Ile Lys Val Ile Asn Ala Ile Ile Lys Lys Tyr Gly Leu
            690                 695                 700

Pro Asn Asp Ile Ile Ile Glu Leu Ala Arg Glu Lys Asn Ser Lys Asp
705                 710                 715                 720

Ala Gln Lys Met Ile Asn Glu Met Gln Lys Arg Asn Arg Gln Thr Asn
                725                 730                 735

Glu Arg Ile Glu Glu Ile Ile Arg Thr Thr Gly Lys Glu Asn Ala Lys
            740                 745                 750

Tyr Leu Ile Glu Lys Ile Lys Leu His Asp Met Gln Glu Gly Lys Cys
            755                 760                 765

Leu Tyr Ser Leu Glu Ala Ile Pro Leu Glu Asp Leu Leu Asn Asn Pro
770                 775                 780

Phe Asn Tyr Glu Val Asp His Ile Ile Pro Arg Ser Val Ser Phe Asp
785                 790                 795                 800

Asn Ser Phe Asn Asn Lys Val Leu Val Lys Gln Glu Glu Asn Ser Lys
                805                 810                 815

Lys Gly Asn Arg Thr Pro Phe Gln Tyr Leu Ser Ser Ser Asp Ser Lys
            820                 825                 830

Ile Ser Tyr Glu Thr Phe Lys Lys His Ile Leu Asn Leu Ala Lys Gly
            835                 840                 845

Lys Gly Arg Ile Ser Lys Thr Lys Lys Glu Tyr Leu Leu Glu Glu Arg
            850                 855                 860

Asp Ile Asn Arg Phe Ser Val Gln Lys Asp Phe Ile Asn Arg Asn Leu
865                 870                 875                 880

Val Asp Thr Arg Tyr Ala Thr Arg Gly Leu Met Asn Leu Leu Arg Ser
                885                 890                 895

Tyr Phe Arg Val Asn Asn Leu Asp Val Lys Val Lys Ser Ile Asn Gly
            900                 905                 910
```

```
Gly Phe Thr Ser Phe Leu Arg Arg Lys Trp Lys Phe Lys Glu Arg
            915                 920                 925

Asn Lys Gly Tyr Lys His His Ala Glu Asp Ala Leu Ile Ile Ala Asn
    930                 935                 940

Ala Asp Phe Ile Phe Lys Glu Trp Lys Lys Leu Asp Lys Ala Lys Lys
945                 950                 955                 960

Val Met Glu Asn Gln Met Phe Glu Lys Gln Ala Glu Ser Met Pro
                965                 970                 975

Glu Ile Glu Thr Glu Gln Glu Tyr Lys Glu Ile Phe Ile Thr Pro His
                980                 985                 990

Gln Ile Lys His Ile Lys Asp Phe Lys Asp Tyr Lys Tyr Ser His Arg
            995                 1000                1005

Val Asp Lys Lys Pro Asn Arg Glu Leu Ile Asn Asp Thr Leu Tyr
    1010                1015                1020

Ser Thr Arg Lys Asp Asp Lys Gly Asn Thr Leu Ile Val Asn Asn
    1025                1030                1035

Leu Asn Gly Leu Tyr Asp Lys Asp Asn Asp Lys Leu Lys Lys Leu
    1040                1045                1050

Ile Asn Lys Ser Pro Glu Lys Leu Leu Met Tyr His His Asp Pro
    1055                1060                1065

Gln Thr Tyr Gln Lys Leu Lys Leu Ile Met Glu Gln Tyr Gly Asp
    1070                1075                1080

Glu Lys Asn Pro Leu Tyr Lys Tyr Tyr Glu Glu Thr Gly Asn Tyr
    1085                1090                1095

Leu Thr Lys Tyr Ser Lys Lys Asp Asn Gly Pro Val Ile Lys Lys
    1100                1105                1110

Ile Lys Tyr Tyr Gly Asn Lys Leu Asn Ala His Leu Asp Ile Thr
    1115                1120                1125

Asp Asp Tyr Pro Asn Ser Arg Asn Lys Val Val Lys Leu Ser Leu
    1130                1135                1140

Lys Pro Tyr Arg Phe Asp Val Tyr Leu Asp Asn Gly Val Tyr Lys
    1145                1150                1155

Phe Val Thr Val Lys Asn Leu Asp Val Ile Lys Lys Glu Asn Tyr
    1160                1165                1170

Tyr Glu Val Asn Ser Lys Cys Tyr Glu Glu Ala Lys Lys Leu Lys
    1175                1180                1185

Lys Ile Ser Asn Gln Ala Glu Phe Ile Ala Ser Phe Tyr Asn Asn
    1190                1195                1200

Asp Leu Ile Lys Ile Asn Gly Glu Leu Tyr Arg Val Ile Gly Val
    1205                1210                1215

Asn Asn Asp Leu Leu Asn Arg Ile Glu Val Asn Met Ile Asp Ile
    1220                1225                1230

Thr Tyr Arg Glu Tyr Leu Glu Asn Met Asn Asp Lys Arg Pro Pro
    1235                1240                1245

Arg Ile Ile Lys Thr Ile Ala Ser Lys Thr Gln Ser Ile Lys Lys
    1250                1255                1260

Tyr Ser Thr Asp Ile Leu Gly Asn Leu Tyr Glu Val Lys Ser Lys
    1265                1270                1275

Lys His Pro Gln Ile Ile Lys Lys Gly Ser Gly Phe Ala Asn Glu
    1280                1285                1290

Leu Gly Pro Arg Leu Met Gly Lys Gly Gly Gly Ser Tyr Gln
    1295                1300                1305

Leu Pro Tyr Val Leu Gly Ser Ala His Gln Gly Cys Leu Pro Pro
```

```
            1310                1315                1320
Phe Pro Ala Asp Val Phe Met Ile Pro Gln Tyr Gly Tyr Leu Thr
    1325                1330                1335
Leu Asn Asn Gly Ser Gln Ala Val Gly Arg Ser Ser Phe Tyr Cys
    1340                1345                1350
Leu Glu Tyr Phe Pro Ser Gln Met Leu Arg Thr Gly Asn Asn Phe
    1355                1360                1365
Glu Phe Ser Tyr Asn Phe Glu Asp Val Pro Phe His Ser Ser Tyr
    1370                1375                1380
Ala His Ser Gln Ser Leu Asp Arg Leu Met Asn Pro Leu Ile Asp
    1385                1390                1395
Gln Tyr Leu Tyr Tyr Leu Ser Arg Thr Gln Ser Thr Gly Gly Thr
    1400                1405                1410
Ala Gly Thr Gln Gln Leu Leu Phe Ser Gln Ala Gly Pro Asn Asn
    1415                1420                1425
Met Ser Ala Gln Ala Lys Asn Trp Leu Pro Gly Pro Cys Tyr Arg
    1430                1435                1440
Gln Gln Arg Val Ser Thr Thr Leu Ser Gln Asn Asn Asn Ser Asn
    1445                1450                1455
Phe Ala Trp Thr Gly Ala Thr Lys Tyr His Leu Asn Gly Arg Asp
    1460                1465                1470
Ser Leu Val Asn Pro Gly Val Ala Met Ala Thr His Lys Asp Asp
    1475                1480                1485
Glu Glu Arg Phe Phe Pro Ser Ser Gly Val Leu Met Phe Gly Lys
    1490                1495                1500
Gln Gly Ala Gly Lys Asp Asn Val Asp Tyr Ser Ser Val Met Leu
    1505                1510                1515
Thr Ser Glu Glu Glu Ile Lys Thr Thr Asn Pro Val Ala Thr Glu
    1520                1525                1530
Gln Tyr Gly Val Val Ala Asp Asn Leu Gln Gln Gln Asn Ala Ala
    1535                1540                1545
Pro Ile Val Gly Ala Val Asn Ser Gln Gly Ala Leu Pro Gly Met
    1550                1555                1560
Val Trp Gln Asn Arg Asp Val Tyr Leu Gln Gly Pro Ile Trp Ala
    1565                1570                1575
Lys Ile Pro His Thr Asp Gly Asn Phe His Pro Ser Pro Leu Met
    1580                1585                1590
Gly Gly Phe Gly Leu Lys His Pro Pro Pro Gln Ile Leu Ile Lys
    1595                1600                1605
Asn Thr Pro Val Pro Ala Asp Pro Pro Thr Thr Phe Ser Gln Ala
    1610                1615                1620
Lys Leu Ala Ser Phe Ile Thr Gln Tyr Ser Thr Gly Gln Val Ser
    1625                1630                1635
Val Glu Ile Glu Trp Glu Leu Gln Lys Glu Asn Ser Lys Arg Trp
    1640                1645                1650
Asn Pro Glu Ile Gln Tyr Thr Ser Asn Tyr Tyr Lys Ser Thr Asn
    1655                1660                1665
Val Asp Phe Ala Val Asn Thr Glu Gly Thr Tyr Ser Glu Pro Arg
    1670                1675                1680
Pro Ile Gly Thr Arg Tyr Leu Thr Arg Asn Leu
    1685                1690

<210> SEQ ID NO 47
```

```
<211> LENGTH: 1694
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 47
```

Met Ala Ser Gly Thr Ser Arg Pro Val Glu Pro Ser Pro Gln Arg Ser
1               5                   10                  15

Pro Asp Ser Ser Thr Gly Ile Gly Lys Lys Gly Gln Gln Pro Ala Lys
            20                  25                  30

Lys Arg Leu Asn Phe Gly Gln Thr Gly Asp Ser Glu Ser Val Pro Asp
        35                  40                  45

Pro Gln Pro Ile Gly Glu Pro Pro Ala Gly Pro Ser Gly Leu Gly Ser
    50                  55                  60

Gly Thr Leu Ala Ala Gly Gly Ala Pro Leu Ala Asp Asn Asn Glu
65                  70                  75                  80

Gly Ala Asp Gly Val Gly Ser Ser Ser Gly Asn Trp His Cys Asp Ser
                85                  90                  95

Thr Trp Leu Gly Asp Arg Val Ile Thr Thr Ser Thr Arg Thr Trp Ala
            100                 105                 110

Leu Pro Thr Tyr Asn Asn His Leu Tyr Lys Gln Ile Ser Asn Gly Thr
        115                 120                 125

Ser Gly Gly Ser Thr Asn Asp Asn Thr Tyr Phe Gly Tyr Ser Thr Pro
    130                 135                 140

Trp Gly Tyr Phe Asp Phe Asn Arg Phe His Cys His Phe Ser Pro Arg
145                 150                 155                 160

Asp Trp Gln Arg Leu Ile Asn Asn Asn Trp Gly Phe Arg Pro Lys Arg
                165                 170                 175

Leu Asn Phe Lys Leu Phe Asn Ile Gln Val Lys Glu Val Thr Gln Asn
            180                 185                 190

Glu Gly Thr Lys Thr Ile Ala Asn Asn Leu Thr Ser Thr Ile Gln Val
        195                 200                 205

Phe Thr Asp Ser Glu Tyr Gln Leu Pro Tyr Val Leu Gly Ser Ala His
    210                 215                 220

Gln Gly Cys Leu Pro Pro Phe Pro Ala Asp Val Phe Met Ile Pro Gln
225                 230                 235                 240

Tyr Gly Tyr Leu Thr Leu Asn Asn Gly Ser Gln Ala Val Gly Arg Ser
                245                 250                 255

Ser Phe Tyr Cys Leu Glu Tyr Phe Pro Ser Gln Met Leu Arg Thr Gly
            260                 265                 270

Asn Asn Phe Glu Phe Ser Tyr Asn Phe Glu Gly Gly Gly Ser Met
        275                 280                 285

Ala Pro Lys Lys Lys Arg Lys Val Gly Ile His Gly Val Pro Ala Ala
    290                 295                 300

Lys Arg Asn Tyr Ile Leu Gly Leu Asp Ile Gly Ile Thr Ser Val Gly
305                 310                 315                 320

Tyr Gly Ile Ile Asp Tyr Glu Thr Arg Asp Val Ile Asp Ala Gly Val
                325                 330                 335

Arg Leu Phe Lys Glu Ala Asn Val Glu Asn Asn Glu Gly Arg Arg Ser
            340                 345                 350

Lys Arg Gly Ala Arg Arg Leu Lys Arg Arg Arg His Arg Ile Gln
        355                 360                 365

```
Arg Val Lys Lys Leu Leu Phe Asp Tyr Asn Leu Leu Thr Asp His Ser
    370             375                 380

Glu Leu Ser Gly Ile Asn Pro Tyr Glu Ala Arg Val Lys Gly Leu Ser
385             390             395                 400

Gln Lys Leu Ser Glu Glu Phe Ser Ala Ala Leu Leu His Leu Ala
                405             410                 415

Lys Arg Arg Gly Val His Asn Val Asn Glu Val Glu Asp Thr Gly
            420             425             430

Asn Glu Leu Ser Thr Lys Glu Gln Ile Ser Arg Asn Ser Lys Ala Leu
        435             440             445

Glu Glu Lys Tyr Val Ala Glu Leu Gln Leu Glu Arg Leu Lys Lys Asp
450             455             460

Gly Glu Val Arg Gly Ser Ile Asn Arg Phe Lys Thr Ser Asp Tyr Val
465             470             475                 480

Lys Glu Ala Lys Gln Leu Leu Lys Val Gln Lys Ala Tyr His Gln Leu
                485             490             495

Asp Gln Ser Phe Ile Asp Thr Tyr Ile Asp Leu Leu Glu Thr Arg Arg
            500             505             510

Thr Tyr Tyr Glu Gly Pro Gly Glu Gly Ser Pro Phe Gly Trp Lys Asp
            515             520             525

Ile Lys Glu Trp Tyr Glu Met Leu Met Gly His Cys Thr Tyr Phe Pro
            530             535             540

Glu Glu Leu Arg Ser Val Lys Tyr Ala Tyr Asn Ala Asp Leu Tyr Asn
545             550             555             560

Ala Leu Asn Asp Leu Asn Asn Leu Val Ile Thr Arg Asp Glu Asn Glu
            565             570             575

Lys Leu Glu Tyr Tyr Glu Lys Phe Gln Ile Ile Glu Asn Val Phe Lys
            580             585             590

Gln Lys Lys Lys Pro Thr Leu Lys Gln Ile Ala Lys Glu Ile Leu Val
            595             600             605

Asn Glu Glu Asp Ile Lys Gly Tyr Arg Val Thr Ser Thr Gly Lys Pro
            610             615             620

Glu Phe Thr Asn Leu Lys Val Tyr His Asp Ile Lys Asp Ile Thr Ala
625             630             635             640

Arg Lys Glu Ile Ile Glu Asn Ala Glu Leu Leu Asp Gln Ile Ala Lys
            645             650             655

Ile Leu Thr Ile Tyr Gln Ser Ser Glu Asp Ile Gln Glu Glu Leu Thr
            660             665             670

Asn Leu Asn Ser Glu Leu Thr Gln Glu Glu Ile Glu Gln Ile Ser Asn
            675             680             685

Leu Lys Gly Tyr Thr Gly Thr His Asn Leu Ser Leu Lys Ala Ile Asn
            690             695             700

Leu Ile Leu Asp Glu Leu Trp His Thr Asn Asp Asn Gln Ile Ala Ile
705             710             715             720

Phe Asn Arg Leu Lys Leu Val Pro Lys Lys Val Asp Leu Ser Gln Gln
            725             730             735

Lys Glu Ile Pro Thr Thr Leu Val Asp Asp Phe Ile Leu Ser Pro Val
            740             745             750

Val Lys Arg Ser Phe Ile Gln Ser Ile Lys Val Ile Asn Ala Ile Ile
            755             760             765

Lys Lys Tyr Gly Leu Pro Asn Asp Ile Ile Glu Leu Ala Arg Glu
            770             775             780

Lys Asn Ser Lys Asp Ala Gln Lys Met Ile Asn Glu Met Gln Lys Arg
```

-continued

```
            785                 790                 795                 800
Asn Arg Gln Thr Asn Glu Arg Ile Glu Glu Ile Ile Arg Thr Thr Gly
                    805                 810                 815
Lys Glu Asn Ala Lys Tyr Leu Ile Glu Lys Ile Lys Leu His Asp Met
                    820                 825                 830
Gln Glu Gly Lys Cys Leu Tyr Ser Leu Glu Ala Ile Pro Leu Glu Asp
                    835                 840                 845
Leu Leu Asn Asn Pro Phe Asn Tyr Glu Val Asp His Ile Ile Pro Arg
                    850                 855                 860
Ser Val Ser Phe Asp Asn Ser Phe Asn Asn Lys Val Leu Val Lys Gln
865                 870                 875                 880
Glu Glu Asn Ser Lys Lys Gly Asn Arg Thr Pro Phe Gln Tyr Leu Ser
                    885                 890                 895
Ser Ser Asp Ser Lys Ile Ser Tyr Glu Thr Phe Lys Lys His Ile Leu
                    900                 905                 910
Asn Leu Ala Lys Gly Lys Gly Arg Ile Ser Lys Thr Lys Lys Glu Tyr
                    915                 920                 925
Leu Leu Glu Glu Arg Asp Ile Asn Arg Phe Ser Val Gln Lys Asp Phe
                    930                 935                 940
Ile Asn Arg Asn Leu Val Asp Thr Arg Tyr Ala Thr Arg Gly Leu Met
945                 950                 955                 960
Asn Leu Leu Arg Ser Tyr Phe Arg Val Asn Asn Leu Asp Val Lys Val
                    965                 970                 975
Lys Ser Ile Asn Gly Gly Phe Thr Ser Phe Leu Arg Arg Lys Trp Lys
                    980                 985                 990
Phe Lys Lys Glu Arg Asn Lys Gly Tyr Lys His His Ala Glu Asp Ala
                    995                 1000                1005
Leu Ile Ile Ala Asn Ala Asp Phe Ile Phe Lys Glu Trp Lys Lys
                    1010                1015                1020
Leu Asp Lys Ala Lys Lys Val Met Glu Asn Gln Met Phe Glu Glu
                    1025                1030                1035
Lys Gln Ala Glu Ser Met Pro Glu Ile Glu Thr Glu Gln Glu Tyr
                    1040                1045                1050
Lys Glu Ile Phe Ile Thr Pro His Gln Ile Lys His Ile Lys Asp
                    1055                1060                1065
Phe Lys Asp Tyr Lys Tyr Ser His Arg Val Asp Lys Lys Pro Asn
                    1070                1075                1080
Arg Glu Leu Ile Asn Asp Thr Leu Tyr Ser Thr Arg Lys Asp Asp
                    1085                1090                1095
Lys Gly Asn Thr Leu Ile Val Asn Asn Leu Asn Gly Leu Tyr Asp
                    1100                1105                1110
Lys Asp Asn Asp Lys Leu Lys Lys Leu Ile Asn Lys Ser Pro Glu
                    1115                1120                1125
Lys Leu Leu Met Tyr His His Asp Pro Gln Thr Tyr Gln Lys Leu
                    1130                1135                1140
Lys Leu Ile Met Glu Gln Tyr Gly Asp Glu Lys Asn Pro Leu Tyr
                    1145                1150                1155
Lys Tyr Tyr Glu Glu Thr Gly Asn Tyr Leu Thr Lys Tyr Ser Lys
                    1160                1165                1170
Lys Asp Asn Gly Pro Val Ile Lys Lys Ile Lys Tyr Tyr Gly Asn
                    1175                1180                1185
Lys Leu Asn Ala His Leu Asp Ile Thr Asp Asp Tyr Pro Asn Ser
                    1190                1195                1200
```

```
Arg Asn Lys Val Val Lys Leu Ser Leu Lys Pro Tyr Arg Phe Asp
1205                1210                1215

Val Tyr Leu Asp Asn Gly Val Tyr Lys Phe Val Thr Val Lys Asn
1220                1225                1230

Leu Asp Val Ile Lys Lys Glu Asn Tyr Tyr Glu Val Asn Ser Lys
1235                1240                1245

Cys Tyr Glu Glu Ala Lys Lys Leu Lys Lys Ile Ser Asn Gln Ala
1250                1255                1260

Glu Phe Ile Ala Ser Phe Tyr Asn Asn Asp Leu Ile Lys Ile Asn
1265                1270                1275

Gly Glu Leu Tyr Arg Val Ile Gly Val Asn Asn Asp Leu Leu Asn
1280                1285                1290

Arg Ile Glu Val Asn Met Ile Asp Ile Thr Tyr Arg Glu Tyr Leu
1295                1300                1305

Glu Asn Met Asn Asp Lys Arg Pro Pro Arg Ile Ile Lys Thr Ile
1310                1315                1320

Ala Ser Lys Thr Gln Ser Ile Lys Lys Tyr Ser Thr Asp Ile Leu
1325                1330                1335

Gly Asn Leu Tyr Glu Val Lys Ser Lys Lys His Pro Gln Ile Ile
1340                1345                1350

Lys Lys Gly Ser Gly Phe Ala Asn Glu Leu Gly Pro Arg Leu Met
1355                1360                1365

Gly Lys Gly Gly Gly Gly Ser Asp Val Pro Phe His Ser Ser Tyr
1370                1375                1380

Ala His Ser Gln Ser Leu Asp Arg Leu Met Asn Pro Leu Ile Asp
1385                1390                1395

Gln Tyr Leu Tyr Tyr Leu Ser Arg Thr Gln Ser Thr Gly Gly Thr
1400                1405                1410

Ala Gly Thr Gln Gln Leu Leu Phe Ser Gln Ala Gly Pro Asn Asn
1415                1420                1425

Met Ser Ala Gln Ala Lys Asn Trp Leu Pro Gly Pro Cys Tyr Arg
1430                1435                1440

Gln Gln Arg Val Ser Thr Thr Leu Ser Gln Asn Asn Asn Ser Asn
1445                1450                1455

Phe Ala Trp Thr Gly Ala Thr Lys Tyr His Leu Asn Gly Arg Asp
1460                1465                1470

Ser Leu Val Asn Pro Gly Val Ala Met Ala Thr His Lys Asp Asp
1475                1480                1485

Glu Glu Arg Phe Phe Pro Ser Ser Gly Val Leu Met Phe Gly Lys
1490                1495                1500

Gln Gly Ala Gly Lys Asp Asn Val Asp Tyr Ser Ser Val Met Leu
1505                1510                1515

Thr Ser Glu Glu Glu Ile Lys Thr Thr Asn Pro Val Ala Thr Glu
1520                1525                1530

Gln Tyr Gly Val Val Ala Asp Asn Leu Gln Gln Gln Asn Ala Ala
1535                1540                1545

Pro Ile Val Gly Ala Val Asn Ser Gln Gly Ala Leu Pro Gly Met
1550                1555                1560

Val Trp Gln Asn Arg Asp Val Tyr Leu Gln Gly Pro Ile Trp Ala
1565                1570                1575

Lys Ile Pro His Thr Asp Gly Asn Phe His Pro Ser Pro Leu Met
1580                1585                1590
```

```
Gly Gly Phe Gly Leu Lys His Pro Pro Gln Ile Leu Ile Lys
    1595                1600                1605

Asn Thr Pro Val Pro Ala Asp Pro Pro Thr Thr Phe Ser Gln Ala
1610                1615                1620

Lys Leu Ala Ser Phe Ile Thr Gln Tyr Ser Thr Gly Gln Val Ser
    1625                1630                1635

Val Glu Ile Glu Trp Glu Leu Gln Lys Glu Asn Ser Lys Arg Trp
1640                1645                1650

Asn Pro Glu Ile Gln Tyr Thr Ser Asn Tyr Tyr Lys Ser Thr Asn
    1655                1660                1665

Val Asp Phe Ala Val Asn Thr Glu Gly Thr Tyr Ser Glu Pro Arg
1670                1675                1680

Pro Ile Gly Thr Arg Tyr Leu Thr Arg Asn Leu
    1685                1690

<210> SEQ ID NO 48
<211> LENGTH: 1694
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 48

Met Ala Ser Gly Thr Ser Arg Pro Val Glu Pro Ser Pro Gln Arg Ser
1               5                   10                  15

Pro Asp Ser Ser Thr Gly Ile Gly Lys Lys Gly Gln Gln Pro Ala Lys
            20                  25                  30

Lys Arg Leu Asn Phe Gly Gln Thr Gly Asp Ser Glu Ser Val Pro Asp
        35                  40                  45

Pro Gln Pro Ile Gly Glu Pro Pro Ala Gly Pro Ser Gly Leu Gly Ser
    50                  55                  60

Gly Thr Leu Ala Ala Gly Gly Ala Pro Leu Ala Asp Asn Asn Glu
65                  70                  75                  80

Gly Ala Asp Gly Val Gly Ser Ser Ser Gly Asn Trp His Cys Asp Ser
                85                  90                  95

Thr Trp Leu Gly Asp Arg Val Ile Thr Thr Ser Thr Arg Thr Trp Ala
            100                 105                 110

Leu Pro Thr Tyr Asn Asn His Leu Tyr Lys Gln Ile Ser Asn Gly Thr
        115                 120                 125

Ser Gly Gly Ser Thr Asn Asp Asn Thr Tyr Phe Gly Tyr Ser Thr Pro
    130                 135                 140

Trp Gly Tyr Phe Asp Phe Asn Arg Phe His Cys His Phe Ser Pro Arg
145                 150                 155                 160

Asp Trp Gln Arg Leu Ile Asn Asn Asn Trp Gly Phe Arg Pro Lys Arg
                165                 170                 175

Leu Asn Phe Lys Leu Phe Asn Ile Gln Val Lys Glu Val Thr Gln Asn
        180                 185                 190

Glu Gly Thr Lys Thr Ile Ala Asn Asn Leu Thr Ser Thr Ile Gln Val
    195                 200                 205

Phe Thr Asp Ser Glu Tyr Gln Leu Pro Tyr Val Leu Gly Ser Ala His
    210                 215                 220

Gln Gly Cys Leu Pro Pro Phe Pro Ala Asp Val Phe Met Ile Pro Gln
225                 230                 235                 240

Tyr Gly Tyr Leu Thr Leu Asn Asn Gly Ser Gln Ala Val Gly Arg Ser
```

```
                245                 250                 255
Ser Phe Tyr Cys Leu Glu Tyr Phe Pro Ser Gln Met Leu Arg Thr Gly
            260                 265                 270

Asn Asn Phe Glu Phe Ser Tyr Asn Phe Glu Asp Val Pro Phe His Ser
            275                 280                 285

Ser Tyr Ala His Ser Gln Ser Leu Asp Arg Leu Met Asn Pro Leu Ile
            290                 295                 300

Asp Gln Tyr Leu Tyr Tyr Leu Ser Arg Thr Gln Ser Thr Gly Gly Thr
305                 310                 315                 320

Ala Gly Thr Gln Gln Leu Leu Phe Ser Gln Ala Gly Pro Asn Asn Met
                325                 330                 335

Ser Ala Gln Ala Lys Asn Trp Leu Pro Gly Pro Cys Tyr Arg Gln Gln
                340                 345                 350

Arg Val Ser Thr Thr Leu Ser Gln Asn Asn Ser Asn Phe Ala Trp
                355                 360                 365

Thr Gly Ala Thr Lys Tyr His Leu Asn Gly Arg Asp Ser Leu Val Asn
            370                 375                 380

Pro Gly Val Ala Met Ala Thr His Lys Asp Asp Glu Glu Arg Phe Phe
385                 390                 395                 400

Pro Ser Ser Gly Val Leu Met Phe Gly Lys Gln Gly Ala Gly Lys Asp
                405                 410                 415

Asn Val Asp Tyr Ser Ser Val Met Leu Thr Ser Glu Glu Ile Lys
            420                 425                 430

Thr Thr Asn Pro Val Ala Thr Glu Gln Tyr Gly Val Val Ala Asp Asn
            435                 440                 445

Leu Gln Gln Gln Asn Ala Ala Pro Ile Val Gly Ala Val Asn Ser Gln
450                 455                 460

Gly Ala Leu Pro Gly Met Val Trp Gln Asn Arg Asp Val Tyr Leu Gln
465                 470                 475                 480

Gly Pro Ile Trp Ala Lys Ile Pro His Thr Asp Gly Asn Phe His Pro
                485                 490                 495

Ser Pro Leu Met Gly Gly Phe Gly Leu Lys His Pro Pro Gln Ile
            500                 505                 510

Leu Ile Lys Asn Thr Pro Val Pro Ala Asp Pro Pro Thr Thr Phe Ser
            515                 520                 525

Gln Ala Lys Leu Ala Ser Phe Ile Thr Gln Tyr Ser Thr Gly Gln Val
            530                 535                 540

Ser Val Glu Gly Gly Gly Ser Met Ala Pro Lys Lys Arg Lys
545                 550                 555                 560

Val Gly Ile His Gly Val Pro Ala Ala Lys Arg Asn Tyr Ile Leu Gly
                565                 570                 575

Leu Asp Ile Gly Ile Thr Ser Val Gly Tyr Gly Ile Ile Asp Tyr Glu
                580                 585                 590

Thr Arg Asp Val Ile Asp Ala Gly Val Arg Leu Phe Lys Glu Ala Asn
                595                 600                 605

Val Glu Asn Asn Glu Gly Arg Arg Ser Lys Arg Gly Ala Arg Arg Leu
            610                 615                 620

Lys Arg Arg Arg Arg His Arg Ile Gln Arg Val Lys Lys Leu Leu Phe
625                 630                 635                 640

Asp Tyr Asn Leu Leu Thr Asp His Ser Glu Leu Ser Gly Ile Asn Pro
                645                 650                 655

Tyr Glu Ala Arg Val Lys Gly Leu Ser Gln Lys Leu Ser Glu Glu Glu
                660                 665                 670
```

```
Phe Ser Ala Ala Leu Leu His Leu Ala Lys Arg Arg Gly Val His Asn
        675                 680                 685

Val Asn Glu Val Glu Glu Asp Thr Gly Asn Glu Leu Ser Thr Lys Glu
690                 695                 700

Gln Ile Ser Arg Asn Ser Lys Ala Leu Glu Glu Lys Tyr Val Ala Glu
705                 710                 715                 720

Leu Gln Leu Glu Arg Leu Lys Lys Asp Gly Glu Val Arg Gly Ser Ile
                725                 730                 735

Asn Arg Phe Lys Thr Ser Asp Tyr Val Lys Glu Ala Lys Gln Leu Leu
            740                 745                 750

Lys Val Gln Lys Ala Tyr His Gln Leu Asp Gln Ser Phe Ile Asp Thr
                755                 760                 765

Tyr Ile Asp Leu Leu Glu Thr Arg Arg Thr Tyr Tyr Glu Gly Pro Gly
770                 775                 780

Glu Gly Ser Pro Phe Gly Trp Lys Asp Ile Lys Glu Trp Tyr Glu Met
785                 790                 795                 800

Leu Met Gly His Cys Thr Tyr Phe Pro Glu Glu Leu Arg Ser Val Lys
                805                 810                 815

Tyr Ala Tyr Asn Ala Asp Leu Tyr Asn Ala Leu Asn Asp Leu Asn Asn
                820                 825                 830

Leu Val Ile Thr Arg Asp Glu Asn Glu Lys Leu Glu Tyr Tyr Glu Lys
                835                 840                 845

Phe Gln Ile Ile Glu Asn Val Phe Lys Gln Lys Lys Lys Pro Thr Leu
850                 855                 860

Lys Gln Ile Ala Lys Glu Ile Leu Val Asn Glu Glu Asp Ile Lys Gly
865                 870                 875                 880

Tyr Arg Val Thr Ser Thr Gly Lys Pro Glu Phe Thr Asn Leu Lys Val
                885                 890                 895

Tyr His Asp Ile Lys Asp Ile Thr Ala Arg Lys Glu Ile Ile Glu Asn
                900                 905                 910

Ala Glu Leu Leu Asp Gln Ile Ala Lys Ile Leu Thr Ile Tyr Gln Ser
            915                 920                 925

Ser Glu Asp Ile Gln Glu Glu Leu Thr Asn Leu Asn Ser Glu Leu Thr
930                 935                 940

Gln Glu Glu Ile Glu Gln Ile Ser Asn Leu Lys Gly Tyr Thr Gly Thr
945                 950                 955                 960

His Asn Leu Ser Leu Lys Ala Ile Asn Leu Ile Leu Asp Glu Leu Trp
                965                 970                 975

His Thr Asn Asp Asn Gln Ile Ala Ile Phe Asn Arg Leu Lys Leu Val
            980                 985                 990

Pro Lys Lys Val Asp Leu Ser Gln Gln Lys Glu Ile Pro Thr Thr Leu
            995                 1000                1005

Val Asp Asp Phe Ile Leu Ser Pro Val Val Lys Arg Ser Phe Ile
    1010                1015                1020

Gln Ser Ile Lys Val Ile Asn Ala Ile Ile Lys Lys Tyr Gly Leu
    1025                1030                1035

Pro Asn Asp Ile Ile Ile Glu Leu Ala Arg Glu Lys Asn Ser Lys
    1040                1045                1050

Asp Ala Gln Lys Met Ile Asn Glu Met Gln Lys Arg Asn Arg Gln
    1055                1060                1065

Thr Asn Glu Arg Ile Glu Glu Ile Ile Arg Thr Thr Gly Lys Glu
    1070                1075                1080
```

```
Asn Ala Lys Tyr Leu Ile Glu Lys Ile Lys Leu His Asp Met Gln
        1085                1090                1095

Glu Gly Lys Cys Leu Tyr Ser Leu Glu Ala Ile Pro Leu Glu Asp
        1100                1105                1110

Leu Leu Asn Asn Pro Phe Asn Tyr Glu Val Asp His Ile Ile Pro
        1115                1120                1125

Arg Ser Val Ser Phe Asp Asn Ser Phe Asn Asn Lys Val Leu Val
        1130                1135                1140

Lys Gln Glu Glu Asn Ser Lys Lys Gly Asn Arg Thr Pro Phe Gln
        1145                1150                1155

Tyr Leu Ser Ser Ser Asp Ser Lys Ile Ser Tyr Glu Thr Phe Lys
        1160                1165                1170

Lys His Ile Leu Asn Leu Ala Lys Gly Lys Gly Arg Ile Ser Lys
        1175                1180                1185

Thr Lys Lys Glu Tyr Leu Leu Glu Glu Arg Asp Ile Asn Arg Phe
        1190                1195                1200

Ser Val Gln Lys Asp Phe Ile Asn Arg Asn Leu Val Asp Thr Arg
        1205                1210                1215

Tyr Ala Thr Arg Gly Leu Met Asn Leu Leu Arg Ser Tyr Phe Arg
        1220                1225                1230

Val Asn Asn Leu Asp Val Lys Val Lys Ser Ile Asn Gly Gly Phe
        1235                1240                1245

Thr Ser Phe Leu Arg Arg Lys Trp Lys Phe Lys Lys Glu Arg Asn
        1250                1255                1260

Lys Gly Tyr Lys His His Ala Glu Asp Ala Leu Ile Ile Ala Asn
        1265                1270                1275

Ala Asp Phe Ile Phe Lys Glu Trp Lys Lys Leu Asp Lys Ala Lys
        1280                1285                1290

Lys Val Met Glu Asn Gln Met Phe Glu Glu Lys Gln Ala Glu Ser
        1295                1300                1305

Met Pro Glu Ile Glu Thr Glu Gln Glu Tyr Lys Glu Ile Phe Ile
        1310                1315                1320

Thr Pro His Gln Ile Lys His Ile Lys Asp Phe Lys Asp Tyr Lys
        1325                1330                1335

Tyr Ser His Arg Val Asp Lys Lys Pro Asn Arg Glu Leu Ile Asn
        1340                1345                1350

Asp Thr Leu Tyr Ser Thr Arg Lys Asp Asp Lys Gly Asn Thr Leu
        1355                1360                1365

Ile Val Asn Asn Leu Asn Gly Leu Tyr Asp Lys Asp Asn Asp Lys
        1370                1375                1380

Leu Lys Lys Leu Ile Asn Lys Ser Pro Glu Lys Leu Leu Met Tyr
        1385                1390                1395

His His Asp Pro Gln Thr Tyr Gln Lys Leu Lys Leu Ile Met Glu
        1400                1405                1410

Gln Tyr Gly Asp Glu Lys Asn Pro Leu Tyr Lys Tyr Tyr Glu Glu
        1415                1420                1425

Thr Gly Asn Tyr Leu Thr Lys Tyr Ser Lys Lys Asp Asn Gly Pro
        1430                1435                1440

Val Ile Lys Lys Ile Lys Tyr Tyr Gly Asn Lys Leu Asn Ala His
        1445                1450                1455

Leu Asp Ile Thr Asp Asp Tyr Pro Asn Ser Arg Asn Lys Val Val
        1460                1465                1470

Lys Leu Ser Leu Lys Pro Tyr Arg Phe Asp Val Tyr Leu Asp Asn
```

```
              1475                1480                1485

Gly Val Tyr Lys Phe Val Thr Val Lys Asn Leu Asp Val Ile Lys
            1490                1495                1500

Lys Glu Asn Tyr Tyr Glu Val Asn Ser Lys Cys Tyr Glu Glu Ala
        1505                1510                1515

Lys Lys Leu Lys Lys Ile Ser Asn Gln Ala Glu Phe Ile Ala Ser
    1520                1525                1530

Phe Tyr Asn Asn Asp Leu Ile Lys Ile Asn Gly Glu Leu Tyr Arg
        1535                1540                1545

Val Ile Gly Val Asn Asn Asp Leu Leu Asn Arg Ile Glu Val Asn
    1550                1555                1560

Met Ile Asp Ile Thr Tyr Arg Glu Tyr Leu Glu Asn Met Asn Asp
    1565                1570                1575

Lys Arg Pro Pro Arg Ile Ile Lys Thr Ile Ala Ser Lys Thr Gln
    1580                1585                1590

Ser Ile Lys Lys Tyr Ser Thr Asp Ile Leu Gly Asn Leu Tyr Glu
    1595                1600                1605

Val Lys Ser Lys Lys His Pro Gln Ile Ile Lys Lys Gly Ser Gly
    1610                1615                1620

Phe Ala Asn Glu Leu Gly Pro Arg Leu Met Gly Lys Gly Gly Gly
    1625                1630                1635

Gly Ser Ile Glu Trp Glu Leu Gln Lys Glu Asn Ser Lys Arg Trp
    1640                1645                1650

Asn Pro Glu Ile Gln Tyr Thr Ser Asn Tyr Tyr Lys Ser Thr Asn
    1655                1660                1665

Val Asp Phe Ala Val Asn Thr Glu Gly Thr Tyr Ser Glu Pro Arg
    1670                1675                1680

Pro Ile Gly Thr Arg Tyr Leu Thr Arg Asn Leu
    1685                1690

<210> SEQ ID NO 49
<211> LENGTH: 1694
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 49

Met Ala Ser Gly Thr Ser Arg Pro Val Glu Pro Ser Pro Gln Arg Ser
1               5                   10                  15

Pro Asp Ser Ser Thr Gly Ile Gly Lys Lys Gly Gln Gln Pro Ala Lys
                20                  25                  30

Lys Arg Leu Asn Phe Gly Gln Thr Gly Asp Ser Glu Ser Val Pro Asp
            35                  40                  45

Pro Gln Pro Ile Gly Glu Pro Pro Ala Gly Pro Ser Gly Leu Gly Ser
        50                  55                  60

Gly Thr Leu Ala Ala Gly Gly Ala Pro Leu Ala Asp Asn Asn Glu
65                  70                  75                  80

Gly Ala Asp Gly Val Gly Ser Ser Gly Asn Trp His Cys Asp Ser
                85                  90                  95

Thr Trp Leu Gly Asp Arg Val Ile Thr Thr Ser Thr Arg Thr Trp Ala
            100                 105                 110

Leu Pro Thr Tyr Asn Asn His Leu Tyr Lys Gln Ile Ser Asn Gly Thr
        115                 120                 125
```

```
Ser Gly Gly Ser Thr Asn Asp Asn Thr Tyr Phe Gly Tyr Ser Thr Pro
        130                 135                 140

Trp Gly Tyr Phe Asp Phe Asn Arg Phe His Cys His Phe Ser Pro Arg
145                 150                 155                 160

Asp Trp Gln Arg Leu Ile Asn Asn Asn Trp Gly Phe Arg Pro Lys Arg
                165                 170                 175

Leu Asn Phe Lys Leu Phe Asn Ile Gln Val Lys Glu Val Thr Gln Asn
                180                 185                 190

Glu Gly Thr Lys Thr Ile Ala Asn Asn Leu Thr Ser Thr Ile Gln Val
            195                 200                 205

Phe Thr Asp Ser Glu Tyr Gln Leu Pro Tyr Val Leu Gly Ser Ala His
        210                 215                 220

Gln Gly Cys Leu Pro Pro Phe Pro Ala Asp Val Phe Met Ile Pro Gln
225                 230                 235                 240

Tyr Gly Tyr Leu Thr Leu Asn Asn Gly Ser Gln Ala Val Gly Arg Ser
                245                 250                 255

Ser Phe Tyr Cys Leu Glu Tyr Phe Pro Ser Gln Met Leu Arg Thr Gly
                260                 265                 270

Asn Asn Phe Glu Phe Ser Tyr Asn Phe Glu Asp Val Pro Phe His Ser
                275                 280                 285

Ser Tyr Ala His Ser Gln Ser Leu Asp Arg Leu Met Asn Pro Leu Ile
        290                 295                 300

Asp Gln Tyr Leu Tyr Tyr Leu Ser Arg Thr Gln Ser Thr Gly Gly Thr
305                 310                 315                 320

Ala Gly Thr Gln Gln Leu Leu Phe Ser Gln Ala Gly Pro Asn Asn Met
                325                 330                 335

Ser Ala Gln Ala Lys Asn Trp Leu Pro Gly Pro Cys Tyr Arg Gln Gln
            340                 345                 350

Arg Val Ser Thr Thr Leu Ser Gln Asn Asn Asn Ser Asn Phe Ala Trp
                355                 360                 365

Thr Gly Ala Thr Lys Tyr His Leu Asn Gly Arg Asp Ser Leu Val Asn
        370                 375                 380

Pro Gly Val Ala Met Ala Thr His Lys Asp Asp Glu Glu Arg Phe Phe
385                 390                 395                 400

Pro Ser Ser Gly Val Leu Met Phe Gly Lys Gln Gly Ala Gly Lys Asp
                405                 410                 415

Asn Val Asp Tyr Ser Ser Val Met Leu Thr Ser Glu Glu Ile Lys
                420                 425                 430

Thr Thr Asn Pro Val Ala Thr Glu Gln Tyr Gly Val Val Ala Asp Asn
        435                 440                 445

Leu Gln Gln Gln Asn Ala Ala Pro Ile Val Gly Ala Val Asn Ser Gln
    450                 455                 460

Gly Ala Leu Pro Gly Met Val Trp Gln Asn Arg Asp Val Tyr Leu Gln
465                 470                 475                 480

Gly Pro Ile Trp Ala Lys Ile Pro His Thr Asp Gly Asn Phe His Pro
                485                 490                 495

Ser Pro Leu Met Gly Gly Phe Gly Leu Lys His Pro Pro Gln Ile
            500                 505                 510

Leu Ile Lys Asn Thr Pro Val Pro Ala Asp Pro Pro Thr Thr Phe Ser
        515                 520                 525

Gln Ala Lys Leu Ala Ser Phe Ile Thr Gln Tyr Ser Thr Gly Gln Val
530                 535                 540
```

```
Ser Val Glu Ile Glu Trp Glu Leu Gly Gly Gly Ser Met Ala Pro
545                 550                 555                 560

Lys Lys Lys Arg Lys Val Gly Ile His Gly Val Pro Ala Ala Lys Arg
            565                 570                 575

Asn Tyr Ile Leu Gly Leu Asp Ile Gly Ile Thr Ser Val Gly Tyr Gly
            580                 585                 590

Ile Ile Asp Tyr Glu Thr Arg Asp Val Ile Asp Ala Gly Val Arg Leu
        595                 600                 605

Phe Lys Glu Ala Asn Val Glu Asn Asn Glu Gly Arg Arg Ser Lys Arg
        610                 615                 620

Gly Ala Arg Arg Leu Lys Arg Arg Arg His Arg Ile Gln Arg Val
625                 630                 635                 640

Lys Lys Leu Leu Phe Asp Tyr Asn Leu Leu Thr Asp His Ser Glu Leu
            645                 650                 655

Ser Gly Ile Asn Pro Tyr Glu Ala Arg Val Lys Gly Leu Ser Gln Lys
            660                 665                 670

Leu Ser Glu Glu Glu Phe Ser Ala Ala Leu Leu His Leu Ala Lys Arg
        675                 680                 685

Arg Gly Val His Asn Val Asn Glu Val Glu Glu Asp Thr Gly Asn Glu
        690                 695                 700

Leu Ser Thr Lys Glu Gln Ile Ser Arg Asn Ser Lys Ala Leu Glu Glu
705                 710                 715                 720

Lys Tyr Val Ala Glu Leu Gln Leu Glu Arg Leu Lys Lys Asp Gly Glu
            725                 730                 735

Val Arg Gly Ser Ile Asn Arg Phe Lys Thr Ser Asp Tyr Val Lys Glu
            740                 745                 750

Ala Lys Gln Leu Leu Lys Val Gln Lys Ala Tyr His Gln Leu Asp Gln
            755                 760                 765

Ser Phe Ile Asp Thr Tyr Ile Asp Leu Leu Glu Thr Arg Arg Thr Tyr
            770                 775                 780

Tyr Glu Gly Pro Gly Glu Gly Ser Pro Phe Gly Trp Lys Asp Ile Lys
785                 790                 795                 800

Glu Trp Tyr Glu Met Leu Met Gly His Cys Thr Tyr Phe Pro Glu Glu
                805                 810                 815

Leu Arg Ser Val Lys Tyr Ala Tyr Asn Ala Asp Leu Tyr Asn Ala Leu
            820                 825                 830

Asn Asp Leu Asn Asn Leu Val Ile Thr Arg Asp Glu Asn Glu Lys Leu
            835                 840                 845

Glu Tyr Tyr Glu Lys Phe Gln Ile Ile Glu Asn Val Phe Lys Gln Lys
        850                 855                 860

Lys Lys Pro Thr Leu Lys Gln Ile Ala Lys Glu Ile Leu Val Asn Glu
865                 870                 875                 880

Glu Asp Ile Lys Gly Tyr Arg Val Thr Ser Thr Gly Lys Pro Glu Phe
            885                 890                 895

Thr Asn Leu Lys Val Tyr His Asp Ile Lys Asp Ile Thr Ala Arg Lys
            900                 905                 910

Glu Ile Ile Glu Asn Ala Glu Leu Leu Asp Gln Ile Ala Lys Ile Leu
        915                 920                 925

Thr Ile Tyr Gln Ser Ser Glu Asp Ile Gln Glu Glu Leu Thr Asn Leu
        930                 935                 940

Asn Ser Glu Leu Thr Gln Glu Glu Ile Glu Gln Ile Ser Asn Leu Lys
945                 950                 955                 960

Gly Tyr Thr Gly Thr His Asn Leu Ser Leu Lys Ala Ile Asn Leu Ile
```

-continued

```
                965                 970                 975
Leu Asp Glu Leu Trp His Thr Asn Asp Asn Gln Ile Ala Ile Phe Asn
                    980                 985                 990
Arg Leu Lys Leu Val Pro Lys Lys Val Asp Leu Ser Gln Gln Lys Glu
        995                 1000                1005
Ile Pro Thr Thr Leu Val Asp Asp Phe Ile Leu Ser Pro Val Val
    1010                1015                1020
Lys Arg Ser Phe Ile Gln Ser Ile Lys Val Ile Asn Ala Ile Ile
    1025                1030                1035
Lys Lys Tyr Gly Leu Pro Asn Asp Ile Ile Glu Leu Ala Arg
    1040                1045                1050
Glu Lys Asn Ser Lys Asp Ala Gln Lys Met Ile Asn Glu Met Gln
    1055                1060                1065
Lys Arg Asn Arg Gln Thr Asn Glu Arg Ile Glu Glu Ile Ile Arg
    1070                1075                1080
Thr Thr Gly Lys Glu Asn Ala Lys Tyr Leu Ile Glu Lys Ile Lys
    1085                1090                1095
Leu His Asp Met Gln Glu Gly Lys Cys Leu Tyr Ser Leu Glu Ala
    1100                1105                1110
Ile Pro Leu Glu Asp Leu Leu Asn Asn Pro Phe Asn Tyr Glu Val
    1115                1120                1125
Asp His Ile Ile Pro Arg Ser Val Ser Phe Asp Asn Ser Phe Asn
    1130                1135                1140
Asn Lys Val Leu Val Lys Gln Glu Glu Asn Ser Lys Lys Gly Asn
    1145                1150                1155
Arg Thr Pro Phe Gln Tyr Leu Ser Ser Ser Asp Ser Lys Ile Ser
    1160                1165                1170
Tyr Glu Thr Phe Lys Lys His Ile Leu Asn Leu Ala Lys Gly Lys
    1175                1180                1185
Gly Arg Ile Ser Lys Thr Lys Lys Glu Tyr Leu Leu Glu Glu Arg
    1190                1195                1200
Asp Ile Asn Arg Phe Ser Val Gln Lys Asp Phe Ile Asn Arg Asn
    1205                1210                1215
Leu Val Asp Thr Arg Tyr Ala Thr Arg Gly Leu Met Asn Leu Leu
    1220                1225                1230
Arg Ser Tyr Phe Arg Val Asn Asn Leu Asp Val Lys Val Lys Ser
    1235                1240                1245
Ile Asn Gly Gly Phe Thr Ser Phe Leu Arg Arg Lys Trp Lys Phe
    1250                1255                1260
Lys Lys Glu Arg Asn Lys Gly Tyr Lys His His Ala Glu Asp Ala
    1265                1270                1275
Leu Ile Ile Ala Asn Ala Asp Phe Ile Phe Lys Glu Trp Lys Lys
    1280                1285                1290
Leu Asp Lys Ala Lys Lys Val Met Glu Asn Gln Met Phe Glu Glu
    1295                1300                1305
Lys Gln Ala Glu Ser Met Pro Glu Ile Glu Thr Glu Gln Glu Tyr
    1310                1315                1320
Lys Glu Ile Phe Ile Thr Pro His Gln Ile Lys His Ile Lys Asp
    1325                1330                1335
Phe Lys Asp Tyr Lys Tyr Ser His Arg Val Asp Lys Lys Pro Asn
    1340                1345                1350
Arg Glu Leu Ile Asn Asp Thr Leu Tyr Ser Thr Arg Lys Asp Asp
    1355                1360                1365
```

Lys Gly Asn Thr Leu Ile Val Asn Asn Leu Asn Gly Leu Tyr Asp
        1370                1375                1380

Lys Asp Asn Asp Lys Leu Lys Lys Leu Ile Asn Lys Ser Pro Glu
        1385                1390                1395

Lys Leu Leu Met Tyr His His Asp Pro Gln Thr Tyr Gln Lys Leu
        1400                1405                1410

Lys Leu Ile Met Glu Gln Tyr Gly Asp Glu Lys Asn Pro Leu Tyr
        1415                1420                1425

Lys Tyr Tyr Glu Glu Thr Gly Asn Tyr Leu Thr Lys Tyr Ser Lys
        1430                1435                1440

Lys Asp Asn Gly Pro Val Ile Lys Lys Ile Lys Tyr Tyr Gly Asn
        1445                1450                1455

Lys Leu Asn Ala His Leu Asp Ile Thr Asp Asp Tyr Pro Asn Ser
        1460                1465                1470

Arg Asn Lys Val Val Lys Leu Ser Leu Lys Pro Tyr Arg Phe Asp
        1475                1480                1485

Val Tyr Leu Asp Asn Gly Val Tyr Lys Phe Val Thr Val Lys Asn
        1490                1495                1500

Leu Asp Val Ile Lys Lys Glu Asn Tyr Tyr Glu Val Asn Ser Lys
        1505                1510                1515

Cys Tyr Glu Glu Ala Lys Lys Leu Lys Lys Ile Ser Asn Gln Ala
        1520                1525                1530

Glu Phe Ile Ala Ser Phe Tyr Asn Asn Asp Leu Ile Lys Ile Asn
        1535                1540                1545

Gly Glu Leu Tyr Arg Val Ile Gly Val Asn Asn Asp Leu Leu Asn
        1550                1555                1560

Arg Ile Glu Val Asn Met Ile Asp Ile Thr Tyr Arg Glu Tyr Leu
        1565                1570                1575

Glu Asn Met Asn Asp Lys Arg Pro Pro Arg Ile Ile Lys Thr Ile
        1580                1585                1590

Ala Ser Lys Thr Gln Ser Ile Lys Lys Tyr Ser Thr Asp Ile Leu
        1595                1600                1605

Gly Asn Leu Tyr Glu Val Lys Ser Lys Lys His Pro Gln Ile Ile
        1610                1615                1620

Lys Lys Gly Ser Gly Phe Ala Asn Glu Leu Gly Pro Arg Leu Met
        1625                1630                1635

Gly Lys Gly Gly Gly Ser Gln Lys Glu Asn Ser Lys Arg Trp
        1640                1645                1650

Asn Pro Glu Ile Gln Tyr Thr Ser Asn Tyr Tyr Lys Ser Thr Asn
        1655                1660                1665

Val Asp Phe Ala Val Asn Thr Glu Gly Thr Tyr Ser Glu Pro Arg
        1670                1675                1680

Pro Ile Gly Thr Arg Tyr Leu Thr Arg Asn Leu
        1685                1690

<210> SEQ ID NO 50
<211> LENGTH: 1083
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 50

```
Met Ala Pro Lys Lys Lys Arg Lys Val Gly Ile His Gly Val Pro Ala
1               5                   10                  15

Ala Lys Arg Asn Tyr Ile Leu Gly Leu Asp Ile Gly Ile Thr Ser Val
            20                  25                  30

Gly Tyr Gly Ile Ile Asp Tyr Glu Thr Arg Asp Val Ile Asp Ala Gly
        35                  40                  45

Val Arg Leu Phe Lys Glu Ala Asn Val Glu Asn Asn Glu Gly Arg Arg
50                  55                  60

Ser Lys Arg Gly Ala Arg Leu Lys Arg Arg Arg His Arg Ile
65                  70                  75                  80

Gln Arg Val Lys Lys Leu Leu Phe Asp Tyr Asn Leu Leu Thr Asp His
                85                  90                  95

Ser Glu Leu Ser Gly Ile Asn Pro Tyr Glu Ala Arg Val Lys Gly Leu
            100                 105                 110

Ser Gln Lys Leu Ser Glu Glu Phe Ser Ala Ala Leu Leu His Leu
        115                 120                 125

Ala Lys Arg Arg Gly Val His Asn Val Asn Glu Val Glu Glu Asp Thr
    130                 135                 140

Gly Asn Glu Leu Ser Thr Lys Glu Gln Ile Ser Arg Asn Ser Lys Ala
145                 150                 155                 160

Leu Glu Glu Lys Tyr Val Ala Glu Leu Gln Leu Glu Arg Leu Lys Lys
                165                 170                 175

Asp Gly Glu Val Arg Gly Ser Ile Asn Arg Phe Lys Thr Ser Asp Tyr
            180                 185                 190

Val Lys Glu Ala Lys Gln Leu Leu Lys Val Gln Lys Ala Tyr His Gln
        195                 200                 205

Leu Asp Gln Ser Phe Ile Asp Thr Tyr Ile Asp Leu Leu Glu Thr Arg
    210                 215                 220

Arg Thr Tyr Tyr Glu Gly Pro Gly Glu Gly Ser Pro Phe Gly Trp Lys
225                 230                 235                 240

Asp Ile Lys Glu Trp Tyr Glu Met Leu Met Gly His Cys Thr Tyr Phe
                245                 250                 255

Pro Glu Glu Leu Arg Ser Val Lys Tyr Ala Tyr Asn Ala Asp Leu Tyr
            260                 265                 270

Asn Ala Leu Asn Asp Leu Asn Asn Leu Val Ile Thr Arg Asp Glu Asn
        275                 280                 285

Glu Lys Leu Glu Tyr Tyr Glu Lys Phe Gln Ile Ile Glu Asn Val Phe
    290                 295                 300

Lys Gln Lys Lys Lys Pro Thr Leu Lys Gln Ile Ala Lys Glu Ile Leu
305                 310                 315                 320

Val Asn Glu Glu Asp Ile Lys Gly Tyr Arg Val Thr Ser Thr Gly Lys
                325                 330                 335

Pro Glu Phe Thr Asn Leu Lys Val Tyr His Asp Ile Lys Asp Ile Thr
            340                 345                 350

Ala Arg Lys Glu Ile Ile Glu Asn Ala Glu Leu Leu Asp Gln Ile Ala
        355                 360                 365

Lys Ile Leu Thr Ile Tyr Gln Ser Ser Glu Asp Ile Gln Glu Glu Leu
    370                 375                 380

Thr Asn Leu Asn Ser Glu Leu Thr Gln Glu Glu Ile Glu Gln Ile Ser
385                 390                 395                 400

Asn Leu Lys Gly Tyr Thr Gly Thr His Asn Leu Ser Leu Lys Ala Ile
                405                 410                 415

Asn Leu Ile Leu Asp Glu Leu Trp His Thr Asn Asp Asn Gln Ile Ala
```

```
               420                 425                 430
Ile Phe Asn Arg Leu Lys Leu Val Pro Lys Val Asp Leu Ser Gln
                435                 440                 445
Gln Lys Glu Ile Pro Thr Thr Leu Val Asp Asp Phe Ile Leu Ser Pro
    450                 455                 460
Val Val Lys Arg Ser Phe Ile Gln Ser Ile Lys Val Ile Asn Ala Ile
465                 470                 475                 480
Ile Lys Lys Tyr Gly Leu Pro Asn Asp Ile Ile Glu Leu Ala Arg
                485                 490                 495
Glu Lys Asn Ser Lys Asp Ala Gln Lys Met Ile Asn Glu Met Gln Lys
                500                 505                 510
Arg Asn Arg Gln Thr Asn Glu Arg Ile Glu Glu Ile Arg Thr Thr
                515                 520                 525
Gly Lys Glu Asn Ala Lys Tyr Leu Ile Glu Lys Ile Lys Leu His Asp
                530                 535                 540
Met Gln Glu Gly Lys Cys Leu Tyr Ser Leu Glu Ala Ile Pro Leu Glu
545                 550                 555                 560
Asp Leu Leu Asn Asn Pro Phe Asn Tyr Glu Val Asp His Ile Ile Pro
                565                 570                 575
Arg Ser Val Ser Phe Asp Asn Ser Phe Asn Asn Lys Val Leu Val Lys
                580                 585                 590
Gln Glu Glu Asn Ser Lys Lys Gly Asn Arg Thr Pro Phe Gln Tyr Leu
                595                 600                 605
Ser Ser Ser Asp Ser Lys Ile Ser Tyr Glu Thr Phe Lys Lys His Ile
                610                 615                 620
Leu Asn Leu Ala Lys Gly Lys Gly Arg Ile Ser Lys Thr Lys Lys Glu
625                 630                 635                 640
Tyr Leu Leu Glu Glu Arg Asp Ile Asn Arg Phe Ser Val Gln Lys Asp
                645                 650                 655
Phe Ile Asn Arg Asn Leu Val Asp Thr Arg Tyr Ala Thr Arg Gly Leu
                660                 665                 670
Met Asn Leu Leu Arg Ser Tyr Phe Arg Val Asn Asn Leu Asp Val Lys
                675                 680                 685
Val Lys Ser Ile Asn Gly Gly Phe Thr Ser Phe Leu Arg Arg Lys Trp
                690                 695                 700
Lys Phe Lys Lys Glu Arg Asn Lys Gly Tyr Lys His His Ala Glu Asp
705                 710                 715                 720
Ala Leu Ile Ile Ala Asn Ala Asp Phe Ile Phe Lys Glu Trp Lys Lys
                725                 730                 735
Leu Asp Lys Ala Lys Lys Val Met Glu Asn Gln Met Phe Glu Glu Lys
                740                 745                 750
Gln Ala Glu Ser Met Pro Glu Ile Glu Thr Glu Gln Glu Tyr Lys Glu
                755                 760                 765
Ile Phe Ile Thr Pro His Gln Ile Lys His Ile Lys Asp Phe Lys Asp
                770                 775                 780
Tyr Lys Tyr Ser His Arg Val Asp Lys Lys Pro Asn Arg Glu Leu Ile
785                 790                 795                 800
Asn Asp Thr Leu Tyr Ser Thr Arg Lys Asp Asp Lys Gly Asn Thr Leu
                805                 810                 815
Ile Val Asn Asn Leu Asn Gly Leu Tyr Asp Lys Asp Asn Asp Lys Leu
                820                 825                 830
Lys Lys Leu Ile Asn Lys Ser Pro Glu Lys Leu Leu Met Tyr His His
                835                 840                 845
```

Asp Pro Gln Thr Tyr Gln Lys Leu Lys Leu Ile Met Glu Gln Tyr Gly
    850                 855                 860

Asp Glu Lys Asn Pro Leu Tyr Lys Tyr Tyr Glu Thr Gly Asn Tyr
865                 870                 875                 880

Leu Thr Lys Tyr Ser Lys Lys Asp Asn Gly Pro Val Ile Lys Ile
                885                 890                 895

Lys Tyr Tyr Gly Asn Lys Leu Asn Ala His Leu Asp Ile Thr Asp Asp
                900                 905                 910

Tyr Pro Asn Ser Arg Asn Lys Val Val Lys Leu Ser Leu Lys Pro Tyr
        915                 920                 925

Arg Phe Asp Val Tyr Leu Asp Asn Gly Val Tyr Lys Phe Val Thr Val
        930                 935                 940

Lys Asn Leu Asp Val Ile Lys Lys Glu Asn Tyr Tyr Glu Val Asn Ser
945                 950                 955                 960

Lys Cys Tyr Glu Glu Ala Lys Lys Leu Lys Lys Ile Ser Asn Gln Ala
                965                 970                 975

Glu Phe Ile Ala Ser Phe Tyr Asn Asn Asp Leu Ile Lys Ile Asn Gly
                980                 985                 990

Glu Leu Tyr Arg Val Ile Gly Val Asn Asn Asp Leu Leu Asn Arg Ile
                995                 1000                1005

Glu Val Asn Met Ile Asp Ile Thr Tyr Arg Glu Tyr Leu Glu Asn
        1010                1015                1020

Met Asn Asp Lys Arg Pro Pro Arg Ile Ile Lys Thr Ile Ala Ser
        1025                1030                1035

Lys Thr Gln Ser Ile Lys Lys Tyr Ser Thr Asp Ile Leu Gly Asn
        1040                1045                1050

Leu Tyr Glu Val Lys Ser Lys His Pro Gln Ile Ile Lys Lys
        1055                1060                1065

Gly Ser Gly Phe Ala Asn Glu Leu Gly Pro Arg Leu Met Gly Lys
        1070                1075                1080

<210> SEQ ID NO 51
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic peptide"

<400> SEQUENCE: 51

Gly Gly Gly Gly Ser
1               5

<210> SEQ ID NO 52
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
     Synthetic oligonucleotide"

<400> SEQUENCE: 52
ggcggaggag gcagc                                                    15

<210> SEQ ID NO 53
<211> LENGTH: 15
<212> TYPE: PRT

-continued

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 53

Gly Gly Gly Gly Ser Gly Gly Gly Gly Ser Gly Gly Gly Gly Ser
1               5                   10                  15

<210> SEQ ID NO 54
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 54

Gly Gly Ser Ser Arg Ser Ser Ser Ser Gly Gly Gly Ser Gly Gly
1               5                   10                  15

Gly Gly

<210> SEQ ID NO 55
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 55

Gly Gly Gly Gly Ser Gly Gly Gly Gly Ser Gly Gly Gly Gly Ser Gly
1               5                   10                  15

Gly Gly Gly Ser
            20

<210> SEQ ID NO 56
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 56

Gly Gly Gly Ser
1

<210> SEQ ID NO 57
<211> LENGTH: 10538
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 57 cgggccccccc ctcgaggtcg acggtatcgg gggagctcgc aggtctccaa ttttgaagcg     60
ggaggtttga acgcgcagcc gccatgccgg ggttttacga gattgtgatt aaggtcccca    120
gcgaccttga cgagcatctg cccggcattt ctgacagctt tgtgaactgg gtggccgaga    180
```

```
aggaatggga gttgccgcca gattctgaca tggatctgaa tctgattgag caggcacccc    240
tgaccgtggc cgagaagctg cagcgcgact ttctgacgga atggcgccgt gtgagtaagg    300
ccccggaggc tcttttcttt gtgcaatttg agaagggaga gagctacttc cacatgcacg    360
tgctcgtgga aaccaccggg gtgaaatcca tggttttggg acgtttcctg agtcagattc    420
gcgaaaaact gattcagaga atttaccgcg ggatcgagcc gactttgcca aactggttcg    480
cggtcacaaa gaccagaaat ggcgccgag gcgggaacaa ggtggtggat gagtgctaca    540
tccccaatta cttgctcccc aaaacccagc ctgagctcca gtgggcgtgg actaatatgg    600
aacagtattt aagcgcctgt ttgaatctca cggagcgtaa acggttggtg gcgcagcatc    660
tgacgcacgt gtcgcagacg caggagcaga acaaagagaa tcagaatccc aattctgatg    720
cgccggtgat cagatcaaaa acttcagcca ggtacatgga gctggtcggg tggctcgtgg    780
acaaggggat tacctcggag aagcagtgga tccaggtgag taattgacaa agccaaacac    840
caccatttgc cgagcacttt agagtttaca ggtttgtttc tcttgaccct caaaacaaac    900
ctgtgaggca tagggagtat tgctatccct taagaattca cccccagtgt gcccatcaaa    960
acctcccagg ctgagtctgc acagttgaag gaggaaggat aggaatggga gggtcgatgg   1020
gtgaaagcat gattctctta accagtccag attatcaggt aatcccttca acaaccacca   1080
cccactccct gggcaatcca gctggagttt acagacagac ttagctggct atagcaccac   1140
cgtgctactc tctgttcttc ctggttgctc aaatgcccta gaaaagtgga acaggtgagc   1200
atcaactcac agggctctat gctggctgct gctgcgaggg atgttatgct atagtaccag   1260
gggccaccat tccataggca cttcctgtgt ttaatacct atatgcttta cttcatctca    1320
tcttcctcca tatcctgaga ggtggttcta ttcttctccc cattttacgg atgaaaaaac    1380
cgagacacag aaaggtgaaa tagcttaaga taaatggtgc cttgcagcct tagactctgg   1440
tggcctctag ttaatgtggg aaattaaggg tgagggatt ggcagctgat ggagggtgca    1500
gggtgccaga cagaggcgtt tagctctgat cccttagcaa tagagagtcc ttgtaggcac   1560
ttggtcaggc gagtgatgcg atgaaagctg tgtttaagaa agattatgct ttctgctgat   1620 ttcataccc caacacccaa gctctgaggc ccctcctcac aggtccttgc agggctggcc    1680
aaaataaagc agcttcactc cgttgtgctg cttttccagct aatgtgtctg tttggcagaa   1740
gtttccctca aaggcagatc agtgaaataa gcagaagcct cgaccccct ttgtcagcca    1800 gagctgctga agtgccttgc cccagggtca ctttgtgtga ggggattaga gagcactggg   1860
gctgccaaga aacactgccg tttctacaga ttagcaggac gctggcttgt ggccttctag   1920
cgaggctcag agctgcggtg gccctagtct gcatgggcta aagacaagct ccatctcctg   1980
tccttgttcc ctccttcctg gcacagccg ccctgcttct tggttctctc tgttggttcc    2040
tgtccgcacg gtagttaggc tggcagcgtg tgtaggattt ggcttagaag attgacaaca   2100
ttgcctttga gccttctttt gctactcctc cctctcccct cccatcagac tcctctctgg   2160
agtctgctct gcgaggcctc tgctctgtgg tatcccagca gccttctcag ccttgacttc   2220 cagaagggg ctgtgcagtg tccggggtgt gcaggcccca gacacggggt aggctcatgg    2280
agatccaagt gctgatctag tgtcaaggct ggcctggaga ctgggctggg ttggtgtctg   2340
cctgctgtgg tcatgtgccc tcccttgggc ctgtatcctc tctccagact tgctgcaggg   2400
agaggtggca gatgtcagcc tagttctggc ctctcagagc agcatggcag ctcccttca    2460 ctcaggccca ggctgggccc tcctgctggc tgacccctgg ggagggtg ctccagagct     2520 ccccaaggaa cagcttcccg aagcagccag gccagcccag aggggctgtg ccaatcctg    2580
```

```
aagctttatg ttcctgctga cattttttct aagttttctc ttgctttcct cttaaatgcc    2640
aatctggaga gtctccgtta ggagaaatgg accccagcca ggaagaagag ttgagttgta    2700
tttaaaacac gagctccccc taaagcatcc ttctttagct tctaaggaga ggcagagact    2760
gacaggcagg actcagcagg aaaaggtacc cccctgacct gctcagtcag gccctaggcc    2820
cagctccacc cagcctgtgg cccccagagt ttcggtaaag agttccctgg gccttaagga    2880
accttgagag agcatttgag gggtgccacc acaaacttgg cagaaaaaac cctcccctc     2940 caagtccagt cctagagaag gagctggcaa ccttgccttg ctttgtaagc aaaagcctct    3000
tagggcttga gctcagatgt agtgtttgag ctgtggctgg tgccctgccc catcagggag    3060
ccaatggtag acatcctatg ggcatctttg ttttccgtaa gagcaggctg tctggggatg    3120
ggccagagga agaggcgacc tggagtcaac caagaggagg ccttaaccaa gccttaacca    3180
cagaggttaa ccaagccttg aaagcgcttc cccctgagca ggcaggaagc actgagtcca    3240
catggttgcc tcgctgtttc atttccttac actcaattct ctcagtcttt aaatgatcac    3300
ttggccttga agttacggat atttggggtc tgaactgaag ttgaagaaaa gaggaaatga    3360
tttaagcttt gtttaagatt aggggccagg tgcggtggct cacgcctgta atcccagcac    3420
cttgggagcc tgaggcgggt ggatcacctg aggtcaggag ttccagacca gcctggccaa    3480
catagcaaaa cccagtctct actaaaaata acaataaaaa aattagccag gtgtggtgac    3540
acatgcctgt aatcccagtt actcaggagg ctgaggcaga attgcttgaa cttgagaggt    3600
ggaggttgta gtgagccaag accgcaccac tgcactccag cctggcgaca gagccagact    3660
ccgtctcaaa acaacaaca aaaagatta gaagaagccc attactgcct tctggccacc     3720
cactcgcaca gacaccaaaa ctgcagccca cacctcgcca tcctcgtgct ctgccctggg    3780 acacccagg cacagtgtgt ccttcgtttt ctgtaagggt gggctgggag cagggacgga    3840
cagggcctgt gggcacctct catggtcact tccttcttgc tcacaggagg accaggcctc    3900
atacatctcc ttcaatgcgg cctccaactc gcggtcccaa atcaaggctg ccttggacaa    3960
tgcgggaaag attatgagcc tgactaaaac cgcccccgac tacctggtgg gccagcagcc    4020
cgtggaggac atttccagca atcggattta taaaattttg gaactaaacg ggtacgatcc    4080
ccaatatgcg gcttccgtct ttctgggatg ggccacgaaa aagttcggca agaggaacac    4140
catctggctg tttgggcctg caactaccgg gaagaccaac atcgcggagg ccatagccca    4200
cactgtgccc ttctacgggt gcgtaaactg gaccaatgag aactttccct tcaacgactg    4260
tgtcgacaag atggtgatct ggtgggagga ggggaagatg accgccaagg tcgtggagtc    4320
ggccaaagcc attctcggag gaagcaaggt gcgcgtggac cagaaatgca agtcctcggc    4380
ccagatagac ccgactcccg tgatcgtcac ctccaacacc aacatgtgcg ccgtgattga    4440
cgggaactca acgaccttcg aacaccagca gccgttgcaa gaccggatgt tcaaatttga    4500
actcacccgc cgtctggatc atgactttgg gaaggtcacc aagcaggaag tcaaagactt    4560
tttccggtgg gcaaaggatc acgtggttga ggtggagcat gaattctacg tcaaaaaggg    4620
tggagccaag aaaagacccg cccccagtga cgcagatata agtgagccca acgggtgcg     4680 cgagtcagtt gcgcagccat cgacgtcaga cgcggaagct tcgatcaact acgcagacag    4740
gtaccaaaac aaatgttctc gtcacgtggg catgaatctg atgctgtttc cctgcagaca    4800
atgcgagaga atgaatcaga attcaaatat ctgcttcact cacggacaga aagactgttt    4860
agagtgcttt cccgtgtcag aatctcaacc cgtttctgtc gtcaaaaagg cgtatcagaa    4920
```

```
actgtgctac attcatcata tcatgggaaa ggtgccagac gcttgcactg cctgcgatct   4980
ggtcaatgtg gatttggatg actgcatctt tgaacaataa atgatttaaa tcaggtatgg   5040
ctgccgatgg ttatcttcca gattggctcg aggacaacct ctctgagggc attcgcgagt   5100
ggtgggacct gaaacctgga gccccgaaac ccaaagccaa ccagcaaaag caggacaacg   5160
gccggggtct ggtgcttcct ggctacaagt acctcggacc cttcaacgga ctcgacaagg   5220
gggagcccgt caacgcggcg gacgcagcgg ccctcgagca cgacaaggcc tacgaccagc   5280
agctccaagc gggtgacaat ccgtacctgc ggtataatca cgccgacgcc gagtttcagg   5340
agcgtctgca agaagatacg tcttttgggg gcaacctcgg gcgcgcagtc ttccaggcca   5400
aaaagcgggt tctcgaacct ctgggcctgg ttgaatcgcc ggttaaggcg ctcctggaa    5460 agaagagacc ggtagagcca tcaccccagc gctctccaga ctcctctacg ggcatcggca   5520
agaaaggcca gcagcccgca aaaagagac tcaattttgg gcagactggc gactcagagt    5580
cagtccccga ccctcaacca atcggagaac caccagcagg ccctctggt ctgggatctg    5640 gtacaatggc tgcaggcggt ggcgctccaa tggcagacaa taacgaaggc gccgacggag   5700
tgggtagttc ctcaggaaat tggcattgcg attccacatg gctgggcgac agagtcatca   5760
ccaccagcac ccgcacctgg gccctgccca cctacaacaa ccacctctac aagcaaatct   5820
ccaacgggac ctcggagga agcaccaacg acaacaccta cttcggctac agcaccccct    5880
gggggtattt tgacttcaac agattccact gccactttc accacgtgac tggcagcgac    5940
tcatcaacaa caactgggga ttccggccca agaggctcaa cttcaagctc ttcaacatcc   6000
aagtcaagga ggtcacgcag aatgaaggca ccaagaccat cgccaataac cttaccagca   6060
cgattcaggt cttacggac tcggaatacc agctcccgta cgtgctcggc tcggcgcacc    6120
agggctgcct gcctccgttc ccggcggacg tcttcatgat tcctcagtac gggtacctga   6180
ctctgaacaa tggcagtcag gctgtgggcc ggtcgtcctt ctactgcctg gagtactttc   6240
cttctcaaat gctgagaacg ggcaacaact ttgaattcag ctacaacttc gaggacgtgc   6300
ccttccacag cagctacgcg cacagccaga gcctggaccg gctgatgaac cctctcatcg   6360
accagtactt gtactacctg tcccggactc aaagcacggg cggtactgca ggaactcagc   6420
agttgctatt ttctcaggcc gggcctaaca acatgtcggc tcaggccaag aactggctac   6480 ccggtcctg ctaccggcag caacgcgtct ccacgacact gtcgcagaac aacaacagca    6540
actttgcctg gacgggtgcc accaagtatc atctgaatgg cagagactct ctggtgaatc   6600
ctggcgttgc catggctacc cacaaggacg acgaagagcg attttttcca tccagcggag   6660
tcttaatgtt tgggaaacag ggagctggaa agacaacgt ggactatagc agcgtgatgc    6720
taaccagcga ggaagaaata aagaccacca cccagtggc cacagaacag tacggcgtgg    6780
tggccgataa cctgcaacag caaaacgccg ctcctattgt agggccgtc aatagtcaag    6840 gagccttacc tggcatggtg tggcagaacc gggacgtgta cctgcagggt cccatctggg   6900
ccaagattcc tcatacggac ggcaactttc atccctcgcc gctgatggga ggctttggac   6960
tgaagcatcc gcctcctcag atcctgatta aaaacacacc tgttcccgcg gatcctccga   7020
ccaccttcag ccaggccaag ctggcttctt tcatcacgca gtacagtacc ggccaggtca   7080
gcgtggagat cgagtgggag ctgcagaagg agaacagcaa acgctggaac ccagagattc   7140
agtacacttc caactactac aaatctacaa atgtggactt tgctgtcaat actgagggta   7200
cttattccga gcctcgcccc attggcaccc gttacctcac ccgtaatctg taattacatg   7260
ttaatcaata aaccggttaa ttcgtttcag ttgaactttg gtctcctgtc cttcttatct   7320
```

```
tatcggttac catagaaact ggttacttat taactgcttg gtgcgcttcg cgataaaaga    7380
cttacgtcat cgggttaccc ctagtgatgg agcggccgct ttcagttgaa ctttggtctc    7440
tgcgtatttc tttcttatct agtttccatg ctctagaggt cctgtattag aggtcacgtg    7500
agtgttttgc gacattttgc gacaccatgt ggtcacgctg ggtatttaag cccgagtgag    7560
cacgcagggt ctccattttg aagcgggagg tttgaacgcg cagccgccaa gccgaattct    7620
gcagatatcc atcacactgg cggccgctcg actagagcgg ccgccaccgc ggtggagctc    7680
cagcttttgt tccctttagt gagggttaat tgcgcgcttg gcgtaatcat ggtcatagct    7740
gtttcctgtg tgaaattgtt atccgctcac aattccacac aacatacgag ccggaagcat    7800
aaagtgtaaa gcctggggtg cctaatgagt gagctaactc acattaattg cgttgcgctc    7860
actgcccgct ttccagtcgg gaaacctgtc gtgccagctg cattaatgaa tcggccaacg    7920
cgcggggaga ggcggtttgc gtattgggcg ctcttccgct tcctcgctca ctgactcgct    7980
gcgctcggtc gttcggctgc ggcgagcggt atcagctcac tcaaaggcgg taatacggtt    8040
atccacagaa tcaggggata acgcaggaaa gaacatgtga gcaaaaggcc agcaaaaggc    8100
caggaaccgt aaaaaggccg cgttgctggc gtttttccat aggctccgcc cccctgacga    8160
gcatcacaaa aatcgacgct caagtcagag gtggcgaaac ccgacaggac tataaagata    8220
ccaggcgttt ccccctggaa gctccctcgt gcgctctcct gttccgaccc tgccgcttac    8280
cggatacctg tccgcctttc tcccttcggg aagcgtggcg ctttctcata gctcacgctg    8340
taggtatctc agttcggtgt aggtcgttcg ctccaagctg ggctgtgtgc acgaaccccc    8400
cgttcagccc gaccgctgcg ccttatccgg taactatcgt cttgagtcca acccggtaag    8460
acacgactta tcgccactgg cagcagccac tggtaacagg attagcagag cgaggtatgt    8520
aggcggtgct acagagttct tgaagtggtg gcctaactac ggctacacta agaacagt    8580
atttggtatc tgcgctctgc tgaagccagt taccttcgga aaaagagttg gtagctcttg    8640
atccggcaaa caaaccaccg ctggtagcgg tggttttttt gtttgcaagc agcagattac    8700
gcgcagaaaa aaaggatctc aagaagatcc tttgatcttt tctacggggt ctgacgctca    8760
gtggaacgaa aactcacgtt aagggatttt ggtcatgaga ttatcaaaaa ggatcttcac    8820
ctagatcctt ttaaattaaa aatgaagttt taaatcaatc taaagtatat atgagtaaac    8880
ttggtctgac agttaccaat gcttaatcag tgaggcacct atctcagcga tctgtctatt    8940
tcgttcatcc atagttgcct gactccccgt cgtgtagata actacgatac gggagggctt    9000
accatctggc cccagtgctg caatgatacc gcgagaccca cgctcaccgg ctccagattt    9060
atcagcaata aaccagccag ccggaagggc cgagcgcaga agtggtcctg caactttatc    9120
cgcctccatc cagtctatta attgttgccg ggaagctaga gtaagtagtt cgccagttaa    9180
tagtttgcgc aacgttgttg ccattgctac aggcatcgtg gtgtcacgct cgtcgtttgg    9240
tatggcttca ttcagctccg gttcccaacg atcaaggcga gttacatgat cccccatgtt    9300
gtgcaaaaaa gcggttagct ccttcggtcc tccgatcgtt gtcagaagta agttggccgc    9360
agtgttatca ctcatggtta tggcagcact gcataattct cttactgtca tgccatccgt    9420
aagatgcttt tctgtgactg gtgagtactc aaccaagtca ttctgagaat agtgtatgcg    9480
gcgaccgagt tgctcttgcc cggcgtcaat acgggataat accgcgccac atagcagaac    9540
tttaaaagtg ctcatcattg gaaaacgttc ttcgggcgca aaactctcaa ggatcttacc    9600
gctgttgaga tccagttcga tgtaacccac tcgtgcaccc aactgatctt cagcatcttt    9660
```

```
tactttcacc agcgtttctg ggtgagcaaa acaggaagg caaaatgccg caaaaaggg     9720 aataagggcg acacggaaat gttgaatact catactcttc cttttcaat attattgaag    9780 catttatcag ggttattgtc tcatgagcgg atacatattt gaatgtattt agaaaaataa   9840
acaaataggg gttccgcgca catttccccg aaaagtgcca cctaaattgt aagcgttaat   9900
attttgttaa aattcgcgtt aaattttgt taaatcagct cattttttaa ccaataggcc    9960
gaaatcggca aaatcccta taaatcaaaa gaatagaccg atagggtt gagtgttgtt     10020 ccagtttgga acaagagtcc actattaaag aacgtggact ccaacgtcaa agggcgaaaa   10080
accgtctatc agggcgatgg cccactacgt gaaccatcac cctaatcaag tttttggg    10140 tcgaggtgcc gtaaagcact aaatcggaac cctaaaggga gccccgatt tagagcttga   10200 cggggaaagc cggcgaacgt ggcgagaaag gaagggaaga aagcgaaagg agcgggcgct   10260
agggcgctgg caagtgtagc ggtcacgctg cgcgtaacca ccacacccgc cgcgcttaat   10320
gcgccgctac agggcgcgtc ccattcgcca ttcaggctgc gcaactgttg ggaagggcga   10380
tcggtgcggg cctcttcgct attacgccag ctggcgaaag gggatgtgc tgcaaggcga    10440 ttaagttggg taacgccagg ttttcccag tcacgacgtt gtaaaacgac ggccagtgag    10500
cgcgcgtaat acgactcact atagggcgaa ttgggtac                          10538

<210> SEQ ID NO 58
<211> LENGTH: 2217
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 58
atggctgccg atggttatct tccagattgg ctcgaggaca acctctctga gggcattcgc    60
gagtggtggg acctgaaacc tggagccccg aaacccaaag ccaaccagca aaagcaggac   120
aacggccggg gtctggtgct tcctggctac aagtacctcg gacccttcaa cggactcgac   180
aagggggagc ccgtcaacgc ggcggacgca gcggccctcg agcacgacaa ggcctacgac   240
cagcagctcc aagcgggtga caatccgtac ctgcggtata tcacgccga cgccgagttt   300 caggagcgtc tgcaagaaga tacgtctttt ggggcaacc tcgggcgcgc agtcttccag   360
gccaaaaagc gggttctcga acctctgggc ctggttgaat cgccggttaa gacggctcct   420
ggaaagaaga gaccggtaga gccatcaccc cagcgctctc cagactcctc tacgggcatc   480
ggcaagaaag gccagcagcc cgcaaaaaag agactcaatt ttgggcagac tggcgactca   540
gagtcagtcc ccgaccctca accaatcgga gaaccaccag caggcccctc tggtctggga   600
tctggtacaa tggctgcagg cggtggcgct ccaatggcag acaataacga aggcgccgac   660
ggagtgggta gttcctcagg aaattggcat gcgattcca catggctggg cgacagagtc   720
atcaccacca gcacccgcac ctgggcccctg cccacctaca caaccacct ctacaagcaa    780 atctccaacg gacctcgggg aggaagcacc aacgacaaca cctacttcgg ctacagcacc   840 ccctggggt attttgactt caacagattc cactgccact tttccaccac tgactggcag   900
cgactcatca acaacaactg gggattccgg cccaagaggc tcaacttcaa gctcttcaac   960
atccaagtca aggaggtcac gcagaatgaa ggcaccaaga ccatcgccaa taaccttacc   1020
agcacgattc aggtctttac ggactcggaa taccagctcc cgtacgtgct cggtcggcg    1080 caccagggct gcctgcctcc gttcccggcg gacgtcttca tgattcctca gtacgggtac   1140
```

```
ctgactctga acaatggcag tcaggctgtg ggccggtcgt ccttctactg cctggagtac   1200
tttccttctc aaatgctgag aacgggcaac aactttgaat tcagctacaa cttcgaggac   1260
gtgcccttcc acagcagcta cgcgcacagc cagagcctgg accggctgat gaaccctctc   1320
atcgaccagt acttgtacta cctgtcccgg actcaaagca cgggcggtac tgcaggaact   1380
cagcagttgc tattttctca ggccgggcct aacaacatgt cggctcaggc caagaactgg   1440
ctacccggtc cctgctaccg gcagcaacgc gtctccacga cactgtcgca gaacaacaac   1500
agcaactttg cctggacggg tgccaccaag tatcatctga atggcagaga ctctctggtg   1560
aatcctggcg ttgccatggc tacccacaag gacgacgaag agcgattttt tccatccagc   1620
ggagtcttaa tgtttgggaa cagggagct ggaaaagaca acgtggacta tagcagcgtg   1680
atgctaacca gcgaggaaga aataaagacc accaacccag tggccacaga acagtacggc   1740
gtggtggccg ataacctgca acagcaaaac gccgctccta ttgtaggggc cgtcaatagt   1800
caaggagcct tacctggcat ggtgtggcag aaccgggacg tgtacctgca gggtcccatc   1860
tgggccaaga ttcctcatac ggacggcaac tttcatccct cgccgctgat gggaggcttt   1920
ggactgaagc atccgcctcc tcagatcctg attaaaaaca cacctgttcc cgcggatcct   1980
ccgaccacct tcaatcaggc caagctggct tctttcatca cgcagtacag taccggccag   2040
gtcagcgtgg agatcgagtg ggagctgcag aaggagaaca gcaaacgctg gaacccagag   2100
attcagtaca cttccaacta ctacaaatct acaaatgtgg actttgctgt caatactgag   2160
ggtacttatt ccgagcctcg ccccattggc acccgttacc tcacccgtaa tctgtaa     2217
```

<210> SEQ ID NO 59
<211> LENGTH: 738
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 59

```
Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asn Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Gln Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Ser Pro Val Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160
```

-continued

```
Gly Lys Lys Gly Gln Gln Pro Ala Lys Lys Arg Leu Asn Phe Gly Gln
                165                 170                 175
Thr Gly Asp Ser Glu Ser Val Pro Asp Pro Gln Pro Ile Gly Glu Pro
            180                 185                 190
Pro Ala Gly Pro Ser Gly Leu Gly Ser Gly Thr Met Ala Ala Gly Gly
        195                 200                 205
Gly Ala Pro Met Ala Asp Asn Asn Glu Gly Ala Asp Gly Val Gly Ser
    210                 215                 220
Ser Ser Gly Asn Trp His Cys Asp Ser Thr Trp Leu Gly Asp Arg Val
225                 230                 235                 240
Ile Thr Thr Ser Thr Arg Thr Trp Ala Leu Pro Thr Tyr Asn Asn His
                245                 250                 255
Leu Tyr Lys Gln Ile Ser Asn Gly Thr Ser Gly Gly Ser Thr Asn Asp
            260                 265                 270
Asn Thr Tyr Phe Gly Tyr Ser Thr Pro Trp Gly Tyr Phe Asp Phe Asn
        275                 280                 285
Arg Phe His Cys His Phe Ser Pro Arg Asp Trp Gln Arg Leu Ile Asn
    290                 295                 300
Asn Asn Trp Gly Phe Arg Pro Lys Arg Leu Asn Phe Lys Leu Phe Asn
305                 310                 315                 320
Ile Gln Val Lys Glu Val Thr Gln Asn Glu Gly Thr Lys Thr Ile Ala
                325                 330                 335
Asn Asn Leu Thr Ser Thr Ile Gln Val Phe Thr Asp Ser Glu Tyr Gln
            340                 345                 350
Leu Pro Tyr Val Leu Gly Ser Ala His Gln Gly Cys Leu Pro Pro Phe
        355                 360                 365
Pro Ala Asp Val Phe Met Ile Pro Gln Tyr Gly Tyr Leu Thr Leu Asn
    370                 375                 380
Asn Gly Ser Gln Ala Val Gly Arg Ser Ser Phe Tyr Cys Leu Glu Tyr
385                 390                 395                 400
Phe Pro Ser Gln Met Leu Arg Thr Gly Asn Asn Phe Glu Phe Ser Tyr
                405                 410                 415
Asn Phe Glu Asp Val Pro Phe His Ser Ser Tyr Ala His Ser Gln Ser
            420                 425                 430
Leu Asp Arg Leu Met Asn Pro Leu Ile Asp Gln Tyr Leu Tyr Tyr Leu
        435                 440                 445
Ser Arg Thr Gln Ser Thr Gly Gly Thr Ala Gly Thr Gln Gln Leu Leu
    450                 455                 460
Phe Ser Gln Ala Gly Pro Asn Asn Met Ser Ala Gln Ala Lys Asn Trp
465                 470                 475                 480
Leu Pro Gly Pro Cys Tyr Arg Gln Gln Arg Val Ser Thr Thr Leu Ser
                485                 490                 495
Gln Asn Asn Asn Ser Asn Phe Ala Trp Thr Gly Ala Thr Lys Tyr His
            500                 505                 510
Leu Asn Gly Arg Asp Ser Leu Val Asn Pro Gly Val Ala Met Ala Thr
        515                 520                 525
His Lys Asp Asp Glu Glu Arg Phe Phe Pro Ser Ser Gly Val Leu Met
    530                 535                 540
Phe Gly Lys Gln Gly Ala Gly Lys Asp Asn Val Asp Tyr Ser Ser Val
545                 550                 555                 560
Met Leu Thr Ser Glu Glu Glu Ile Lys Thr Thr Asn Pro Val Ala Thr
                565                 570                 575
Glu Gln Tyr Gly Val Val Ala Asp Asn Leu Gln Gln Gln Asn Ala Ala
```

```
                580             585             590
Pro Ile Val Gly Ala Val Asn Ser Gln Gly Ala Leu Pro Gly Met Val
            595                 600             605

Trp Gln Asn Arg Asp Val Tyr Leu Gln Gly Pro Ile Trp Ala Lys Ile
610             615                 620

Pro His Thr Asp Gly Asn Phe His Pro Ser Pro Leu Met Gly Gly Phe
625                 630                 635                 640

Gly Leu Lys His Pro Pro Gln Ile Leu Ile Lys Asn Thr Pro Val
                645             650                 655

Pro Ala Asp Pro Pro Thr Thr Phe Asn Gln Ala Lys Leu Ala Ser Phe
                660             665                 670

Ile Thr Gln Tyr Ser Thr Gly Gln Val Ser Val Glu Ile Glu Trp Glu
            675                 680             685

Leu Gln Lys Glu Asn Ser Lys Arg Trp Asn Pro Glu Ile Gln Tyr Thr
            690                 695             700

Ser Asn Tyr Tyr Lys Ser Thr Asn Val Asp Phe Ala Val Asn Thr Glu
705                 710                 715                 720

Gly Thr Tyr Ser Glu Pro Arg Pro Ile Gly Thr Arg Tyr Leu Thr Arg
                725             730                 735

Asn Leu

<210> SEQ ID NO 60
<211> LENGTH: 136
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 60

Cys Leu Ser Tyr Asp Thr Glu Ile Leu Thr Val Glu Tyr Gly Phe Leu
1               5                   10                  15

Pro Ile Gly Lys Ile Val Glu Glu Arg Ile Glu Cys Thr Val Tyr Thr
            20                  25                  30

Val Asp Lys Asn Gly Phe Val Tyr Thr Gln Pro Ile Ala Gln Trp His
        35                  40                  45

Asn Arg Gly Glu Gln Glu Val Phe Glu Tyr Cys Leu Glu Asp Gly Ser
    50                  55                  60

Ile Ile Arg Ala Thr Lys Asp His Lys Phe Met Thr Thr Asp Gly Gln
65                  70                  75                  80

Met Leu Pro Ile Asp Glu Ile Phe Glu Arg Gly Leu Asp Leu Lys Gln
                85                  90                  95

Val Asp Gly Leu Pro Val Lys Ile Ile Ser Arg Lys Ser Leu Gly Thr
            100                 105                 110

Gln Asn Val Tyr Asp Ile Gly Val Glu Lys Asp His Asn Phe Leu Leu
        115                 120                 125

Lys Asn Gly Leu Val Ala Ser Asn
    130                 135

<210> SEQ ID NO 61
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 6xHis tag"
```

```
<400> SEQUENCE: 61

His His His His His His
1               5
```

What is claimed is:

1. A modified viral capsid protein comprising a viral capsid protein having a Cas9 protein conjugated to the interior of the viral capsid protein, wherein the Cas9 protein is conjugated to a viral protein 2 (VP2) at amino acid position 228, 350, 419, 684, or 689 of SEQ ID NO: 59.

2. The modified viral capsid protein of claim 1, further comprising one or more linkers.

3. The modified viral capsid protein of claim 2, wherein the one or more linkers comprise SEQ ID NO: 31, SEQ ID NO: 32, SEQ ID NO: 33, SEQ ID NO: 34, SEQ ID NO: 35, or SEQ ID NO: 51.

4. The modified viral capsid protein of claim 1, wherein the Cas9 protein has been conjugated to the interior of the viral capsid protein via modular intein based assembly.

5. The modified viral capsid protein of claim 1, wherein the Cas9 protein is conjugated to VP2 at amino acid position 228, 350, 419, 684, or 689 of SEQ ID NO: 59 via one or more linkers.

6. The modified viral capsid protein of claim 1, wherein the modified capsid protein comprises SEQ ID NO: 45, SEQ ID NO: 46, SEQ ID NO: 47, SEQ ID NO: 48, or SEQ ID NO: 49.

7. The modified viral capsid protein of claim 1, wherein the modified capsid protein comprises SEQ ID NO: 39.

8. An isolated polynucleotide encoding a modified viral capsid protein comprising a viral capsid protein having a Cas9 protein conjugated to the interior of the viral capsid protein, wherein the Cas9 protein is conjugated to VP2 at amino acid position 228, 350, 419, 684, or 689 of SEQ ID NO: 59 via one or more linkers.

9. An isolated vector or host cell comprising the isolated polynucleotide of claim 8.

10. A recombinant viral particle comprising a modified capsid wherein the modified capsid comprises the modified viral capsid protein of claim 1.

11. The recombinant viral particle of claim 10, further comprising a polynucleotide encapsidated within the modified capsid.

12. The recombinant viral particle of claim 11, wherein the polynucleotide comprises a polynucleotide encoding one or more guide RNAs (gRNAs).

13. The recombinant viral particle of claim 12, wherein the polynucleotide comprising the polynucleotide encoding the one or more gRNAs comprises:
    a. a fusion polynucleotide encoding CRISPR RNA (crRNA) and trans-activating CRISPR RNA (tracrRNA); or
    b. a polynucleotide encoding CRISPR RNA (crRNA) and trans-activating CRIPSPR RNA (tracrRNA).

14. The recombinant viral particle of claim 10, further comprising a therapeutic polynucleotide.

15. A recombinant expression system for the generation of a modified viral particle comprising Cas9 on the interior of the viral capsid, wherein the Cas9 protein is fused to VP2 at amino acid position 228, 350, 419, 684, or 689 of SEQ ID NO: 59, the recombinant expression system comprising:
    (a) a plasmid comprising a DNA sequence encoding a fusion protein, the fusion protein comprising the Cas9 and an N-terminal fragment of a split intein;
    (b) a plasmid comprising a DNA sequence encoding a fusion protein, the fusion protein comprising a viral capsid protein and a C-terminal fragment of a split intein; and
    (c) a helper plasmid.

16. The recombinant expression system of claim 15, wherein the Cas9 protein is fused to VP2 at amino acid position 228, 350, 419, 684, or 689 of SEQ ID NO: 59 via one or more linkers.

17. A method of producing modified AAV expressing Cas9 on the interior of the viral capsid comprising transfecting one or more cells with the recombinant expression system of claim 15.

18. An isolated tissue comprising the modified viral capsid protein of claim 1.

19. A non-human transgenic animal comprising the modified viral capsid protein of claim 1.

20. A method of gene editing or gene regulation comprising contacting a cell with the recombinant viral particle of claim 10.

21. A method of gene editing or gene regulation comprising contacting a cell with the recombinant viral particle of claim 10 and a second viral particle comprising a polynucleotide.

22. The method of claim 21, wherein the polynucleotide comprises a polynucleotide encoding one or more guide RNAs (gRNAs).

23. The method of claim 22, wherein the polynucleotide encoding the one or more gRNAs comprises:
    a. a fusion polynucleotide comprising CRISPR RNA (crRNA) and trans-activating CRIPSPR RNA (tracrRNA); or
    b. a polynucleotide comprising CRISPR RNA (crRNA) and trans-activating CRIPSPR RNA (tracrRNA).

24. The method of claim 21, further comprising a therapeutic polynucleotide.

25. The method of claim 24, wherein the therapeutic polynucleotide comprises a repair template.

26. The method of claim 20, wherein the contacting is in vitro, in vivo, or ex vivo.

* * * * *